United States Patent
Kaldor et al.

(10) Patent No.: US 11,407,737 B2
(45) Date of Patent: Aug. 9, 2022

(54) INHIBITORS OF RAF KINASES

(71) Applicant: Kinnate Biopharma Inc., San Diego, CA (US)

(72) Inventors: Stephen W. Kaldor, San Diego, CA (US); Toufike Kanouni, Rancho Santa Fe, CA (US); John Tyhonas, San Diego, CA (US); Eric Murphy, San Marcos, CA (US); Jason Cox, Rancho Santa Fe, CA (US); Robert Kania, Del Mar, CA (US)

(73) Assignee: KINNATE BIOPHARMA INC., San Diego, CA (US)

( * ) Notice: Subject to any disclaimer, the term of this patent is extended or adjusted under 35 U.S.C. 154(b) by 0 days.

(21) Appl. No.: 17/477,260

(22) Filed: Sep. 16, 2021

(65) Prior Publication Data

US 2022/0089569 A1    Mar. 24, 2022

Related U.S. Application Data

(60) Provisional application No. 63/080,268, filed on Sep. 18, 2020.

(51) Int. Cl.
| | | |
|---|---|---|
| *C07D 401/14* | (2006.01) | |
| *C07D 413/14* | (2006.01) | |
| *C07D 401/12* | (2006.01) | |
| *C07D 471/08* | (2006.01) | |
| *C07D 265/30* | (2006.01) | |
| *C07D 417/14* | (2006.01) | |

(52) U.S. Cl.
CPC ......... *C07D 401/14* (2013.01); *C07D 401/12* (2013.01); *C07D 413/14* (2013.01); *C07D 417/14* (2013.01)

(58) Field of Classification Search
CPC .. C07D 401/14; C07D 413/14; C07D 401/12; C07D 471/08; C07D 265/30
See application file for complete search history.

(56) References Cited

U.S. PATENT DOCUMENTS

| | | |
|---|---|---|
| 5,846,514 A | 12/1998 | Foster et al. |
| 6,334,997 B1 | 1/2002 | Foster et al. |
| 10,927,111 B2 | 2/2021 | Kaldaor et al. |
| 11,098,031 B1 | 8/2021 | Kaldor et al. |
| 2004/0157827 A1 | 8/2004 | Pevarello et al. |
| 2005/0256174 A1 | 11/2005 | Wood et al. |
| 2007/0054916 A1 | 3/2007 | Patel et al. |
| 2007/0244120 A1 | 10/2007 | Dumas et al. |
| 2008/0114006 A1 | 5/2008 | Flynn et al. |
| 2009/0036419 A1 | 2/2009 | Chen et al. |
| 2009/0054436 A1 | 2/2009 | Borzilleri et al. |
| 2011/0183997 A1 | 7/2011 | Chianelli et al. |
| 2012/0040951 A1 | 2/2012 | Chuaqui et al. |
| 2015/0119392 A1 | 4/2015 | Flynn et al. |
| 2016/0075727 A1 | 3/2016 | Burger et al. |
| 2017/0260207 A1 | 9/2017 | Aversa et al. |
| 2019/0175606 A1 | 6/2019 | Aversa et al. |
| 2021/0246135 A1 | 8/2021 | Kaldor et al. |

FOREIGN PATENT DOCUMENTS

| | | |
|---|---|---|
| WO | WO-03068229 A1 | 8/2003 |
| WO | WO-2006071940 A2 | 7/2006 |
| WO | WO-2008034008 A2 | 3/2008 |
| WO | WO-2013184119 A1 | 12/2013 |
| WO | WO-2014151616 A1 | 9/2014 |
| WO | WO-2016038581 A1 | 3/2016 |
| WO | WO-2020168172 A1 | 8/2020 |
| WO | WO-2020198058 A1 | 10/2020 |
| WO | WO-2020227020 A1 | 11/2020 |

OTHER PUBLICATIONS

Anastassiadis et al. Comprehensive assay of kinase catalytic activity reveals features of kinase inhibitor selectivity. Nat Biotechnol. 29(11):1039-45 (2011).
Berge et al. Pharmaceutical Salts. Journal of Pharmaceutical Sciences 66(1): 1-19 (Jan. 1977).
CAS Chemical Structure Search #3191415 Updated (Apr. 2020).
CAS Chemical Structure Search dated Apr. 24, 2019.
Co-pending U.S. Appl. No. 17/213,036, inventors Kaldor; Stephen W. et al., filed on Mar. 25, 2021.
Evans. Synthesis of radiolabeled compounds. J Radioanal Chem 64(1-2):9-32 (1981).
Henry et al. Discovery of 1-(3,3-dimethylbutyl)-3-(2-fluoro-4-methyl-5-(7-methyl-2-(methylamino)pyrido[2,3-d]pyrimidin-6-yl)phenyl)urea (LY3009120) as a pan-RAF inhibitor with minimal paradoxical activation and activity against BRAF or RAS mutant tumor cells. J Med Chem 58:4165-4179 (2015).
Kabalka et al. The Synthesis of Radiolabeled Compounds via Organometallic Intermediates. Tetrahedron 45(21):6601-6621 (1989).
PCT/US2020/024009 International Search Report and Written Opinion dated Jul. 28, 2020.
PCT/US2020/024009 Invitation to Pay Additional Fees dated Jun. 2, 2020.
PCT/US2020/030786 International Search Report and Written Opinion dated Sep. 14, 2020.
PCT/US2020/030786 Invitation to Pay Additional Fees dated Jul. 14, 2020.
PCT/US2020/057132 International Search Report and Written Opinion dated Feb. 9, 2021.
Rosse. Pyridyl Isonicotinamide Inhibitors of RAF Kinase. ACS Med. Chem. Lett. 7:1022-1023 (2016).
Science IP Report dated Jul. 13, 2020 (873 pgs).
Lv et al. Design, synthesis and biological evaluation of novel 4-alkynylquinoline derivatives as PI3K/mTOR dual inhibitors. Eur J Med Chem 99:36-50 (2015).

(Continued)

*Primary Examiner* — Samira J Jean-Louis
(74) *Attorney, Agent, or Firm* — Wilson Sonsini Goodrich & Rosati

(57) ABSTRACT

Provided herein are inhibitors of receptor tyrosine kinase effector, RAF, pharmaceutical compositions comprising said compounds, and methods for using said compounds for the treatment of diseases.

30 Claims, No Drawings

(56) References Cited

OTHER PUBLICATIONS

Nishiguchi et al. Design and Discovery of N-(2-Methyl-5'-morpholino-6'-((tetrahydro-2H-pyran-4-yl)oxy)-[3,3'-bipyridin]-5-yl)-3-(trifluoromethyl)benzamide (RAF709): A Potent, Selective, and Efficacious RAF Inhibitor Targeting RAS Mutant Cancers. J Med Chem 60(12):4869-4881 (2017).

PCT/US2021/050690 International Search Report and Written Opinion dated Dec. 27, 2021.

PCT/US2021/054403 International Search Report and Written Opinion dated Dec. 28, 2021.

Ramurthy et al. Design and Discovery of N-(3-(2-(2-Hydroxyethoxy)-6-morpholinopyridin-4-yl)-4-methylphenyl)-2-(trifluoromethyl)isonicotinamide, a Selective, Efficacious, and Well-Tolerated RAF Inhibitor Targeting RAS Mutant Cancers: The Path to the Clinic. J Med Chem 63(5):2013-2027 (2020).

Reg/Caplus and Marpat. Science IP Report dated Sep. 17, 2020.

INHIBITORS OF RAF KINASES

CROSS-REFERENCE TO RELATED APPLICATION

This application claims benefit of U.S. Patent Application No. 63/080,268, filed on Sep. 18, 2020 which is incorporated by reference in its entirety.

BACKGROUND

RAF kinase functions in the Ras-Raf-MEK-ERK mitogen activated protein kinase (MAPK) pathway (also known as MAPK/ERK pathway) by phosphorylating and activating MEK. By altering the levels and activities of transcription factors, MAPK leads to altered transcription of genes that are important for the cell cycle. Deregulation of MAPK activity occurs frequently in tumors. Accordingly, therapies that target RAF kinase activity are desired for use in the treatment of cancer and other disorders characterized by aberrant MAPK/ERK pathway signaling.

BRIEF SUMMARY OF THE INVENTION

Provided herein are inhibitors of the receptor tyrosine kinase effector Raf (RAF), pharmaceutical compositions comprising said compounds, and methods for using said compounds for the treatment of diseases.

One embodiment provides a compound, or pharmaceutically acceptable salt or solvate thereof, having the structure of Formula (I):

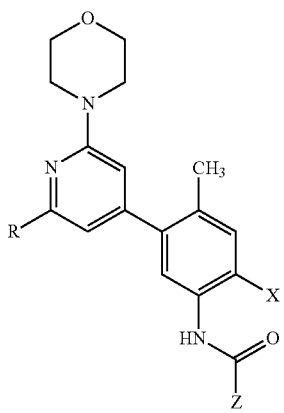

(I)

wherein,
R is selected from optionally substituted C1-C8 alkyl, optionally substituted C2-C8 alkenyl, optionally substituted C2-C8 alkynyl, optionally substituted C3-C6 cycloalkyl, optionally substituted C4-C8 cycloalkylalkyl, optionally substituted C3-C6 heterocyclyl, optionally substituted C4-C8 heterocyclylalkyl, optionally substituted C6 aryl, optionally substituted 5- or 6-membered heteroaryl, or —CON($R^1$)$_2$—;
$R^1$ is selected from H or optionally substituted C1-C8 alkyl, wherein, optionally, two $R^1$ substituents join to form a ring;
X is H or F;
Z is selected from:
(a) —$NR^aR^b$, wherein $R^a$ is selected from H, optionally substituted alkyl, optionally substituted C3-C6 alkenyl, optionally substituted C3-C6 alkynyl, optionally substituted C3-C6 cycloalkyl, optionally substituted C3-C6 cycloalkylalkyl, optionally substituted heterocyclyl, or optionally substituted heterocyclylalkyl; and $R^b$ is selected from optionally substituted alkyl, optionally substituted C3-C6 alkenyl, optionally substituted C3-C6 alkynyl, optionally substituted C3-C6 cycloalkyl, optionally substituted C3-C6 cycloalkylalkyl, optionally substituted C4-C6 heterocyclyl, or optionally substituted heterocyclylalkyl;

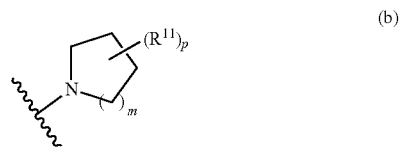

(b)

wherein m is 0, 1, 2, or 3; p is 0, 1, 2, 3, or 4; and
each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —SO$_2$alkyl, optionally substituted C3-C6 cycloalkylalkyl, optionally substituted heterocyclyl, or optionally substituted heterocyclylalkyl; or two $R^{11}$ groups together form an oxo;

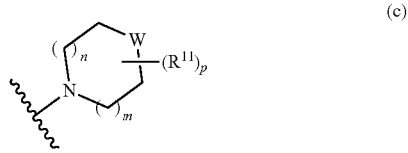

(c)

wherein m is 0, 1, 2, or 3; n is 0, 1, 2, or 3; p is 0, 1, 2, 3, or 4; W is O, S, S(O), SO$_2$, NH or N (optionally substituted C1-C6 alkyl); and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two $R^{11}$ groups together form an oxo;

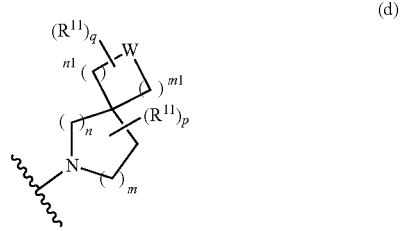

(d)

wherein m is 0, 1, or 2; n is 0, 1, or 2; m1 is 0, 1, or 2; n1 is 0, 1, or 2 provided both m1 and n1 are not both 0; p is 0, 1, or 2; and q is 0, 1 or 2; W is O, S, S(O), SO$_2$, NH or N (optionally substituted C1-C6 alkyl), CH$_2$, CHR$^{11}$, or C(R$^{11}$)$_2$; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO₂alkyl, optionally substituted C3-C6 cycloalkylalkyl, optionally substituted heterocyclyl, or optionally substituted heterocyclylalkyl, or two R¹¹ groups together form an oxo;

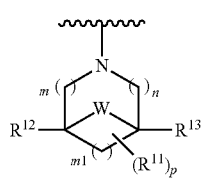

(e)

wherein m is 0, 1, or 2; n is 0, 1, or 2; m1 is 1, or 2; p is 0, 1, 2, or 3; W is O, S, S(O), SO₂, NH or N (optionally substituted C1-C6 alkyl), CH₂, CHR¹¹, —CH₂—CH₂—, —CH₂—CHR¹¹—, —CH₂—C(R¹¹)₂—, —CHR¹¹—CH₂—, —C(R¹)₂—CH₂—, —NH—CH₂—, —NH—CHR¹¹—, —NH—C(R¹¹)₂—, —CH₂—NH—, —CHR¹¹—NH—, —C(R¹¹)₂—NH—, —N(R¹¹)—CH₂—, —N(R¹¹)—CR¹¹—, —N(R¹¹)—C(R¹¹)₂—, —CH₂—N(R¹¹)—, —CHR¹¹—N(R¹¹)—, —C(R¹¹)₂—N(R¹¹)—, —O—CH₂—, or —CH₂—O—; each R¹¹ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO₂alkyl, optionally substituted C3-C6 cycloalkylalkyl, optionally substituted heterocyclyl, or optionally substituted heterocyclylalkyl, or two R¹¹ groups together form an oxo; and R¹² and R¹³ are each independently selected from H, or optionally substituted C1-C6 alkyl;

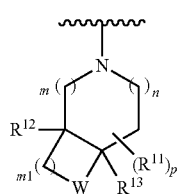

(f)

or

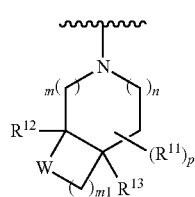

wherein m is 0, 1, or 2; n is 0, 1, or 2; m1 is 0, 1, or 2; p is 0, 1, or 2; W is O, S, S(O), SO₂, NH or N (optionally substituted C1-C6 alkyl), CH₂, CHR¹¹, or C(R¹¹)₂; each R¹¹ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO₂alkyl, optionally substituted C3-C6 cycloalkylalkyl, optionally substituted heterocyclyl, or optionally substituted heterocyclylalkyl, or two R¹¹ groups together form an oxo; and R¹² and R¹³ are each independently selected from H, or optionally substituted C1-C6 alkyl;

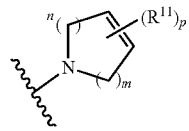

(g)

wherein m is 0, 1, 2, or 3; n is 0, 1, 2, or 3; p is 0, 1, 2, 3, or 4; and each R¹¹ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —SO₂alkyl, optionally substituted C3-C6 cycloalkylalkyl, optionally substituted heterocyclyl, or optionally substituted heterocyclylalkyl; or two R¹¹ groups together form an oxo;

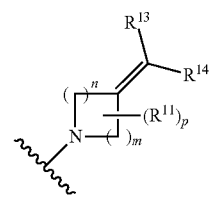

(h)

wherein m is 1, 2, or 3; n is 1, 2, or 3; p is 0, 1, or 2; and each R¹³ or R¹⁴ is independently selected from hydrogen, halogen, —CN, optionally substituted C1-C6 alkyl, or optionally substituted C3-C6 cycloalkyl; each R¹¹ is independently selected from —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO₂alkyl, optionally substituted C3-C6 cycloalkylalkyl, optionally substituted heterocyclyl, or optionally substituted heterocyclylalkyl; or (i)

wherein m is 0, 1, or 2; n is 0, 1, or 2; m1 is 0, 1, or 2; p is 0, 1, or 2; and q is 0, 1 or 2; W is O, S, S(O), SO₂, NH or N (optionally substituted C1-C6 alkyl), CH₂, CHR¹¹, or C(R¹¹)₂; and each R¹¹ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO₂alkyl, optionally substituted C3-C6 cycloalkylalkyl, optionally substituted heterocyclyl, or optionally substituted heterocyclylalkyl, or two geminal $R^{11}$ groups together form an oxo.

One embodiment provides a pharmaceutical composition comprising a compound of Formula (I), or pharmaceutically acceptable salt or solvate thereof, and at least one pharmaceutically acceptable excipient.

One embodiment provides a method of treating a disease or disorder in a patient in need thereof comprising administering to the patient a compound of Formula (I), or pharmaceutically acceptable salt or solvate thereof. Another embodiment provides the method wherein the disease or disorder is cancer.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluorom- "Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises two carbon atoms (e.g., $C_2$ alkenylene). In other embodiments, an alkenylene comprises five to eight carbon atoms (e.g., $C_5$-$C_8$ alkenylene). In other embodiments, an alkenylene comprises three to five carbon atoms (e.g., $C_3$-$C_5$ alkenylene). Unless stated otherwise specifically in the specification, an alkenylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —OC(O)—$N(R^a)_2$, —$N(R^a)$C(O)$R^a$, —$N(R^a)$S(O)$_t R^a$ (where t is 1 or 2), —S(O)$_t OR^a$ (where t is 1 or 2), —S(O)$_t R^a$ (where t is 1 or 2) and —S(O)$_t N(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)$S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t N(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^e$-aryl where $R^e$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Carbocyclylalkyl" refers to a radical of the formula —R$^c$-carbocyclyl where R$^c$ is an alkylene chain as defined above. The alkylene chain and the carbocyclyl radical is optionally substituted as defined above.

"Carbocyclylalkynyl" refers to a radical of the formula —R$^c$-carbocyclyl where R$^c$ is an alkynylene chain as defined above. The alkynylene chain and the carbocyclyl radical is optionally substituted as defined above.

"Carbocyclylalkoxy" refers to a radical bonded through an oxygen atom of the formula —O—R$^c$-carbocyclyl where R$^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

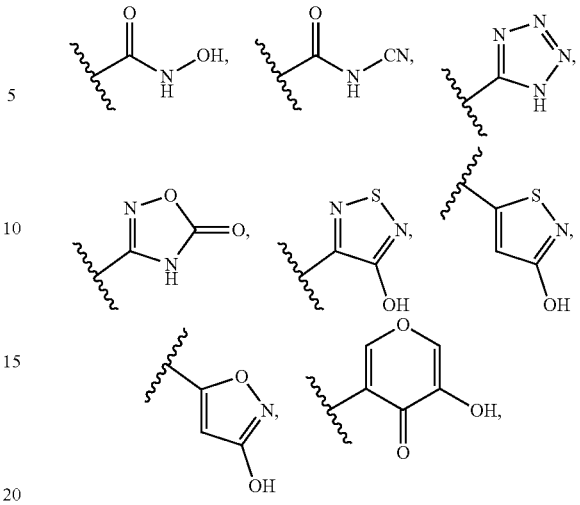

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—

$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

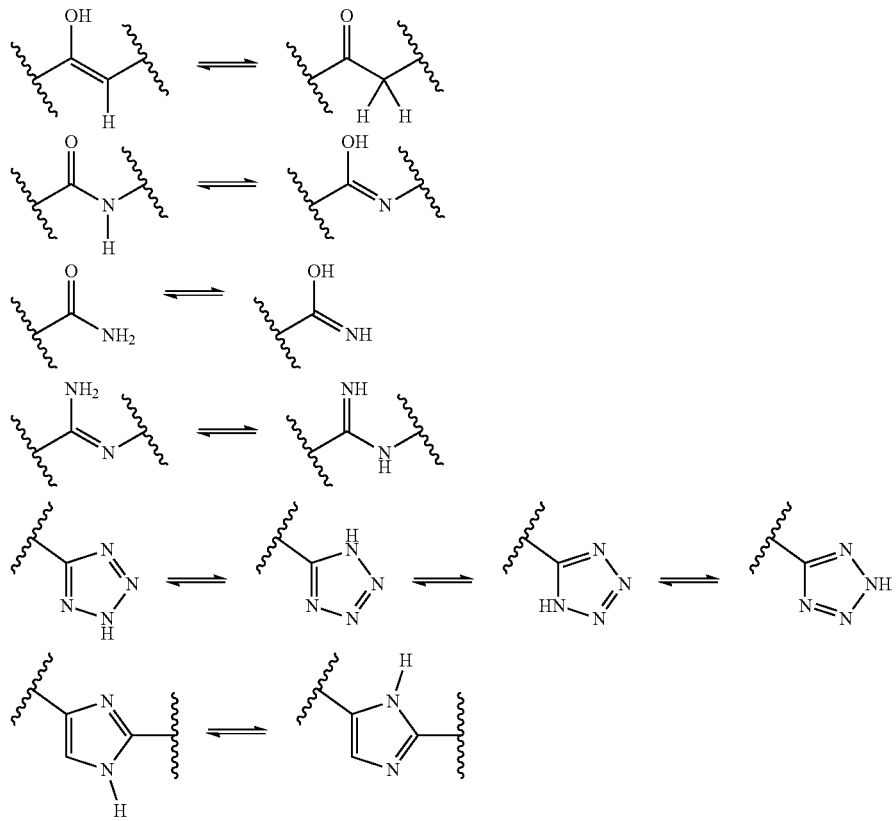

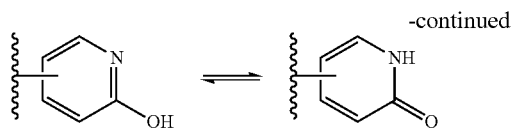

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. In some embodiments, isotopic substitution with $^{18}F$ is contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-$d_3$ ($CD_3I$), are readily available and may be employed to transfer a deuterium-substituted carbon atom under nucleophilic substitution reaction conditions to the reaction substrate. The use of $CD_3I$ is illustrated, by way of example only, in the reaction schemes below.

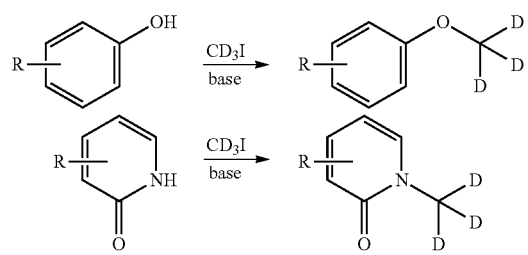

Deuterium-transfer reagents, such as lithium aluminum deuteride ($LiAlD_4$), are employed to transfer deuterium under reducing conditions to the reaction substrate. The use of $LiAlD_4$ is illustrated, by way of example only, in the reaction schemes below.

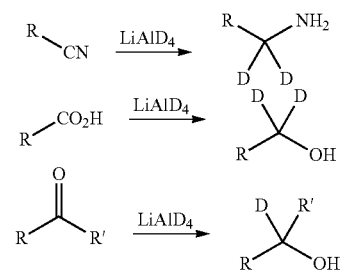

Deuterium gas and palladium catalyst are employed to reduce unsaturated carbon-carbon linkages and to perform a reductive substitution of aryl carbon-halogen bonds as illustrated, by way of example only, in the reaction schemes below.

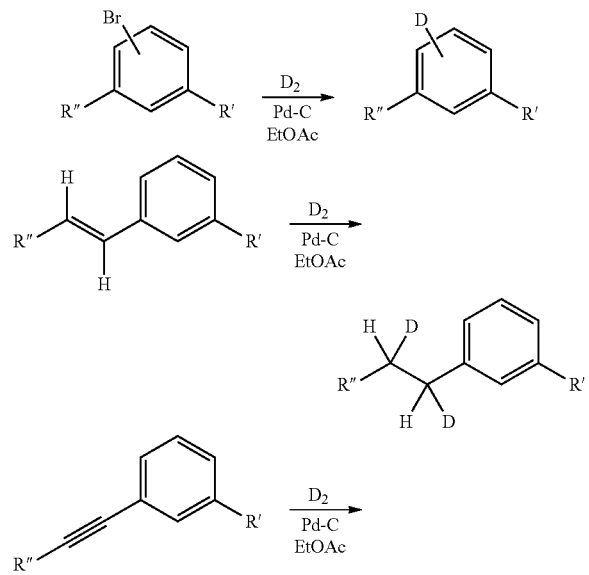

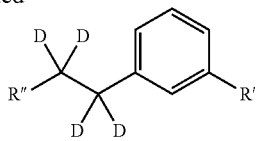

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1$H hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the heteroaromatic RAF inhibitory compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. The compounds provided herein optionally exist in either unsolvated as well as solvated forms. The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

The RAF Family of Kinases

The RAF kinases are a family of serine/thronine protein kinases constitute core components of the RAS-RAF-MEK-ERK mitogen activated protein kinase (MAPK) signalling cascade (also known as the MAPK/ERK pathway), a pathway that mediates signals from cell surface receptors to the nucleus to regulate cell growth, differentiation and survival. The RAF proteins are related to retroviral oncogenes and are structurally conserved from metazoans to mammals, as is the MAPK/ERK pathway. Their dysregulation leads to uncontrolled cellular proliferation, survival and dedifferentiation. Consequently, RAF kinases are altered or inappropriately activated in a majority of cancers.

The MAPK/ERK signalling pathway is a network of proteins in the cell that communicates a signal from a receptor on the surface of the cell to the DNA in the nucleus of the cell. The signal starts when a signaling molecule binds to the receptor on the cell surface and ends when the DNA in the nucleus expresses a protein and produces some change in the cell, such as cell division. The pathway includes many proteins, which communicate by adding phosphate groups to a neighboring protein, which acts as a molecular "on" or "off" switch, and overall the pathway can be divided into 3 steps: (i) Ras activation, (ii) a kinase signal transduction cascade, and (iii) regulation of translation and transcription. Briefly, an extracellular mitogen or a signaling molecule binds to the membrane receptor. This allows Ras (a small GTPase) to swap its GDP for a GTP and become active. Activated Ras activates the protein kinase activity of RAF kinase. RAF kinase phosphorylates and activates MEK (MEK1 and MEK2). MEK then phosphorylates and activates a MAPK (also known as ERK). MAPK activation regulates activities of several transcription factors and also alters the translation of mRNA to proteins. By altering the levels and activities of transcription factors, MAPK leads to altered transcription of genes that are important for the cell cycle.

There are three known mammalian RAF isoforms: C-RAF (also known as RAF-1, or c-RAF-1), B-RAF, and A-RAF. All RAF kinases share a common modular structure consisting of 3 conserved regions (CR1, CR2, and CR3) with distinct functions. CR1 contains (i) a Ras-binding domain (RBD), which is necessary for the interaction with Ras and with membrane phospholipids required for membrane recruitment, and (ii) a cysteine-rich domain (CRD), which is a secondary Ras-binding site and also necessary for the interaction of CR1 with the kinase domain for RAF autoinhibition. CR2 contains important inhibitory phosphorylation sites participating in the negative regulation of Ras binding and RAF activation. CR3 features the kinase domain, including the activation segment, whose phosphorylation is crucial for kinase activation.

Functionally, the RAF structure can be split into a regulatory N-terminal region, containing the RBD, which is critical for activation as well as inhibitory phosphorylation sites, and a catalytic C-terminal region, which includes phosphorylation sites necessary for the kinase activation. The regulatory domain restrains the activity of the kinase domain, and its removal results in constitutive oncogenic activation. However, the activity of the isolated C-RAF kinase domain is subjected to further regulation and can be stimulated by phorbol esters, v-Src, and phosphorylation.

The common and key step in the activation of all 3 RAF kinase isoforms is membrane recruitment by a Ras family protein. The RAF kinases are located in the cytosol in their inactive state when bound to 14-3-3 proteins. In the presence of active Ras, they translocate to the plasma membrane. Membrane translocation triggers further activation events, such as the binding of PP2A to dephosphorylate the inhibitory pS259 site in RAF-1 (and presumably the corresponding sites in A-RAF and B-RAF) and the co-localization with the kinases responsible for the multiple activating phosphorylations. The sequences forming the binding interface are well conserved in the RAF as well as Ras family indicating that several members of the Ras family have the ability to bind RAF kinases. H-Ras, N-Ras, and K-Ras stimulate all 3 RAF isoforms and are the only Ras proteins that activate B-RAF. In contrast, A-RAF is also activated by R-Ras3, while C-RAF responds weakly to R-Ras3, Rit, and TC21 as well. But, all RAF kinases share MEK1/2 kinases as substrates. MEK1/2 in turn activate ERK1/2, and this pathway regulates many cellular functions such as cell proliferation, differentiation, migration, or apoptosis.

C-RAF

C-RAF was first to be identified and is a ubiquitously expressed isoform. In humans, C-RAF is encoded by the RAF1 gene. C-RAF also has a known splice variant preferentially expressed in the muscle and brain. C-RAF plays a critical role in mediating the cellular effects of growth factor signals. In the inactive state, C-RAF exists in a closed conformation in which the N-terminal regulatory region folds over and occludes the catalytic region. This conformation is stabilized by a 14-3-3 dimer binding to an N-terminal site, phospho-S259 (pS259), and a C-terminal site, pS621. Dephosphorylation of pS259 at the cell membrane by specific phosphatases (PP2A, PP1) releases 14-3-3 from its N-terminal binding site in C-RAF, thereby allowing conformational changes to occur that unmask the RBD and CRD domains in the CR1 region to enable Ras binding and membrane recruitment.

B-RAF

B-RAF is encoded in humans by the BRAF gene, also known as proto-oncogene B-RAF and v-RAF murine sarcoma viral oncogene homolog B. Alternative splicing gives rise to multiple B-RAF isoforms which are differentially expressed in various tissues. Whereas activation of A-RAF and C-RAF requires both phosphorylation and dephosphorylation of certain residues, as well as binding to other proteins, B-RAF becomes activated immediately upon translocation to the plasma membrane. B-RAF exhibits higher basal kinase activity than A-RAF and C-RAF. B-RAF requires Ras and 14-3-3 binding for its activation, and is inhibited or activated by PKA depending on the levels of 14-3-3 expression, which need to be high for permitting activation. B-RAF activity is also regulated by splicing. B-RAF isoforms containing exon 8b are more phosphorylated on the inhibitory S365 site, leading to an increased interaction with 14-3-3 and strengthening the inhibitory interaction between N-terminal regulatory domain and kinase domain, altogether resulting in lower kinase activity.

A-RAF

Serine/threonine-protein kinase A-RAF or A-RAF is an enzyme encoded by the ARAF gene in humans. There are 2 known splice isoforms of A-RAF-DA-RAF1 and D-RAF2. They lack the kinase domain and act as dominant inhibitory mutants of Ras and ARF GTPases. DA-RAF1 is a positive regulator of myogenic differentiation by mediating the inhibition of the ERK pathway required for differentiation. There are several ways A-RAF is different from the other RAF kinases. A-RAF is the only steroid hormone-regulated Raf isoform. In addition, the A-RAFprotein has amino acid substitutions in a negatively charged region upstream of the kinase domain (N-region), which contributes to its low basal activity. A-RAF is also only weakly activated by oncogenic H-Ras and Src and also displays low kinase activity towards MEK (the lowest kinase activity towards MEK proteins in the Raf kinase family). In addition to phosphorylating MEK, A-RAF also inhibits MST2, a tumor suppressor and proapoptotic kinase not found in the MAPK pathway. By inhibiting MST2, A-RAF prevents apoptosis from occurring. However, this inhibition is only occurs when the splice factor heterogenous nuclear ribonucleoprotein H (hnRNP H) maintains the expression of a full-length A-RAF protein. Tumorous cells often overexpress hnRNP H which leads to full-length expression of A-Raf which then inhibits apoptosis, allowing cancerous cells that should be destroyed to stay alive. A-RAF also binds to pyruvate kinase M2 (PKM2), again outside the MAPK pathway. PKM2 is an isozyme of pyruvate kinase that is responsible for the Warburg effect in cancer cells. A-RAF upregulates the activity of PKM2 by promoting a conformational change in PKM2. This causes PKM2 to transition from its low-activity dimeric form to a highly active tetrameric form. This causes more glucose carbons to be converted to pyruvate and lactate, producing energy for the cell, linking A-Raf to energy metabolism regulation and cell transformation, both of which are very important in tumorigenesis.

RAF Kinase Inhibitors

Aberrant activation of the MAPK/ERK pathway is frequently found in various cancers and is a target for cancer therapeutics. In particular, B-RAF has emerged as one of the most attractive molecular targets for cancer therapeutics because somatic mutations of B-RAF have frequently been found in human tumors. Approximately 20% of all cancer samples tested to date harbor mutations in B-RAF. B-RAF-V600E, a missense mutation in the kinase domain generated by the substitution of glutamic acid with valine at position 600 is the most common B-RAF mutation. C-RAF is mutated in ~1% of the various tumor types tested and the rate of mutations in A-RAF is even lower. B-RAF and C-RAF form both homo- and heterodimers as part of their activation mechanism and A-RAF stabilizes the B-RAF:C-RAF complexes to sustain signaling efficiency. Also, it is C-RAF, not B-RAF, that transmits signals from oncogenic RAS to MEK. Therefore, in different contexts, each of the RAF isoforms act as a potential therapeutic target.

Sorafenib was the first RAF inhibitor to enter clinical trials. Sorafenib is a broad specificity drug that inhibits additional kinases, including vascular endothelial growth factor receptor family (VEGFR-2 and VEGFR-3), platelet-derived growth factor receptor family (PDGFR-b and KIT) and FLT3. Clinical trials showed no correlation between the clinical responses with B-RAF mutation status, indicating it is a poor inhibitor of B-RAF. This led to the development of a new generation of B-RAF inhibitors, including, but not limited to vemurafenib, SB-590885, and dabrafenib (GSK2118436). Although the initial results of the clinical studies in B-RAF-mutant melanoma were encouraging, as clinical testing began in other B-RAF-mutated cancers (such as thyroid and colorectal cancers) it became apparent that tumors of different cell types harboring B-RAF mutations responded differently to selective B-RAF inhibition. Moreover, the existence of both primary and secondary resistance to RAF inhibition poses as one of the greatest challenge to the progress of RAF kinase inhibitor therapy. The mechanisms of resistance fall into two broad categories. Intrinsic/primary resistance is displayed by approximately 50% of patients. The other 50% of the patients initially respond (>30% tumor shrinkage) to RAF inhibitor but subsequently develop progressive disease associated with acquired/secondary resistance to RAF inhibitor. These two categories are not mutually exclusive because nearly all responders have remaining disease and, thus, may display intrinsic resistance. The determinants of primary RAF inhibitor resistance seem to vary with tumor type, with alteration in RTK signaling also being involved. Potential mechanisms of secondary B-RAF inhibitor resistance include, but are not limited to, reactivation of ERK1/2 pathways, upregulation of RTK signaling, the upregulation of receptor tyrosine kinases, mutations in RAS, and upregulation of COT. B-Raf alternative splicing and amplification of B-RAF-V600E have also been implicated in ~30 and 20% of patients, respectively. Moreover, RAF kinase inhibitors cause paradoxical activation of the MAPK pathway, which, in some instances, leads to the development of secondary RAS mutation-driven malignancies. As such, there is a need in the field for new RAF kinase inhibitors that overcome the existing pitfalls and challenges posed by the current inhibitors.

Heteroaromatic RAF Inhibitory Compounds

In one aspect, provided herein is a heteroaromatic RAF inhibitory compound.

One embodiment provides a compound, or pharmaceutically acceptable salt or solvate thereof, having the structure of Formula (I):

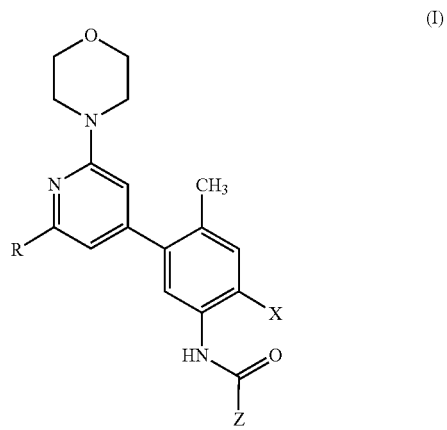

wherein,

R is selected from optionally substituted C1-C8 alkyl, optionally substituted C2-C8 alkenyl, optionally substituted C2-C8 alkynyl, optionally substituted C3-C6 cycloalkyl, optionally substituted C4-C8 cycloalkylalkyl, optionally substituted C3-C6 heterocyclyl, optionally substituted C4-C8 heterocyclylalkyl, optionally substituted C6 aryl, optionally substituted 5- or 6-membered heteroaryl, or —CON($R^1$)$_2$—;

$R^1$ is selected from H or optionally substituted C1-C8 alkyl, wherein, optionally, two $R^1$ substituents join to form a ring;

X is H or F;

Z is selected from:

(a) —$NR^aR^b$, wherein $R^a$ is selected from H, optionally substituted alkyl, optionally substituted C3-C6 alkenyl, optionally substituted C3-C6 alkynyl, optionally substituted C3-C6 cycloalkyl, optionally substituted C3-C6 cycloalkylalkyl, optionally substituted heterocyclyl, or optionally substituted heterocyclylalkyl; and $R^b$ is selected from optionally substituted alkyl, optionally substituted C3-C6 alkenyl, optionally substituted C3-C6 alkynyl, optionally substituted C3-C6 cycloalkyl, optionally substituted C3-C6 cycloalkylalkyl, optionally substituted C4-C6 heterocyclyl, or optionally substituted heterocyclylalkyl;

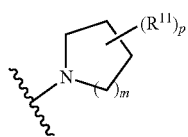
(b)

wherein m is 0, 1, 2, or 3; p is 0, 1, 2, 3, or 4; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —$SO_2$alkyl, optionally substituted C3-C6 cycloalkylalkyl, optionally substituted heterocyclyl, or optionally substituted heterocyclylalkyl; or two $R^{11}$ groups together form an oxo;

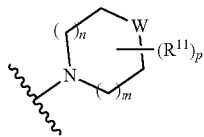
(c)

wherein m is 0, 1, 2, or 3; n is 0, 1, 2, or 3; p is 0, 1, 2, 3, or 4; W is O, S, S(O), $SO_2$, NH or N (optionally substituted C1-C6 alkyl); and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —$SO_2$alkyl, optionally substituted C3-C6 cycloalkylalkyl, optionally substituted heterocyclyl, or optionally substituted heterocyclylalkyl, or two $R^{11}$ groups together form an oxo;

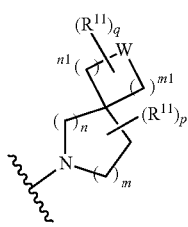
(d)

wherein m is 0, 1, or 2; n is 0, 1, or 2; m1 is 0, 1, or 2; n1 is 0, 1, or 2 provided both m1 and n1 are not both 0; p is 0, 1, or 2; and q is 0, 1 or 2; W is O, S, S(O), $SO_2$, NH or N (optionally substituted C1-C6 alkyl), $CH_2$, $CHR^{11}$, or $C(R^{11})_2$; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —$SO_2$alkyl, optionally substituted C3-C6 cycloalkylalkyl, optionally substituted heterocyclyl, or optionally substituted heterocyclylalkyl, or two $R^{11}$ groups together form an oxo;

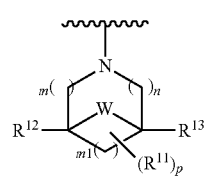
(e)

wherein m is 0, 1, or 2; n is 0, 1, or 2; m1 is 1, or 2; p is 0, 1, 2, or 3; W is O, S, S(O), $SO_2$, NH or N (optionally substituted C1-C6 alkyl), $CH_2$, $CHR^{11}$, —$CH_2$—$CH_2$—, —$CH_2$—$CHR^{11}$—, —$CH_2$—$C(R^{11})_2$—, —$CHR^{11}$—$CH_2$—, —$C(R^{11})_2$—$CH_2$—, —NH—$CH_2$—, —NH—$CHR^{11}$—, —NH—$C(R^{11})_2$—, —$CH_2$—NH—, —$CHR^{11}$—NH—, —$C(R^{11})_2$—NH—, —$N(R^{11})$—$CH_2$—, —$N(R^{11})$—$CR^{11}$—, —$N(R^{11})$—$C(R^{11})_2$—, —$CH_2$—$N(R^{11})$—, —$CHR^{11}$—$N(R^{11})$—, —$C(R^{11})_2$—$N(R^{11})$—, —O—$CH_2$—, or —$CH_2$—O—; each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —$SO_2$alkyl, optionally substituted C3-C6 cycloalkylalkyl, optionally substituted heterocyclyl, or optionally substituted heterocyclylalkyl, or two $R^{11}$ groups together form an oxo; and $R^{12}$ and $R^{13}$ are each independently selected from H, or optionally substituted C1-C6 alkyl;

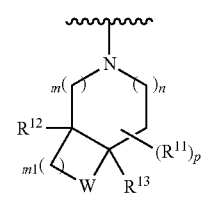
(f)

or

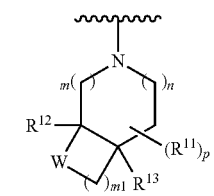

wherein m is 0, 1, or 2; n is 0, 1, or 2; m1 is 0, 1, or 2; p is 0, 1, or 2; W is O, S, S(O), $SO_2$, NH or N (optionally substituted C1-C6 alkyl), $CH_2$, $CHR^{11}$, or $C(R^{11})_2$; each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —$SO_2$alkyl, optionally substituted C3-C6 cycloalkylalkyl, optionally substituted heterocyclyl, or optionally substituted heterocyclylalkyl, or two $R^{11}$ groups together form an oxo; and $R^{12}$ and $R^{13}$ are each independently selected from H, or optionally substituted C1-C6 alkyl;

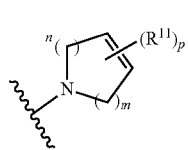
(g)

wherein m is 0, 1, 2, or 3; n is 0, 1, 2, or 3; p is 0, 1, 2, 3, or 4; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —SO$_2$alkyl, optionally substituted C3-C6 cycloalkylalkyl, optionally substituted heterocyclyl, or optionally substituted heterocyclylalkyl; or two $R^{11}$ groups together form an oxo;

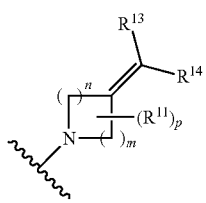
(h)

wherein m is 1, 2, or 3; n is 1, 2, or 3; p is 0, 1, or 2; and each $R^{13}$ or $R^{14}$ is independently selected from hydrogen, halogen, —CN, optionally substituted C1-C6 alkyl, or optionally substituted C3-C6 cycloalkyl; each $R^{11}$ is independently selected from —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl; or

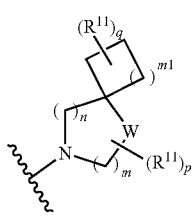
(i)

wherein m is 0, 1, or 2; n is 0, 1, or 2; m1 is 0, 1, or 2; p is 0, 1, or 2; and q is 0, 1 or 2; W is O, S, S(O), SO$_2$, NH or N (optionally substituted C1-C6 alkyl), CH$_2$, CHR$^{11}$, or C(R$^{11}$)$_2$; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl; or two geminal $R^{11}$ groups together form an oxo.

One embodiment provides a compound, or pharmaceutically acceptable salt or solvate thereof, having the structure of Formula (II):

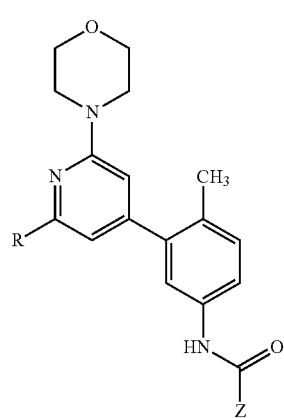
(II)

wherein,

R is selected from optionally substituted C1-C8 alkyl, optionally substituted C2-C8 alkenyl, optionally substituted C2-C8 alkynyl, optionally substituted C3-C6 cycloalkyl, optionally substituted C4-C8 cycloalkylalkyl, optionally substituted C3-C6 heterocyclyl, optionally substituted C4-C8 heterocyclylalkyl, optionally substituted C6 aryl, optionally substituted 5- or 6-membered heteroaryl, or —

$R^1$ is selected from H or optionally substituted C1-C8 alkyl, wherein, optionally, two $R^1$ substituents join to form a ring;

Z is selected from:

(a) —NR$^a$R$^b$, wherein R$^a$ is selected from H, optionally substituted alkyl, optionally substituted C3-C6 alkenyl, optionally substituted C3-C6 alkynyl, optionally substituted C3-C6 cycloalkyl, optionally substituted C3-C6 cycloalkylalkyl, optionally substituted heterocyclyl, or optionally substituted heterocyclylalkyl; and R$^b$ is selected from optionally substituted alkyl, optionally substituted C3-C6 alkenyl, optionally substituted C3-C6 alkynyl, optionally substituted C3-C6 cycloalkyl, optionally substituted C3-C6 cycloalkylalkyl, optionally substituted C4-C6 heterocyclyl, or optionally substituted heterocyclylalkyl;

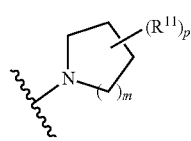
(b)

wherein m is 0, 1, 2, or 3; p is 0, 1, 2, 3, or 4; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —SO$_2$alkyl, optionally substituted C3-C6 cycloalkylalkyl, optionally substituted heterocyclyl, or optionally substituted heterocyclylalkyl; or two $R^{11}$ groups together form an oxo;

(c)

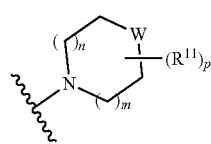

wherein m is 0, 1, 2, or 3; n is 0, 1, 2, or 3; p is 0, 1, 2, 3, or 4; W is O, S, S(O), SO$_2$, NH or N (optionally substituted C1-C6 alkyl); and each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two R$^{11}$ groups together form an oxo;

(d)

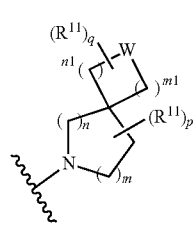

wherein m is 0, 1, or 2; n is 0, 1, or 2; m1 is 0, 1, or 2; n1 is 0, 1, or 2 provided both m1 and n1 are not both 0; p is 0, 1, or 2; and q is 0, 1 or 2; W is O, S, S(O), SO$_2$, NH or N (optionally substituted C1-C6 alkyl), CH$_2$, CHR$^{11}$, or C(R$^{11}$)$_2$; and each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two R$^{11}$ groups together form an oxo;

(e)

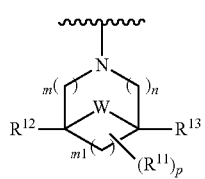

wherein m is 0, 1, or 2; n is 0, 1, or 2; m1 is 1, or 2; p is 0, 1, 2, or 3; W is O, S, S(O), SO$_2$, NH or N (optionally substituted C1-C6 alkyl), CH$_2$, CHR$^{11}$, —CH$_2$—CH$_2$—, —CH$_2$—CHR$^{11}$—, —CH$_2$—C(R$^{11}$)$_2$—, —CHR$^{11}$—CH$_2$—, —C(R$^{11}$)$_2$—CH$_2$—, —NH—CH$_2$—, —NH—CHR$^{11}$—, —NH—C(R$^{11}$)$_2$—, —CH$_2$—NH—, —CHR$^{11}$—NH—, —C(R$^{11}$)$_2$—NH—, —N(R$^{11}$)—CH$_2$—, —N(R$^{11}$)—CHR$^{11}$—, —N(R$^{11}$)—C(R$^{11}$)$_2$—, —CH$_2$—N(R$^{11}$)—, —CHR$^{11}$—N(R$^{11}$)—, —C(R$^{11}$)$_2$—N(R$^{11}$)—, —O—CH$_2$—, or —CH$_2$—O—; each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two R$^{11}$ groups together form an oxo; and R$^{12}$ and R$^{13}$ are each independently selected from H, or optionally substituted C1-C6 alkyl;

(f)

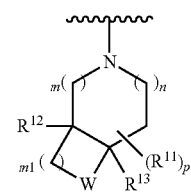

or

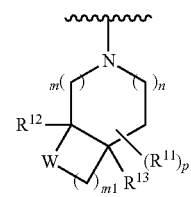

wherein m is 0, 1, or 2; n is 0, 1, or 2; m1 is 0, 1, or 2; p is 0, 1, or 2; W is O, S, S(O), SO$_2$, NH or N (optionally substituted C1-C6 alkyl), CH$_2$, CHR$^{11}$, or C(R$^{11}$)$_2$; each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two R$^{11}$ groups together form an oxo; and R$^{12}$ and R$^{13}$ are each independently selected from H, or optionally substituted C1-C6 alkyl;

(g)

wherein m is 0, 1, 2, or 3; n is 0, 1, 2, or 3; p is 0, 1, 2, 3, or 4; and each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —SO$_2$alkyl, optionally substituted C3-C6 cycloalkylalkyl, optionally substituted heterocyclyl, or optionally substituted heterocyclylalkyl; or two R$^{11}$ groups together form an oxo;

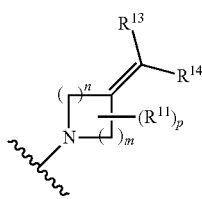
(h)

wherein m is 1, 2, or 3; n is 1, 2, or 3; p is 0, 1, or 2; and each $R^{13}$ or $R^{14}$ is independently selected from hydrogen, halogen, —CN, optionally substituted C1-C6 alkyl, or optionally substituted C3-C6 cycloalkyl; each $R^{11}$ is independently selected from —OH, halogen, optionally substituted C1-C6 alkyl, optionally substituted C3-C6 cycloalkyl, optionally substituted C1-C6 alkoxy, optionally substituted C2-C6 alkynyl, optionally substituted —$SO_2$alkyl, optionally substituted C3-C6 cycloalkylalkyl, optionally substituted heterocyclyl, or optionally substituted heterocyclylalkyl; or

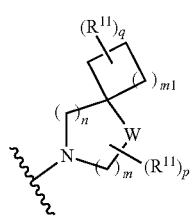
(i)

wherein m is 0, 1, or 2; n is 0, 1, or 2; m1 is 0, 1, or 2; p is 0, 1, or 2; and q is 0, 1 or 2; W is O, S, S(O), $SO_2$, NH or N (optionally substituted C1-C6 alkyl), $CH_2$, $CHR^{11}$, or $C(R^{11})_2$; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —$SO_2$alkyl, optionally substituted C3-C6 cycloalkylalkyl, optionally substituted heterocyclyl, or optionally substituted heterocyclylalkyl, or two geminal $R^{11}$ groups together form an oxo.

One embodiment provides the compound of Formula (I) or (II), or pharmaceutically acceptable salt or solvate thereof, wherein Z is

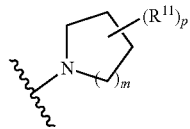

wherein m is 0, 1, 2, or 3; p is 0, 1, 2, 3, or 4; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —$SO_2$alkyl, optionally substituted C3-C6 cycloalkylalkyl, optionally substituted heterocyclyl, or optionally substituted heterocyclylalkyl; or two $R^{11}$ groups together form an oxo.

One embodiment provides the compound of Formula (I) or (II), or pharmaceutically acceptable salt or solvate thereof, wherein m is 0. One embodiment provides the compound of Formula (I) or (II), or pharmaceutically acceptable salt or solvate thereof, wherein m is 1. One embodiment provides the compound of Formula (I) or (II), or pharmaceutically acceptable salt or solvate thereof, wherein m is 2. One embodiment provides the compound of Formula (I) or (II), or pharmaceutically acceptable salt or solvate thereof, wherein m is 3. One embodiment provides the compound of Formula (I) or (II), or pharmaceutically acceptable salt or solvate thereof, wherein p is 0. One embodiment provides the compound of Formula (I) or (II), or pharmaceutically acceptable salt or solvate thereof, wherein p is 1. One embodiment provides the compound of Formula (I) or (II), or pharmaceutically acceptable salt or solvate thereof, wherein p is 2. One embodiment provides the compound of Formula (I) or (II), or pharmaceutically acceptable salt or solvate thereof, wherein p is 3. One embodiment provides the compound of Formula (I) or (II), or pharmaceutically acceptable salt or solvate thereof, wherein $R^{11}$ is optionally substituted C1-C6 alkyl, or optionally substituted C3-C6 cycloalkyl. One embodiment provides the compound of Formula (I) or (II), or pharmaceutically acceptable salt or solvate thereof, wherein the optionally substituted C1-C6 alkyl, or optionally substituted C3-C6 cycloalkyl is substituted with at least a halogen. One embodiment provides the compound of Formula (I) or (II), or pharmaceutically acceptable salt or solvate thereof, wherein the optionally substituted C1-C6 alkyl is an optionally substituted C2 alkyl substituted with at least one halogen. One embodiment provides the compound of Formula (I) or (II), or pharmaceutically acceptable salt or solvate thereof, wherein the optionally substituted C2 alkyl is a 3,3,3-trifluoroethyl group. One embodiment provides the compound of Formula (I) or (II), or pharmaceutically acceptable salt or solvate thereof, wherein the optionally substituted C2 alkyl is a 3,3,3-trifluoroethyl group, and m is 1. One embodiment provides the compound of Formula (I) or (II), or pharmaceutically acceptable salt or solvate thereof, wherein Z is 3-(2,2,2-trifluoroethyl)pyrrolidin-1-yl.

One embodiment provides the compound of Formula (I) or (II), or pharmaceutically acceptable salt or solvate thereof, wherein Z is —$NR^aR^b$, wherein $R^a$ is selected from H, optionally substituted alkyl, optionally substituted C3-C6 alkenyl, optionally substituted C3-C6 alkynyl, optionally substituted C3-C6 cycloalkyl, optionally substituted C3-C6 cycloalkylalkyl, optionally substituted heterocyclyl, or optionally substituted heterocyclylalkyl; and $R^b$ is selected from optionally substituted alkyl, optionally substituted C3-C6 alkenyl, optionally substituted C3-C6 alkynyl, optionally substituted C3-C6 cycloalkyl, optionally substituted C3-C6 cycloalkylalkyl, optionally substituted C4-C6 heterocyclyl, or optionally substituted heterocyclylalkyl.

One embodiment provides the compound of Formula (I) or (II), or pharmaceutically acceptable salt or solvate thereof, wherein Z is

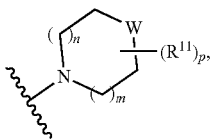

wherein m is 0, 1, 2, or 3; n is 0, 1, 2, or 3; p is 0, 1, 2, 3, or 4; W is O, S, S(O), $SO_2$, NH or N (optionally substituted C1-C6 alkyl); and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two R$^{11}$ groups together form an oxo.

One embodiment provides the compound of Formula (I) or (II), or pharmaceutically acceptable salt or solvate thereof, wherein Z is

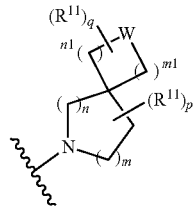

wherein m is 0, 1, or 2; n is 0, 1, or 2; m1 is 0, 1, or 2; n1 is 0, 1, or 2 provided both m1 and n1 are not both 0; p is 0, 1, or 2; and q is 0, 1 or 2; W is O, S, S(O), SO$_2$, NH or N (optionally substituted C1-C6 alkyl), CH$_2$, CHR$^{11}$, or C(R$^{11}$)$_2$; and each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two R$^{11}$ groups together form an oxo.

One embodiment provides the compound of Formula (I) or (II), or pharmaceutically acceptable salt or solvate thereof, wherein Z is

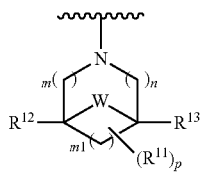

wherein m is 0, 1, or 2; n is 0, 1, or 2; m1 is 1, or 2; p is 0, 1, 2, or 3; W is O, S, S(O), SO$_2$, NH or N (optionally substituted C1-C6 alkyl), CH$_2$, CHR$^{11}$, —CH$_2$—CH$_2$—, —CH$_2$—CHR$^{11}$—, —CH$_2$—C(R$^{11}$)$_2$—, —CHR$^{11}$—CH$_2$—, —C(R$^{11}$)$_2$—CH$_2$—, —NH—CH$_2$—, —NH—CHR$^{11}$—, —NH—C(R$^{11}$)$_2$—, —CH$_2$—NH—, —CHR$^{11}$—NH—, —C(R$^{11}$)$_2$—NH—, —N(R$^{11}$)—CH$_2$—, —N(R$^{11}$)—CHR$^{11}$—, —N(R$^{11}$)—C(R$^{11}$)$_2$—, —CH$_2$—N(R$^{11}$)—, —CHR$^{11}$—N(R$^{11}$)—, —C(R$^{11}$)$_2$—N(R$^{11}$)—, —O—CH$_2$—, or —CH$_2$—O—; each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two R$^{11}$ groups together form an oxo; and R$^{12}$ and R$^{13}$ are each independently selected from H, or optionally substituted C1-C6 alkyl.

One embodiment provides the compound of Formula (I) or (II), wherein Z is

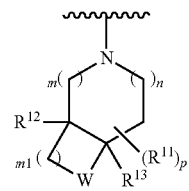

or

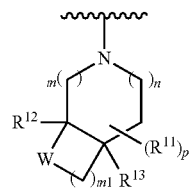

wherein m is 0, 1, or 2; n is 0, 1, or 2; m1 is 0, 1, or 2; p is 0, 1, or 2; W is O, S, S(O), SO$_2$, NH or N (optionally substituted C1-C6 alkyl), CH$_2$, CHR$^{11}$, or C(R$^{11}$)$_2$; each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two R$^{11}$ groups together form an oxo; and R$^{12}$ and R$^{13}$ are each independently selected from H, or optionally substituted C1-C6 alkyl.

One embodiment provides the compound of Formula (I) or (II), or pharmaceutically acceptable salt or solvate thereof, wherein Z is

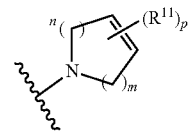

wherein m is 0, 1, 2, or 3; n is 0, 1, 2, or 3; p is 0, 1, 2, 3, or 4; and each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —SO$_2$alkyl, optionally substituted C3-C6 cycloalkylalkyl, optionally substituted heterocyclyl, or optionally substituted heterocyclylalkyl; or two R$^{11}$ groups together form an oxo. One embodiment provides the compound of Formula (I) or (II), or pharmaceutically acceptable salt or solvate thereof, wherein n is 1; m is 1; and R$^{11}$ is optionally substituted C1-C6 alkyl. One embodiment provides the compound of Formula (I) or (II), or pharmaceutically acceptable salt or solvate thereof, wherein p is 1. One embodiment provides the compound of Formula (I) or (II), or pharmaceutically acceptable salt or solvate thereof, wherein the optionally substituted C1-C6 alkyl is a —CF$_3$ group.

One embodiment provides the compound of Formula (I) or (II), or pharmaceutically acceptable salt or solvate thereof, wherein Z is

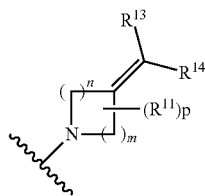

wherein m is 1, 2, or 3; n is 1, 2, or 3; p is 0, 1, or 2; and each $R^{13}$ or $R^{14}$ is independently selected from hydrogen, halogen, —CN, optionally substituted C1-C6 alkyl, or optionally substituted C3-C6 cycloalkyl; each $R^{11}$ is independently selected from —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl.

One embodiment provides the compound of Formula (I) or (II), or pharmaceutically acceptable salt or solvate thereof, wherein Z is

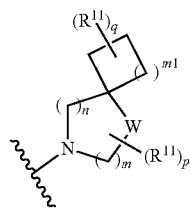

wherein m is 0, 1, or 2; n is 0, 1, or 2; m1 is 0, 1, or 2; p is 0, 1, or 2; and q is 0, 1 or 2; W is O, S, S(O), SO$_2$, NH or N (optionally substituted C1-C6 alkyl), CH$_2$, CHR$^{11}$, or C(R$^{11}$)$_2$; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two geminal $R^{11}$ groups together form an oxo.

One embodiment provides the compound of Formula (I) or (II), or pharmaceutically acceptable salt or solvate thereof, wherein R is optionally substituted C1-C8 alkyl. One embodiment provides the compound of Formula (I) or (II), or pharmaceutically acceptable salt or solvate thereof, wherein R is optionally substituted C2-C8 alkenyl. One embodiment provides the compound of Formula (I) or (II), or pharmaceutically acceptable salt or solvate thereof, wherein R is optionally substituted C2-C8 alkynyl. One embodiment provides the compound of Formula (I) or (II), or pharmaceutically acceptable salt or solvate thereof, wherein R is optionally substituted C3-C6 cycloalkyl. One embodiment provides the compound of Formula (I) or (II), or pharmaceutically acceptable salt or solvate thereof, wherein R is optionally substituted C4-C8 cycloalkylalkyl. One embodiment provides the compound of Formula (I) or (II), or pharmaceutically acceptable salt or solvate thereof, wherein R is optionally substituted C3-C6 heterocyclyl. One embodiment provides the compound of Formula (I) or (II), or pharmaceutically acceptable salt or solvate thereof, wherein R is optionally substituted C4-C8 heterocyclylalkyl. One embodiment provides the compound of Formula (I) or (II), or pharmaceutically acceptable salt or solvate thereof, wherein R is optionally substituted C6 aryl. One embodiment provides the compound of Formula (I) or (II), or pharmaceutically acceptable salt or solvate thereof, wherein R is optionally substituted 5-membered heteroaryl. One embodiment provides the compound of Formula (I) or (II), or pharmaceutically acceptable salt or solvate thereof, wherein the optionally substituted 5-membered heteroaryl is an optionally substituted pyrazole, oxazole, or thiazole. One embodiment provides the compound of Formula (I) or (II), or pharmaceutically acceptable salt or solvate thereof, wherein R is optionally substituted 6-membered heteroaryl. One embodiment provides the compound of Formula (I) or (II), or pharmaceutically acceptable salt or solvate thereof, wherein the optionally substituted 6-membered heteroaryl is an optionally substituted pyridine or pyrimidine. One embodiment provides the compound of Formula (I) or (II), or pharmaceutically acceptable salt or solvate thereof, wherein R is an optionally substituted pyrazole. One embodiment provides the compound of Formula (I) or (II), or pharmaceutically acceptable salt or solvate thereof, wherein R is an optionally substituted pyrazol-4-yl, or optionally substituted pyrazol-5-yl. One embodiment provides the compound of Formula (I) or (II), or pharmaceutically acceptable salt or solvate thereof, wherein R is

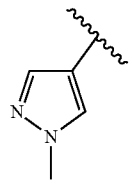 [SMILES: *c1cnn(C)c1]

or

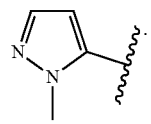

One embodiment provides the compound of Formula (I) or (II), or pharmaceutically acceptable salt or solvate thereof, wherein R is —CON(R$^1$)$_2$—, and $R^1$ is selected from H or optionally substituted C1-C8 alkyl. One embodiment provides the compound of Formula (I) or (II), or pharmaceutically acceptable salt or solvate thereof, wherein R is —CON(R$^1$)$_2$—, and wherein the two $R^1$ substituents are optionally substituted C1-C8 alkyl and join to form a ring.

One embodiment provides the compound of Formula (I), or pharmaceutically acceptable salt or solvate thereof, wherein X is H.

One embodiment provides the compound of Formula (I), or pharmaceutically acceptable salt or solvate thereof, wherein X is F.

In some embodiments, the heteroaromatic RAF kinase inhibitory compound as described herein has a structure provided in Table 1.

TABLE 1
| Synthetic Chemistry Example | Compound Structure | Compound Name |
|---|---|---|
| 1 | 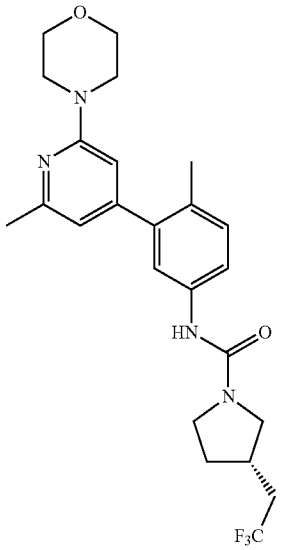 [SMILES: Cc1cc(-c2cc(NC(=O)N3CC[C@@H](CC(F)(F)F)C3)ccc2C)cc(N2CCOCC2)n1] | (3S)-N-[4-methyl-3-[2-methyl-6-(morpholin-4-yl)pyridin-4-yl]phenyl]-3-(2,2,2-trifluoroethyl)pyrrolidine-1-carboxamide |
| 2 | 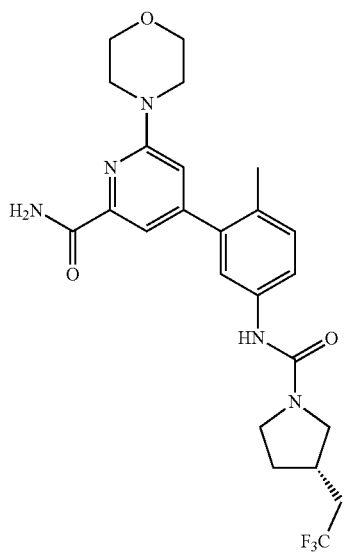 [SMILES: Cc1ccc(NC(=O)N2CC[C@@H](CC(F)(F)F)C2)cc1-c1cc(C(N)=O)nc(N2CCOCC2)c1] | 4-[2-methyl-5-[(3S)-3-(2,2,2-trifluoroethyl)pyrrolidine-1-carbonylamino]phenyl]-6-(morpholin-4-yl)pyridine-2-carboxamide |

TABLE 1-continued

| Synthetic Chemistry Example | Compound Structure | Compound Name |
|---|---|---|
| 3 | 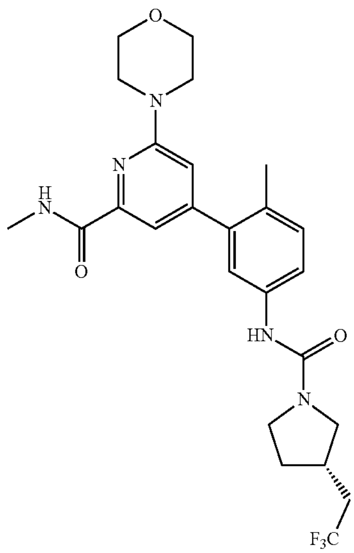 [SMILES: CNC(=O)c1cc(-c2cc(NC(=O)N3CC[C@@H](CC(F)(F)F)C3)ccc2C)cc(N2CCOCC2)n1] | N-methyl-4-[2-methyl-5-[(3S)-3-(2,2,2-trifluoroethyl)pyrrolidine-1-carbonylamino]phenyl]-6-(morpholin-4-yl)pyridine-2-carboxamide |
| 4 | 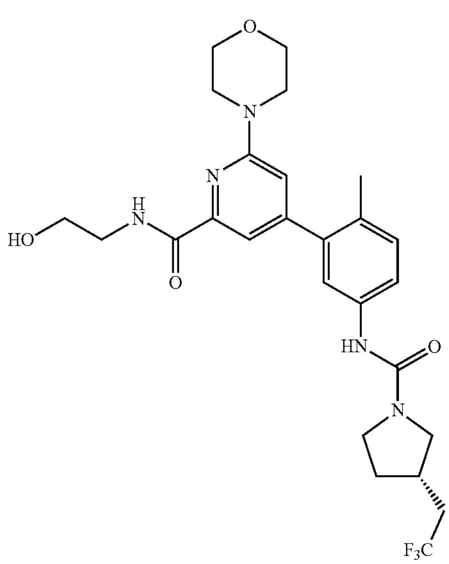 [SMILES: Cc1ccc(NC(=O)N2CC[C@@H](CC(F)(F)F)C2)cc1-c1cc(C(=O)NCCO)nc(N2CCOCC2)c1] | N-(2-hydroxyethyl)-4-[2-methyl-5-[(3S)-3-(2,2,2-trifluoroethyl)pyrrolidine-1-carbonylamino]phenyl]-6-(morpholin-4-yl)pyridine-2-carboxamide |

TABLE 1-continued

| Synthetic Chemistry Example | Compound Structure | Compound Name |
|---|---|---|
| 5 | 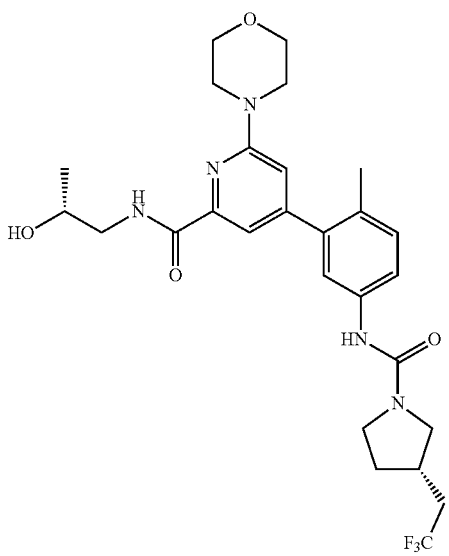 [SMILES: Cc1ccc(NC(=O)N2CC[C@@H](CC(F)(F)F)C2)cc1-c1cc(C(=O)NC[C@@H](C)O)nc(N2CCOCC2)c1] | N-[(2R)-2-hydroxypropyl]-4-[2-methyl-5-[(3S)-3-(2,2,2-trifluoroethyl)pyrrolidine-1-carbonylamino]phenyl]-6-(morpholin-4-yl)pyridine-2-carboxamide |
| 6 | 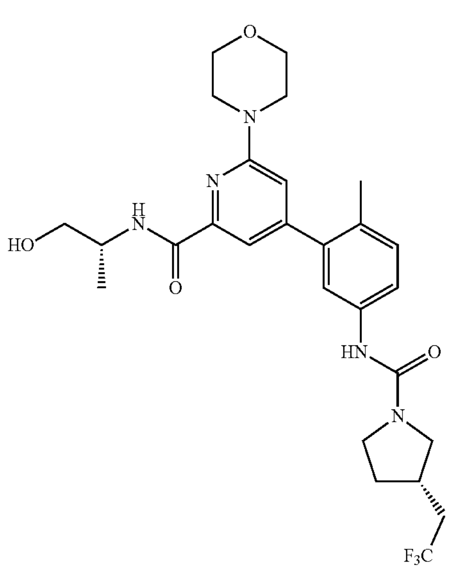 [SMILES: Cc1ccc(NC(=O)N2CC[C@@H](CC(F)(F)F)C2)cc1-c1cc(C(=O)N[C@H](C)CO)nc(N2CCOCC2)c1] | N-[(2R)-1-hydroxypropan-2-yl]-4-[2-methyl-5-[(3S)-3-(2,2,2-trifluoroethyl)pyrrolidine-1-carbonylamino]phenyl]-6-(morpholin-4-yl)pyridine-2-carboxamide |

TABLE 1-continued
| Synthetic Chemistry Example | Compound Structure | Compound Name |
|---|---|---|
| 7 | 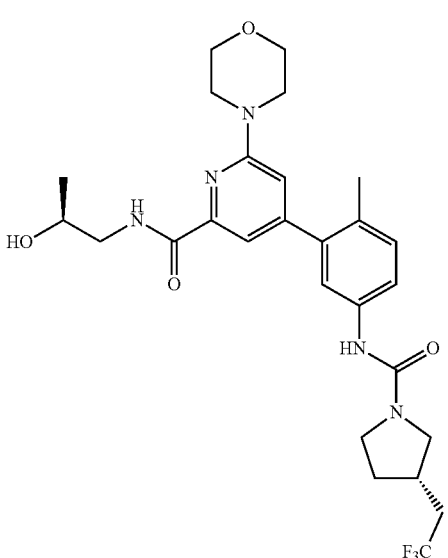 [SMILES: Cc1ccc(NC(=O)N2CC[C@@H](CC(F)(F)F)C2)cc1-c1cc(C(=O)NC[C@H](C)O)nc(N2CCOCC2)c1] | N-[(2S)-2-hydroxypropyl]-4-[2-methyl-5-[(3S)-3-(2,2,2-trifluoroethyl)pyrrolidine-1-carbonylamino]phenyl]-6-(morpholin-4-yl)pyridine-2-carboxamide |
| 8 | 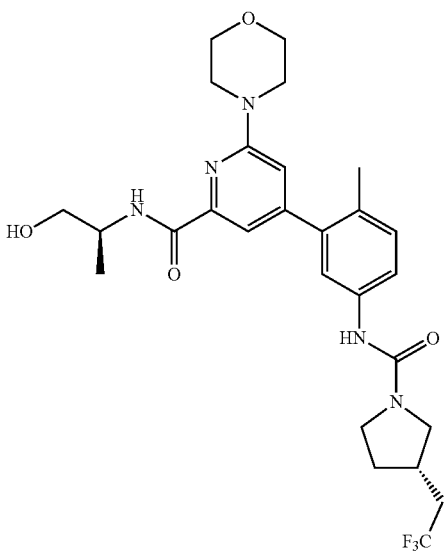 | N-[(2S)-1-hydroxypropan-2-yl]-4-[2-methyl-5-[(3S)-3-(2,2,2-trifluoroethyl)pyrrolidine-1-carbonylamino]phenyl]-6-(morpholin-4-yl)pyridine-2-carboxamidel |

TABLE 1-continued

| Synthetic Chemistry Example | Compound Structure | Compound Name |
|---|---|---|
| 9 | 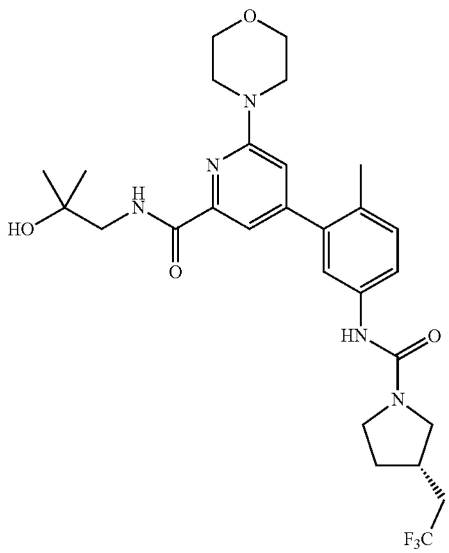 [SMILES: Cc1ccc(NC(=O)N2CC[C@@H](CC(F)(F)F)C2)cc1-c1cc(C(=O)NCC(C)(C)O)nc(N2CCOCC2)c1] | N-(2-hydroxy-2-methyl propyl)-4-[2-methyl-5-[(3S)-3-(2,2,2-trifluoroethyl)pyrrolidine-1-carbonylamino]phenyl]-6-(morpholin-4-yl)pyridine-2-carboxamide |
| 10 | 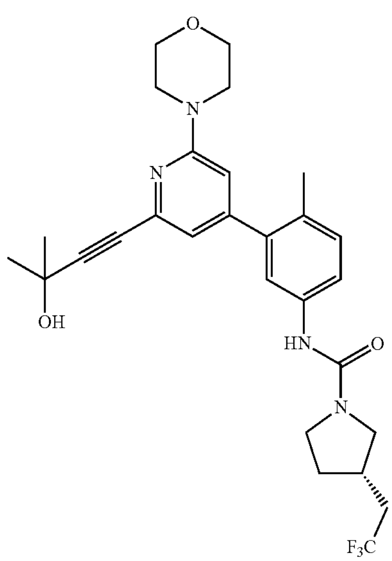 [SMILES: Cc1ccc(NC(=O)N2CC[C@@H](CC(F)(F)F)C2)cc1-c1cc(C#CC(C)(C)O)nc(N2CCOCC2)c1] | (3S)-N-[3-[2-(3-hydroxy-3-methylbut-1-yn-1-yl)-6-(morpholin-4-yl)pyridin-4-yl]-4-methylphenyl]-3-(2,2,2-trifluoroethyl)pyrrolidine-1-carboxamide |

TABLE 1-continued
| Synthetic Chemistry Example | Compound Structure | Compound Name |
|---|---|---|
| 11 | 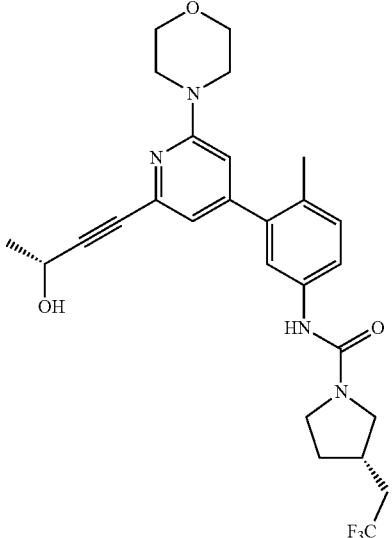 | (3S)-N-(3-[2-[(3R)-3-hydroxybut-1-yn-1-yl]-6-(morpholin-4-yl)pyridin-4-yl]-4-methylphenyl)-3-(2,2,2-trifluoroethyl)pyrrolidine-1-carboxamide |
| 12 | 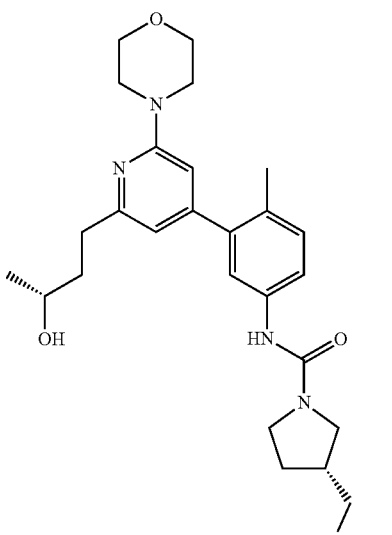 | (3S)-N-(3-[2-[(3R)-3-hydroxybutyl]-6-(morpholin-4-yl)pyridin-4-yl]-4-methylphenyl)-3-(2,2,2-trifluoroethyl)pyrrolidine-1-carboxamide |

TABLE 1-continued
| Synthetic Chemistry Example | Compound Structure | Compound Name |
|---|---|---|
| 13 | 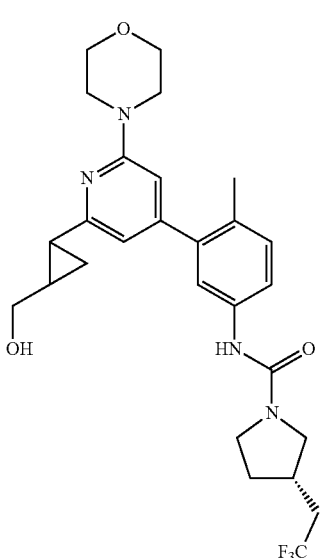 | (3S)-N-(3-[2-[(1R,2S)-2-(hydroxymethyl)cyclopropyl]-6-(morpholin-4-yl)pyridin-4-yl]-4-methylphenyl)-3-(2,2,2-trifluoroethyl)pyrrolidine-1-carboxamide |
| 14 | 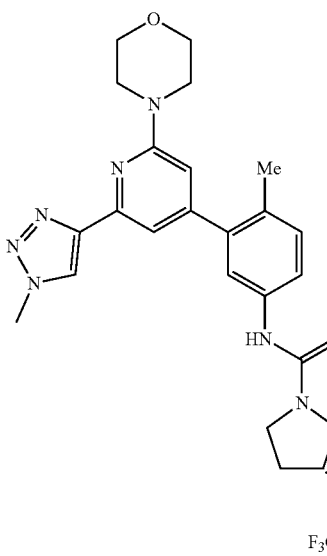 | (3S)-N-[4-methyl-3-[2-(1-methyl-1,2,3-triazol-4-yl)-6-(morpholin-4-yl)pyridin-4-yl]phenyl]-3-(2,2,2-trifluoroethyl)pyrrolidine-1-carboxamide |

TABLE 1-continued
| Synthetic Chemistry Example | Compound Structure | Compound Name |
|---|---|---|
| 15 | 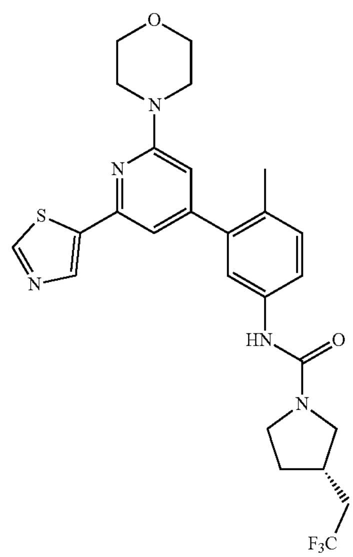 [SMILES: Cc1ccc(NC(=O)N2CC[C@@H](CC(F)(F)F)C2)cc1-c1cc(-c2cncs2)nc(N2CCOCC2)c1] | (3S)-N-[4-methyl-3-[2-(morpholin-4-yl)-6-(1,3-thiazol-5-yl)pyridin-4-yl]phenyl]-3-(2,2,2-trifluoroethyl)pyrrolidine-1-carboxamide |
| 16 | 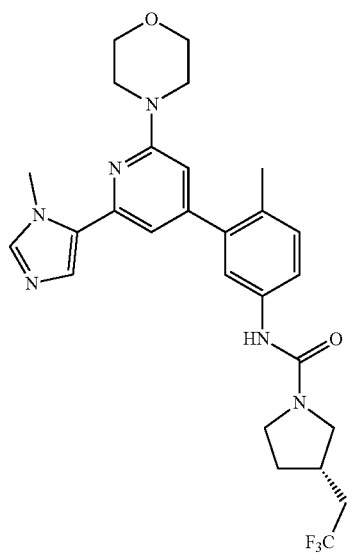 [SMILES: Cc1ccc(NC(=O)N2CC[C@@H](CC(F)(F)F)C2)cc1-c1cc(-c2cncn2C)nc(N2CCOCC2)c1] | (3S)-N-[4-methyl-3-[2-(3-methylimidazol-4-yl)-6-(morpholin-4-yl)pyridin-4-yl]phenyl]-3-(2,2,2-trifluoroethyl)pyrrolidine-1-carboxamide |

TABLE 1-continued

| Synthetic Chemistry Example | Compound Structure | Compound Name |
|---|---|---|
| 17 | 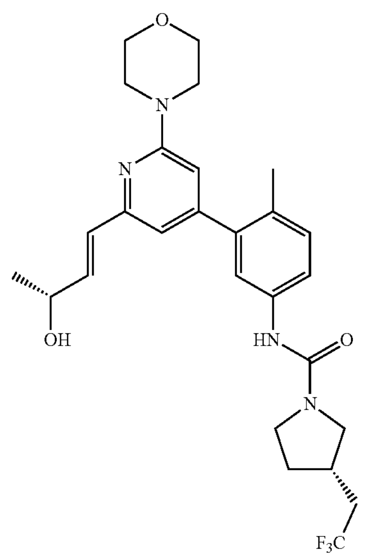 [SMILES: Cc1ccc(NC(=O)N2CC[C@@H](CC(F)(F)F)C2)cc1-c1cc(/C=C/[C@@H](C)O)nc(N2CCOCC2)c1] | (3S)-N-(3-[2-[(1E,3R)-3-hydroxybut-1-en-1-yl]-6-(morpholin-4-yl)pyridin-4-yl]-4-methylphenyl)-3-(2,2,2-trifluoroethyl)pyrrolidine-1-carboxamide |
| 18 | 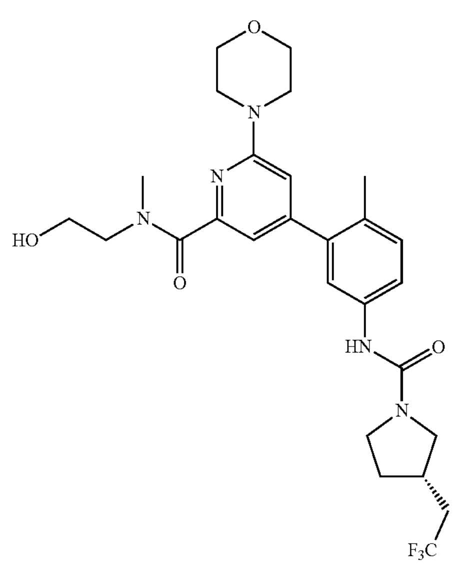 [SMILES: Cc1ccc(NC(=O)N2CC[C@@H](CC(F)(F)F)C2)cc1-c1cc(C(=O)N(C)CCO)nc(N2CCOCC2)c1] | N-(2-hydroxyethyl)-N-methyl-4-[2-methyl-5-[(3S)-3-(2,2,2-trifluoroethyl)pyrrolidine-1-carbonylamino]phenyl]-6-(morpholin-4-yl)pyridine-2-carboxamide |

TABLE 1-continued

| Synthetic Chemistry Example | Compound Structure | Compound Name |
|---|---|---|
| 19 | 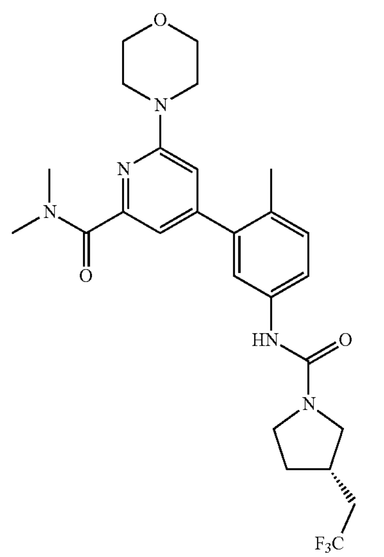 [SMILES: Cc1ccc(NC(=O)N2CC[C@@H](CC(F)(F)F)C2)cc1-c1cc(C(=O)N(C)C)nc(N2CCOCC2)c1] | N,N-dimethyl-4-[2-methyl-5-[(3S)-3-(2,2,2-trifluoroethyl)pyrrolidine-1-carbonylamino]phenyl]-6-(morpholin-4-yl)pyridine-2-carboxamide |
| 20 | 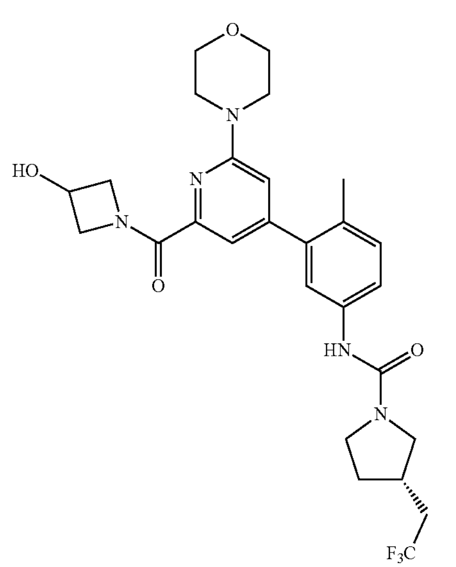 [SMILES: Cc1ccc(NC(=O)N2CC[C@@H](CC(F)(F)F)C2)cc1-c1cc(C(=O)N2CC(O)C2)nc(N2CCOCC2)c1] | (3S)-N-[3-[2-(3-hydroxyazetidine-1-carbonyl)-6-(morpholin-4-yl)pyridin-4-yl]-4-methylphenyl]-3-(2,2,2-trifluoroethyl)pyrrolidine-1-carboxamide |

TABLE 1-continued
| Synthetic Chemistry Example | Compound Structure | Compound Name |
|---|---|---|
| 21 | 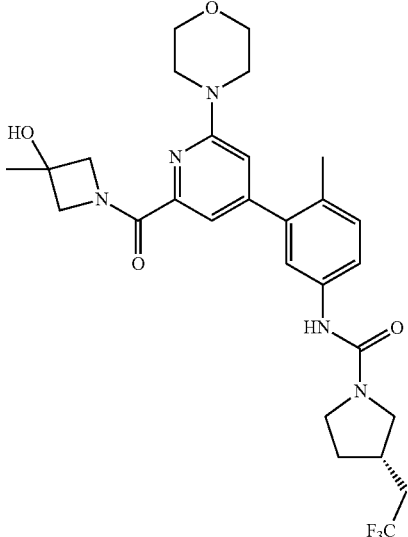 [SMILES: Cc1ccc(NC(=O)N2CC[C@@H](CC(F)(F)F)C2)cc1-c1cc(C(=O)N2CC(C)(O)C2)nc(N2CCOCC2)c1] | (3S)-N-[3-[2-(3-hydroxy-3-methylazetidine-1-carbonyl)-6-(morpholin-4-yl)pyridin-4-yl]-4-methylphenyl]-3-(2,2,2-trifluoroethyl)pyrrolidine-1-carboxamide |
| 22 | 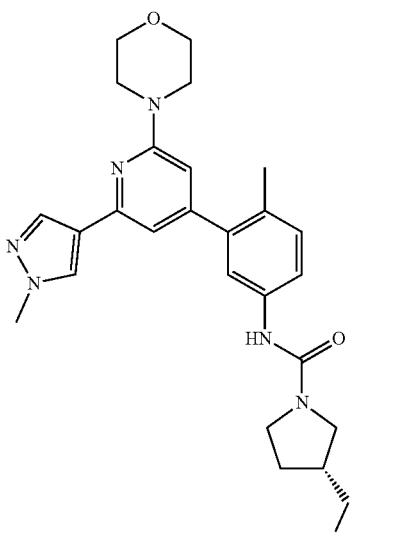 | (3S)-N-[4-methyl-3-[2-(l-methylpyrazol-4-yl)-6-(morpholin-4-yl)pyridin-4-yl]phenyl]-3-(2,2,2-trifluoroelhyl)pyrrolidine-1-carboxamide |

TABLE 1-continued

| Synthetic Chemistry Example | Compound Structure | Compound Name |
|---|---|---|
| 23 | 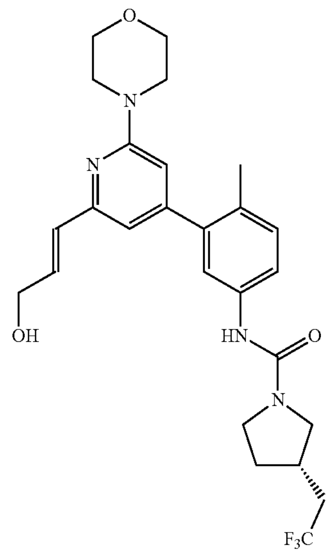 [SMILES: Cc1ccc(NC(=O)N2CC[C@@H](CC(F)(F)F)C2)cc1-c1cc(/C=C/CO)nc(N2CCOCC2)c1] | (3S)-N-(3-[2-[(1E)-3-hydroxyprop-1-en-1-yl]-6-(morpholin-4-yl)pyridin-4-yl]-4-methylphenyl)-3-(2,2,2-trifluoroethyl)pyrrolidine-1-carboxamide |
| 24 | 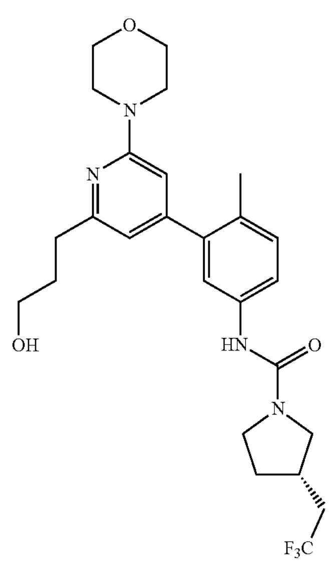 [SMILES: Cc1ccc(NC(=O)N2CC[C@@H](CC(F)(F)F)C2)cc1-c1cc(CCCO)nc(N2CCOCC2)c1] | (3S)-N-[3-[2-(3-hydroxypropyl)-6-(morpholin-4-yl)pyridin-4-yl]-4-methylphenyl]-3-(2,2,2-trifluoroethyl)pyrrolidine-1-carboxamide |

TABLE 1-continued
| Synthetic Chemistry Example | Compound Structure | Compound Name |
|---|---|---|
| 25 | 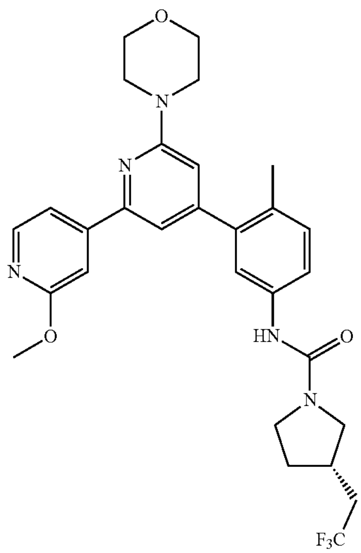 [SMILES: COc1cc(-c2cc(-c3cc(NC(=O)N4CC[C@@H](CC(F)(F)F)C4)ccc3C)cc(N3CCOCC3)n2)ccn1] | (3S)-N-[3-[2-methoxy-6-(morpholin-4-yl)-[2,4-bipyridin]-4-yl]-4-methylphenyl]-3-(2,2,2-trifluoroethyl)pyrrolidine-1-carboxamide |
| 26 | 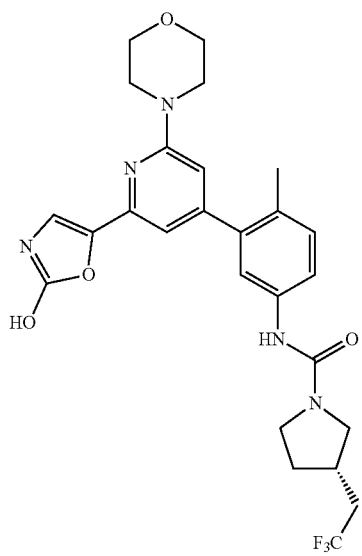 [SMILES: Cc1ccc(NC(=O)N2CC[C@@H](CC(F)(F)F)C2)cc1-c1cc(-c2cnc(O)o2)nc(N2CCOCC2)c1] | (3S)-N-[3-[2-(2-hydroxy-1,3-oxazol-5-yl)-6-(morpholin-4-yl)pyridin-4-yl]-4-methylphenyl]-3-(2,2,2-trifluoroethyl)pyrrolidine-1-carboxamide |

TABLE 1-continued
| Synthetic Chemistry Example | Compound Structure | Compound Name |
|---|---|---|
| 27 | 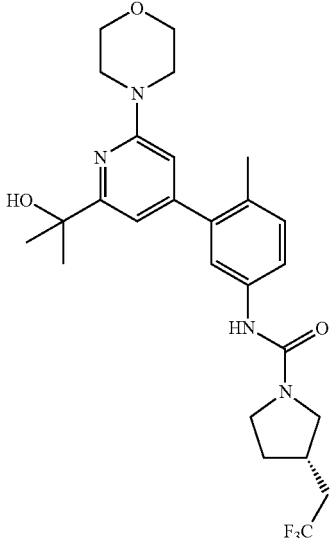 [SMILES: Cc1ccc(NC(=O)N2CC[C@@H](CC(F)(F)F)C2)cc1-c1cc(N2CCOCC2)nc(C(C)(C)O)c1] | (3S)-N-[3-[2-(2-hydroxypropan-2-yl)-6-(morpliolin-4-yl)pyridin-4-yl]-4-methylphenyl]-3-(2,2,2-trifluoroethyl)pyrrolidine-1-carboxamide |
| 28 | 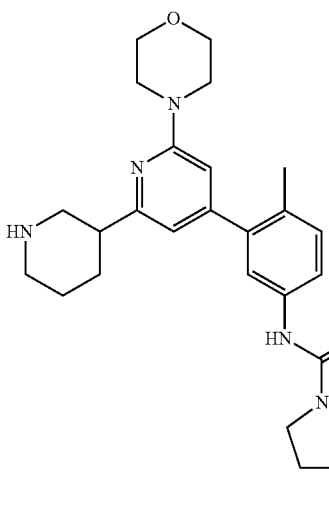 | (3S)-N-4-methyl-3-[2-(morpholin-4-yl) 6-(piperidin-3-yl)pyridin-4-yl]phenyl]-3 (2,2,2-trifluoroethyl)pyrrolidine-1-carboxamide |

TABLE 1-continued
| Synthetic Chemistry Example | Compound Structure | Compound Name |
|---|---|---|
| 29 | 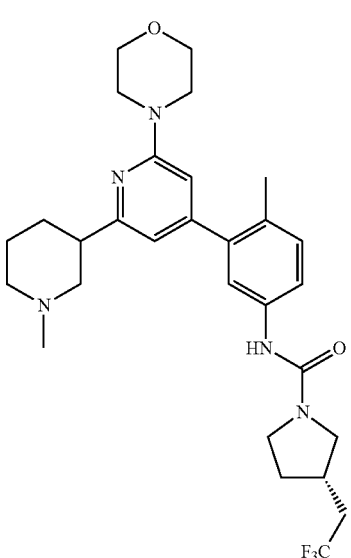 [SMILES: Cc1ccc(NC(=O)N2CC[C@@H](CC(F)(F)F)C2)cc1-c1cc(C2CCCN(C)C2)nc(N2CCOCC2)c1] | (3S)-N-[3-(2-[[(2R)-2-hydroxypropyl](methyl)amino]-6-(morpholin-4-yl)pyridin-4-yl)-4-methylphenyl]-3-(2,2,2-trifluoroethyl)pyrrolidine-1-carboxamide |
| 30 | 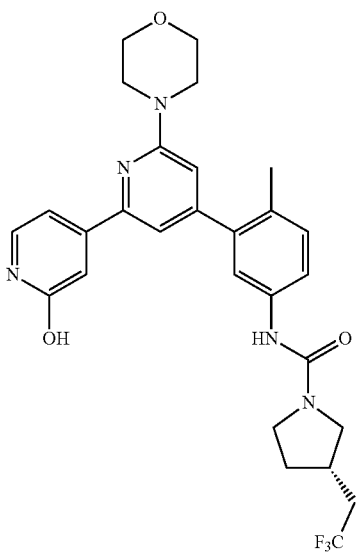 [SMILES: Cc1ccc(NC(=O)N2CC[C@@H](CC(F)(F)F)C2)cc1-c1cc(-c2ccnc(O)c2)nc(N2CCOCC2)c1] | (3S)-N-[3-[2-hydroxy-6-(morpholin-4-yl)-[2,4-bipyridin]-4-yl]-4-methylphenyl]-3-(2,2,2-trifluoroethyl)pyrrolidine-1-carboxamide |

TABLE 1-continued

| Synthetic Chemistry Example | Compound Structure | Compound Name |
|---|---|---|
| 31 | 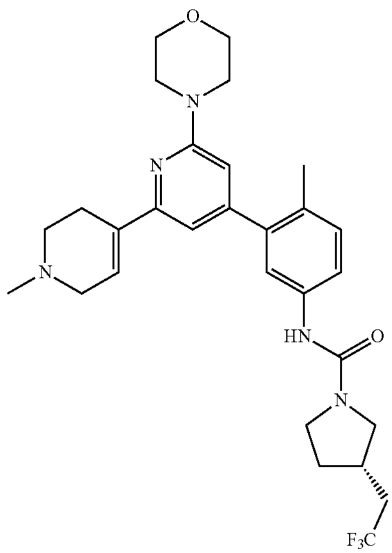 [SMILES: Cc1ccc(NC(=O)N2CC[C@@H](CC(F)(F)F)C2)cc1-c1cc(C2=CCN(C)CC2)nc(N2CCOCC2)c1] | (3S)-N-[4-methyl-3-[1'-methyl-6-(morpholin-4-yl)-3',6'-dihydro-2'H-[2,4'-bipyridin]-4-yl]phenyl]-3-(2,2,2-trifluoroethyl)pyrrolidine-1-carboxamide |
| 32 | 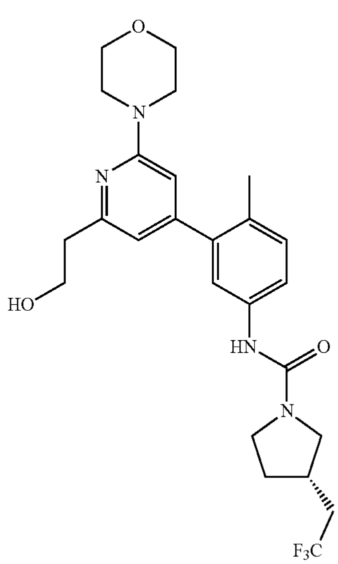 [SMILES: Cc1ccc(NC(=O)N2CC[C@@H](CC(F)(F)F)C2)cc1-c1cc(CCO)nc(N2CCOCC2)c1] | (3S)-N-[3-[2-(2-hydroxyethyl)-6-(morpholin-4-yl)pyridin-4-yl]-4-methylphenyl]-3-(2,2,2-trifluoroethyl)pyrrolidine-1-carboxamide |

TABLE 1-continued
| Synthetic Chemistry Example | Compound Structure | Compound Name |
|---|---|---|
| 33 | 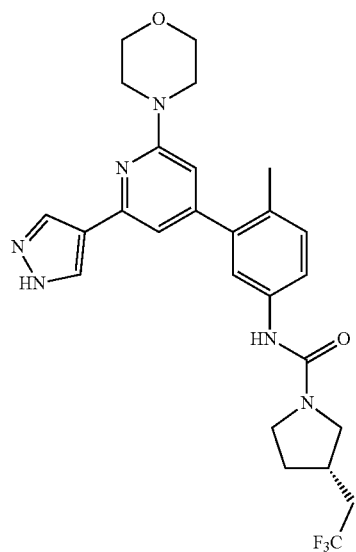 [SMILES: Cc1ccc(NC(=O)N2CC[C@@H](CC(F)(F)F)C2)cc1-c1cc(-c2cn[nH]c2)nc(N2CCOCC2)c1] | (3S)-N-[4-methyl-3-[2-(morpholin-4-yl)-6-(1H-pyrazol-4-yl)pyridin-4-yl]phenyl]-3-(2,2,2-trifluoroethyl)pyrrolidine-1-carboxamide |
| 34 | 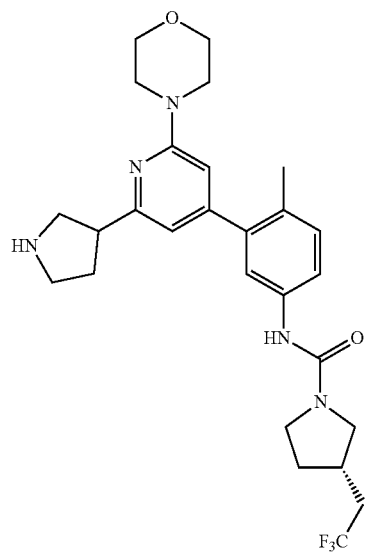 [SMILES: Cc1ccc(NC(=O)N2CC[C@@H](CC(F)(F)F)C2)cc1-c1cc(C2CCNC2)nc(N2CCOCC2)c1] | (3S)-N-(4-methyl-3-(2-morpholino-6-(pyrrolidin-3-yl)pyridin-4-yl)phenyl)-3-(2,2,2-trifluoroethyl)pyrrolidine-1-carboxamide |

TABLE 1-continued

| Synthetic Chemistry Example | Compound Structure | Compound Name |
|---|---|---|
| 35 | 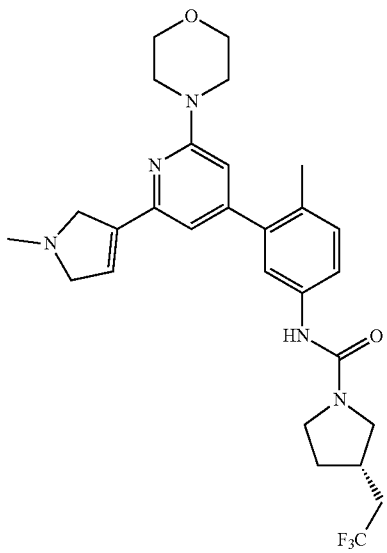 [SMILES: Cc1ccc(NC(=O)N2CC[C@@H](CC(F)(F)F)C2)cc1-c1cc(C2=CCN(C)C2)nc(N2CCOCC2)c1] | (3S)-N-[4-methyl-3-[2-(1-methyl-2,5-dihydropyrrol-3-yl)-6-(morpholin-4-yl)pyridin-4-yl]phenyl]-3-(2,2,2-trifluoroethyl)pyrrolidine-1-carboxamide |
| 36 | 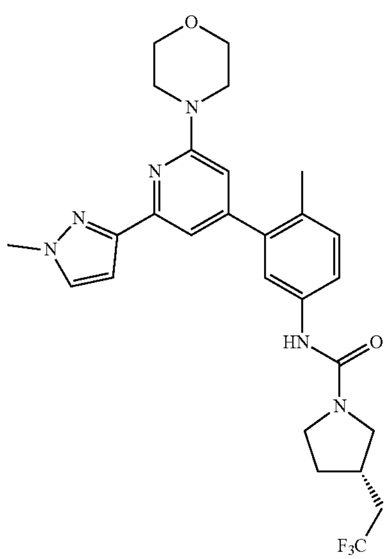 [SMILES: Cc1ccc(NC(=O)N2CC[C@@H](CC(F)(F)F)C2)cc1-c1cc(-c2ccn(C)n2)nc(N2CCOCC2)c1] | (3S)-N-[4-methyl-3-[2-(1-methylpyrazol-3-yl)-6-(morpholin-4-yl)pyridin-4-yl]phenyl]-3-(2,2,2-trifluoroethyl)pyrrolidine-1-carboxamide |

TABLE 1-continued

| Synthetic Chemistry Example | Compound Structure | Compound Name |
|---|---|---|
| 37 | 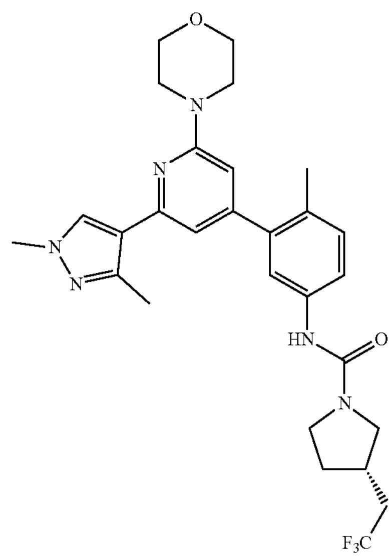 [SMILES: Cc1ccc(NC(=O)N2CC[C@@H](CC(F)(F)F)C2)cc1-c1cc(-c2cn(C)nc2C)nc(N2CCOCC2)c1] | (3S)-N-[3-[2-(1,3-dimethylpyrazol-4-yl)-6-(morpholin-4-yl)pyridin-4-yl]-4-methylphenyl]-3-(2,2,2-trifluoroethyl)pyrrolidine-1-carboxamide |
| 38 | 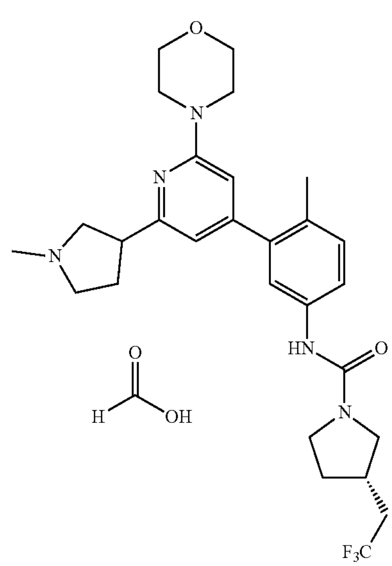 [SMILES: Cc1ccc(NC(=O)N2CC[C@@H](CC(F)(F)F)C2)cc1-c1cc(C2CCN(C)C2)nc(N2CCOCC2)c1 ; O=CO] | (3S)-N-(4-methyl-3-(2-(1-methylpyrrolidin-3-yl)-6-morpholinopyridin-4-yl)phenyl)-3-(2,2,2-trifluoroethyl)pyrrolidine-1-carboxamide formate |

TABLE 1-continued
| Synthetic Chemistry Example | Compound Structure | Compound Name |
|---|---|---|
| 39 | 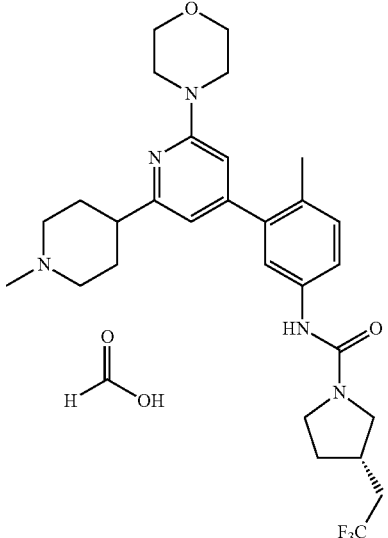 | (S)-N-(4-methyl-3-(2-(1-methylpiperidin-4-yl)-6-morpholinopyridin-4-yl)phenyl)-3-(2,2,2-trifluoroethyl)pyrrolidine-1-carboxamide formate |
| 40 | 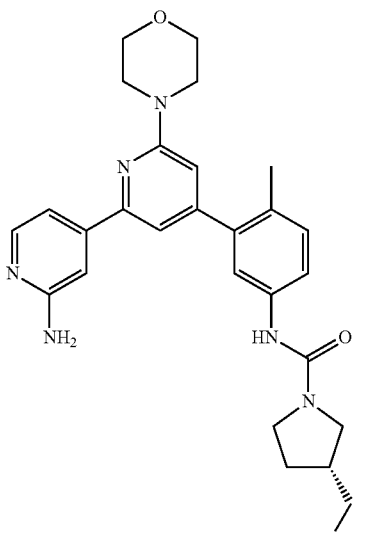 | (3S)-N-[3-[2'-amino-6-(morpholin-4-yl)-[2,4'-bipyridin]-4-yl]-4-methylphenyl]-3-(2,2,2-trifluoroethyl)pyrrolidine-1-carboxamide |

TABLE 1-continued

| Synthetic Chemistry Example | Compound Structure | Compound Name |
|---|---|---|
| 41 | 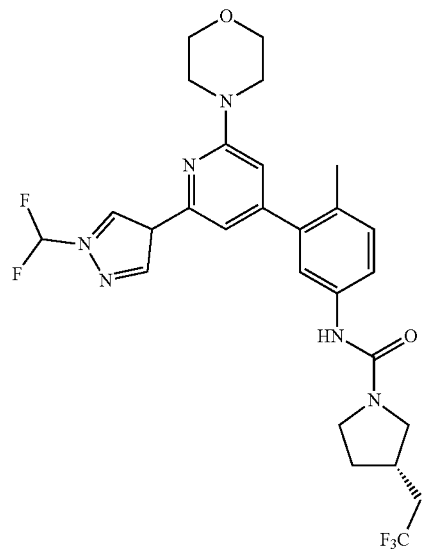 | (3S)-N-(3-[2-[1-(difluoromethyl)pyrazol-4-yl]-6-(morpholin-4-yl)pyridin-4-yl]-4-methylphenyl)-3-(2,2,2-trifluoroethyl)pyrrolidine-1-carboxamide |
| 42 | 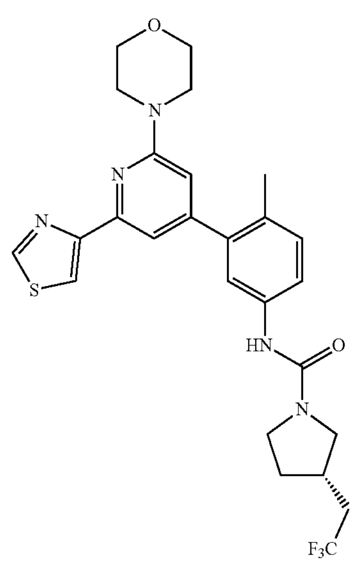 [SMILES: Cc1ccc(NC(=O)N2CC[C@@H](CC(F)(F)F)C2)cc1-c1cc(-c2cscn2)nc(N2CCOCC2)c1] | (3S)-N-[4-methyl-3-[2-(morpholin-4-yl)-6-(1,3-thiazol-4-yl)pyridin-4-yl]phenyl]-3-(2,2,2-trifluoroethyl)pyrrolidine-1-carboxamide |

TABLE 1-continued

| Synthetic Chemistry Example | Compound Structure | Compound Name |
|---|---|---|
| 43 | 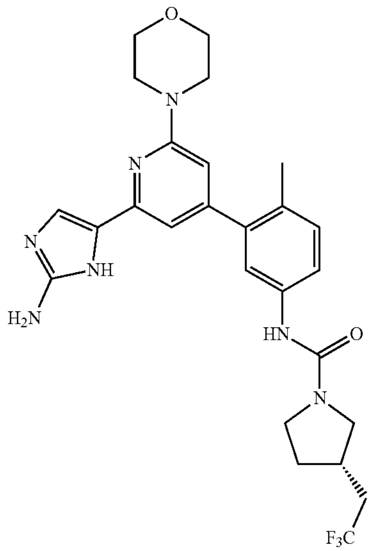 [SMILES: Cc1ccc(NC(=O)N2CC[C@@H](CC(F)(F)F)C2)cc1-c1cc(-c2cnc(N)[nH]2)nc(N2CCOCC2)c1] | (3S)-N-[3-[2-(2-amino-3H-imidazol-4-yl)-6-(morpholin-4-yl)pyridin-4-yl]-4-methylphenyl]-3-(2,2,2-trifluoroethyl)pyrrolidine-1-carboxamide |
| 44 | 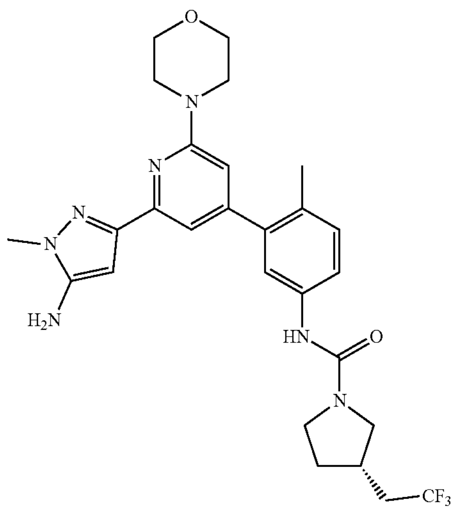 [SMILES: Cc1ccc(NC(=O)N2CC[C@@H](CC(F)(F)F)C2)cc1-c1cc(-c2cc(N)n(C)n2)nc(N2CCOCC2)c1] | (3S)-N-[3-[2-(5-amino-1-methylpyrazol-3-yl)-6-(morpholin-4-yl)pyridin-4-yl]-4-methylphenyl]-3-(2,2,2-trifluoroethyl)pyrrolidine-1-carboxamide |
| 45 | 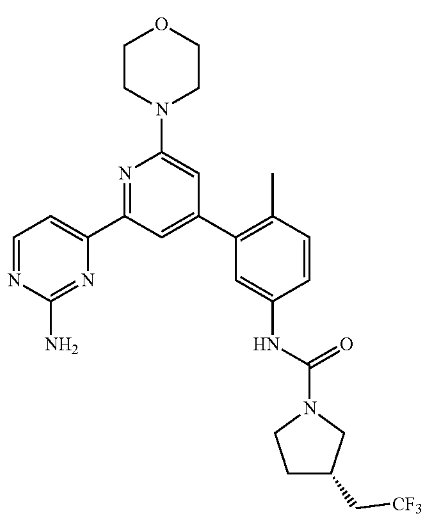 [SMILES: Cc1ccc(NC(=O)N2CC[C@@H](CC(F)(F)F)C2)cc1-c1cc(-c2ccnc(N)n2)nc(N2CCOCC2)c1] | (3S)-N-[3-[2-(2-aminopyrimidin-4-yl)-6-(morpholin-4-yl)pyridin-4-yl]-4-methylphenyl]-3-(2,2,2-trifluoroethyl)pyrrolidine-1-carboxamide |

TABLE 1-continued

| Synthetic Chemistry Example | Compound Structure | Compound Name |
|---|---|---|
| 46 | 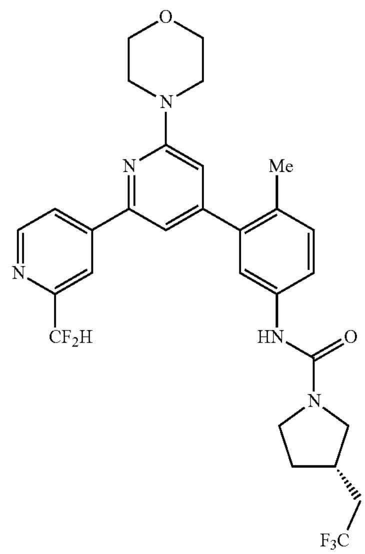 [SMILES: Cc1ccc(NC(=O)N2CC[C@@H](CC(F)(F)F)C2)cc1-c1cc(-c2ccnc(C(F)F)c2)nc(N2CCOCC2)c1] | (3S)-N-[3-[2'-(difluoromethyl)-6-(morpholin-4-yl)-[2,4'-bipyridin]-4-yl]-4-methylphenyl]-3-(2,2,2-trifluoroethyl)pyrrolidine-1-carboxamide |
| 47 | 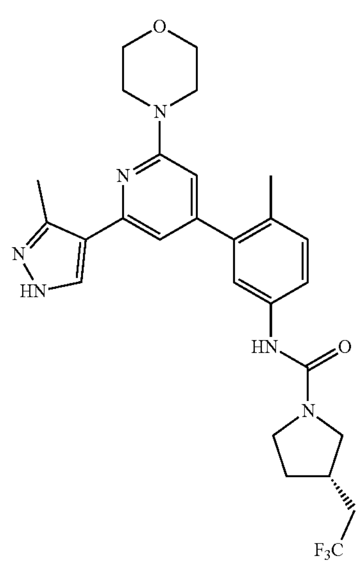 [SMILES: Cc1ccc(NC(=O)N2CC[C@@H](CC(F)(F)F)C2)cc1-c1cc(-c2c[nH]nc2C)nc(N2CCOCC2)c1] | (3S)-N-[4-methyl-3-[2-(3-methyl-1H-pyrazol-4-yl)-6-(morpholin-4-yl)pyridin-4-yl]phenyl]-3-(2,2,2-trifluoroethyl)pyrrolidine-1-carboxamide |

TABLE 1-continued

| Synthetic Chemistry Example | Compound Structure | Compound Name |
|---|---|---|
| 48 | 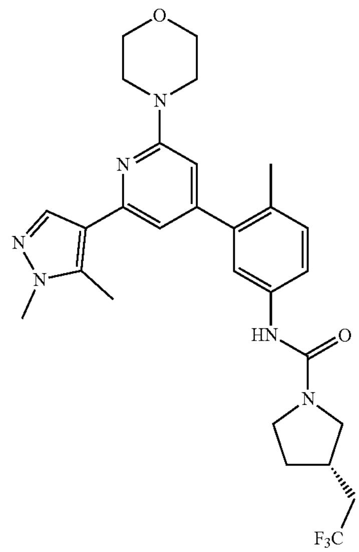 [SMILES: Cc1ccc(NC(=O)N2CC[C@@H](CC(F)(F)F)C2)cc1-c1cc(-c2cnn(C)c2C)nc(N2CCOCC2)c1] | (3S)-N-[3-[2-(1,5-dimethylpyrazol-4-yl)-6-(morpholin-4-yl)pyridin-4-yl]-4-methylphenyl]-3-(2,2,2-trifluoroethyl)pyrrolidine-1-carboxamide |
| 49 | 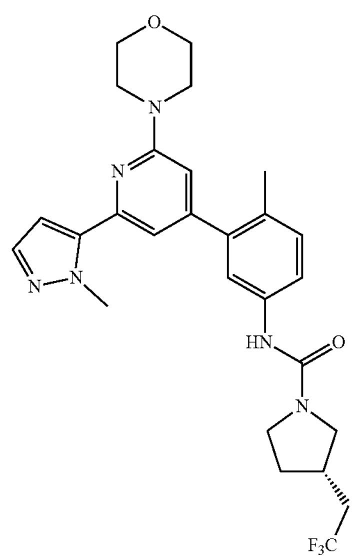 [SMILES: Cc1ccc(NC(=O)N2CC[C@@H](CC(F)(F)F)C2)cc1-c1cc(-c2ccnn2C)nc(N2CCOCC2)c1] | (3S)-N-[4-methyl-3-[2-(2-methylpyrazol-3-yl)-6-(morpholin-4-yl)pyridin-4-yl]phenyl]-3-(2,2,2-trifluoroethyl)pyrrolidine-1-carboxamide |

TABLE 1-continued
| Synthetic Chemistry Example | Compound Structure | Compound Name |
|---|---|---|
| 50 | 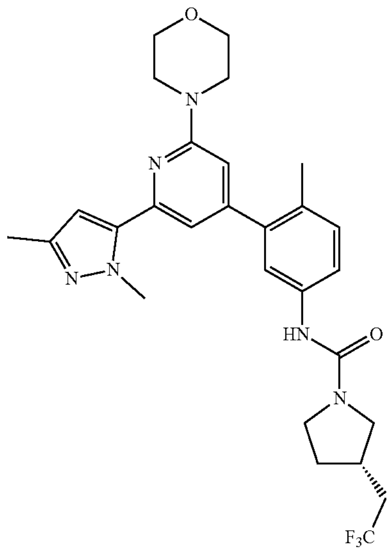 [SMILES: Cc1cc(-c2cc(-c3cc(NC(=O)N4CC[C@@H](CC(F)(F)F)C4)ccc3C)cc(N3CCOCC3)n2)n(C)n1] | (3S)-N-[3-[2-(2,5-dimethylpyrazol-3-yl)-6-(morpholin-4-yl)pyridin-4-yl]-4-methylphenyl]-3-(2,2,2-trifluoroethyl)pyrrolidine-1-carboxamide |
| 51 | 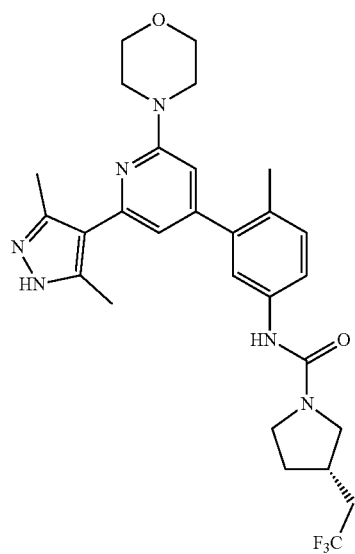 [SMILES: Cc1ccc(NC(=O)N2CC[C@@H](CC(F)(F)F)C2)cc1-c1cc(-c2c(C)n[nH]c2C)nc(N2CCOCC2)c1] | (3S)-N-[3-[2-(3,5-dimethyl-1H-pyrazol-4-yl)-6-(morpholirt-4-yl)pyridin-4-yl]-4-methylphenyl]-3-(2,2,2-trifluoroethyl)pyrrolidine-1-carboxamide |

TABLE 1-continued
| Synthetic Chemistry Example | Compound Structure | Compound Name |
|---|---|---|
| 52 | 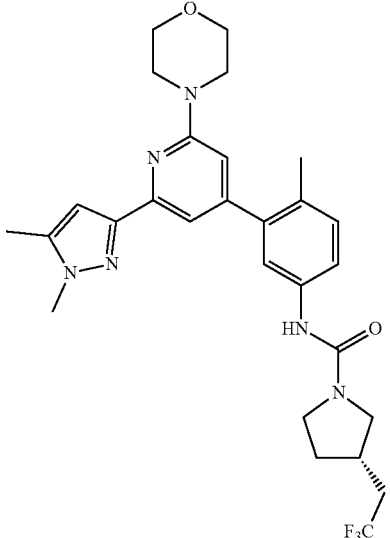 [SMILES: Cc1ccc(NC(=O)N2CC[C@@H](CC(F)(F)F)C2)cc1-c1cc(-c2cc(C)n(C)n2)nc(N2CCOCC2)c1] | (3S)-N-[3-[2-(1,5-dimethylpyrazol-3-yl)-6-(morpholin-4-yl)pyridin-4-yl]-4-methylphenyl]-3-(2,2,2-trifluoroethyl)pyrrolidine-1-carboxamide |
| 53 | 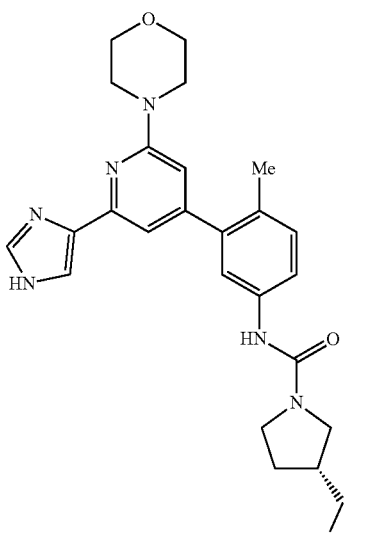 | (3S)-N-[3-[2-(1H-imidazol-4-yl)-6-(morpholin-4-yl)pyridin-4-yl]-4-methylphenyl]-3-(2,2,2-trifluoroethyl)pyrrolidine-1-carboxamide |

TABLE 1-continued

| Synthetic Chemistry Example | Compound Structure | Compound Name |
|---|---|---|
| 54 | 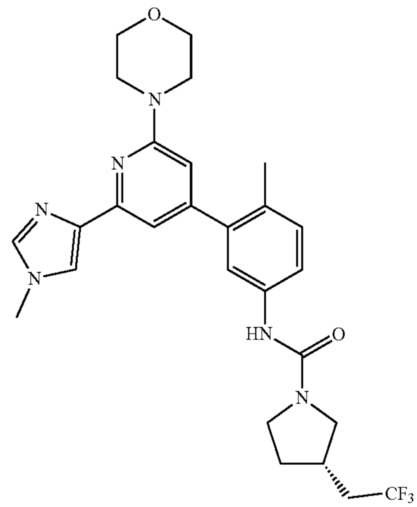 [SMILES: Cc1ccc(NC(=O)N2CC[C@@H](CC(F)(F)F)C2)cc1-c1cc(-c2cn(C)cn2)nc(N2CCOCC2)c1] | (3S)-N-{4-methyl-3-[2-(1-methylimidazol-4-yl)-6-(morpholin-4-yl)pyridin-4-yl]phenyl}-3-(2,2,2-trifluoroethyl)pyrrolidine-1-carboxamide |
| 55 | 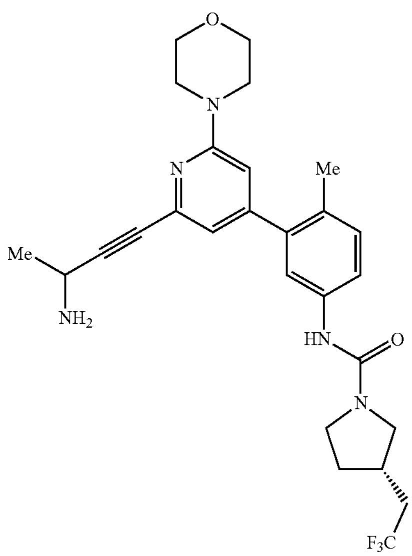 [SMILES: Cc1ccc(NC(=O)N2CC[C@@H](CC(F)(F)F)C2)cc1-c1cc(C#CC(C)N)nc(N2CCOCC2)c1] | (3S)-N-{3-[2-(3-aminobut-1-yn-1-yl)-6-(morpholin-4-yl)pyridin-4-yl]-4-methylphenyl}-3-(2,2,2-trifluoroethyl)pyrrolidine-1-carboxamide |
| 56 | 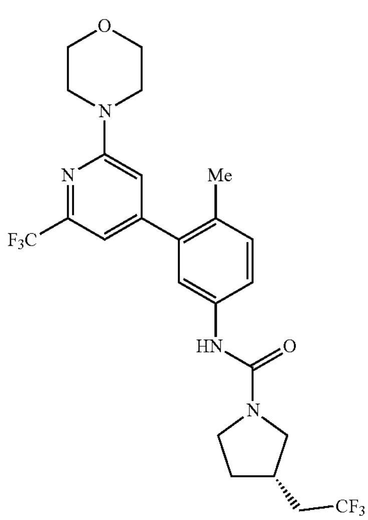 [SMILES: Cc1ccc(NC(=O)N2CC[C@@H](CC(F)(F)F)C2)cc1-c1cc(N2CCOCC2)nc(C(F)(F)F)c1] | (3S)-N-[4-methyl-3-[2-(morpholin-4-yl)-6-(trifluoromethyl)pyridin-4-yl]phenyl]-3-(2,2,2-trifluoroethyl)pyrrolidine-1-carboxamide |

TABLE 1-continued

| Synthetic Chemistry Example | Compound Structure | Compound Name |
|---|---|---|
| 57 | 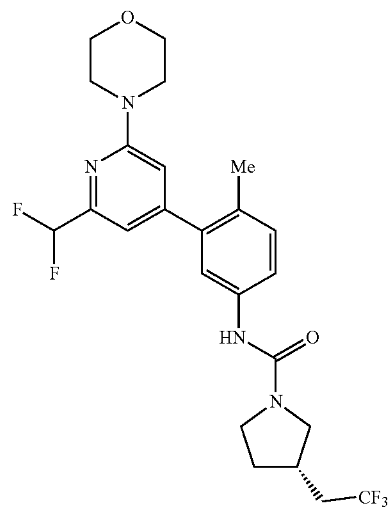 [SMILES: Cc1ccc(NC(=O)N2CC[C@@H](CC(F)(F)F)C2)cc1-c1cc(C(F)F)nc(N2CCOCC2)c1] | (3S)-N-{3-[2-(difluoromethyl)-6-(morpholin-4-yl)pyridin-4-yl]-4-methylphenyl}-3-(2,2,2-trifluoroethyl)pyrrolidine-1-carboxamide |
| 58 | 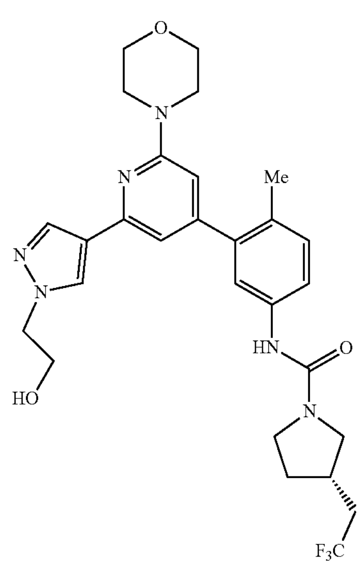 [SMILES: Cc1ccc(NC(=O)N2CC[C@@H](CC(F)(F)F)C2)cc1-c1cc(-c2cnn(CCO)c2)nc(N2CCOCC2)c1] | (3S)-N-(3-(2-(1-(2-hydroxyethyl)-1H-pyrazol-4-yl)-6-morpholinopyridin-4-yl)-4-methylphenyl)-3-(2,2,2-trifluoroethyl)pyrrolidine-1-carboxamide |

TABLE 1-continued

| Synthetic Chemistry Example | Compound Structure | Compound Name |
|---|---|---|
| 59 | 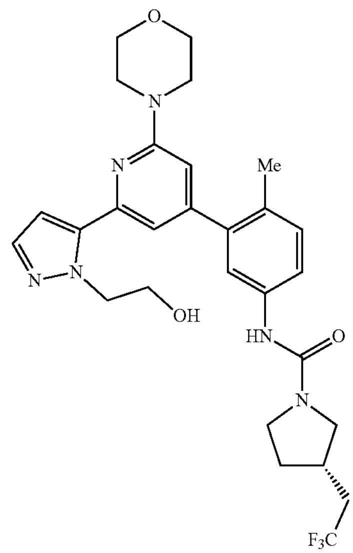 [SMILES: Cc1ccc(NC(=O)N2CC[C@@H](CC(F)(F)F)C2)cc1-c1cc(-c2ccnn2CCO)nc(N2CCOCC2)c1] | (3S)-N-(3-{2-[2-(2-hydroxyethyl)pyrazol-3-yl]-6-(morpholin-4-yl)pyridin-4-yl}-4-methylphenyl)-3-(2,2,2-trifluoroethyl)pyrrolidine-1-carboxamide |
| 60 | 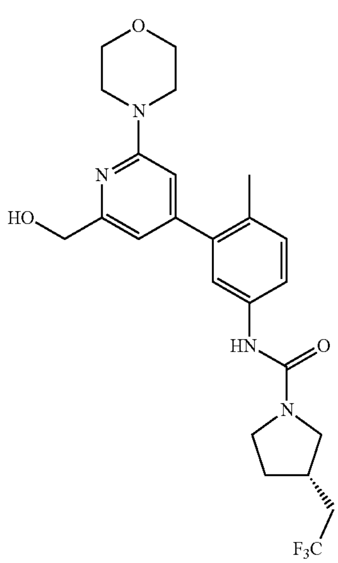 [SMILES: Cc1ccc(NC(=O)N2CC[C@@H](CC(F)(F)F)C2)cc1-c1cc(CO)nc(N2CCOCC2)c1] | (3S)-N-[3-[2-(hydroxymethyl)-6-(morpholin-4-yl)pyridin-4-yl]-4-methylphenyl]-3-(2,2,2-trifluoroethyl)pyrrolidine-1-carboxamide |

TABLE 1-continued

| Synthetic Chemistry Example | Compound Structure | Compound Name |
|---|---|---|
| 61 | 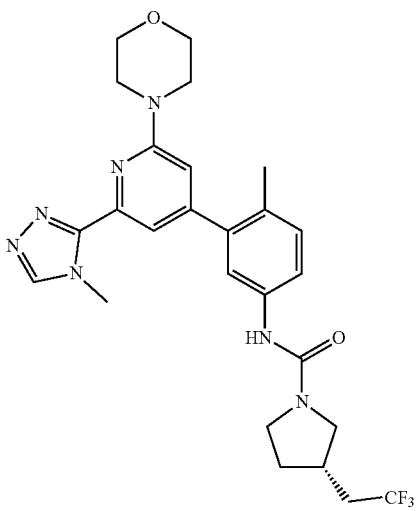 [SMILES: Cc1ccc(NC(=O)N2CC[C@@H](CC(F)(F)F)C2)cc1-c1cc(-c2nncn2C)nc(N2CCOCC2)c1] | (3S)-N-(4-methyl-3-[2-(4-methyl-1,2,4-triazol-3-yl)-6-(morpholin-4-yl)pyridin-4-yl]phenyl}-3-(2,2,2-trifluoroethyl)pyrrolidine-1-carboxamide |
| 62 | 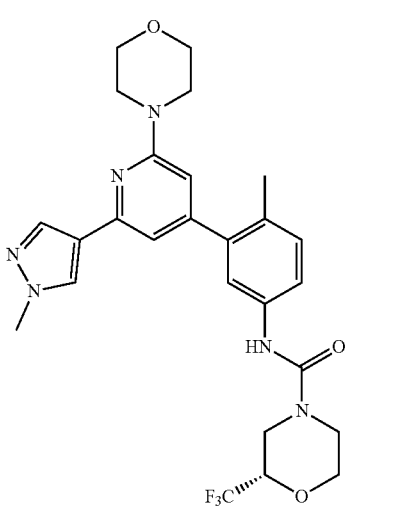 [SMILES: Cc1ccc(NC(=O)N2CCO[C@H](C(F)(F)F)C2)cc1-c1cc(-c2cnn(C)c2)nc(N2CCOCC2)c1] | (2S)-N-{4-methyl-3-[2-(1-methylpyrazol-4-yl)-6-(morpholin-4-yl)pyridin-4-yl]phenyl}-2-(trifluoromethyl)morpholine-4-carboxamide |
| 63 | 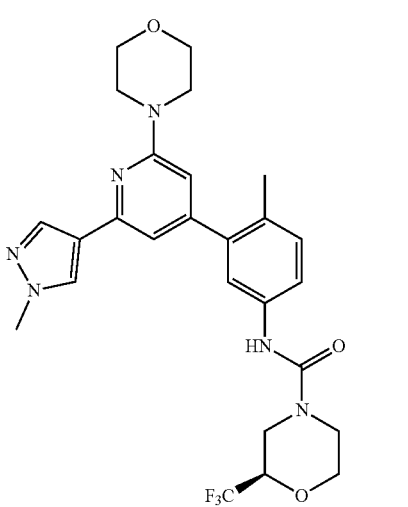 [SMILES: Cc1ccc(NC(=O)N2CCO[C@@H](C(F)(F)F)C2)cc1-c1cc(-c2cnn(C)c2)nc(N2CCOCC2)c1] | (2R)-N-{4-methyl-3-[2-(1-methylpyrazol-4-yl)-6-(morpholin-4-yl)pyridin-4-yl]phenyl}-2-(trifluoromethyl)morpholine-4-carboxamide |

TABLE 1-continued

| Synthetic Chemistry Example | Compound Structure | Compound Name |
|---|---|---|
| 64 | 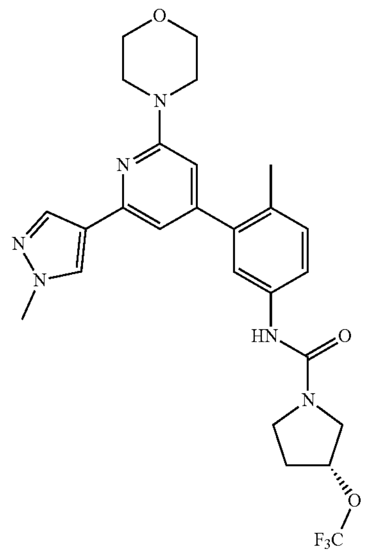 [SMILES: Cc1ccc(NC(=O)N2CC[C@@H](OC(F)(F)F)C2)cc1-c1cc(-c2cnn(C)c2)nc(N2CCOCC2)c1] | (3R)-N-{4-methyl-3-[2-(1-methylpyrazol-4-yl)-6-(morpholin-4-yl)pyridin-4-yl]phenyl}-3-(trifluoromethoxy)pyrrolidine-1-carboxamide |
| 65 | 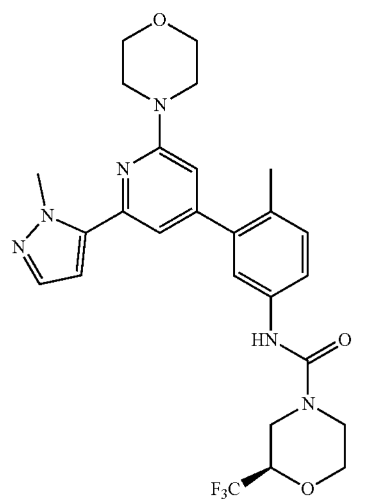 [SMILES: Cc1ccc(NC(=O)N2CCO[C@@H](C(F)(F)F)C2)cc1-c1cc(-c2ccnn2C)nc(N2CCOCC2)c1] | (2R)-N-{4-methyl-3-[2-(2-methylpyrazol-3-yl)-6-(morpholin-4-yl)pyridin-4-yl]phenyl}-2-(trifluoromethyl)morpholine-4-carboxamide |
| 66 | 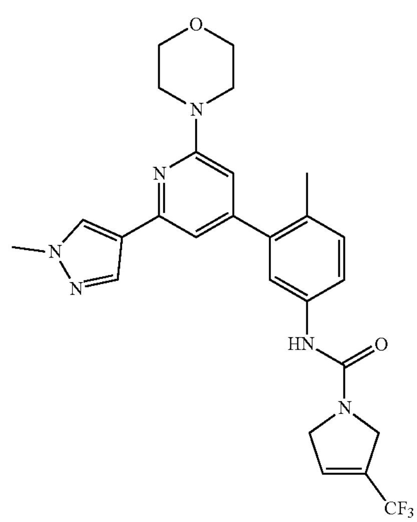 [SMILES: Cc1ccc(NC(=O)N2CC=C(C(F)(F)F)C2)cc1-c1cc(-c2cnn(C)c2)nc(N2CCOCC2)c1] | N-{4-methyl-3-[2-(1-methylpyrazol-4-yl)-6-(morpholin-4-yl)pyridin-4-yl]phenyl}-3-(trifluoromethyl)-2,5-dihydropyrrole-1-carboxamide |

TABLE 1-continued

| Synthetic Chemistry Example | Compound Structure | Compound Name |
|---|---|---|
| 67 | 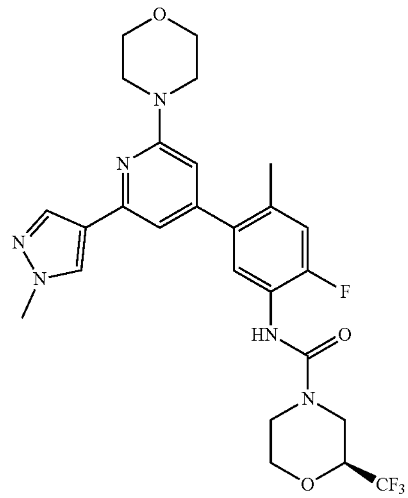 [SMILES: Cc1cc(F)c(NC(=O)N2CCO[C@H](C(F)(F)F)C2)cc1-c1cc(-c2cnn(C)c2)nc(N2CCOCC2)c1] | (2S)-N-{2-fluoro-4-methyl-5-[2-(1-methylpyrazol-4-yl)-6-(morpholin-4-yl)pyridin-4-yl]phenyl}-2-(trifluoromethyl)morpholine-4-carboxamide |
| 68 | 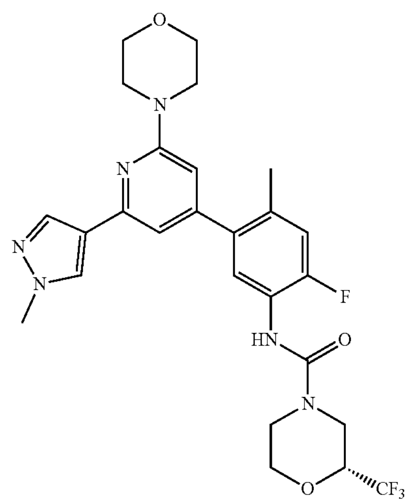 [SMILES: Cc1cc(F)c(NC(=O)N2CCO[C@@H](C(F)(F)F)C2)cc1-c1cc(-c2cnn(C)c2)nc(N2CCOCC2)c1] | (2R)-N-{2-fluoro-4-methyl-5-[2-(1-methylpyrazol-4-yl)-6-(morpholin-4-yl)pyridin-4-yl]phenyl}-2-(trifluoromethyl)morpholine-4-carboxamide |
| 69 | 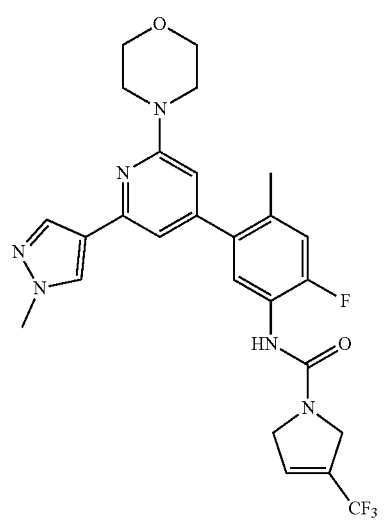 [SMILES: Cc1cc(F)c(NC(=O)N2CC=C(C(F)(F)F)C2)cc1-c1cc(-c2cnn(C)c2)nc(N2CCOCC2)c1] | N-{2-fluoro-4-methyl-5-[2-(1-methylpyrazol-4-yl)-6-(morpholin-4-yl)pyridin-4-yl]phenyl}-3-(trifluoromethyl)-2,5-dihydropyrrole-carboxamide |

TABLE 1-continued
| Synthetic Chemistry Example | Compound Structure | Compound Name |
|---|---|---|
| 70 | 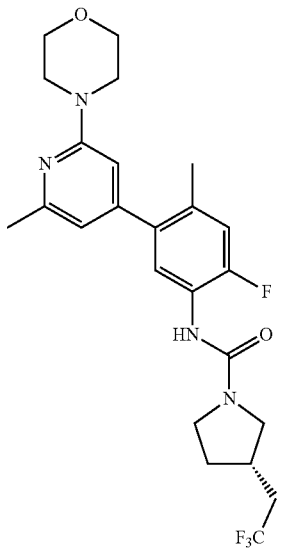 [SMILES: Cc1cc(-c2cc(NC(=O)N3CC[C@@H](CC(F)(F)F)C3)c(F)cc2C)cc(N2CCOCC2)n1] | (3S)-N-{2-fluoro-4-methyl-5-[2-methyl 6-(morpholin-4-yl)pyridin-4-yl]phenyl} 3-(2,2,2-trifluoroethyl)pyrrolidine-1-carboxamide |
| 71 | 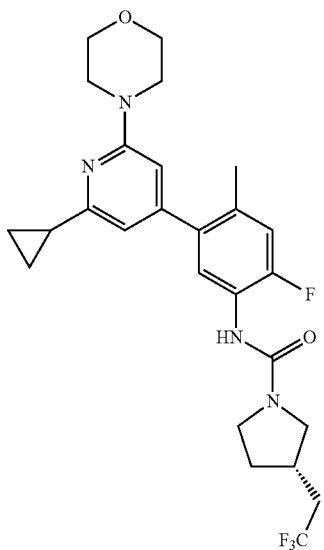 [SMILES: Cc1cc(F)c(NC(=O)N2CC[C@@H](CC(F)(F)F)C2)cc1-c1cc(C2CC2)nc(N2CCOCC2)c1] | (3S)-N-{5-[2-cyclopropyl-6-(morpholin-4-yl)pyridin-4-yl]-2-fluoro-4-methylphenyl}-3-(2,2,2-trifluoroethyl)pyrrolidine-1-carboxamide |

TABLE 1-continued
| Synthetic Chemistry Example | Compound Structure | Compound Name |
|---|---|---|
| 72 | 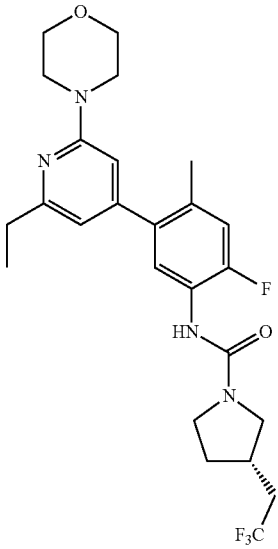 [SMILES: CCc1cc(-c2cc(NC(=O)N3CC[C@@H](CC(F)(F)F)C3)c(F)cc2C)cc(N2CCOCC2)n1] | (3S)-N-{5-[2-ethyl-6-(morpholin-4-yl)pyridin-4-yl]-2-fluoro-4-methylphenyl}-3-(2,2,2-trifluoroethyl)pyrrolidine-1-carboxamide |
| 73 | 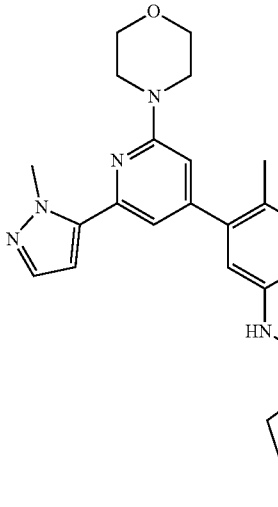 | N-{2-fluoro-4-methyl-5-[2-(2-methylpyrazol-3-yl)-6-(morpholin-4-yl)pyridin-4-yl]phenyl}-3-(trifluoromethyl)-2,5-dihydropyrrole-carboxamide |

TABLE 1-continued

| Synthetic Chemistry Example | Compound Structure | Compound Name |
|---|---|---|
| 74 | 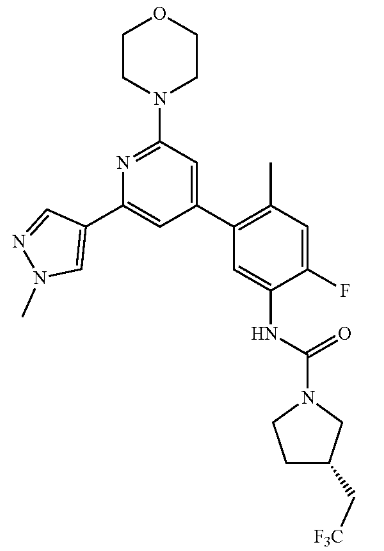 [SMILES: Cc1cc(F)c(NC(=O)N2CC[C@@H](CC(F)(F)F)C2)cc1-c1cc(-c2cnn(C)c2)nc(N2CCOCC2)c1] | (3S)-N-{2-fluoro-4-melhyl-5-[2-(1-methylpyrazol-4-yl)-6-(morpholin-4-yl)pyridin-4-yl]phenyl}-3-(2,2,2-trifluoroethyl)pyrrolidine-1-carboxamide |
| 75 | 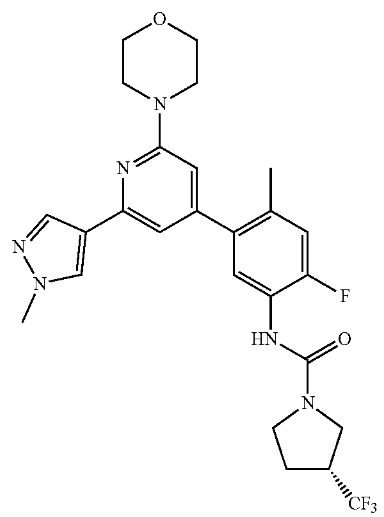 [SMILES: Cc1cc(F)c(NC(=O)N2CC[C@@H](C(F)(F)F)C2)cc1-c1cc(-c2cnn(C)c2)nc(N2CCOCC2)c1] | (3R)-N-{2-fluoro-4-methyl-5-[2-(1-methylpyrazol-4-yl)-6-(morpholin-4-yl)pyridin-4-yl]phenyl}-3-(trifluoromethyl)pyrrolidine-1-carboxamide |
| 76 | 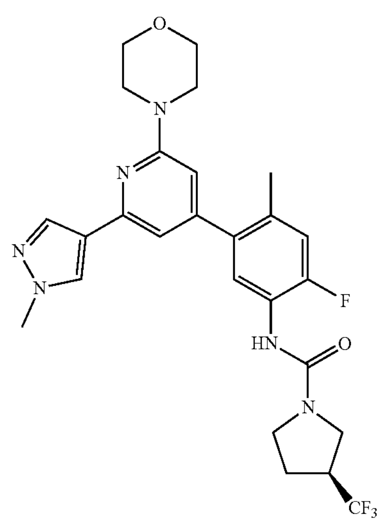 [SMILES: Cc1cc(F)c(NC(=O)N2CC[C@H](C(F)(F)F)C2)cc1-c1cc(-c2cnn(C)c2)nc(N2CCOCC2)c1] | (3S)-N-{2-fluoro-4-methyl-5-[2-(1-methylpyrazol-4-yl)-6-(morpholin-4-yl)pyridin-4-yl]phenyl}-3-(trifluoromethyl)pyrrolidine-1-carboxamide |

TABLE 1-continued
| Synthetic Chemistry Example | Compound Structure | Compound Name |
|---|---|---|
| 77 | 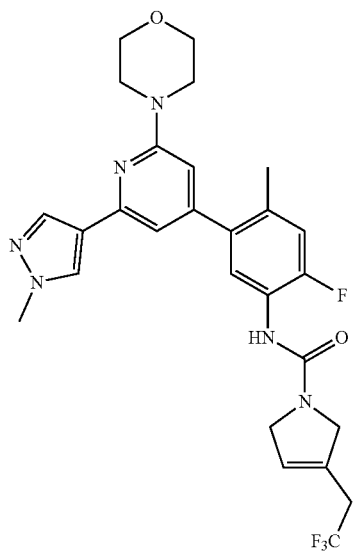 [SMILES: Cc1cc(F)c(NC(=O)N2CC=C(CC(F)(F)F)C2)cc1-c1cc(-c2cnn(C)c2)nc(N2CCOCC2)c1] | N-{2-fluoro-4-methyl-5-[2-(1-methylpyrazol-4-yl)-6-(morpholin-4-yl)pyridin-4-yl]phenyl}-3-(2,2,2-trifluoroethyl)-2,5-dihydropyrrole-1-carboxamide |
| 78 | 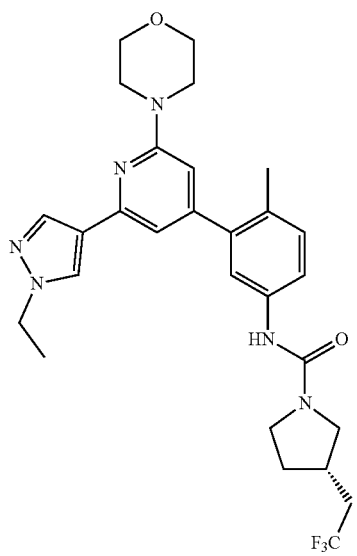 [SMILES: CCn1cc(-c2cc(-c3cc(NC(=O)N4CC[C@@H](CC(F)(F)F)C4)ccc3C)cc(N3CCOCC3)n2)cn1] | (3S)-N-{3-[2-(1-ethylpyrazol-4-yl)-6-(morpholin-4-yl)pyridin-4-yl]-4-methylphenyl}-3-(2,2,2-trifluoroethyl)pyrrolidine-1-carboxamide |

TABLE 1-continued
| Synthetic Chemistry Example | Compound Structure | Compound Name |
|---|---|---|
| 79 | 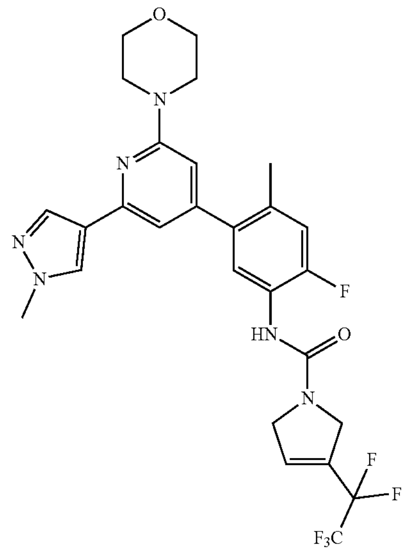 [SMILES: Cc1cc(F)c(NC(=O)N2CC=C(C(F)(F)C(F)(F)F)C2)cc1-c1cc(-c2cnn(C)c2)nc(N2CCOCC2)c1] | N-{2-fluoro-4-methyl-5-[2-(1-methylpyrazol-4-yl)-6-(morpholin-4-yl)pyridin-4-yl]phenyl}-3-(1,1,2,2,2-pentafluoroethyl)-2,5-dihydropyrrole-1-carboxamide |
| 80 | 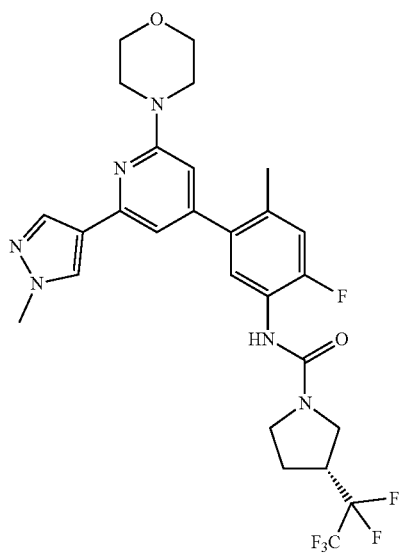 [SMILES: Cc1cc(F)c(NC(=O)N2CC[C@@H](C(F)(F)C(F)(F)F)C2)cc1-c1cc(-c2cnn(C)c2)nc(N2CCOCC2)c1] | (3R)-N-{2-fluoro-4-methyl-5-[2-(1-methylpyrazol-4-yl)-6-(morpholin-4-yl)pyridin-4-yl]phenyl}-3-(1,1,2,2,2-pentafluoroethyl)pyrrolidine-1-carboxamide (absolute chiral configuration was not determined) |

TABLE 1-continued

| Synthetic Chemistry Example | Compound Structure | Compound Name |
|---|---|---|
| 81 | 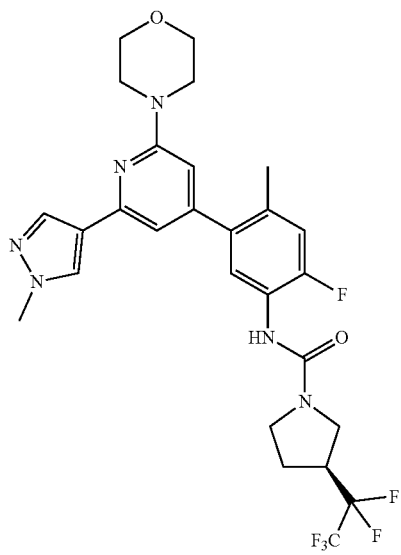 [SMILES: Cc1cc(F)c(NC(=O)N2CC[C@H](C(F)(F)C(F)(F)F)C2)cc1-c1cc(-c2cnn(C)c2)nc(N2CCOCC2)c1] | (3S)-N-{2-fluoro-4-methyl-5-[2-(1-methylpyrazol-4-yl)-6-(morpholin-4-yl)pyridin-4-yl]phenyl}-3-(1,1,2,2,2-pentafluoroethyl)pyrrolidine-1-carboxamide (absolute chiral configuration was not determined) |
| 82 | 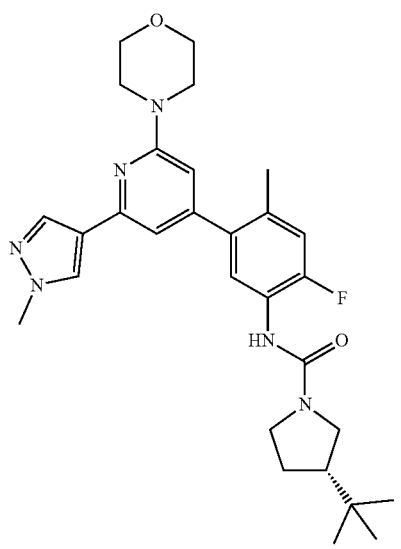 [SMILES: Cc1cc(F)c(NC(=O)N2CC[C@@H](C(C)(C)C)C2)cc1-c1cc(-c2cnn(C)c2)nc(N2CCOCC2)c1] | (3S)-3-tert-butyl-N-{2-fluoro-4-methyl-5-[2-(1-methylpyrazol-4-yl)-6-(morpholin-4-yl)pyridin-4-yl]phenyl}pyrrolidine-1-carboxamide (absolute chiral configuration was not determined) |

TABLE 1-continued

| Synthetic Chemistry Example | Compound Structure | Compound Name |
|---|---|---|
| 83 | 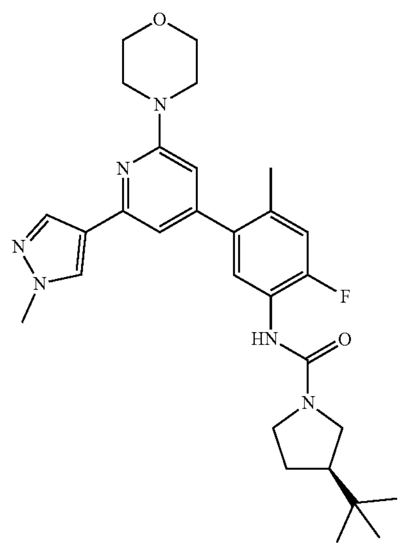 [SMILES: Cc1cc(F)c(NC(=O)N2CC[C@H](C(C)(C)C)C2)cc1-c1cc(-c2cnn(C)c2)nc(N2CCOCC2)c1] | (3R)-3-tertyl-N-{2-fluoro-4-methyl-5-[2-(1-methylpyrazol-4-yl)-6-(morpholin-4-yl)pyridin-4-yl]phenyl}pyrrolidine-1-carboxamide (absolute chiral configuration was not determined) |
| 84 | 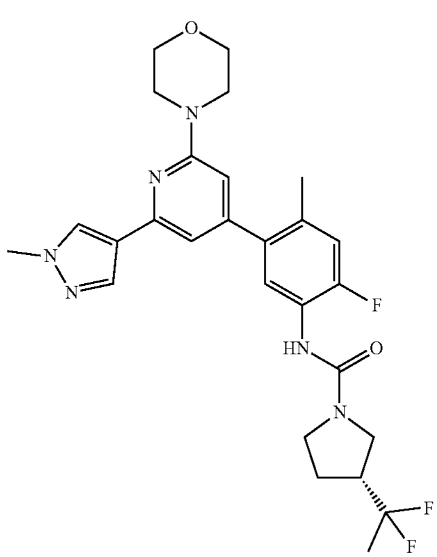 [SMILES: Cc1cc(F)c(NC(=O)N2CC[C@@H](C(C)(F)F)C2)cc1-c1cc(-c2cnn(C)c2)nc(N2CCOCC2)c1] | (3R)-3-(1,1-difluoroethyl)-N-{2-fluoro-4-methyl-5-[2-(1-methylpyrazol-4-yl)-6-(morpholin-4-yl)pyridin-4-yl]phenyl}pyrrolidine-1-carboxamide (absolute chiral configuration was not determined) |

TABLE 1-continued

| Synthetic Chemistry Example | Compound Structure | Compound Name |
|---|---|---|
| 85 | 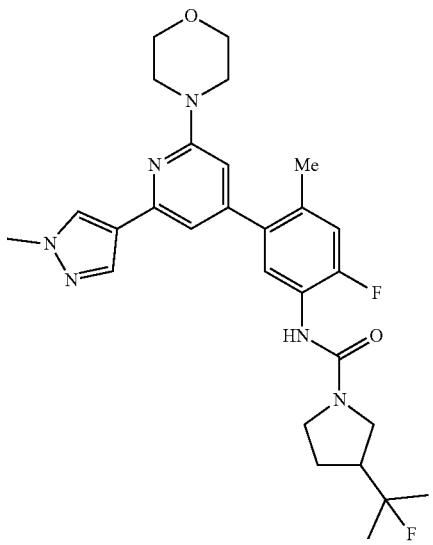 [SMILES: Cc1cc(F)c(NC(=O)N2CCC(C(C)(C)F)C2)cc1-c1cc(-c2cnn(C)c2)nc(N2CCOCC2)c1] | N-{2-fluoro-4-methyl-5-[2-(1-methylpyrazol-4-yl)-6-(morpholin-4-yl)pyridin-4-yl]phenyl}-3-(2-fluoropropan-2-yl)pyrrolidine-1-carboxamide |

Preparation of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference useful for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Pharmaceutical Compositions

In certain embodiments, the heteroaromatic RAF kinase inhibitory compound described herein is administered as a pure chemical. In other embodiments, the heteroaromatic RAF kinase inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, Pa. (2005)).

Provided herein is a pharmaceutical composition comprising at least one heteroaromatic RAF kinase inhibitory compound as described herein, or a stereoisomer, pharmaceutically acceptable salt, hydrate, or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject or the patient) of the composition.

One embodiment provides a pharmaceutical composition comprising a pharmaceutically acceptable excipient and a compound of Formula (I) or (II), or a pharmaceutically acceptable salt or solvate thereof.

One embodiment provides a method of preparing a pharmaceutical composition comprising mixing a compound of Formula (I) or (II), or a pharmaceutically acceptable salt or solvate thereof, and a pharmaceutically acceptable carrier.

In certain embodiments, the heteroaromatic RAF kinase inhibitory compound as described by Formula (I) or (II), or a pharmaceutically acceptable salt or solvate thereof, is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., Remington: The Science and Practice of Pharmacy (Gennaro, 21$^{st}$ Ed. Mack Pub. Co., Easton, Pa. (2005)).

In some embodiments, the heteroaromatic RAF kinase inhibitory compound as described by Formula (I) or (II), or pharmaceutically acceptable salt or solvate thereof, is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising at least one heteroaromatic RAF kinase inhibitory compound as described herein differs depending upon the subject or patient's (e.g., human) condition. In some embodiments, such factors include general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Methods of Treatment

One embodiment provides a compound of Formula (I) or (II), or a pharmaceutically acceptable salt or solvate thereof, for use in a method of treatment of the human or animal body.

One embodiment provides a compound of Formula (I) or (II), or a pharmaceutically acceptable salt or solvate thereof, for use in a method of treatment of cancer or neoplastic disease.

One embodiment provides a use of a compound of Formula (I) or (II), or a pharmaceutically acceptable salt or solvate thereof, in the manufacture of a medicament for the treatment of cancer or neoplastic disease.

In some embodiments, described herein is a method of treating cancer in a patient in need thereof comprising administering to the patient a compound of Formula (I) or (II), or a pharmaceutically acceptable salt or solvate thereof. In some embodiments, described herein is a method of treating cancer in a patient in need thereof comprising administering to the patient a pharmaceutical composition comprising a compound of Formula (I) or (II), or a pharmaceutically acceptable salt or solvate thereof, and a pharmaceutically acceptable excipient.

Provided herein is the method wherein the pharmaceutical composition is administered orally. Provided herein is the method wherein the pharmaceutical composition is administered by injection.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

In some embodiments, the heteroaromatic RAF kinase inhibitory compounds disclosed herein are synthesized according to the following examples. As used below, and throughout the description of the invention, the following abbreviations, unless otherwise indicated, shall be understood to have the following meanings:

| | |
|---|---|
| ° C. | degrees Celsius |
| $\delta_H$ | chemical shift in parts per million downfield from tetramethylsilane |
| DCM | dichloromethane ($CH_2Cl_2$) |
| DMF | dimethylformamide |

| | |
|---|---|
| DMSO | dimethylsulfoxide |
| EA | ethyl acetate |
| ESI | electrospray ionization |
| Et | ethyl |
| g | gram(s) |
| h | hour(s) |
| HPLC | high performance liquid chromatography |
| Hz | hertz |
| J | coupling constant (in NMR spectrometry) |
| LCMS | liquid chromatography mass spectrometry |
| μ | micro |
| m | multiplet (spectral); meter(s); milli |
| M | molar |
| M+ | parent molecular ion |
| Me | methyl |
| MHz | megahertz |
| min | minute(s) |
| mol | mole(s); molecular (as in mol wt) |
| mL | milliliter |
| MS | mass spectrometry |
| nm | nanometer(s) |
| NMR | nuclear magnetic resonance |
| pH | potential of hydrogen; a measure of the acidity or basicity of an aqueous solution |
| PE | petroleum ether |
| RT | room temperature |
| s | singlet (spectral) |
| t | triplet (spectral) |
| T | temperature |
| TFA | trifluoroacetic acid |
| THF | tetrahydrofuran |

Example 1: (3S)—N-[4-methyl-3-[2-methyl-6-(morpholin-4-yl)pyridin-4-yl]phenyl]-3-(2,2,2-trifluoroethyl)pyrrolidine-1-carboxamide Synthetic Scheme

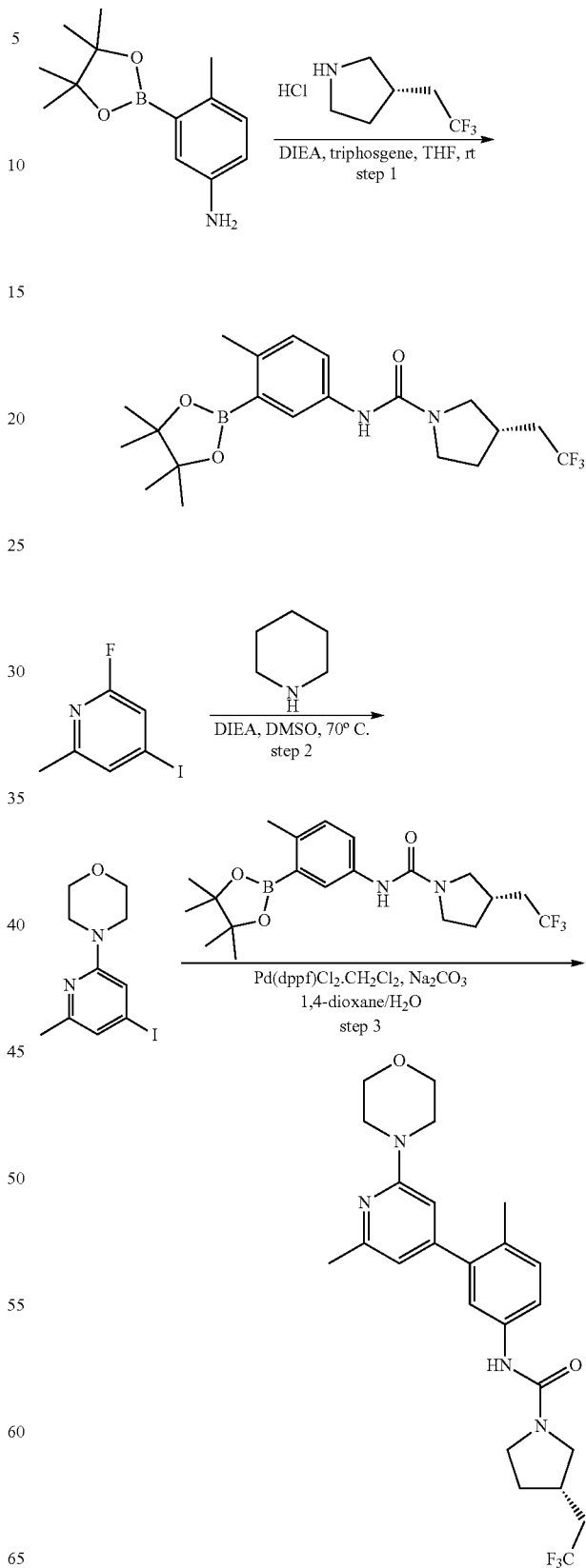

121

Preparation 1A: (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide

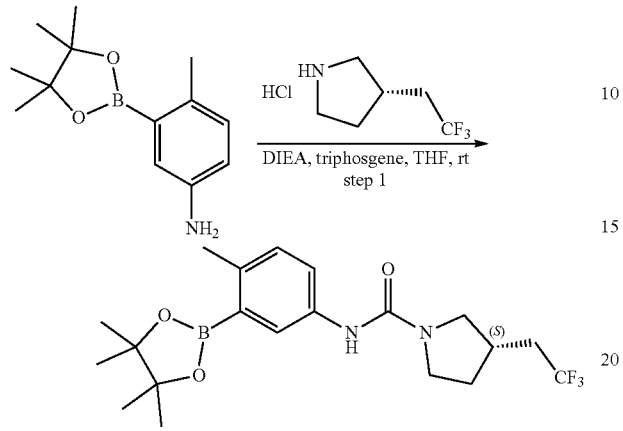

To a stirred solution of 4-methyl-3-(4,4,5,5-tetramethyl-1,3,2-dioxaborolan-2-yl)aniline (11.0 g, 47.186 mmol, 1.00 equiv) in THF (1000 mL) were added DIEA (30.5 g, 235.930 mmol, 5.00 equiv) and triphosgene (5.6 g, 18.874 mmol, 0.40 equiv) at ambient temperature under nitrogen atmosphere. The resulting mixture was stirred at ambient temperature for 30 min. To this was added a solution of (3S)-3-(2,2,2-trifluoroethyl)pyrrolidine hydrochloride (8.95 g, 47.186 mmol, 1.00 equiv) in THF (100 mL). The resulting mixture was stirred at ambient temperature for 3 h. The reaction mixture was concentrated under reduced pressure. The residue was purified by silica gel column chromatography, eluted with EtOAc in PE (5%-45%) to afford (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (16.3 g, 84%) as a white solid. MS ESI calculated for $C_{20}H_{28}BF_3N_2O_3$ $[M+H]^+$, 413.21, found 413.25. $^1$H NMR (300 MHz, chloroform-d) δ 7.75 (dd, J=8.4, 2.7 Hz, 1H), 7.44 (d, J=2.7 Hz, 1H), 7.14 (d, J=8.4 Hz, 1H), 6.14 (s, 1H), 3.86-3.74 (m, 1H), 3.69-3.56 (m, 1H), 3.43 (td, J=9.6, 6.6 Hz, 1H), 3.11 (t, J=9.6 Hz, 1H), 2.58 (dd, J=16.5, 8.4 Hz, 1H), 2.50 (s, 3H), 2.37-2.18 (m, 3H), 1.82-1.75 (m, 1H), 1.36 (s, 12H). $^{19}$F NMR (282 MHz, chloroform-d) δ -64.95.

Preparation 1B: (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide

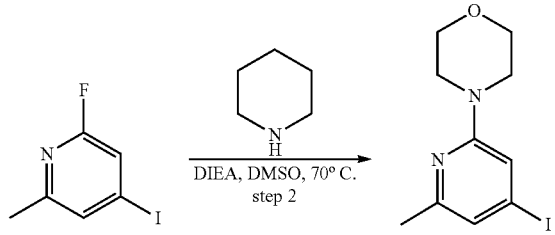

122

To a mixture of 2-fluoro-4-iodo-6-methylpyridine (1.00 g, 4.219 mmol) in DMSO (10 mL) were added morpholine (0.37 g, 4.219 mmol) and DIEA (0.6 g, 4.641 mmol). The resulting mixture was stirred for 16 h at 70° C. The resulting mixture was diluted with water (100 mL) and extracted with EtOAc (3×50 mL). The combined organic layers were washed with brine (100 mL), dried over anhydrous $Na_2SO_4$. After filtration, the filtrate was concentrated under reduced pressure. The residue was purified by silica gel column chromatography, eluted with 25% EtOAc in PE to afford 4-(4-iodo-6-methylpyridin-2-yl)morpholine (1.01 g, 79%) as an off-white solid. MS ESI calculated for $C_{10}H_{13}IN_2O$ $[M+H]^+$, 305.01, found 304.90. $^1$H NMR (400 MHz, chloroform-d) δ 6.93 (s, 1H), 6.82 (s, 1H), 3.83-3.81 (m, 4H), 3.52-3.49 (m, 4H), 2.36 (s, 3H).

Example 1: (3S)—N-[4-methyl-3-[2-methyl-6-(morpholin-4-yl)pyridin-4-yl]phenyl]-3-(2,2,2-trifluoroethyl)pyrrolidine-1-carboxamide

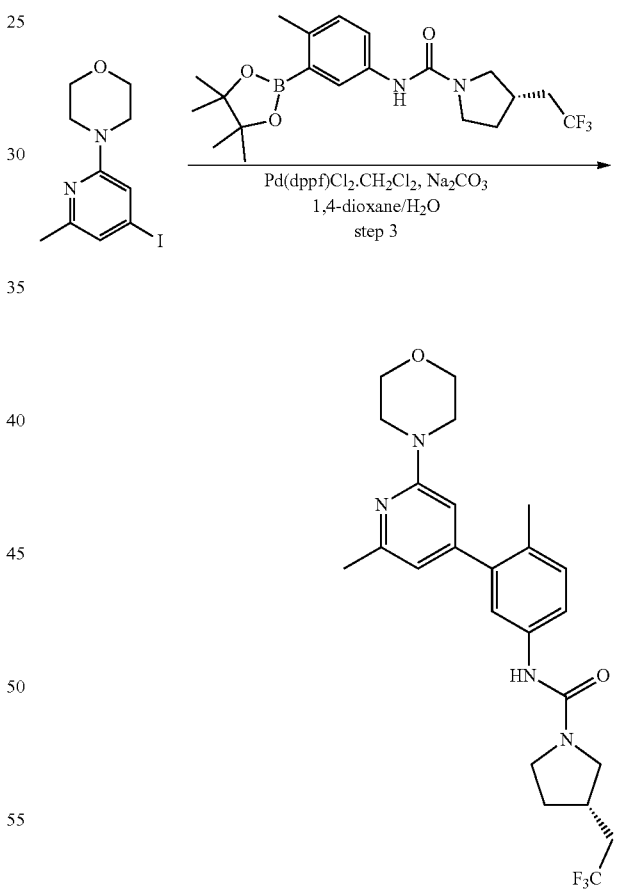

To a solution of 4-(4-iodo-6-methylpyridin-2-yl)morpholine (141 mg, 0.463 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (191 mg, 0.463 mmol) in 1,4-dioxane (4 mL) and $H_2O$ (1 mL) were added $Na_2CO_3$ (147 mg, 1.388 mmol) and Pd(dppf)$Cl_2$·$CH_2Cl_2$ (38 mg, 0.046 mmol). The resulting mixture was stirred for 2 h at 80° C. under nitrogen atmosphere and then concentrated under reduced pressure. The residue was purified silica gel column chromatography, eluted with EtOAc/EtOH (3/1) in PE (0-17%) to afford (3S)—N-[4-methyl-3-[2-methyl-6-(morpholin-4-yl)pyridin-4-yl]phenyl]-3-(2,2,2-trifluoroethyl)pyrrolidine-1-carboxamide (158 mg, 73%) as an off-white solid. MS ESI calculated for $C_{24}H_{29}F_3N_4O_2$ [M+H]$^+$, 463.22 found 463.25. $^1$H NMR (300 MHz, DMSO-d$_6$) δ 8.16 (s, 1H), 7.47 (m, 1H), 7.38 (m, 1H), 7.14 (m, 1H), 6.52 (s, 2H), 3.73-3.65 (m, 5H), 3.56-3.43 (m, 6H), 3.32-3.25 (m, 2H), 3.03 (t, J=9.4 Hz, 1H), 2.44 (s, 1H), 2.37 (s, 3H), 2.18-2.00 (m, 4H), 1.72-1.60 (m, 1H). $^{19}$F NMR (282 MHz, DMSO-d$_6$) δ −63.35 (3F).

Example 2: 4-[2-methyl-5-[(3S)-3-(2,2,2-trifluoroethyl)pyrrolidine-1-carbonylamino]phenyl]-6-(morpholin-4-yl)pyridine-2-carboxamide Synthetic Scheme

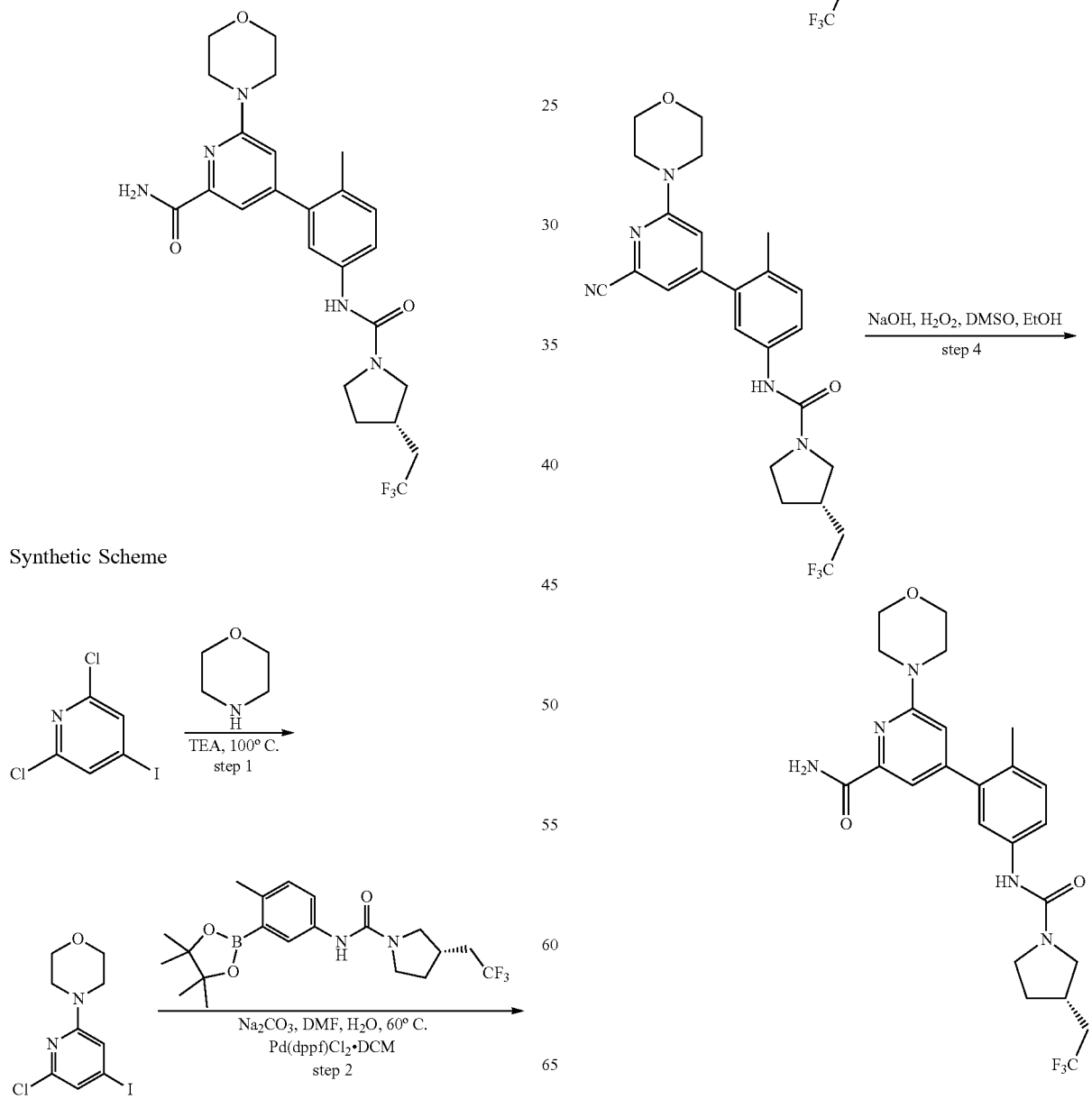

Preparation 2A: 4-(6-chloro-4-iodopyridin-2-yl)morpholine

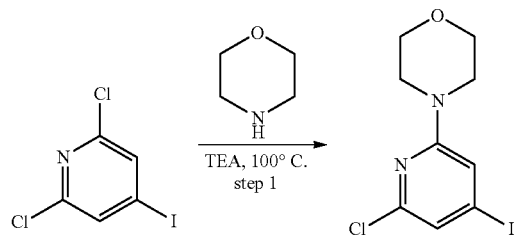 [SMILES: Clc1cc(I)cc(Cl)n1 ; C1COCCN1 ; Clc1cc(I)cc(N2CCOCC2)n1]

A mixture of 2,6-dichloro-4-iodopyridine (8.50 g, 31.035 mmol), TEA (3.14 g, 31.035 mmol) and morpholine (2.70 g, 30.991 mmol) was stirred for 2 h at 100° C. under nitrogen atmosphere. The resulting mixture was diluted with EtOAc (200 mL) and washed with sat. NaHCO$_3$ (3×100 mL). The combined organic layers were concentrated under reduced pressure. The residue was purified by silica gel column chromatography, eluted with hexane/EtOAc (5/1) to afford 4-(6-chloro-4-iodopyridin-2-yl)morpholine (4.28 g, 42%) as a white solid. MS ESI calculated for C$_9$H$_{10}$ClIN$_2$O [M+H]$^+$, 324.95, found 324.95. $^1$H NMR (400 MHz, DMSO-d$_6$) δ 7.19-7.18 (m, 1H), 7.09-7.08 (m, 1H), 3.67-3.65 (m, 4H), 3.47-3.45 (m, 4H).

Preparation 2B: (3S)—N-[3-[2-chloro-6-(morpholin-4-yl)pyridin-4-yl]-4-methylphenyl]-3-(2,2,2-trifluoroethyl)pyrrolidine-1-carboxamide To a stirred mixture of 4-(6-chloro-4-iodopyridin-2-yl)morpholine (200.00 mg, 0.616 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (254 mg, 0.616 mmol), Na$_2$CO$_3$ (196 mg, 1.849 mmol) in DMF (6.00 mL) and H$_2$O (1.50 mL) was added Pd(dppf)Cl$_2$·CH$_2$Cl$_2$ (50 mg, 0.062 mmol) under nitrogen atmosphere. The resulting mixture was stirred for 2 h at 60 degrees C. under nitrogen atmosphere. The resulting mixture was diluted with H$_2$O (80 mL). The resulting mixture was extracted with EA (3×80 mL). The combined organic layers were washed with brine (2×50 mL), dried over anhydrous Na$_2$SO$_4$. After filtration, the filtrate was concentrated under reduced pressure. The residue was purified by silica gel column chromatography, eluted with hexane/EtOAc/EtOH (4/3/1) to afford (3S)—N-[3-[2-chloro-6-(morpholin-4-yl)pyridin-4-yl]-4-methylphenyl]-3-(2,2,2-trifluoroethyl)pyrrolidine-1-carboxamide (395 mg, crude) as a light brown oil. MS ESI calculated for C$_{23}$H$_{26}$ClF$_3$N$_4$O$_2$ [M+H]$^+$, 483.17, found 483.35.

Preparation 2C: (3S)—N-[3-[2-cyano-6-(morpholin-4-yl)pyridin-4-yl]-4-methylphenyl]-3-(2,2,2-trifluoroethyl)pyrrolidine-1-carboxamide

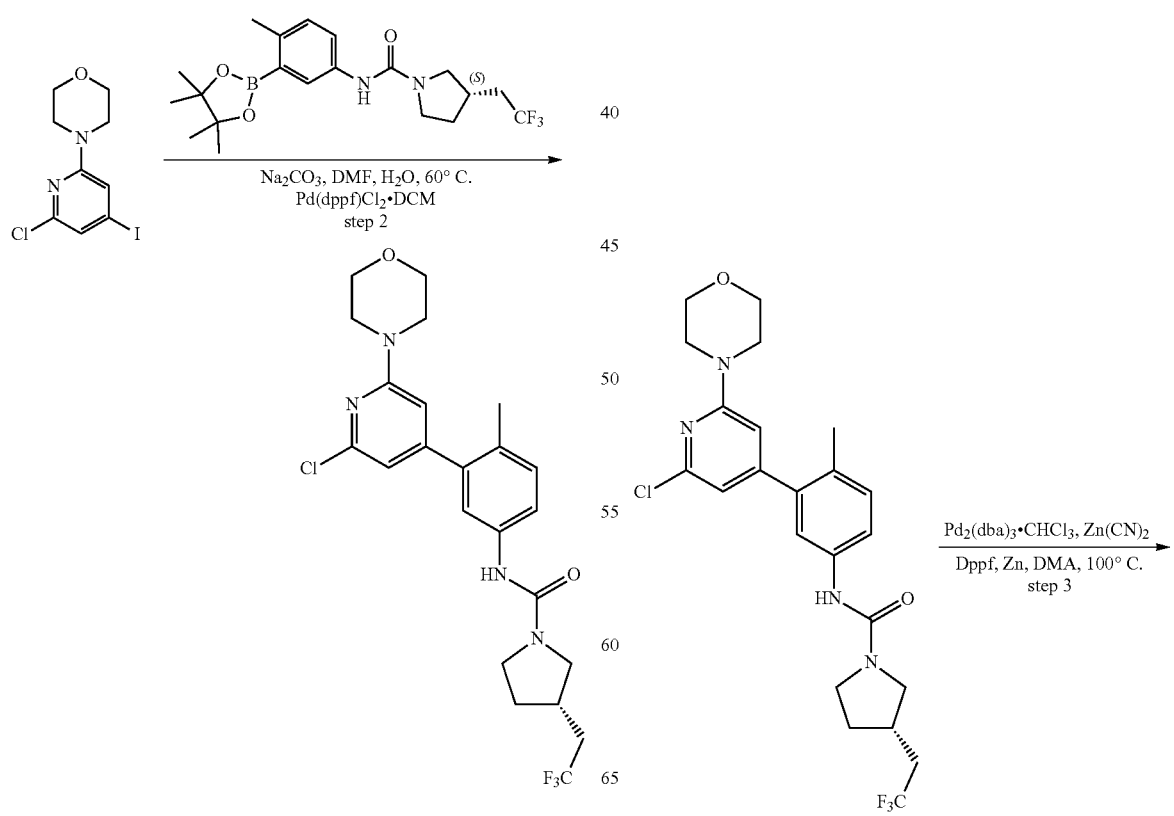

Example 2: 4-[2-methyl-5-[(3S)-3-(2,2,2-trifluoro-ethyl)pyrrolidine-1-carbonylamino]phenyl]-6-(morpholin-4-yl)pyridine-2-carboxamide

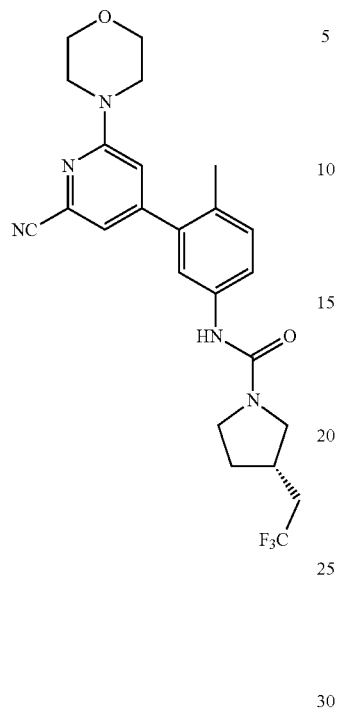

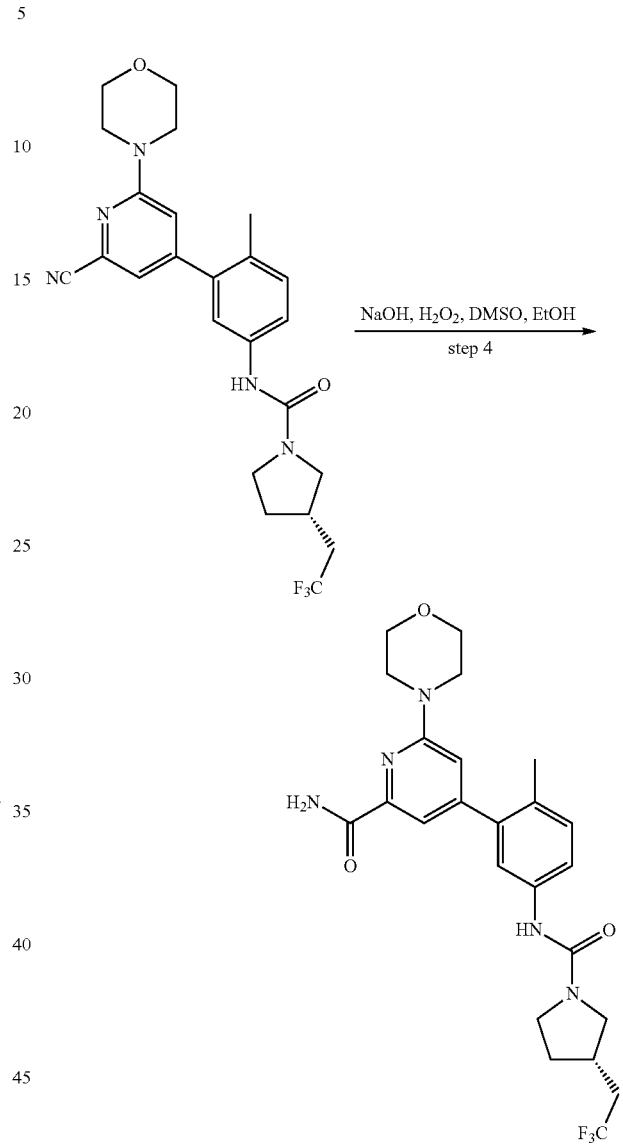

To a stirred mixture of (3S)—N-[3-[2-chloro-6-(morpholin-4-yl)pyridin-4-yl]-4-methylphenyl]-3-(2,2,2-trifluoroethyl)pyrrolidine-1-carboxamide (320 mg, 0.663 mmol) in DMA (8 mL) were added Zn (43.34 mg, 0.663 mmol), dppf (146 mg, 0.265 mmol), Zn(CN)$_2$ (47 mg, 0.398 mmol) and Pd$_2$(dba)$_3$.CHCl$_3$ (137 mg) under nitrogen atmosphere. The resulting mixture was stirred for 2 h at 100 degrees C. under nitrogen atmosphere. The resulting mixture was diluted with H$_2$O (100 mL). The resulting mixture was extracted with EtOAc (3×100 mL). The combined organic layers were washed with brine (100 mL), dried over anhydrous Na$_2$SO$_4$. After filtration, the filtrate was concentrated under reduced pressure. The residue was purified by silica gel column chromatography, eluted with hexane/EtOAc/EtOH (4/3/1). The crude product was purified by Prep-HPLC with the following conditions (Column: XBridge Prep C18 OBD Column, 19×150 mm Sum; Mobile Phase A: water (10 MMOL/L NH$_4$HCO$_3$), Mobile Phase B: CH$_3$CN; Flow rate: 20 mL/min; Gradient: 50% B to 85% B in 5.8 min; 210/254 nm to afford (3S)—N-[3-[2-cyano-6-(morpholin-4-yl)pyridin-4-yl]-4-methylphenyl]-3-(2,2,2-trifluoroethyl)pyrrolidine-1-carboxamide (78 mg, 24%) as a white solid. MS ESI calculated for C$_{24}$H$_{26}$F$_3$N$_5$O$_2$[M+H]$^+$, 474.20, found 474.20. $^1$H NMR (400 MHz, DMSO-d$_6$) δ 8.21 (s, 1H), 7.53-7.51 (m, 1H), 7.42-7.41 (m, 1H), 7.25-7.25 (m, 1H), 7.19-7.17 (m, 1H), 7.09 (s, 1H), 3.71-3.51 (m, 10H), 3.31-3.28 (m, 1H), 3.05-3.00 (m, 1H), 2.52-2.34 (m, 3H), 2.18 (s, 3H), 2.11-2.05 (m, 1H), 1.72-1.61 (m, 1H). $^{19}$F NMR (376 MHz, d$_6$-DMSO) δ −63.37-64.12 (3F).

To a solution of (3S)—N-[3-[2-cyano-6-(morpholin-4-yl)pyridin-4-yl]-4-methylphenyl]-3-(2,2,2-trifluoroethyl)pyrrolidine-1-carboxamide (125 mg, 0.264 mmol) in EtOH (2.5 mL), DMSO (0.5 mL) was added NaOH (0.6 mL, 0.5 M, 0.300 mmol), H$_2$O$_2$ (72 uL, 30%) at 0 degrees C. The reaction mixture was stirred for 30 min at 0 degrees C. and diluted with water (30 mL). The resulting mixture was extracted with EtOAc (3×20 mL). The combined organic layers were washed with brine (2×20 mL), dried over anhydrous Na$_2$SO$_4$. After filtration, the filtrate was concentrated under reduced pressure. The residue was purified by silica gel column chromatography, eluted with PE/EtOAc/EtOH (4/3/1) to afford 4-[2-methyl-5-[(3S)-3-(2,2,2-trifluoroethyl)pyrrolidine-1-carbonylamino]phenyl]-6-(morpholin-4-yl)pyridine-2-carboxamide (123 mg, 95%) as an off-white solid. MS ESI calculated for C$_{24}$H$_{28}$F$_3$N$_5$O$_3$[M+H]$^+$, 492.21, found 492.20. $^1$H NMR (400 MHz, DMSO-d$_6$) δ 8.20 (s, 1H), 8.04 (s, 1H), 7.56-7.50 (m, 2H), 7.42-7.41 (m, 1H), 7.26 (s, 1H), 7.18-7.16 (m, 1H), 6.92 (m, 1H), 3.73-3.62 (m, 5H), 3.61-3.51 (m, 5H), 3.33-3.31 (m, 1H), 3.03-3.00 (m, 1H), 2.52-2.34 (m, 3H), 2.18 (s, 3H), 2.17-2.07 (m, 1H), 1.17-1.15 (m, 1H). $^{19}$F NMR (376 MHz, DMSO-$d_6$) δ −63.37 (3F).
Example 3: N-methyl-4-[2-methyl-5-[(3S)-3-(2,2,2-trifluoroethyl)pyrrolidine-1-carbonylamino]phenyl]-6-(morpholin-4-yl)pyridine-2-carboxamide
Synthetic Scheme
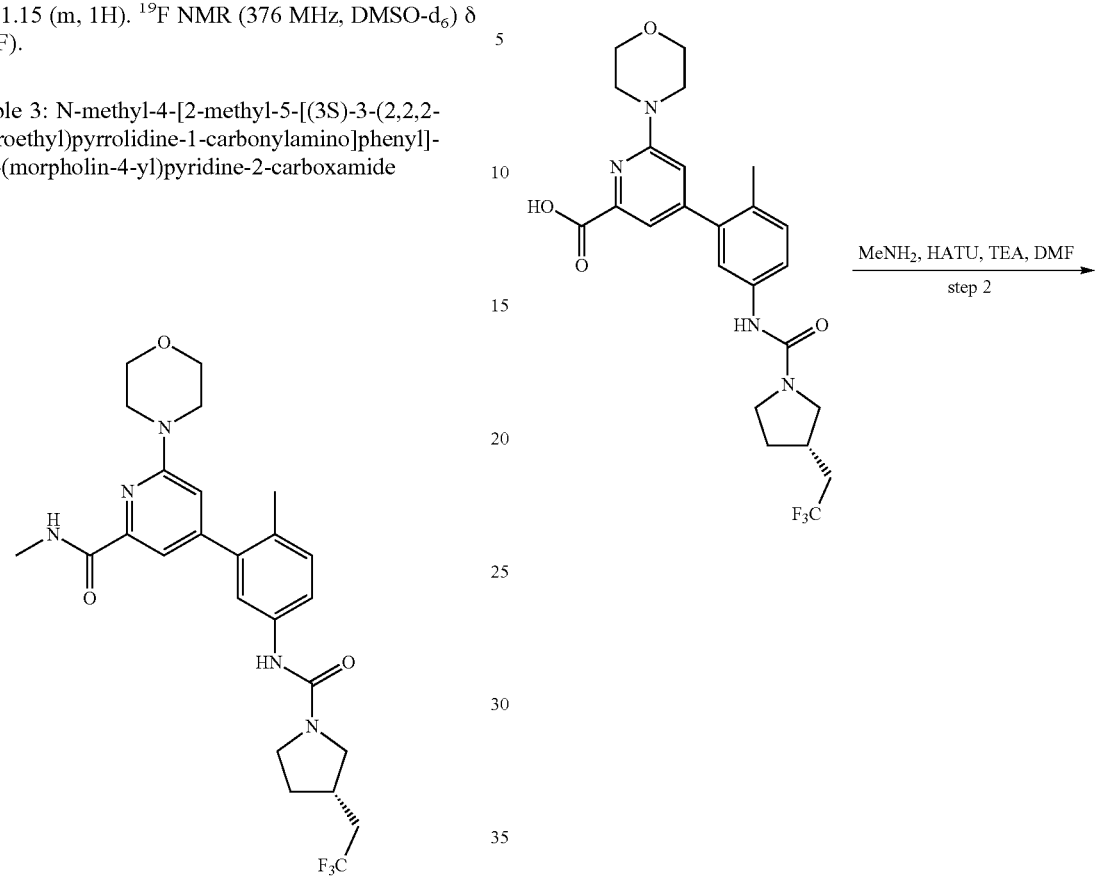
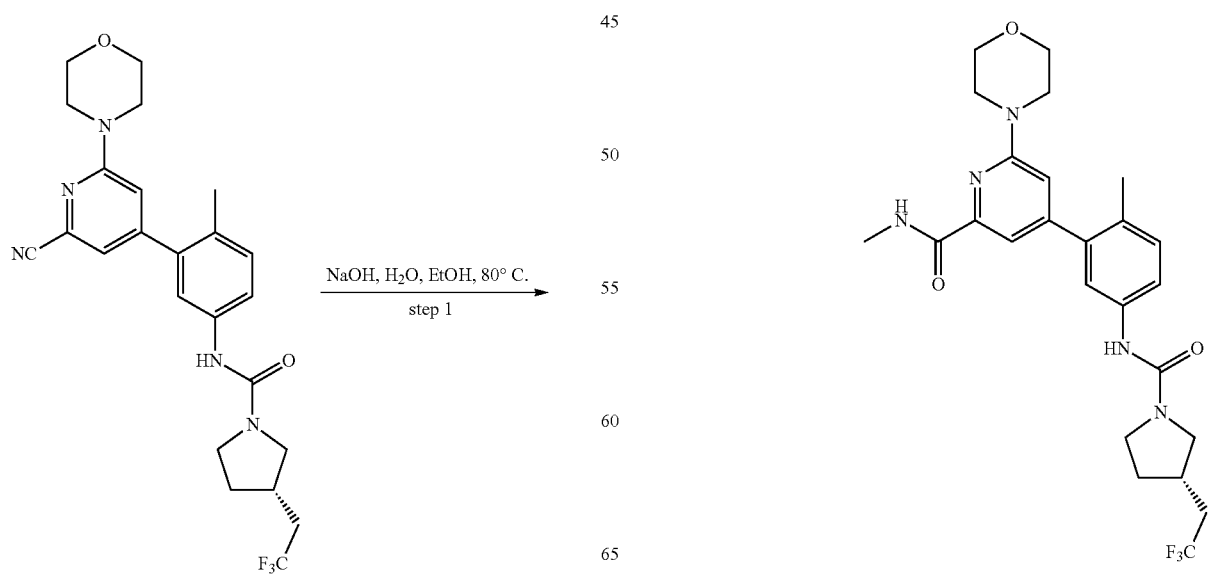

Preparation 3A: (S)-4-(2-methyl-5-(3-(2,2,2-trifluoroethyl)pyrrolidine-1-carboxamido)phenyl)-6-morpholinopicolinic Acid

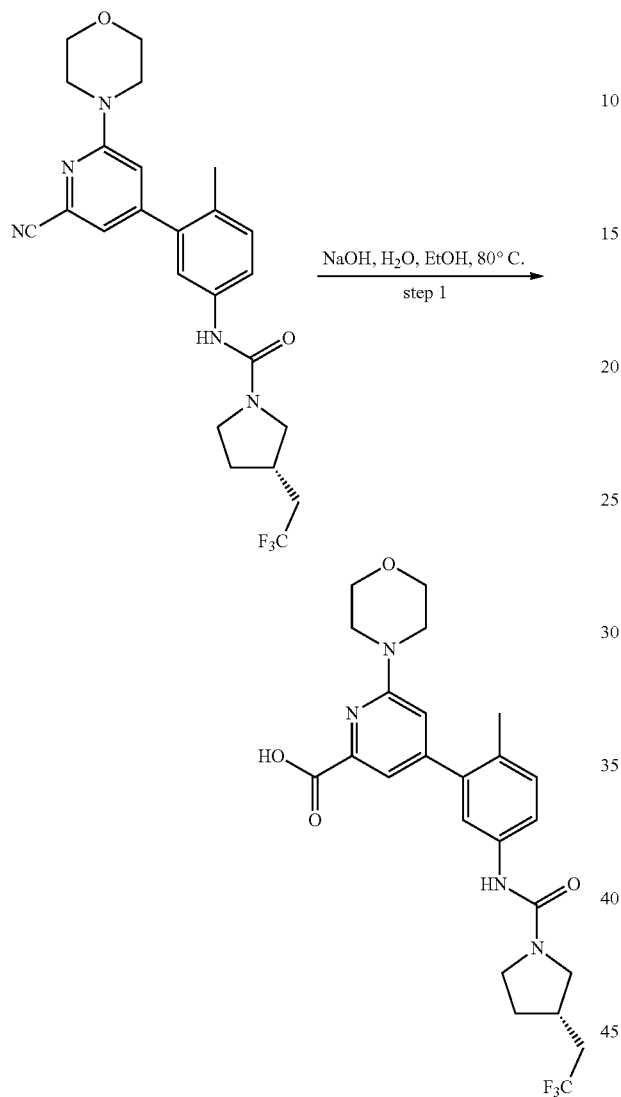

To a solution of (3S)—N-[3-[2-cyano-6-(morpholin-4-yl)pyridin-4-yl]-4-methylphenyl]-3-(2,2,2-trifluoroethyl)pyrrolidine-1-carboxamide (2 g, 4.224 mmol, 1.00 equiv) in EtOH (40 mL) was added NaOH (5%) (40 mL). The solution was stirred at 80 degrees C. for 12 h. The mixture was acidified to pH 6 with 6 M hydrochloric acid. The resulting mixture was concentrated under reduced pressure. The resulting mixture was filtered, the filter cake was washed with methanol (3×100 mL). The filtrate was concentrated under reduced pressure. The crude product was purified by Prep-HPLC with the following conditions (Column: XBridge Shield RP18 OBD Column, 30*150 mm, 5 um; Mobile Phase A: water (0.5% TFA), Mobile Phase B: $CH_3CN$; Flow rate: 60 mL/min; Gradient: 25% B to 65% B in 25 min; 220 nm to afford (S)-4-(2-methyl-5-(3-(2,2,2-trifluoroethyl)pyrrolidine-1-carboxamido)phenyl)-6-morpholinopicolinic acid (1.8 g, 87%) as a light yellow solid. MS ESI calculated for $C_{24}H_{27}F_3N_4O_4$ [M+H]$^+$, 493.20, found 493.25. $^1$H NMR (300 MHz, Methanol-$d_4$) δ 7.46 (d, J=1.1 Hz, 1H), 7.37 (d, J=6.9 Hz, 2H), 7.23 (d, J=8.9 Hz, 1H), 7.02 (d, J=1.2 Hz, 1H), 3.88-3.74 (m, 5H), 3.71-3.58 (m, 5H), 3.37-3.34 (m, 3H), 3.14 (t, J=9.8 Hz, 1H), 2.60-2.50 (m, 1H), 2.44-2.28 (m, 1H), 2.25 (s, 3H), 1.87-1.71 (m, 1H).

Example 3: N-methyl-4-[2-methyl-5-[(3S)-3-(2,2,2-trifluoroethyl)pyrrolidine-1-carbonylamino]phenyl]-6-(morpholin-4-yl)pyridine-2-carboxamide

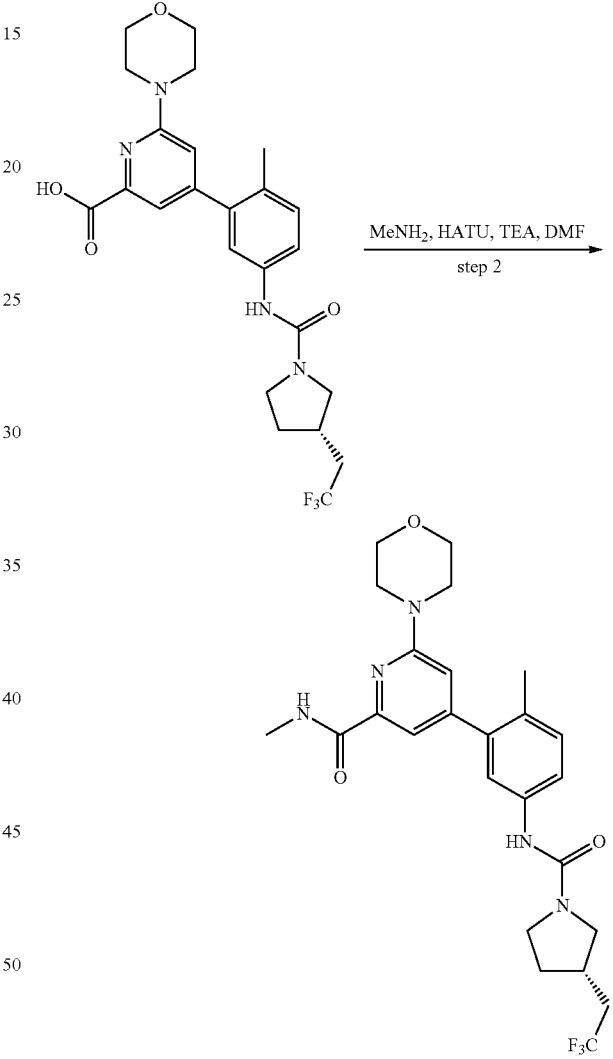

A mixture of 4-[2-methyl-5-[(3S)-3-(2,2,2-trifluoroethyl)pyrrolidine-1-carbonylamino]phenyl]-6-(morpholin-4-yl)pyridine-2-carboxylic acid (200 mg, 0.406 mmol), HATU (232 mg, 0.609 mmol) and $CH_3NH_2$ (2 M in THF) (0.4 mL, 0.812 mmol) in DMF (5 mL) was stirred for 2 h at room temperature. The mixture was purified by reverse flash chromatography with the following conditions: Column: $C^{18}$ Column 120 g; Mobile Phase A: water (10 mmol/L $NH_4HCO_3$), Mobile Phase B: $CH_3CN$; Flow rate: 60 mL/min; Gradient: 40% B to 70% B in 35 min; 254/220 nm to afford N-methyl-4-[2-methyl-5-[(3S)-3-(2,2,2-trifluoroethyl)pyrrolidine-1-carbonylamino]phenyl]-6-(morpholin- 4-yl)pyridine-2-carboxamide (145 mg, 70%) as a white solid. MS ESI calculated for $C_{25}H_{30}F_3N_5O_3[M+H]^+$, 506.23, found 506.25. $^1$H NMR (400 MHz, DMSO-$d_6$) δ 8.56 (m, 1H), 8.20 (s, 1H), 7.51 (m, 1H), 7.42 (m, 1H), 7.25 (m, 1H), 7.17 (m, 1H), 6.90 (m, 1H), 3.73 (m, 4H), 3.67 (m, 1H), 3.61 (m, 4H), 3.53 (m, 1H), 3.32-3.27 (m, 1H), 3.03 (t, J=9.4 Hz, 1H), 2.83 (d, J=4.8 Hz, 3H), 2.49-2.36 (m, 3H), 2.17 (s, 3H), 2.13-2.05 (m, 1H), 1.71-1.59 (m, 1H). $^{19}$F NMR (376 MHz, DMSO-$d_6$) δ −63.37 (3F).

Example 4: N-(2-hydroxyethyl)-4-[2-methyl-5-[(3S)-3-(2,2,2-trifluoroethyl)pyrrolidine-1-carbonylamino]phenyl]-6-(morpholin-4-yl)pyridine-2-carboxamide

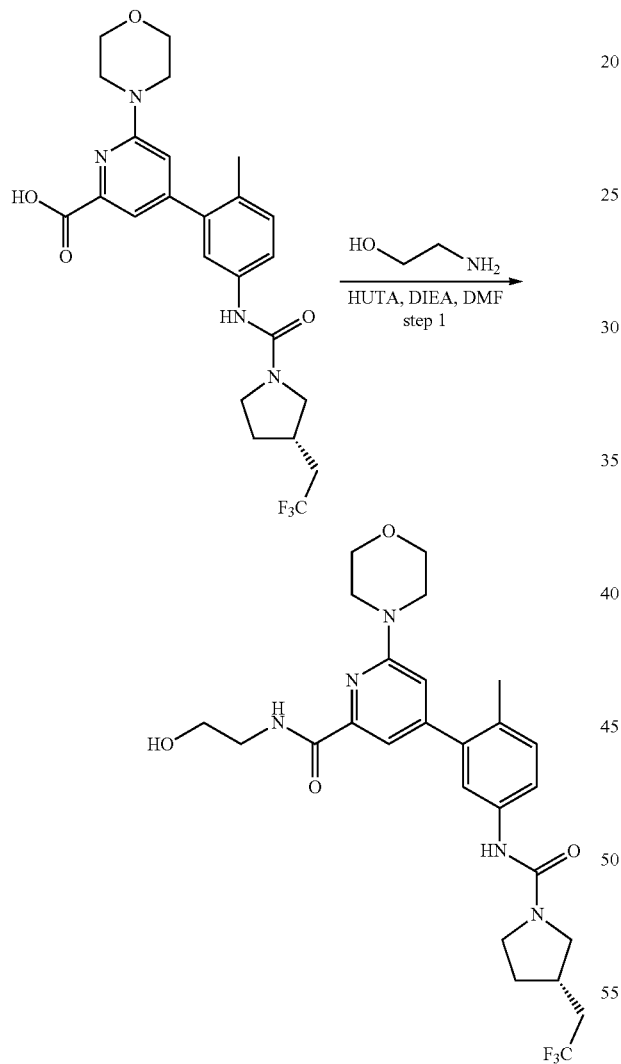

To a stirred mixture of 4-[2-methyl-5-[(3S)-3-(2,2,2-trifluoroethyl)pyrrolidine-1-carbonylamino]phenyl]-6-(morpholin-4-yl)pyridine-2-carboxylic acid (150 mg, 0.305 mmol) and ethanolamine (24 mg, 0.396 mmol) in DMF (2 mL) were added DIEA (120 mg, 0.914 mmol) and HATU (140 mg, 0.365 mmol) at room temperature. The resulting mixture was stirred for 2 h at room temperature. The residue was purified by reverse flash chromatography with the following conditions: column, C18 silica gel; mobile phase, CH$_3$CN in water, 40% to 50% gradient in 10 min; detector, UV 254 nm to afford N-(2-hydroxyethyl)-4-[2-methyl-5-[(3S)-3-(2,2,2-trifluoroethyl)pyrrolidine-1-carbonylamino] phenyl]-6-(morpholin-4-yl)pyridine-2-carboxamide (130 mg, 82%) as an off-white solid. MS ESI calculated for $C_{26}H_{32}F_3N_5O_4[M+H]^+$, 536.24, found 536.15. $^1$H NMR (400 MHz, CD$_3$OD-$d_4$) δ 7.43 (d, J=0.8 Hz, 1H), 7.38-7.35 (m, 2H), 7.38-7.21 (m, 1H), 6.94 (s, 1H), 3.86-3.74 (m, 7H), 3.66-3.56 (m, 7H), 3.48-3.41 (m, 1H), 3.16-3.11 (m, 1H), 2.57-2.53 (m, 1H), 2.43-2.34 (m, 2H), 2.26-2.21 (m, 4H), 1.80-1.75 (m, 1H). $^{19}$F NMR (400 MHz, CD$_3$OD-$d_4$) δ −63.47 (3F).

Example 5: N-[(2R)-2-hydroxypropyl]-4-[2-methyl-5-[(3S)-3-(2,2,2-trifluoroethyl)pyrrolidine-1-carbonylamino]phenyl]-6-(morpholin-4-yl)pyridine-2-carboxamide

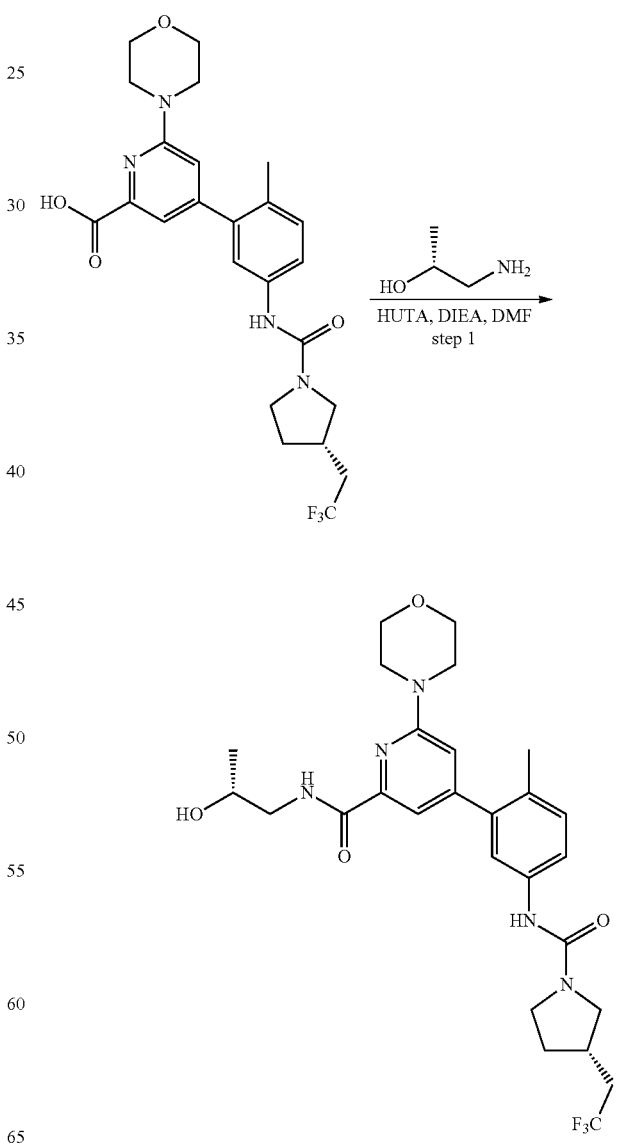

To a stirred mixture of 4-[2-methyl-5-[(3S)-3-(2,2,2-trifluoroethyl)pyrrolidine-1-carbonylamino]phenyl]-6-(morpholin-4-yl)pyridine-2-carboxylic acid (150 mg, 0.305 mmol), HATU (139 mg, 0.365 mmol) and DIEA (118 mg, 0.914 mmol) in DMF (3 mL) was added (R)-1-amino-2-propanol (30 mg, 0.396 mmol. The resulting mixture was stirred for 1 h at room temperature. The residue was purified by reverse phase flash chromatography with the following conditions: Column: Spherical C18, 20-40 um, 120 g; Mobile Phase A: water (plus 5 mM $NH_4HCO_3$); Mobile Phase B: $CH_3CN$; Flow rate: 60 mL/min; Gradient: 5%-5% B, 10 min, 35% B-60% B gradient in 30 min; Detector: 220 nm to afford N-[(2R)-2-hydroxypropyl]-4-[2-methyl-5-[(3S)-3-(2,2,2-trifluoroethyl)pyrrolidine-1-carbonylamino]phenyl]-6-(morpholin-4-yl)pyridine-2-carboxamide (133 mg, 80%) as an off-white solid. MS ESI calculated for $C_{27}H_{34}F_3N_5O_4$ [M+H]$^+$, 550.26, found 550.35. $^1$H NMR (300 MHz, DMSO-$d_6$) δ 8.24-8.10 (m, 2H), 7.53-7.51 (m, 1H), 7.45-7.41 (m, 1H), 7.30-7.26 (m, 1H), 7.20-7.16 (m, 1H), 6.96-6.93 (m, 1H), 4.89-4.85 (m, 1H), 4.11-3.92 (m, 1H), 3.83-3.63 (m, 5H), 3.62-3.37 (m, 7H), 3.03 (t, J=9.3 Hz, 1H), 2.48-2.34 (m, 4H), 2.18 (s, 3H), 2.17-2.05 (m, 1H), 1.78-1.55 (m, 1H), 1.18 (d, J=6.6 Hz, 3H). $^{19}$F NMR (282 MHz, DMSO-$d_6$) δ −63.36 (3F).

Example 6: N-[(2R)-1-hydroxyproyan-2-yl]-4-[2-methyl-5-[(3S)-3-(2,2,2-trifluoroethyl)pyrrolidine-1-carbonylamino]phenyl]-6-(morpholin-4-yl)pyridine-2-carboxamide

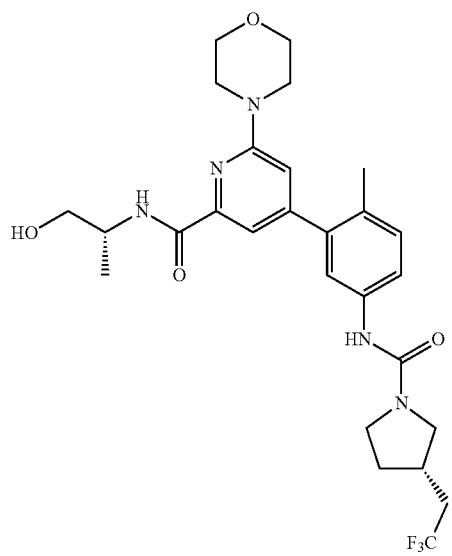

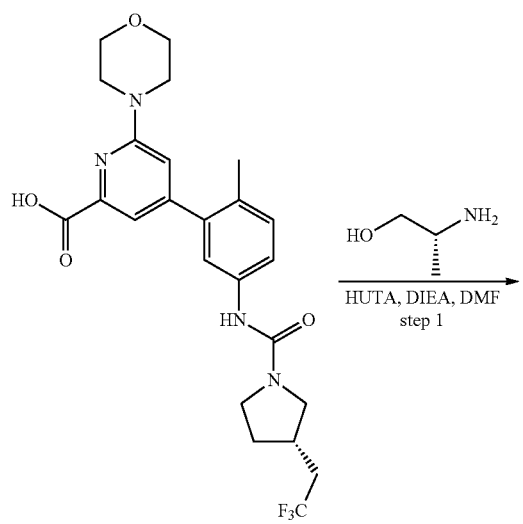

To a stirred mixture of 4-[2-methyl-5-[(3S)-3-(2,2,2-trifluoroethyl)pyrrolidine-1-carbonylamino]phenyl]-6-(morpholin-4-yl)pyridine-2-carboxylic acid (150 mg, 0.305 mmol) and HATU (139 mg, 0.365 mmol) and DIEA (118 mg, 0.914 mmol) in DMF (3 mL) was added (R)-(−)-2-amino-1-propanol (30 mg, 0.396 mmol). The resulting mixture was stirred for 1 h at room temperature. The residue was purified by reverse phase flash chromatography with the following conditions: Column: Spherical C18, 20-40 um, 120 g; Mobile Phase A: water (plus 5 mM $NH_4HCO_3$); Mobile Phase B: $CH_3CN$; Flow rate: 60 mL/min; Gradient: 5%-5% B, 10 min, 38% B-60% B gradient in 30 min; Detector: 220 nm to afford N-[(2R)-1-hydroxypropan-2-yl]-4-[2-methyl-5-[(3S)-3-(2,2,2-trifluoroethyl)pyrrolidine-1-carbonylamino]phenyl]-6-(morpholin-4-yl)pyridine-2-carboxamide (126 mg, 75%) as an off-white solid. MS ESI calculated for $C_{27}H_{34}F_3N_5O_4$[M+H]$^+$, 550.26, found 550.35. $^1$H NMR (300 MHz, DMSO-$d_6$) δ 8.25-8.08 (m, 2H), 7.54-7.50 (m, 1H), 7.45-7.41 (m, 1H), 7.30-7.26 (m, 1H), 7.20-7.17 (m, 1H), 6.96-6.93 (m, 1H), 4.87 (t, J=5.4 Hz, 1H), 4.13-3.92 (m, 1H), 3.83-3.63 (m, 5H), 3.62-3.39 (m, 7H), 3.03 (t, J=9.3 Hz, 1H), 2.48-2.32 (m, 4H), 2.18 (s, 4H), 1.70-1.66 (m, 1H), 1.18 (d, J=6.9 Hz, 3H). $^{19}$F NMR (282 MHz, DMSO-$d_6$) δ −63.36 (3F).

Example 7: N-[(2S)-2-hydroxypropyl]-4-[2-methyl-5-[(3S)-3-(2,2,2-trifluoroethyl)pyrrolidine-1-carbonylamino]phenyl]-6-(morpholin-4-yl)pyridine-2-carboxamide

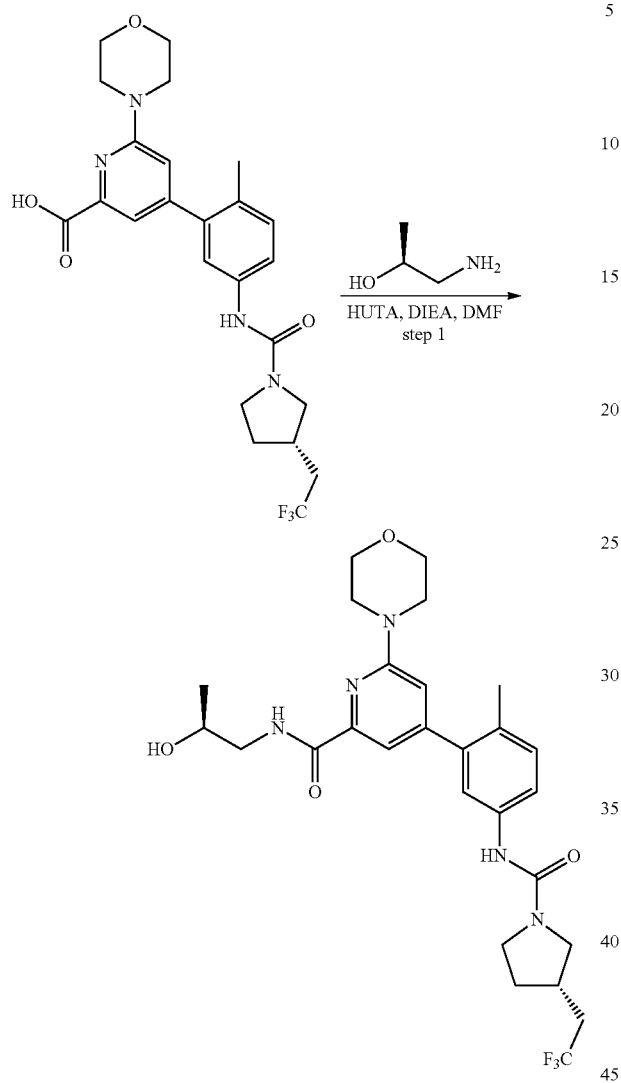

To a stirred solution of 4-[2-methyl-5-[(3S)-3-(2,2,2-trifluoroethyl)pyrrolidine-1-carbonylamino]phenyl]-6-(morpholin-4-yl)pyridine-2-carboxylic acid (150 mg, 0.305 mmol), DIEA (118 mg, 0.914 mmol) and HATU (139 mg, 0.365 mmol) in DMF (3 mL) was added (2S)-1-aminopropan-2-ol (30 mg, 0.396 mmol) at room temperature. The resulting mixture was stirred for 2 h at room temperature. The resulting mixture was concentrated under reduced pressure. The residue product was purified by reverse phase flash with the following conditions (Column: Spherical C18, 20-40 um, 120 g; Mobile Phase A: water (plus 10 mM NH$_4$CO$_3$); Mobile Phase B: CH$_3$CN; Flow rate: 60 mL/min; Gradient of B: 5%, 10 min; 5%~35%, 5 min; 35%~55%, 20 min; 75%~95%, 5 min, Detector: 220 nm) to afford N-[(2S)-2-hydroxypropyl]-4-[2-methyl-5-[(3S)-3-(2,2,2-trifluoroethyl)pyrrolidine-1-carbonylamino]phenyl]-6-(morpholin-4-yl)pyridine-2-carboxamide (117 mg, 70%) as an off-white solid. MS ESI calculated for C$_{27}$H$_{34}$F$_3$N$_5$O$_4$ [M+H]$^+$, 550.26, found 550.10. $^1$H NMR (300 MHz, DMSO-d$_6$) δ 8.49 (t, J=6.1 Hz, 1H), 8.20 (s, 1H), 7.53-7.51 (m, 1H), 7.43 (d, J=2.3 Hz, 1H), 7.28 (d, J=1.1 Hz, 1H), 7.18 (d, J=8.4 Hz, 1H), 6.94 (d, J=1.2 Hz, 1H), 4.84 (d, J=4.7 Hz, 1H), 3.88-3.47 (m, 11H), 3.42-3.25 (m, 2H), 3.22-3.12 (m, 1H), 3.05-2.99 (m, 1H), 2.50-2.40 (m, 3H), 2.18 (s, 3H), 2.17-2.02 (m, 1H), 1.69-1.63 (m, 1H), 1.08 (d, J=6.2 Hz, 3H). $^{19}$F NMR (282 MHz, DMSO-d$_6$) δ −63.33 (3F).

Example 8: N-[(2S)-1-hydroxypropan-2-yl]-4-[2-methyl-5-[(3S)-3-(2,2,2-trifluoroethyl)pyrrolidine-1-carbonylamino]phenyl]-6-(morpholin-4-yl)pyridine-2-carboxamide

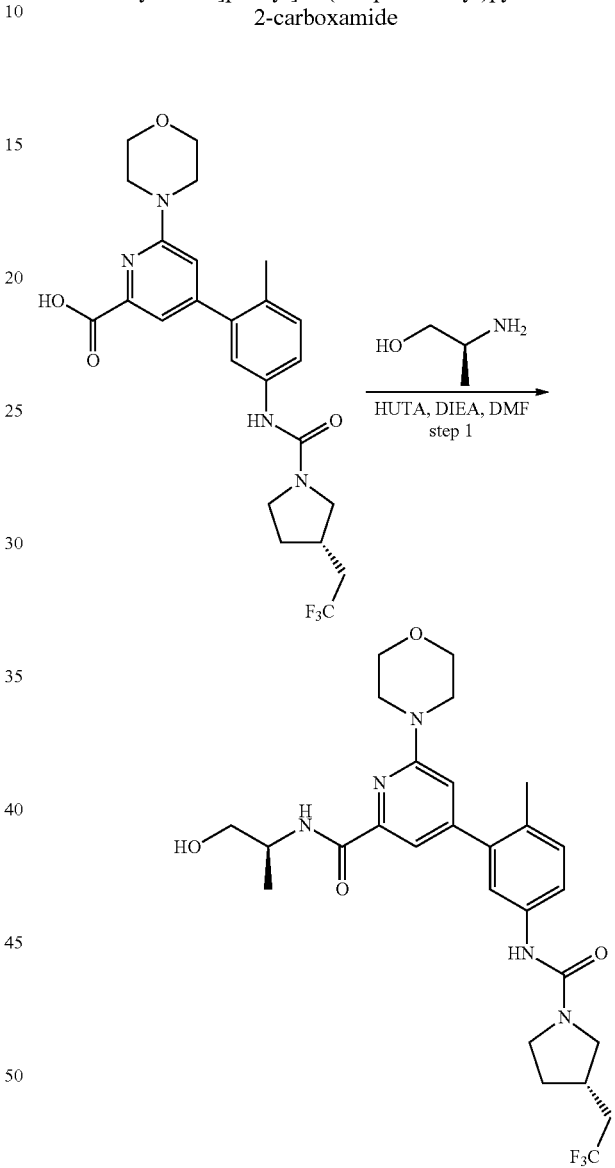

To a stirred solution of 4-[2-methyl-5-[(3S)-3-(2,2,2-trifluoroethyl)pyrrolidine-1-carbonylamino]phenyl]-6-(morpholin-4-yl)pyridine-2-carboxylic acid (150 mg, 0.305 mmol) and HATU (139 mg, 0.365 mmol) in DMF (2 mL) were added (2S)-2-aminopropan-1-ol (30 mg, 0.396 mmol) and DIEA (118 mg, 0.914 mmol) at room temperature. The resulting mixture was stirred for 2 h at room temperature. The reaction was quenched by the addition of water (0.1 mL). The residue was purified by reverse flash chromatography with the following conditions: column, C18 silica gel; mobile phase, CH$_3$CN in water (0.1% NH$_4$HCO$_3$), 35% to 60% gradient in 20 min; detector, UV 254 nm to afford N-[(2S)-1-hydroxypropan-2-yl]-4-[2-methyl-5-[(3S)-3-(2,2,2-trifluoroethyl)pyrrolidine-1-carbonylamino]phenyl]-6-(morpholin-4-yl)pyridine-2-carboxamide (114 mg, 68%) as an off-white solid. MS ESI calculated for $C_7H_{34}F_3N_5O_4$ [M+H]$^+$, 550.26, found 550.10. $^1$H NMR (400 MHz, DMSO-d$_6$) δ 8.22-8.12 (m, 2H), 7.51-7.49 (m, 1H), 7.42 (d, J=2.3 Hz, 1H), 7.28 (d, J=1.2 Hz, 1H), 7.17 (d, J=8.4 Hz, 1H), 6.94 (d, J=1.3 Hz, 1H), 4.86 (t, J=5.6 Hz, 1H), 4.05-3.96 (m, 1H), 3.74-3.65 (m, 5H), 3.62-3.42 (m, 7H), 3.49-3.40 (m, 1H), 3.03 (t, J=9.4 Hz, 1H), 2.50-2.39 (m, 3H), 2.18 (s, 3H), 2.13-2.05 (m, 1H), 1.71-1.62 (m, 1H), 1.18 (d, J=6.7 Hz, 3H). $^{19}$F NMR (376 MHz, DMSO-d$_6$) δ -63.36 (3F).

Example 9: N-(2-hydroxy-2-methylpropyl)-4-[2-methyl-5-[(3S)-3-(2,2,2-trifluoroethyl)pyrrolidine-1-carbonylamino]phenyl]-6-(morpholin-4-yl)pyridine-2-carboxamide mmol) in DMF (2 mL) were added DIEA (120 mg, 0.914 mmol) and HATU (140 mg, 0.365 mmol) at room temperature. The resulting mixture was stirred for 2 h at room temperature and purified by reverse flash chromatography with the following conditions: column, C18 silica gel; mobile phase, CH$_3$CN in water, 40% to 50% gradient in 10 min; detector, UV 254 nm to afford N-(2-hydroxy-2-methylpropyl)-4-[2-methyl-5-[(3S)-3-(2,2,2-trifluoroethyl)pyrrolidine-1-carbonylamino]phenyl]-6-(morpholin-4-yl)pyridine-2-carboxamide (116 mg, 67%) as an off-white solid. MS ESI calculated for $C_{28}H_{36}F_3N_5O_4$[M+H]$^+$, 564.27 found 564.15. $^1$H NMR (400 MHz, CD$_3$OD) δ 7.44 (s, 1H), 7.38-7.36 (m, 2H), 7.23-7.21 (m, 1H), 6.97 (s, 1H), 3.86-3.77 (m, 5H), 3.65-3.63 (m, 5H), 3.47-3.41 (m, 3H), 3.14 (t, J=9.7 Hz, 1H), 2.55-2.53 (m, 1H), 2.43-2.36 (m, 2H), 2.24-2.22 (m, 4H), 1.79-1.74 (m, 1H), 1.27 (s, 6H). $^{19}$F NMR (400 MHz, CD$_3$OD) δ -63.47 (3F).

Example 10: (3S)—N-[3-[2-(3-hydroxy-3-methylbut-1-yn-1-yl)-6-(morpholin-4-yl)pyridin-4-yl]-4-methylphenyl]-3-(2,2,2-trifluoroethyl)pyrrolidine-1-carboxamide

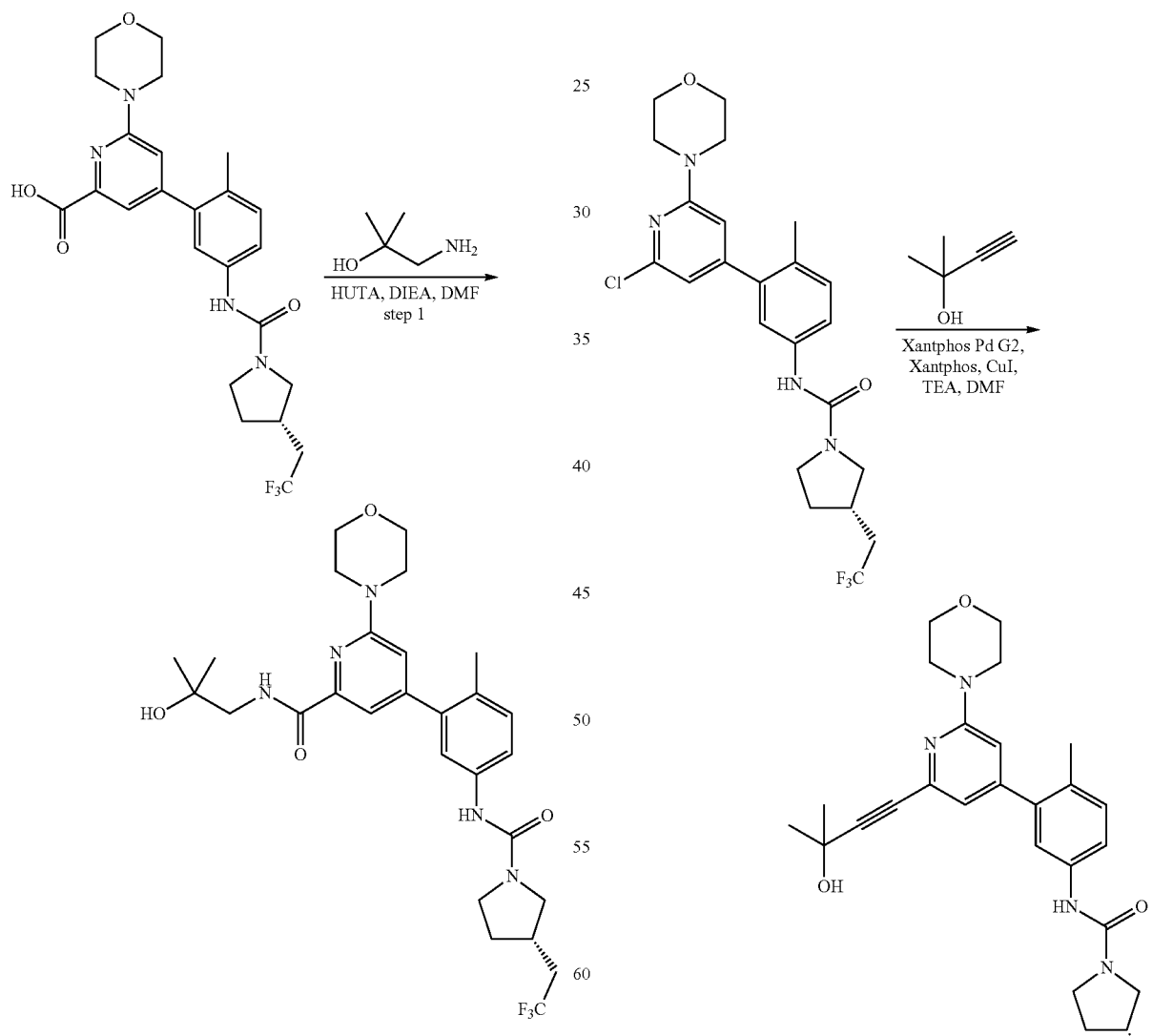

To a stirred mixture of 4-[2-methyl-5-[(3S)-3-(2,2,2-trifluoroethyl)pyrrolidine-1-carbonylamino]phenyl]-6-(morpholin-4-yl)pyridine-2-carboxylic acid (150 mg, 0.305 mmol) and 1-amino-2-methylpropan-2-ol (35 mg, 0.396

To a stirred solution of (3S)—N-[3-[2-chloro-6-(morpholin-4-yl)pyridin-4-yl]-4-methylphenyl]-3-(2,2,2-trifluoroethyl)pyrrolidine-1-carboxamide (300 mg, 0.621 mmol) and 2-methyl-3-butyn-2-ol (156 mg, 1.864 mmol) in DMF (3 mL) were added XantPhos (36 mg, 0.062 mmol), 2nd Generation XantPhos precatalyst (55 mg, 0.062 mmol), TEA (0.26 mL, 2.560 mmol) and CuI (59 mg, 0.311 mmol) under nitrogen atmosphere. The resulting mixture was stirred for 16 h at 90 degrees C. under nitrogen atmosphere. The mixture was allowed to cool down to room temperature. The reaction was quenched by the addition of water (30 mL). The resulting mixture was extracted with EtOAc (3×20 mL). The combined organic layers were washed with brine (20 mL), dried over anhydrous $Na_2SO_4$. After filtration, the filtrate was concentrated under reduced pressure. The residue was purified by silica gel column chromatography, eluted with PE/EtOAc/EtOH (4/3/1) to afford (3S)—N-[3-[2-(3-hydroxy-3-methylbut-1-yn-1-yl)-6-(morpholin-4-yl)pyridin-4-yl]-4-methylphenyl]-3-(2,2,2-trifluoroethyl)pyrrolidine-1-carboxamide (247 mg, 75%) as a light yellow solid. MS ESI calculated for $C_{28}H_{33}F_3N_4O_3[M+H]^+$, 531.25, found 531.15. $^1$H NMR (400 MHz, DMSO-$d_6$) δ 8.17 (s, 1H), 7.52-7.46 (m, 1H), 7.40 (d, J=2.4 Hz, 1H), 7.15 (d, J=8.4 Hz, 1H), 6.73 (d, J=1.2 Hz, 1H), 6.67 (d, J=1.1 Hz, 1H), 5.54 (s, 1H), 3.73-3.62 (m, 5H), 3.58-3.44 (m, 5H), 3.33-3.25 (m, 1H), 3.07-2.98 (m, 1H), 2.51-2.34 (m, 3H), 2.18 (s, 3H), 2.10 (m, 1H), 1.72-1.63 (m, 1H), 1.46 (s, 6H). $^{19}$F NMR (376 MHz, DMSO-$d_6$) −63.37 (3F).

Example 11: (3S)—N-(3-[2-[(3R)-3-hydroxybut-1-yn-1-yl]-6-(morpholin-4-yl)pyridin-4-yl]-4-methylphenyl)-3-(2,2,2-trifluoroethyl)pyrrolidine-1-carboxamide

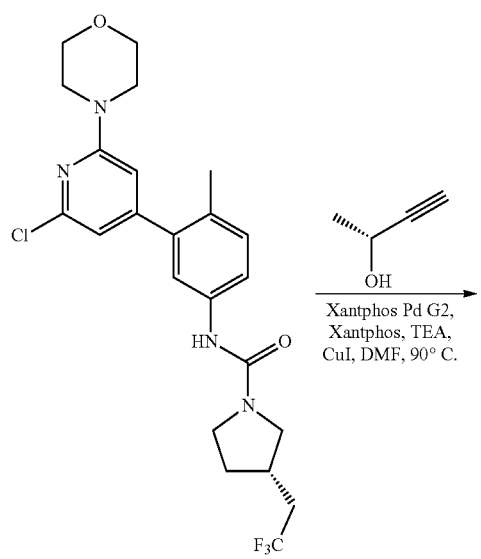

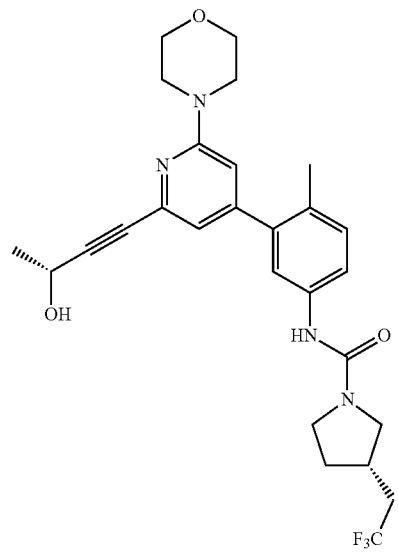

A mixture of (3S)—N-[3-[2-chloro-6-(morpholin-4-yl)pyridin-4-yl]-4-methylphenyl]-3-(2,2,2-trifluoroethyl)pyrrolidine-1-carboxamide (300 mg, 0.621 mmol), (2R)-but-3-yn-2-ol (87 mg, 1.242 mmol), 2nd Generation XantPhos precatalyst (55 mg, 0.062 mmol), XantPhos (36 mg, 0.062 mmol), TEA (189 mg, 1.864 mmol) and CuI (6 mg, 0.031 mmol) in DMF (8 mL) was stirred at 90 degrees C. for 16 h under $N_2$ atmosphere. The mixture was allowed to cool down to room temperature. The reaction was quenched by the addition of water (50 mL). The resulting mixture was extracted with EtOAc (3×30 mL). The combined organic layers were washed with brine (3×20 mL), dried over anhydrous $Na_2SO_4$. After filtration, the filtrate was concentrated under reduced pressure. The residue was purified by Prep-TLC with PE/EtOAc (1/1). The crude was purified by reverse flash chromatography with the following conditions: Column: C18 Column 120 g; Mobile Phase A: water (10 mmol/L $NH_4HCO_3$), Mobile Phase B: $CH_3CN$; Flow rate: 50 mL/min; Gradient: 30% B to 60% B in 30 min; 254/220 nm to afford (3S)—N-(3-[2-[(3R)-3-hydroxybut-1-yn-1-yl]-6-(morpholin-4-yl)pyridin-4-yl]-4-methylphenyl)-3-(2,2,2-trifluoroethyl)pyrrolidine-1-carboxamide (124 mg, 39%) as a white solid. MS ESI calculated for $C_{27}H_{31}F_3N_4O_3$ $[M+H]^+$, 517.23 found 517.20. $^1$H NMR (400 MHz, DMSO-$d_6$) δ 8.17 (s, 1H), 7.48-7.46 (m, 1H), 7.40 (d, J=2.3 Hz, 1H), 7.15 (d, J=8.4 Hz, 1H), 6.74 (d, J=1.2 Hz, 1H), 6.70 (d, J=1.1 Hz, 1H), 5.53 (d, J=5.4 Hz, 1H), 4.59-4.54 (m, 1H), 3.68-3.64 (m, 5H), 3.56-3.44 (m, 5H), 3.31 (d, J=6.6 Hz, 1H), 3.02 (t, J=9.4 Hz, 1H), 2.49-2.35 (m, 3H), 2.18 (s, 3H), 2.14-2.04 (m, 1H), 1.66-1.64 (m, 1H), 1.38 (d, J=6.6 Hz, 3H). $^{19}$F NMR (376 MHz, DMSO-$d_6$) δ −63.37 (3F).

143

Example 12: (3S)—N-(3-[2-[(3R)-3-hydroxybutyl]-6-(morpholin-4-yl)pyridin-4-yl]-4-methylphenyl)-3-(2,2,2-trifluoroethyl)pyrrolidine-1-carboxamide

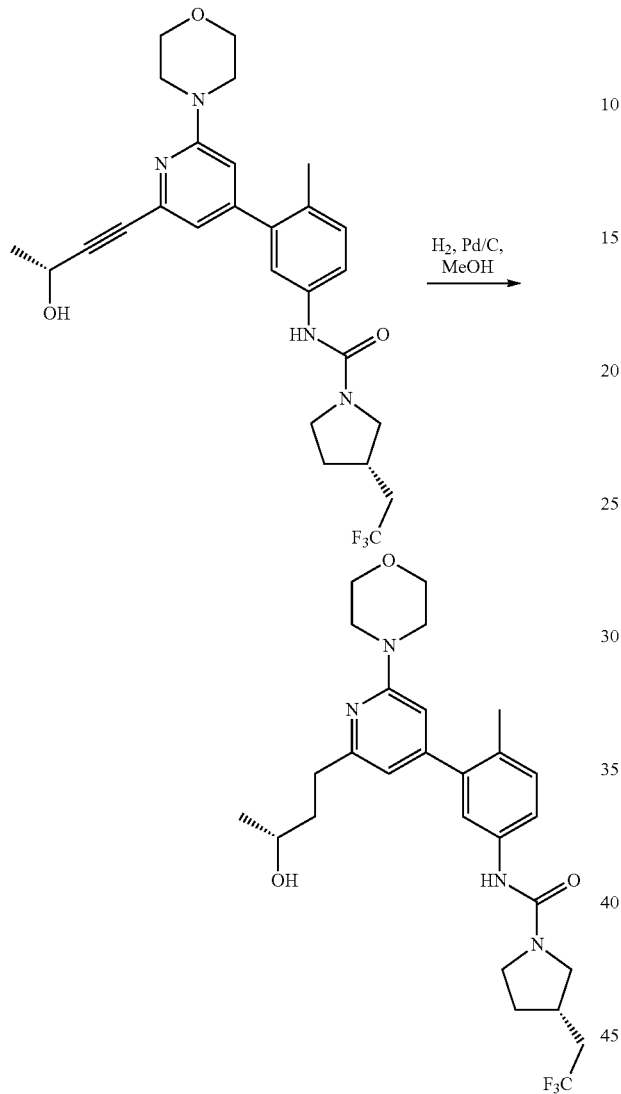

To a solution of (3S)—N-(3-[2-[(3R)-3-hydroxybut-1-yn-1-yl]-6-(morpholin-4-yl)pyridin-4-yl]-4-methylphenyl)-3-(2,2,2-trifluoroethyl)pyrrolidine-1-carboxamide (150 mg, 0.290 mmol) in MeOH (5 mL) was added Pd/C (309 mg, 2.900 mmol) under nitrogen atmosphere. The mixture was stirred at room temperature for 1 h under hydrogen atmosphere. The resulting mixture was filtered, and the filter cake was washed with MeOH (3×50 mL). The filtrate was concentrated under reduced pressure. The residue was purified by reverse flash chromatography with the following conditions: Column: C18 Column 120 g; Mobile Phase A: water (10 mmol/L $NH_4HCO_3$), Mobile Phase B: $CH_3CN$; Flow rate: 60 mL/min; Gradient: 30% B to 65% B in 30 min; 254/220 nm to afford (3S)—N-(3-[2-[(3R)-3-hydroxybutyl]-6-(morpholin-4-yl)pyridin-4-yl]-4-methylphenyl)-3-(2,2,2-trifluoroethyl)pyrrolidine-1-carboxamide (80 mg, 53%) as a white solid. MS ESI calculated for $C_7H_{35}F_3N_4O_3$ $[M+H]^+$, 521.27 found 521.20. $^1$H NMR (400 MHz, DMSO-$d_6$) δ 8.16 (s, 1H), 7.46-7.44 (m, 1H), 7.36 (d, J=2.4 Hz, 1H), 7.13 (d, J=8.4 Hz, 1H), 6.52-6.47 (m, 2H), 4.47 (d, J=4.7 Hz, 1H), 3.75-3.60 (m, 6H), 3.57-3.42 (m, 5H), 3.33-3.26 (m, 1H), 3.02 (t, J=9.4 Hz, 1H), 2.75-2.58 (m, 2H), 2.47-2.39 (m, 3H), 2.16 (s, 3H), 2.12-2.04 (m, 1H), 1.76-1.60 (m, 3H), 1.09 (d, J=6.2 Hz, 3H). $^{19}$F NMR (376 MHz, DMSO-$d_6$) δ −63.37 (3F).

Example 13: (3S)—N-(3-[2-[(1R,2S)-2-(hydroxymethyl)cyclopropyl]-6-(morpholin-4-yl)pyridin-4-yl]-4-methylphenyl)-3-(2,2,2-trifluoroethyl)pyrrolidine-1-carboxamide

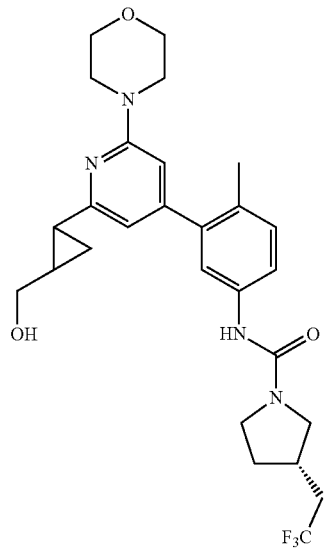 [SMILES: Cc1ccc(NC(=O)N2CC[C@@H](CC(F)(F)F)C2)cc1-c1cc(C2CC2CO)nc(N2CCOCC2)c1]

Synthetic Scheme

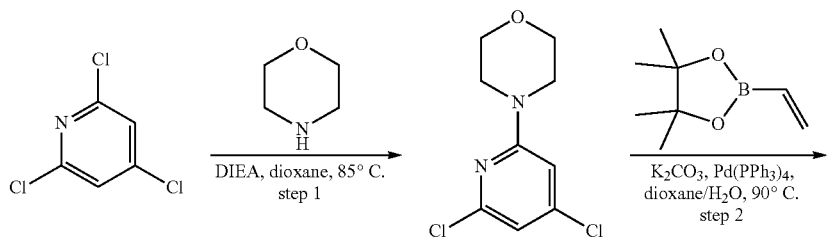

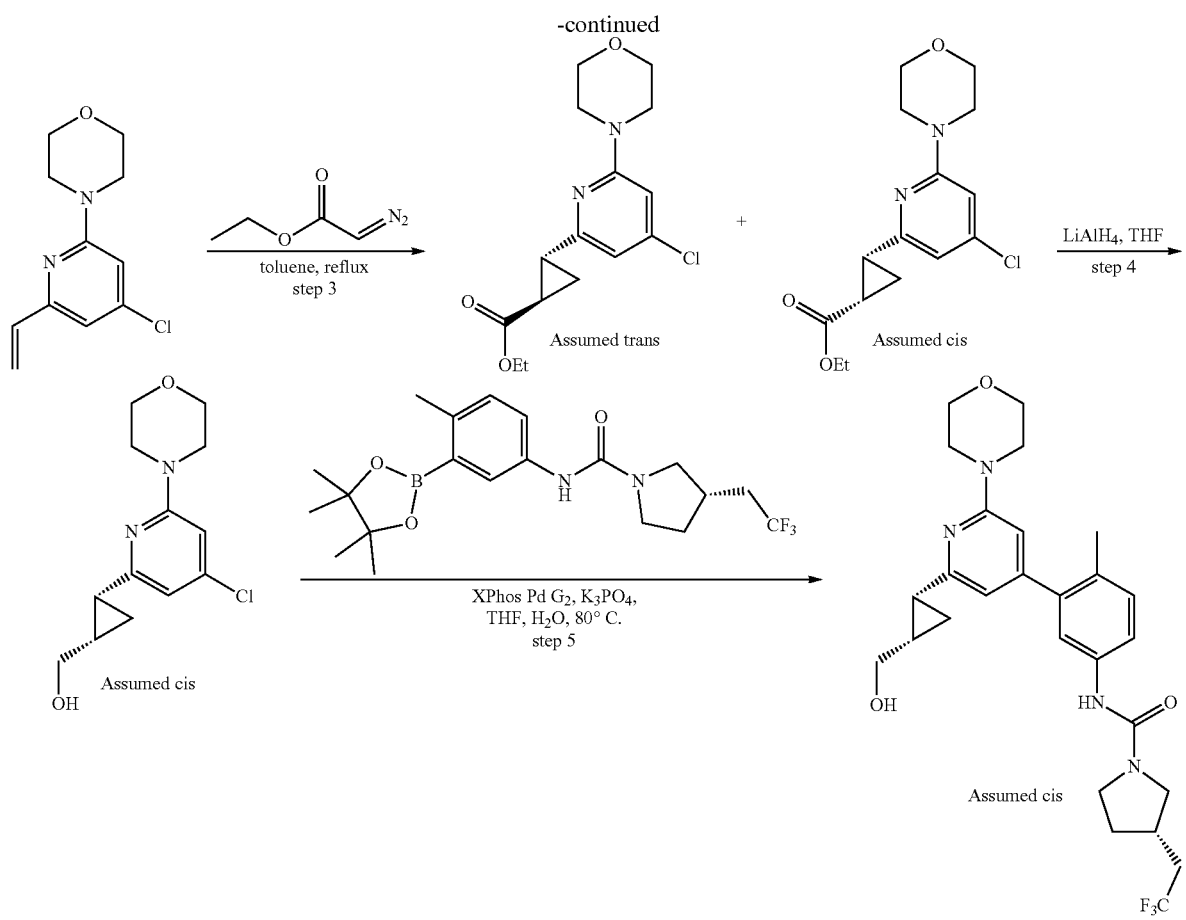

Preparation 13A:
4-(4,6-dichloropyridin-2-yl)morpholine

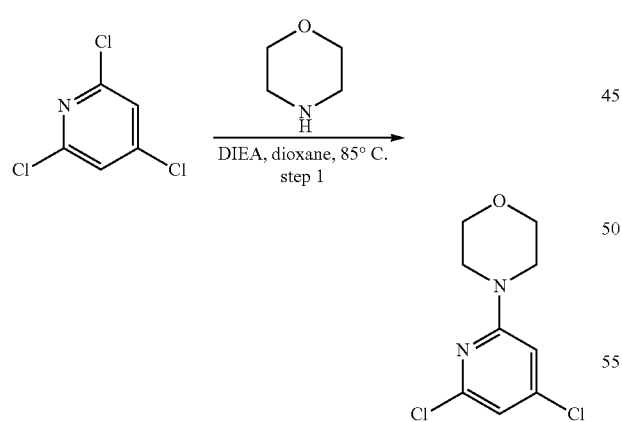

A mixture of 2,4,6-trichloropyridine (30.0 g, 164.447 mmol, 1.00 equiv), morpholine (14.3 mL, 164.449 mmol) and DIEA (28.6 mL, 221.626 mmol) in 1,4-dioxane (160 mL) was stirred for 16 h at 85 degrees C. The mixture was allowed to cool down to room temperature. The reaction was quenched with water (300 mL). The resulting mixture was extracted with EtOAc (3×200 mL). The combined organic layers were washed with brine (300 mL), dried over anhydrous Na₂SO₄. After filtration, the filtrate was concentrated under reduced pressure. The residue was purified by silica gel column chromatography, eluted with EtOAc in PE (15%) to afford 4-(4,6-dichloropyridin-2-yl)morpholine (19.5 g, 51%) as an off-white solid. MS ESI calculated for $C_9H_{10}Cl_2N_2O$ [M+H]⁺, 233.02, found 232.90. ¹H NMR (400 MHz, Chloroform-d) δ 6.67 (d, J=1.3 Hz, 1H), 6.48 (d, J=1.3 Hz, 1H), 3.83-3.76 (m, 4H), 3.56-3.49 (m, 4H).

Preparation 13B:
4-(4-chloro-6-ethenylpyridin-2-yl)morpholine

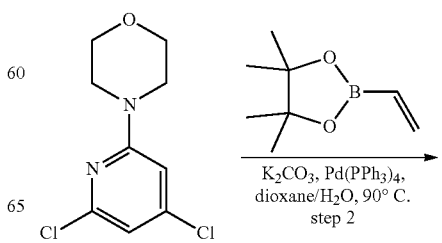

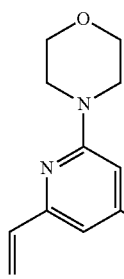

A mixture of 4-(4,6-dichloropyridin-2-yl)morpholine (3.00 g, 12.871 mmol), 2-ethenyl-4,4,5,5-tetramethyl-1,3,2-dioxaborolane (2.18 g, 14.158 mmol), Pd(PPh₃)₄ (1.49 g, 1.287 mmol) and K₂CO₃ (5.34 g, 38.612 mmol, 3 equiv) in 1,4-dioxane (32 mL) and H₂O (8 mL) was stirred for 3 h at 90° C. under nitrogen atmosphere. The mixture was quenched with water (100 mL). The resulting mixture was extracted with EtOAc (3×50 mL). The combined organic layers were washed with brine (100 mL), dried over anhydrous Na₂SO₄. After filtration, the filtrate was concentrated under reduced pressure. The residue was purified by silica gel column chromatography, eluted with EtOAc in PE (15%) to afford 4-(4-chloro-6-ethenylpyridin-2-yl)morpholine (2.65 g, 92%) as yellow oil. MS ESI calculated for $C_{11}H_{13}ClN_2O$ [M+H]⁺, 225.07, found 225.10. ¹H NMR (300 MHz, Chloroform-d) δ 6.68-6.59 (m, 2H), 6.52 (s, 1H), 6.25-6.19 (m, 1H), 5.46-5.42 (m, 1H), 3.84-3.79 (m, 4H), 3.58-3.54 (m, 4H).

Preparation 13C: ethyl (1R,2R and 1S,2S)-2-(4-chloro-6-morpholinopyridin-2-yl)cyclopropane-1-carboxylate and ethyl (1S,2R and 1R,2S)-2-(4-chloro-6-morpholinopyridin-2-yl)cyclopropane-1-carboxylate

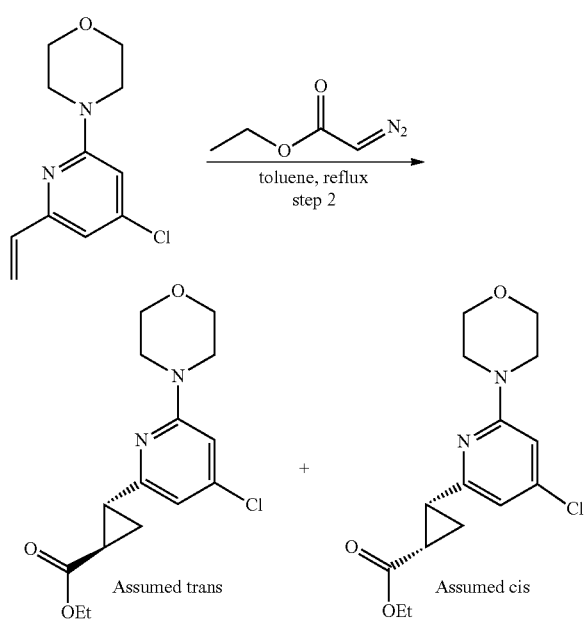

A solution of 4-(4-chloro-6-ethenylpyridin-2-yl)morpholine (1.00 g, 4.451 mmol) and ethyl diazoacetate (1.52 g, 13.352 mmol) in toluene (28 mL) was stirred for 16 h at 100° C. under nitrogen atmosphere. The resulting mixture was concentrated under vacuum. The residue was purified by silica gel column chromatography, eluted with EtOAc/PE (0-20%) to afford ethyl (1R,2R and 1S,2S)-2-(4-chloro-6-morpholinopyridin-2-yl)cyclopropane-1-carboxylate (850 mg, 61%) as an off-white solid. MS ESI calculated for $C_{15}H_{19}ClN_2O_3$[M+H]⁺, 311.11, found 311.00. ¹H NMR (400 MHz, Chloroform-d) δ 6.66-6.60 (m, 1H), 6.43-6.42 (m, 1H), 4.25-4.12 (m, 2H), 3.85-3.78 (m, 4H), 3.52-3.45 (m, 4H), 2.47-2.42 (m, 1H), 2.24-2.20 (m, 1H), 1.59-1.51 (m, 2H), 1.31-1.27 (m, 3H). Also afforded ethyl (1S,2R and 1R,2S)-2-(4-chloro-6-morpholinopyridin-2-yl)cyclopropane-1-carboxylate (370 mg, 27%) as a yellow solid. MS ESI calculated for $C_{15}H_{19}ClN_2O_3$[M+H]⁺, 311.11, found 311.00. ¹H NMR (400 MHz, Chloroform-d) δ 6.68 (s, 1H), 6.43 (s, 1H), 4.00-3.94 (m, 2H), 3.82-3.76 (m, 4H), 3.73-3.43 (m, 4H), 2.53-2.46 (m, 1H), 2.14-2.06 (m, 1H), 1.81-1.76 (m, 1H), 1.36-1.28 (m, 1H), 1.12-1.08 (m, 3H).

Preparation 13D: ((1R,2S and 1S,2R)-2-(4-chloro-6-morpholinopyridin-2-yl)cyclopropyl)methanol

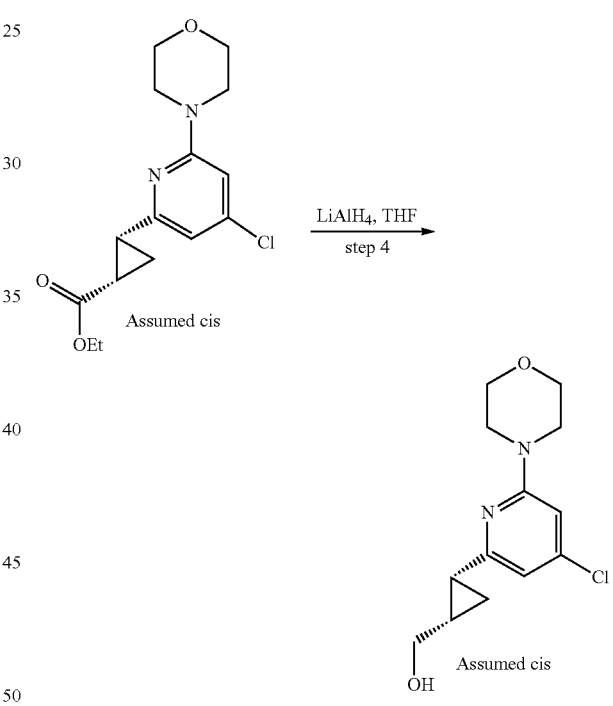

To a stirred solution of ethyl (1S,2R and 1R,2S)-2-(4-chloro-6-morpholinopyridin-2-yl)cyclopropane-1-carboxylate (350 mg, 1.126 mmol) in THF (8 mL) was added LiAlH₄ (85 mg, 2.252 mmol) in portions at 0 degrees C. The resulting mixture was stirred for 2 h at room temperature. The reaction was quenched by the addition of water (0.1 mL), NaOH (15%, 0.1 mL) and water (0.3 mL) at 0 degrees C. The resulting mixture was extracted with EtOAc (3×15 mL). The combined organic layers were washed with brine (30 mL), dried over anhydrous Na₂SO₄. After filtration, the filtrate was concentrated under reduced pressure. The residue was purified by silica gel column chromatography, eluted with EtOAc in PE (50%) to ((1R,2S and 1S,2R)-2-(4-chloro-6-morpholinopyridin-2-yl)cyclopropyl)methanol (300 mg, 99%) as an off-white solid. MS ESI calculated for $C_{13}H_{17}ClN_2O_2$[M+H]⁺, 269.10, found 269.05. ¹H NMR (400 MHz, DMSO-d$_6$) δ 6.77-6.76 (m, 1H), 6.67-6.66 (m, 1H), 4.27-4.24 (m, 1H), 3.68-3.54 (m, 2H), 3.52-3.33 (m, 8H), 2.15-2.10 (m, 1H), 1.42-1.38 (m, 1H), 1.20-1.12 (m, 1H), 1.00-0.95 (m, 1H).

Example 13: (3S)—N-(3-[2-[(1R,2S)-2-(hydroxymethyl)cyclopropyl]-6-(morpholin-4-yl)pyridin-4-yl]-4-methylphenyl)-3-(2,2,2-trifluoroethyl)pyrrolidine-1-carboxamide

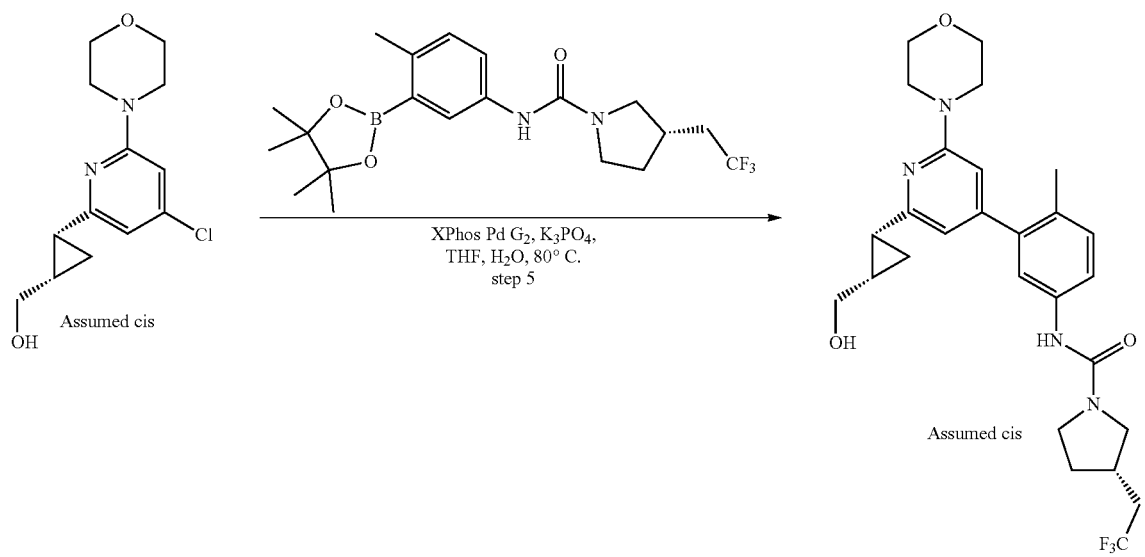 [SMILES: OC[C@H]1C[C@H]1c1cc(Cl)cc(N2CCOCC2)n1 ; Cc1ccc(NC(=O)N2CC[C@@H](CC(F)(F)F)C2)cc1B1OC(C)(C)C(C)(C)O1 ; Cc1ccc(NC(=O)N2CC[C@@H](CC(F)(F)F)C2)cc1-c1cc([C@@H]2C[C@@H]2CO)nc(N2CCOCC2)c1]

A mixture of ((1R,2S and 1S,2R)-2-(4-chloro-6-morpholinopyridin-2-yl)cyclopropyl)methanol, (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (337 mg, 0.819 mmol), 2nd Generation XPhos precatalyst (59 mg, 0.074 mmol), K$_3$PO$_4$ (316 mg, 1.488 mmol), THF (10 mL) and H$_2$O (1 mL) was stirred for 2 h at 80 degrees C. under nitrogen atmosphere. The reaction mixture was cooled to room temperature and concentrated under reduced pressure. The residue was purified by silica gel column chromatography, eluted with EA/EtOH (3/1) in PE (45%). The crude product was purified by prep-HPLC with the following conditions: Column: XBridge Prep Phenyl OBD Column, 19×150 mm, 5 um; Mobile Phase A: water (10 mmol/L NH$_4$HCO$_3$), Mobile Phase B: CH$_3$CN; Flow rate: 20 mL/min; Gradient: 40 B to 65 B in 5.3 min; 254/210 nm to afford (3S)—N-(3-[2-[(1R,2S)-2-(hydroxymethyl)cyclopropyl]-6-(morpholin-4-yl)pyridin-4-yl]-4-methylphenyl)-3-(2,2,2-trifluoroethyl)pyrrolidine-1-carboxamide (187 mg, 49%) as an off-white solid. MS ESI calculated for C$_{27}$H$_{33}$F$_3$N$_4$O$_3$ [M+H]$^+$, 519.25, found 519.15. $^1$H NMR (400 MHz, chloroform-d) δ 7.33-7.31 (m, 2H), 7.28-7.20 (m 1H), 6.71 (s, 1H), 6.44 (s, 1H), 6.15 (s, 1H), 4.01-3.97 (m, 1H), 3.85-3.80 (m, 5H), 3.68-3.62 (m, 1H), 3.51-3.42 (m, 5H), 3.35-3.33 (m, 1H), 3.16-3.11 (m, 1H), 2.60-2.56 (m, 1H), 2.31-2.23 (m, 7H), 1.79-1.74 (m, 2H), 1.14-1.04 (m, 2H). $^{19}$F NMR (376 MHz, chloroform-d) 6-64.95 (3F).

Example 14: (3S)—N-(3-[2-[(1E)-3-hydroxyprop-1-en-1-yl]-6-(morpholin-4-yl)pyridin-4-yl]-4-methylphenyl)-3-(2,2,2-trifluoroethyl)pyrrolidine-1-carboxamide

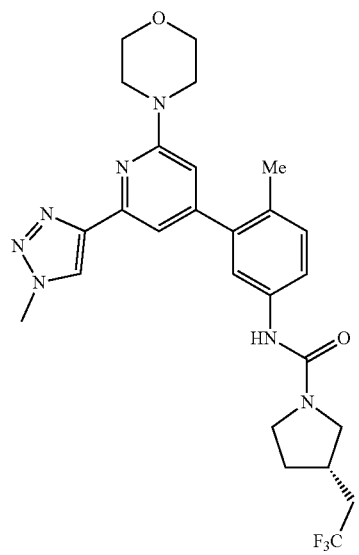

Synthetic Scheme

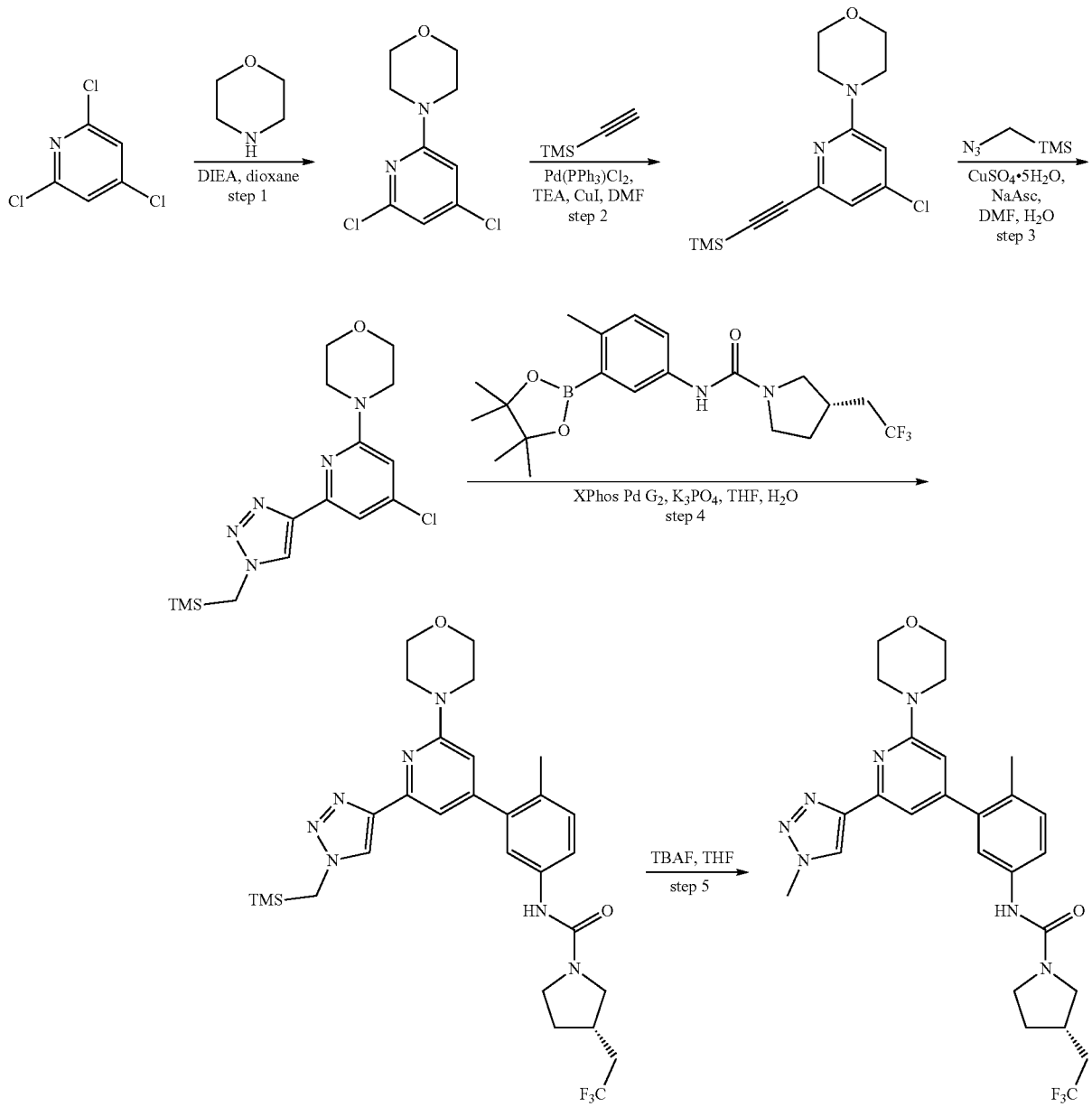

Preparation 14A:
4-(4,6-dichloropyridin-2-yl)morpholine

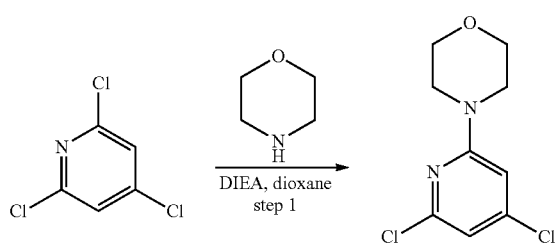 [SMILES: Clc1cc(Cl)nc(Cl)c1 ; C1COCCN1 ; Clc1cc(Cl)nc(N2CCOCC2)c1]

A mixture of 2,4,6-trichloropyridine (29.20 g, 160.06 mmol), morpholine (14 mL, 160.06 mmol) and DIEA (28 mL, 215.72 mmol) in 1,4-dioxane (160 mL) was stirred for 16 h at 85° C. The mixture was allowed to cool down to room temperature. The reaction was quenched with water (300 mL). The resulting mixture was extracted with EA (3×200 mL). The combined organic layers were washed with brine (300 mL), dried over anhydrous Na$_2$SO$_4$. After filtration, the filtrate was concentrated under reduced pressure. The residue was purified by silica gel column chromatography, eluted with EA/PE (15/85) to afford 4-(4,6-dichloropyridin-2-yl)morpholine (19.10 g, 51%) as an off-white solid. MS ESI calculated for C$_9$H$_{10}$Cl$_2$N$_2$O [M+H]$^+$, 233.02, found 232.90. $^1$H NMR (400 MHz, Chloroform-d) δ 6.67 (d, J=1.3 Hz, 1H), 6.48 (d, J=1.3 Hz, 1H), 3.83-3.76 (m, 4H), 3.56-3.49 (m, 4H).

Preparation 14B: 4-[4-chloro-6-[2-(trimethylsilyl)ethynyl]pyridin-2-yl]morpholine

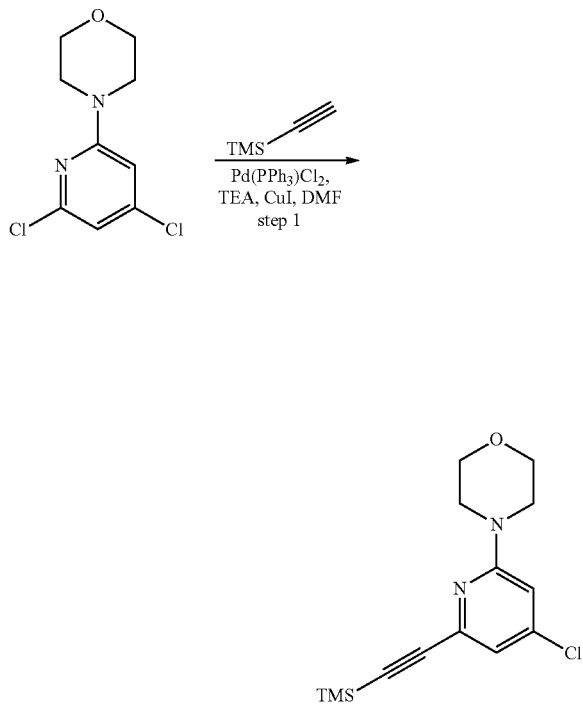

A mixture of 4-(4,6-dichloropyridin-2-yl)morpholine (2.00 g, 8.58 mmol), trimethylsilylacetylene (0.84 g, 8.55 mmol), CuI (0.33 g, 1.72 mmol), Pd(PPh₃)₂Cl₂ (0.60 g, 0.86 mmol) and TEA (2.60 g, 25.69 mmol) in DMF (20 mL) was stirred for 16 h at 80° C. under nitrogen atmosphere. The resulting mixture was quenched water (100 mL). The resulting mixture was extracted with EA (2×100 mL). The combined organic layers were washed with brine (100 mL), dried over anhydrous Na₂SO₄. After filtration, the filtrate was concentrated under reduced pressure. The residue was purified by silica gel column chromatography, eluted with PE/EA (1/1) to afford 4-[4-chloro-6-[2-(trimethylsilyl)ethynyl]pyridin-2-yl]morpholine (2.50 g, 87%) as yellow oil. MS ESI calculated for $C_{14}H_{19}ClN_2OSi$ [M+H]⁺, 295.10; found 295.30. ¹H NMR (400 MHz, Chloroform-d) δ 6.87 (s, 1H), 6.58 (s, 1H), 3.82-3.80 (m, 4H), 3.56-3.54 (m, 4H), 0.29-0.26 (m, 9H).

Preparation 14C: tert-butyl 3-[(5-bromopyrimidin-2-yl)(methyl)amino]pyrrolidine-1-carboxylate

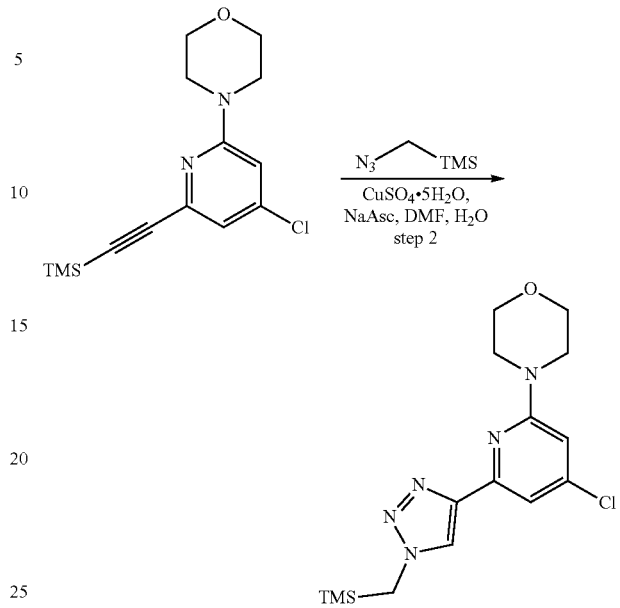

To a mixture of 4-[4-chloro-6-[2-(trimethylsilyl)ethynyl]pyridin-2-yl]morpholine (500 mg, 1.696 mmol) and (azidomethyl)trimethylsilane (438 mg, 3.392 mmol) in DMF (7.5 mL) were added CuSO₄.5H₂O (42 mg, 0.170 mmol) in H₂O (1.5 mL) and sodium ascorbate (135 mg, 0.678 mmol) in H₂O (1.5 mL). The resulting mixture was stirred for 16 h at room temperature under nitrogen atmosphere. The reaction was diluted with NH₄Cl (sat.)/NH₄OH (10/1, 10 mL). The resulting mixture was extracted with EA (2×50 mL). The combined organic layers were washed with brine (100 mL), dried over anhydrous Na₂SO₄. After filtration, the filtrate was concentrated under reduced pressure. The residue was purified by silica gel column chromatography, eluted with PE/EA (1/1) to afford 4-(4-chloro-6-[1-[(trimethylsilyl)methyl]-1,2,3-triazol-4-yl]pyridin-2-yl)morpholine (390 mg, 62%) as an off-white solid. MS ESI calculated for $C_{15}H_{22}ClN_5OSi$ [M+H]⁺, 352.13, found 352.55. ¹H NMR (400 MHz, Chloroform-d) δ 7.91 (s, 1H), 7.58 (s, 1H), 6.57 (s, 1H), 3.97 (s, 2H), 3.87-3.84 (m, 4H), 3.58-3.56 (m, 4H), 0.21-0.19 (m, 9H).

Preparation 14D: (3S)—N-[4-methyl-3-[2-(morpholin-4-yl)-6-[1-[(trimethylsilyl)methyl]-1,2,3-triazol-4-yl]pyridin-4-yl]phenyl]-3-(2,2,2-trifluoroethyl)pyrrolidine-1-carboxamide

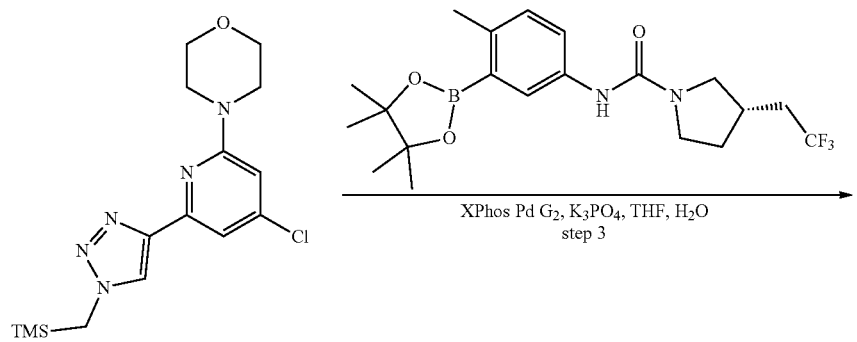

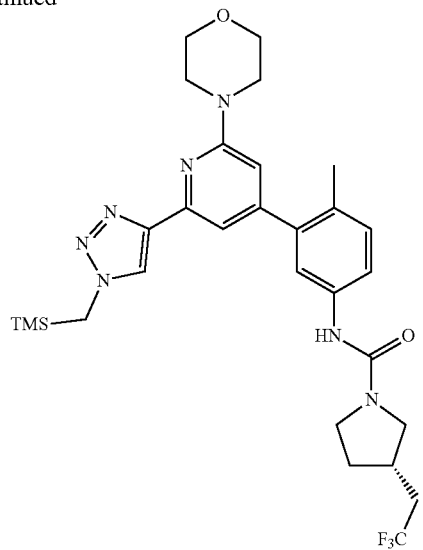

A mixture of 4-(4-chloro-6-[1-[(trimethylsilyl)methyl]-1,2,3-triazol-4-yl]pyridin-2-yl)morpholine (200 mg, 0.568 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (187 mg, 0.455 mmol), $2^{nd}$ Generation XPhos precatalyst (45 mg, 0.057 mmol) and $K_3PO_4$ (241 mg, 1.137 mmol) in THF (2 mL) and $H_2O$ (0.2 mL) was stirred for 2 h at 80° C. under nitrogen atmosphere. The reaction was quenched with water (10 mL). The resulting mixture was extracted with EA (2×5 mL). The combined organic layers were washed with brine (5 mL), dried over anhydrous $Na_2SO_4$. After filtration, the filtrate was concentrated under reduced pressure. The residue was purified by silica gel column chromatography, eluted with PE/EA (1/1) to afford (3S)—N-[4-methyl-3-[2-(morpholin-4-yl)-6-[1-[(trimethylsilyl)methyl]-1,2,3-triazol-4-yl]pyridin-4-yl]phenyl]-3-(2,2,2-trifluoroethyl)pyrrolidine-1-carboxamide (250 mg, crude) as an off-white solid. MS ESI calculated for $C_{29}H_{38}F_3N_7O_2Si$ [M+H]$^+$, 602.28, found 602.45.

Example 14: (S)—N-(4-methyl-3-(2-(1-methyl-1H-1,2,3-triazol-4-yl)-6-morpholinopyridin-4-yl)phenyl)-3-(2,2,2-trifluoroethyl)pyrrolidine-1-carboxamide

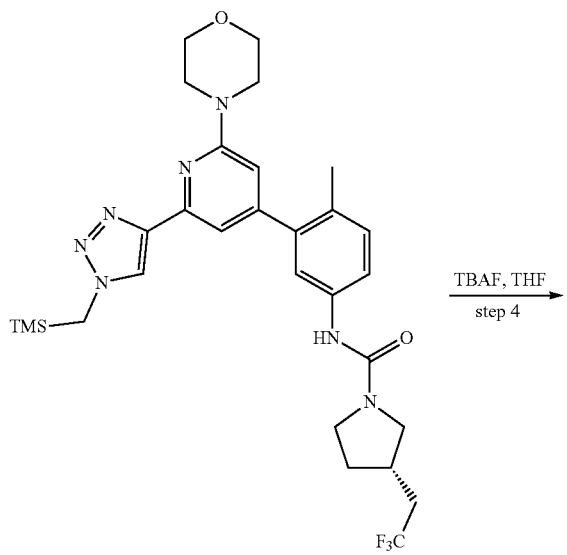

TBAF, THF
step 4

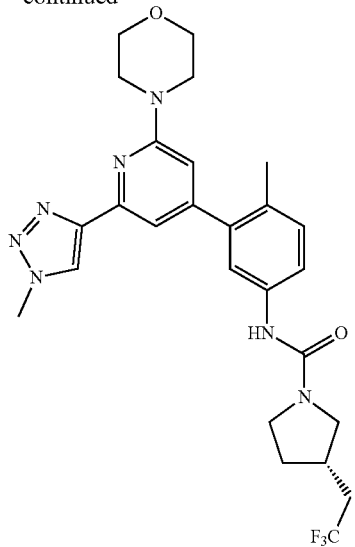

To a mixture of (3S)—N-[4-methyl-3-[2-(morpholin-4-yl)-6-[1-[(trimethylsilyl)methyl]-1,2,3-triazol-4-yl]pyridin-4-yl]phenyl]-3-(2,2,2-trifluoroethyl)pyrrolidine-1-carboxamide (200 mg, 0.332 mmol) in THF (2 mL) was added TBAF (174 mg, 0.665 mmol). The reaction mixture was stirred for 2 h at room temperature. The resulting mixture was quenched with water (10 mL) and extracted with EA (2×10 mL). The combined organic layers were washed with brine (5 mL), dried over anhydrous $Na_2SO_4$. After filtration, the filtrate was concentrated under reduced pressure. The residue was purified by silica gel column chromatography, eluted with PE/EA/EtOH (4/3/1) to afford (S)—N-(4-methyl-3-(2-(1-methyl-1H-1,2,3-triazol-4-yl)-6-morpholinopyridin-4-yl)phenyl)-3-(2,2,2-trifluoroethyl)pyrrolidine-1-carboxamide (127.4 mg, 70%) as an off-white solid. MS ESI calculated for $C_{26}H_{30}F_3N_7O_2$[M+H]$^+$, 530.24, found 530.35; H NMR (300 MHz, DMSO-$d_6$) δ 8.54 (s, 1H), 8.20 (s, 1H), 7.52 (dd, J=8.2, 2.3 Hz, 1H), 7.47 (d, J=2.3 Hz, 1H), 7.28 (d, J=1.1 Hz, 1H), 7.19 (d, J=8.4 Hz, 1H), 6.70 (d, J=1.2 Hz, 1H), 4.12 (s, 3H), 3.77-3.73 (m, 4H), 3.72-3.65

(m, 1H), 3.64-3.50 (m, 5H), 3.34-3.28 (m, 1H), 3.04 (t, J=9.3 Hz, 1H), 2.50-2.37 (m, 3H), 2.23 (s, 3H), 2.14-2.06 (m, 1H), 1.74-1.61 (m, 1H). $^{19}$F NMR (282 MHz, Chloroform-d) 6-63.36 (3F).

Example 15: (3S)—N-[4-methyl-3-[2-(morpholin-4-yl)-6-(1,3-thiazol-5-yl)pyridin-4-yl]phenyl]-3-(2,2,2-trifluoroethyl)pyrrolidine-1-carboxamide

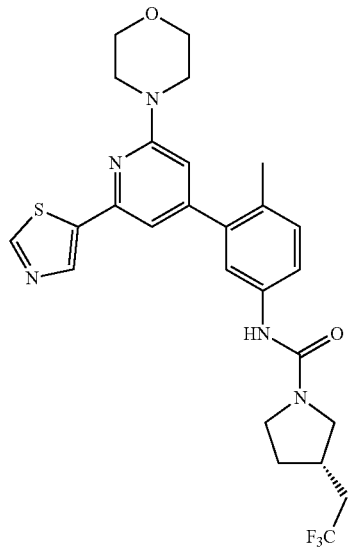 [SMILES: Cc1ccc(NC(=O)N2CC[C@@H](CC(F)(F)F)C2)cc1-c1cc(-c2cncs2)nc(N2CCOCC2)c1]

Synthetic Scheme

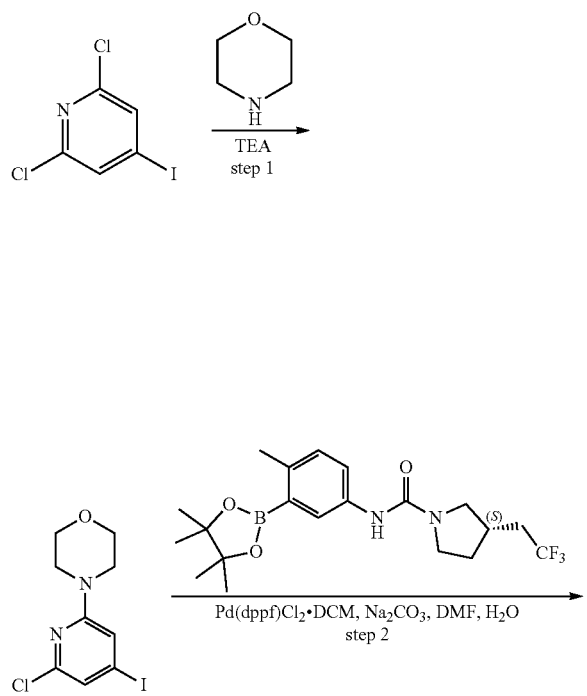

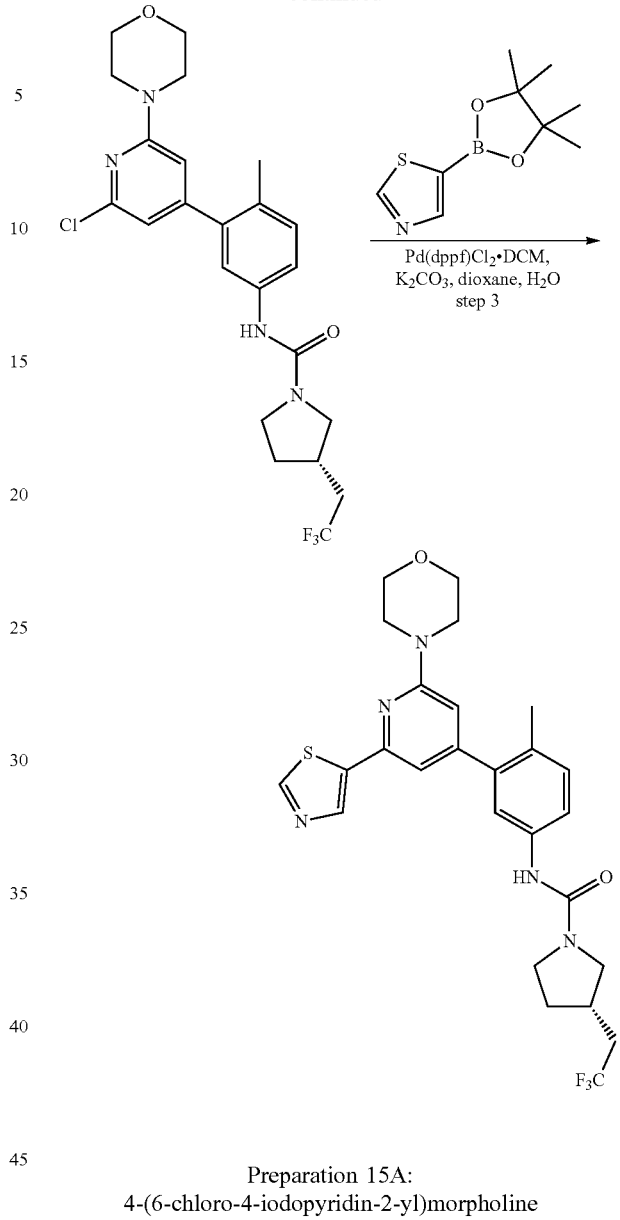

Preparation 15A:
4-(6-chloro-4-iodopyridin-2-yl)morpholine

A mixture of 2,6-dichloro-4-iodopyridine (8.50 g, 31.035 mmol), TEA (3.14 g, 31.035 mmol) and morpholine (2.70 g, 30.991 mmol) was stirred for 2 h at 100° C. under nitrogen atmosphere. The resulting mixture was diluted with EA (200 mL), washed with sat. NaHCO$_3$ (3×100 mL), and concentrated under reduced pressure. The residue was purified by silica gel column chromatography, eluted with hexane/EA (5/1) to afford 4-(6-chloro-4-iodopyridin-2-yl)morpholine (4.28 g, 42%) as a white solid. MS ESI calculated for C$_9$H$_{10}$ClIN$_2$O [M+H]$^+$, 324.95, found 324.95. $^1$H NMR (400 MHz, DMSO-d$_6$) δ 7.19-7.18 (m, 1H), 7.09-7.08 (m, 1H), 3.67-3.65 (m, 4H), 3.47-3.45 (m, 4H).

Preparation 15B: (3S)—N-[3-[2-chloro-6-(morpholin-4-yl)pyridin-4-yl]-4-methylphenyl]-3-(2,2,2-trifluoroethyl)pyrrolidine-1-carboxamide

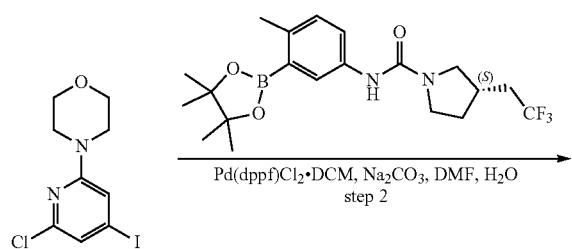

Example 15: (3S)—N-[4-methyl-3-[2-(morpholin-4-yl)-6-(1,3-thiazol-5-yl)pyridin-4-yl]phenyl]-3-(2,2,2-trifluoroethyl)pyrrolidine-1-carboxamide

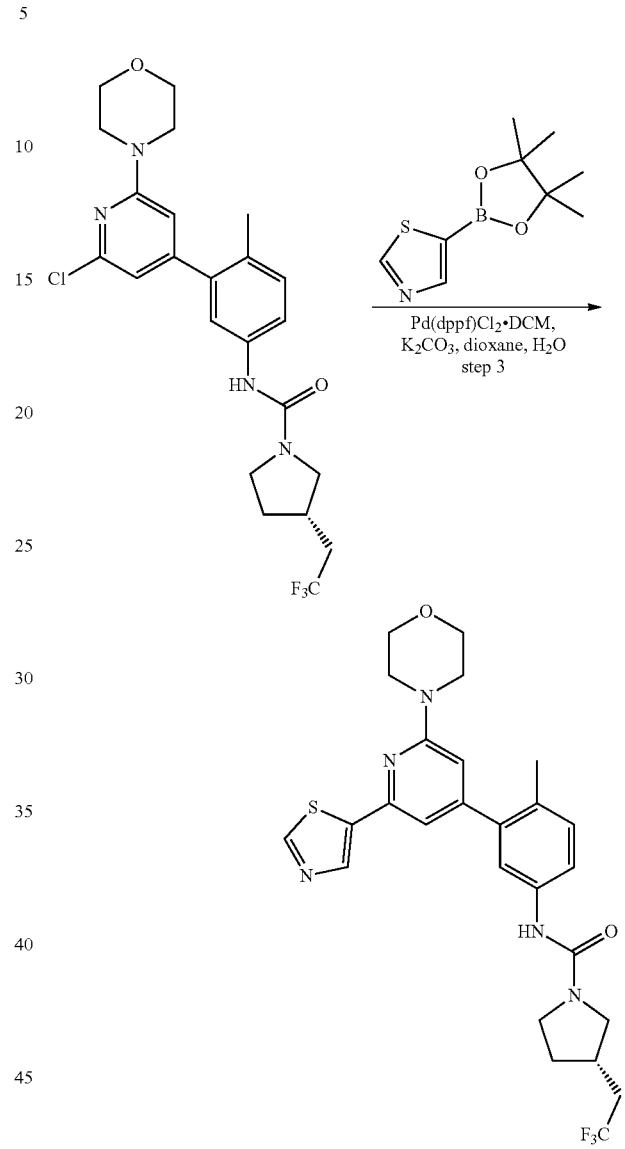

To a stirred mixture of 4-(6-chloro-4-iodopyridin-2-yl)morpholine (200 mg, 0.616 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (254 mg, 0.616 mmol), Na$_2$CO$_3$ (196 mg, 1.849 mmol) in DMF (6 mL) and H$_2$O (1.5 mL) was added Pd(dppf)Cl$_2$.CH$_2$Cl$_2$ (50 mg, 0.062 mmol) under nitrogen atmosphere. The resulting mixture was stirred for 2 h at 60° C. under nitrogen atmosphere. The resulting mixture was diluted with H$_2$O (80 mL). The resulting mixture was extracted with EA (3×80 mL). The combined organic layers were washed with brine (2×50 mL), dried over anhydrous Na$_2$SO$_4$. After filtration, the filtrate was concentrated under reduced pressure. The residue was purified by silica gel column chromatography, eluted with hexane/EA/EtOH (4/3/1) to afford (3S)—N-[3-[2-chloro-6-(morpholin-4-yl)pyridin-4-yl]-4-methylphenyl]-3-(2,2,2-trifluoroethyl)pyrrolidine-1-carboxamide (395 mg, crude) as a light brown oil. MS ESI calculated for C$_{23}$H$_{26}$ClF$_3$N$_4$O$_2$ [M+H]$^+$, 483.17, found 483.35.

A mixture of 5-(4,4,5,5-tetramethyl-1,3,2-dioxaborolan-2-yl)-1,3-thiazole (131 mg, 0.621 mmol), (3S)—N-[3-[2-chloro-6-(morpholin-4-yl)pyridin-4-yl]-4-methylphenyl]-3-(2,2,2-trifluoroethyl)pyrrolidine-1-carboxamide (150 mg, 0.311 mmol), Pd(dppf)Cl$_2$.CH$_2$Cl$_2$ (25 mg, 0.031 mmol) and K$_2$CO$_3$ (128 mg, 0.932 mmol) in dioxane (4 mL) and H$_2$O (1 mL) was stirred for 2 h at 80° C. under nitrogen atmosphere. The mixture was allowed to cool down to room temperature. The residue was purified by Prep-TLC with PE/EA (1/1). The residue was purified by reverse phase flash chromatography with the following conditions: Column: Spherical C18, 20-40 μm, 120 g; Mobile Phase A: Water (plus 5 mM NH$_4$HCO$_3$); Mobile Phase B: CH$_3$CN; Flow rate: 60 mL/min; Gradient: 30% B-70% B; Detector: 220 nm to afford (3S)—N-[4-methyl-3-[2-(morpholin-4-yl)-6-(1,3-thiazol-5-yl)pyridin-4-yl]phenyl]-3-(2,2,2-trifluoroethyl)pyrrolidine-1-carboxamide (118 mg, 71%) as an off-white solid. MS ESI calculated for C$_{26}$H$_{28}$F$_3$N$_5$O$_2$S [M+H]$^+$, 532.19, found 532.20. ¹H NMR (400 MHz, DMSO-d₆) δ 9.09 (s, 1H), 8.57 (s, 1H), 8.19 (s, 1H), 7.52 (dd, J=8.3, 2.3 Hz, 1H), 7.43 (d, J=2.2 Hz, 1H), 7.28 (d, J=0.9 Hz, 1H), 7.18 (d, J=8.4 Hz, 1H), 6.68 (s, 1H), 3.75-3.71 (m, 5H), 3.58-3.48 (m, 5H), 3.33-3.28 (m, 1H), 3.03 (t, J=9.4 Hz, 1H), 2.50-2.38 (m, 3H), 2.21 (s, 3H), 2.11-2.07 (m, 1H), 1.73-1.59 (m, 1H); ¹⁹F NMR (376 MHz, DMSO-d₆) δ −63.36 (3F).

Example 16: (3S)—N-[4-methyl-3-[2-(3-methylimidazol-4-yl)-6-(morpholin-4-yl)pyridin-4-yl]phenyl]-3-(2,2,2-trifluoroethyl)pyrrolidine-1-carboxamide

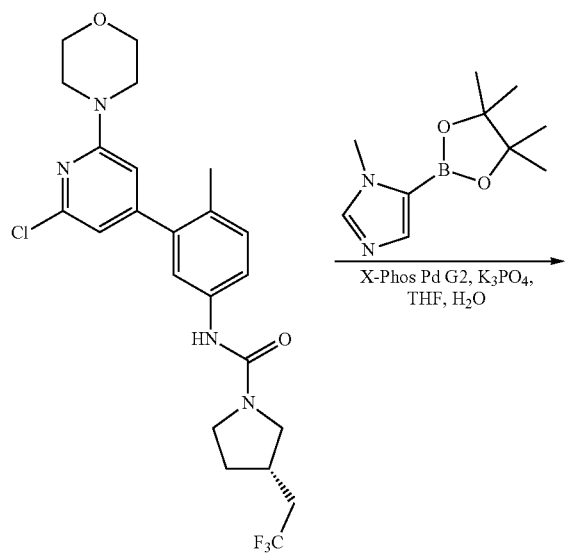

A mixture of 1-methyl-5-(4,4,5,5-tetramethyl-1,3,2-dioxaborolan-2-yl)imidazole (103 mg, 0.497 mmol), (3S)—N-[3-[2-chloro-6-(morpholin-4-yl)pyridin-4-yl]-4-methylphenyl]-3-(2,2,2-trifluoroethyl)pyrrolidine-1-carboxamide (120 mg, 0.248 mmol), 2$^{nd}$ Generation XPhos precatalyst (20 mg, 0.025 mmol) and K₃PO₄ (105 mg, 0.497 mmol) in dioxane (4 mL) and H₂O (1 mL) was stirred at 80° C. for 2 h under nitrogen atmosphere. The mixture was allowed to cool down to room temperature. The resulting mixture was diluted with EA (10 mL) and washed with brine (3×10 mL), dried over anhydrous Na₂SO₄. After filtration, the filtrate was concentrated under reduced pressure. The residue was purified by silica gel column chromatography, eluted with PE/EA (1/1). The crude product was purified by reverse flash chromatography with the following conditions: Column: C18 Column 120 g; Mobile Phase A: Water (10 mmol/L NH₄HCO₃), Mobile Phase B: CH₃CN; Flow rate: 80 mL/min; Gradient: 40% B to 70% B; 254/220 nm to afford (3S)—N-[4-methyl-3-[2-(3-methylimidazol-4-yl)-6-(morpholin-4-yl)pyridin-4-yl]phenyl]-3-(2,2,2-trifluoroethyl)pyrrolidine-1-carboxamide (124.4 mg, 81%) as a white solid. MS ESI calculated for C₂₇H₃₁F₃N₆O₂ [M+H]⁺, 529.25 found 529.30; ¹H NMR (400 MHz, DMSO-d₆) δ 8.17 (s, 1H), 7.71 (d, J=1.1 Hz, 1H), 7.51-7.48 (m, 2H), 7.42 (d, J=2.3 Hz, 1H), 7.16 (d, J=8.4 Hz, 1H), 7.00 (d, J=1.0 Hz, 1H), 6.61 (d, J=1.1 Hz, 1H), 3.98 (s, 3H), 3.75-3.65 (m, 5H), 3.57-3.47 (m, 5H), 3.32-3.26 (m, 1H), 3.03 (t, J=9.4 Hz, 1H), 2.49-2.35 (m, 3H), 2.20 (s, 3H), 2.10-2.05 (m, 1H), 1.70-1.62 (m, 1H); ¹⁹F NMR (376 MHz, DMSO-d₆) δ −63.38 (3F).

Example 17: (3S)—N-(3-[2-[(1E,3R)-3-hydroxybut-1-en-1-yl]-6-(morpholin-4-yl)pyridin-4-yl]-4-methylphenyl)-3-(2,2,2-trifluoroethyl)pyrrolidine-1-carboxamide

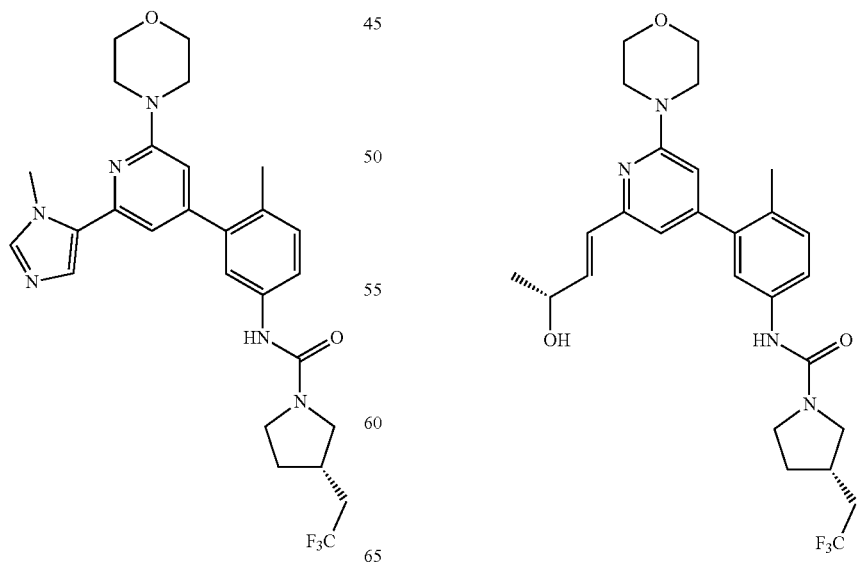

Synthetic Scheme

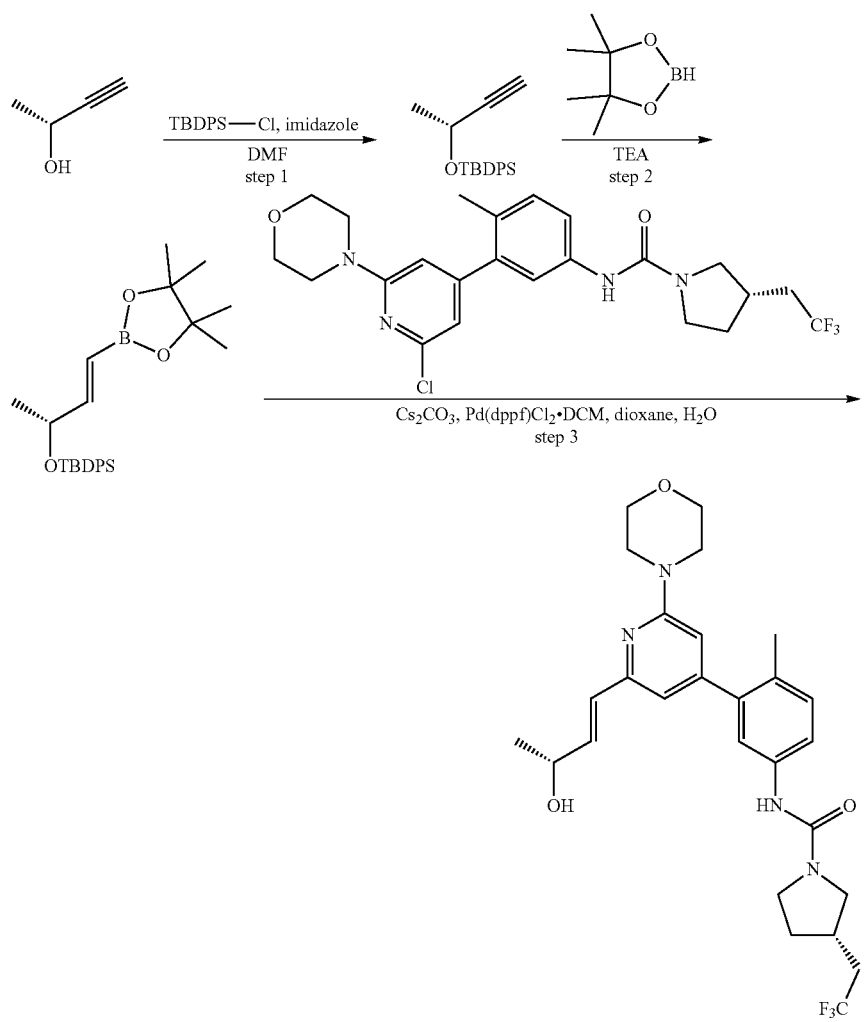

Preparation 17A: [(2R)-but-3-yn-2-yloxy](tert-butyl)diphenylsilane

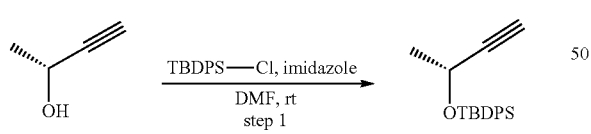

To a solution of (2R)-but-3-yn-2-ol (5.00 g, 71.34 mmol) and imidazole (9.71 g, 142.67 mmol) in DMF (50 mL) was added TBDPS-Cl (29.41 g, 107.00 mmol) at 0° C. The mixture was stirred for 4 h at room temperature. The mixture was diluted with water (500 mL) and extracted with EtOAc (3×100 mL). The combined extracts were washed with brine (100 mL), dried over anhydrous sodium sulfate, filtered and concentrated under reduced pressure. The residue was purified by silica gel column chromatography, eluted with EA in PE (8%) to afford [(2R)-but-3-yn-2-yloxy](tert-butyl)diphenylsilane (21 g, 95%) as colorless oil. $C_{20}H_{24}OSi$. $^1H$ NMR (400 MHz, $CDCl_3$) δ 7.81-7.72 (m, 4H), 7.48-7.40 (m, 6H), 4.53-4.48 (m, 1H), 2.38-2.37 (m, 1H), 1.45-1.43 (m, 3H), 1.15 (s, 9H).

Preparation 17B: tert-butyldiphenyl[[(2R,3E)-4-(4,4,5,5-tetramethyl-1,3,2-dioxaborolan-2-yl)but-3-en-2-yl]oxy]silane

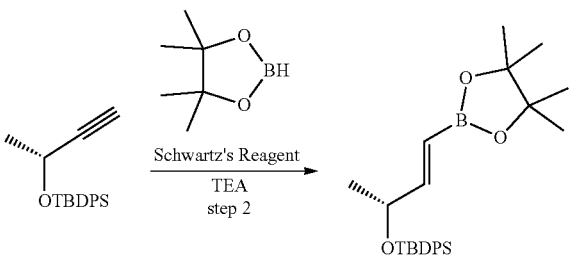

A mixture of [(2R)-but-3-yn-2-yloxy](tert-butyl)diphenylsilane (5.00 g, 16.21 mmol), 4,4,5,5-tetramethyl-1,3,2-dioxaborolane (2.18 g, 0.02 mmol), bis(cyclopentadienyl)

zirconium chloride hydride (0.42 g, 1.62 mmol) and TEA (0.16 g, 1.62 mmol) was stirred for 16 h at 60° C. under nitrogen atmosphere. The mixture was allowed to cool down to room temperature. The resulting mixture was diluted with hexane (10 mL). The solid was removed by filtering over a short pad of silica gel and washed with hexane (3×10 mL). The filtrate was concentrated under reduced pressure to afford tert-butyldiphenyl[[(2R,3E)-4-(4,4,5,5-tetramethyl-1,3,2-dioxaborolan-2-yl)but-3-en-2-yl]oxy]silane (6.00 g, 85%) as colorless oil. $C_{26}H_{37}BO_3Si$. $^1H$ NMR (400 MHz, $CDCl_3$) δ 7.76-7.62 (m, 4H), 7.46-7.33 (m, 6H), 6.65-6.60 (m, 1H), 5.70-5.64 (m, 1H), 4.43-4.33 (m, 1H), 1.32 (s, 12H), 1.10-1.09 (m, 12H).

Example 17: (S)—N-(3-(2-((R,E)-3-hydroxybut-1-en-1-yl)-6-morpholinopyridin-4-yl)-4-methylphenyl)-3-(2,2,2-trifluoroethyl)pyrrolidine-1-carboxamide A mixture of (3S)—N-[3-[2-chloro-6-(morpholin-4-yl)pyridin-4-yl]-4-methylphenyl]-3-(2,2,2-trifluoroethyl)pyrrolidine-1-carboxamide (600 mg, 1.242 mmol), tert-butyldiphenyl[[(2R,3E)-4-(4,4,5,5-tetramethyl-1,3,2-dioxaborolan-2-yl)but-3-en-2-yl]oxy]silane (1627 mg, 3.727 mmol), $Cs_2CO_3$ (1214 mg, 3.727 mmol), Pd(dppf)$Cl_2 \cdot CH_2Cl_2$ (101 mg, 0.124 mmol), dioxane (20 mL) and $H_2O$ (2 mL) was stirred for 16 h at 100° C. under nitrogen atmosphere. The resulting mixture was concentrated under reduced pressure. The residue was purified by silica gel column chromatography, eluted with EA followed by purification by prep-HPLC with the following conditions: Column: SunFire Prep C18 OBD Column, 19×150 mm 5um 10 nm; Mobile Phase A: water (0.1% FA), Mobile Phase B: acetonitrile; Flow rate: 20 mL/min; Gradient: 30 B to 55 B in 4.3 min; 254/210 nm to afford (S)—N-(3-(2-((R,E)-3-hydroxybut-1-en-1-yl)-6-morpholinopyridin-4-yl)-4-methylphenyl)-3-(2,2,2-trifluoroethyl)pyrrolidine-1-carboxamide (86 mg, 13%) as a light yellow solid. MS ESI calculated for $C27H_{33}F_3N_4O_3$ $[M+H]^+$, 519.25, found 519.10. $^1H$ NMR (400 MHz, DMSO-$d_6$) δ 8.16 (s, 1H), 7.47-7.46 (m, 1H), 7.39-7.38 (m, 1H), 7.15-7.13 (m, 1H), 6.73-6.71 (m, 1H), 6.62-6.58 (m, 2H), 6.50-6.46 (m, 1H), 4.90-4.89 (m, 1H), 4.44-4.34 (m, 1H), 3.73-3.70 (m, 5H), 3.52-3.50 (m, 5H), 3.34-3.30 (m, 1H), 3.00-2.99 (m, 1H), 2.51-2.50 (m, 3H), 2.17-2.00 (m, 4H), 1.50-1.45 (m, 1H) 1.22 (d, J=6.4 Hz, 3H). $^{19}F$ NMR (376 MHz, DMSO-$d_6$) δ −63.37 (3F).

Example 18: N-(2-hydroxyethyl)-N-methyl-4-[2-methyl-5-[(3S)-3-(2,2,2-trifluoroethyl)pyrrolidine-1-carbonylamino]phenyl]-6-(morpholin-4-yl)pyridine-2-carboxamide

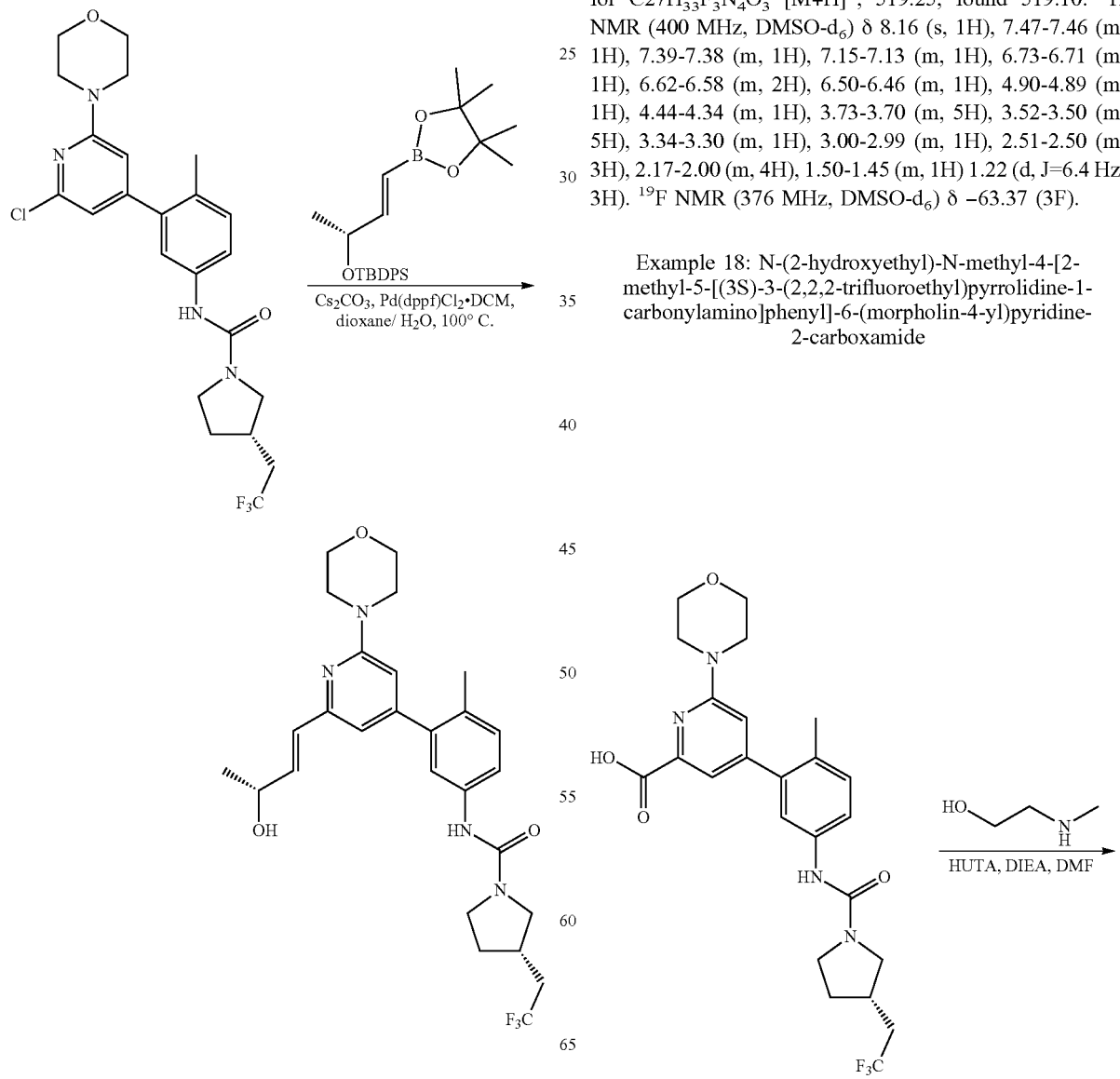

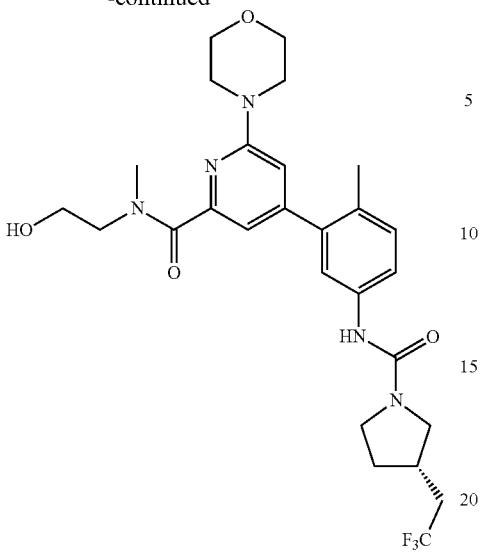

A mixture of 4-[2-methyl-5-[(3S)-3-(2,2,2-trifluoroethyl)pyrrolidine-1-carbonylamino]phenyl]-6-(morpholin-4-yl)pyridine-2-carboxylic acid (100 mg, 0.203 mmol), methylethanolamine (20 mg, 0.264 mmol), HATU (93 mg, 0.244 mmol) and DIEA (79 mg, 0.609 mmol) in DMF (2 mL) was stirred for 16 h at room temperature. The residue was purified by reverse phase Flash chromatography with the following conditions: Column: WelFlash™ C18, 20-40 μm, 120 g; Eluent A: water (plus 10 mmol/L $NH_4HCO_3$); Eluent B: $CH_3CN$; Gradient: 30%-50% B in 25 min; Flow rate: 60 mL/min; Detector: 220/254 nm to afford N-(2-hydroxyethyl)-N-methyl-4-[2-methyl-5-[(3S)-3-(2,2,2-trifluoroethyl)pyrrolidine-1-carbonylamino]phenyl]-6-(morpholin-4-yl)pyridine-2-carboxamide (80 mg, 72%) as a white solid. MS ESI calculated for $C_7H_{34}F_3N_5O_4$ $[M+H]^+$, 550.26 found 550.20. $^1H$ NMR (400 MHz, chloroform-d) δ 7.34 (d, J=7.7 Hz, 2H), 7.19 (d, J=8.1 Hz, 1H), 7.01-6.91 (m, 1H), 6.65 (s, 1H), 6.35 (d, J=9.5 Hz, 1H), 3.96-3.71 (m, 8H), 3.70-3.39 (m, 8H), 3.21-3.09 (m, 4H), 2.64-2.49 (m, 1H), 2.34-2.20 (m, 6H), 1.81-1.70 (m, 1H). $^{19}F$ NMR (376 MHz, chloroform-d) 6-64.94 (3F).

Example 19: N, N-dimethyl-4-[2-methyl-5-[(3S)-3-(2,2,2-trifluoroethyl)pyrrolidine-1-carbonylamino]phenyl]-6-(morpholin-4-yl)pyridine-2-carboxamide

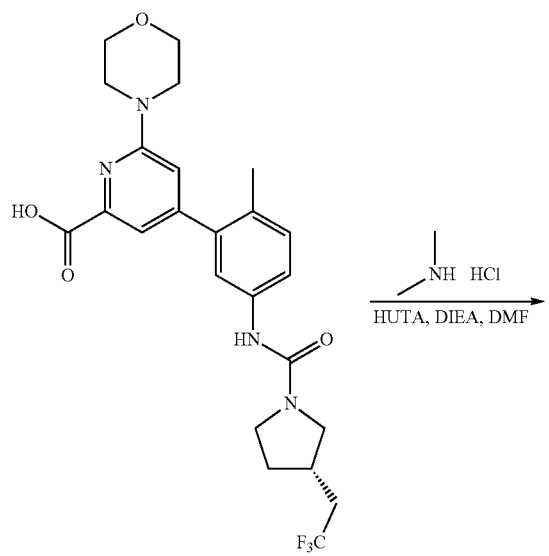

A mixture of 4-[2-methyl-5-[(3S)-3-(2,2,2-trifluoroethyl)pyrrolidine-1-carbonylamino]phenyl]-6-(morpholin-4-yl)pyridine-2-carboxylic acid (100 mg, 0.203 mmol), dimethylamine hydrochloride (22 mg, 0.264 mmol), HATU (93 mg, 0.244 mmol) and DIEA (105 mg, 0.812 mmol) in DMF (2 mL) was stirred for 16 h at room temperature. The residue was purified by reverse phase Flash chromatography with the following conditions: Column: WelFlash™ C18, 20-40 μm, 120 g; Eluent A: water (plus 10 mmol/L $NH_4HCO_3$); Eluent B: $CH_3CN$; Gradient: 30%-50% B in 25 min; Flow rate: 60 mL/min; Detector: 220/254 nm to afford N, N-dimethyl-4-[2-methyl-5-[(3S)-3-(2,2,2-trifluoroethyl)pyrrolidine-1-carbonylamino]phenyl]-6-(morpholin-4-yl)pyridine-2-carboxamide (74 mg, 70%) as a white solid. MS ESI calculated for $C_{26}H_{32}F_3N_5O_3[M+H]^+$, 520.25 found 520.25. $^1H$ NMR (400 MHz, DMSO-$d_6$) δ 8.18 (s, 1H), 7.49-7.47 (m, 1H), 7.42 (d, J=2.3 Hz, 1H), 7.16 (d, J=8.5 Hz, 1H), 6.79 (d, J=1.2 Hz, 1H), 6.73 (d, J=0.8 Hz, 1H), 3.69-3.61 (m, 5H), 3.51-3.45 (m, 5H), 3.34-3.31 (m, 1H), 3.07-2.98 (m, 7H), 2.49-2.39 (m, 3H), 2.19 (s, 3H), 2.15-2.06 (m, 1H), 1.66-1.62 (m, 1H). $^{19}F$ NMR (376 MHz, DMSO-$d_6$) δ −63.37 (3F).

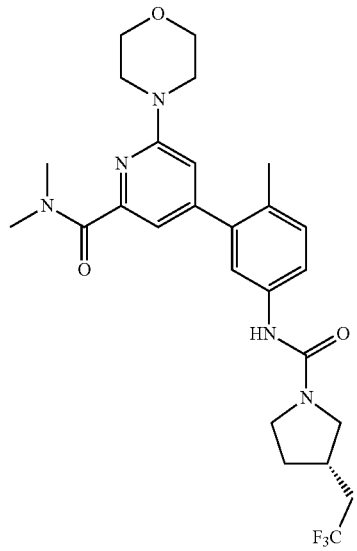

Example 20: (3S)—N-[3-[2-(3-hydroxyazetidine-1-carbonyl)-6-(morpholin-4-yl)pyridin-4-yl]-4-methylphenyl]-3-(2,2,2-trifluoroethyl)pyrrolidine-1-carboxamide

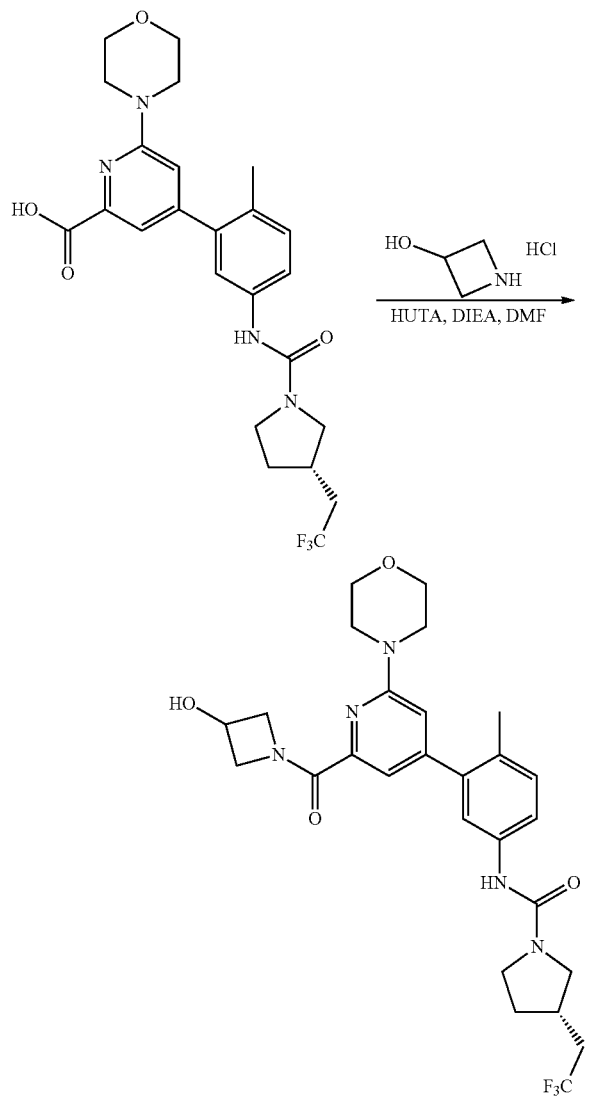

A mixture of 4-[2-methyl-5-[(3S)-3-(2,2,2-trifluoroethyl)pyrrolidine-1-carbonylamino]phenyl]-6-(morpholin-4-yl)pyridine-2-carboxylic acid (100 mg, 0.203 mmol), azetidin-3-ol hydrochloride (29 mg, 0.264 mmol), HATU (93 mg, 0.244 mmol) and DIEA (105 mg, 0.812 mmol) in DMF (2 mL) was stirred for 16 h at room temperature. The residue was purified by reverse phase Flash chromatography with the following conditions: Column: WelFlash™ C18, 20-40 μm, 120 g; Eluent A: water (plus 10 mmol/L NH$_4$HCO$_3$); Eluent B: CH$_3$CN; Gradient: 30%-50% B in 25 min; Flow rate: 60 mL/min; Detector: 220/254 nm to afford (3S)—N-[3-[2-(3-hydroxyazetidine-1-carbonyl)-6-(morpholin-4-yl)pyridin-4-yl]-4-methylphenyl]-3-(2,2,2-trifluoroethyl)pyrrolidine-1-carboxamide (69 mg, 62%) as a white solid. MS ESI calculated for C$_{27}$H$_{32}$F$_3$N$_5$O$_4$ [M+H]$^+$, 548.24, found 548.25. $^1$H NMR (400 MHz, DMSO-d$_6$) δ 8.18 (s, 1H), 7.48-7.46 (m, 1H), 7.39 (d, J=2.3 Hz, 1H), 7.19 (d, J=1.1 Hz, 1H), 7.14 (d, J=8.4 Hz, 1H), 6.88 (d, J=1.2 Hz, 1H), 5.70 (d, J=6.4 Hz, 1H), 4.81-4.78 (m, 1H), 4.55-4.42 (m, 1H), 4.34-4.31 (m, 1H), 4.23-4.21 (m, 1H), 3.80-3.60 (m, 6H), 3.53-3.47 (m, 5H), 3.00 (t, J=9.3 Hz, 1H), 3.15-2.90 (m, 1H), 2.45-2.31 (m, 3H), 2.15 (s, 3H), 2.11-2.01 (m, 1H), 1.65-1.50 (m, 1H). $^{19}$F NMR (376 MHz, DMSO-d$_6$) δ −63.37 (3F).

Example 21: (3S)—N-[3-[2-(3-hydroxy-3-methylazetidine-1-carbonyl)-6-(morpholin-4-yl)pyridin-4-yl]-4-methylphenyl]-3-(2,2,2-trifluoroethyl)pyrrolidine-1-carboxamide

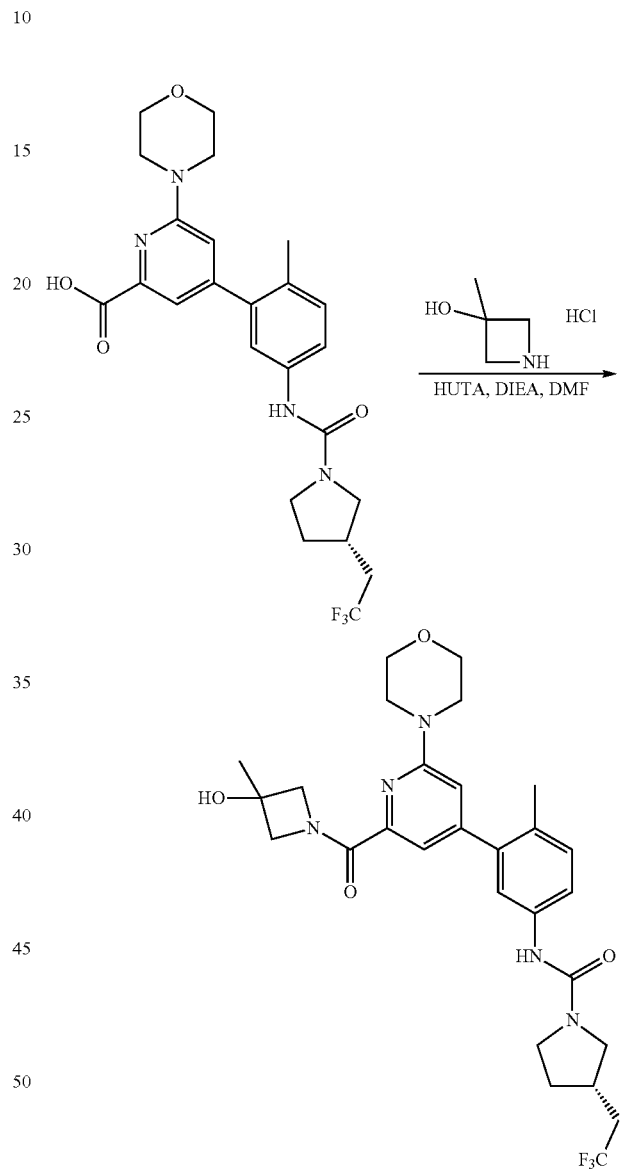

A mixture of 4-[2-methyl-5-[(3S)-3-(2,2,2-trifluoroethyl)pyrrolidine-1-carbonylamino]phenyl]-6-(morpholin-4-yl)pyridine-2-carboxylic acid (100 mg, 0.203 mmol), 3-methylazetidin-3-ol hydrochloride (33 mg, 0.264 mmol), HATU (93 mg, 0.244 mmol), DIEA (105 mg, 0.812 mmol) and DMF (2 mL) was stirred for 16 h at room temperature. The residue was purified by reverse phase Flash chromatography with the following conditions: Column: WelFlash™ C18, 20-40 μm, 120 g; Eluent A: water (plus 10 mmol/L NH$_4$HCO$_3$); Eluent B: CH$_3$CN; Gradient: 30%-50% B in 25 min; Flow rate: 60 mL/min; Detector: 220/254 nm to afford (3S)—N-[3-[2-(3-hydroxy-3-methylazetidine-1-carbonyl)-6-(morpholin-4-yl)pyridin-4-yl]-4-methylphenyl]-3-(2,2,2- trifluoroethyl)pyrrolidine-1-carboxamide (75 mg, 66%) as a white solid. MS ESI calculated for $C_{28}H_{34}F_3N_5O_4[M+H]^+$, 562.26 found 562.30. $^1$H NMR (400 MHz, DMSO-d$_6$) δ 8.19 (s, 1H), 7.49-7.47 (m, 1H), 7.42 (d, J=2.3 Hz, 1H), 7.23 (d, J=1.1 Hz, 1H), 7.17 (d, J=8.4 Hz, 1H), 6.90 (d, J=1.2 Hz, 1H), 5.66 (s, 1H), 4.50-4.46 (m, 2H), 3.90-3.87 (m, 2H), 3.78-3.64 (m, 5H), 3.51 (t, J=5.0 Hz, 5H), 3.12-3.11 (m, 1H), 3.02 (t, J=9.4 Hz, 1H), 2.50-2.44 (m, 3H), 2.17 (s, 3H), 2.12-2.03 (m, 1H), 1.67-1.65 (m, 1H), 1.41 (s, 3H). $^{19}$F NMR (376 MHz, DMSO-d$_6$) δ −63.37 (3F).

Example 22: (3S)—N-[4-methyl-3-[2-(1-methylpyrazol-4-yl)-6-(morpholin-4-yl)pyridin-4-yl]phenyl]-3-(2,2,2-trifluoroethyl)pyrrolidine-1-carboxamide

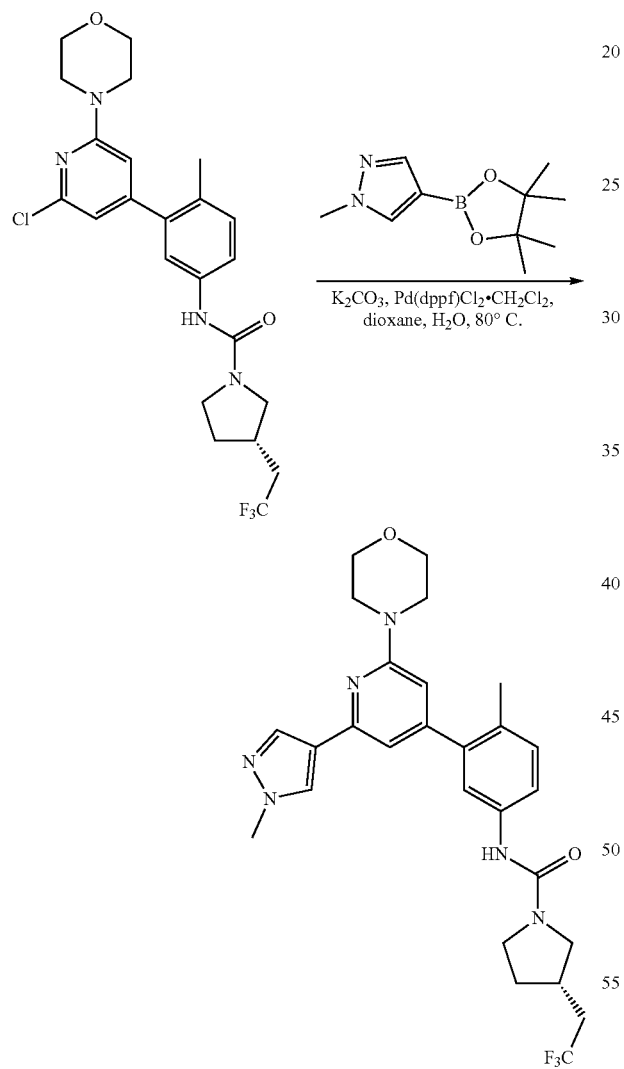

A mixture of (3S)—N-[3-[2-chloro-6-(morpholin-4-yl)pyridin-4-yl]-4-methylphenyl]-3-(2,2,2-trifluoroethyl)pyrrolidine-1-carboxamide (50 mg, 0.104 mmol), 1-methyl-4-(4,4,5,5-tetramethyl-1,3,2-dioxaborolan-2-yl)pyrazole (43 mg, 0.207 mmol), 1,4-dioxane (1 mL), H$_2$O (0.25 mL), K$_2$CO$_3$ (43 mg, 0.311 mmol) and Pd(dppf)Cl$_2$·CH$_2$Cl$_2$ (8 mg, 0.010 mmol) was stirred for 16 h at 80 degrees C. under nitrogen atmosphere. The reaction was quenched by the addition of water (10 mL. The resulting mixture was extracted with EtOAc (3×30 mL). The combined organic layers were washed with brine (2×20 mL), dried over anhydrous Na$_2$SO$_4$. After filtration, the filtrate was concentrated under reduced pressure. The residue was purified by Prep-TLC with PE/EtOAc (5/1) to afford (3S)—N-[4-methyl-3-[2-(1-methylpyrazol-4-yl)-6-(morpholin-4-yl)pyridin-4-yl]phenyl]-3-(2,2,2-trifluoroethyl)pyrrolidine-1-carboxamide (66 mg, 90%) as a white solid. MS ESI calculated for $C_7H_{31}F_3N_6O_2$ [M+H]$^+$, 529.25, found 529.30. $^1$H NMR (400 MHz, chloroform-d) δ 7.92 (s, 2H), 7.37-7.35 (m, 2H), 7.30-7.27 (m, 1H), 7.22 (d, J=7.9 Hz, 1H), 6.84 (s, 1H), 6.42 (s, 1H), 3.97 (s, 3H), 3.88-3.82 (m, 5H), 3.62-3.55 (m, 5H), 3.46-3.41 (m, 1H), 3.14-3.10 (m, 1H), 2.58-2.55 (m, 1H), 2.27-2.23 (m, 6H), 1.77-1.74 (m, 1H). $^{19}$F NMR (376 MHz, chloroform-d) 6-64.95 (3F).

Example 23: (3S)—N-(3-[2-[(1E)-3-hydroxyprop-1-en-1-yl]-6-(morpholin-4-yl)pyridin-4-yl]-4-methylphenyl)-3-(2,2,2-trifluoroethyl)pyrrolidine-1-carboxamide

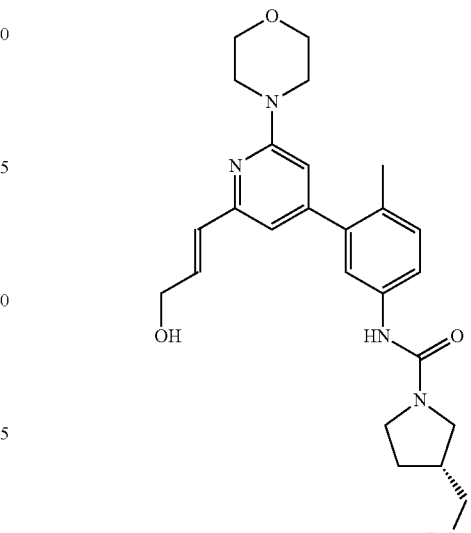

Synthetic Scheme

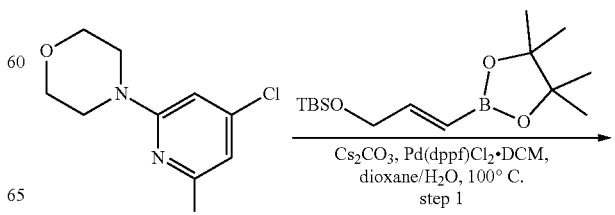

step 1

-continued

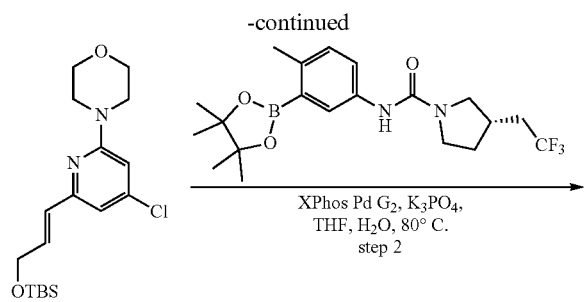

XPhos Pd G₂, K₃PO₄,
THF, H₂O, 80° C.
step 2

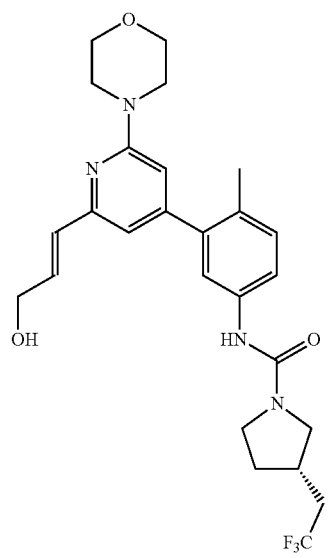

Preparation 23A: Step 1: (E)-4-(6-(3-((tert-butyldimethylsilyl)oxy)prop-1-en-1-yl)-4-chloropyridin-2-yl)morpholine

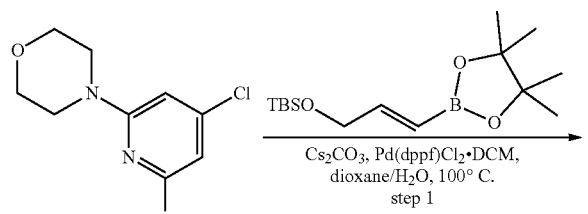

Cs₂CO₃, Pd(dppf)Cl₂·DCM,
dioxane/H₂O, 100° C.
step 1

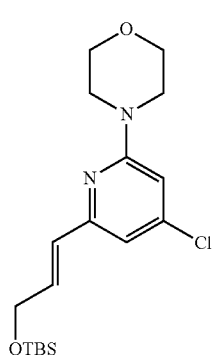

A mixture of 4-(4,6-dichloropyridin-2-yl)morpholine (0.60 g, 2.57 mmol) and tert-butyldimethyl[[(2E)-3-(4,4,5,5-tetramethyl-1,3,2-dioxaborolan-2-yl)prop-2-en-1-yl]oxy]silane (0.77 g, 2.57 mmol), 1,4-dioxane (6 mL), H₂O (0.6 mL), Cs₂CO₃ (3.00 g, 7.67 mmol) and Pd(dppf)Cl₂·CH₂C₂ (0.21 g, 0.26 mmol) was stirred for 16 h at 100° C. under nitrogen atmosphere. The reaction was quenched by the addition of water (20 mL). The resulting mixture was extracted with EtOAc (3×20 mL). The combined organic layers were washed with brine (20 mL), dried over anhydrous Na₂SO₄. After filtration, the filtrate was concentrated under reduced pressure. The residue was purified by silica gel column chromatography, eluted with PE/EtOAc (10/1) to afford (E)-4-(6-(3-((tert-butyldimethylsilyl)oxy)prop-1-en-1-yl)-4-chloropyridin-2-yl)morpholine (0.70 g, 74%) as a yellow oil. MS ESI calculated for $C_{18}H_{29}ClN_2O_2Si$ [M+H]⁺, 369.17, found 369.20. ¹H NMR (400 MHz, DMSO) δ 6.87-6.81 (m, 1H), 6.62 (d, J=1.4 Hz, 1H), 6.57-6.47 (m, 2H), 4.41 (dd, J=4.5, 2.0 Hz, 2H), 3.86-3.80 (m, 4H), 3.59-3.52 (m, 4H), 0.97 (s, 9H), 0.13 (s, 6H).

Example 23: (3S)—N-(3-[2-[(1E)-3-hydroxyprop-1-en-1-yl]-6-(morpholin-4-yl)pyridin-4-yl]-4-methylphenyl)-3-(2,2,2-trifluoroethyl)pyrrolidine-1-carboxamide

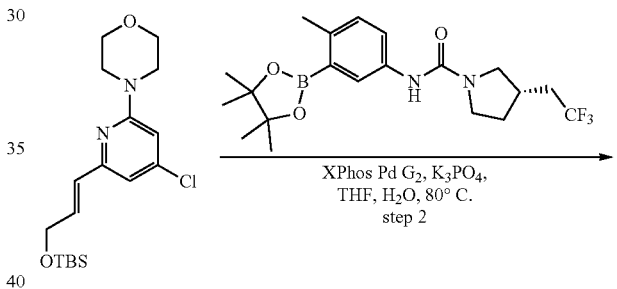

XPhos Pd G₂, K₃PO₄,
THF, H₂O, 80° C.
step 2

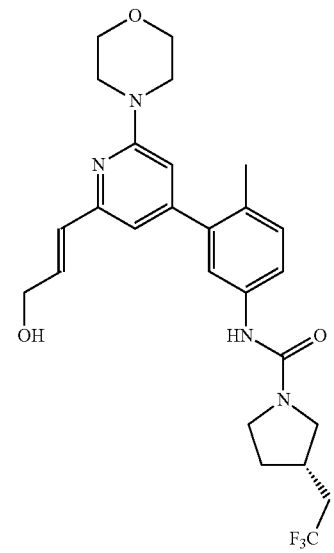 [SMILES: Cc1ccc(NC(=O)N2CC[C@@H](CC(F)(F)F)C2)cc1-c1cc(/C=C/CO)nc(N2CCOCC2)c1]

To a stirred solution of 4-[6-[(1E)-3-[(tert-butyldimethyl-silyl)oxy]prop-1-en-1-yl]-4-chloropyridin-2-yl]morpholine (400 mg, 1.084 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (447 mg, 1.084 mmol) in THF (4 mL) and H₂O (0.5 mL) were added XPhos palladium(II) biphenyl-2-amine chloride (85 mg, 0.108 mmol) and K₃PO₄ (460 mg, 2.168 mmol) under nitrogen atmosphere. The resulting mixture was stirred for 16 h at 80 degrees C. under nitrogen atmosphere. The mixture was allowed to cool down to room temperature. The reaction was quenched by the addition of water (20 mL). The resulting mixture was extracted with EtOAc (3×20 mL). The combined organic layers were washed with brine (2×10 mL), dried over anhydrous Na₂SO₄. After filtration, the filtrate was concentrated under reduced pressure. The residue was purified by silica gel column chromatography, eluted with PE/EtOAc/EtOH (12/3/1). The crude product was purified by Prep-HPLC with the following conditions Column: XBridge Prep C18 OBD Column, 19×150 mm, 5 um; Mobile Phase A: water (10 mmol/L NH₄HCO₃), Mobile Phase B: ACN; Flow rate: 20 mL/min; Gradient: 40 B to 60 B in 4.3 min; 254/210 nm to afford (3S)—N-(3-[2-[(1E)-3-hydroxyprop-1-en-1-yl]-6-(morpholin-4-yl)pyridin-4-yl]-4-methylphenyl)-3-(2,2,2-trifluoroethyl)pyrrolidine-1-carboxamide (97 mg, 18%) as a white solid. MS ESI calculated for C₂₆H₃₁F₃N₄O₃[M+H]⁺, 505.23, found 505.05. ¹H NMR (400 MHz, DMSO-d₆) δ 8.15 (s, 1H), 7.47-7.45 (m, 1H), 7.39 (d, J=2.3 Hz, 1H), 7.14 (d, J=8.4 Hz, 1H), 6.82-6.80 (m, 1H), 6.63 (d, J=1.0 Hz, 1H), 6.58 (d, J=1.1 Hz, 1H), 6.54-6.52 (m, 1H), 4.89 (t, J=5.5 Hz, 1H), 4.16 (t, J=4.7 Hz, 2H), 3.69-3.64 (m, 5H), 3.57-3.48 (m, 5H), 3.36-3.25 (m, 1H), 3.02 (t, J=9.4 Hz, 1H), 2.51-2.34 (m, 3H), 2.17 (s, 3H), 2.13-2.05 (m, 1H), 1.66 (m, 1H). ¹⁹F NMR (376 MHz, DMSO-d₆) δ −63.37 (3F).

Example 24: (3S)—N-[3-[2-(3-hydroxypropyl)-6-(morpholin-4-yl)pyridin-4-yl]-4-methylphenyl]-3-(2,2,2-trifluoroethyl)pyrrolidine-1-carboxamide

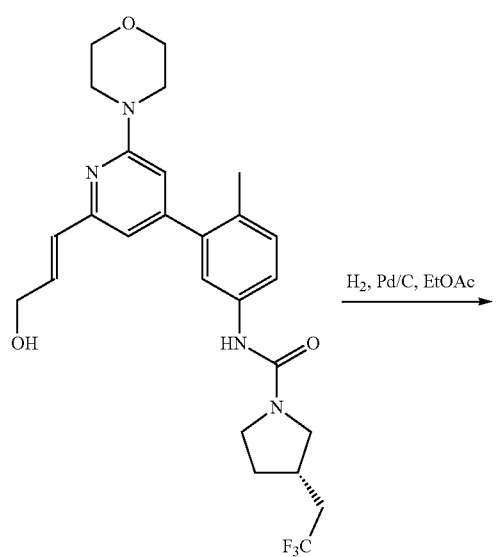

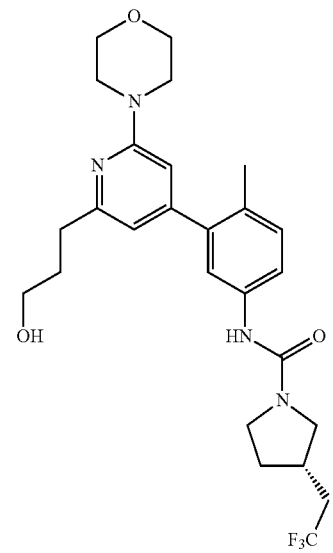

To a stirred mixture of (3S)—N-(3-[2-[(1E)-3-hydroxyprop-1-en-1-yl]-6-(morpholin-4-yl)pyridin-4-yl]-4-methylphenyl)-3-(2,2,2-trifluoroethyl)pyrrolidine-1-carboxamide (80 mg, 0.159 mmol) in EtOAc (2 mL) was added Pd/C (17 mg, 0.016 mmol, 10%) under hydrogen atmosphere. The resulting mixture was stirred for 3 h at room temperature under hydrogen atmosphere. The resulting mixture was filtered, the filter cake was washed with EtOAc (3×20 mL). The filtrate was concentrated under reduced pressure. The residue was purified by Prep-HPLC with the following conditions Column: XBridge Prep C18 OBD Column, 5 um, 19*150 mm; Mobile Phase A: water (10 mmol/L NH₄HCO₃), Mobile Phase B: CH₃CN; Flow rate: 20 mL/min; Gradient: 40 B to 60 B in 4.3 min; 254/210 nm to afford (3S)—N-[3-[2-(3-hydroxypropyl)-6-(morpholin-4-yl)pyridin-4-yl]-4-methylphenyl]-3-(2,2,2-trifluoroethyl)pyrrolidine-1-carboxamide (15 mg, 18%) as a white solid. MS ESI calculated for C₂₆H₃₃F₃N₄O₃[M+H]⁺, 507.25, found 507.05. ¹H NMR (400 MHz, DMSO-d₆) δ 8.16 (s, 1H), 7.46-7.44 (m, 1H), 7.38 (d, J=2.3 Hz, 1H), 7.14 (d, J=8.4 Hz, 1H), 6.54-6.51 (m, 2H), 3.68-3.64 (m, 5H), 3.57-3.28 (m, 9H), 3.02 (t, J=9.4 Hz, 1H), 2.66 (t, J=7.6 Hz, 2H), 2.51-2.34 (m, 3H), 2.17 (s, 3H), 2.13-2.05 (m, 1H), 1.83-1.78 (m, 2H), 1.66-1.62 (m, 1H). ¹⁹F NMR (376 MHz, DMSO-d₆) δ −63.37 (3F).

Example 25: (3S)—N-[3-[2-methoxy-6-(morpholin-4-yl)-[2,4-bipyridin]-4-yl]-4-methylphenyl]-3-(2,2,2-trifluoroethyl)pyrrolidine-1-carboxamide

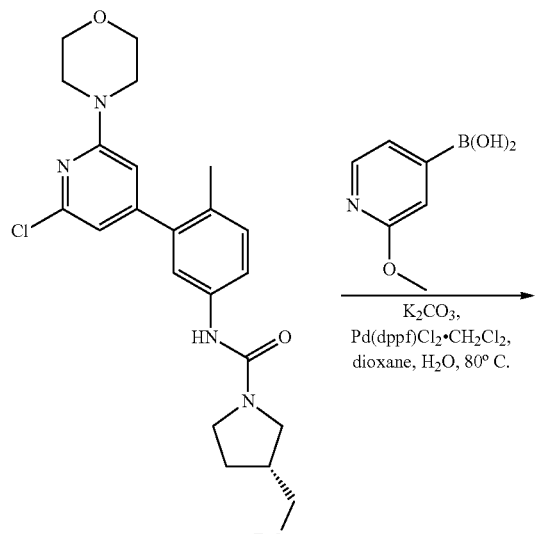

A mixture of (3S)—N-[3-[2-chloro-6-(morpholin-4-yl)pyridin-4-yl]-4-methylphenyl]-3-(2,2,2-trifluoroethyl)pyrrolidine-1-carboxamide (50 mg, 0.104 mmol), 2-methoxypyridin-4-ylboronic acid (32 mg, 0.207 mmol), 1,4-dioxane (1 mL), H$_2$O (0.25 mL), K$_2$CO$_3$ (43 mg, 0.311 mmol) and Pd(dppf)Cl$_2$.CH$_2$Cl$_2$ (8 mg, 0.010 mmol) was stirred for 2 h at 80 degrees C. under nitrogen atmosphere. The reaction was quenched by the addition of water (5 mL) at room temperature. The resulting mixture was extracted with EtOAc (3×20 mL). The combined organic layers were washed with brine (2×5 mL), dried over anhydrous Na$_2$SO$_4$. After filtration, the filtrate was concentrated under reduced pressure. The residue was purified by Prep-TLC with PE/EtOAc (1/1) to afford (3S)—N-[3-[2-methoxy-6-(morpholin-4-yl)-[2,4-bipyridin]-4-yl]-4-methylphenyl]-3-(2,2,2-trifluoroethyl)pyrrolidine-1-carboxamide (22.5 mg, 39%) as a white solid. MS ESI calculated for C$_{29}$H$_{32}$F$_3$N$_5$O$_3$ [M+H]$^+$, 556.25 found 556.30. $^1$H NMR (400 MHz, chloroform-d) δ 8.25 (d, J=5.4 Hz, 1H), 7.51 (d, J=5.4 Hz, 1H), 7.44 (s, 1H), 7.40-7.31 (m, 2H), 7.23 (d, J=8.1 Hz, 1H), 7.15 (d, J=1.0 Hz, 1H), 6.64 (d, J=0.9 Hz, 1H), 6.15 (s, 1H), 4.04 (s, 3H), 3.92-3.79 (m, 5H), 3.66-3.62 (m, 5H), 3.49-3.44 (m, 1H), 3.14 (t, J=9.4 Hz, 1H), 2.58-2.53 (m, 1H), 2.26-2.13 (m, 6H), 1.82-1.72 (m, 1H). $^{19}$F NMR (376 MHz, chloroform-d) 6-64.96 (3F).

Example 26: (3S)—N-[3-[2-(2-hydroxy-1,3-oxazol-5-yl)-6-(morpholin-4-yl)pyridin-4-yl]-4-methylphenyl]-3-(2,2,2-trifluoroethyl)pyrrolidine-1-carboxamide

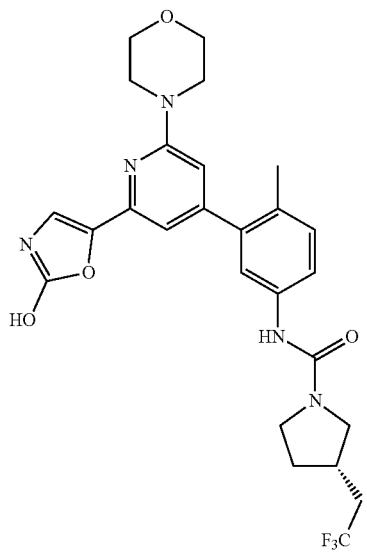 [SMILES: Cc1ccc(NC(=O)N2CC[C@@H](CC(F)(F)F)C2)cc1-c1cc(-c2cnc(O)o2)nc(N2CCOCC2)c1]

Synthetic Scheme

-continued

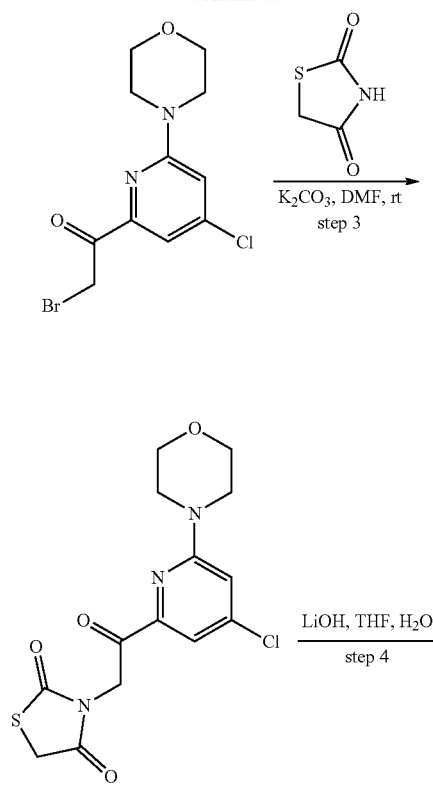

Preparation 26A: 4-[4-chloro-6-(1-ethoxyethenyl)pyridin-2-yl]morpholine

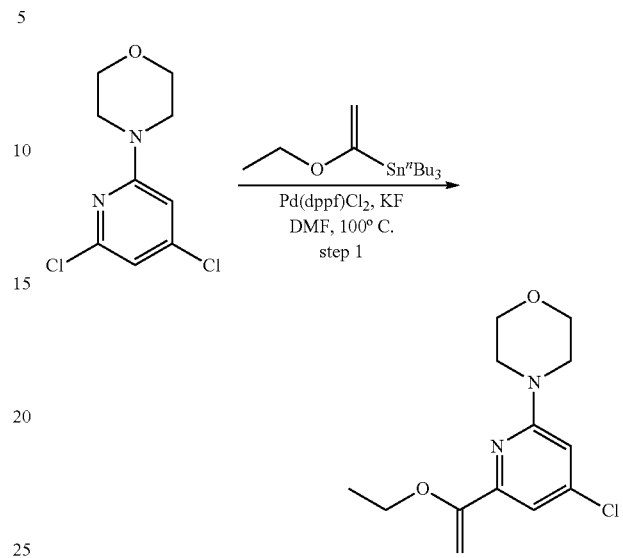

To a stirred solution of 4-(4,6-dichloropyridin-2-yl)morpholine (2 g, 8.580 mmol) and tributyl(1-ethoxyethenyl)stannane (3 g, 8.580 mmol) in DMF (20 mL) were added Pd(dppf)Cl$_2$·CH$_2$Cl$_2$ (0.70 g, 0.858 mmol) and KF (1 g, 17.161 mmol) at room temperature. The resulting mixture was stirred for 2 h at 100° C. under nitrogen atmosphere. The mixture was allowed to cool down to room temperature. The reaction was quenched by the addition of water (50 mL). The resulting mixture was extracted with EtOAc (3×50 mL). The combined organic layers were washed with brine (150 mL), dried over anhydrous Na$_2$SO$_4$. After filtration, the filtrate was concentrated under reduced pressure. The residue was purified by silica gel column chromatography, eluted with PE/EtOAc (5:1) to afford 4-[4-chloro-6-(1-ethoxyethenyl)pyridin-2-yl]morpholine (1.6 g, 69%) as a off-white solid. MS ESI calculated for C$_{13}$H$_{17}$ClN$_2$O$_2$[M+H]$^+$, 269.10; found 269.15. $^1$H NMR (300 MHz, chloroform-d) δ 7.09 (d, J=1.6 Hz, 1H), 6.60-6.43 (m, 1H), 5.39 (d, J=1.7 Hz, 1H), 4.32 (d, J=1.7 Hz, 1H), 3.94 (q, J=7.0 Hz, 2H), 3.86-3.77 (m, 4H), 3.60-3.54 (m, 4H), 1.40-1.30 (m, 3H).

Preparation 26B: 2-bromo-1-[4-chloro-6-(morpholin-4-yl)pyridin-2-yl]ethanone

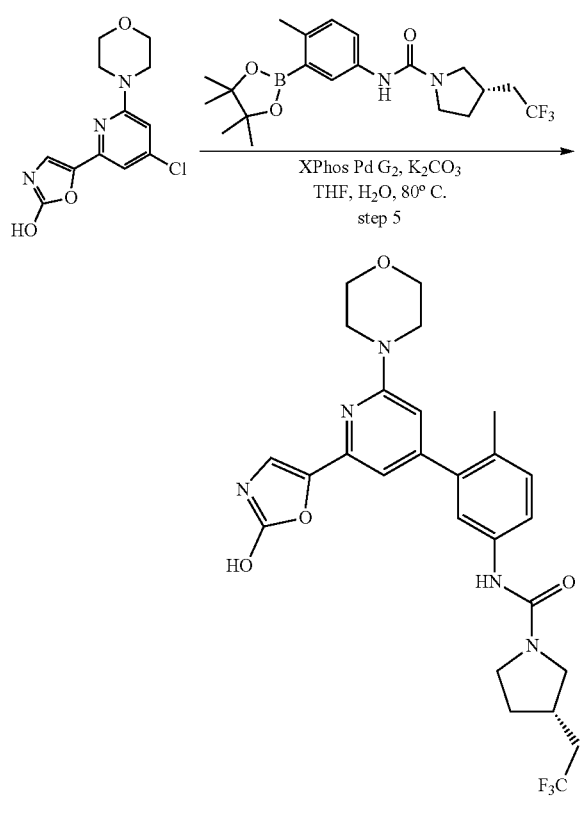

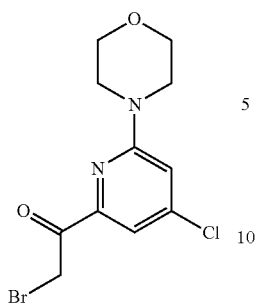

To a stirred solution of 4-[4-chloro-6-(1-ethoxyethenyl)pyridin-2-yl]morpholine (850 mg, 3.163 mmol) in THF (10 mL) and $H_2O$ (1 mL) was added NBS (563 mg, 3.163 mmol) at 0° C. The resulting mixture was stirred for 2 h at room temperature. The resulting mixture was concentrated under reduced pressure. The reaction was diluted with water (20 mL). The resulting mixture was extracted with EtOAc (3×20 mL). The combined organic layers were washed with brine (20 mL), dried over anhydrous $Na_2SO_4$. After filtration, the filtrate was concentrated under reduced pressure. The residue was purified by silica gel column chromatography, eluted with PE/EtOAc (5/1) to afford 2-bromo-1-[4-chloro-6-(morpholin-4-yl)pyridin-2-yl]ethanone (550 mg, 54%) as a light yellow solid. MS ESI calculated for $C_{11}H_{12}BrClN_2O_2$ [M+H]$^+$: 318.98, 320.98; found 318.95, 320.95. $^1$H NMR (400 MHz, chloroform-d) δ 7.44 (d, J=1.5 Hz, 1H), 6.84 (d, J=1.5 Hz, 1H), 4.73 (s, 2H), 3.91-3.83 (m, 4H), 3.63-3.54 (m, 4H).

Preparation 26C: 3-[2-[4-chloro-6-(morpholin-4-yl)pyridin-2-yl]-2-oxoethyl]-1,3-thiazolidine-2,4-dione

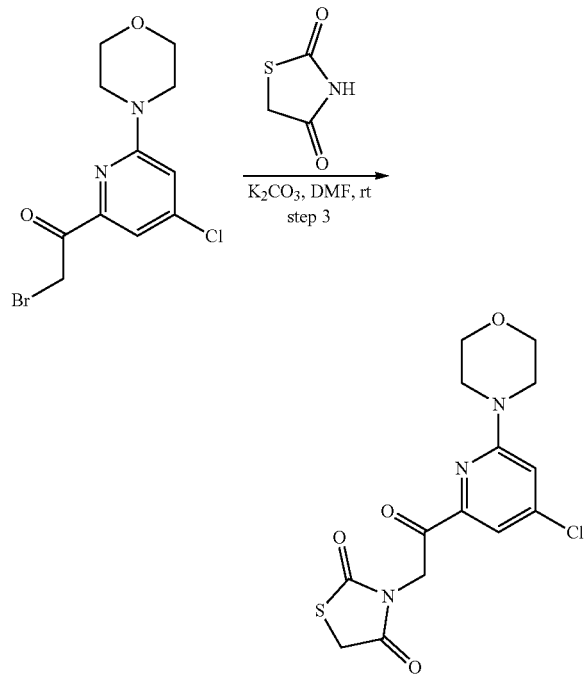

To a stirred solution of 2-bromo-1-[4-chloro-6-(morpholin-4-yl)pyridin-2-yl]ethanone (500 mg, 1.565 mmol) and $K_2CO_3$ (432 mg, 3.129 mmol) in DMF (5 mL) was added 2,4-thiazolidinedione (219 mg, 1.877 mmol) at room temperature. The resulting mixture was stirred for 2 h at room temperature. The reaction was quenched with water (10 mL) at room temperature. The resulting mixture was extracted with EtOAc (3×10 mL). The combined organic layers were washed with brine (10 mL), dried over anhydrous $Na_2SO_4$. After filtration, the filtrate was concentrated under reduced pressure to afford 3-[2-[4-chloro-6-(morpholin-4-yl)pyridin-2-yl]-2-oxoethyl]-1,3-thiazolidine-2,4-dione (450 mg, 81%) as a light yellow solid. MS ESI calculated for $C_{14}H_{14}ClN_3O_4S$ [M+H]$^+$356.04; found 356.10. $^1$H NMR (400 MHz, chloroform-d) δ 7.37 (d, J=1.5 Hz, 1H), 6.85 (d, J=1.5 Hz, 1H), 5.22 (s, 2H), 4.11 (s, 2H), 3.90-3.83 (m, 4H), 3.63-3.56 (m, 4H).

Preparation 26D: 5-[4-chloro-6-(morpholin-4-yl)pyridin-2-yl]-1,3-oxazol-2-ol

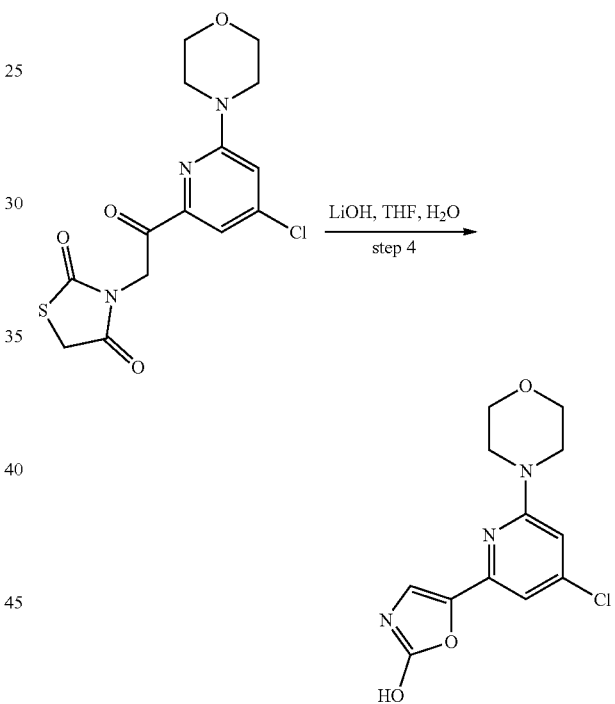

To a stirred solution of 3-[2-[4-chloro-6-(morpholin-4-yl)pyridin-2-yl]-2-oxoethyl]-1,3-thiazolidine-2,4-dione (480 mg, 1.349 mmol) in THF (5 mL) and $H_2O$ (2.3 mL) was added LiOH.$H_2O$ (2.7 mL, 2.698 mmol, 1 N). The resulting mixture was stirred for 2 h at room temperature. The mixture was allowed to cool down to 0 degrees C. To this was added HCl (1 N, 2.7 mL). The resulting mixture was concentrated under reduced pressure. The residue was purified by reverse flash chromatography with the following conditions: column, C18 column; mobile phase, $CH_3CN$ in water, 25% to 60% gradient in 20 min; detector, 254 nm to afford 5-[4-chloro-6-(morpholin-4-yl)pyridin-2-yl]-1,3-oxazol-2-ol (150 mg, 39%) as a light yellow solid. MS ESI calculated for $C_{12}H_{12}ClN_3O_3$ [M+H]$^+$282.06; found 282.10. $^1$H NMR (300 MHz, DMSO-d$_6$) δ 11.10 (s, 1H), 7.59 (s, 1H), 6.78-6.75 (m, 2H), 3.67 (t, J=4.8 Hz, 4H), 3.51 (t, J=4.8 Hz, 4H).

Example 26: (3S)—N-[3-[2-(2-hydroxy-1,3-oxazol-5-yl)-6-(morpholin-4-yl)pyridin-4-yl]-4-methylphenyl]-3-(2,2,2-trifluoroethyl)pyrrolidine-1-carboxamide

Example 27: (3S)—N-[3-[2-(2-hydroxypropan-2-yl)-6-(morpholin-4-yl)pyridin-4-yl]-4-methylphenyl]-3-(2,2,2-trifluoroethyl)pyrrolidine-1-carboxamide

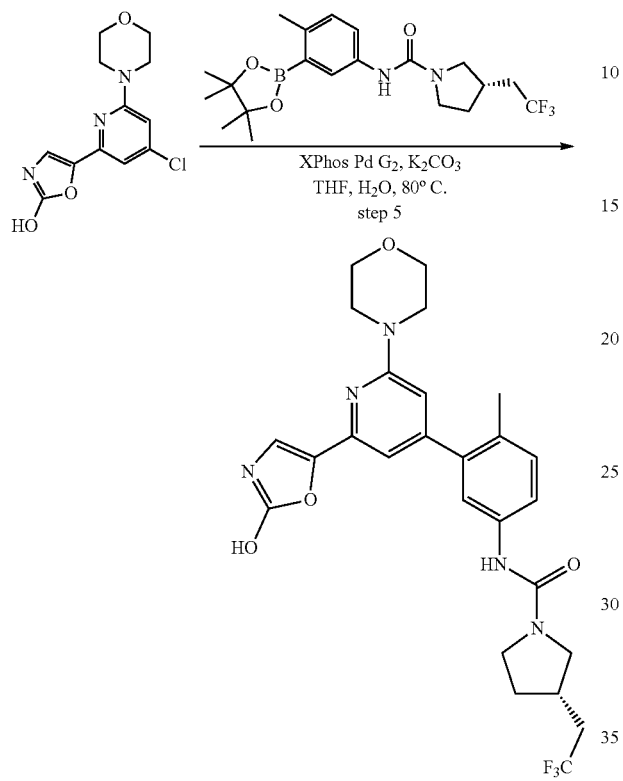

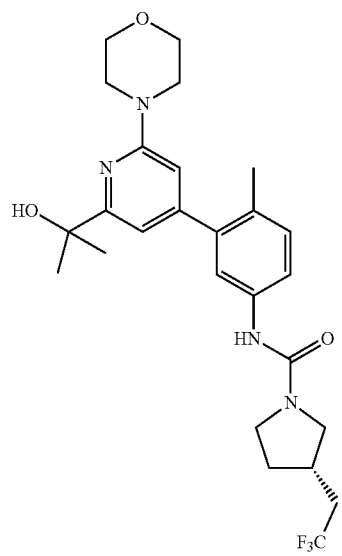 [SMILES: Cc1ccc(NC(=O)N2CC[C@@H](CC(F)(F)F)C2)cc1-c1cc(N2CCOCC2)nc(C(C)(C)O)c1]

Synthetic Scheme

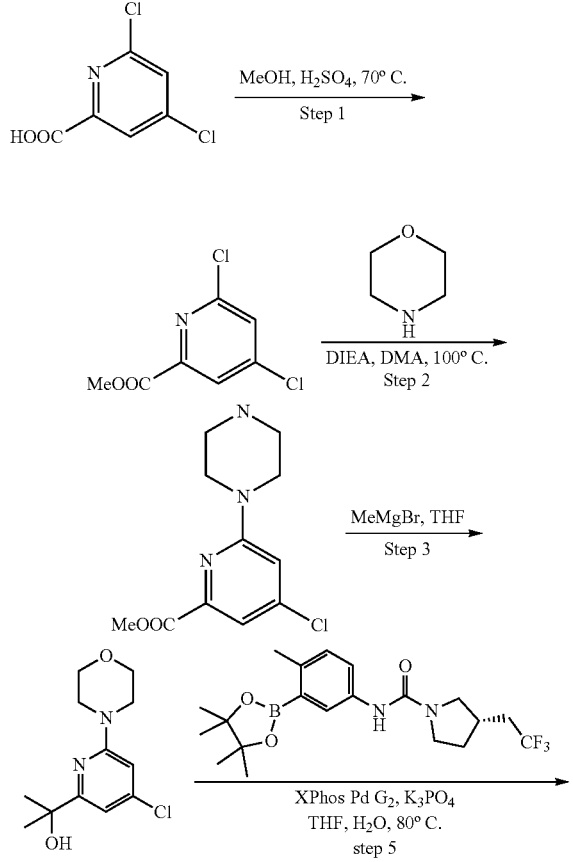

To a stirred solution of 5-[4-chloro-6-(morpholin-4-yl)pyridin-2-yl]-1,3-oxazol-2-ol (140 mg, 0.497 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (205 mg, 0.497 mmol) in THF (4 mL) and H$_2$O (0.4 mL) were added K$_2$CO$_3$ (206 mg, 1.491 mmol) and XPhos palladium(II) biphenyl-2-amine chloride (39 mg, 0.050 mmol) under nitrogen atmosphere. The resulting mixture was stirred for 16 h at 80 degrees C. under nitrogen atmosphere. The mixture was allowed to cool down to room temperature. The reaction was quenched with water (15 mL) at room temperature. The resulting mixture was extracted with EtOAc (3×15 mL). The combined organic layers were washed with brine (15 mL), dried over anhydrous Na$_2$SO$_4$. After filtration, the filtrate was concentrated under reduced pressure. The residue was purified by silica gel column chromatography, eluted with PE/EtOAc/EtOH (6/3/1) to afford (3S)—N-[3-[2-(2-hydroxy-1,3-oxazol-5-yl)-6-(morpholin-4-yl)pyridin-4-yl]-4-methylphenyl]-3-(2,2,2-trifluoroethyl)pyrrolidine-1-carboxamide (66 mg, 25%) as a light yellow solid. MS ESI calculated for C$_{28}$H$_{28}$F$_3$N$_5$O$_4$ [M+H]$^+$ 532.21, found 532.05. $^1$H NMR (400 MHz, DMSO-d$_6$) δ 11.01 (d, J=2.1 Hz, 1H), 8.18 (s, 1H), 7.57-7.47 (m, 2H), 7.41 (d, J=2.3 Hz, 1H), 7.16 (d, J=8.4 Hz, 1H), 6.70 (d, J=1.1 Hz, 1H), 6.64 (d, J=1.1 Hz, 1H), 3.73-3.66 (m, 5H), 3.53-3.51 (m, 5H), 3.33-3.30 (m, 1H), 3.03 (t, J=9.4 Hz, 1H), 2.51-2.34 (m, 3H), 2.19 (s, 3H), 2.13-2.05 (m, 1H), 1.66 (m, 1H). $^{19}$F NMR (376 MHz, DMSO-d$_6$) δ −63.37 (3F).

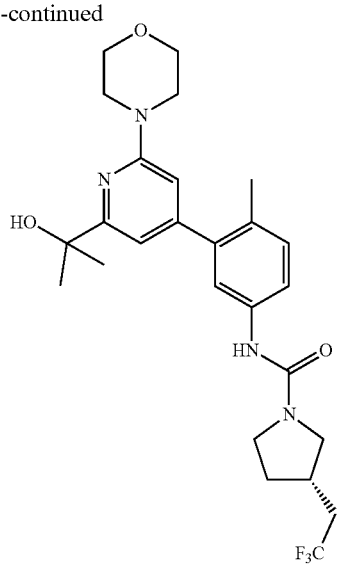

Preparation 27A: methyl 4,6-dichloropyridine-2-carboxylate

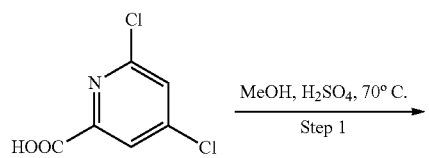

A mixture of 4,6-dichloropyridine-2-carboxylic acid (5.0 g, 26.04 mmol) and H$_2$SO$_4$ (2 mL) in MeOH (100 mL) was stirred for 16 h at 70 degrees C. The resulting mixture was concentrated under reduced pressure and diluted with water (50 mL). The pH value was adjusted to 8 with NaHCO$_3$ (sat.). The precipitated solids were collected by filtration, washed with water (2×30 mL), and dried in an oven under reduced pressure to afford methyl 4,6-dichloropyridine-2-carboxylate (5.2 g, 97%) as an off-white solid. $^1$H NMR (400 MHz, chloroform-d) 6 (d, J=1.7 Hz, 1H), 7.57 (d, J=1.7 Hz, 1H), 4.03 (s, 3H).

Preparation 27B: Methyl 4-chloro-6-(morpholin-4-yl)pyridine-2-carboxylate

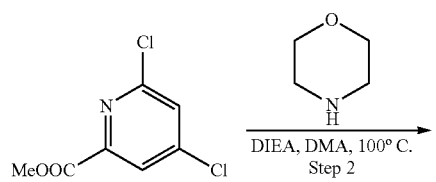

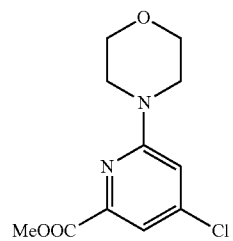

A mixture of methyl 4,6-dichloropyridine-2-carboxylate (2.00 g, 9.71 mmol), morpholine (1.01 g, 11.65 mmol) and DIEA (3.76 g, 29.12 mmol) in DMA (20 mL) was stirred for 4 h at 100 degrees C. The mixture was allowed to cool down to room temperature. The reaction was quenched with water (50 mL). The resulting mixture was extracted with EtOAc (50 mL). The organic layer was washed with brine (30 mL), dried over anhydrous Na$_2$SO$_4$. After filtration, the filtrate was concentrated under reduced pressure. The residue was purified by silica gel column chromatography, eluted with hexane/EtOAc (3/1) to afford methyl 4-chloro-6-(morpholin-4-yl)pyridine-2-carboxylate (0.5 g, 20%) as a yellow solid. MS ESI calculated for C$_{11}$H$_{13}$ClN$_2$O$_3$ [M+H]$^+$, 257.06 found 256.95. $^1$H NMR (400 MHz, chloroform-d) δ 7.44 (d, J=1.5 Hz, 1H), 6.77 (d, J=1.5 Hz, 1H), 3.95 (s, 3H), 3.86-3.77 (m, 4H), 3.60-3.55 (m, 4H).

Preparation 27C: 2-[4-chloro-6-(morpholin-4-yl)pyridin-2-yl]propan-2-ol

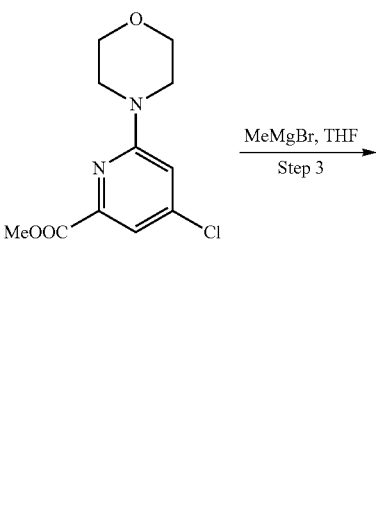

To a stirred solution of methyl 4-chloro-6-(morpholin-4-yl)pyridine-2-carboxylate (500 mg, 1.948 mmol) in THF (5 mL) was added MeMgBr (in 2-MeTHF, 3 M) (0.31 mL, 2.691 mmol) dropwise at −10 degrees C. under nitrogen atmosphere. The resulting mixture was stirred for 1 h at room temperature under nitrogen atmosphere. The reaction was quenched by the addition of sat. NH$_4$Cl (aq.) (20 mL). The resulting mixture was extracted with EtOAc (3×20 mL). The combined organic layers were washed with brine (10 mL), dried over anhydrous Na$_2$SO$_4$. After filtration, the filtrate was concentrated under reduced pressure. The residue was purified by silica gel column chromatography, eluted with PE/EtOAc (6/1) to afford 2-[4-chloro-6-(morpholin-4-yl)pyridin-2-yl]propan-2-ol (395 mg, 79%) as an off-white solid. MS ESI calculated for $C_{12}H_{17}ClN_2O_2[M+H]^+$, 257.10 found 257.20. $^1H$ NMR (400 MHz, chloroform-d) δ 6.72 (d, J=1.4 Hz, 1H), 6.52 (d, J=1.4 Hz, 1H), 4.76 (s, 1H), 3.87-3.82 (m, 4H), 3.57-3.52 (m, 4H), 1.51 (s, 6H).

Example 27: (3S)—N-[3-[2-(2-hydroxypropan-2-yl)-6-(morpholin-4-yl)pyridin-4-yl]-4-methylphenyl]-3-(2,2,2-trifluoroethyl)pyrrolidine-1-carboxamide methylphenyl]-3-(2,2,2-trifluoroethyl)pyrrolidine-1-carboxamide (159 mg, 40%) as a white solid. MS ESI calculated for $C_{26}H_{33}F_3N_4O_3[M+H]^+$, 507.25 found 507.30. $^1H$ NMR (400 MHz, DMSO-$d_6$) δ 8.16 (s, 1H), 7.46-7.44 (m, 1H), 7.38 (d, J=2.3 Hz, 1H), 7.14 (d, J=8.4 Hz, 1H), 6.89 (d, J=1.1 Hz, 1H), 6.54 (d, J=1.2 Hz, 1H), 5.06 (s, 1H), 3.76-3.61 (m, 5H), 3.56-3.44 (m, 5H), 3.30-3.28 (m, 1H), 3.02 (t, J=9.4 Hz, 1H), 2.49-2.38 (m, 3H), 2.17 (s, 3H), 2.13-2.03 (m, 1H), 1.66-1.64 (m, 1H), 1.43 (s, 6H). $^{19}F$ NMR (376 MHz, DMSO-$d_6$) δ −63.37 (3F).

Example 28: (3S)—N-[4-methyl-3-[2-(morpholin-4-yl)-6-(piperidin-3-yl)pyridin-4-yl]phenyl]-3-(2,2,2-trifluoroethyl)pyrrolidine-1-carboxamide

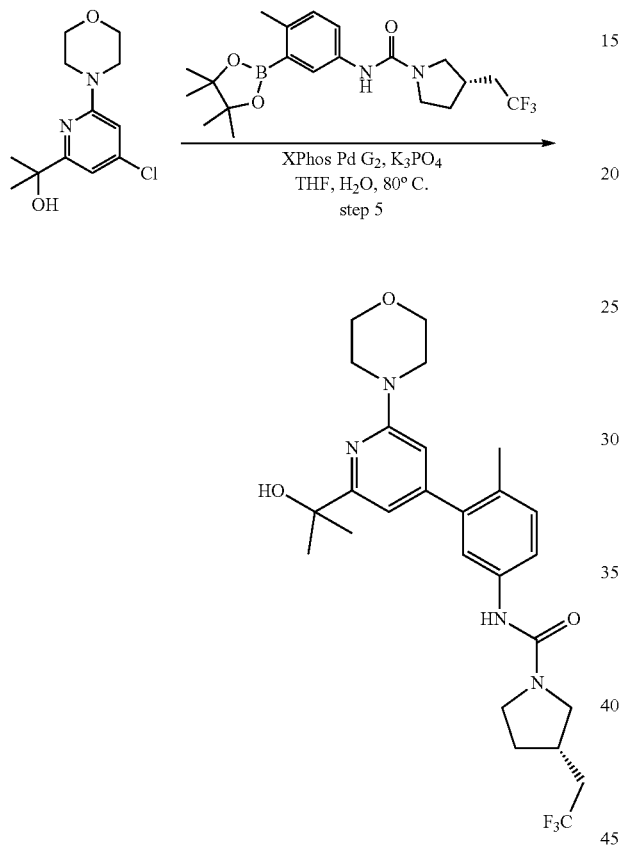

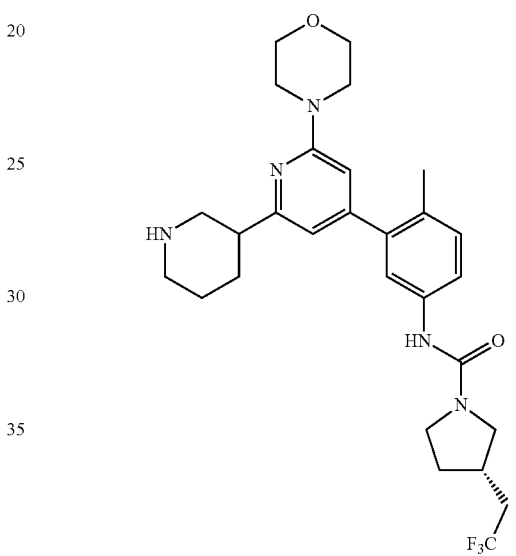

Synthetic Scheme

A mixture of 2-[4-chloro-6-(morpholin-4-yl)pyridin-2-yl]propan-2-ol (200 mg, 0.779 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (321 mg, 0.779 mmol), $K_3PO_4$ (331 mg, 1.558 mmol) in THF (2 mL) and $H_2O$ (0.2 mL) was stirred for 3 h at 80 degrees C. under nitrogen atmosphere. The mixture was allowed to cool down to room temperature. The reaction was quenched by the addition of water (20 mL) at room temperature. The resulting mixture was extracted with EtOAc (2×20 mL). The combined organic layers were washed with brine (20 mL), dried over anhydrous $Na_2SO_4$. After filtration, the filtrate was concentrated under reduced pressure. The residue was purified by reverse phase Flash chromatography with the following conditions: Column: WelFlash™ C18, 20-40 μm, 120 g; Eluent A: water (plus 10 mmol/L FA); Eluent B: $CH_3CN$; Gradient: 30%-50% B in 25 min; Flow rate: 60 mL/min; Detector: 220/254 nm to afford (3S)—N-[3-[2-(2-hydroxypropan-2-yl)-6-(morpholin-4-yl)pyridin-4-yl]-4-

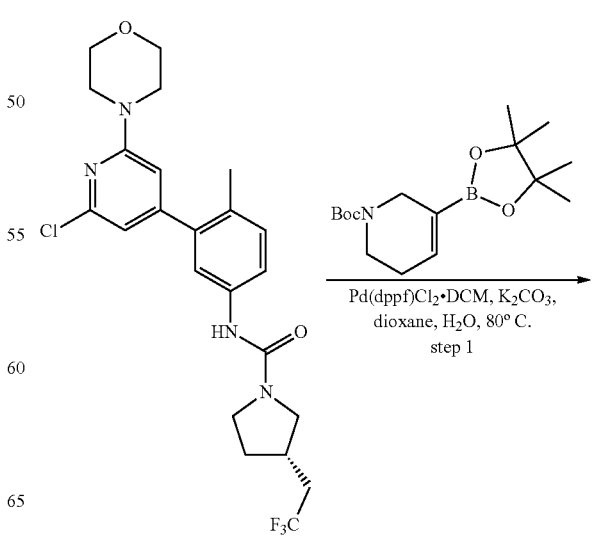

189

-continued

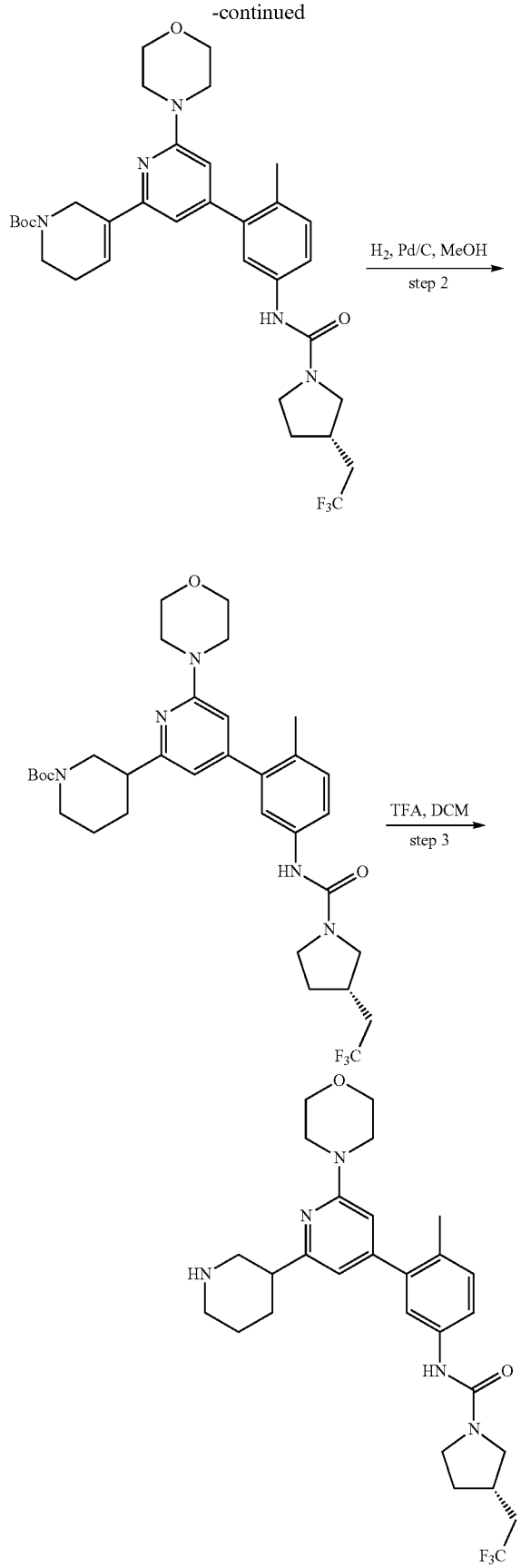

190

Preparation 28A: tert-butyl 4-[2-methyl-5-[(3S)-3-(2,2,2-trifluoroethyl)pyrrolidine-1-carbonylamino]phenyl]-6-(morpholin-4-yl)-5′,6′-dihydro-2′H-[2,3′-bipyridine]-1′-carboxylate

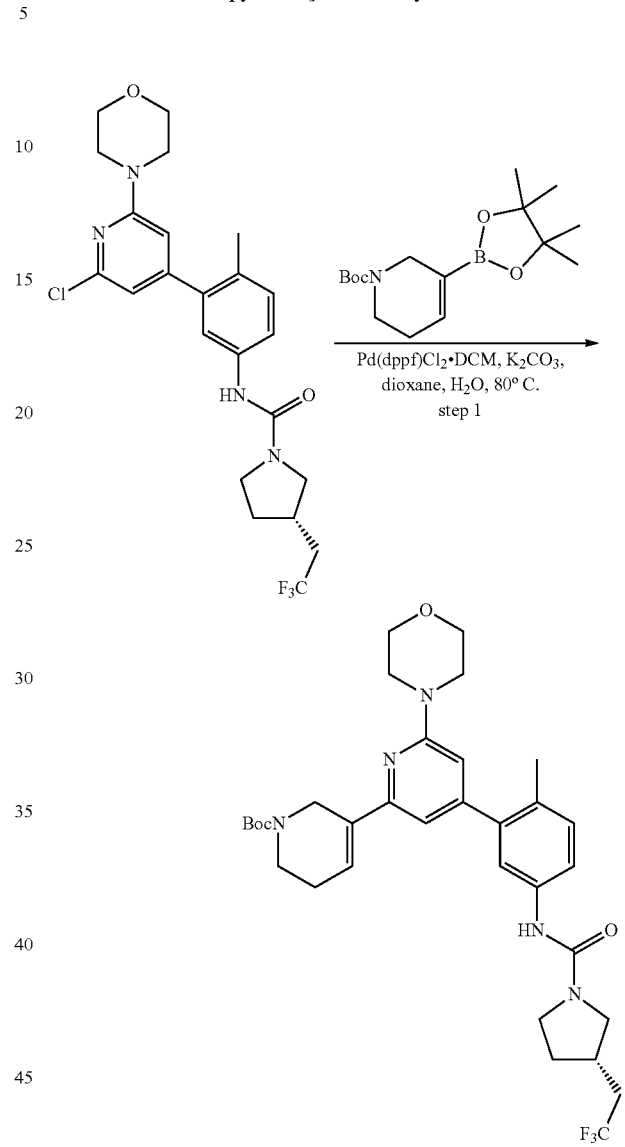

A mixture of (3S)—N-[3-[2-chloro-6-(morpholin-4-yl)pyridin-4-yl]-4-methylphenyl]-3-(2,2,2-trifluoroethyl)pyrrolidine-1-carboxamide (300 mg, 0.621 mmol), tert-butyl 3-(4,4,5,5-tetramethyl-1,3,2-dioxaborolan-2-yl)-5,6-dihydro-2H-pyridine-1-carboxylate (384 mg, 1.242 mmol), Pd(dppf)Cl$_2$.CH$_2$Cl$_2$ (51 mg, 0.062 mmol) and K$_2$CO$_3$ (258 mg, 1.864 mmol) in dioxane (4 mL) and H$_2$O (1 mL) was stirred at 80 degrees C. for 2 h under N$_2$ atmosphere. The mixture was allowed to cool down to room temperature. The resulting mixture was quenched with H$_2$O (10 mL) and extracted with EtOAc (3×10 mL). The combined organic layers were washed with brine (3×20 mL), dried over anhydrous Na$_2$SO$_4$. After filtration, the filtrate was concentrated under reduced pressure. The residue was purified by silica gel column chromatography, eluted with PE/EtOAc (1/1) to afford tert-butyl 4-[2-methyl-5-[(3S)-3-(2,2,2-trifluoroethyl)pyrrolidine-1-carbonylamino]phenyl]-6-(morpholin-4-yl)-5,6-dihydro-2H-[2,3-bipyridine]-1-carboxylate (350 mg, 89%) as yellow oil. MS ESI calculated for $C_{33}H_{42}F_3N_5O_4[M+H]^+$, 630.32 found 630.30. $^1$H NMR (400 MHz, chloroform-d) δ 7.37 (s, 1H), 7.19 (d, J=8.3 Hz, 2H), 6.77-6.75 (m, 1H), 6.47 (d, J=1.0 Hz, 1H), 6.23 (s, 1H), 4.43-4.41 (m, 2H), 3.84 (t, J=4.7 Hz, 4H), 3.82-3.78 (m, 1H), 3.70-3.53 (m, 8H), 3.45-3.42 (m, 1H), 3.13 (t, J=9.5 Hz, 1H), 2.57-2.50 (m, 1H), 2.35-2.24 (m, 4H), 2.22 (s, 3H), 2.09 (d, J=0.9 Hz, 1H), 1.80-1.71 (m, 1H), 1.51 (s, 9H).

Preparation 28B: tert-butyl 3-(4-[2-methyl-5-[(3S)-3-(2,2,2-trifluoroethyl)pyrrolidine-1-carbonylamino]phenyl]-6-(morpholin-4-yl)pyridin-2-yl)piperidine-1-carboxylate

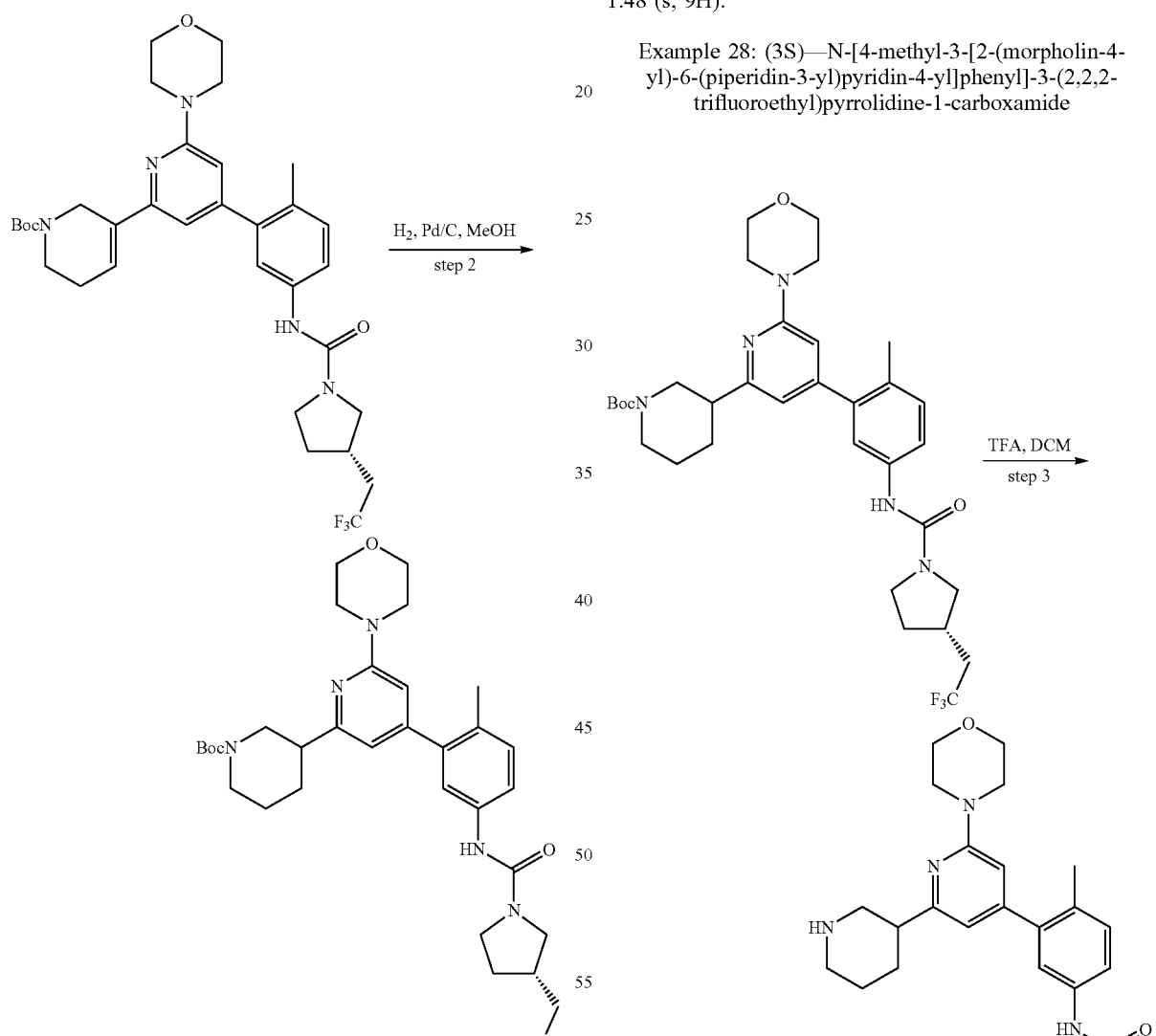

A mixture of tert-butyl 4-[2-methyl-5-[(3S)-3-(2,2,2-trifluoroethyl)pyrrolidine-1-carbonylamino]phenyl]-6-(morpholin-4-yl)-5,6-dihydro-2H-[2,3-bipyridine]-1-carboxylate (330 mg, 0.524 mmol), Pd/C (558 mg, 5.240 mmol) in MeOH (5 mL) stirred at room temperature for 1 h under H$_2$ atmosphere. The resulting mixture was filtered, and the filter cake was washed with methanol (3×50 mL). The filtrate was concentrated under reduced pressure. The residue was purified by silica gel column chromatography, eluted with PE/EtOAc/EtOH (8/3/1 to 4/3/1) to afford tert-butyl 3-(4-[2-methyl-5-[(3S)-3-(2,2,2-trifluoroethyl)pyrrolidine-1-carbonylamino]phenyl]-6-(morpholin-4-yl)pyridin-2-yl)piperidine-1-carboxylate (280 mg, 85%) as a white solid. MS ESI calculated for $C_{33}H_{44}F_3N_5O_4[M+H]^+$, 632.33 found 632.35. $^1$H NMR (400 MHz, chloroform-d) δ 7.36 (s, 1H), 7.19 (d, J=8.3 Hz, 2H), 6.52 (s, 1H), 6.42 (s, 1H), 6.22 (s, 1H), 4.37-4.22 (m, 1H), 4.19-4.08 (m, 1H), 3.88-3.83 (m, 4H), 3.82-3.77 (m, 1H), 3.64 (m, 1H), 3.55 (t, J=4.9 Hz, 4H), 3.45-3.41 (m, 1H), 3.13 (t, J=9.4 Hz, 1H), 2.98-2.95 (m, 1H), 2.80-2.69 (m, 2H), 2.57-2.55 (m, 1H), 2.27-2.24 (m, 3H), 2.22 (s, 3H), 2.07-2.03 (m, 1H), 1.76-1.72 (m, 4H), 1.48 (s, 9H).

Example 28: (3S)—N-[4-methyl-3-[2-(morpholin-4-yl)-6-(piperidin-3-yl)pyridin-4-yl]phenyl]-3-(2,2,2-trifluoroethyl)pyrrolidine-1-carboxamide A mixture of tert-butyl 3-(4-[2-methyl-5-[(3S)-3-(2,2,2-trifluoroethyl)pyrrolidine-1-carbonylamino]phenyl]-6-(morpholin-4-yl)pyridin-2-yl)piperidine-1-carboxylate (280 mg, 0.443 mmol) and TFA (1 mL) in DCM (5 mL) stirred at room temperature for 2 h. The resulting mixture was concentrated under reduced pressure. The residue was purified by reverse flash chromatography with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 40% B to 70% B in 30 min; 254/220 nm to afford (3S)—N-[4-methyl-3-[2-(morpholin-4-yl)-6-(piperidin-3-yl)pyridin-4-yl]phenyl]-3-(2,2,2-trifluoroethyl)pyrrolidine-1-carboxamide (160 mg, 68%) as a light pink solid. MS ESI calculated for C$_{28}$H$_{36}$F$_3$N$_5$O$_2$[M+H]$^+$, 532.28, found 532.15. $^1$H NMR (400 MHz, DMSO-d$_6$) δ 8.14 (s, 1H), 7.46-7.44 (m, 1H), 7.36 (d, J=2.3 Hz, 1H), 7.13 (d, J=8.4 Hz, 1H), 6.51 (s, 1H), 6.48 (s, 1H), 3.75-3.62 (m, 5H), 3.56-3.44 (m, 5H), 3.33-3.28 (m, 2H), 3.11-2.99 (m, 2H), 2.95-2.87 (m, 1H), 2.72-2.58 (m, 2H), 2.50-2.35 (m, 4H), 2.16 (s, 3H), 2.10-2.03 (m, 1H), 1.97-1.88 (m, 1H), 1.73-1.57 (m, 3H), 1.45 (m, 1H). $^{19}$F NMR (376 MHz, DMSO-d$_6$) δ −63.37 (3F).

Example 29: (3S)—N-[4-methyl-3-[2-(1-methylpiperidin-3-yl)-6-(morpholin-4-yl)pyridin-4-yl]phenyl]-3-(2,2,2-trifluoroethyl)pyrrolidine-1-carboxamide

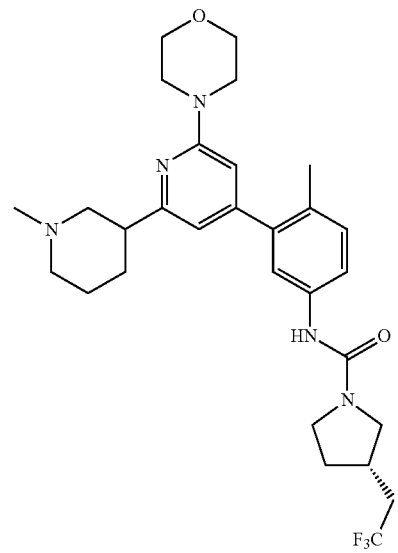

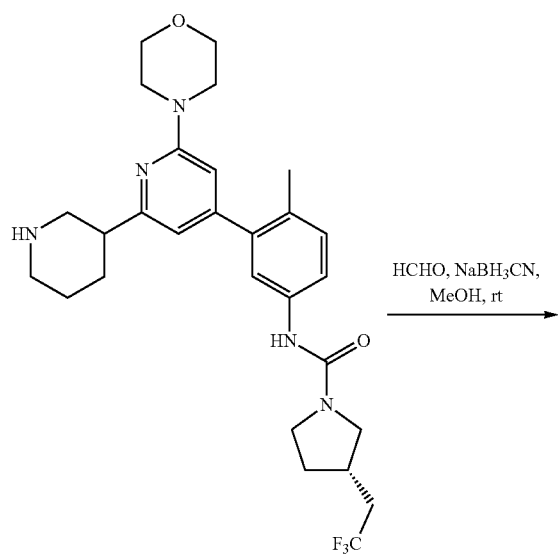

A mixture of (3S)—N-[4-methyl-3-[2-(morpholin-4-yl)-6-(piperidin-3-yl)pyridin-4-yl]phenyl]-3-(2,2,2-trifluoroethyl)pyrrolidine-1-carboxamide (150 mg, 0.282 mmol), HCHO (34 mg, 0.423 mmol, 37%) and NaBH$_3$CN (35 mg, 0.564 mmol) in MeOH (5 mL) stirred at room temperature for 2 h. The resulting mixture was concentrated under reduced pressure. The residue was purified by reverse flash chromatography with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 40% B to 70% B in 40 min; 254/220 nm to afford (3S)—N-[4-methyl-3-[2-(1-methylpiperidin-3-yl)-6-(morpholin-4-yl)pyridin-4-yl]phenyl]-3-(2,2,2-trifluoroethyl)pyrrolidine-1-carboxamide (69 mg, 45%) as a white solid. MS ESI calculated for C$_{29}$H$_{38}$F$_3$N$_5$O$_2$ [M+H]$^+$, 546.30 found 546.30. $^1$H NMR (400 MHz, DMSO-d$_6$) δ 8.14 (s, 1H), 7.46-7.44 (m, 1H), 7.35 (d, J=2.3 Hz, 1H), 7.13 (d, J=8.4 Hz, 1H), 6.52 (s, 1H), 6.51 (s, 1H), 3.75-3.62 (m, 5H), 3.57-3.42 (m, 5H), 3.30-3.28 (m, 1H), 3.02 (t, J=9.4 Hz, 1H), 2.91-2.87 (m, 1H), 2.78-2.75 (m, 2H), 2.49-2.36 (m, 3H), 2.18 (s, 3H), 2.16 (s, 3H), 2.12-1.98 (m, 2H), 1.85-1.82 (m, 2H), 1.72-1.43 (m, 4H). $^{19}$F NMR (376 MHz, DMSO-d$_6$) δ −63.37 (3F).

Example 30: (3S)—N-[3-[2-hydroxy-6-(morpholin-4-yl)-[2,4-bipyridin]-4-yl]-4-methylphenyl]-3-(2,2,2-trifluoroethyl)pyrrolidine-1-carboxamide

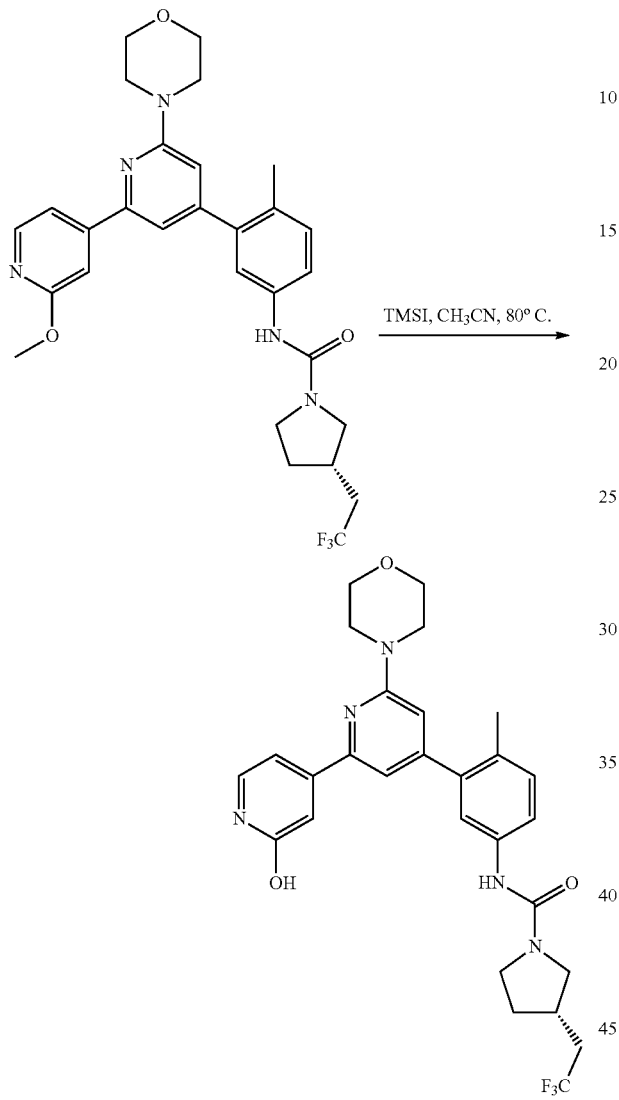

A mixture of (3S)—N-[3-[2-methoxy-6-(morpholin-4-yl)-[2,4-bipyridin]-4-yl]-4-methylphenyl]-3-(2,2,2-trifluoroethyl)pyrrolidine-1-carboxamide (100 mg, 0.180 mmol) and TMSI (72 mg, 0.360 mmol) in CH$_3$CN (2 mL) was stirred for 2 h at 80 degrees C. The reaction was quenched by the addition of water (10 mL) at room temperature. The resulting mixture was extracted with EtOAc (3×30 mL). The combined organic layers were washed with brine (2×5 mL), dried over anhydrous Na$_2$SO$_4$. After filtration, the filtrate was concentrated under reduced pressure. The residue was purified by Prep-TLC with PE/EtOAc (1/1) to afford (3S)—N-[3-[2-hydroxy-6-(morpholin-4-yl)-[2,4-bipyridin]-4-yl]-4-methylphenyl]-3-(2,2,2-trifluoroethyl)pyrrolidine-1-carboxamide (50.9 mg, 52%) as a white solid. MS ESI calculated for C$_{28}$H$_{30}$F$_3$N$_5$O$_3$[M+H]$^+$542.23, found 542.25. $^1$H NMR (400 MHz, chloroform-d) δ 7.49-7.48 (m, 1H), 7.38-7.33 (m, 5H), 7.15-7.04 (m, 2H), 6.66 (s, 1H), 6.25 (s, 1H), 3.87-3.85 (m, 5H), 3.65-3.63 (m, 5H), 3.40-3.35 (m, 1H), 3.14-3.12 (m, 1H), 2.59-2.56 (m, 1H), 2.25-1.78 (m, 6H), 1.80-1.75 (m, 1H). $^{19}$F NMR (376 MHz, chloroform-d) 6-64.96 (3F).

Example 31: (3S)—N-[4-methyl-3-[1'-methyl-6-(morpholin-4-yl)-3',6'-dihydro-2'H-[2,4'-bipyridin]-4-yl]phenyl]-3-(2,2,2-trifluoroethyl)pyrrolidine-1-carboxamide

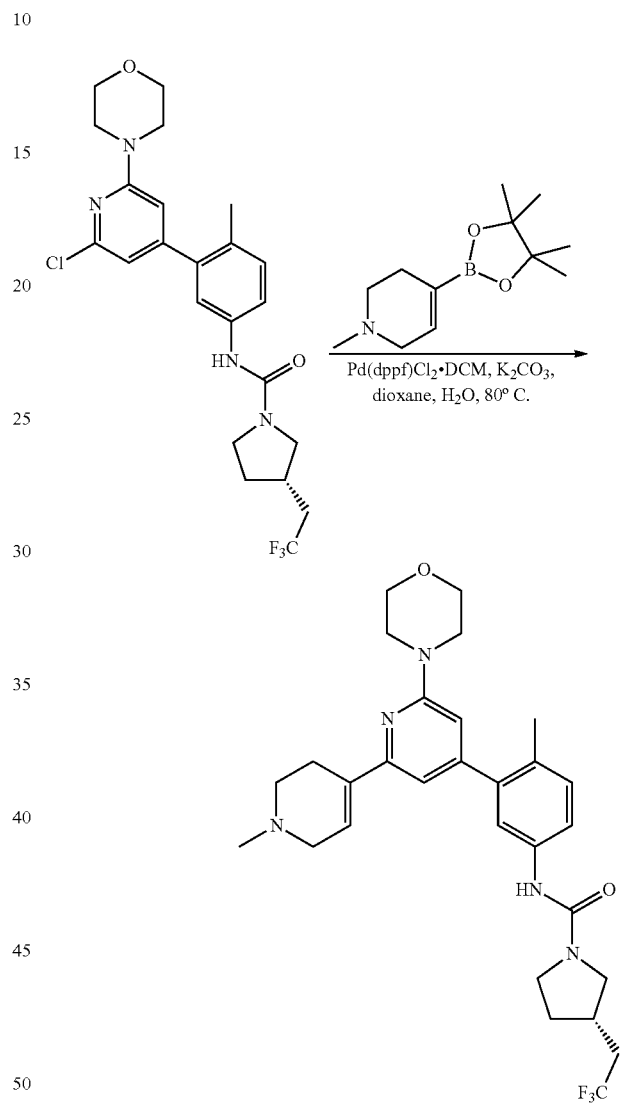

To a stirred mixture of (3S)—N-[3-[2-chloro-6-(morpholin-4-yl)pyridin-4-yl]-4-methylphenyl]-3-(2,2,2-trifluoroethyl)pyrrolidine-1-carboxamide (200 mg, 0.414 mmol) and 1-methyl-4-(4,4,5,5-tetramethyl-1,3,2-dioxaborolan-2-yl)-3,6-dihydro-2H-pyridine (231 mg, 1.035 mmol) in dioxane (4 mL) and H$_2$O (1 mL) were added Pd(dppf)Cl$_2$.CH$_2$Cl$_2$ (34 mg, 0.041 mmol) and K$_2$CO$_3$ (115 mg, 0.828 mmol) under nitrogen atmosphere. The resulting mixture was stirred at 80 degrees C. for 2 h under nitrogen atmosphere. The mixture was allowed to cool down to room temperature. The mixture was concentrated under reduced pressure. The residue was purified by reverse phase flash chromatography with the following conditions: Column: Spherical C18, 20-40 um, 120 g; Mobile Phase A: water (plus 5 mM NH$_4$HCO$_3$); Mobile Phase B: CH$_3$CN; Flow rate: 50 mL/min; Gradient: 5%-5% B, 10 min, 30% B-70% B gradient in 30 min; Detector: 220 nm to afford (3S)—N-[4-methyl-3-[1-methyl-6-(morpholin-4-yl)-3,6-dihydro-2H-[2,4-bipyridin]-4-yl]phenyl]-3-(2,2,2-trifluoroethyl)pyrrolidine-1-carboxamide (68 mg, 30%) as a yellow solid. MS ESI calculated for $C_{29}H_{36}F_3N_5O_2$ [M+H]$^+$, 544.28, found 544.15. $^1$H NMR (400 MHz, DMSO-d$_6$) δ 8.15 (s, 1H), 7.48-7.46 (m, 1H), 7.38 (d, J=2.3 Hz, 1H), 7.14 (d, J=8.4 Hz, 1H), 6.73 (s, 1H), 6.69 (dd, J=3.2, 3.2 Hz, 1H), 6.59 (s, 1H), 3.75-3.63 (m, 5H), 3.51-3.48 (m, 5H), 3.30-3.28 (m, 1H), 3.07-2.98 (m, 3H), 2.54-2.34 (m, 7H), 2.28 (s, 3H), 2.17 (s, 3H), 2.14-2.03 (m, 1H), 1.73-1.60 (m, 1H). $^{19}$F NMR (376 MHz, DMSO-d$_6$) δ −63.37 (3F).

Example 32: (3S)—N-[3-[2-(2-hydroxyethyl)-6-(morpholin-4-yl)pyridin-4-yl]-4-methylphenyl]-3-(2,2,2-trifluoroethyl)pyrrolidine-1-carboxamide

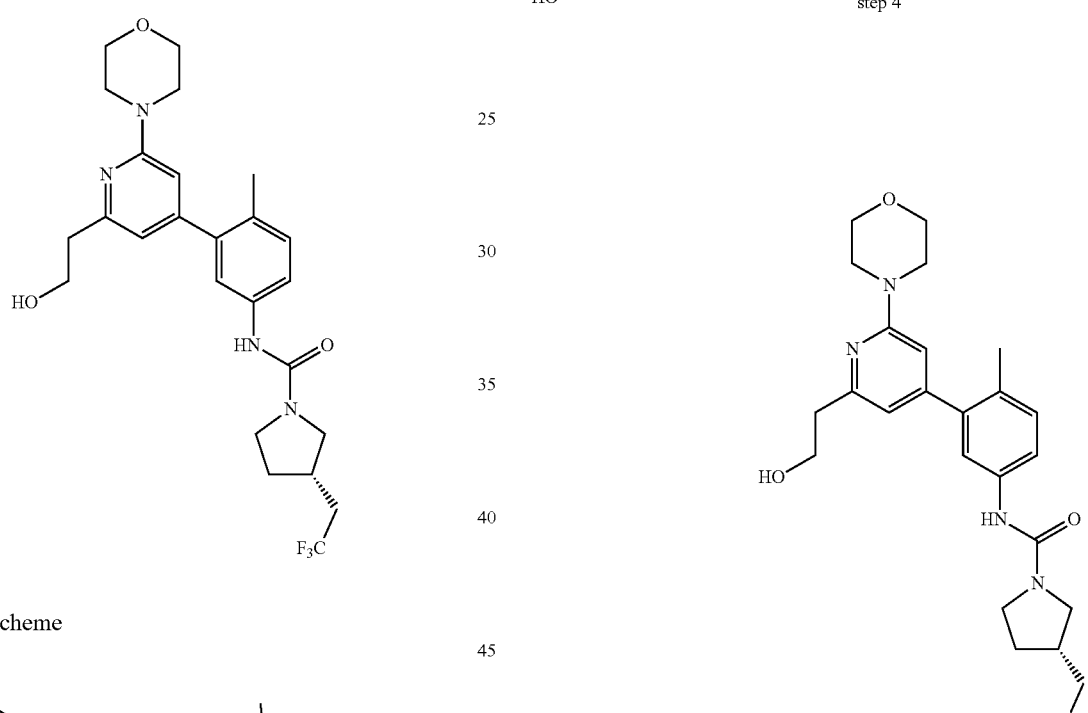

Synthetic Scheme

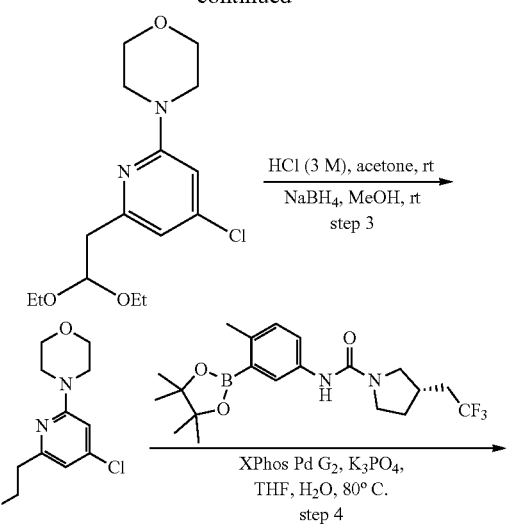

Preparation 32A: 4-[4-chloro-6-[(E)-2-ethoxyethenyl]pyridin-2-yl]morpholine

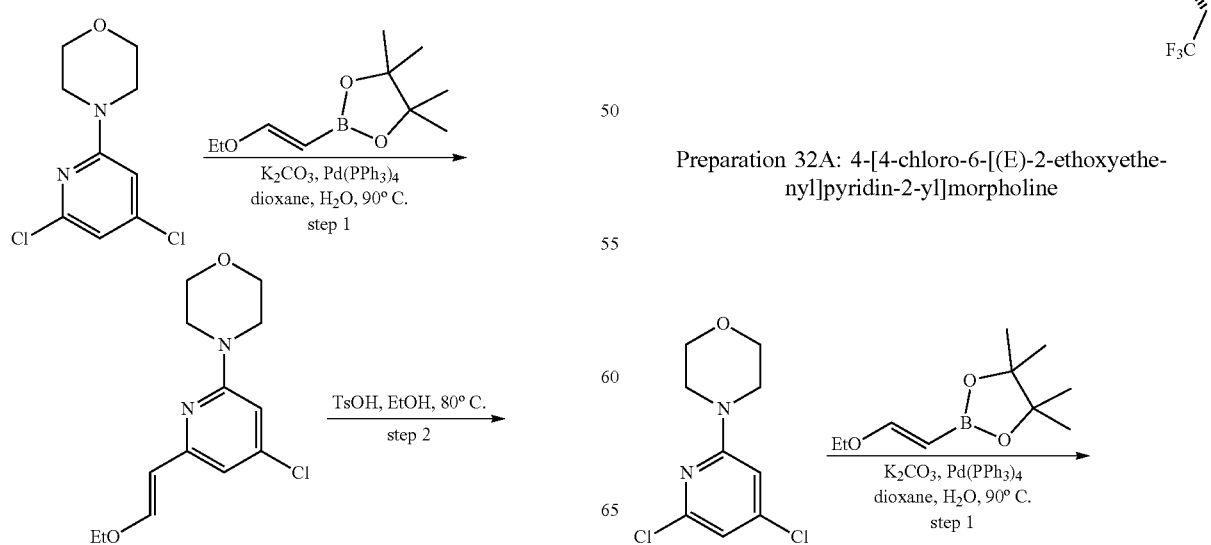

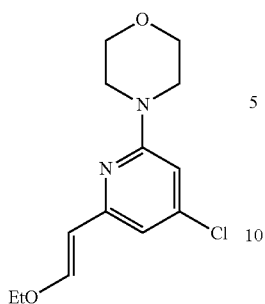

A mixture of 4-(4,6-dichloropyridin-2-yl)morpholine (1.30 g, 5.58 mmol), 2-[(E)-2-ethoxyethenyl]-4,4,5,5-tetramethyl-1,3,2-dioxaborolane (1.33 g, 6.69 mmol), Pd(PPh$_3$)$_4$ (0.64 g, 0.56 mmol) and K$_2$CO$_3$ (2.31 g, 16.72 mmol) in dioxane (12 mL) and H$_2$O (3 mL) was stirred for 16 h at 90 degrees C. under nitrogen atmosphere. The mixture was allowed to cool down to room temperature. The resulting mixture was diluted with water (30 mL). The resulting mixture was extracted with EtOAc (2×20 mL). The combined organic layers were washed with brine (30 mL), dried over anhydrous Na$_2$SO$_4$. After filtration, the filtrate was concentrated under reduced pressure. The residue was purified by silica gel column chromatography, eluted with PE/EtOAc (5/1) to afford 4-[4-chloro-6-[(E)-2-ethoxyethenyl]pyridin-2-yl]morpholine (0.95 g, 63%) as yellow oil. MS ESI calculated for C$_{13}$H$_{17}$ClN$_2$O$_2$[M+H]$^+$, 269.10 found 269.15. $^1$H NMR (400 MHz, chloroform-d) 6 (d, J=12.5 Hz, 1H), 6.43 (d, J=1.4 Hz, 1H), 6.38 (d, J=1.5 Hz, 1H), 5.70 (d, J=12.5 Hz, 1H), 3.95-3.91 (m, 2H), 3.86-3.78 (m, 4H), 3.55-3.48 (m, 4H), 1.37 (t, J=7.0 Hz, 3H).

Preparation 32B: 4-[4-chloro-6-(2,2-diethoxyethyl)pyridin-2-yl]morpholine

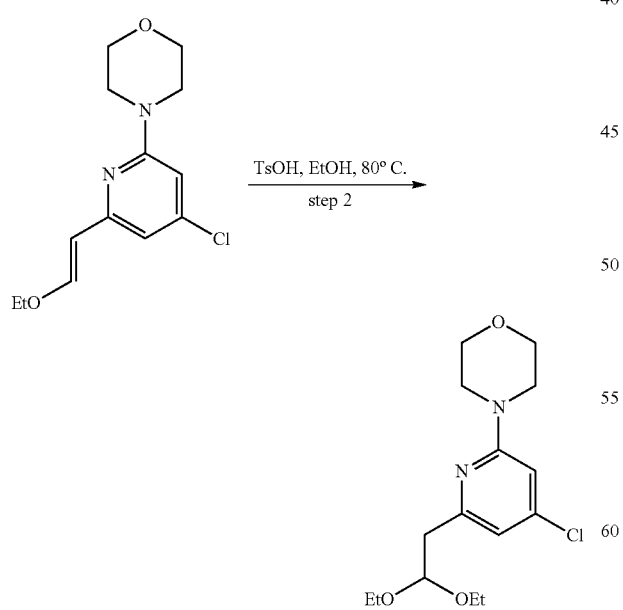

A mixture of 4-[4-chloro-6-[(E)-2-ethoxyethenyl]pyridin-2-yl]morpholine (850 mg, 3.185 mmol) and TsOH (55 mg, 0.319 mmol) in EtOH (15 mL) was stirred for 16 h at 80 degrees C. The resulting mixture was concentrated under reduced pressure. The residue was purified by silica gel column chromatography, eluted with PE/EtOAc (5/1) to afford 4-[4-chloro-6-(2,2-diethoxyethyl)pyridin-2-yl]morpholine (800 mg, 80%) as a yellow oil. C$_{15}$H$_{23}$ClN$_2$O$_3$, $^1$H NMR (400 MHz, chloroform-d) δ 6.61 (d, J=1.5 Hz, 1H), 6.45 (d, J=1.5 Hz, 1H), 4.92 (t, J=5.7 Hz, 1H), 3.83-3.79 (m, 4H), 3.58-3.42 (m, 8H), 2.94 (d, J=5.7 Hz, 2H), 1.17 (t, J=7.0 Hz, 6H).

Preparation 32C: 2-[4-chloro-6-(morpholin-4-yl)pyridin-2-yl]ethanol

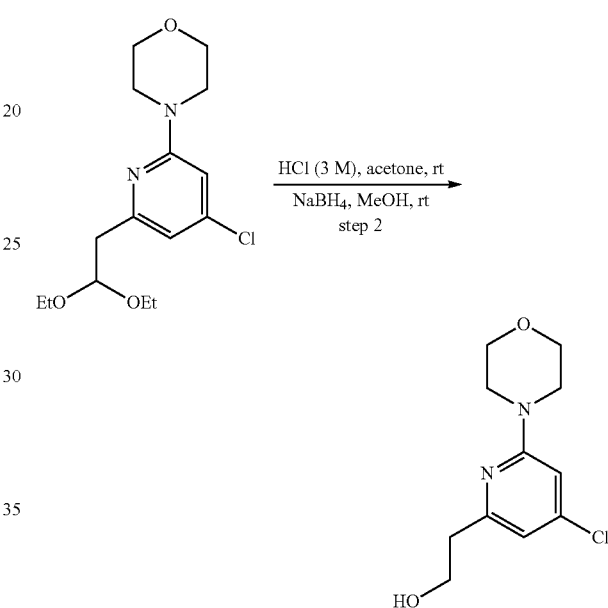

A mixture of 4-[4-chloro-6-(2,2-diethoxyethyl)pyridin-2-yl]morpholine (800 mg, 2.541 mmol) and HCl (aq, 3 M) (5 mL) in acetone (5 mL) was stirred for 3 h at room temperature. The mixture was neutralized to pH 7 with saturated NaHCO$_3$ (sat.). The resulting mixture was extracted with CH$_2$Cl$_2$ (3×20 mL). The combined organic layers were washed with brine (10 mL), dried over anhydrous Na$_2$SO$_4$. After filtration, the filtrate was concentrated under reduced pressure. To the above mixture was added MeOH (5 mL) and NaBH$_4$ (144 mg, 3.811 mmol) at room temperature. The resulting mixture was stirred for additional 2 h at room temperature. The reaction was quenched by the addition of water (20 mL). The resulting mixture was extracted with CH$_2$Cl$_2$ (3×20 mL). The combined organic layers were washed with brine (10 mL), dried over anhydrous Na$_2$SO$_4$. After filtration, the filtrate was concentrated under reduced pressure. The residue was purified by silica gel column chromatography, eluted with PE/EtOAc (2/1) to afford 2-[4-chloro-6-(morpholin-4-yl)pyridin-2-yl]ethanol (410 mg, 66%) as a yellow solid. MS ESI calculated for C$_{11}$H$_{15}$ClN$_2$O$_2$[M+H]$^+$, 243.08 found 243.15. $^1$H NMR (300 MHz, chloroform-d) δ 6.57 (d, J=1.5 Hz, 1H), 6.53 (d, J=1.5 Hz, 1H), 4.09 (s, 1H), 3.98 (t, J=5.5 Hz, 2H), 3.86-3.80 (m, 4H), 3.48-3.41 (m, 4H), 2.88 (t, J=5.4 Hz, 2H).

Example 32: (3S)—N-[3-[2-(2-hydroxyethyl)-6-(morpholin-4-yl)pyridin-4-yl]-4-methylphenyl]-3-(2,2,2-trifluoroethyl)pyrrolidine-1-carboxamide

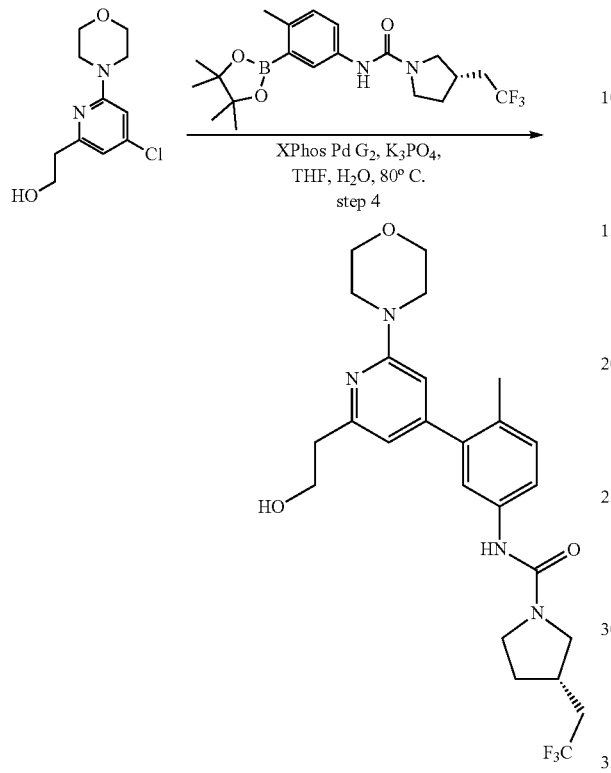

A mixture of 2-[4-chloro-6-(morpholin-4-yl)pyridin-2-yl]ethanol (200 mg, 0.824 mmol), Chloro(2-dicyclohexylphosphino-2',4',6'-triisopropyl-1,1'-biphenyl)[2-(2'-amino-1,1'-biphenyl)]palladium(II) (65 mg, 0.082 mmol), K$_3$PO$_4$ (350 mg, 1.648 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (340 mg, 0.824 mmol) in THF (2 mL) and H$_2$O (0.2 mL) was stirred for 3 h at 80 degrees C. under nitrogen atmosphere. The mixture was allowed to cool down to room temperature. The reaction was quenched by the addition of water (20 mL). The resulting mixture was extracted with EtOAc (2×20 mL). The combined organic layers were washed with brine (20 mL), dried over anhydrous Na$_2$SO$_4$. After filtration, the filtrate was concentrated under reduced pressure. The residue was purified by reverse phase Flash chromatography with the following conditions: Column: WelFlash™ C18, 20-40 µm, 120 g; Eluent A: water (plus 10 mmol/L FA); Eluent B: CH$_3$CN; Gradient: 30%-50% B in 25 min; Flow rate: 60 mL/min; Detector: 220/254 nm to afford (3S)—N-[3-[2-(2-hydroxyethyl)-6-(morpholin-4-yl)pyridin-4-yl]-4-methylphenyl]-3-(2,2,2-trifluoroethyl)pyrrolidine-1-carboxamide (100 mg, 25%) as a white solid. MS ESI calculated for C$_{25}$H$_{31}$F$_3$N$_4$O$_3$[M+H]$^+$, 493.23 found 493.30. $^1$H NMR (400 MHz, DMSO-d$_6$) δ 8.15 (s, 1H), 7.46-7.44 (m, 1H), 7.37 (d, J=2.3 Hz, 1H), 7.14 (d, J=8.4 Hz, 1H), 6.53 (s, 2H), 4.60 (s, 1H), 3.80-3.63 (m, 7H), 3.55-3.45 (m, 5H), 3.30-3.22 (m, 1H), 3.02 (t, J=9.5 Hz, 1H), 2.78 (t, J=6.9 Hz, 2H), 2.42-2.40 (m, 3H), 2.16 (s, 3H), 2.08-2.00 (m, 1H), 1.67-1.65 (m, 1H). $^{19}$F NMR (376 MHz, DMSO-d$_6$) δ −63.37 (3F).

Example 33: (3S)—N-[4-methyl-3-[2-(morpholin-4-yl)-6-(1H-pyrazol-4-yl)pyridin-4-yl]phenyl]-3-(2,2,2-trifluoroethyl)pyrrolidine-1-carboxamide

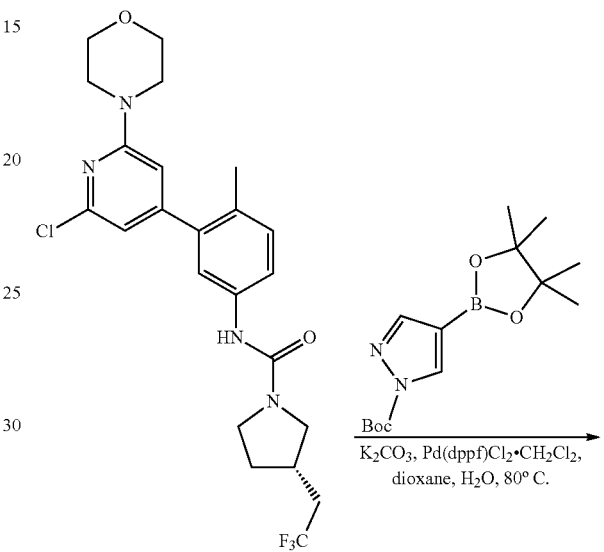

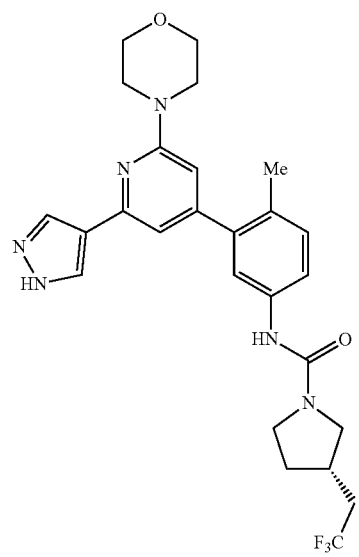

A mixture of tert-butyl 4-(4,4,5,5-tetramethyl-1,3,2-dioxaborolan-2-yl)pyrazole-1-carboxylate (150 mg, 0.510 mmol), (3S)—N-[3-[2-chloro-6-(morpholin-4-yl)pyridin-4-yl]-4-methylphenyl]-3-(2,2,2-trifluoroethyl)pyrrolidine-1-carboxamide (739 mg, 1.530 mmol), Pd(dppf)Cl$_2$·CH$_2$Cl$_2$ (42 mg, 0.051 mmol) and K$_2$CO$_3$ (211 mg, 1.530 mmol) in dioxane (4 mL) and H$_2$O (1 mL) was stirred at 80 degrees C. for 16 h under N$_2$ atmosphere. The mixture was allowed to cool down to room temperature. The resulting mixture was quenched with water (10 mL) and extracted with EtOAc (3×10 mL). The combined organic layers were washed with brine (3×5 mL), dried over anhydrous Na$_2$SO$_4$. After filtration, the filtrate was concentrated under reduced pressure. The residue was purified by reverse flash chromatography with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 40% B to 70% B in 40 min; 254/220 nm to afford (3S)—N-[4-methyl-3-[2-(morpholin-4-yl)-6-(1H-pyrazol-4-yl)pyridin-4-yl]phenyl]-3-(2,2,2-trifluoroethyl)pyrrolidine-1-carboxamide (99 mg, 38%) as a white solid. MS ESI calculated for C$_{26}$H$_{29}$F$_3$N$_6$O$_2$[M+H]$^+$, 515.23 found 515.20. $^1$H NMR (400 MHz, DMSO-d$_6$) δ 12.96 (s, 1H), 8.28 (s, 1H), 8.16 (s, 1H), 8.04 (s, 1H), 7.50-7.48 (m, 1H), 7.40 (d, J=2.3 Hz, 1H), 7.15 (d, J=8.4 Hz, 1H), 6.97 (d, J=1.0 Hz, 1H), 6.49 (d, J=1.1 Hz, 1H), 3.73-3.67 (m, 5H), 3.53-3.48 (m, 5H), 3.32-3.27 (m, 1H), 3.02 (t, J=9.4 Hz, 1H), 2.49-2.37 (m, 3H), 2.19 (s, 3H), 2.14-2.02 (m, 1H), 1.70-1.59 (m, 1H). $^{19}$F NMR (376 MHz, DMSO-d$_6$) δ −63.37 (3F).

Example 34: (3S)—N-[4-methyl-3-[2-(morpholin-4-yl)-6-(pyrrolidin-3-yl)pyridin-4-yl]phenyl]-3-(2,2,2-trifluoroethyl)pyrrolidine-1-carboxamide Synthetic Scheme

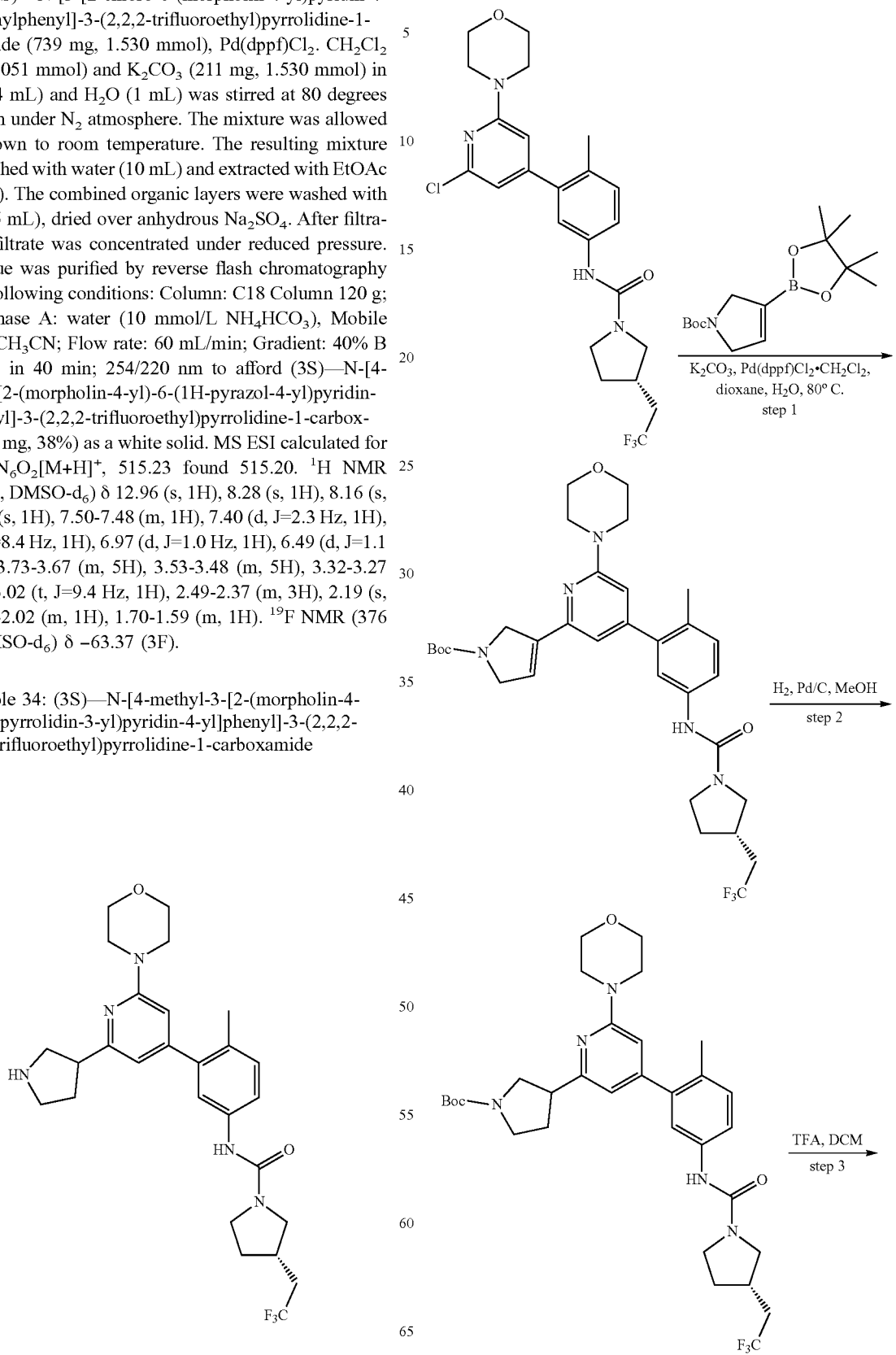

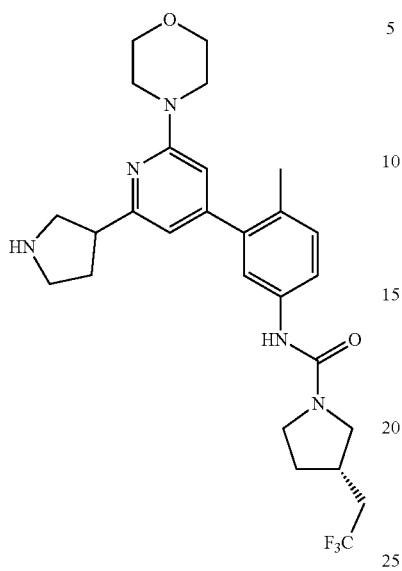

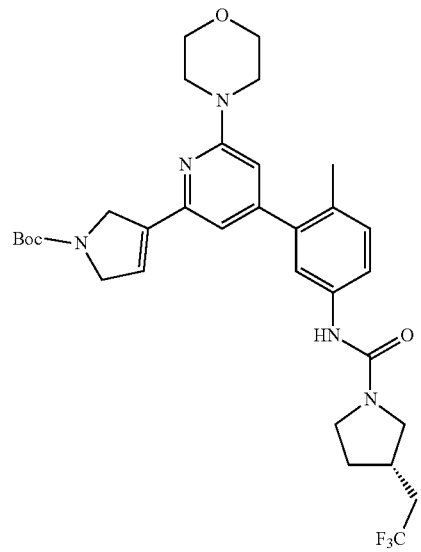

Preparation 34A: tert-butyl 3-(4-[2-methyl-5-[(3S)-3-(2,2,2-trifluoroethyl)pyrrolidine-1-carbonylamino]phenyl]-6-(morpholin-4-yl)pyridin-2-yl)-2,5-dihydropyrrole-1-carboxylate

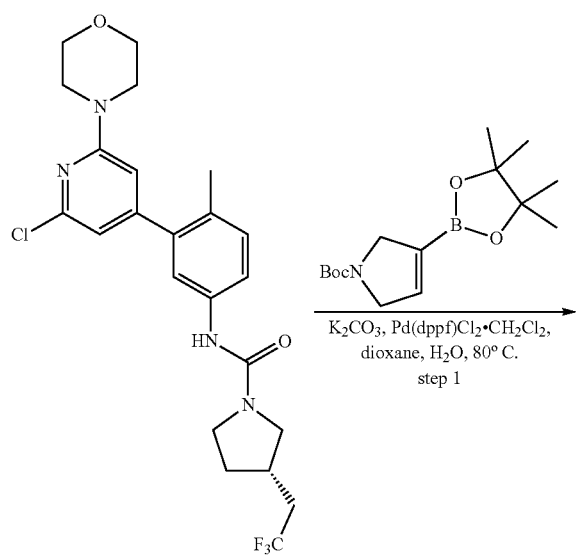

To a stirred mixture of (3S)—N-[3-[2-chloro-6-(morpholin-4-yl)pyridin-4-yl]-4-methylphenyl]-3-(2,2,2-trifluoroethyl)pyrrolidine-1-carboxamide (300 mg, 0.621 mmol) and tert-butyl 3-(4,4,5,5-tetramethyl-1,3,2-dioxaborolan-2-yl)-2,5-dihydropyrrole-1-carboxylate (367 mg, 1.242 mmol) in dioxane (4 mL) and H$_2$O (1 mL) were added Pd(dppf)Cl$_2$·CH$_2$Cl$_2$ (51 mg, 0.062 mmol) and K$_2$CO$_3$ (172 mg, 1.242 mmol) under nitrogen atmosphere. The resulting mixture was stirred at 80 degrees C. for 2 h under nitrogen atmosphere. The mixture was allowed to cool down to room temperature. The resulting mixture was concentrated under reduced pressure. The residue was purified by reverse phase flash chromatography with the following conditions: Column: Spherical C18, 20-40 um, 120 g; Mobile Phase A: water (plus 5 mM NH$_4$HCO$_3$); Mobile Phase B: CH$_3$CN; Flow rate: 50 mL/min; Gradient: 5%-5% B, 10 min, 30% B-70% B gradient in 30 min; Detector: 220 nm to afford tert-butyl 3-(4-[2-methyl-5-[(3S)-3-(2,2,2-trifluoroethyl)pyrrolidine-1-carbonylamino]phenyl]-6-(morpholin-4-yl)pyridin-2-yl)-2,5-dihydropyrrole-1-carboxylate (267 mg, 70%) as an off-white solid. MS ESI calculated for C$_{32}$H$_{40}$F$_3$N$_5$O$_4$[M+H]$^+$, 616.30, found 616.35. $^1$H NMR (400 MHz, chloroform-d) δ 7.38-7.27 (m, 2H), 7.18 (d, J=8.2 Hz, 1H), 6.67 (d, J=20.1 Hz, 1H), 6.54-6.38 (m, 2H), 6.25 (d, J=6.9 Hz, 1H), 4.57-4.55 (m, 1H), 4.48-4.46 (m, 1H), 4.34-4.30 (m, 2H), 3.81-3.75 (m, 5H), 3.67-3.44 (m, 6H), 3.11-3.09 (m, 1H), 2.55-2.50 (m, 1H), 2.33-2.16 (m, 6H), 1.73-1.70 (m, 1H), 1.53-1.50 (s, 9H).

Preparation 34B: tert-butyl 3-(4-[2-methyl-5-[(3S)-3-(2,2,2-trifluoroethyl)pyrrolidine-1-carbonylamino]phenyl]-6-(morpholin-4-yl)pyridin-2-yl)pyrrolidine-1-carboxylate

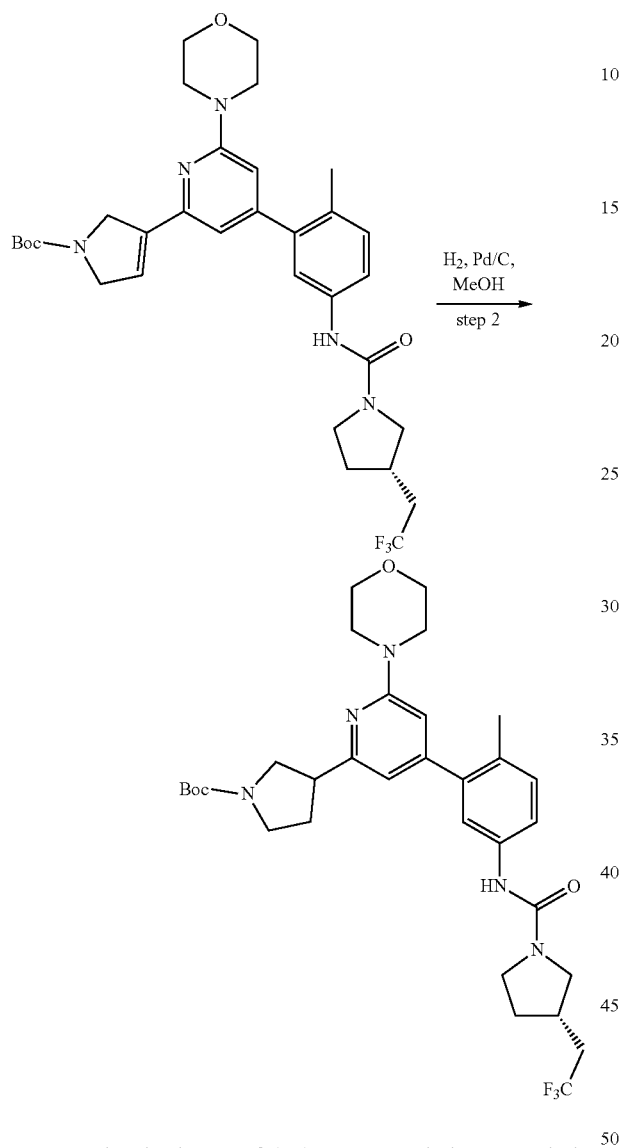

To a stirred mixture of (3S)—N-[4-methyl-3-[1-methyl-6-(morpholin-4-yl)-3,6-dihydro-2H-[2,4-bipyridin]-4-yl]phenyl]-3-(2,2,2-trifluoroethyl)pyrrolidine-1-carboxamide (110 mg, 0.202 mmol) in MeOH (3 mL) was added Pd/C (50 mg) under $N_2$ atmosphere. The resulting mixture was stirred for 30 min at room temperature under hydrogen atmosphere. The resulting mixture was filtered, the filter cake was washed with MeOH (3×10 mL). The filtrate was concentrated under reduced pressure. The residue was purified by silica gel column chromatography, eluted with PE/EtOAc (3/2 to 3/7) to afford tert-butyl 3-(4-[2-methyl-5-[(3S)-3-(2,2,2-trifluoroethyl)pyrrolidine-1-carbonylamino]phenyl]-6-(morpholin-4-yl)pyridin-2-yl)pyrrolidine-1-carboxylate (189 mg, 71%) as a white solid. MS ESI calculated for $C_{32}H_{42}F_3N_5O_4[M+H]^+$, 618.32, found 618.35. $^1$H NMR (400 MHz, chloroform-d) δ 7.37-7.24 (m, 2H), 7.18 (d, J=8.5 Hz, 1H), 6.52 (s, 1H), 6.43 (s, 1H), 6.22 (s, 1H), 3.87-3.69 (m, 6H), 3.67-3.59 (m, 2H), 3.54-3.34 (m, 8H), 3.12-3.10 (m, 1H), 2.56-2.52 (m, 1H), 2.27-2.17 (m, 7H), 1.82-1.68 (m, 2H), 1.49 (s, 9H).

Example 34: (3S)—N-[4-methyl-3-[2-(morpholin-4-yl)-6-(pyrrolidin-3-yl)pyridin-4-yl]phenyl]-3-(2,2,2-trifluoroethyl)pyrrolidine-1-carboxamide

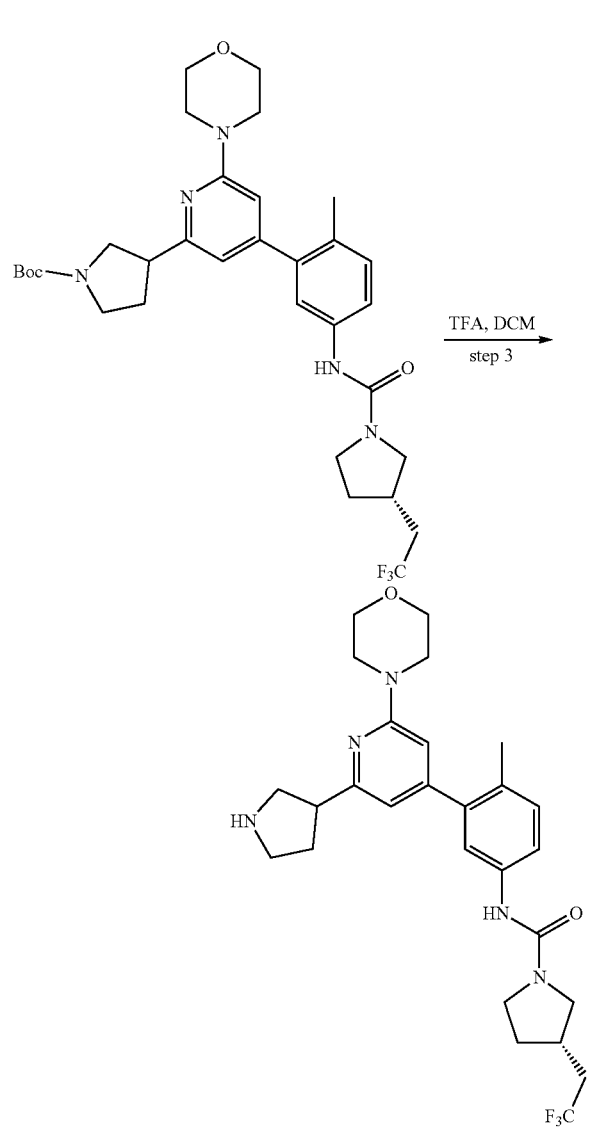

To a stirred mixture of tert-butyl 3-(4-[2-methyl-5-[(3S)-3-(2,2,2-trifluoroethyl)pyrrolidine-1-carbonylamino]phenyl]-6-(morpholin-4-yl)pyridin-2-yl)pyrrolidine-1-carboxylate (150 mg, 0.243 mmol) in DCM (3 mL) were added TFA (1 mL) at room temperature. The resulting mixture was stirred for 2 h and concentrated under reduced pressure. The residue was purified by reverse phase flash chromatography with the following conditions: Column: Spherical C18, 20-40 um, 120 g; Mobile Phase A: water (plus 10% $NH_4HCO_3$); Mobile Phase B: $CH_3CN$; Flow rate: 50 mL/min; Gradient: 5%-5% B, 10 min, 30% B-70% B gradient in 30 min; Detector: 220 nm to afford ((3S)—N-[4-methyl-3-[2-(morpholin-4-yl)-6-(pyrrolidin-3-yl)pyridin-4-yl]phenyl]-3-(2,2,2-trifluoroethyl)pyrrolidine-1-carboxamide (11.5 mg, 9%) as an off-white solid. MS ESI calculated for $C_{27}H_{34}F_3N_5O_2$ [M+H]$^+$, 518.27, found 518.25. $^1$H NMR (400 MHz, DMSO-d$_6$) δ 8.16 (s, 1H), 7.44-7.42 (m, 1H), 7.39 (d, J=2.3 Hz, 1H), 7.14 (d, J=8.3 Hz, 1H), 6.59 (s, 1H), 6.57 (s, 1H), 3.68-3.62 (m, 5H), 3.48-2.97 (m, 15H), 2.51-2.34 (m, 2H), 2.16-1.93 (m, 5H), 1.73-1.58 (m, 1H). $^{19}$F NMR (376 MHz, DMSO-d$_6$) δ −63.37 (3F).
Example 35: (3S)—N-[4-methyl-3-[2-(1-methyl-2,5-dihydropyrrol-3-yl)-6-(morpholin-4-yl)pyridin-4-yl]phenyl]-3-(2,2,2-trifluoroethyl)pyrrolidine-1-carboxamide
Synthetic Scheme
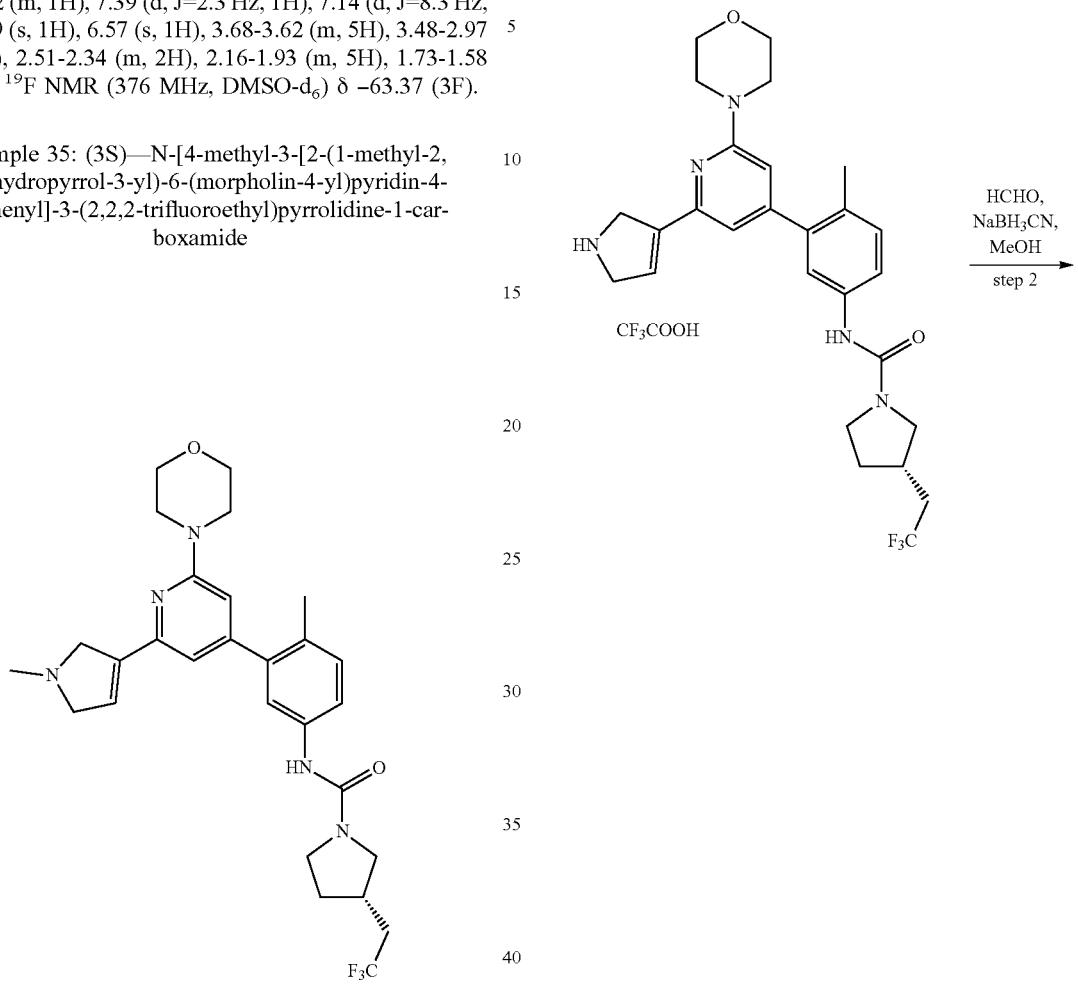
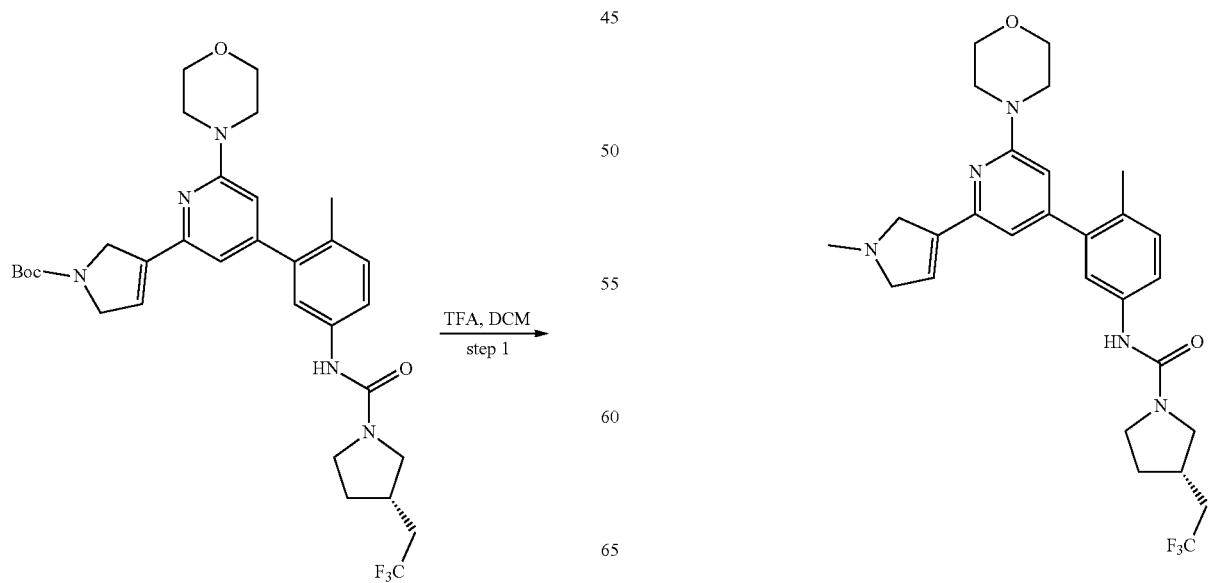

211

Preparation 35A: (3S)—N-[4-methyl-3-[2-(morpholin-4-yl)-6-(pyrrolidin-3-yl)pyridin-4-yl]phenyl]-3-(2,2,2-trifluoroethyl)pyrrolidine-1-carboxamide

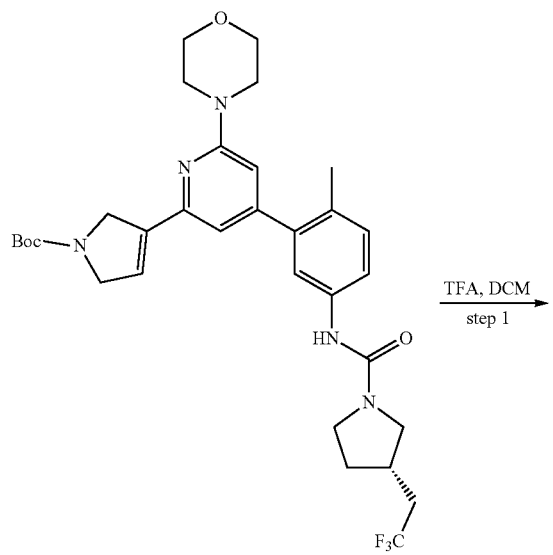

212

Example 35: (3S)—N-[4-methyl-3-[2-(1-methyl-2,5-dihydropyrrol-3-yl)-6-(morpholin-4-yl)pyridin-4-yl]phenyl]-3-(2,2,2-trifluoroethyl)pyrrolidine-1-carboxamide

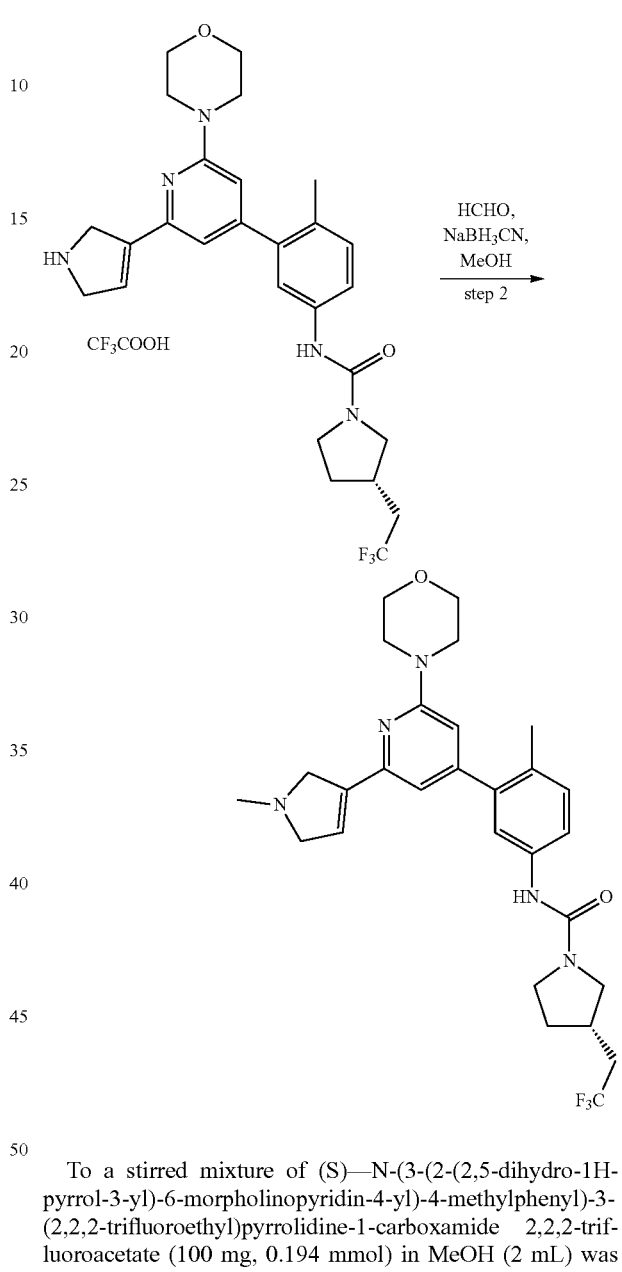

To a stirred mixture of tert-butyl (S)-3-(4-(2-methyl-5-(3-(2,2,2-trifluoroethyl)pyrrolidine-1-carboxamido)phenyl)-6-morpholinopyridin-2-yl)-2,5-dihydro-1H-pyrrole-1-carboxylate (150 mg, 0.243 mmol) in DCM (3 mL) were added TFA (1 mL) at room temperature. The resulting mixture was stirred for 2 h and concentrated under reduced pressure to afford (S)—N-(3-(2-(2,5-dihydro-1H-pyrrol-3-yl)-6-morpholinopyridin-4-yl)-4-methylphenyl)-3-(2,2,2-trifluoroethyl)pyrrolidine-1-carboxamide 2,2,2-trifluoroacetate (150 mg, crude) as an off-white solid. MS ESI calculated for $C_{29}H_{33}F_6N_5O_4$ [M+H]$^+$, 516.25, found 516.25.

To a stirred mixture of (S)—N-(3-(2-(2,5-dihydro-1H-pyrrol-3-yl)-6-morpholinopyridin-4-yl)-4-methylphenyl)-3-(2,2,2-trifluoroethyl)pyrrolidine-1-carboxamide 2,2,2-trifluoroacetate (100 mg, 0.194 mmol) in MeOH (2 mL) was added formaldehyde (9 mg, 0.291 mmol) and NaBH$_3$CN (25 mg, 0.388 mmol). The resulting mixture was stirred for 1 h at room temperature. The mixture was concentrated under reduced pressure. The residue was purified by reverse phase flash chromatography with the following conditions: Column: Spherical C18, 20-40 um, 120 g; Mobile Phase A: water (plus 5 mM NH$_4$NO$_3$); Mobile Phase B: CH$_3$CN; Flow rate: 50 mL/min; Gradient: 5%-5% B, 10 min, 30% B-70% B gradient in 30 min; Detector: 220 nm to afford (3S)—N-[4-methyl-3-[2-(1-methyl-2,5-dihydropyrrol-3-yl)-6-(morpholin-4-yl)pyridin-4-yl]phenyl]-3-(2,2,2-trifluoroethyl)pyrrolidine-1-carboxamide (50 mg, 50%) as a white solid. MS ESI calculated for $C_{28}H_{34}F_3N_5O_2$[M+H]$^+$, 530.27, found 530.25. ¹H NMR (400 MHz, chloroform-d) δ 7.36-7.34 (m, 1H), 7.26 (d, J=2.4 Hz, 1H), 7.20 (d, J=8.3 Hz, 1H), 6.68 (d, J=1.0 Hz, 1H), 6.46 (d, J=1.2 Hz, 2H), 6.15 (s, 1H), 3.94-3.92 (m, 2H), 3.86-3.77 (m, 5H), 3.72-3.59 (m, 3H), 3.63-3.52 (m, 4H), 3.45-3.42 (m, 1H), 3.13-3.10 (m, 1H), 2.59-2.56 (m, 4H), 2.35-2.22 (m, 3H), 2.21 (s, 3H), 1.76-1.72 (m, 1H). ¹⁹F NMR (376 MHz, chloroform-d) 6-64.95 (3F).

Example 36: (3S)—N-[4-methyl-3-[2-(1-methylpyrazol-3-yl)-6-(morpholin-4-yl)pyridin-4-yl]phenyl]-3-(2,2,2-trifluoroethyl)pyrrolidine-1-carboxamide

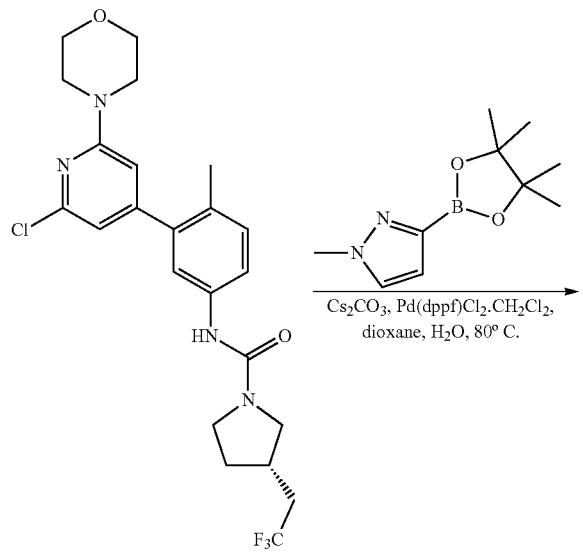

To a stirred mixture of (3S)—N-[3-[2-chloro-6-(morpholin-4-yl)pyridin-4-yl]-4-methylphenyl]-3-(2,2,2-trifluoroethyl)pyrrolidine-1-carboxamide (130 mg, 0.269 mmol), 1-methyl-3-(4,4,5,5-tetramethyl-1,3,2-dioxaborolan-2-yl)pyrazole (84 mg, 0.404 mmol) and Cs₂CO₃ (263 mg, 0.808 mmol) in dioxane (2 mL) and H₂O (0.5 mL) was added Pd(dppf)Cl₂·CH₂Cl₂ (21 mg, 0.027 mmol) under air atmosphere. The reaction mixture was stirred for 16 h at 80 degrees C. under N₂ atmosphere. The resulting mixture was diluted with water (10 mL). The resulting mixture was extracted with EtOAc (3×10 mL). The combined organic layers were washed with brine (2×10 mL), dried over anhydrous Na₂SO₄. After filtration, the filtrate was concentrated under reduced pressure. The residue was purified by silica gel column chromatography, eluted with PE/EtOAc/EtOH (4/3/1) to afford (3S)—N-[4-methyl-3-[2-(1-methylpyrazol-3-yl)-6-(morpholin-4-yl)pyridin-4-yl]phenyl]-3-(2,2,2-trifluoroethyl)pyrrolidine-1-carboxamide (135 mg, 94%) as a white solid. MS ESI calculated for $C_{27}H_{31}F_3N_6O_2$ [M+H]⁺, 529.25, found 529.25; ¹H NMR (400 MHz, chloroform-d) δ 7.47-7.45 (m, 1H), 7.41 (d, J=2.2 Hz, 1H), 7.34 (d, J=0.9 Hz, 1H), 7.25-7.17 (m, 2H), 6.93 (s, 1H), 6.54 (s, 1H), 6.15 (s, 1H), 3.97 (s, 3H), 3.89 (t, J=4.8 Hz, 4H), 3.82-3.80 (m, 1H), 3.65-3.60 (m, 5H), 3.46-3.42 (m, 1H), 3.13 (t, J=9.4 Hz, 1H), 2.57-2.55 (m, 1H), 2.36-2.23 (m, 6H), 1.78-1.75 (m, 1H).). ¹⁹F NMR (282 MHz, chloroform-d) 6-64.95 (3F).

Example 37: (3S)—N-[3-[2-(1,3-dimethylpyrazol-4-yl)-6-(morpholin-4-yl)pyridin-4-yl]-4-methylphenyl]-3-(2,2,2-trifluoroethyl)pyrrolidine-1-carboxamide

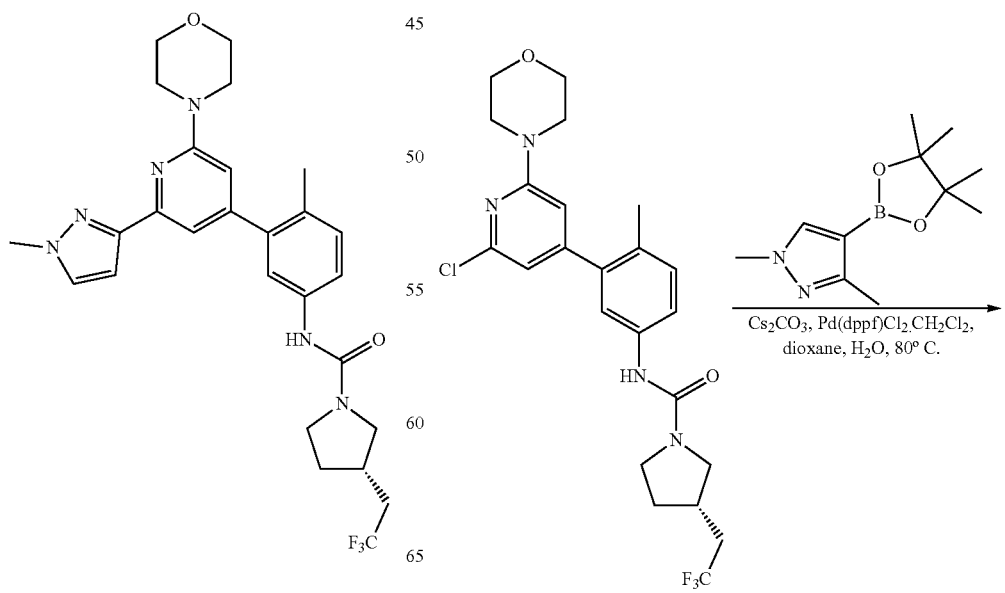

215
-continued

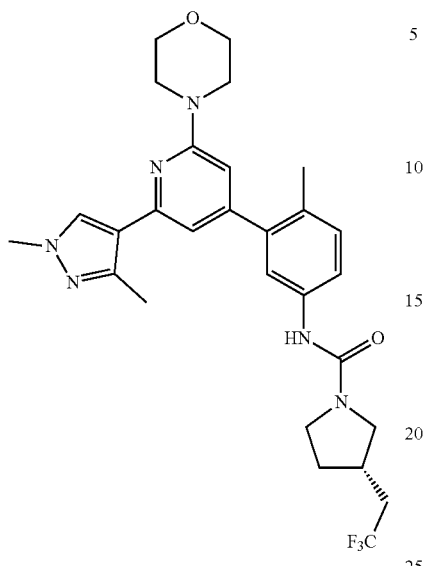

To a stirred mixture of (3 S)—N-[3-[2-chloro-6-(morpholin-4-yl)pyridin-4-yl]-4-methylphenyl]-3-(2,2,2-trifluoroethyl)pyrrolidine-1-carboxamide (130 mg, 0.269 mmol), 1,3-dimethyl-4-(4,4,5,5-tetramethyl-1,3,2-dioxaborolan-2-yl)pyrazole (89 mg, 0.404 mmol) and Cs$_2$CO$_3$ (263 mg, 0.808 mmol) in dioxane (2 mL) and H$_2$O (0.5 mL) was added Pd(dppf)Cl$_2$.CH$_2$Cl$_2$ (22 mg, 0.027 mmol). The reaction mixture was stirred for 16 h at 80 degrees C. under N$_2$ atmosphere. The resulting mixture was diluted with water (10 mL). The resulting mixture was extracted with EtOAc (3×10 mL). The combined organic layers were washed with brine (2×10 mL), dried over anhydrous Na$_2$SO$_4$. After filtration, the filtrate was concentrated under reduced pressure. The residue was purified by silica gel column chromatography, eluted with PE/EtOAc/EtOH (4/3/1) to afford (3S)—N-[3-[2-(1,3-dimethylpyrazol-4-yl)-6-(morpholin-4-yl)pyridin-4-yl]-4-methylphenyl]-3-(2,2,2-trifluoroethyl)pyrrolidine-1-carboxamide (139 mg, 94%) as a white solid. MS ESI calculated for C$_{28}$H$_{33}$F$_3$N$_6$O$_2$[M+H]$^+$, 543.26, found 543.25; $^1$H NMR (400 MHz, chloroform-d) δ 7.79 (s, 1H), 7.39-7.30 (m, 2H), 7.22 (d, J=8.2 Hz, 1H), 6.80 (d, J=1.1 Hz, 1H), 6.43 (s, 1H), 6.13 (s, 1H), 3.90-3.80 (m, 8H), 3.70-3.57 (m, 5H), 3.46-3.44 (m, 1H), 3.14 (t, J=9.4 Hz, 1H), 2.56-2.54 (m, 4H), 2.32-2.23 (m, 6H), 1.77-1.75 (m, 1H). $^{19}$F NMR (282 MHz, chloroform-d) δ-64.95 (3F).

Example 38: (3S)—N-(4-methyl-3-(2-(1-methylpyrrolidin-3-yl)-6-morpholinopyridin-4-yl)phenyl)-3-(2,2,2-trifluoroethyl)pyrrolidine-1-carboxamide formate

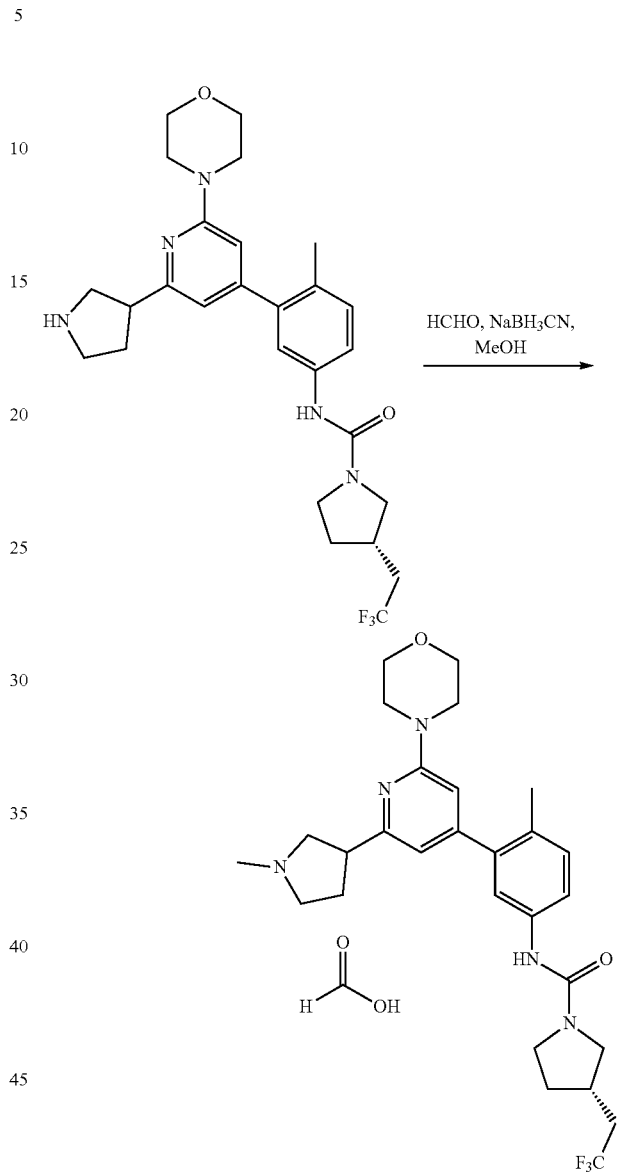

To a stirred mixture of (3S)—N-[4-methyl-3-[2-(morpholin-4-yl)-6-(pyrrolidin-3-yl)pyridin-4-yl]phenyl]-3-(2,2,2-trifluoroethyl)pyrrolidine-1-carboxamide (120 mg, 0.232 mmol) and formaldehyde (10 mg, 0.348 mmol) in MeOH (3 mL) was added NaBH$_3$CN (29 mg, 0.464 mmol). The resulting mixture was stirred for 6 h at room temperature and concentrated under reduced pressure. The residue was purified by Prep-HPLC with the following conditions: Column: C18 Column 120 g; Mobile Phase A: water (plus 5% FA), Mobile Phase B: CH$_3$CN; Flow rate: 80 mL/min; Gradient: 40% B to 70% B in 40 min; 254/220 nm to afford (3S)—N-(4-methyl-3-(2-(1-methylpyrrolidin-3-yl)-6-morpholinopyridin-4-yl)phenyl)-3-(2,2,2-trifluoroethyl)pyrrolidine-1-carboxamide formate (54 mg, 69%) as an off-white solid. MS ESI calculated for C$_{29}$H$_{38}$F$_3$N$_5$O$_4$ [M−HCOO]$^+$, 532.28, found 532.15. $^1$H NMR (400 MHz, DMSO-d$_6$) δ 8.17 (s, 1H), 8.15 (s, 1H), 7.45 (d, J=8.0 Hz, 1H), 7.37 (s, 1H), 7.14 (d, J=7.6 Hz, 1H), 6.55-6.52 (m, 2H), 3.71-3.65 (m, 6H), 3.48-3.40 (m, 5H), 3.11-3.02 (m, 4H), 2.92-2.65 (m, 4H), 2.40-2.35 (m, 4H), 2.15-2.07 (s, 6H), 1.67-1.65 (m, 1H).). $^{19}$F NMR (376 MHz, DMSO-$d_6$) δ −63.37 (3F).

Example 39: (S)—N-(4-methyl-3-(2-(1-methylpiperidin-4-yl)-6-morpholinopyridin-4-yl)phenyl)-3-(2,2,2-trifluoroethyl)pyrrolidine-1-carboxamide formate

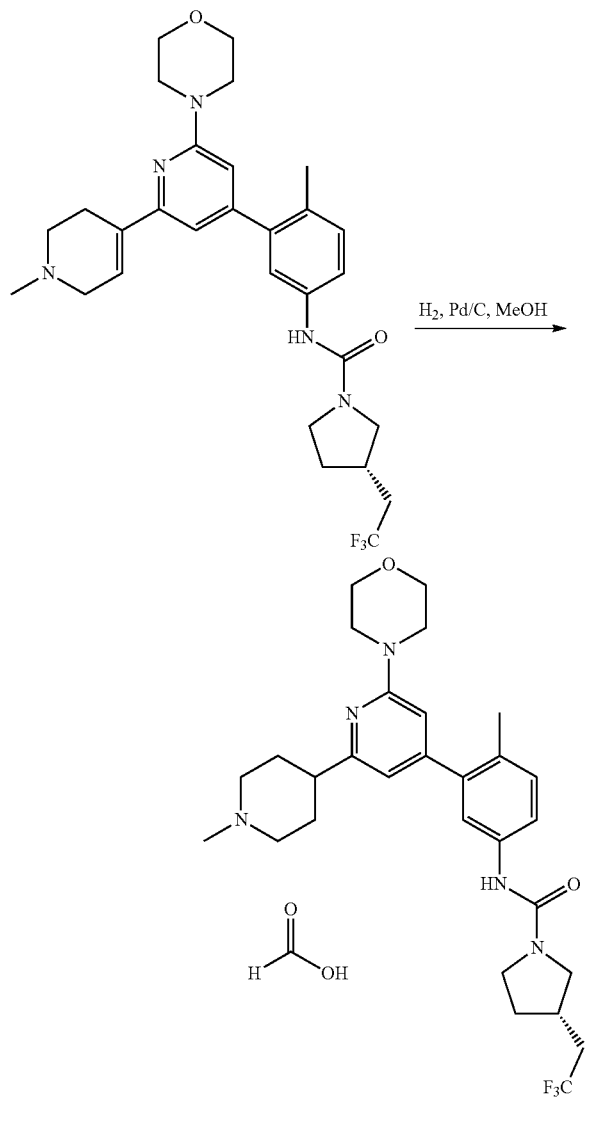

To a stirred mixture of (3S)—N-[4-methyl-3-[1-methyl-6-(morpholin-4-yl)-3,6-dihydro-2H-[2,4-bipyridin]-4-yl]phenyl]-3-(2,2,2-trifluoroethyl)pyrrolidine-1-carboxamide (110 mg, 0.202 mmol) in MeOH (3 mL) was added Pd/C (50 mg). The resulting mixture was stirred for 30 min at room temperature under hydrogen atmosphere. The resulting mixture was filtered, and the filter cake was washed with MeOH (3×10 mL). The filtrate was concentrated under reduced pressure. The residue was purified by reverse phase flash chromatography with the following conditions: Column: Spherical C18, 20-40 um, 120 g; Mobile Phase A: water (plus 5% FA); Mobile Phase B: CH$_3$CN; Flow rate: 50 mL/min; Gradient: 5%5% B, 10 min, 30% B70% B gradient in 30 min; Detector: 220 nm to afford (S)—N-(4-methyl-3-(2-(1-methylpiperidin-4-yl)-6-morpholinopyridin-4-yl)phenyl)-3-(2,2,2-trifluoroethyl)pyrrolidine-1-carboxamide formate (72 mg, 62%) as a white solid. MS ESI calculated for C$_{30}$H$_{40}$F$_3$N$_5$O$_4$[M−HCOO]$^+$, 546.30, found 546.25. $^1$H NMR (400 MHz, DMSO-$d_6$) δ 8.25 (s, 1H), 8.15 (s, 1H), 7.45 (m, 1H), 7.37 (d, J=2.3 Hz, 1H), 7.13 (d, J=8.4 Hz, 1H), 6.52 (s, 1H), 6.51 (s, 1H), 3.74-3.62 (m, 5H), 3.57-3.44 (m, 5H), 3.31-3.29 (m, 1H), 3.00-2.97 (m, 3H), 2.57-2.55 (m, 1H), 2.51-2.34 (m, 3H), 2.32 (s, 3H), 2.22-2.05 (m, 6H), 1.87-1.75 (m, 4H), 1.73-1.58 (m, 1H).). $^{19}$F NMR (376 MHz, DMSO-$d_6$) δ −63.37 (3F).

Example 40: (3S)—N-[3-[2'-amino-6-(morpholin-4-yl)-[2,4'-bipyridin]-4-yl]-4-methylphenyl]-3-(2,2,2-trifluoroethyl)pyrrolidine-1-carboxamide

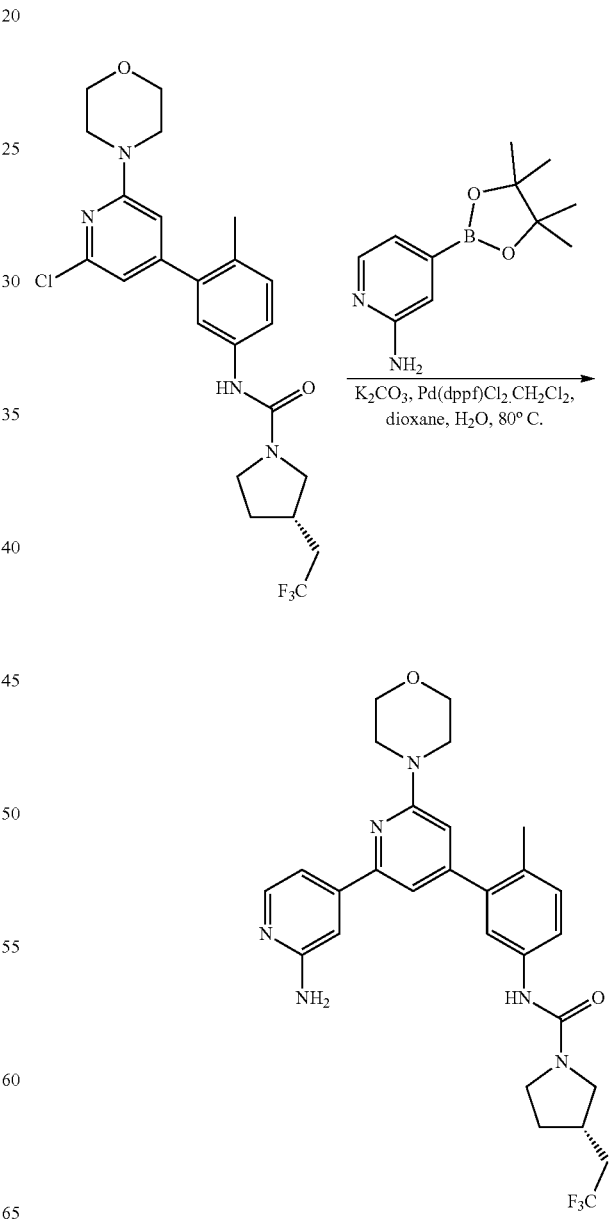

A mixture of 4-(4,4,5,5-tetramethyl-1,3,2-dioxaborolan-2-yl)pyridin-2-amine (109 mg, 0.497 mmol), (3S)—N-[3-[2-chloro-6-(morpholin-4-yl)pyridin-4-yl]-4-methylphenyl]-3-(2,2,2-trifluoroethyl)pyrrolidine-1-carboxamide (120 mg, 0.248 mmol), Pd(dppf)Cl$_2$·CH$_2$Cl$_2$ (20 mg, 0.025 mmol) and K$_2$CO$_3$ (103 mg, 0.745 mmol) in dioxane (4 mL) and H$_2$O (1 mL) was stirred at 80 degrees C. for 16 h under N$_2$ atmosphere. The mixture was allowed to cool down to room temperature. The resulting mixture was quenched with water (10 mL) and extracted with EtOAc (3×10 mL). The combined organic layers were washed with brine (3×10 mL), dried over anhydrous Na$_2$SO$_4$. After filtration, the filtrate was concentrated under reduced pressure. The residue was purified by silica gel column chromatography, eluted with PE/EtOAc/EtOH (4/3/1 to 2/3/1). The crude product was purified by reverse flash chromatography with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 40% B to 70% B in 40 min; 254/220 nm to afford (3S)—N-[3-[2'-amino-6-(morpholin-4-yl)-[2,4'-bipyridin]-4-yl]-4-methylphenyl]-3-(2,2,2-trifluoroethyl)pyrrolidine-1-carboxamide (99 mg, 74%) as a white solid. MS ESI calculated for C$_{28}$H$_{31}$F$_3$N$_6$O$_2$[M+H]$^+$, 541.25 found 541.20. $^1$H NMR (400 MHz, DMSO-d$_6$) δ 8.18 (s, 1H), 7.97 (d, J=5.4 Hz, 1H), 7.51-7.49 (m, 1H), 7.44 (d, J=2.3 Hz, 1H), 7.18 (t, J=4.1 Hz, 2H), 7.13 (d, J=3.8 Hz, 2H), 6.78 (s, 1H), 5.97 (s, 2H), 3.79-3.72 (m, 4H), 3.68-3.53 (m, 6H), 3.30-3.29 (m, 1H), 3.03 (t, J=9.4 Hz, 1H), 2.42-2.35 (m, 3H), 2.21 (s, 3H), 2.13-2.05 (m, 1H), 1.71-1.60 (m, 1H). $^{19}$F NMR (376 MHz, DMSO-d$_6$) δ −63.37 (3F).

Example 41: (3S)—N-(3-[2-[1-(difluoromethyl)pyrazol-4-yl]-6-(morpholin-4-yl)pyridin-4-yl]-4-methylphenyl)-3-(2,2,2-trifluoroethyl)pyrrolidine-1-carboxamide

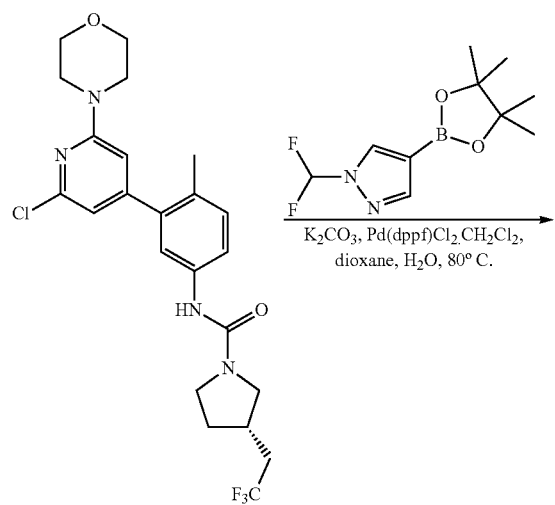

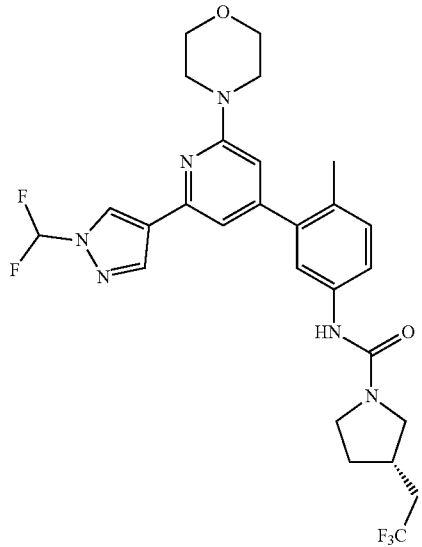

A mixture of 1-(difluoromethyl)-4-(4,4,5,5-tetramethyl-1,3,2-dioxaborolan-2-yl)pyrazole (121 mg, 0.497 mmol), (3S)—N-[3-[2-chloro-6-(morpholin-4-yl)pyridin-4-yl]-4-methylphenyl]-3-(2,2,2-trifluoroethyl)pyrrolidine-1-carboxamide (120 mg, 0.248 mmol), Pd(dppf)Cl$_2$·CH$_2$Cl$_2$ (20 mg, 0.025 mmol) and K$_2$CO$_3$ (103 mg, 0.745 mmol) in dioxane (4 mL) and H$_2$O (1 mL) was stirred at 80 degrees C. for 16 h under N$_2$ atmosphere. The mixture was allowed to cool down to room temperature. The resulting mixture was quenched with water (10 mL) and extracted with EtOAc (20 mL). The combined organic layers were washed with brine (3×10 mL), dried over anhydrous Na$_2$SO$_4$. After filtration, the filtrate was concentrated under reduced pressure. The residue was purified by silica gel column chromatography, eluted with hexane/EtOAc/EtOH (8/3/1 to 4/3/1). The crude product was purified by reverse flash chromatography with the following conditions: Column: C$^{18}$ Column 120 g; Mobile Phase A: water (10 mmol/L NH$_4$HCO$_3$), Mobile Phase B: CH$_3$CN; Flow rate: 60 mL/min; Gradient: 40% B to 70% B in 40 min; 254/220 nm to afford (3S)—N-(3-[2-[1-(difluoromethyl)pyrazol-4-yl]-6-(morpholin-4-yl)pyridin-4-yl]-4-methylphenyl)-3-(2,2,2-trifluoroethyl)pyrrolidine-1-carboxamide (89 mg, 63%) as a white solid. MS ESI calculated for C$_{27}$H$_{29}$F$_5$N$_6$O$_2$[M+H]$^+$, 565.23 found 565.15. $^1$H NMR (400 MHz, DMSO-d$_6$) δ 8.80 (s, 1H), 8.38 (s, 1H), 8.18 (s, 1H), 7.84 (t, J=59.2 Hz, 1H), 7.51-7.49 (m, 1H), 7.42 (d, J=2.3 Hz, 1H), 7.17 (d, J=8.4 Hz, 1H), 7.11 (d, J=1.0 Hz, 1H), 6.61 (d, J=1.1 Hz, 1H), 3.77-3.63 (m, 5H), 3.54-3.51 (m, 5H), 3.32-3.27 (m, 1H), 3.03 (t, J=9.2 Hz, 1H), 2.50-2.36 (m, 3H), 2.20 (s, 3H), 2.09-2.07 (m, 1H), 1.66-1.61 (m, 1H). $^{19}$F NMR (376 MHz, DMSO-d$_6$) δ −63.38 (3F), −94.24 (2F).

Example 42: (3S)—N-[4-methyl-3-[2-(morpholin-4-yl)-6-(1,3-thiazol-4-yl)pyridin-4-yl]phenyl]-3-(2,2,2-trifluoroethyl)pyrrolidine-1-carboxamide
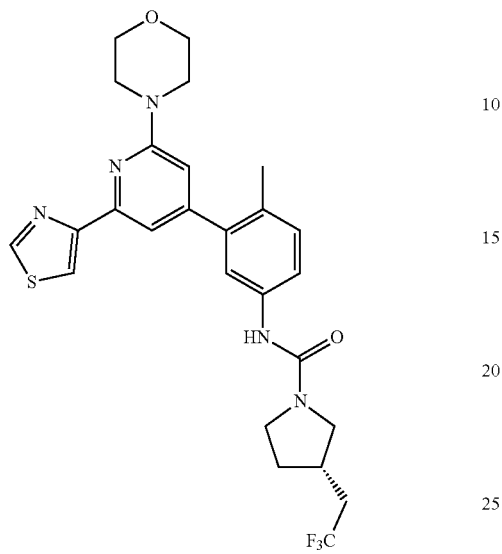
Synthetic Scheme
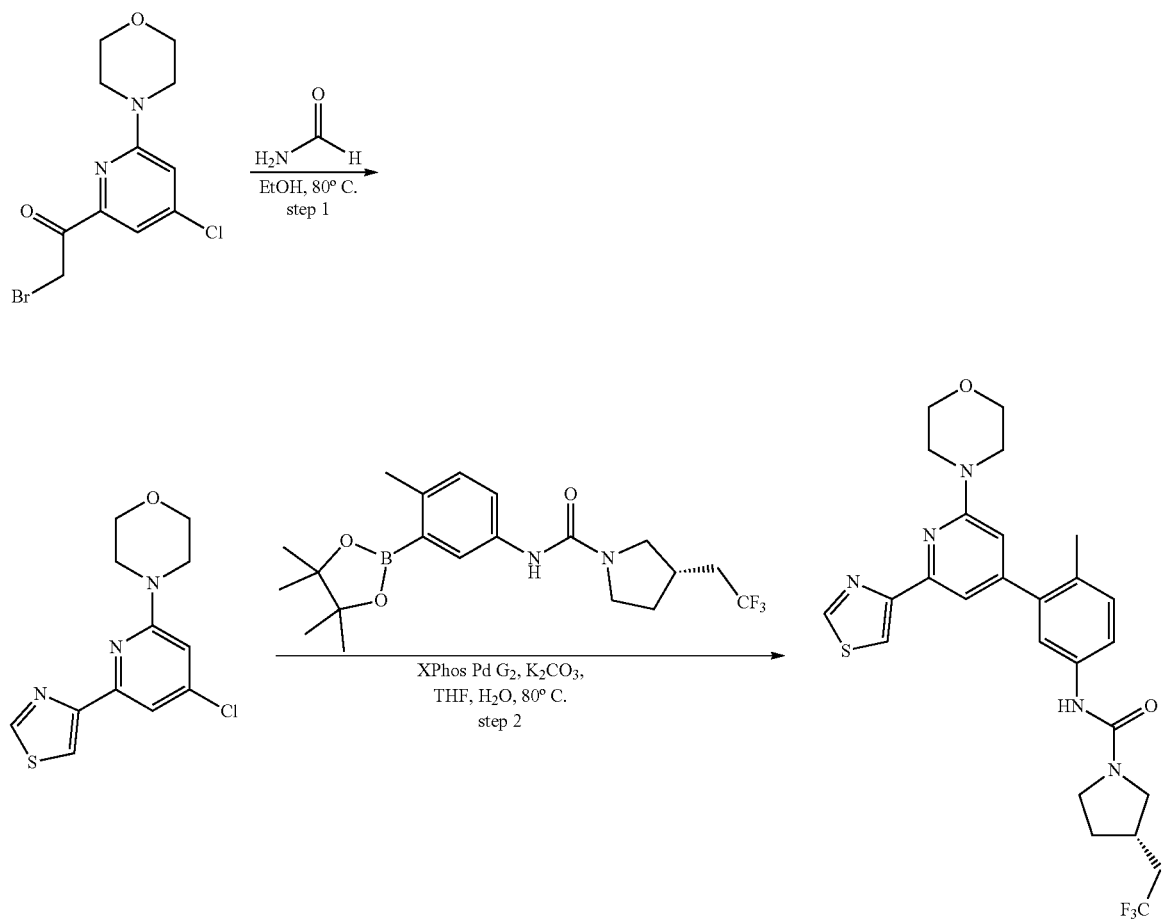

Preparation 42A: 4-[4-chloro-6-(1,3-thiazol-4-yl)pyridin-2-yl]morpholine

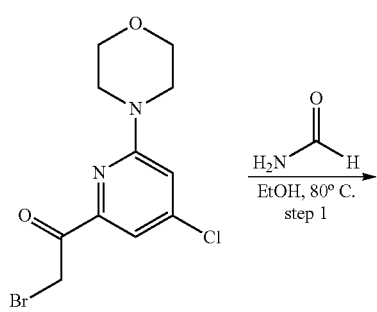

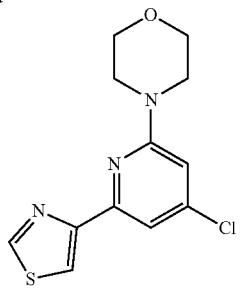

To a stirred mixture of 2-bromo-1-[4-chloro-6-(morpholin-4-yl)pyridin-2-yl]ethanone (500 mg, 1.565 mmol) in EtOH (1 mL) was added thioformamide (115 mg, 1.877 mmol). The resulting mixture was stirred for 16 h at 80 degrees C. The resulting mixture was concentrated under reduced pressure. The residue was purified by silica gel column chromatography, eluted with PE/EtOAc (5/1) to afford 4-[4-chloro-6-(1,3-thiazol-4-yl)pyridin-2-yl]morpholine (177 mg, 40%) as a yellow solid. MS ESI calculated for $C_{12}H_{12}ClN_3OS$ $[M+H]^+$, 282.04; found 282.10. $^1H$ NMR (400 MHz, chloroform-d) δ 8.87 (d, J=2.2 Hz, 1H), 8.12 (d, J=2.2 Hz, 1H), 7.61 (d, J=1.5 Hz, 1H), 6.63 (d, J=1.5 Hz, 1H), 3.87-3.81 (m, 4H), 3.66-3.54 (m, 4H).

Example 42: (3S)—N-[4-methyl-3-[2-(morpholin-4-yl)-6-(1,3-thiazol-4-yl)pyridin-4-yl]phenyl]-3-(2,2,2-trifluoroethyl)pyrrolidine-1-carboxamide

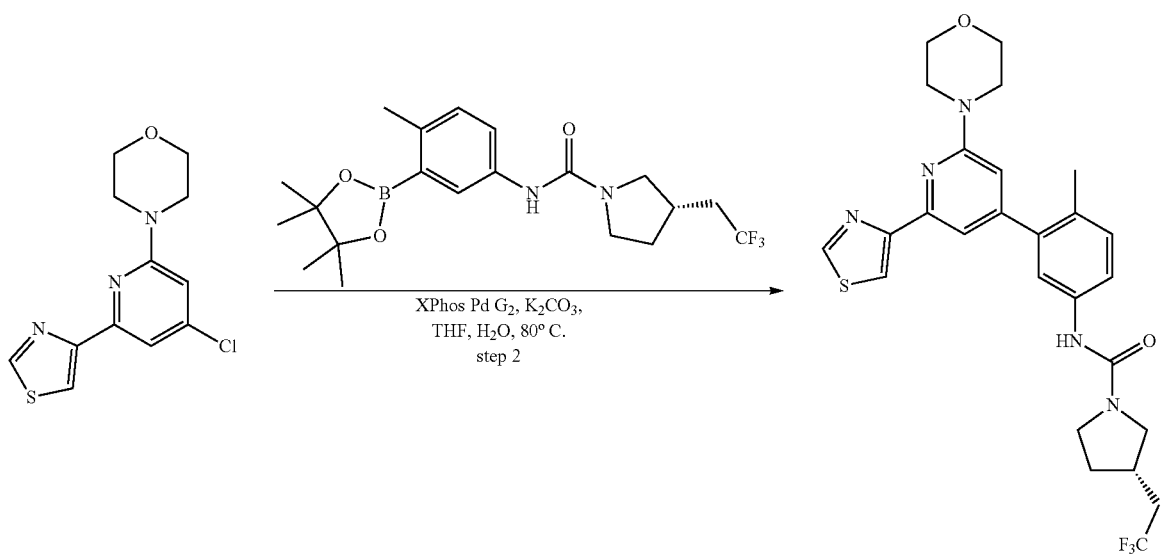 [SMILES: Clc1cc(-c2cscn2)nc(N2CCOCC2)c1 ; Cc1ccc(NC(=O)N2CC[C@@H](CC(F)(F)F)C2)cc1B1OC(C)(C)C(C)(C)O1 ; Cc1ccc(NC(=O)N2CC[C@@H](CC(F)(F)F)C2)cc1-c1cc(-c2cscn2)nc(N2CCOCC2)c1]

To a stirred mixture of 4-[4-chloro-6-(1,3-thiazol-4-yl)pyridin-2-yl]morpholine (100 mg, 0.355 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (146 mg, 0.355 mmol) in THF (1 mL) and H$_2$O (0.1 mL) were added K$_2$CO$_3$ (147 mg, 1.065 mmol) and XPhos palladium(II) biphenyl-2-amine chloride (56 mg, 0.071 mmol). The resulting mixture was stirred for 16 h at 80 degrees C. under nitrogen atmosphere. The resulting mixture was concentrated under reduced pressure. The resulting mixture was quenched with water (50 mL) and extracted with EtOAc (3×20 mL). The combined organic layers were washed with brine (2×10 mL), dried over anhydrous Na$_2$SO$_4$. After filtration, the filtrate was concentrated under reduced pressure. The residue was purified by reverse flash chromatography with the following conditions: column, C18 silica gel; mobile phase, CH$_3$CN in water (10 mM NH$_4$HCO$_3$), 30% to 75% gradient in 20 min; detector, UV 254 nm to afford (3S)—N-[4-methyl-3-[2-(morpholin-4-yl)-6-(1,3-thiazol-4-yl)pyridin-4-yl]phenyl]-3-(2,2,2-trifluoroethyl)pyrrolidine-1-carboxamide (113 mg, 60%) as a white solid. MS ESI calculated for C$_{26}$H$_{28}$F$_3$N$_5$O$_2$S [M+H]$^+$, 532.19, found 532.15. $^1$H NMR (300 MHz, DMSO-d$_6$) δ 9.19 (d, J=2.1 Hz, 1H), 8.31 (d, J=2.1 Hz, 1H), 8.21 (s, 1H), 7.53-7.51 (m, 1H), 7.47 (d, J=2.3 Hz, 1H), 7.41 (d, J=1.0 Hz, 1H), 7.19 (d, J=8.3 Hz, 1H), 6.75 (d, J=1.2 Hz, 1H), 3.76-3.66 (m, 5H), 3.61-3.54 (m, 5H), 3.31-3.30 (m, 1H), 3.04-2.46 (m, 1H), 2.50-2.35 (m, 3H), 2.21 (s, 3H), 2.18-1.99 (m, 1H), 1.70-1.64 (m, 1H). $^{19}$F NMR (282 MHz, DMSO-d$_6$) δ −63.37 (3F).

Example 43: (3S)—N-[3-[2-(2-amino-3H-imidazol-4-yl)-6-(morpholin-4-yl)pyridin-4-yl]-4-methylphenyl]-3-(2,2,2-trifluoroethyl)pyrrolidine-1-carboxamide

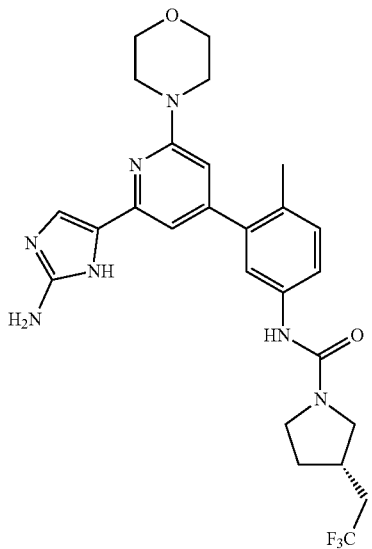 [SMILES: Cc1ccc(NC(=O)N2CC[C@@H](CC(F)(F)F)C2)cc1-c1cc(-c2cnc(N)[nH]2)nc(N2CCOCC2)c1]

Synthetic Scheme

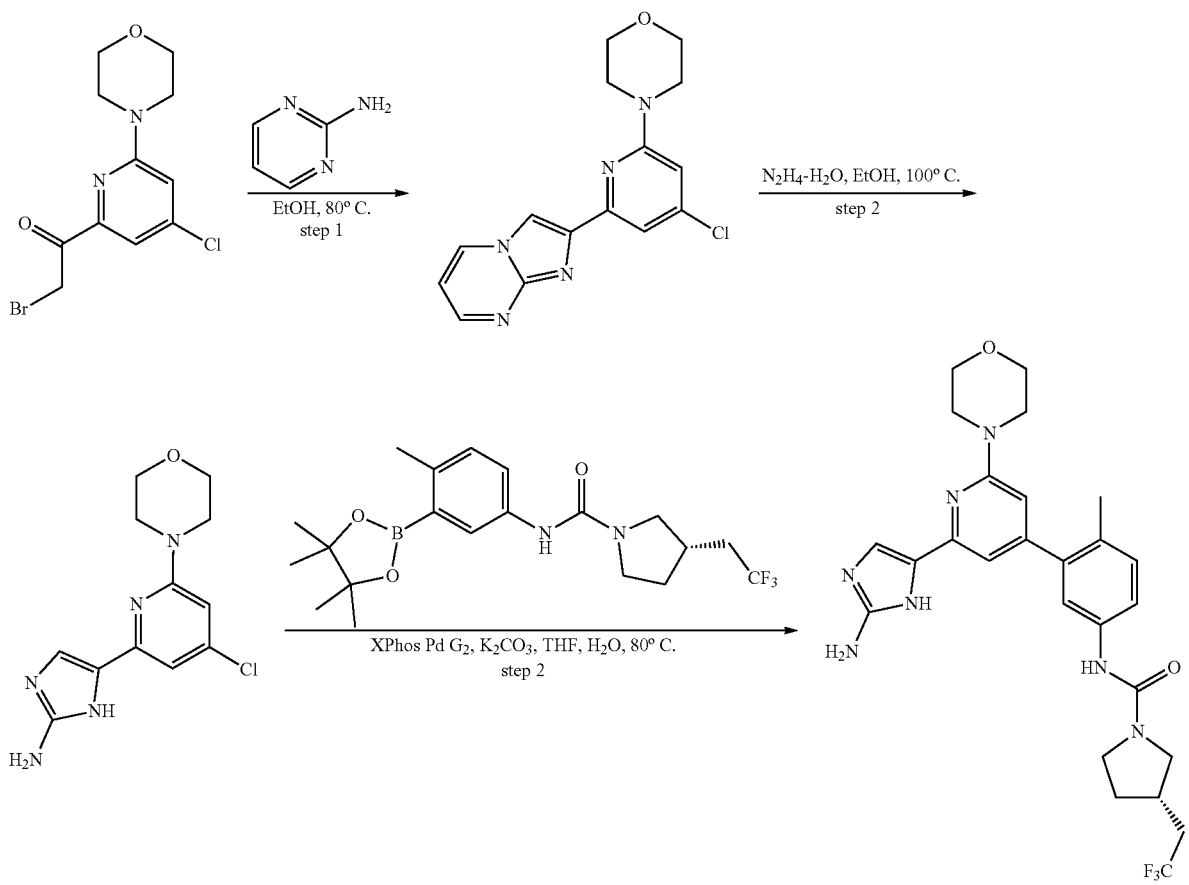

227

Preparation 43A: 4-(4-chloro-6-[imidazo[1,2-a]pyrimidin-2-yl]pyridin-2-yl)morpholine

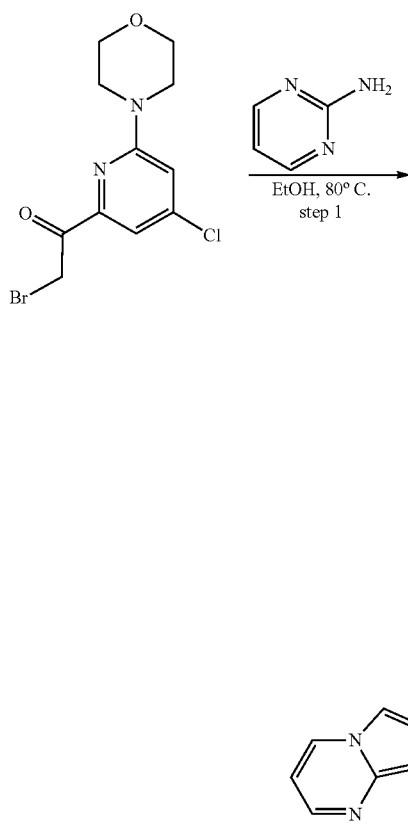

To a stirred solution of 2-bromo-1-[4-chloro-6-(morpholin-4-yl)pyridin-2-yl]ethanone (2.00 g, 6.26 mmol) in EtOH (20 mL) was added 2-aminopyrimidine (0.60 g, 6.26 mmol). The resulting mixture was stirred for 16 h at 80 degrees C. The mixture was allowed to cool down to room temperature. The solid was collected by filtered and dried under vacuum to afford 4-(4-chloro-6-[imidazo[1,2-a]pyrimidin-2-yl]pyridin-2-yl)morpholine (1.80 g, crude) as a light orange solid. MS ESI calculated for $C_{15}H_{14}ClN_5O$ [M+H]$^+$, 316.09; found 316.15. $^1$H NMR (300 MHz, DMSO-d$_6$) δ 9.26-9.24 (m, 1H), 8.97-8.95 (m, 1H), 8.83 (d, J=2.2 Hz, 1H), 7.68-7.49 (m, 2H), 7.05 (d, J=1.5 Hz, 1H), 3.72-3.66 (m, 8H).

228

Preparation 43B: 4-[4-chloro-6-(morpholin-4-yl)pyridin-2-yl]-3H-imidazol-2-amine

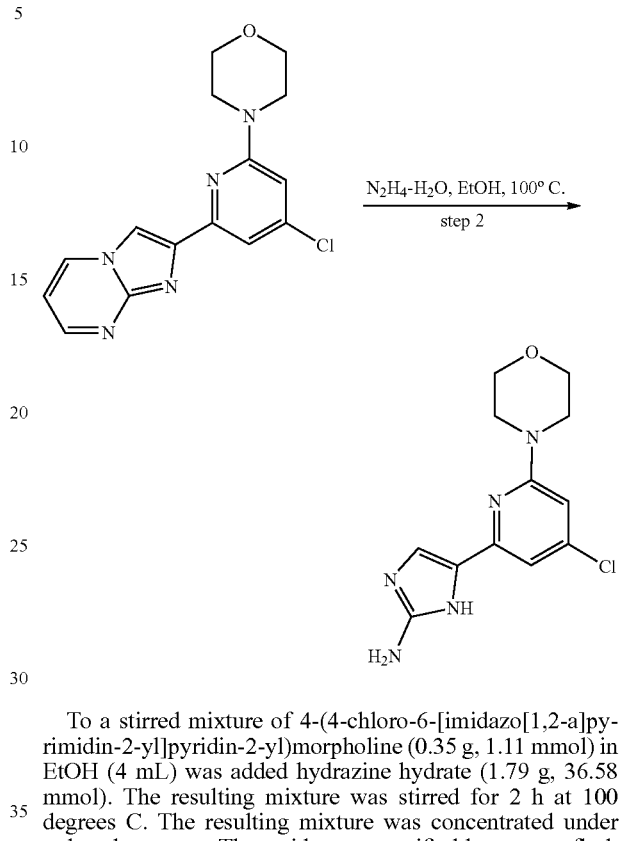

To a stirred mixture of 4-(4-chloro-6-[imidazo[1,2-a]pyrimidin-2-yl]pyridin-2-yl)morpholine (0.35 g, 1.11 mmol) in EtOH (4 mL) was added hydrazine hydrate (1.79 g, 36.58 mmol). The resulting mixture was stirred for 2 h at 100 degrees C. The resulting mixture was concentrated under reduced pressure. The residue was purified by reverse flash chromatography with the following conditions: column, C18 silica gel; mobile phase, $CH_3CN$ in water (0.1% $NH_4HCO_3$), 20% to 50% gradient in 20 min; detector, UV 254 nm to afford 4-[4-chloro-6-(morpholin-4-yl)pyridin-2-yl]-3H-imidazol-2-amine (0.27 g, 68%) as a light yellow solid. MS ESI calculated for $C_{12}H_{14}ClN_5O$ [M+H]$^+$, 280.09; found 280.10. $^1$H NMR (400 MHz, DMSO-d$_6$) δ 10.56 (s, 1H), 7.13 (s, 1H), 6.94 (s, 1H), 6.59 (s, 1H), 5.38 (s, 2H), 3.70-3.68 (m, 4H), 3.51-3.49 (m, 4H).

Example 43: (3S)—N-[3-[2-(2-amino-3H-imidazol-4-yl)-6-(morpholin-4-yl)pyridin-4-yl]-4-methylphenyl]-3-(2,2,2-trifluoroethyl)pyrrolidine-1-carboxamide

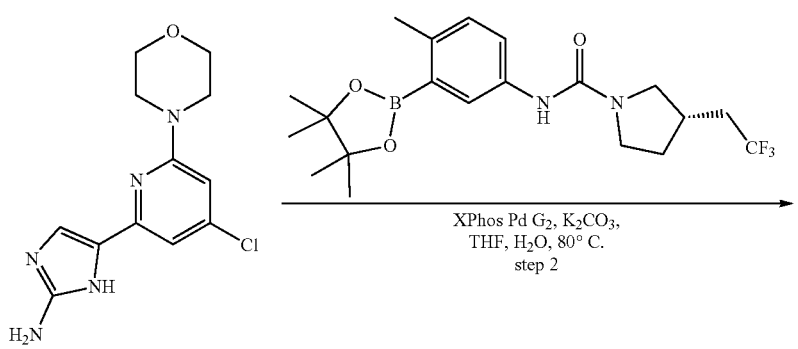

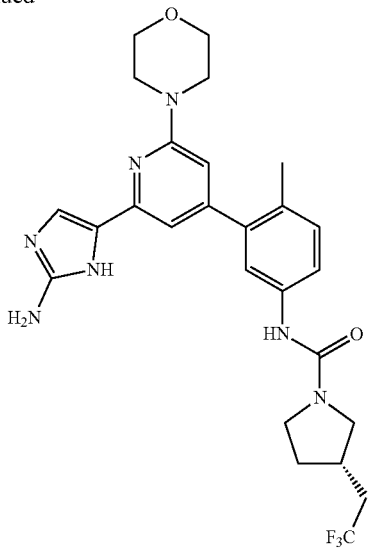

To a stirred solution of 4-[4-chloro-6-(morpholin-4-yl)pyridin-2-yl]-3H-imidazol-2-amine (100 mg, 0.357 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (147 mg, 0.357 mmol) in THF (1 mL) and H$_2$O (0.1 mL) were added K$_2$CO$_3$ (148 mg, 1.072 mmol) and XPhos palladium(II) biphenyl-2-amine chloride (56 mg, 0.071 mmol) under nitrogen atmosphere. The resulting mixture was stirred for 16 h at 80 degrees C. under nitrogen atmosphere. The mixture was allowed to cool down to room temperature. The reaction was quenched by the addition of water (15 mL). The resulting mixture was extracted with EtOAc (3×15 mL). The combined organic layers were washed with brine (10 mL), dried over anhydrous Na$_2$SO$_4$. After filtration, the filtrate was concentrated under reduced pressure. The residue was purified by silica gel column chromatography, eluted with PE/EtOAc/EtOH (1/12/4). The crude product was purified by reverse flash chromatography with the following conditions: column, C18 silica gel; mobile phase, CH$_3$CN in water (0.1% NH$_4$HCO$_3$), 30% to 60% gradient in 20 min; detector, UV 254 nm to afford (3S)—N-[3-[2-(2-amino-3H-imidazol-4-yl)-6-(morpholin-4-yl)pyridin-4-yl]-4-methylphenyl]-3-(2,2,2-trifluoroethyl)pyrrolidine-1-carboxamide (32.7 mg, 17%) as an off-white solid. MS ESI calculated for C$_{26}$H$_{30}$F$_3$N$_7$O$_2$[M+H]$^+$, 530.24, found 530.25. $^1$H NMR (400 MHz, DMSO-d$_6$) δ 10.61 (brs, 1H), 8.17 (s, 1H), 7.49-7.47 (m, 1H), 7.41 (d, J=2.3 Hz, 1H), 7.20-7.09 (m, 2H), 6.90 (s, 1H), 6.41 (s, 1H), 5.40 (brs, 2H), 3.73-3.70 (m, 5H), 3.53-3.50 (m, 5H), 3.30-3.28 (m, 1H), 3.10-2.97 (m, 1H), 2.44-2.35 (m, 3H), 2.20 (s, 3H), 2.09-2.06 (m, 1H), 1.73-1.60 (m, 1H). $^{19}$F NMR (282 MHz, DMSO-d$_6$) δ −63.36 (3F).

Example 45: (3S)—N-[3-[2-(2-aminopyrimidin-4-yl)-6-(morpholin-4-yl)pyridin-4-yl]-4-methylphenyl]-3-(2,2,2-trifluoroethyl)pyrrolidine-1-carboxamide

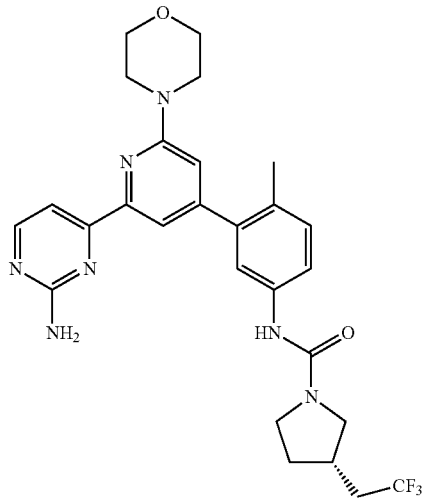 [SMILES: Cc1ccc(NC(=O)N2CC[C@@H](CC(F)(F)F)C2)cc1-c1cc(-c2ccnc(N)n2)nc(N2CCOCC2)c1]

Synthetic Scheme

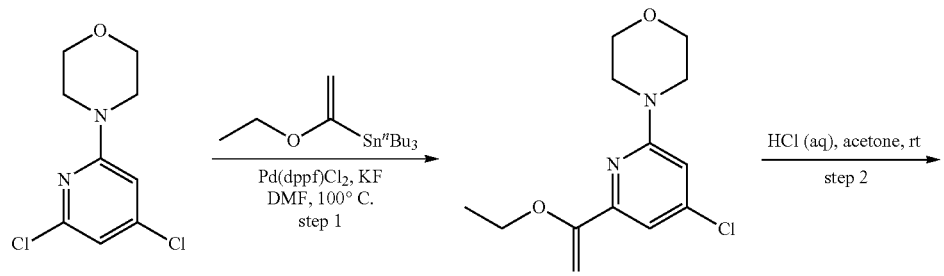

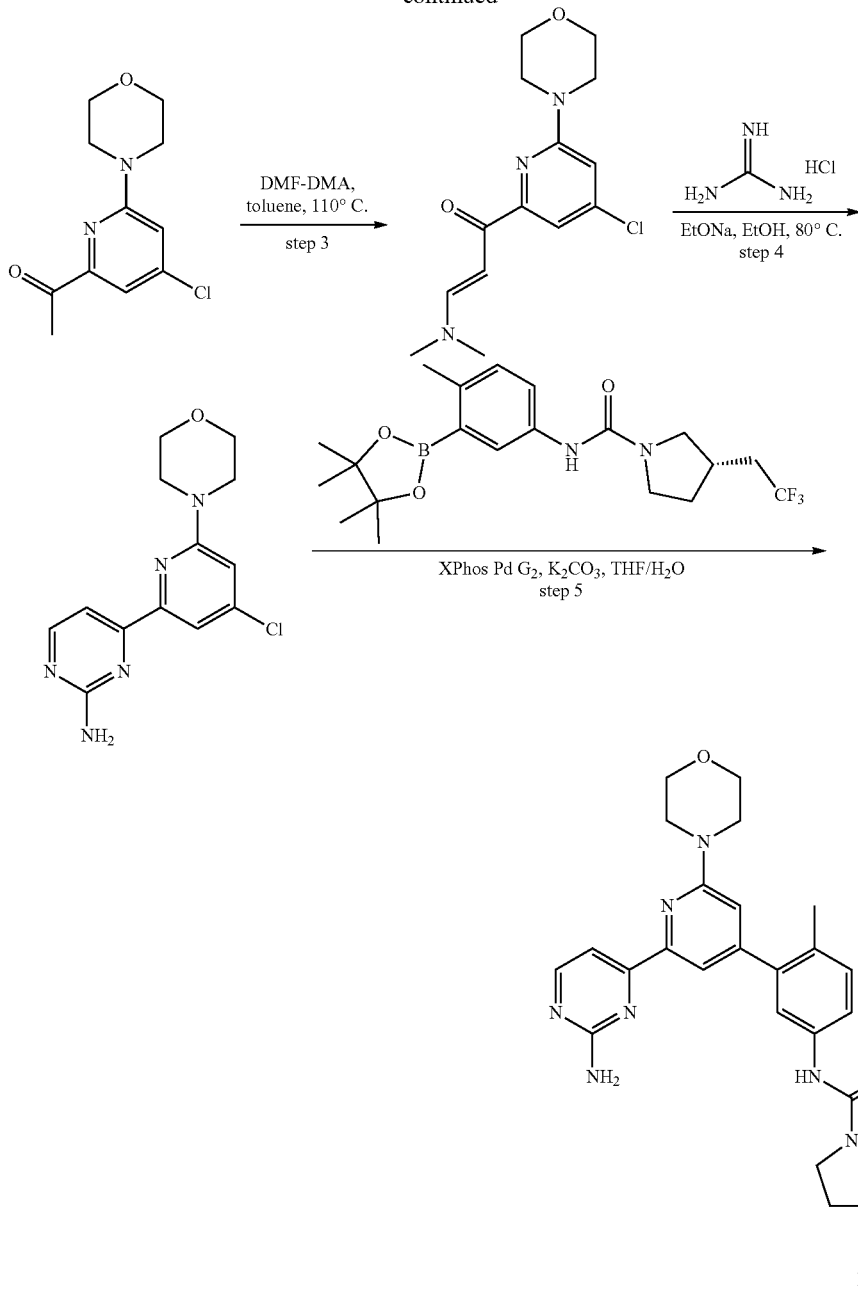
Preparation 45A: 4-[4-chloro-6-(1-ethoxyethenyl)pyridin-2-yl]morpholine
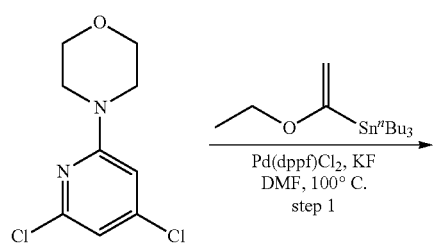
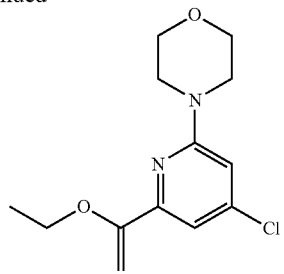
To a stirred solution of 4-(4,6-dichloropyridin-2-yl)morpholine (2 g, 8.580 mmol) and tributyl(1-ethoxyethenyl)

stannane (3 g, 8.580 mmol) in DMF (20 mL) were added Pd(dppf)Cl$_2$.CH$_2$Cl$_2$ (0.70 g, 0.858 mmol) and KF (1 g, 17.161 mmol) at room temperature. The resulting mixture was stirred for 2 h at 100° C. under nitrogen atmosphere. The mixture was allowed to cool down to room temperature. The reaction was quenched by the addition of water (50 mL). The resulting mixture was extracted with EA (3×50 mL). The combined organic layers were washed with brine (150 mL), dried over anhydrous Na$_2$SO$_4$. After filtration, the filtrate was concentrated under reduced pressure. The residue was purified by silica gel column chromatography, eluted with PE/EA (5/1) to afford 4-[4-chloro-6-(1-ethoxyethenyl)pyridin-2-yl]morpholine (1.6 g, 69%) as a off-white solid. MS ESI calculated for C$_{13}$H$_{17}$ClN$_2$O$_2$[M+H]$^+$, 269.10; found 269.15; $^1$H NMR (300 MHz, chloroform-d) δ 7.09 (d, J=1.6 Hz, 1H), 6.60-6.43 (m, 1H), 5.39 (d, J=1.7 Hz, 1H), 4.32 (d, J=1.7 Hz, 1H), 3.94 (q, J=7.0 Hz, 2H), 3.86-3.77 (m, 4H), 3.60-3.54 (m, 4H), 1.40-1.30 (m, 3H).

Preparation 45B: 1-[4-chloro-6-(morpholin-4-yl)pyridin-2-yl]ethanone

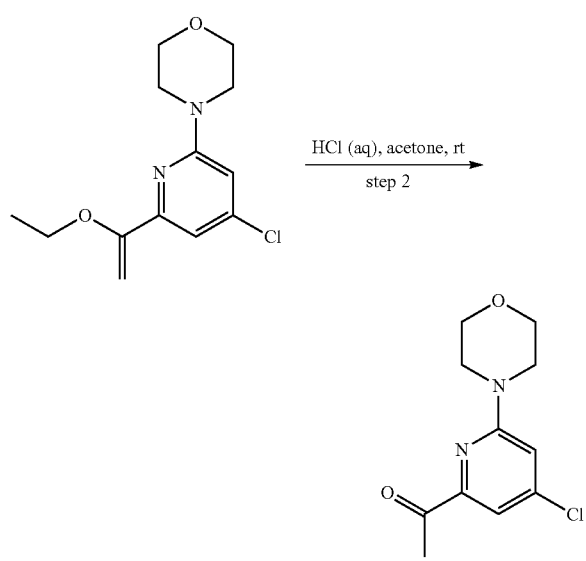

To a stirred mixture of 4-[4-chloro-6-(1-ethoxyethenyl)pyridin-2-yl]morpholine (1.5 g, 5.58 mmol) in acetone (15 mL) was added HCl (15 mL, 1 M). The resulting mixture was stirred for 2 h at room temperature. The resulting mixture was concentrated under reduced pressure. The mixture was basified to pH 7 with NaOH (15 mL, 1 M). The resulting mixture was extracted with DCM (3×25 mL). The combined organic layers were washed with brine (2×15 mL), dried over anhydrous Na$_2$SO$_4$. After filtration, the filtrate was concentrated under reduced pressure. The residue was purified by silica gel column chromatography, eluted with PE/EA (7/1) to afford 1-[4-chloro-6-(morpholin-4-yl)pyridin-2-yl]ethanone (1.2 g, 89%) as an off-white solid. MS ESI calculated for C$_{11}$H$_{13}$ClN$_2$O$_2$[M+H]$^+$, 241.07; found 241.45; $^1$H NMR (400 MHz, Chloroform-d) δ 7.39 (d, J=1.5 Hz, 1H), 6.80 (d, J=1.5 Hz, 1H), 3.90-3.83 (m, 4H), 3.63-3.56 (m, 4H), 2.64 (s, 3H).

Preparation 45C: 1-[4-chloro-6-(morpholin-4-yl)pyridin-2-yl]-3-(dimethylamino)prop-2-en-1-one

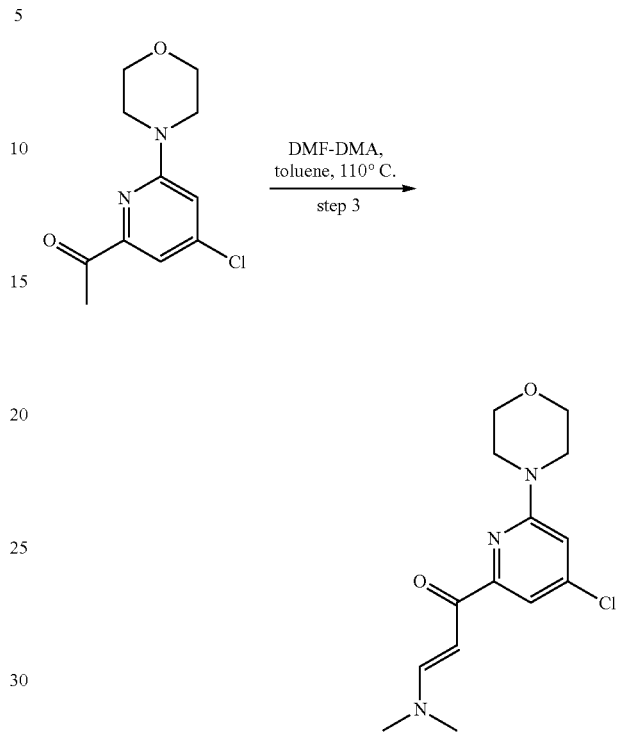

To a stirred mixture of 1-[4-chloro-6-(morpholin-4-yl)pyridin-2-yl]ethanone (0.50 g, 2.08 mmol) in toluene (1 mL) was added (dimethoxymethyl)dimethylamine (1.00 g, 10.39 mmol). The resulting mixture was stirred for 16 h at 110° C. The resulting mixture was concentrated under reduced pressure to afford 1-(4-chloro-6-morpholinopyridin-2-yl)-3-(dimethylamino)prop-2-en-1-one (0.50 g, 81%) as a yellow solid. MS ESI calculated for C$_{14}$H$_{18}$ClN$_3$O$_2$[M+H]$^+$, 296.11, found 296.15; $^1$H NMR (400 MHz, Chloroform-d) δ 7.90 (d, J=12.7 Hz, 1H), 7.54 (d, J=1.6 Hz, 1H), 6.71 (d, J=1.6 Hz, 1H), 6.34 (d, J=12.7 Hz, 1H), 3.90-3.80 (m, 4H), 3.64-3.55 (m, 4H), 3.19 (s, 3H), 2.99 (s, 3H).

Preparation 45D: 4-[4-chloro-6-(morpholin-4-yl)pyridin-2-yl]pyrimidin-2-amine

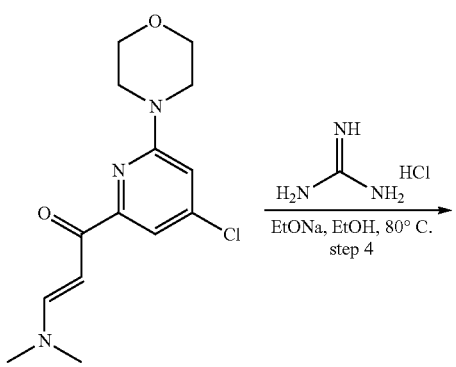

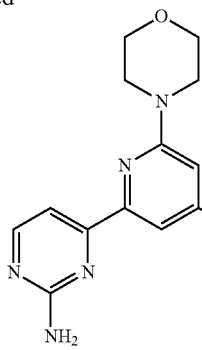

To a solution of 1-(4-chloro-6-morpholinopyridin-2-yl)-3-(dimethylamino)prop-2-en-1-one (500 mg, 1.691 mmol) and guanidine hydrochloride (484 mg, 5.072 mmol) in EtOH (5 mL) was added EtONa (1 mL, 21.640 mmol, 18%) at room temperature. The resulting mixture was stirred for 16 h at 80° C. The mixture was allowed to cool down to room temperature. The resulting mixture was diluted with water (20 mL) and extracted with EA (3×20 mL). The combined organic layers were washed with brine (2×10 mL), dried over anhydrous Na$_2$SO$_4$. After filtration, the filtrate was concentrated under reduced pressure. The residue was purified by silica gel column chromatography, eluted with petroleum ether/EtOAc/EtOH (8/3/1) to afford 4-[4-chloro-6-(morpholin-4-yl)pyridin-2-yl]pyrimidin-2-amine (259 mg, 53%) as a yellow solid. MS ESI calculated for C$_{13}$H$_{14}$ClN$_5$O [M+H]$^+$, 292.09; found 292.10. $^1$H NMR (400 MHz, DMSO-d$_6$) δ 8.39 (d, J=5.0 Hz, 1H), 7.62 (d, J=1.5 Hz, 1H), 7.41 (d, J=5.0 Hz, 1H), 7.08 (d, J=1.6 Hz, 1H), 6.77 (s, 2H), 3.73-3.71 (m, 4H), 3.60-3.58 (m, 4H).

Example 45: (3S)—N-[3-[2-(2-aminopyrimidin-4-yl)-6-(morpholin-4-yl)pyridin-4-yl]-4-methylphenyl]-3-(2,2,2-trifluoroethyl)pyrrolidine-1-carboxamide

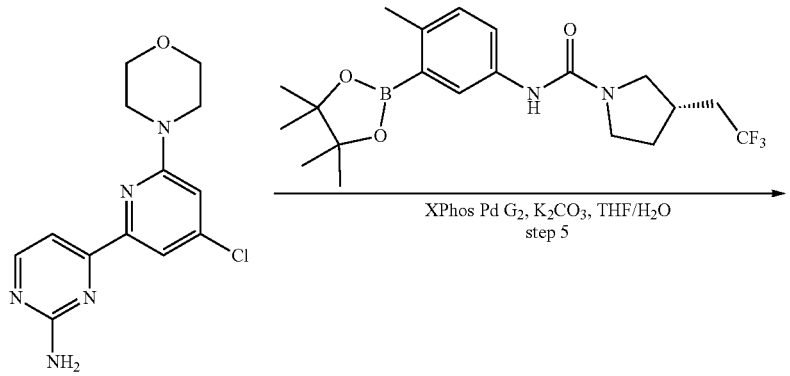

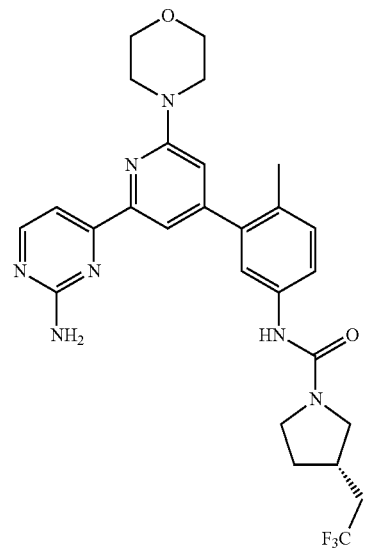

A mixture of 4-[4-chloro-6-(morpholin-4-yl)pyridin-2-yl]pyrimidin-2-amine (100 mg, 0.343 mmol), $K_2CO_3$ (142 mg, 1.028 mmol), $2^{nd}$ Generation XPhos precatalyst (54 mg, 0.069 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (141 mg, 0.343 mmol) in THF (1 mL) and $H_2O$ (0.1 mL) was stirred for 16 h at 80° C. under nitrogen atmosphere. The mixture was allowed to cool down to room temperature. The resulting mixture was diluted with EA (30 mL), washed with brine (2×10 mL), and dried over anhydrous $Na_2SO_4$. After filtration, the filtrate was concentrated under reduced pressure. The residue was purified by silica gel column chromatography, eluted with PE/EA/EtOH (4/3/1) to afford (3S)—N-[3-[2-(2-aminopyrimidin-4-yl)-6-(morpholin-4-yl)pyridin-4-yl]-4-methylphenyl]-3-(2,2,2-trifluoroethyl)pyrrolidine-1-carboxamide (78 mg, 42%) as an off-white solid. MS ESI calculated for $C_{27}H_{30}F_3N_7O_2$ $[M+H]^+$, 542.24, found 542.20. $^1H$ NMR (300 MHz, DMSO-$d_6$) δ 8.39 (d, J=5.1 Hz, 1H), 8.21 (s, 1H), 7.65 (d, J=1.1 Hz, 1H), 7.56-7.43 (m, 3H), 7.19 (d, J=8.4 Hz, 1H), 6.90 (s, 1H), 6.68 (brs, 2H), 3.76-3.62 (m, 5H), 3.61-3.45 (m, 5H), 3.32-3.22 (m, 1H), 3.04 (t, J=9.3 Hz, 1H), 2.50-2.40 (m, 3H), 2.20 (s, 3H), 2.15-1.98 (m, 1H), 1.70-1.60 (m, 1H). $^{19}F$ NMR (282 MHz, DMSO-$d_6$) δ −63.36 (3F).

Example 46: (3S)—N-[3-[2'-(difluoromethyl)-6-(morpholin-4-yl)-[2,4'-bipyridin]-4-yl]-4-methylphenyl]-3-(2,2,2-trifluoroethyl)pyrrolidine-1-carboxamide

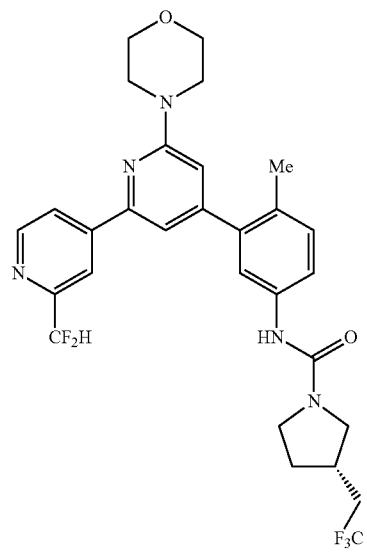 [SMILES: Cc1ccc(NC(=O)N2CC[C@@H](CC(F)(F)F)C2)cc1-c1cc(-c2ccnc(C(F)F)c2)nc(N2CCOCC2)c1]

Synthetic Scheme

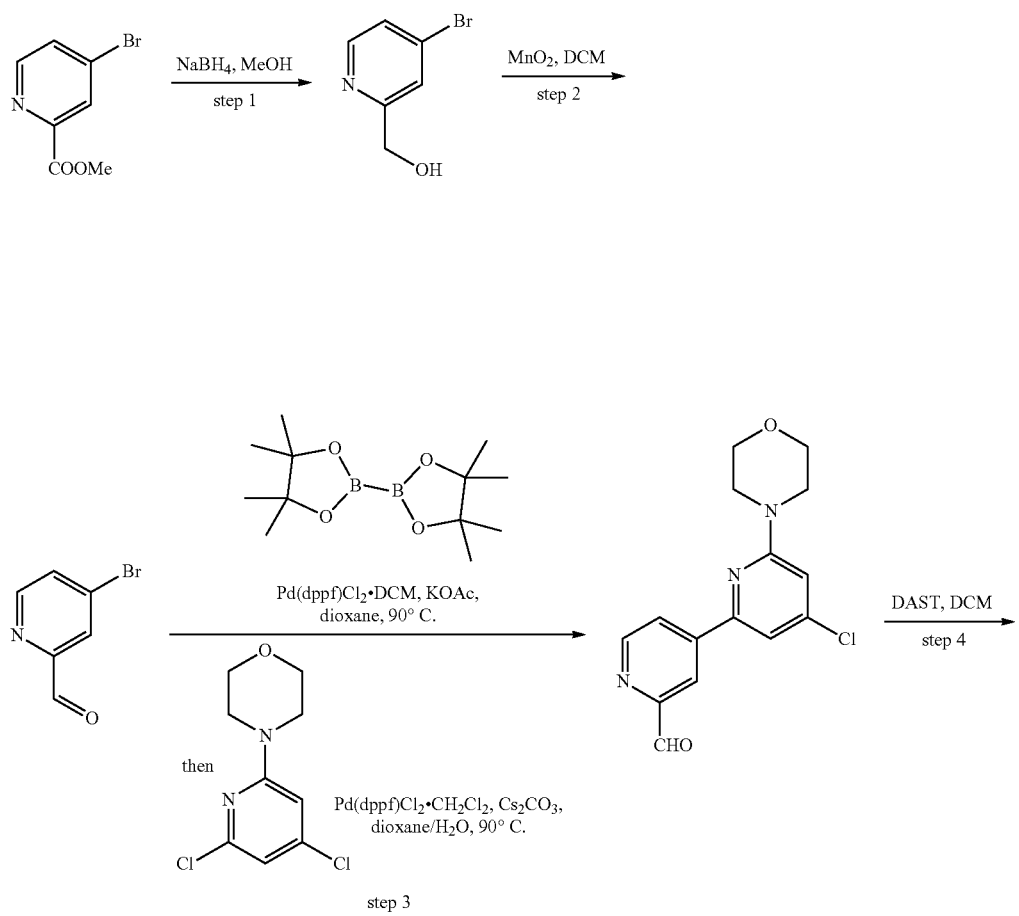

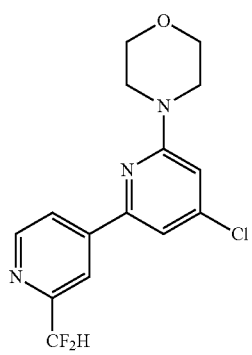
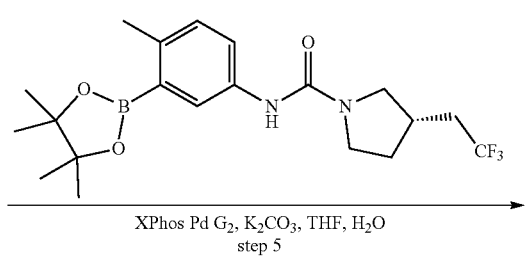

XPhos Pd G₂, K₂CO₃, THF, H₂O
step 5

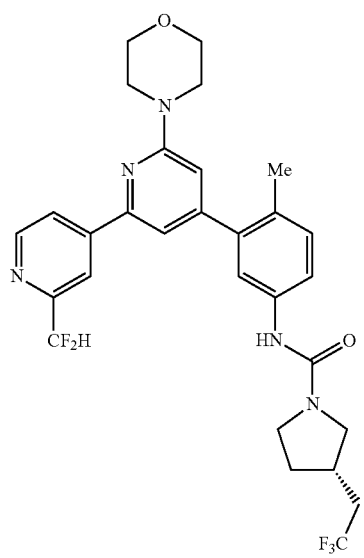

Preparation 46A: (4-bromopyridin-2-yl)methanol

Preparation 46B: 4-bromopyridine-2-carbaldehyde

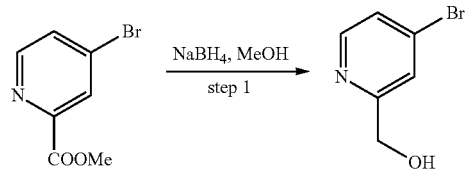 [SMILES: COC(=O)c1cc(Br)ccn1 ; OCc1cc(Br)ccn1]

A mixture of methyl 4-bromopyridine-2-carboxylate (3.00 g, 13.89 mmol) and NaBH₄ (1.31 g, 34.72 mmol) in MeOH (50 mL) was stirred for 30 min at 50° C. The resulting mixture was concentrated under reduced pressure and diluted with water (50 mL). The resulting mixture was extracted with DCM (2×20 mL). The combined organic layers were washed with brine (20 mL) and dried over anhydrous Na₂SO₄. After filtration, the filtrate was concentrated under reduced pressure to afford (4-bromopyridin-2-yl)methanol (2.27 g, 87%) as yellow oil. MS ESI calculated for C₆H₆BrNO [M+H]⁺, 187.96, 189.96; found 187.90, 189.85. ¹H NMR (400 MHz, Chloroform-d) δ 8.34 (d, J=5.4 Hz, 1H), 7.53 (d, J=1.8 Hz, 1H), 7.37 (dd, J=5.4, 1.9 Hz, 1H), 4.74 (s, 2H), 4.18 (s, 1H).

A mixture of (4-bromopyridin-2-yl)methanol (2.20 g, 11.70 mmol) and MnO₂ (10.17 g, 117.01 mmol) in DCM (100 mL) was stirred for 16 h at room temperature. The resulting mixture was filtered, the filter cake was washed with DCM (2×20 mL). The filtrate was concentrated under reduced pressure. The residue was purified by silica gel column chromatography, eluted with PE/EA (3/1) to afford 4-bromopyridine-2-carbaldehyde (1.80 g, 83%) as yellow oil. MS ESI calculated for C₆H₄BrNO [M+H]⁺, 185.95, 187.95; found 186.10, 188.10. H NMR (400 MHz, Chloroform-d) δ 10.04 (s, 1H), 8.61 (s, 1H), 8.10 (s, 1H), 7.70 (s, 1H).

Preparation 46C: 4-chloro-6-morpholino-[2,4'-bipyridine]-2'-carbaldehyde

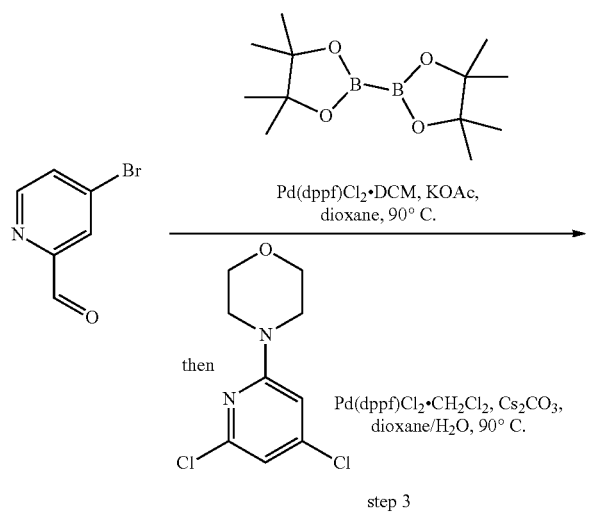

A mixture of 4-bromopyridine-2-carbaldehyde (1.20 g, 6.45 mmol), Pd(dppf)Cl$_2$·CH$_2$Cl$_2$ (0.52 g, 0.64 mmol), KOAc (1.27 g, 12.90 mmol) and bis(pinacolato)diboron (2.46 g, 9.68 mmol) in dioxane (36 mL) was stirred for 2 h at 90° C. under nitrogen atmosphere. The resulting mixture was allowed to cool down to room temperature. To this were added 4-(4,6-dichloropyridin-2-yl)morpholine (1.25 g, 5.36 mmol), Pd(dppf)Cl$_2$·CH$_2$Cl$_2$ (0.44 g, 0.54 mmol), Cs$_2$CO$_3$ (3.49 g, 10.73 mmol) and H$_2$O (8 mL) under nitrogen atmosphere. The resulting mixture was stirred for 3 h at 90° C. under nitrogen atmosphere. The resulting mixture was diluted with water (100 mL). The resulting mixture was extracted with EA (3×50 mL). The combined organic layers were washed with brine (30 mL), dried over anhydrous Na$_2$SO$_4$. After filtration, the filtrate was concentrated under reduced pressure. The residue was purified by silica gel column chromatography, eluted with PE/EA (3/1) to afford 4-chloro-6-morpholino-[2,4'-bipyridine]-2'-carbaldehyde (1.00 g, 61%) as a yellow solid. MS ESI calculated for C$_{15}$H$_{14}$ClN$_3$O$_2$[M+H]$^+$, 304.08; found 304.15. $^1$H NMR (400 MHz, Chloroform-d) δ 10.18 (s, 1H), 8.88 (dd, J=5.1, 0.9 Hz, 1H), 8.50 (dd, J=1.8, 0.8 Hz, 1H), 8.13 (dd, J=5.1, 1.8 Hz, 1H), 7.26 (d, J=1.3 Hz, 1H), 6.72 (d, J=1.3 Hz, 1H), 3.93-3.79 (m, 4H), 3.66-3.64 (m, 4H).

Preparation 46D: 4-(4-chloro-2'-(difluoromethyl)-[2,4'-bipyridin]-6-yl)morpholine

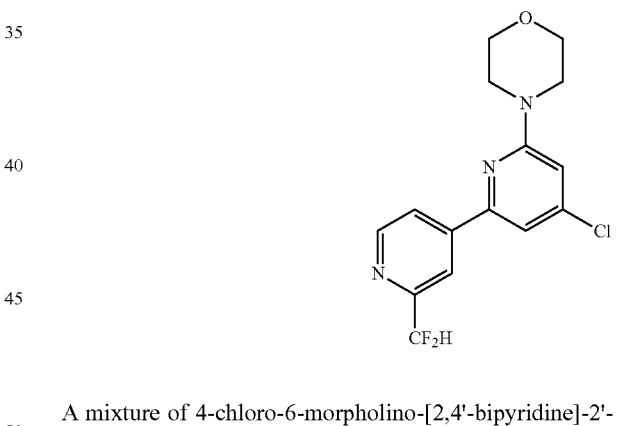

A mixture of 4-chloro-6-morpholino-[2,4'-bipyridine]-2'-carbaldehyde (500 mg, 1.646 mmol) and DAST (531 mg, 3.292 mmol) in DCM (10 mL) was stirred for 16 h at room temperature. The reaction was quenched with water (50 mL). The resulting mixture was extracted with DCM (50 mL). The combined organic layers were washed with brine (30 mL), dried over anhydrous Na$_2$SO$_4$. After filtration, the filtrate was concentrated under reduced pressure. The residue was purified by silica gel column chromatography, eluted with PE/EA (5/1) to afford 4-(4-chloro-2'-(difluoromethyl)-[2,4'-bipyridin]-6-yl)morpholine (320 mg, 60%) as a yellow solid. MS ESI calculated for C$_{15}$H$_{14}$ClF$_2$N$_3$O [M+H]$^+$, 326.08; found 326.15. $^1$H NMR (400 MHz, Chloroform-d) δ $^1$H NMR (400 MHz, Chloroform-d) δ 8.75 (dd, J=5.2, 0.8 Hz, 1H), 8.22-8.17 (m, 1H), 7.98 (m, 1H), 7.23 (d, J=1.4 Hz, 1H), 6.74 (t, J=55.5 Hz, 1H), 6.71 (d, J=1.2 Hz, 1H), 3.91-3.84 (m, 4H), 3.69-3.62 (m, 4H). $^{19}$F NMR (282 MHz, Chloroform-d) δ-115.74 (2F).

Example 46: (3S)—N-[3-[2'-(difluoromethyl)-6-(morpholin-4-yl)-[2,4'-bipyridin]-4-yl]-4-methylphenyl]-3-(2,2,2-trifluoroethyl)pyrrolidine-1-carboxamide

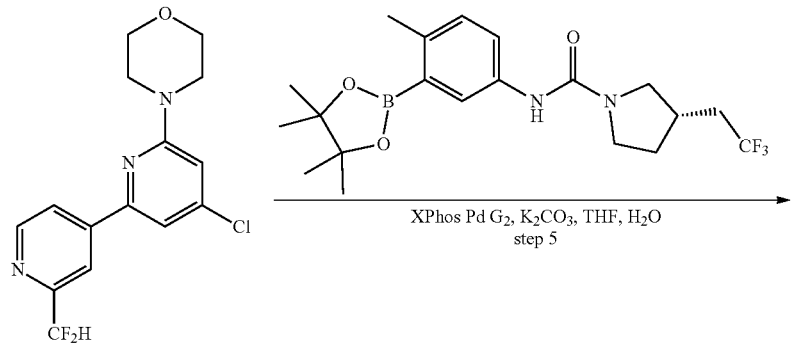

XPhos Pd G₂, K₂CO₃, THF, H₂O
step 5

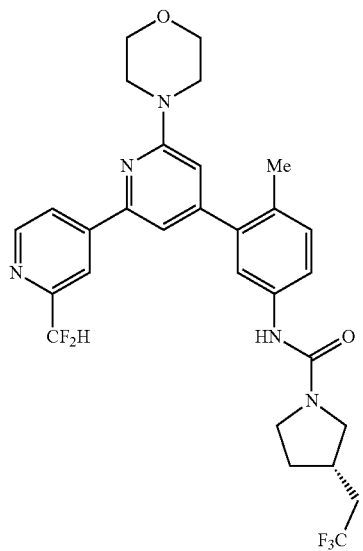

A mixture of 4-chloro-2-(difluoromethyl)-6-(morpholin-4-yl)-2,4-bipyridine (120 mg, 0.368 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (152 mg, 0.368 mmol), 2$^{nd}$ Generation XPhos precatalyst (29 mg, 0.037 mmol) and K₃PO₄ (156 mg, 0.737 mmol) in THF (2 mL) and H₂O (0.4 mL) was stirred for 2 h at 80° C. under nitrogen atmosphere. The mixture was allowed to cool down to room temperature. The resulting mixture was quenched with water (20 mL). The resulting mixture was extracted with DCM (20 mL). The organic layer was washed with brine (10 mL) and dried over anhydrous Na₂SO₄. After filtration, the filtrate was concentrated under reduced pressure. The residue was purified by reverse phase Flash chromatography with the following conditions: Column: WelFlash™ C18, 20-40 μm, 120 g; Eluent A: Water (10 mmol/L NH₄HCO₃); Eluent B: CH₃CN; Gradient: 55%-75% B in 25 min; Flow rate: 60 mL/min; Detector: 220/254 nm to afford (3S)—N-[3-[2'-(difluoromethyl)-6-(morpholin-4-yl)-[2,4'-bipyridin]-4-yl]-4-methylphenyl]-3-(2,2,2-trifluoroethyl)pyrrolidine-1-carboxamide (102 mg, 48%) as a white solid. MS ESI calculated for C29H30F5N5O2 [M+H]$^+$, 576.23 found 576.30; $^1$H NMR (300 MHz, DMSO-d₆) δ 8.75 (d, J=5.2 Hz, 1H), 8.36 (s, 1H), 8.29-8.23 (m, 1H), 8.18 (s, 1H), 7.56-7.42 (m, 3H), 7.17 (s, 1H), 7.01 (t, J=54.9 Hz, 1H), 6.87 (s, 1H), 3.84-3.46 (m, 10H), 3.34-3.25 (m, 1H), 3.02 (t, J=9.3 Hz, 1H), 2.50-2.40 (m, 3H), 2.21 (s, 3H), 2.10-2.05 (m, 1H), 1.70-1.60 (m, 1H); $^{19}$F NMR (282 MHz, DMSO-d₆) δ −63.36 (3F), −115.17 (2F).

Example 47: (3S)—N-[4-methyl-3-[2-(3-methyl-1H-pyrazol-4-yl)-6-(morpholin-4-yl)pyridin-4-yl]phenyl]-3-(2,2,2-trifluoroethyl)pyrrolidine-1-carboxamide

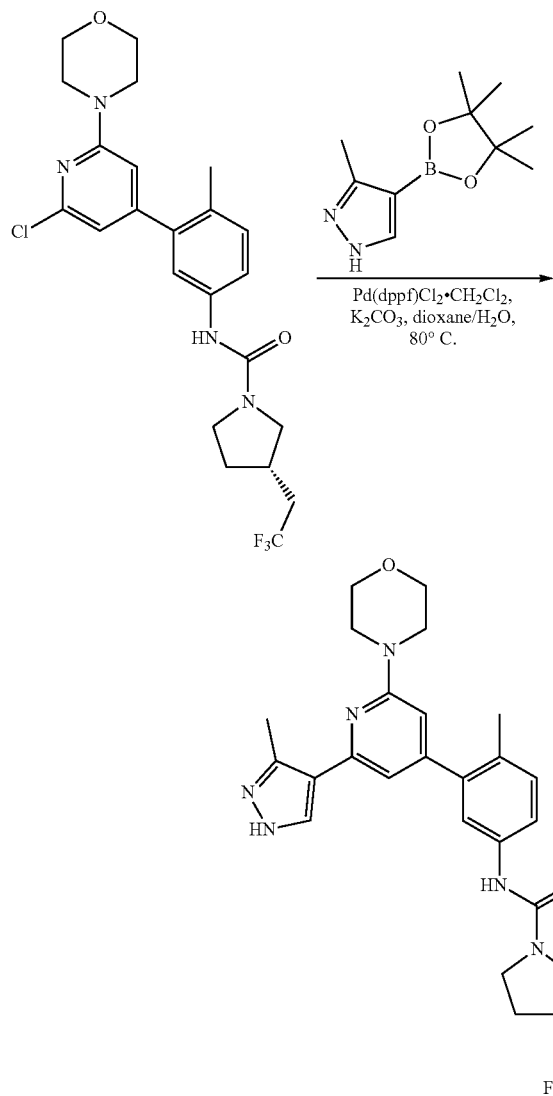

A mixture of (3S)—N-[3-[2-chloro-6-(morpholin-4-yl)pyridin-4-yl]-4-methylphenyl]-3-(2,2,2-trifluoroethyl)pyrrolidine-1-carboxamide (120 mg, 0.248 mmol) and 3-methyl-4-(4,4,5,5-tetramethyl-1,3,2-dioxaborolan-2-yl)-1H-pyrazole (78 mg, 0.373 mmol) in dioxane (4 mL) and $H_2O$ (1 mL), Pd(dppf)$Cl_2 \cdot CH_2Cl_2$ (20 mg, 0.025 mmol) and $K_2CO_3$ (69 mg, 0.497 mmol) was stirred at 80° C. for 2 h under nitrogen atmosphere. The mixture was concentrated under reduced pressure. The residue was purified by Prep-TLC with PE/EA (1/1). The crude product was purified by reverse phase flash chromatography with the following conditions: Column: Spherical C18, 20-40 µm, 120 g; Mobile Phase A: Water (5 mM $NH_4HCO_3$); Mobile Phase B: $CH_3CN$; Flow rate: 50 mL/min; Gradient: 30% B-70% B; Detector: 254 nm to afford (3S)—N-[4-methyl-3-[2-(3-methyl-1H-pyrazol-4-yl)-6-(morpholin-4-yl)pyridin-4-yl]phenyl]-3-(2,2,2-trifluoroethyl)pyrrolidine-1-carboxamide (86.6 mg, 66%) as a white solid. MS ESI calculated for $C_{27}H_{31}F_3N_6O_2$ [M+H]$^+$, 529.25, found 529.20. $^1$H NMR (300 MHz, DMSO-d$_6$) δ 12.63 (s, 1H), 8.17 (s, 1H), 8.03 (brs, 1H), 7.50 (d, J=8.1 Hz, 1H), 7.42 (s, 1H), 7.17 (d, J=8.1 Hz, 1H), 6.91 (s, 1H), 6.50 (s, 1H), 3.80-3.65 (m, 5H), 3.56-3.50 (m, 5H), 3.32-3.25 (m, 1H), 3.04 (t, J=9.3 Hz, 1H), 2.56 (s, 3H), 2.50-2.40 (m, 3H), 2.21 (s, 3H), 2.11-2.05 (m, 1H), 1.70-1.60 (m, 1H). $^{19}$F NMR (282 MHz, DMSO-d$_6$) δ −63.35 (3F).

Example 48: (3S)—N-[3-[2-(1,5-dimethylpyrazol-4-yl)-6-(morpholin-4-yl)pyridin-4-yl]-4-methylphenyl]-3-(2,2,2-trifluoroethyl)pyrrolidine-1-carboxamide

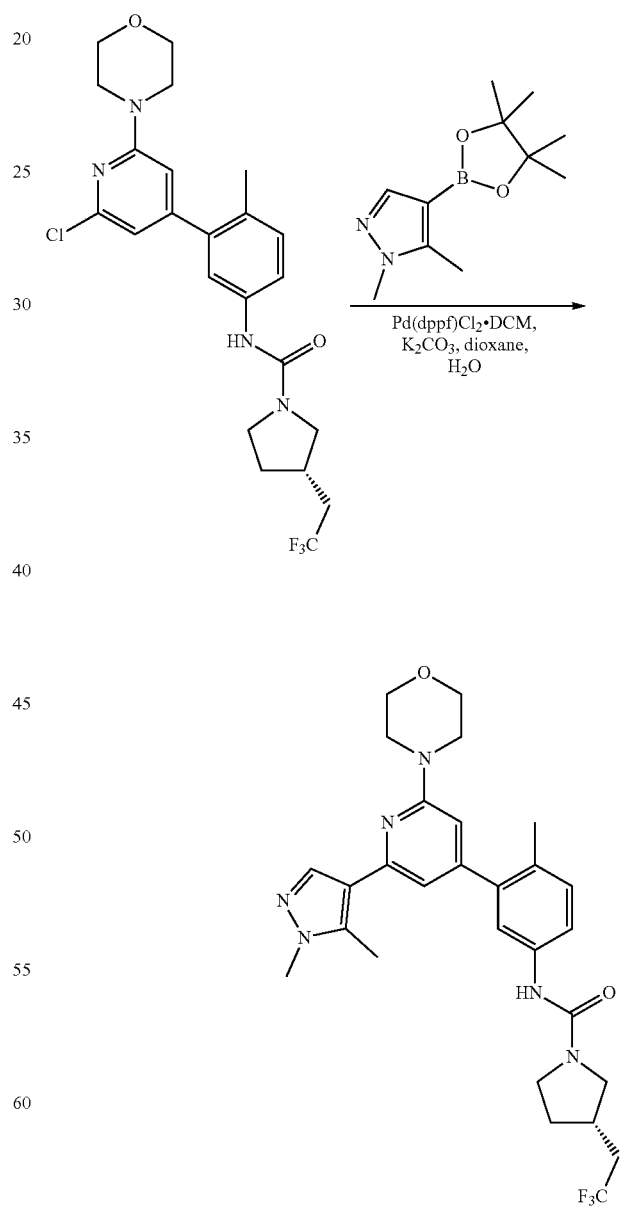

A mixture of (3S)—N-[3-[2-chloro-6-(morpholin-4-yl)pyridin-4-yl]-4-methylphenyl]-3-(2,2,2-trifluoroethyl)pyrrolidine-1-carboxamide (120 mg, 0.248 mmol) and 1,5-dimethyl-4-(4,4,5,5-tetramethyl-1,3,2-dioxaborolan-2-yl)pyrazole (83 mg, 0.372 mmol), dioxane (2 mL), H$_2$O (0.5 mL), Pd(dppf)Cl$_2$.CH$_2$Cl$_2$ (20 mg, 0.025 mmol) and K$_2$CO$_3$ (68 mg, 0.496 mmol) was stirred for 2 h at 80° C. under nitrogen atmosphere. The mixture was concentrated under reduced pressure. The residue was purified by Prep-TLC with PE/EA/EtOH (4/3/1). The crude product was purified by reverse phase flash chromatography with the following conditions: Column: Spherical C18, 20-40 μm, 120 g; Mobile Phase A: Water (5 mM NH$_4$HCO$_3$); Mobile Phase B: CH$_3$CN; Flow rate: 50 mL/min; Gradient: 30% B-70% B; Detector: 254 nm to afford (3S)—N-[3-[2-(1,5-dimethylpyrazol-4-yl)-6-(morpholin-4-yl)pyridin-4-yl]-4-methylphenyl]-3-(2,2,2-trifluoroethyl)pyrrolidine-1-carboxamide (73.7 mg, 55%) as a white solid. MS ESI calculated for C$_{28}$H$_{33}$F$_3$N$_6$O$_2$[M+H]$^+$, 543.26, found 543.25; $^1$H NMR (400 MHz, DMSO-d$_6$) δ 8.16 (s, 1H), 7.85 (s, 1H), 7.49 (dd, J=8.3, 2.3 Hz, 1H), 7.40 (d, J=2.3 Hz, 1H), 7.15 (d, J=8.4 Hz, 1H), 6.87 (d, J=1.0 Hz, 1H), 6.51 (d, J=1.1 Hz, 1H), 3.78 (s, 3H), 3.77-3.63 (m, 5H), 3.55-3.50 (m, 5H), 3.37-3.26 (m, 1H), 3.03 (t, J=9.4 Hz, 1H), 2.62 (s, 3H), 2.51-2.34 (m, 3H), 2.20 (s, 3H), 2.10-2.05 (m, 1H), 1.73-1.61 (m, 1H). $^{19}$F NMR (376 MHz, DMSO-d$_6$) δ −63.37 (3F).

Example 49: (3S)—N-[4-methyl-3-[2-(2-methylpyrazol-3-yl)-6-(morpholin-4-yl)pyridin-4-yl]phenyl]-3-(2,2,2-trifluoroethyl)pyrrolidine-1-carboxamide

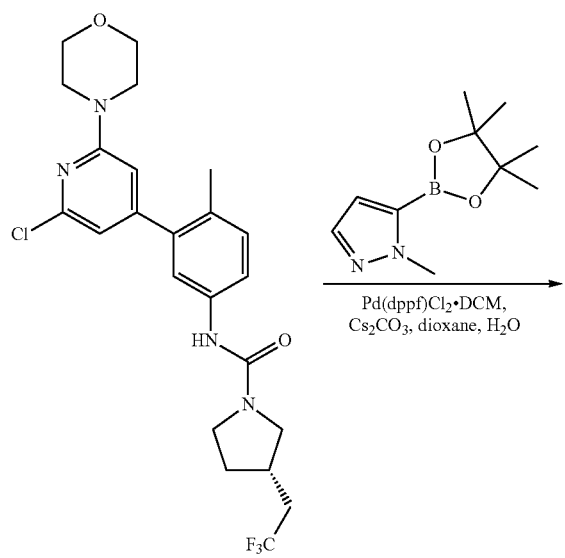

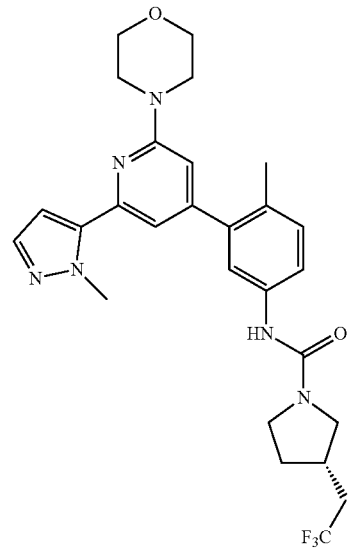

A mixture of (3S)—N-[3-[2-chloro-6-(morpholin-4-yl)pyridin-4-yl]-4-methylphenyl]-3-(2,2,2-trifluoroethyl)pyrrolidine-1-carboxamide (140 mg, 0.290 mmol), 1-methyl-5-(4,4,5,5-tetramethyl-1,3,2-dioxaborolan-2-yl)pyrazole (121 mg, 0.580 mmol), Pd(dppf)Cl$_2$. CH$_2$Cl$_2$ (24 mg, 0.029 mmol) and Cs$_2$CO$_3$ (189 mg, 0.580 mmol) in dioxane (4 mL) and H$_2$O (1 mL) was stirred at 80° C. for 16 h. The mixture was allowed to cool down to room temperature. The resulting mixture was diluted with EA (20 mL), washed with brine (3×10 mL), and dried over anhydrous Na$_2$SO$_4$. After filtration, the filtrate was concentrated under reduced pressure. The residue was purified by silica gel column chromatography, eluted with PE/EA/EtOH (8/3/1 to 4/3/1). The crude product was purified by reverse flash chromatography with the following conditions: Column: C18 Column 120 g; Mobile Phase A: Water (10 mmol/L NH$_4$HCO$_3$), Mobile Phase B: CH$_3$CN; Flow rate: 80 mL/min; Gradient: 30% B to 70% B; 254/220 nm to afford (3S)—N-[4-methyl-3-[2-(2-methylpyrazol-3-yl)-6-(morpholin-4-yl)pyridin-4-yl]phenyl]-3-(2,2,2-trifluoroethyl)pyrrolidine-1-carboxamide (128.8 mg, 84%) as a white solid. MS ESI calculated for C$_{27}$H$_{31}$F$_3$N$_6$O$_2$ [M+H]$^+$, 529.25 found 529.15. $^1$H NMR (400 MHz, DMSO-d$_6$) δ 8.18 (s, 1H), 7.50 (dd, J=8.3, 2.3 Hz, 1H), 7.44 (d, J=1.9 Hz, 2H), 7.17 (d, J=8.4 Hz, 1H), 7.05 (d, J=1.0 Hz, 1H), 6.78 (d, J=2.0 Hz, 1H), 6.73 (s, 1H), 4.19 (s, 3H), 3.77-3.71 (m, 4H), 3.70-3.66 (m, 1H), 3.57-3.51 (m, 5H), 3.30-3.25 (m, 1H), 3.03 (t, J=9.4 Hz, 1H), 2.49-2.36 (m, 3H), 2.21 (s, 3H), 2.10-2.05 (m, 1H), 1.70-1.60 (m, 1H). $^{19}$F NMR (376 MHz, DMSO-d$_6$) δ −63.38 (3F).

Example 50: (3S)—N-[3-[2-(2,5-dimethylpyrazol-3-yl)-6-(morpholin-4-yl)pyridin-4-yl]-4-methylphenyl]-3-(2,2,2-trifluoroethyl)pyrrolidine-1-carboxamide

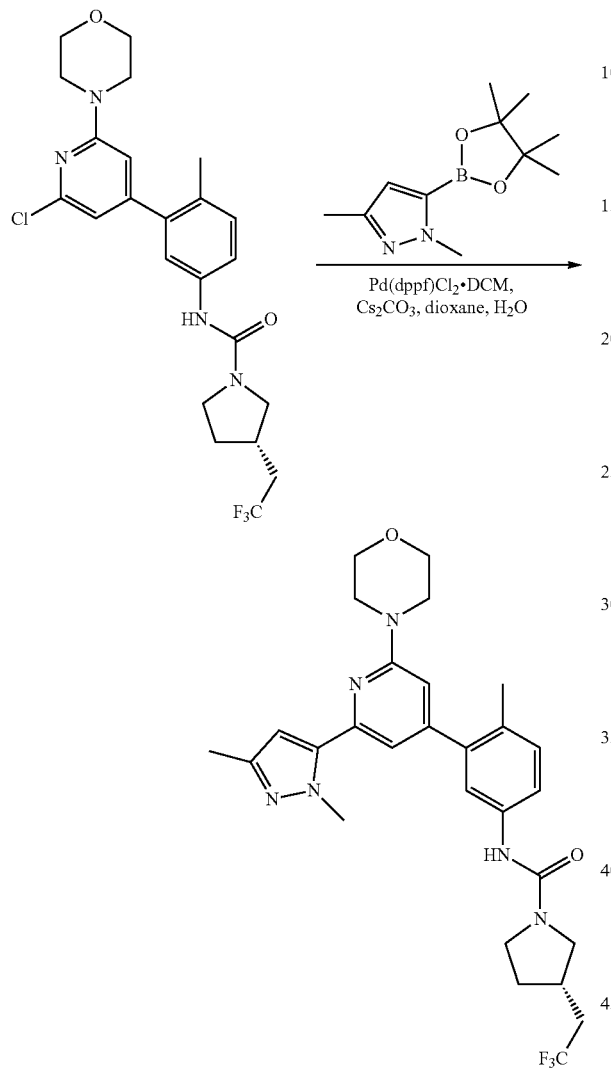

A mixture of (3S)—N-[3-[2-chloro-6-(morpholin-4-yl)pyridin-4-yl]-4-methylphenyl]-3-(2,2,2-trifluoroethyl)pyrrolidine-1-carboxamide (140 mg, 0.290 mmol), 1,3-dimethyl-5-(4,4,5,5-tetramethyl-1,3,2-dioxaborolan-2-yl)pyrazole (129 mg, 0.580 mmol), Pd(dppf)Cl$_2$·CH$_2$Cl$_2$ (24 mg, 0.029 mmol) and Cs$_2$CO$_3$ (189 mg, 0.580 mmol) in dioxane (4 mL) and H$_2$O (1 mL) was stirred at 80° C. for 16 h under N$_2$ atmosphere. The mixture was allowed to cool down to room temperature. The resulting mixture was diluted with EA (10 mL), washed with brine (3×5 mL), and dried over anhydrous Na$_2$SO$_4$. After filtration, the filtrate was concentrated under reduced pressure. The residue was purified by silica gel column chromatography, eluted with PE/EA/EtOH (8/3/1 to 4/3/1). The crude product was purified by reverse flash chromatography with the following conditions: Column: C18 Column 120 g; Mobile Phase A: Water (10 mmol/L NH$_4$HCO$_3$), Mobile Phase B: CH$_3$CN; Flow rate: 60 mL/min; Gradient: 30% B to 70% B; 254/220 nm to afford (3S)—N-[3-[2-(2,5-dimethylpyrazol-3-yl)-6-(morpholin-4-yl)pyridin-4-yl]-4-methylphenyl]-3-(2,2,2-trifluoroethyl)pyrrolidine-1-carboxamide (100 mg, 64%) as a white solid. MS ESI calculated for C$_{28}$H$_{33}$F$_3$N$_6$O$_2$[M+H]$^+$, 543.26 found 543.25; $^1$H NMR (400 MHz, DMSO-d$_6$) δ 8.17 (s, 1H), 7.50 (dd, J=8.3, 2.3 Hz, 1H), 7.44 (d, J=2.3 Hz, 1H), 7.17 (d, J=8.4 Hz, 1H), 6.99 (d, J=1.0 Hz, 1H), 6.71 (d, J=1.1 Hz, 1H), 6.54 (s, 1H), 4.10 (s, 3H), 3.76-3.71 (m, 4H), 3.70-3.65 (m, 1H), 3.58-3.51 (m, 5H), 3.31-3.26 (m, 1H), 3.03 (t, J=9.4 Hz, 1H), 2.48-2.36 (m, 3H), 2.21 (s, 3H), 2.16 (s, 3H), 2.13-2.04 (m, 1H), 1.70-1.60 (m, 1H). $^{19}$F NMR (376 MHz, DMSO-d$_6$) δ −63.38 (3F).

Example 51: (3S)—N-[3-[2-(3,5-dimethyl-1H-pyrazol-4-yl)-6-(morpholin-4-yl)pyridin-4-yl]-4-methylphenyl]-3-(2,2,2-trifluoroethyl)pyrrolidine-1-carboxamide

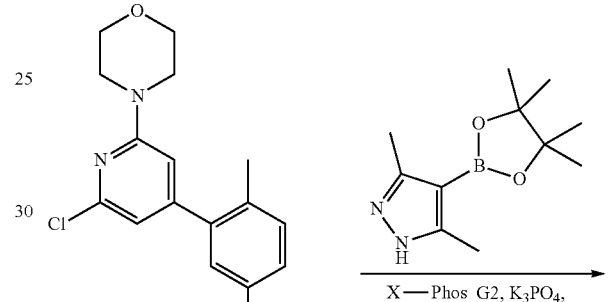

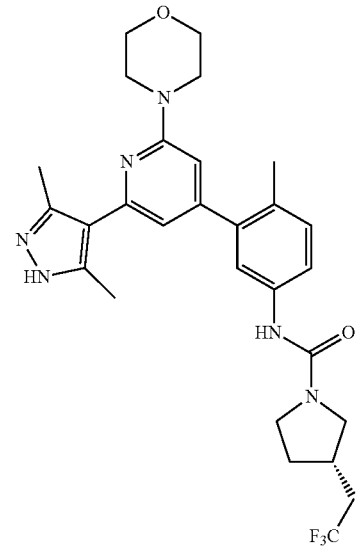

A mixture of (3S)—N-[3-[2-chloro-6-(morpholin-4-yl)pyridin-4-yl]-4-methylphenyl]-3-(2,2,2-trifluoroethyl)pyrrolidine-1-carboxamide (120 mg, 0.248 mmol) and 3,5-dimethyl-4-(4,4,5,5-tetramethyl-1,3,2-dioxaborolan-2-yl)-1H-pyrazole (110 mg, 0.496 mmol) in dioxane (4 mL) and H$_2$O (1 mL), 2$^{nd}$ Generation XPhos precatalyst (20 mg, 0.025 mmol) and K$_3$PO$_4$ (106 mg, 0.497 mmol) was stirred for 2 h at 80° C. under nitrogen atmosphere. The mixture was concentrated under reduced pressure. The residue was purified by Prep-TLC with PE/EA/EtOH (4/3/1). The crude product was purified by reverse phase flash chromatography with the following conditions: Column: Spherical C18, 20-40 μm, 120 g; Mobile Phase A: Water (5 mM NH$_4$HCO$_3$); Mobile Phase B: CH$_3$CN; Flow rate: 50 mL/min; Gradient: 30% B-70% B; Detector: 220 nm. The fractions containing the desired product were collected at 58% B and concentrated under reduced pressure to afford (3S)—N-[3-[2-(3,5-dimethyl-1H-pyrazol-4-yl)-6-(morpholin-4-yl)pyridin-4-yl]-4-methylphenyl]-3-(2,2,2-trifluoroethyl)pyrrolidine-1-carboxamide (62.3 mg, 46%) as a white solid. MS ESI calculated for C$_{28}$H$_{33}$F$_3$N$_6$O$_2$[M+H]$^+$, 543.26, found 543.20; $^1$H NMR (300 MHz, DMSO-d$_6$) δ 12.30 (s, 1H), 8.15 (s, 1H), 7.53-7.40 (m, 2H), 7.16 (d, J=8.3 Hz, 1H), 6.64 (s, 1H), 6.52 (s, 1H), 3.75-3.65 (m, 5H), 3.60-3.47 (m, 5H), 3.30-3.25 (m, 1H), 3.03 (t, J=9.4 Hz, 1H), 2.50-2.40 (m, 3H), 2.37 (s, 6H), 2.23 (s, 3H), 2.10-2.05 (m, 1H), 1.70-1.60 (m, 1H). $^{19}$F NMR (282 MHz, DMSO-d$_6$) δ −63.35 (3F).

Example 52: (3S)—N-[3-[2-(1,5-dimethylpyrazol-3-yl)-6-(morpholin-4-yl)pyridin-4-yl]-4-methylphenyl]-3-(2,2,2-trifluoroethyl)pyrrolidine-1-carboxamide Synthetic Scheme

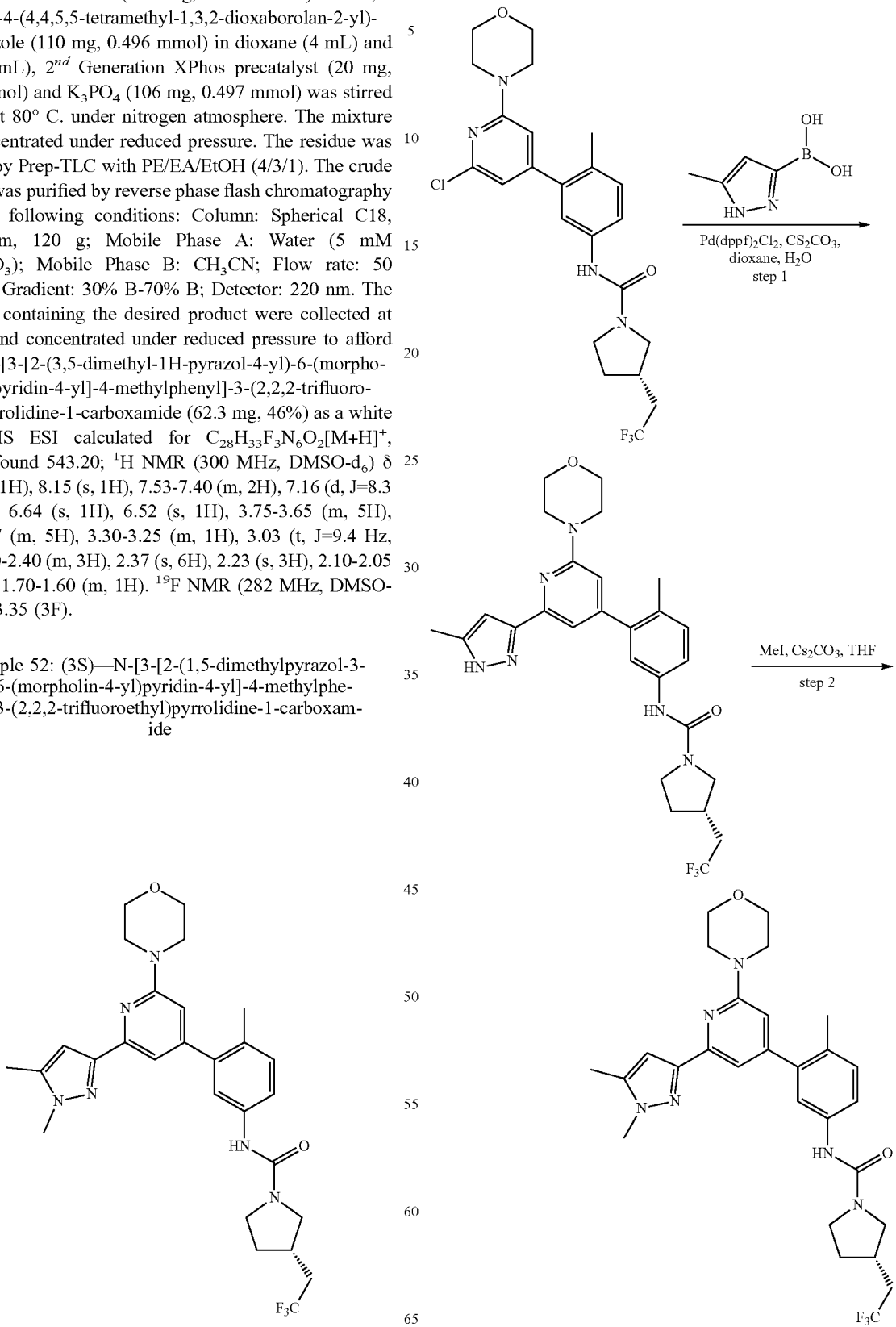

253

Preparation 52A: (3S)—N-[4-methyl-3-[2-(5-methyl-1H-pyrazol-3-yl)-6-(morpholin-4-yl)pyridin-4-yl]phenyl]-3-(2,2,2-trifluoroethyl)pyrrolidine-1-carboxamide

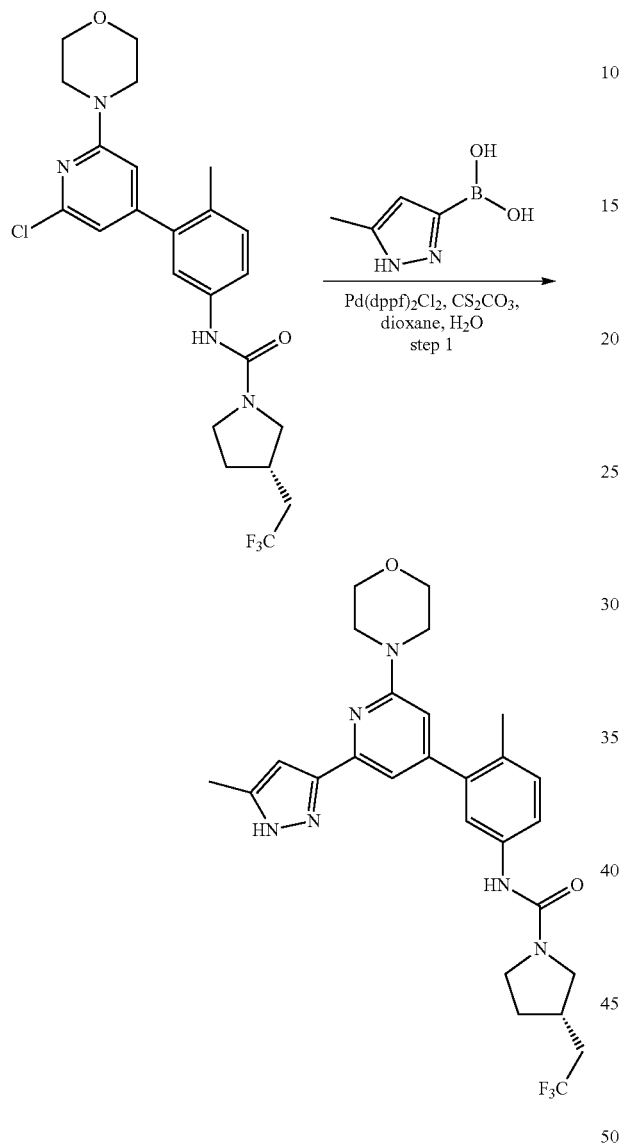

A mixture of (3S)—N-[3-[2-chloro-6-(morpholin-4-yl)pyridin-4-yl]-4-methylphenyl]-3-(2,2,2-trifluoroethyl)pyrrolidine-1-carboxamide (500 mg, 1.214 mmol) and 5-methyl-1H-pyrazol-3-ylboronic acid (306 mg, 2.428 mmol), Pd(dppf)Cl$_2$·CH$_2$Cl$_2$ (99 mg, 0.121 mmol) and Cs$_2$CO$_3$ (792 mg, 2.428 mmol) in dioxane (8 mL) and H$_2$O (2 mL) was stirred for 2 h at 80° C. under nitrogen atmosphere. The mixture was concentrated under reduced pressure. The residue was purified by silica gel column chromatography, eluted with PE/EA/EtOH (4/3/1) to afford (3S)—N-[4-methyl-3-[2-(5-methyl-1H-pyrazol-3-yl)-6-(morpholin-4-yl)pyridin-4-yl]phenyl]-3-(2,2,2-trifluoroethyl)pyrrolidine-1-carboxamide (600 mg, 93%) as a white solid. MS ESI calculated for C$_{27}$H$_{31}$F$_3$N$_6$O$_2$[M+H]$^+$, 529.25, found 529.30. $^1$H NMR (400 MHz, Chloroform-d) δ 7.37 (dd, J=8.2, 2.4 Hz, 1H), 7.30 (d, J=2.4 Hz, 1H), 7.20 (d, J=8.3 Hz, 1H), 7.03-6.99 (m, 1H), 6.53-6.46 (m, 2H),

254

6.32 (s, 1H), 3.89-3.74 (m, 5H), 3.68-3.55 (m, 5H), 3.45-3.41 (m, 1H), 3.11 (t, J=9.5 Hz, 1H), 2.57-2.52 (m, 1H), 2.35 (s, 3H), 2.33-2.17 (m, 6H), 1.80-1.65 (m, 1H). $^{19}$F NMR (376 MHz, DMSO-d$_6$) δ −64.88 (3F).

Example 52: (3S)—N-[3-[2-(1,5-dimethylpyrazol-3-yl)-6-(morpholin-4-yl)pyridin-4-yl]-4-methylphenyl]-3-(2,2,2-trifluoroethyl)pyrrolidine-1-carboxamide

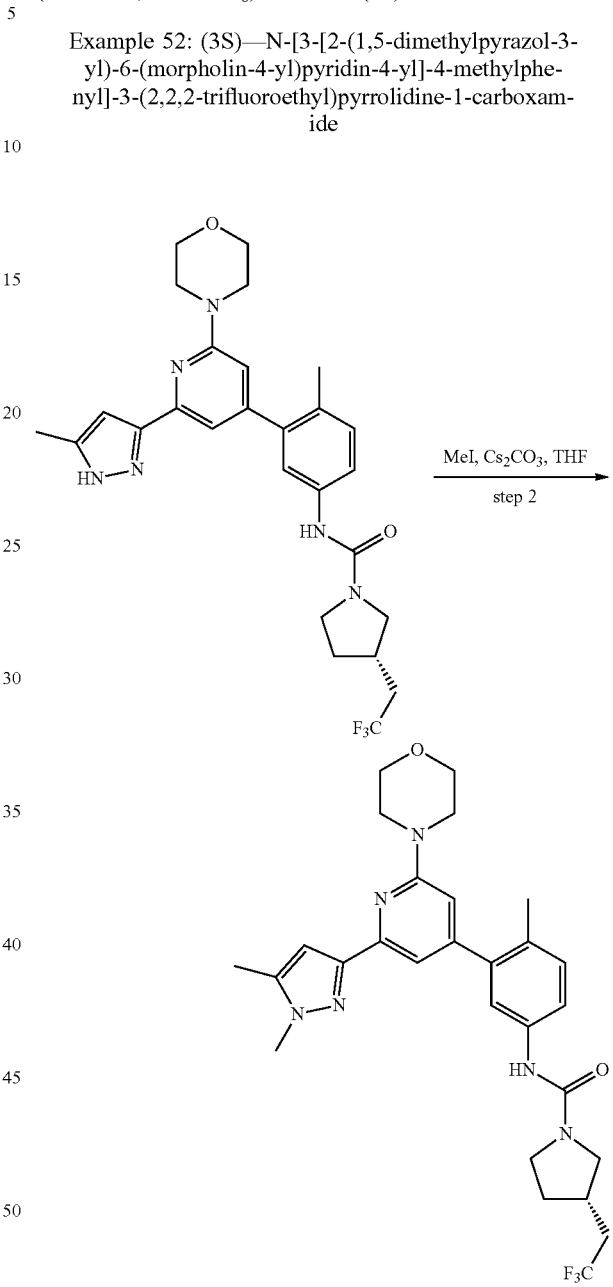

To a stirred mixture of (3S)—N-[4-methyl-3-[2-(5-methyl-1H-pyrazol-3-yl)-6-(morpholin-4-yl)pyridin-4-yl]phenyl]-3-(2,2,2-trifluoroethyl)pyrrolidine-1-carboxamide (300 mg, 0.568 mmol) and Cs$_2$CO$_3$ (370 mg, 1.135 mmol) in THF (5 mL) was added MeI (120 mg, 0.851 mmol). The resulting mixture was stirred for 2 h at 50° C. The mixture was concentrated under reduced pressure. The residue was purified by silica gel column chromatography, eluted with PE/EA/EtOH (4/3/1). The crude product was purified by Prep-HPLC with the following conditions: Column: SunFire Prep C18 OBD Column, 19×150 mm, 5 μm; Mobile Phase A: Water (0.05% TFA), Mobile Phase B: CH$_3$CN; Flow rate: 20 mL/min; Gradient: 40% B-60% B; 254/210 nm to afford (3S)—N-[3-[2-(1,5-dimethylpyrazol-3-yl)-6-(morpholin-4-yl)pyridin-4-yl]-4-methylphenyl]-3-(2,2,2-trifluoroethyl)pyrrolidine-1-carboxamide (120 mg, 39%) as a white solid. MS ESI calculated for $C_{28}H_{33}F_3N_6O_2[M+H]^+$, 543.26, found 543.25; $^1$H NMR (400 MHz, DMSO-$d_6$) δ $^1$H NMR (400 MHz, DMSO-$d_6$) δ 8.19 (s, 1H), 7.48 (d, J=2.0 Hz, 1H), 7.43 (d, J=2.0 Hz, 1H), 7.16 (d, J=8.4 Hz, 1H), 7.13 (s, 1H), 6.61 (s, 1H), 6.59 (s, 1H), 3.79-3.70 (m, 8H), 3.57-3.52 (m, 5H), 3.03 (t, J=9.4 Hz, 1H), 2.50-2.40 (m, 4H), 2.29 (s, 3H), 2.20 (s, 3H), 2.13-2.05 (m, 1H), 1.71-1.61 (m, 1H). $^{19}$F NMR (376 MHz, DMSO-$d_6$) δ −63.38 (3F).

Example 53: (3S)—N-[3-[2-(1H-imidazol-4-yl)-6-(morpholin-4-yl)pyridin-4-yl]-4-methylphenyl]-3-(2,2,2-trifluoroethyl)pyrrolidine-1-carboxamide

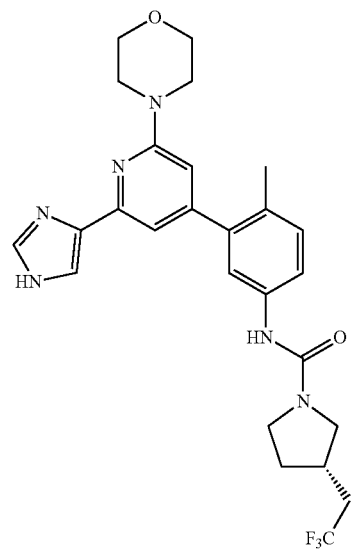 [SMILES: Cc1ccc(NC(=O)N2CC[C@@H](CC(F)(F)F)C2)cc1-c1cc(-c2c[nH]cn2)nc(N2CCOCC2)c1]

Synthetic Scheme

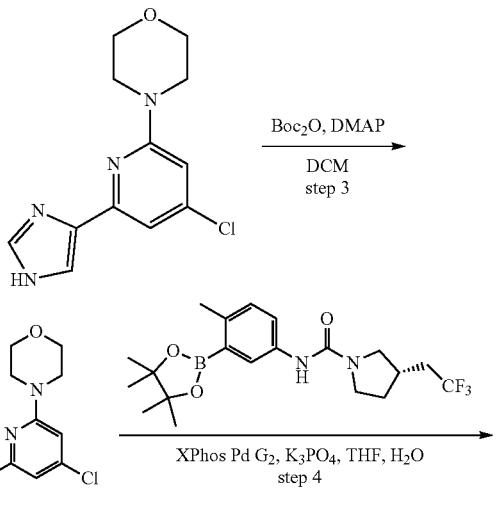

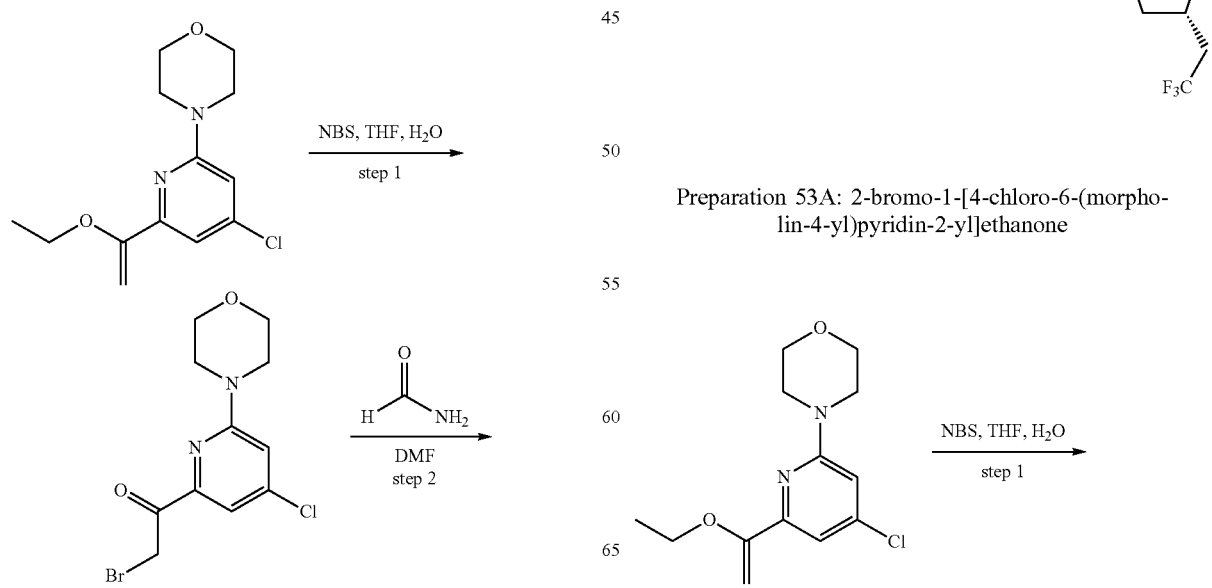

Preparation 53A: 2-bromo-1-[4-chloro-6-(morpholin-4-yl)pyridin-2-yl]ethanone

257

-continued

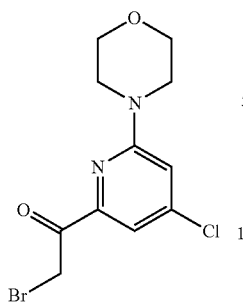

To a stirred solution of 4-[4-chloro-6-(1-ethoxyethenyl)pyridin-2-yl]morpholine (850 mg, 3.163 mmol) in THF (10 mL) and H$_2$O (1 mL) was added NBS (563 mg, 3.163 mmol) at 0° C. The resulting mixture was stirred for 2 h at room temperature. The resulting mixture was concentrated under reduced pressure. The reaction was diluted with water (20 mL). The resulting mixture was extracted with EA (3×20 mL). The combined organic layers were washed with brine (20 mL), dried over anhydrous Na$_2$SO$_4$. After filtration, the filtrate was concentrated under reduced pressure. The residue was purified by silica gel column chromatography, eluted with PE/EA (5/1) to afford 2-bromo-1-[4-chloro-6-(morpholin-4-yl)pyridin-2-yl]ethanone (550 mg, 54%) as a light yellow solid. MS ESI calculated for C$_{11}$H$_{12}$BrClN$_2$O$_2$ [M+H]$^+$: 318.98, 320.98; found 318.95, 320.95; $^1$H NMR (400 MHz, Chloroform-d) δ 7.44 (d, J=1.5 Hz, 1H), 6.84 (d, J=1.5 Hz, 1H), 4.73 (s, 2H), 3.91-3.83 (m, 4H), 3.63-3.54 (m, 4H).

Preparation 53B: 4-[4-chloro-6-(1H-imidazol-4-yl)pyridin-2-yl]morpholine

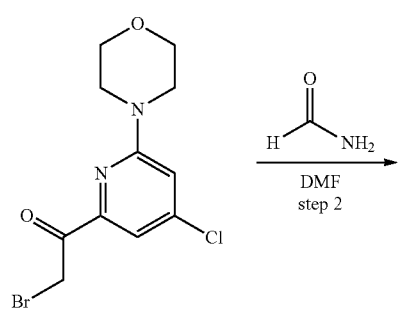

258

A mixture of 2-bromo-1-[4-chloro-6-(morpholin-4-yl)pyridin-2-yl]ethanone (2.00 g, 6.26 mmol) and formamide (1.41 g, 31.29 mmol) in DMF (20 mL) was stirred at 150° C. for 3 h. The mixture was allowed to cool down to room temperature. The mixture was purified by reverse flash chromatography with the following conditions: Column: C18 Column 330 g; Mobile Phase A: Water (10 mmol/L NH$_4$HCO$_3$), Mobile Phase B: CH$_3$CN; Flow rate: 80 mL/min; Gradient: 30% B to 70% B; 254/220 nm to afford 4-[4-chloro-6-(1H-imidazol-4-yl)pyridin-2-yl]morpholine (0.50 g, 30%) as a white solid. MS ESI calculated for C$_{12}$H$_{13}$ClN$_4$O [M+H]$^+$, 265.08 found 265.00. $^1$H NMR (400 MHz, DMSO-d$_6$) δ 12.34 (s, 1H), 7.72 (s, 1H), 7.66 (s, 1H), 7.18 (s, 1H), 6.71 (d, J=1.6 Hz, 1H), 3.72-3.68 (m, 4H), 3.55-3.51 (m, 4H).

Preparation 53C: tert-butyl 4-[4-chloro-6-(morpholin-4-yl)pyridin-2-yl]imidazole-1-carboxylate

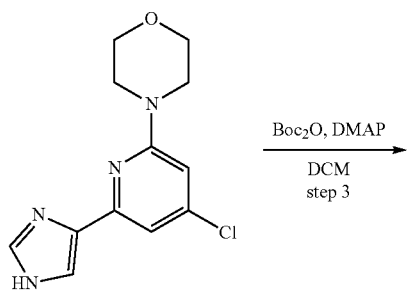

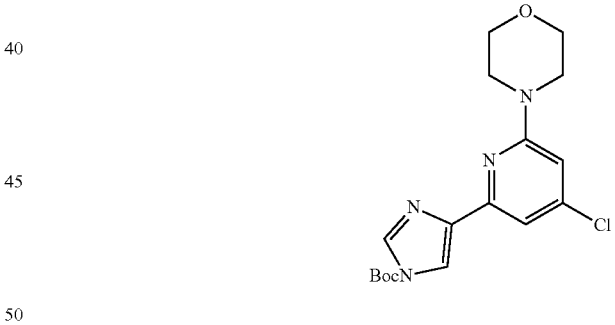

A mixture of 4-[4-chloro-6-(1H-imidazol-4-yl)pyridin-2-yl]morpholine (100 mg, 0.378 mmol), Boc$_2$O (123 mg, 0.567 mmol) and DMAP (5 mg, 0.038 mmol) in DCM (2 mL) was stirred at room temperature for 1 h. The reaction was quenched by the addition of water (1 mL). The resulting mixture was extracted with DCM (5 mL), washed with brine (3×2 mL), and dried over anhydrous Na$_2$SO$_4$. After filtration, the filtrate was concentrated under reduced pressure. The residue was purified by silica gel column chromatography, eluted with PE/EA (1/1) to afford tert-butyl 4-[4-chloro-6-(morpholin-4-yl)pyridin-2-yl]imidazole-1-carboxylate (130 mg, 94%) as a white solid. MS ESI calculated for C$_{17}$H$_{21}$ClN$_4$O$_3$[M+H]$^+$, 365.13 found 365.20; $^1$H NMR (400 MHz, Chloroform-d) δ 8.11 (d, J=1.4 Hz, 1H), 7.91 (d, J=1.4 Hz, 1H), 7.41 (d, J=1.5 Hz, 1H), 6.55 (d, J=1.6 Hz, 1H), 3.87-3.84 (m, 4H), 3.63-3.50 (m, 4H), 1.67 (s, 9H).

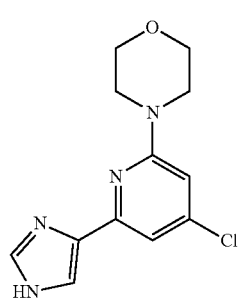

Example 53: (3S)—N-[3-[2-(1H-imidazol-4-yl)-6-(morpholin-4-yl)pyridin-4-yl]-4-methylphenyl]-3-(2,2,2-trifluoroethyl)pyrrolidine-1-carboxamide

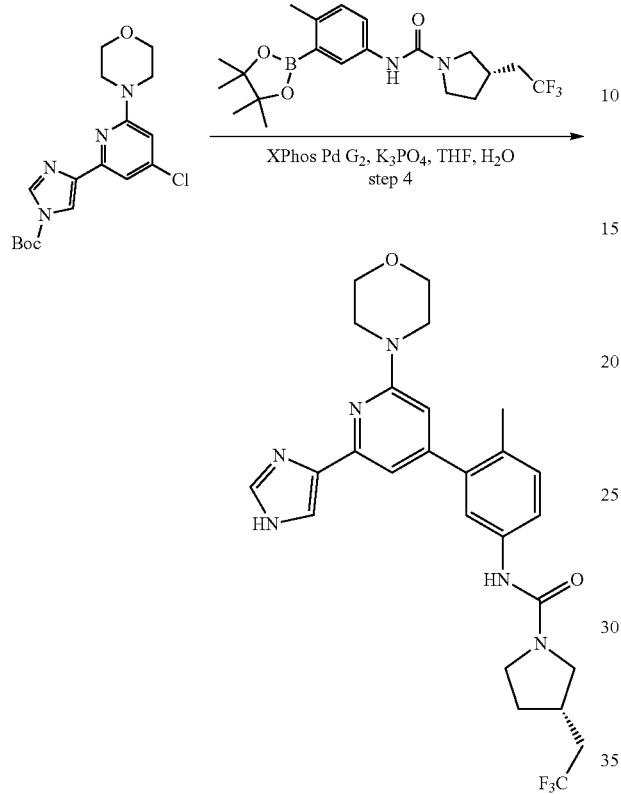

Example 54: (3S)—N-{4-methyl-3-[2-(1-methylimidazol-4-yl)-6-(morpholin-4-yl)pyridin-4-yl]phenyl}-3-(2,2,2-trifluoroethyl)pyrrolidine-1-carboxamide

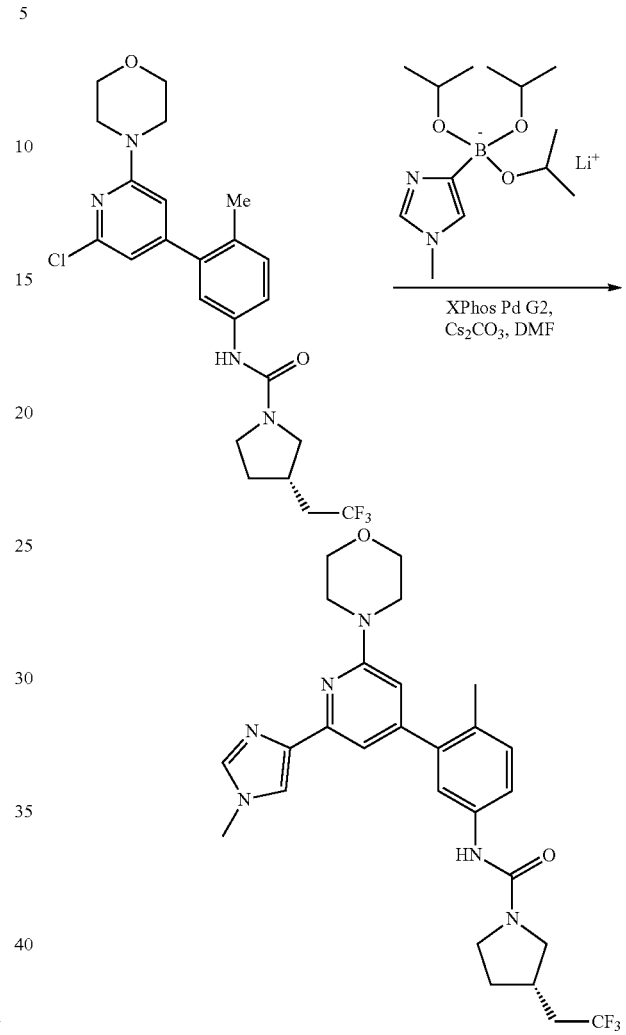

A mixture of tert-butyl 4-[4-chloro-6-(morpholin-4-yl)pyridin-2-yl]imidazole-1-carboxylate (170 mg, 0.467 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (150 mg, 0.364 mmol), $2^{nd}$ Generation XPhos precatalyst (74 mg, 0.093 mmol) and $K_3PO_4$ (198 mg, 0.934 mmol) in THF (5 mL) and $H_2O$ (0.5 mL) was stirred at 100° C. for 16 h under nitrogen atmosphere. The mixture was allowed to cool down to room temperature. The resulting mixture was diluted with EA (20 mL), washed with brine (3×5 mL), and dried over anhydrous $Na_2SO_4$. After filtration, the filtrate was concentrated under reduced pressure. The residue was purified by silica gel column chromatography, eluted with PE/EA (1/1). The crude product was purified by reverse flash chromatography with the following conditions: Column: C18 Column 120 g; Mobile Phase A: Water (10 mmol/L $NH_4HCO_3$), Mobile Phase B: $CH_3CN$; Flow rate: 60 mL/min; Gradient: 30% B to 70% B; 254/220 nm to afford (3S)—N-[3-[2-(1H-imidazol-4-yl)-6-(morpholin-4-yl)pyridin-4-yl]-4-methylphenyl]-3-(2,2,2-trifluoroethyl)pyrrolidine-1-carboxamide (52.7 mg, 28%) as a white solid. MS ESI calculated for $C_{26}H_{29}F_3N_6O_2$ [M+H]$^+$, 515.23, found 515.15; $^1H$ NMR (300 MHz, DMSO-$d_6$) δ 12.35 (brs, 1H), 8.17 (s, 1H), 7.71 (s, 1H), 7.62 (s, 1H), 7.49 (dd, J=8.1, 1.8 Hz, 1H), 7.41 (d, J=1.8 Hz, 1H), 7.21-7.11 (m, 2H), 6.53 (s, 1H), 3.81-3.64 (m, 5H), 3.58-3.50 (m, 5H), 3.30-3.24 (m, 1H), 3.02 (t, J=9.3 Hz, 1H), 2.50-2.40 (m, 3H), 2.22 (s, 3H), 2.16-2.05 (m, 1H), 1.70-1.60 (m, 1H). $^{19}F$ NMR (282 MHz, DMSO-$d_6$) δ −63.35 (3F).

A mixture of (3S)—N-{3-[2-chloro-6-(morpholin-4-yl)pyridin-4-yl]-4-methylphenyl}-3-(2,2,2-trifluoroethyl)pyrrolidine-1-carboxamide (150 mg, 0.311 mmol), lithium triisopropoxy(1-methylimidazol-4-yl)boranuide (171 mg, 0.622 mmol), 2nd Generation XPhos Precatalyst (24 mg, 0.031 mmol) and $Cs_2CO_3$ (202 mg, 0.622 mmol) in DMF (2 mL) was stirred for 16 h at 100° C. under nitrogen atmosphere. The mixture was allowed to cool down to room temperature. The resulting mixture was concentrated under reduced pressure. The residue was purified by Prep-TLC with DCM/MeOH (10/1). The crude product was purified by reverse phase Flash chromatography with the following conditions: Column: WelFlash™ C18-I, 20-40 μm, 120 g; Eluent A: Water (10 mmol/L $NH_4HCO_3$); Eluent B: $CH_3CN$; Gradient: 25% B to 45% B; Flow rate: 60 mL/min; Detector: 220/254 nm to afford (3S)—N-{4-methyl-3-[2-(1-methylimidazol-4-yl)-6-(morpholin-4-yl)pyridin-4-yl]phenyl}-3-(2,2,2-trifluoroethyl)pyrrolidine-1-carboxamide (12 mg, 7%) as a white solid. MS ESI calculated for $C_{28}H_{34}F_3N_5O_4$ [M+H]$^+$, 529.25 found 529.35; $^1H$ NMR (400 MHz, DMSO-$d_6$) δ 8.18 (s, 1H), 7.66 (d, J=1.2 Hz, 1H), 7.61 (d, J=0.8 Hz, 1H), 7.49 (dd, J=8.4, 2.0 Hz, 1H), 7.42 (d, J=2.0 Hz, 1H), 7.16 (d, J=8.4 Hz, 1H), 7.15 (s, 1H), 6.54 (s, 1H), 3.79-3.64 (m, 8H), 3.58-4.51 (m, 5H), 3.31-3.24 (m, 1H), 3.03 (t, J=9.3 Hz, 1H), 2.50-2.40 (m, 3H), 2.20 (s, 2H), 2.10-2.06 (m, 1H), 1.71-1.61 (m, 1H). $^{19}$F NMR (376 MHz, DMSO-$d_6$) δ −63.37 (3F).
Example 55: (3S)—N-{3-[2-(3-aminobut-1-yn-1-yl)-6-(morpholin-4-yl)pyridin-4-yl]-4-methylphenyl}-3-(2,2,2-trifluoroethyl)pyrrolidine-1-carboxamide
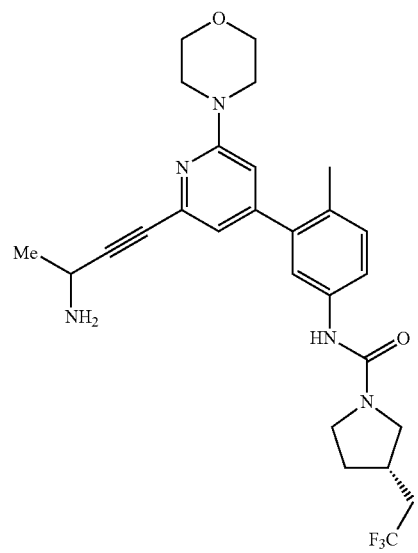 [SMILES: Cc1ccc(NC(=O)N2CC[C@@H](CC(F)(F)F)C2)cc1-c1cc(C#CC(C)N)nc(N2CCOCC2)c1]
Synthetic Scheme
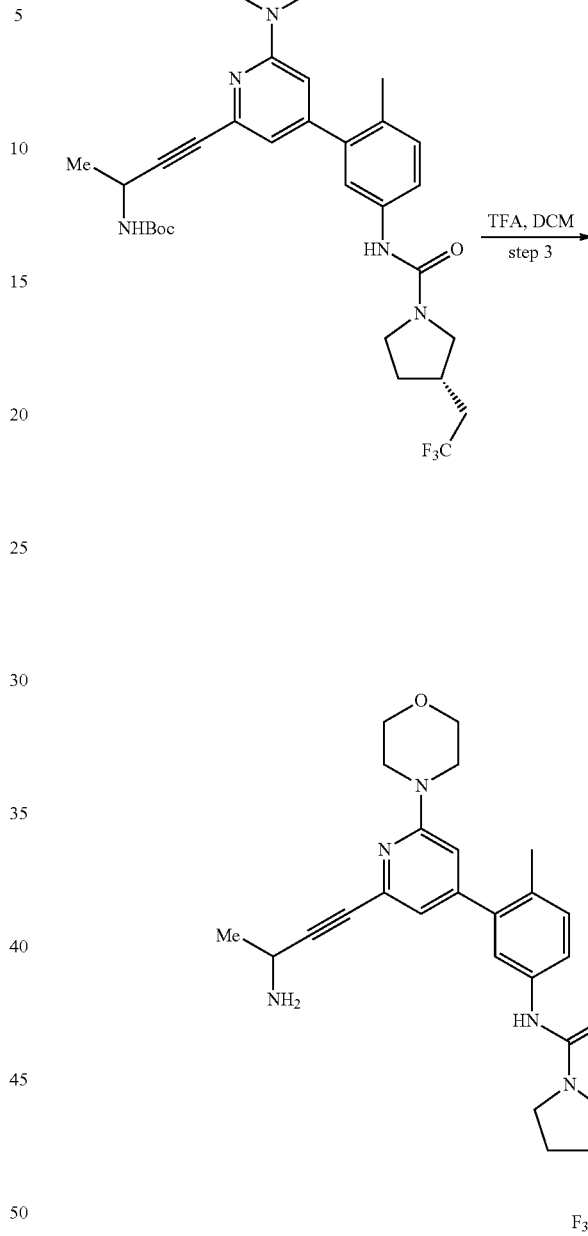
Preparation 55A: tert-butyl N-[4-[4-chloro-6-(morpholin-4-yl)pyridin-2-yl]but-3-yn-2-yl]carbamate
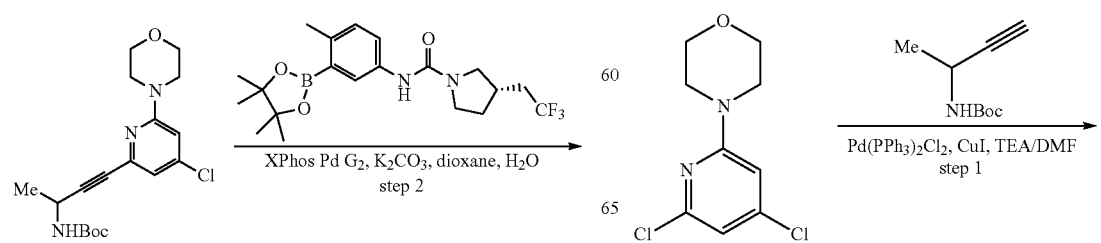

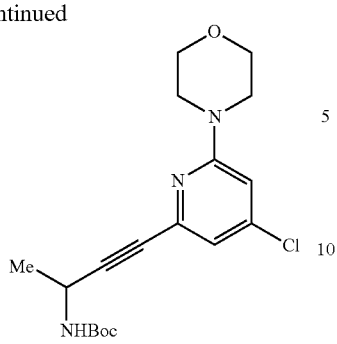

To a stirred solution of 4-(4,6-dichloropyridin-2-yl)morpholine (570 mg, 2.445 mmol) and tert-butyl N-(but-3-yn-2-yl)carbamate (828 mg, 4.891 mmol) in TEA (1.5 mL) and DMF (6 mL) were added Pd(PPh$_3$)$_2$Cl$_2$ (172 mg, 0.245 mmol) and CuI (93 mg, 0.489 mmol). The resulting mixture was stirred for 16 h at 80° C. under nitrogen atmosphere. The mixture was allowed to cool down to room temperature. The resulting mixture was diluted with EA (100 mL), washed with brine (2×50 mL), and dried over anhydrous Na$_2$SO$_4$. After filtration, the filtrate was concentrated under reduced pressure. The residue was purified by silica gel column chromatography, eluted with PE/EA (5/1) to afford tert-butyl N-[4-[4-chloro-6-(morpholin-4-yl)pyridin-2-yl]but-3-yn-2-yl]carbamate (850 mg, 95%) as a yellow solid. MS ESI calculated for C$_{18}$H$_{24}$ClN$_3$O$_3$[M+H]$^+$, 366.15, found 366.20; $^1$H NMR (400 MHz, Chloroform-d) δ 6.81 (s, 1H), 6.58 (s, 1H), 4.90-4.75 (m, 1H), 3.82-3.80 (m, 4H), 3.56-3.53 (m, 4H), 1.51-1.48 (m, 12H).

Preparation 55B: tert-butyl N-[4-(4-[2-methyl-5-[(3S)-3-(2,2,2-trifluoroethyl)pyrrolidine-1-carbonylamino]phenyl]-6-(morpholin-4-yl)pyridin-2-yl)but-3-yn-2-yl]carbamate

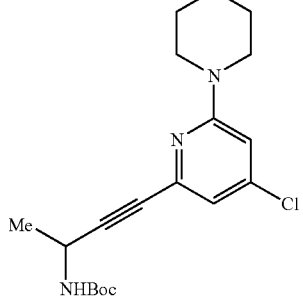
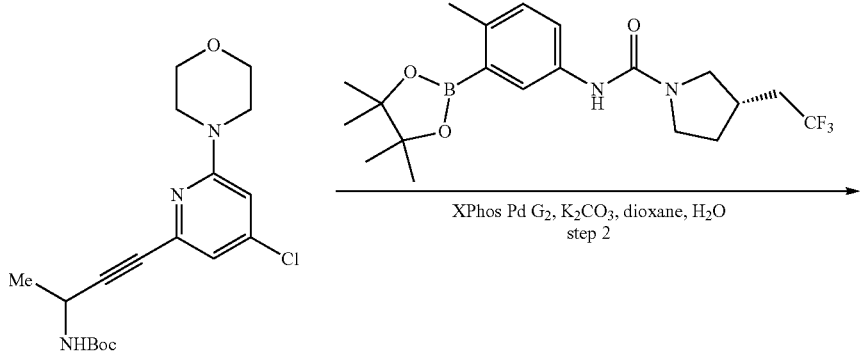

XPhos Pd G$_2$, K$_2$CO$_3$, dioxane, H$_2$O
step 2

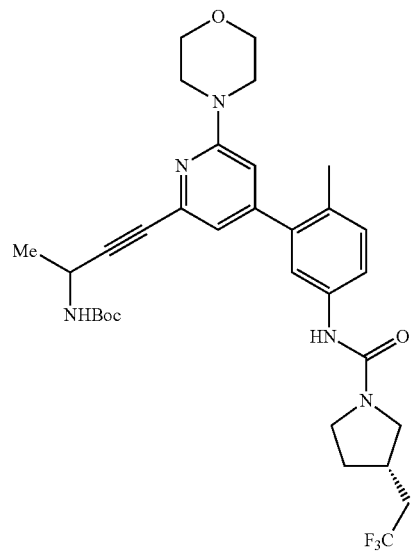

To a stirred solution of tert-butyl N-[4-[4-chloro-6-(morpholin-4-yl)pyridin-2-yl]but-3-yn-2-yl]carbamate (100 mg, 0.273 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (101 mg, 0.246 mmol) in dioxane (1 mL) and H$_2$O (0.25 mL) were added K$_2$CO$_3$ (113 mg, 0.819 mmol) and 2nd Generation XPhos Precatalyst (22 mg, 0.027 mmol) under nitrogen atmosphere. The resulting mixture was stirred for 2 h at 80° C. under nitrogen atmosphere. The resulting mixture was concentrated under reduced pressure. The residue was purified by silica gel column chromatography, eluted with PE/EA (2/3) to afford tert-butyl N-[4-(4-[2-methyl-5-[(3S)-3-(2,2,2-trifluoroethyl)pyrrolidine-1-carbonylamino]phenyl]-6-(morpholin-4-yl)pyridin-2-yl)but-3-yn-2-yl]carbamate (150 mg, crude) as a yellow solid. MS ESI calculated for C$_{32}$H$_{40}$F$_3$N$_5$O$_4$[M+H]$^+$, 616.30, found 616.55.

Example 55: (3S)—N-{3-[2-(3-aminobut-1-yn-1-yl)-6-(morpholin-4-yl)pyridin-4-yl]-4-methylphenyl}-3-(2,2,2-trifluoroethyl)pyrrolidine-1-carboxamide

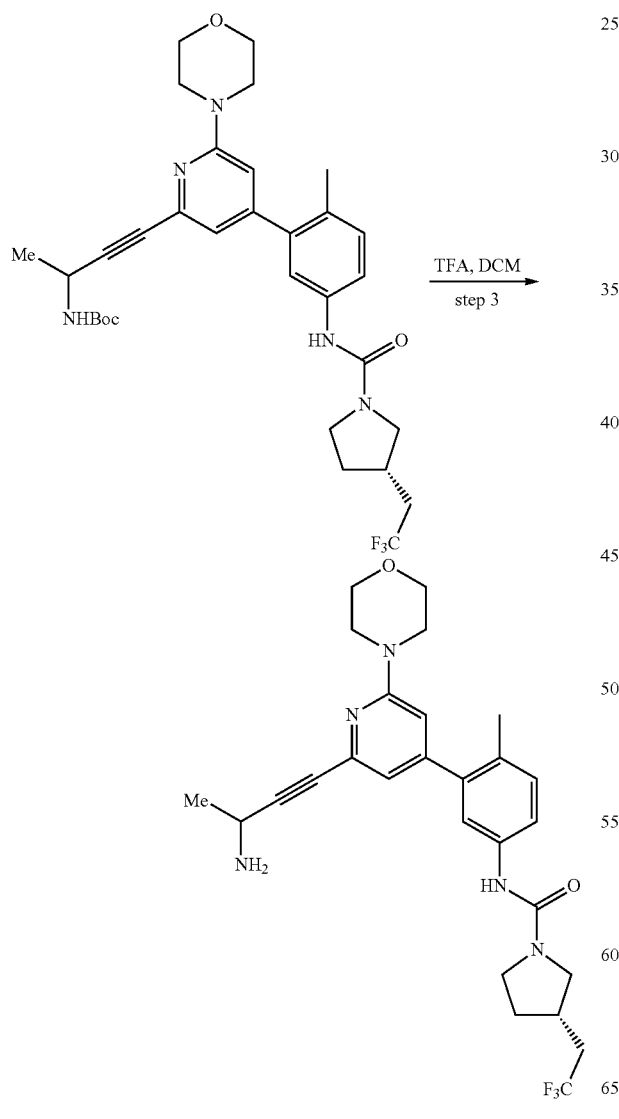

To a stirred solution of tert-butyl N-[4-(4-{2-methyl-5-[(3S)-3-(2,2,2-trifluoroethyl)pyrrolidine-1-carbonylamino]phenyl}-6-(morpholin-4-yl)pyridin-2-yl)but-3-yn-2-yl]carbamate (260 mg, 0.422 mmol) in DCM (5 mL) was added TFA (1 mL) dropwise at 0° C. The resulting solution was stirred for 2 h at room temperature. The reaction was quenched with NaHCO$_3$ (sat., 20 mL). The resulting mixture was extracted with ethyl acetate (3×20 mL). The combined organic layers were washed with brine (20 mL), dried over anhydrous Na$_2$SO$_4$. After filtration, the filtrate was concentrated under reduced pressure. The residue was purified by reverse flash chromatography with the following conditions: Column: C18 Column 120 g; Mobile Phase A: Water (10 mmol/L NH$_4$HCO$_3$), Mobile Phase B: CH$_3$CN; Flow rate: 60 mL/min; Gradient: 30% B to 70% B; 254/220 nm to afford (3S)—N-{3-[2-(3-aminobut-1-yn-1-yl)-6-(morpholin-4-yl)pyridin-4-yl]-4-methylphenyl}-3-(2,2,2-trifluoroethyl)pyrrolidine-1-carboxamide (124.1 mg, 56%) as an off-white solid. MS ESI calculated for C$_{27}$H$_{32}$F$_3$N$_5$O$_2$ [M+H]$^+$, 516.25, found 516.15; $^1$H NMR (400 MHz, Chloroform-d) δ 7.32-7.28 (m, 2H), 7.19 (d, J=9.2 Hz, 1H), 6.81 (s, 1H), 6.52 (s, 1H), 6.16 (s, 1H), 3.96 (q, J=6.9 Hz, 1H), 3.86-3.77 (m, 5H), 3.66-3.61 (m, 1H), 3.57-3.53 (m, 4H), 3.47-3.43 (m, 1H), 3.13 (t, J=9.4 Hz, 1H), 2.63-2.51 (m, 1H), 2.33-2.20 (m, 6H), 1.81-1.69 (m, 1H), 1.48 (d, J=6.8 Hz, 3H). $^{19}$F NMR (376 MHz, Chloroform-d) 6-64.96 (3F).

Example 56: (3S)—N-[4-methyl-3-[2-(morpholin-4-yl)-6-(trifluoromethyl)pyridin-4-yl]phenyl]-3-(2,2,2-trifluoroethyl)pyrrolidine-1-carboxamide

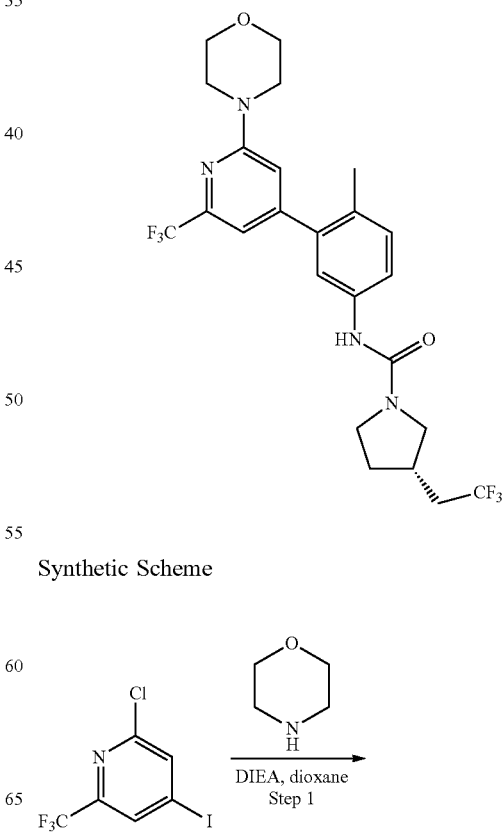

Synthetic Scheme

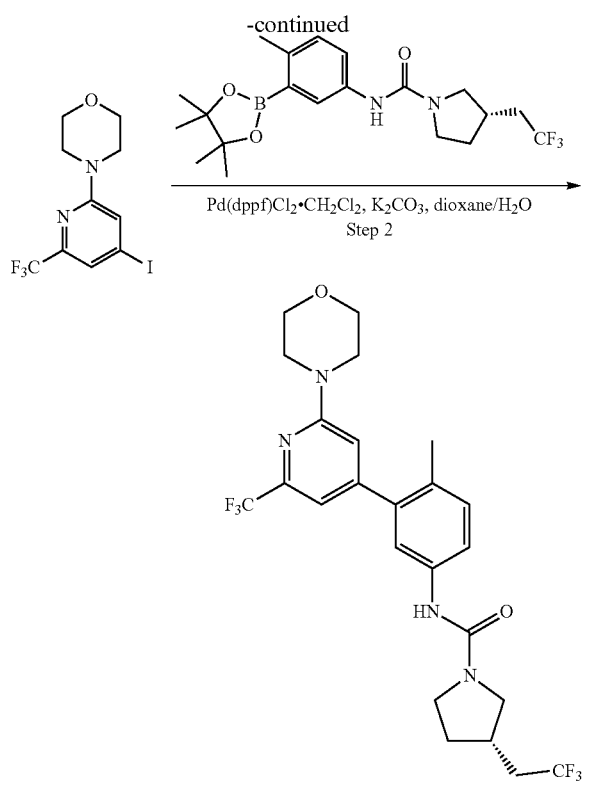

Preparation 56A: 4-[4-iodo-6-(trifluoromethyl)pyridin-2-yl]morpholine

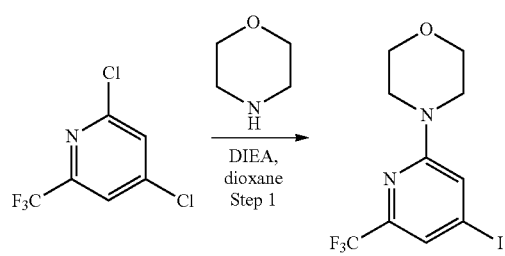

To a stirred solution of 2-chloro-4-iodo-6-(trifluoromethyl)pyridine (400 mg, 1.301 mmol) and DIEA (336 mg, 2.602 mmol) in dioxane (4 mL) was added morpholine (136 mg, 1.561 mmol). The resulting mixture was stirred for 16 h at 80° C. The mixture was allowed to cool down to room temperature. The reaction was quenched by the addition of water (50 mL). The resulting mixture was extracted with EA (3×50 mL). The combined organic layers were washed with brine (50 mL), dried over anhydrous $Na_2SO_4$. After filtration, the filtrate was concentrated under reduced pressure. The residue was purified by silica gel column chromatography, eluted with PE/EA (1/1) to afford 4-[4-iodo-6-(trifluoromethyl)pyridin-2-yl]morpholine (260 mg, 56%) as a white solid. MS ESI calculated for $C_{10}H_{10}F_3IN_2O$ [M+H]$^+$, 358.98; found 359.00; $^1$H NMR (300 MHz, Chloroform-d) δ 7.32 (d, J=1.1 Hz, 1H), 7.16 (s, 1H), 3.87-3.78 (m, 4H), 3.63-3.54 (m, 4H). $^{19}$F NMR (282 MHz, Chloroform-d) 6-68.92 (3F).

Example 56: (3S)—N-[4-methyl-3-[2-(morpholin-4-yl)-6-(trifluoromethyl)pyridin-4-yl]phenyl]-3-(2,2,2-trifluoroethyl)pyrrolidine-1-carboxamide

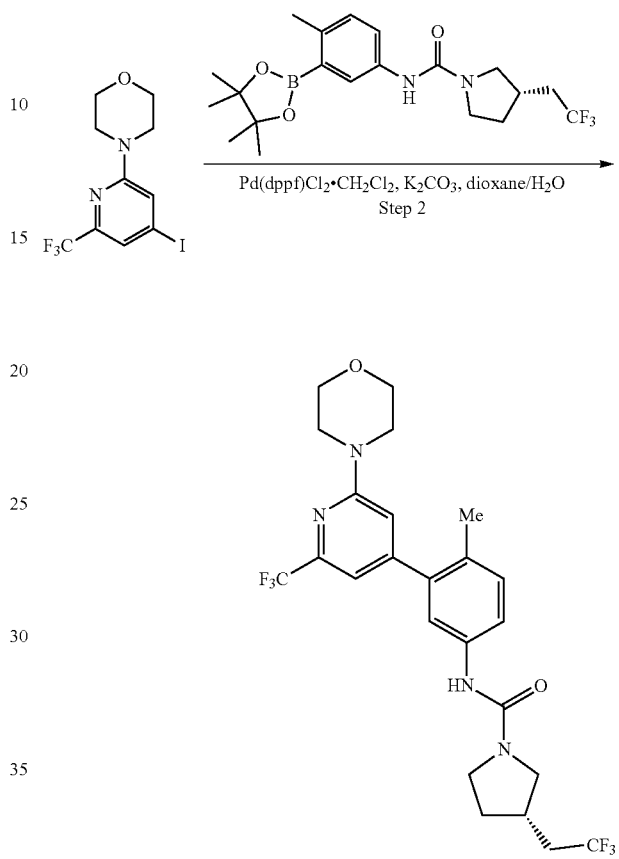

To a stirred solution of 4-[4-iodo-6-(trifluoromethyl)pyridin-2-yl]morpholine (150 mg, 0.419 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (155 mg, 0.377 mmol) in dioxane (2 mL) and $H_2O$ (0.3 mL) were added $K_2CO_3$ (174 mg, 1.257 mmol) and Pd(dppf)Cl$_2$.CH$_2$Cl$_2$ (34 mg, 0.042 mmol) under nitrogen atmosphere. The resulting mixture was stirred for 2 h at 80° C. under nitrogen atmosphere. The mixture was allowed to cool down to room temperature. The resulting mixture was quenched with water (50 mL) and extracted with EA (3×50 mL). The combined organic layers were washed with brine (2×30 mL), dried over anhydrous $Na_2SO_4$. After filtration, the filtrate was concentrated under reduced pressure. The residue was purified by silica gel column chromatography, eluted with PE/EA/EtOH (1/3/1) to afford (3S)—N-[4-methyl-3-[2-(morpholin-4-yl)-6-(trifluoromethyl)pyridin-4-yl]phenyl]-3-(2,2,2-trifluoroethyl)pyrrolidine-1-carboxamide (91 mg, 42%) as a white solid. MS ESI calculated for $C_{24}H_{26}F_6N_4O_2$[M+H]$^+$, 517.10; found 517.10; H NMR (300 MHz, DMSO-d$_6$) δ 8.21 (s, 1H), 7.54 (dd, J=8.3, 2.3 Hz, 1H), 7.43 (d, J=2.3 Hz, 1H), 7.19 (d, J=8.4 Hz, 1H), 7.04 (s, 1H), 7.01 (s, 1H), 3.77-3.63 (m, 5H), 3.63-3.48 (m, 5H), 3.40-3.30 (m, 1H), 3.04 (t, J=9.3 Hz, 1H), 2.51-2.38 (m, 3H), 2.20 (s, 3H), 2.10-2.02 (m, 1H), 1.73-1.61 (m, 1H). $^{19}$F NMR (282 MHz, DMSO-d$_6$) δ −63.36 (3F), −67.17 (3F).

Example 57: (3S)—N-{3-[2-(difluoromethyl)-6-(morpholin-4-yl)pyridin-4-yl]-4-methylphenyl}-3-(2,2,2-trifluoroethyl)pyrrolidine-1-carboxamide

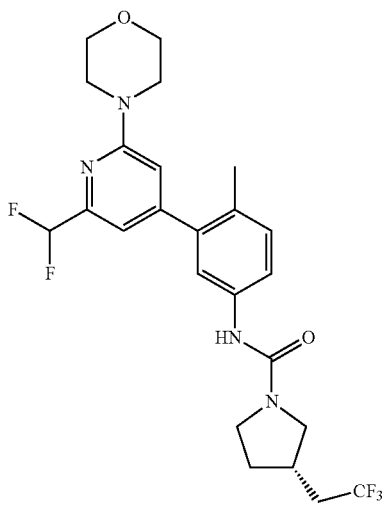 [SMILES: Cc1ccc(NC(=O)N2CC[C@@H](CC(F)(F)F)C2)cc1-c1cc(C(F)F)nc(N2CCOCC2)c1]

Synthetic Scheme

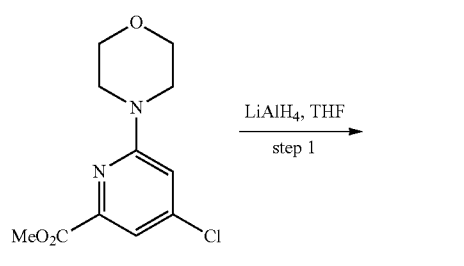

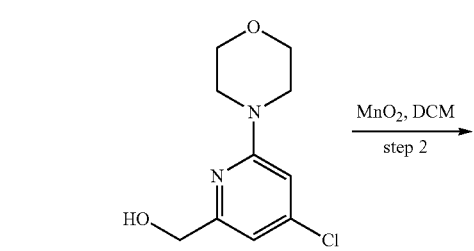

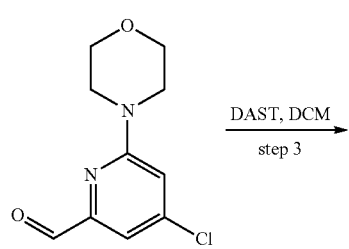

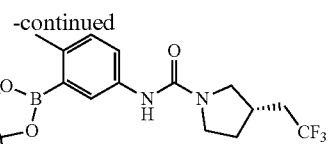

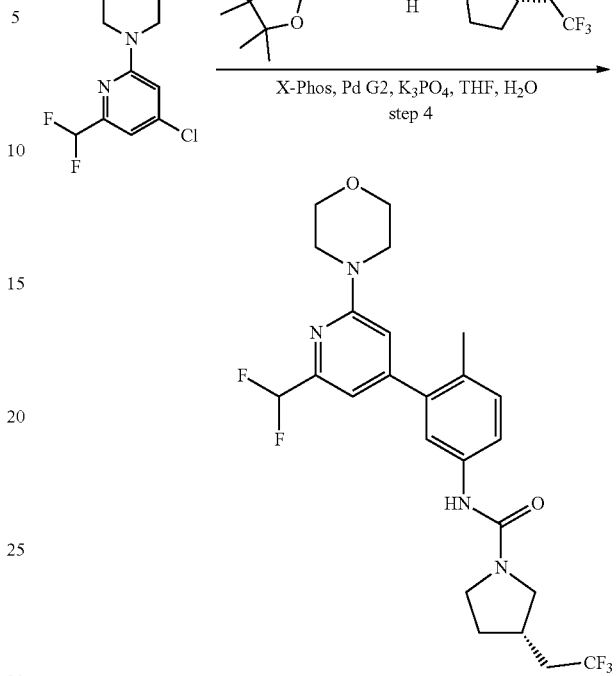

Preparation 57A: 4-chloro-6-(morpholin-4-yl)pyridin-2-yl]methanol

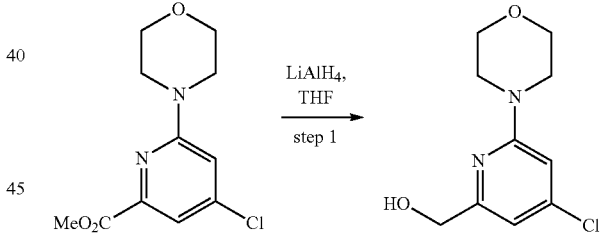

To a stirred solution of methyl 4-chloro-6-(morpholin-4-yl)pyridine-2-carboxylate (1.5 g, 5.844 mmol) in THF (15 mL) was added LiAlH₄ (0.33 g, 8.765 mmol) at −10° C. under nitrogen atmosphere. The resulting mixture was stirred for 1 h at −10° C. under nitrogen atmosphere. The reaction was quenched by the addition of water (10 mL) at −10° C. The resulting mixture was filtered. The filtrate was concentrated under reduced pressure and extracted with EA (3×50 mL). The combined organic layers were washed with brine (50 mL), dried over anhydrous Na₂SO₄. After filtration, the filtrate was concentrated under reduced pressure. The residue was purified by silica gel column chromatography, eluted with PE/EA (1/1) to afford 4-chloro-6-(morpholin-4-yl)pyridin-2-yl]methanol (0.7 g, 52%) as a white solid. MS ESI calculated for $C_{10}H_{13}ClN_2O_2[M+H]^+$, 229.07; found 229.15; ¹H NMR (400 MHz, Chloroform-d) δ 6.62 (dd, J=1.6, 0.8 Hz, 1H), 6.53 (s, 1H), 4.62 (s, 2H), 3.87-3.81 (m, 4H), 3.59-3.55 (m, 4H).

Preparation 57B: 4-chloro-6-(morpholin-4-yl)pyridine-2-carbaldehyde

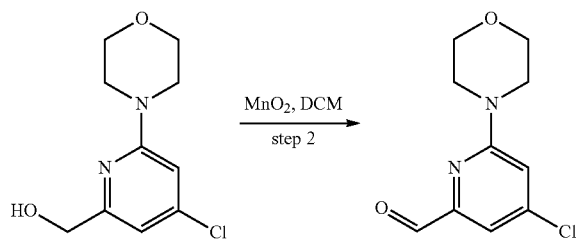 [SMILES: OCc1cc(Cl)cc(N2CCOCC2)n1 ; O=Cc1cc(Cl)cc(N2CCOCC2)n1]

To a stirred mixture of [4-chloro-6-(morpholin-4-yl)pyridin-2-yl]methanol (0.90 g, 3.94 mmol) in DCM (15 mL) was added MnO$_2$ (3.00 g, 39.36 mmol). The resulting mixture was stirred for 16 h at room temperature. The resulting mixture was filtered, the filter cake was washed with DCM (4×20 mL). The filtrate was concentrated under reduced pressure. The residue was purified by silica gel column chromatography, eluted with PE/EA (3/1) to afford 4-chloro-6-(morpholin-4-yl)pyridine-2-carbaldehyde (650 mg, 73%) as a light yellow solid. MS ESI calculated for C$_{10}$H$_{11}$ClN$_2$O$_2$[M+H]$^+$, 227.05; found 227.05; $^1$H NMR (400 MHz, DMSO-d$_6$) δ 9.78 (d, J=0.7 Hz, 1H), 7.26 (d, J=1.5 Hz, 1H), 7.19 (t, J=1.3 Hz, 1H), 3.73-3.69 (m, 4H), 3.62-3.58 (m, 4H).

Preparation 57C: 4-[4-chloro-6-(difluoromethyl)pyridin-2-yl]morpholine

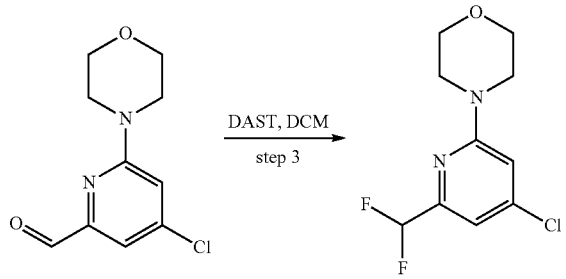 [SMILES: O=Cc1cc(Cl)cc(N2CCOCC2)n1 ; FC(F)c1cc(Cl)cc(N2CCOCC2)n1]

To a stirred solution of 4-chloro-6-(morpholin-4-yl)pyridine-2-carbaldehyde (300 mg, 1.324 mmol) in DCM (5 mL) was added DAST (320 mg, 1.986 mmol) at 0° C. under nitrogen atmosphere. The resulting mixture was stirred for 2 h at room temperature under nitrogen atmosphere. The mixture was basified to pH 8 with NaHCO$_3$ (sat., 2 mL) at 0° C. The resulting mixture was diluted with water (20 mL) and extracted with DCM (3×20 mL). The combined organic layers were washed with brine (20 mL), dried over anhydrous Na$_2$SO$_4$. After filtration, the filtrate was concentrated under reduced pressure. The residue was purified by silica gel column chromatography, eluted with PE/EA (5/1) to afford 4-[4-chloro-6-(difluoromethyl)pyridin-2-yl]morpholine (250 mg, 76%) as an off-white solid. MS ESI calculated for C$_{10}$H$_{11}$ClF$_2$N$_2$O [M+H]$^+$, 249.05; found 249.05; $^1$H NMR (300 MHz, Chloroform-d) δ 6.97 (d, J=1.4 Hz, 1H), 6.69 (s, 1H), 6.42 (t, J=55.6 Hz, 1H), 3.93-3.74 (m, 4H), 3.59-3.55 (m, 4H). $^{19}$F NMR (282 MHz, Chloroform-d) δ -117.03 (2F).

Example 57: (3S)—N-{3-[2-(difluoromethyl)-6-(morpholin-4-yl)pyridin-4-yl]-4-methylphenyl}-3-(2,2,2-trifluoroethyl)pyrrolidine-1-carboxamide

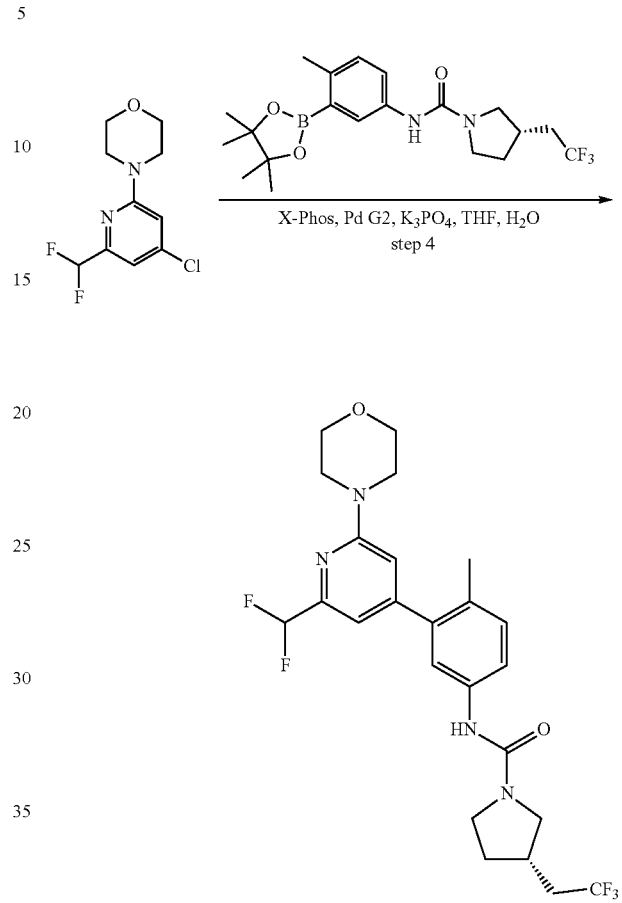

To a stirred solution of 4-[4-chloro-6-(difluoromethyl)pyridin-2-yl]morpholine (150 mg, 0.603 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (224 mg, 0.543 mmol) in THF (2 mL) and H$_2$O (0.2 mL) were added K$_3$PO$_4$ (256 mg, 1.206 mmol) and 2$^{nd}$ Generation XPhos precatalyst (47 mg, 0.060 mmol) under nitrogen atmosphere. The resulting mixture was stirred for 2 h at 80° C. under nitrogen atmosphere. The resulting mixture was diluted with EA (150 mL). The organic layer was washed with brine (2×30 mL) and dried over anhydrous Na$_2$SO$_4$. After filtration, the filtrate was concentrated under reduced pressure. The residue was purified by silica gel column chromatography, eluted with PE/EA/EtOH (1/3/1) to afford (3S)—N-{3-[2-(difluoromethyl)-6-(morpholin-4-yl)pyridin-4-yl]-4-methylphenyl}-3-(2,2,2-trifluoroethyl)pyrrolidine-1-carboxamide (90 mg, 30%) as a white solid. MS ESI calculated for C$_{24}$H$_{27}$F$_5$N$_4$O$_2$ [M+H]$^+$, 499.21, found 499.25; $^1$H NMR (400 MHz, DMSO-d$_6$) δ 8.19 (s, 1H), 7.51 (dd, J=8.3, 2.3 Hz, 1H), 7.41 (d, J=2.3 Hz, 1H), 7.17 (d, J=8.3 Hz, 1H), 6.89 (s, 1H), 6.85 (s, 1H), 6.79 (t, J=55.4 Hz, 1H), 3.74-3.62 (m, 5H), 3.57-3.47 (m, 5H), 3.30-3.25 (m, 1H), 3.02 (t, J=9.4 Hz, 1H), 2.50-2.33 (m, 3H), 2.17 (s, 3H), 2.12-2.04 (m, 1H), 1.65-1.64 (m, 1H). $^{19}$F NMR (376 MHz, DMSO-d$_6$) δ -63.76 (3F). $^{19}$F NMR (376 MHz, DMSO-d$_6$) δ -63.37 (3F), 6-116.08 (2F).

Example 58: (3S)—N-(3-(2-(1-(2-hydroxyethyl)-1H-pyrazol-4-yl)-6-morpholinopyridin-4-yl)-4-methylphenyl)-3-(2,2,2-trifluoroethyl)pyrrolidine-1-carboxamide

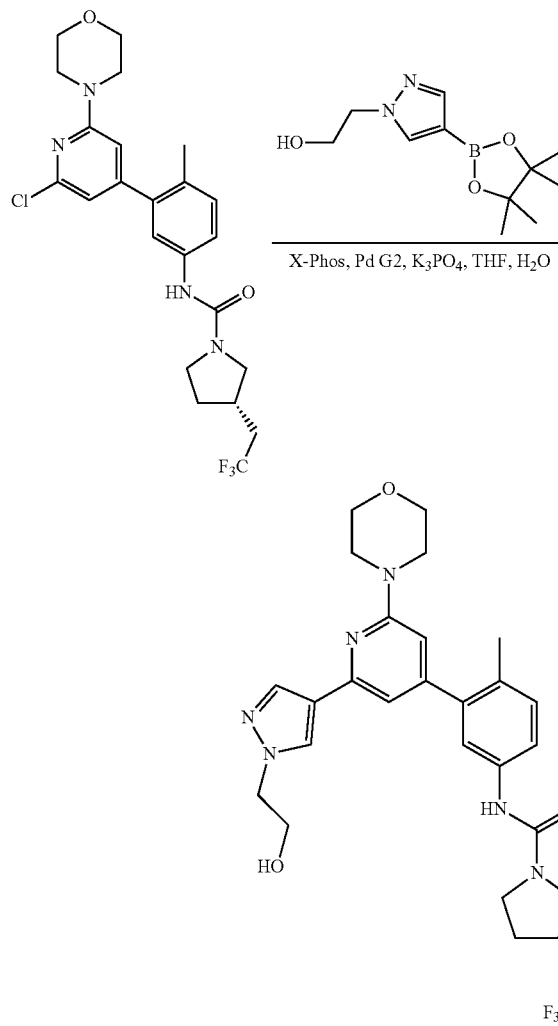

A mixture of (3S)-3-(2,2,2-trifluoroethyl)pyrrolidine-1-carbonylamino]phenyl}-6-(morpholin-4-yl)pyridin-2-yl)pyrazol-1-yl]piperidine-1-carboxylate (150 mg, 0.36 mmol), 2-(4-(4,4,5,5-tetramethyl-1,3,2-dioxaborolan-2-yl)-1H-pyrazol-1-yl)ethan-1-ol (173 mg, 0.73 mmol), $2_n$a Generation XPhos Precatalyst (34 mg, 0.043 mmol) and $K_3PO_4$ (91 mg, 0.430 mmol) in THF (5 mL) and $H_2O$ (0.5 mL) was stirred at 80 degrees C. for 16 h under $N_2$ atmosphere. The mixture was allowed to cool down to room temperature. The resulting mixture was diluted with EA (10 mL) and washed with brine (3×5 mL), dried over anhydrous $Na_2SO_4$. After filtration, the filtrate was concentrated under reduced pressure. The residue was purified by silica gel column chromatography, eluted with PE/EA (1/1). The crude product was purified by reverse flash chromatography with the following conditions: Column: C18 Column 120 g; Mobile Phase A: water (10 mmol/L $NH_4HCO_3$), Mobile Phase B: $CH_3CN$; Flow rate: 50 mL/min; Gradient: 30% B to 70% B; 254/220 nm to afford (3S)—N-(3-(2-(1-(2-hydroxyethyl)-1H-pyrazol-4-yl)-6-morpholinopyridin-4-yl)-4-methylphenyl)-3-(2,2,2-trifluoroethyl)pyrrolidine-1-carboxamide (122.1 mg, 60%) as a white solid. MS ESI calculated for $C_{28}H_{33}F_3N_6O_3[M+H]^+$, 559.26, found 559.25. $^1$H NMR (300 MHz, DMSO-$d_6$) δ 8.25 (s, 1H), 8.17 (s, 1H), 8.00 (s, 1H), 7.51 (dd, J=8.3, 2.3 Hz, 1H), 7.41 (d, J=2.3 Hz, 1H), 7.17 (d, J=8.4 Hz, 1H), 6.96-6.91 (m, 1H), 6.52-6.47 (m, 1H), 4.92 (t, J=5.3 Hz, 1H), 4.18 (t, J=5.6 Hz, 2H), 3.82-3.64 (m, 7H), 3.60-3.50 (m, 5H), 3.31-3.27 (m, 1H), 3.04 (t, J=9.4 Hz, 1H), 2.50-2.41 (m, 3H), 2.21 (s, 3H), 2.15-2.03 (m, 1H), 1.70-1.63 (m, 1H). $^{19}$F NMR (282 MHz, DMSO-$d_6$) δ −63.32 (3F).

Example 59: (3S)—N-(3-{2-[2-(2-hydroxyethyl)pyrazol-3-yl]-6-(morpholin-4-yl)pyridin-4-yl}-4-methylphenyl)-3-(2,2,2-trifluoroethyl)pyrrolidine-1-carboxamide

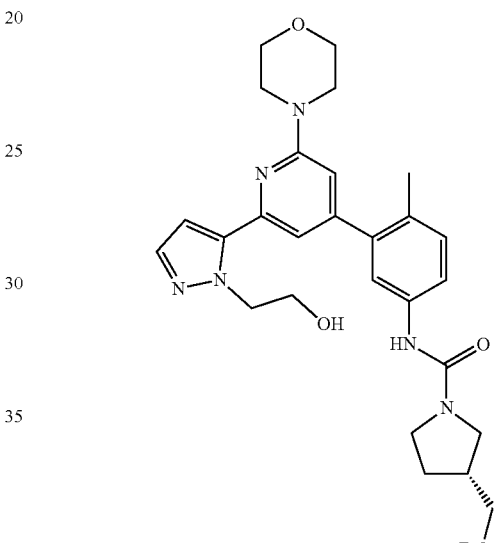

Synthetic Scheme

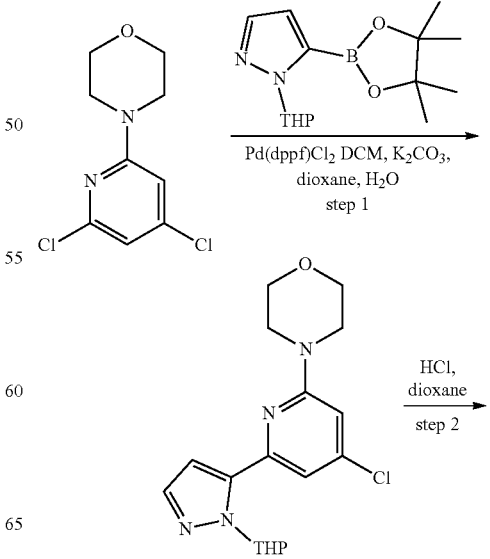

275

-continued

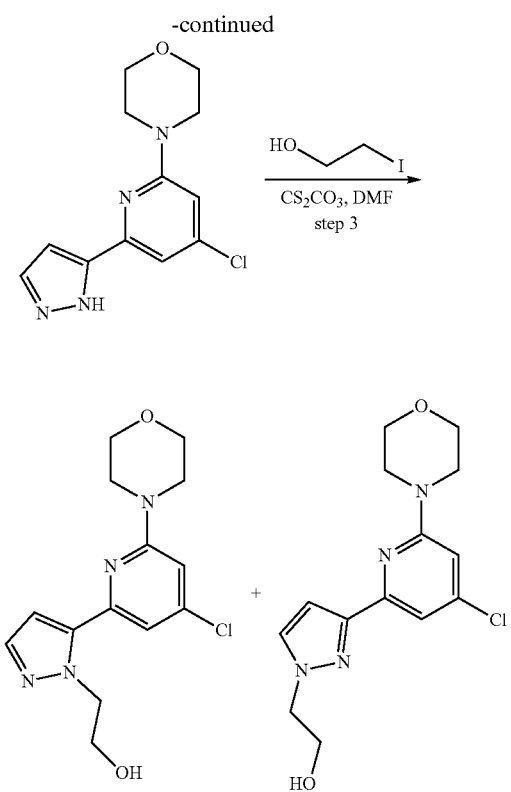

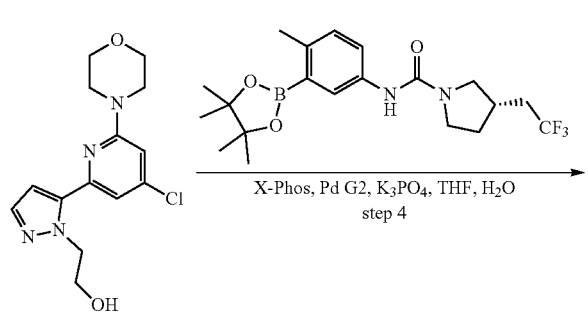

276

Preparation 59A: 4-[4-chloro-6-[2-(oxan-2-yl)pyrazol-3-yl]pyridin-2-yl]morpholine

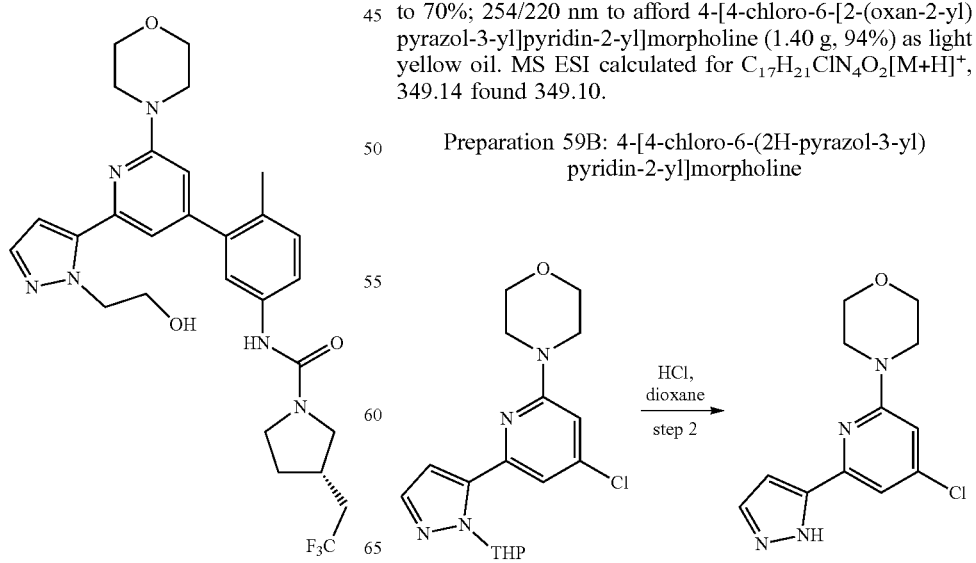

A mixture of 1-(oxan-2-yl)-5-(4,4,5,5-tetramethyl-1,3,2-dioxaborolan-2-yl)pyrazole (1.79 g, 6.43 mmol), 4-(4,6-dichloropyridin-2-yl)morpholine (1.00 g, 4.29 mmol), Pd(dppf)Cl$_2$.CH$_2$Cl$_2$ (0.35 g, 0.64 mmol) and K$_2$CO$_3$ (1.78 g, 12.87 mmol) in dioxane (8 mL) and H$_2$O (2 mL), the mixture was stirred at 80° C. for 16 h under nitrogen atmosphere. The mixture was allowed to cool down to room temperature. The resulting mixture was diluted with EA (50 mL) and washed with brine (3×20 mL), dried over anhydrous Na$_2$SO$_4$. After filtration, the filtrate was concentrated under reduced pressure. The residue was purified by silica gel column chromatography, eluted with PE/EA/EtOH (4/3/1). The crude was purified by reverse flash chromatography with the following conditions: Column: C18 Column 120 g; Mobile Phase A: water (10 mmol/L NH$_4$HCO$_3$), Mobile Phase B: CH$_3$CN; Flow rate: 50 mL/min; Gradient: 30% B to 70%; 254/220 nm to afford 4-[4-chloro-6-[2-(oxan-2-yl)pyrazol-3-yl]pyridin-2-yl]morpholine (1.40 g, 94%) as light yellow oil. MS ESI calculated for C$_{17}$H$_{21}$ClN$_4$O$_2$[M+H]$^+$, 349.14 found 349.10.

Preparation 59B: 4-[4-chloro-6-(2H-pyrazol-3-yl)pyridin-2-yl]morpholine

To a stirred solution of 4-[4-chloro-6-[2-(oxan-2-yl)pyrazol-3-yl]pyridin-2-yl]morpholine (1.40 g, 4.01 mmol) in dioxane (10 mL) was added HCl in dioxane (4 M, 10 mL) dropwise at room temperature. The mixture was stirred at room temperature for 30 min. The mixture was basified to pH 8 with saturated NaHCO$_3$ (aq.). The resulting mixture was extracted with EA (50 mL). The combined organic layers were washed with brine (3×30 mL), dried over anhydrous Na$_2$SO$_4$. After filtration, the filtrate was concentrated under reduced pressure. The residue was purified by silica gel column chromatography, eluted with PE/EA (1/1) to afford 4-[4-chloro-6-(2H-pyrazol-3-yl)pyridin-2-yl]morpholine (0.90 g, 85%) as a white solid. MS ESI calculated for C$_{12}$H$_{13}$ClN$_4$O [M+H]$^+$, 265.08; found 265.15. $^1$H NMR (400 MHz, DMSO-d$_6$) δ 7.69 (brs, 1H), 7.24 (d, J=1.5 Hz, 1H), 6.83-6.82 (m, 2H), 3.72-3.69 (m, 4H), 3.59-3.57 (m, 4H).

Preparation 59C: 2-(5-(4-chloro-6-morpholinopyridin-2-yl)-1H-pyrazol-1-yl)ethan-1-ol and 2-(3-(4-chloro-6-morpholinopyridin-2-yl)-1H-pyrazol-1-yl)ethan-1-ol

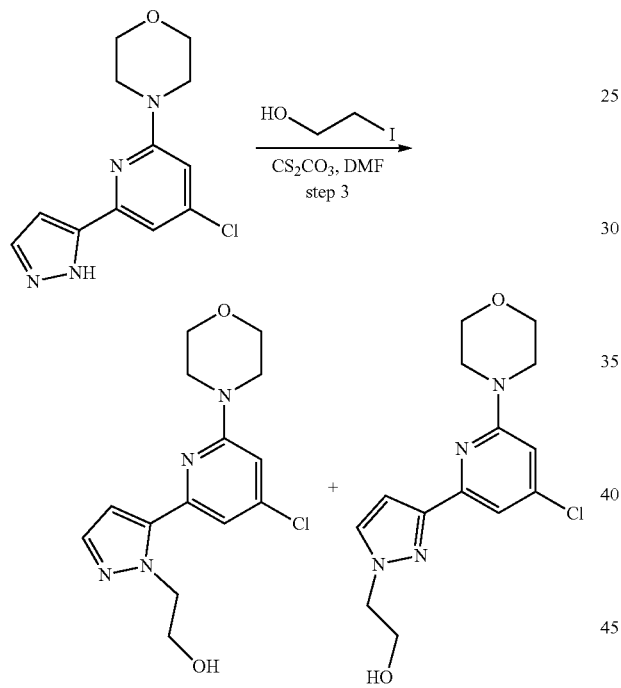

A mixture of 4-[4-chloro-6-(2H-pyrazol-3-yl)pyridin-2-yl]morpholine (400 mg, 1.511 mmol), 2-iodo-ethanol, (590 mg, 3.432 mmol) and Cs$_2$CO$_3$ (1120 mg, 3.432 mmol) in DMF (4 mL), the mixture was stirred at 80° C. for 16 h. The mixture was allowed to cool down to room temperature. The mixture was purified by reverse flash chromatography with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 30% B to 70% B; 254/220 nm to afford 2-(5-(4-chloro-6-morpholinopyridin-2-yl)-1H-pyrazol-1-yl)ethan-1-ol (95 mg, 18%) as a white solid. MS ESI calculated for C$_{14}$H$_{17}$ClN$_4$O$_2$ [M+H]$^+$, 309.10, found 309.05. $^1$H NMR (400 MHz, DMSO-d$_6$) δ 7.49 (d, J=1.9 Hz, 1H), 7.18 (d, J=1.4 Hz, 1H), 6.94 (d, J=1.5 Hz, 1H), 6.80 (d, J=2.0 Hz, 1H), 4.83-4.71 (m, 1H), 4.63 (t, J=6.6 Hz, 2H), 3.73-3.68 (m, 6H), 3.55-3.52 (m, 4H).

Also afforded 2-(3-(4-chloro-6-morpholinopyridin-2-yl)-1H-pyrazol-1-yl)ethan-1-ol (344 mg, 65%) as a white solid. MS ESI calculated for C$_{14}$H$_{17}$ClN$_4$O$_2$[M+H]$^+$, 309.10, found 309.05. $^1$H NMR (400 MHz, DMSO-d$_6$) δ 7.76 (d, J=2.2 Hz, 1H), 7.20 (d, J=1.5 Hz, 1H), 6.81 (d, J=1.6 Hz, 1H), 6.76 (d, J=2.3 Hz, 1H), 4.20 (t, J=5.6 Hz, 2H), 3.78 (t, J=5.6 Hz, 2H), 3.73-3.70 (m, 4H), 3.56-3.53 (m, 4H).

Example 59: (3S)—N-(3-{2-[2-(2-hydroxyethyl)pyrazol-3-yl]-6-(morpholin-4-yl)pyridin-4-yl}-4-methylphenyl)-3-(2,2,2-trifluoroethyl)pyrrolidine-1-carboxamide

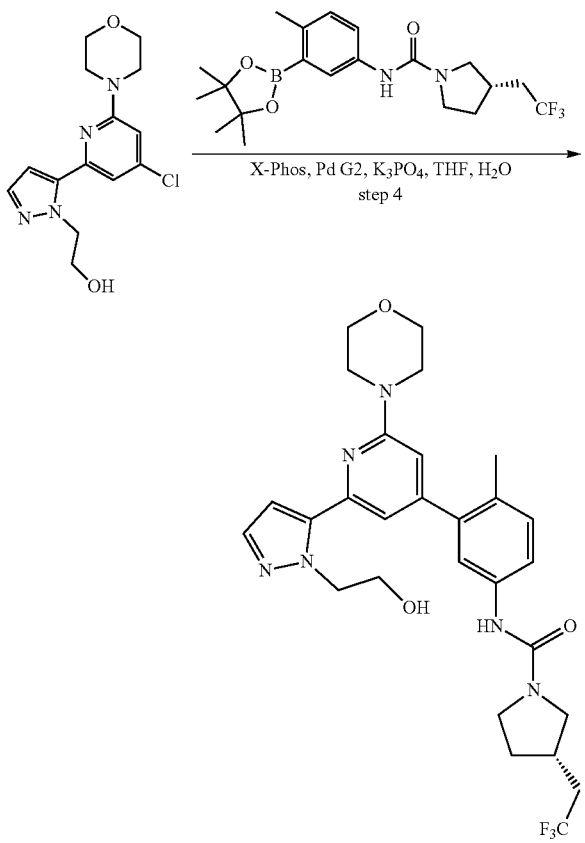

A mixture of 2-(5-(4-chloro-6-morpholinopyridin-2-yl)-1H-pyrazol-1-yl)ethan-1-ol (95 mg, 0.308 mmol), (3S)—N-{4-methyl-3-[2-(morpholin-4-yl)-6-(4,4,5,5-tetramethyl-1,3,2-dioxaborolan-2-yl)pyridin-4-yl]phenyl}-3-(2,2,2-trifluoroethyl)pyrrolidine-1-carboxamide (127 mg, 0.308 mmol), 2$^{nd}$ Generation XPhos Precatalyst (48 mg, 0.062 mmol) and K$_3$PO$_4$ (131 mg, 0.616 mmol) in THF (5 mL) and H$_2$O (0.5 mL) was stirred at 80° C. for 2 h under nitrogen atmosphere. The mixture was allowed to cool down to room temperature. The resulting mixture was diluted with EA (20 mL) and washed with brine (3×10 mL), dried over anhydrous Na$_2$SO$_4$. After filtrate was concentrated under reduced pressure. The residue was purified by silica gel column chromatography, eluted with PE/EA (1/1). The crude was purified by reverse flash chromatography with the following conditions: Column: C18 Column 120 g; Mobile Phase A: water (10 mmol/L NH$_4$HCO$_3$), Mobile Phase B: CH$_3$CN; Flow rate: 60 mL/min; Gradient: 30% B to 70% B; 254/220 nm to afford (3S)—N-(3-{2-[2-(2-hydroxyethyl)pyrazol-3-yl]-6-(morpholin-4-yl)pyridin-4-yl}-4-methylphenyl)-3-(2,2,2-trifluoroethyl)pyrrolidine-1-carboxamide (77 mg, 45%) as a white solid. MS ESI calculated for C$_{28}$H$_{33}$F$_3$N$_6$O$_3$[M+H]$^+$, 559.26, found 559.25. $^1$H NMR (300 MHz, DMSO-d$_6$) δ 8.18 (s, 1H), 7.56-7.40 (m, 3H), 7.18 (d, J=8.5 Hz, 1H), 7.05 (d, J=1.0 Hz, 1H), 6.76-6.74 (m, 2H), 4.82 (t, J=5.4 Hz, 1H), 4.70 (t, J=6.7 Hz, 2H), 3.79-3.64

(m, 7H), 3.57-3.51 (m, 5H), 3.03 (t, J=9.4 Hz, 1H), 2.50-2.42 (m, 3H), 2.22 (s, 3H), 2.15-2.04 (m, 1H), 1.70-1.64 (m, 1H). $^{19}$F NMR (282 MHz, DMSO-d$_6$) δ −63.36 (3F).

Example 60: (3S)—N-[3-[2-(hydroxymethyl)-6-(morpholin-4-yl)pyridin-4-yl]-4-methylphenyl]-3-(2,2,2-trifluoroethyl)pyrrolidine-1-carboxamide

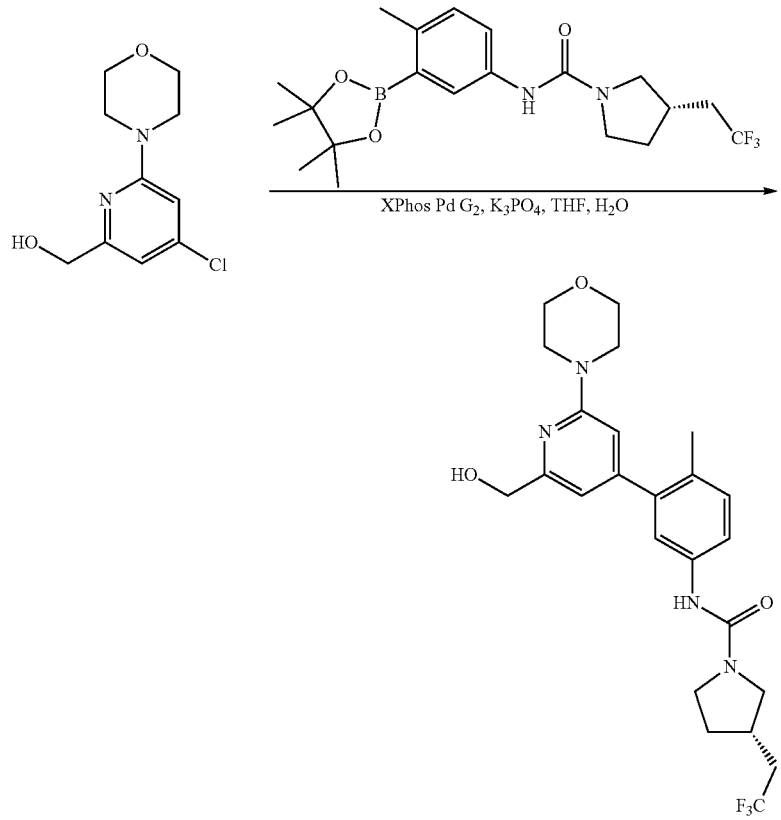

To a stirred solution of [4-chloro-6-(morpholin-4-yl)pyridin-2-yl]methanol (100 mg, 0.437 mmol) and (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (162 mg, 0.394 mmol) in THF (2 mL) and H$_2$O (0.4 mL) were added K$_3$PO$_4$ (278 mg, 1.312 mmol) and 2$^{nd}$ Generation XPhos precatalyst (34 mg, 0.044 mmol) at room temperature under nitrogen atmosphere. The resulting mixture was stirred for 2 h at 80° C. under nitrogen atmosphere. The resulting mixture was diluted with EA (150 mL). The combined organic layers were washed with brine (2×30 mL), dried over anhydrous Na$_2$SO$_4$. After filtration, the filtrate was concentrated under reduced pressure. The residue was purified by silica gel column chromatography, eluted with PE/EA/EtOH (1/3/1) to afford (3S)—N-[3-[2-(hydroxymethyl)-6-(morpholin-4-yl)pyridin-4-yl]-4-methylphenyl]-3-(2,2,2-trifluoroethyl)pyrrolidine-1-carboxamide (106.2 mg, 51%) as a white solid. MS ESI calculated for C$_{24}$H$_{29}$F$_3$N$_4$O$_3$ [M+H]$^+$, 479.22, found 479.20; $^1$H NMR (300 MHz, DMSO-d$_6$) δ 8.17 (s, 1H), 7.47 (dd, J=8.2, 2.3 Hz, 1H), 7.41 (d, J=2.3 Hz, 1H), 7.16 (d, J=8.4 Hz, 1H), 6.74 (s, 1H), 6.57 (s, 1H), 5.25 (t, J=5.9 Hz, 1H), 4.46 (d, J=5.9 Hz, 2H), 3.73-3.65 (m, 5H), 3.60-3.43 (m, 5H), 3.35-3.25 (m, 1H), 3.04 (t, J=9.4 Hz, 1H), 2.50-2.42 (m, 3H), 2.18 (s, 3H), 2.10-2.04 (m, 1H), 1.73-1.60 (m, 1H). $^{19}$F NMR (282 MHz, DMSO-d$_6$) δ −63.38 (3F).

Example 61: (3S)—N-{4-methyl-3-[2-(4-methyl-1,2,4-triazol-3-yl)-6-(morpholin-4-yl)pyridin-4-yl]phenyl}-3-(2,2,2-trifluoroethyl)pyrrolidine-1-carboxamide

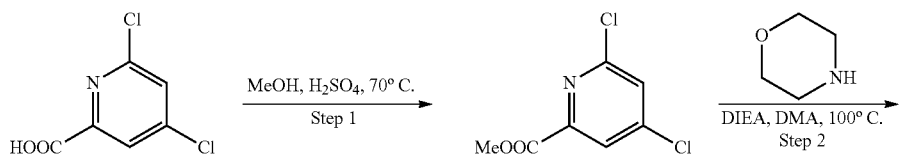

-continued
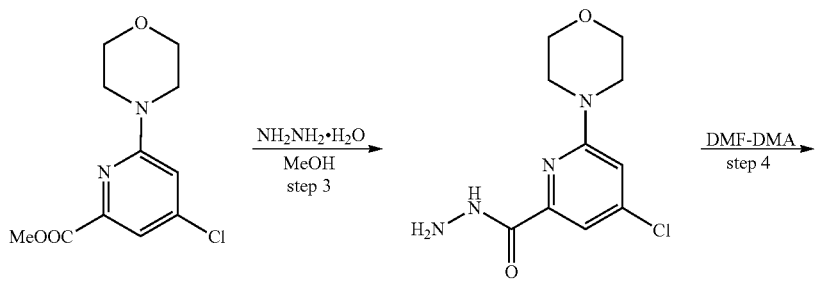
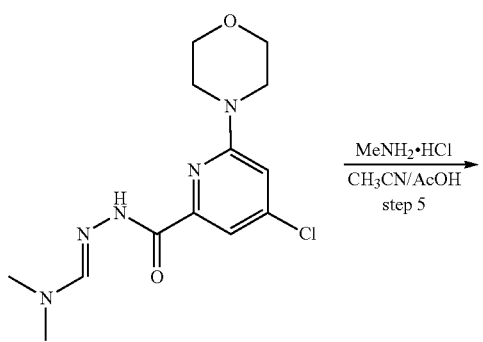
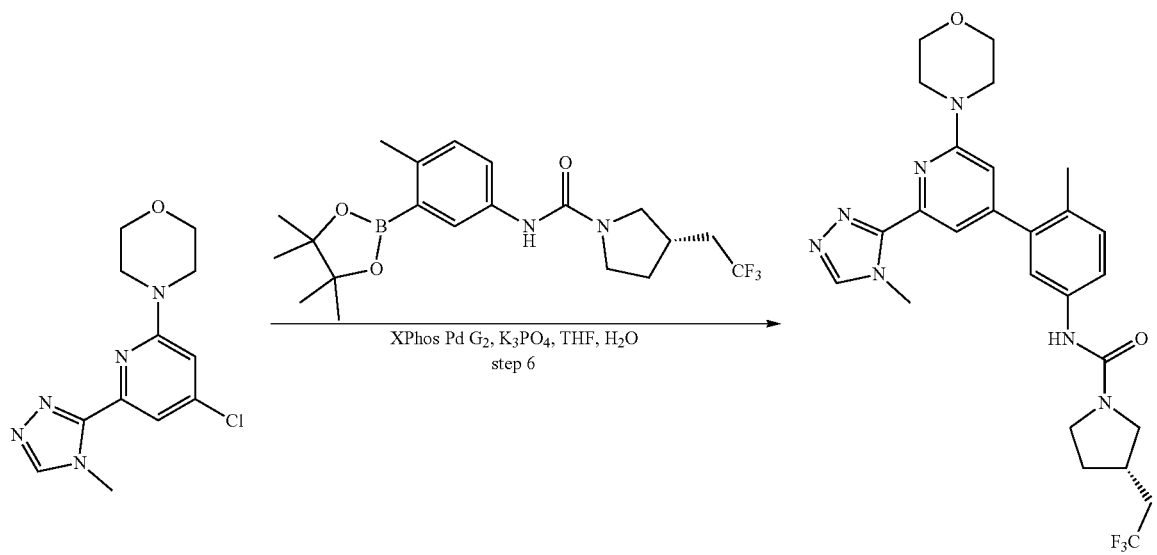

Preparation 61A: methyl 4,6-dichloropyridine-2-carboxylate

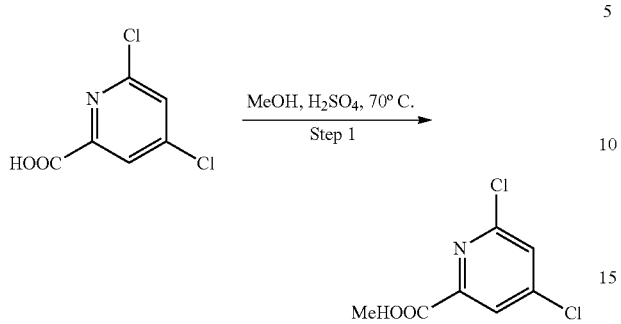

A mixture of 4,6-dichloropyridine-2-carboxylic acid (5.0 g, 26.04 mmol) and H$_2$SO$_4$ (2 mL) in MeOH (100 mL) was stirred for 16 h at 70 degrees C. The resulting mixture was concentrated under reduced pressure and diluted with water (50 mL). The pH value was adjusted to 8 with NaHCO$_3$ (sat.). The precipitated solids were collected by filtration, washed with water (2×30 mL), and dried in an oven under reduced pressure to afford methyl 4,6-dichloropyridine-2-carboxylate (5.2 g, 97%) as an off-white solid. $^1$H NMR (400 MHz, CDCl$_3$) δ (d, J=1.7 Hz, 1H), 7.57 (d, J=1.7 Hz, 1H), 4.03 (s, 3H).

Preparation 61B: Methyl 4-chloro-6-(morpholin-4-yl)pyridine-2-carboxylate

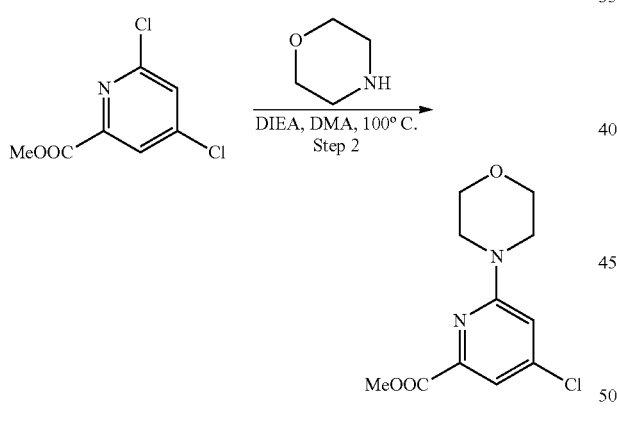

A mixture of methyl 4,6-dichloropyridine-2-carboxylate (2.00 g, 9.71 mmol), morpholine (1.01 g, 11.65 mmol) and DIEA (3.76 g, 29.12 mmol) in DMA (20 mL) was stirred for 4 h at 100 degrees C. The mixture was allowed to cool down to room temperature. The reaction was quenched with water (50 mL). The resulting mixture was extracted with EtOAc (50 mL). The organic layer was washed with brine (30 mL), dried over anhydrous Na$_2$SO$_4$. After filtration, the filtrate was concentrated under reduced pressure. The residue was purified by silica gel column chromatography, eluted with hexane/EtOAc (3/1) to afford methyl 4-chloro-6-(morpholin-4-yl)pyridine-2-carboxylate (0.5 g, 20%) as a yellow solid. MS ESI calculated for C$_{11}$H$_{13}$ClN$_2$O$_3$ [M+H]$^+$, 257.06 found 256.95. $^1$H NMR (400 MHz, CDCl$_3$) δ 7.44 (d, J=1.5 Hz, 1H), 6.77 (d, J=1.5 Hz, 1H), 3.95 (s, 3H), 3.86-3.77 (m, 4H), 3.60-3.55 (m, 4H).

Preparation 61C: 4-chloro-6-(morpholin-4-yl)pyridine-2-carbohydrazide

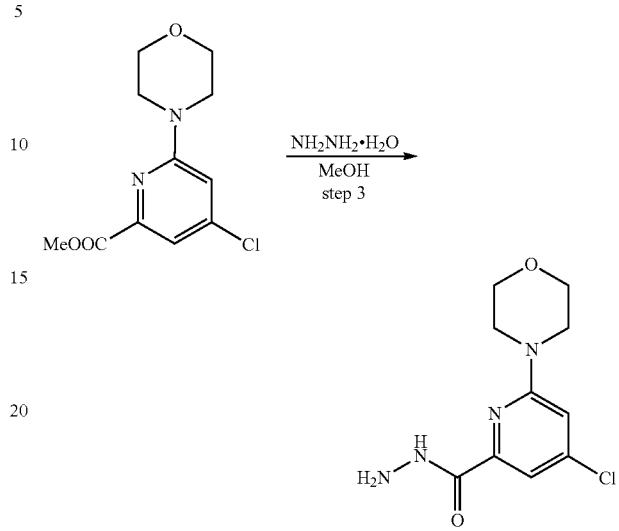

A solution of methyl methyl 4-chloro-6-(morpholin-4-yl)pyridine-2-carboxylate (500 mg, 1.948 mmol) and NH$_2$NH$_2$.H$_2$O (488 mg, 9.740 mmol) in MeOH (10 mL) was stirred for 16 h at 70° C. The mixture was allowed to cool down to room temperature. The precipitated solids were collected by filtration and washed with MeOH (3×2 mL) to afford 4-chloro-6-(morpholin-4-yl)pyridine-2-carbohydrazide (370 mg, 74%) as an off-white solid. MS ESI calculated for C$_{10}$H$_{13}$ClN$_4$O$_2$[M+H]$^+$, 257.07, found 257.00. $^1$H NMR (400 MHz, DMSO-d$_6$) δ 9.81 (brs, 1H), 7.21 (s, 1H), 7.08 (s, 1H), 4.56 (brs, 2H), 3.69-3.60 (m, 8H).

Preparation 61D: 4-chloro-N-[(dimethylamino)methylidene]-6-(morpholin-4-yl)pyridine-2-carbohydrazide

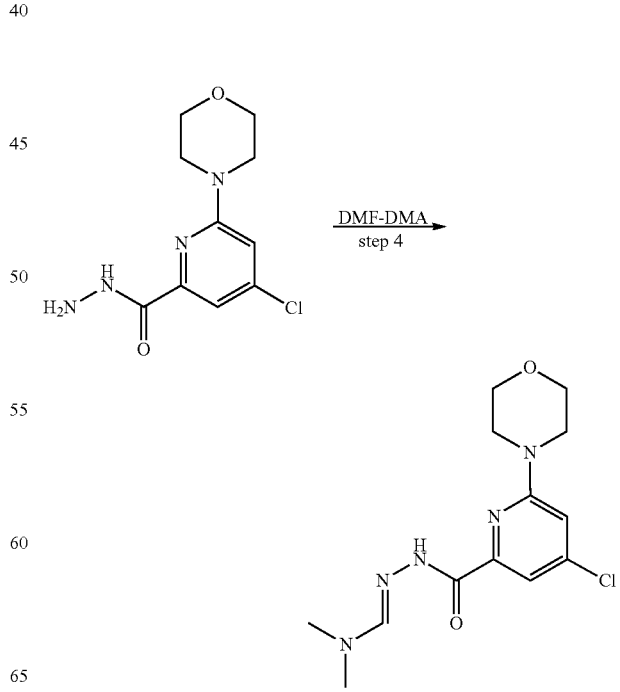

285

A mixture of 4-chloro-6-(morpholin-4-yl)pyridine-2-carbohydrazide (300 mg, 1.169 mmol) in N,N-dimethylformamide dimethyl acetal (3 mL) was stirred for 16 h at 100° C. under nitrogen atmosphere. The mixture was allowed to cool down to room temperature. The precipitated solids were collected by filtration and washed with diethyl ether (3×5 mL) to afford 4-chloro-N-[(dimethylamino)methylidene]-6-(morpholin-4-yl)pyridine-2-carbohydrazide (335 mg, 92%) as an off-white solid. MS ESI calculated for $C_{13}H_{18}ClN_5O_2$ [M+H]$^+$, 312.11, found 312.10. $^1$H NMR (300 MHz, CDCl$_3$) δ 9.70 (s, 1H), 8.14 (s, 1H), 7.59-7.56 (m, 1H), 6.77-6.75 (m, 1H), 3.86-3.82 (m, 4H), 3.55-3.52 (m, 4H), 3.00 (s, 6H).

Preparation 61E: 4-[4-chloro-6-(4-methyl-1,2,4-triazol-3-yl)pyridin-2-yl]morpholine

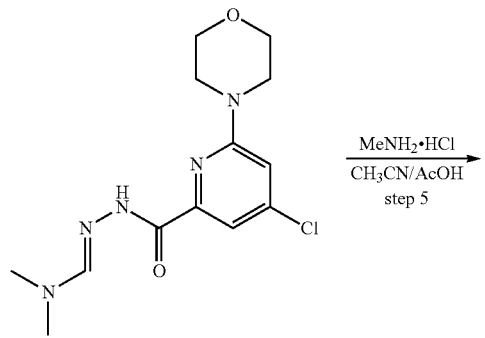

286

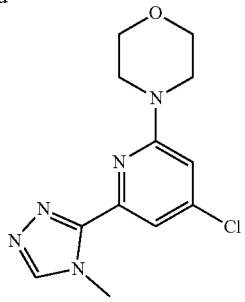

A mixture of 4-chloro-N-[(dimethylamino)methylidene]-6-(morpholin-4-yl)pyridine-2-carbohydrazide (200 mg, 0.641 mmol) and CH$_3$NH$_2$·HCl (216.56 mg, 3.205 mmol) in CH$_3$CN (4 mL) and AcOH (1 mL) was stirred for 3 h at 90° C. The resulting mixture was filtered, the filter cake was washed with CH$_3$CN (3×2 mL). The combined filtrate was concentrated under reduced pressure. The residue was triturated in EtOAc (10 mL) to afford 4-[4-chloro-6-(4-methyl-1,2,4-triazol-3-yl)pyridin-2-yl]morpholine (220 mg, 98%) as an off-white solid. MS ESI calculated for $C_{12}H_{14}ClN_5O$ [M+H]$^+$, 280.09, found 280.00. $^1$H NMR (300 MHz, CD$_3$OD) δ 8.55 (s, 1H), 7.48 (d, J=1.5 Hz, 1H), 6.99 (d, J=1.5 Hz, 1H), 4.09 (s, 3H), 3.84-3.79 (m, 4H), 3.62-3.59 (m, 4H).

Example 61: (3S)—N-{4-methyl-3-[2-(4-methyl-1,2,4-triazol-3-yl)-6-(morpholin-4-yl)pyridin-4-yl]phenyl}-3-(2,2,2-trifluoroethyl)pyrrolidine-1-carboxamide

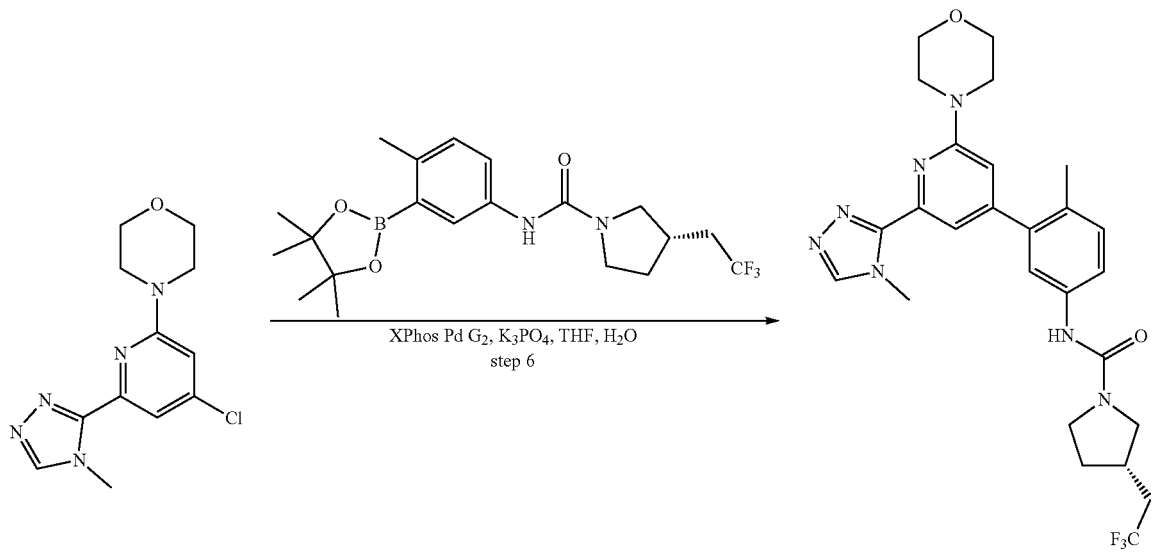 [SMILES: Cn1cnnc1-c1cc(Cl)cc(N2CCOCC2)n1 ; Cc1ccc(NC(=O)N2CC[C@@H](CC(F)(F)F)C2)cc1B1OC(C)(C)C(C)(C)O1 ; Cc1ccc(NC(=O)N2CC[C@@H](CC(F)(F)F)C2)cc1-c1cc(-c2nncn2C)nc(N2CCOCC2)c1]

A mixture of 4-[4-chloro-6-(4-methyl-1,2,4-triazol-3-yl)pyridin-2-yl]morpholine (100 mg, 0.357 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (118 mg, 0.286 mmol), potassium phosphate (152 mg, 0.714 mmol), chloro(2-dicyclohexylphosphino-2',4',6'-triisopropyl-1,1'-biphenyl)[2-(2'-amino-1,1'-biphenyl)]palladium(II) (2$^{nd}$ Generation XPhos precatalyst) (28 mg, 0.036 mmol), tetrahydrofuran (2 mL) and H$_2$O (0.2 mL) was stirred for 12 h at 80° C. under nitrogen atmosphere. The reaction mixture was cooled to room temperature and concentrated under reduced pressure. The residue was purified by prep-HPLC with the following conditions: Column: XBridge Prep C18 OBD Column, 19×150 mm, 5 μm; Mobile Phase A: water (10 mM NH$_4$HCO$_3$), Mobile Phase B: acetonitrile; Flow rate: 20 mL/min; Gradient: 40% B to 60% B; 254/210 nm to afford (3S)—N-{4-methyl-3-[2-(4-methyl-1,2,4-triazol-3-yl)-6-(morpholin-4-yl)pyridin-4-yl]phenyl}-3-(2,2,2-trifluoroethyl)pyrrolidine-1-carboxamide (30.5 mg, 16%) as an off-white solid. MS ESI calculated for C$_{26}$H$_{30}$F$_3$N$_7$O$_2$[M+H]$^+$, 530.24, found 530.15. $^1$H NMR (400 MHz, DMSO-d$_6$) δ 8.59 (s, 1H), 8.21 (s, 1H), 7.53-7.47 (m, 2H), 7.41 (s, 1H), 7.19 (d, J=8.4 Hz, 1H), 6.87 (s, 1H), 4.04 (s, 3H), 3.76-3.66 (m, 5H), 3.57-3.52 (m, 5H), 3.33-3.31 (m, 1H), 3.03 (t, J=9.6 Hz, 1H), 2.53-2.41 (m, 3H), 2.23 (s, 3H), 2.10-2.02 (m, 1H), 1.79-1.60 (m, 1H). 19F NMR (376 MHz, DMSO-d$_6$) δ −63.37 (3F).

Example 62: (2S)—N-{4-methyl-3-[2-(1-methylpyrazol-4-yl)-6-(morpholin-4-yl)pyridin-4-yl]phenyl}-2-(trifluoromethyl)morpholine-4-carboxamide

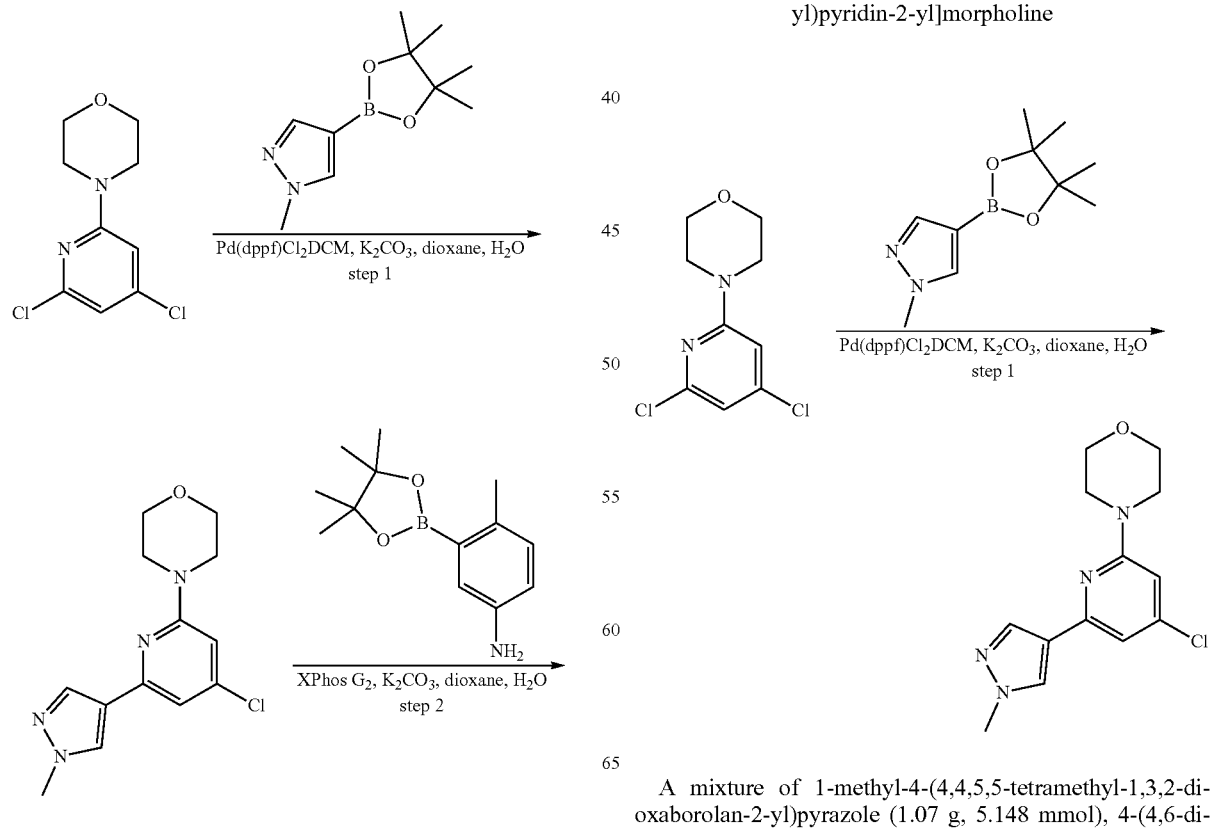

Preparation 62A: 4-[4-chloro-6-(1-methylpyrazol-4-yl)pyridin-2-yl]morpholine

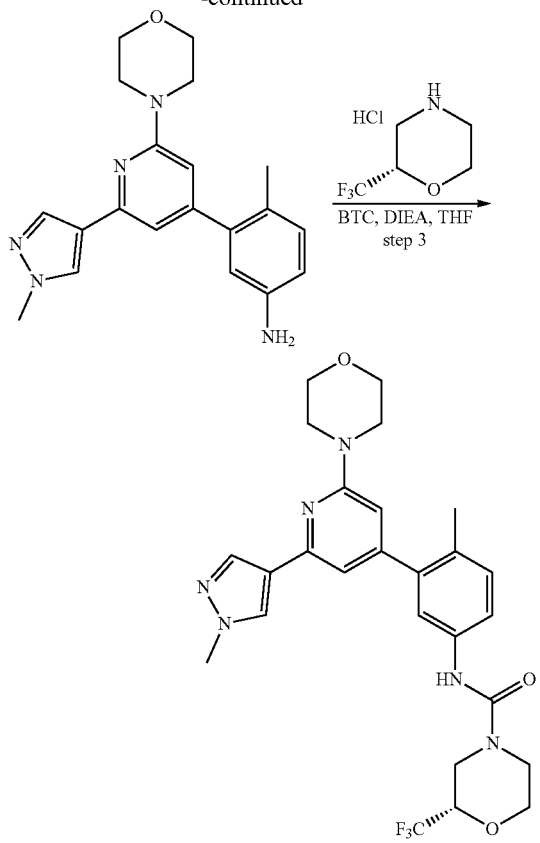

A mixture of 1-methyl-4-(4,4,5,5-tetramethyl-1,3,2-dioxaborolan-2-yl)pyrazole (1.07 g, 5.148 mmol), 4-(4,6-dichloropyridin-2-yl)morpholine (1 g, 4.290 mmol), 1,1'-bis(diphenylphosphino)ferrocene-palladium(II) dichloride dichloromethane complex (352 mg, 0.431 mmol) and potassium carbonate (1.78 g, 12.870 mmol) in dioxane (8 mL) and H$_2$O (2 mL) was stirred at 80° C. for 16 h under nitrogen atmosphere. The resulting mixture was diluted with water (50 mL) and extracted with EtOAc (3×50 mL). The combined organic layers were washed with brine (3×20 mL), dried over anhydrous Na$_2$SO$_4$. After filtration, the filtrate was concentrated under reduced pressure. The residue was purified by silica gel column chromatography, eluted with petroleum ether/EtOAc (1/1) to afford 4-[4-chloro-6-(1-methylpyrazol-4-yl)pyridin-2-yl]morpholine (892 mg, 75%) as a yellow solid. MS ESI calculated for C$_{13}$H$_{15}$ClN$_4$O [M+H]$^+$, 279.09; found 279.05. $^1$H NMR (400 MHz, CDCl$_3$) δ 7.90 (s, 1H), 7.85 (s, 1H), 6.84 (d, J=1.2 Hz, 1H), 6.45 (d, J=1.2 Hz, 1H), 3.95 (s, 3H), 3.87-3.81 (m, 4H), 3.60-3.53 (m, 4H).

Preparation 62B: 4-methyl-3-[2-(1-methylpyrazol-4-yl)-6-(morpholin-4-yl)pyridin-4-yl]aniline

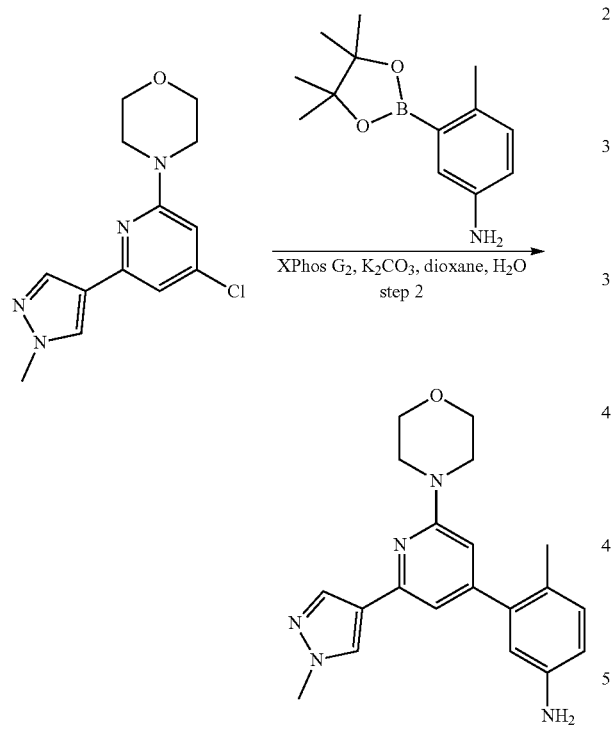

A mixture of 4-[4-chloro-6-(1-methylpyrazol-4-yl)pyridin-2-yl]morpholine (440 mg, 1.579 mmol), potassium carbonate (655 mg, 4.737 mmol), 4-methyl-3-(4,4,5,5-tetramethyl-1,3,2-dioxaborolan-2-yl)aniline (368 mg, 1.579 mmol) and chloro(2-dicyclohexylphosphino-2',4',6'-triisopropyl-1,1'-biphenyl)[2-(2'-amino-1,1'-biphenyl)]palladium(II) (2$^{nd}$ Generation XPhos precatalyst) (124 mg, 0.158 mmol) in dioxane (4 mL) and H$_2$O (1 mL) was stirred for 16 h at 80° C. under nitrogen atmosphere. The reaction was quenched by the addition of water (50 mL). The resulting mixture was extracted with EtOAc (3×40 mL). The combined organic layers were washed with saturated brine (3×40 mL), dried over anhydrous Na$_2$SO$_4$. After filtration, the filtrate was concentrated under reduced pressure. The residue was purified by silica gel column chromatography, eluted with petroleum ether/EtOAc (1/1) to afford 4-methyl-3-[2-(1-methylpyrazol-4-yl)-6-(morpholin-4-yl)pyridin-4-yl]aniline (360 mg, 65%) as a light yellow solid. MS ESI calculated for C$_{20}$H$_{23}$N$_5$O [M+H]$^+$, 350.19, found 350.15. $^1$H NMR (400 MHz, CDCl$_3$) δ 7.93-7.91 (m, 2H), 7.08 (d, J=8.0 Hz, 1H), 6.84 (d, J=1.2 Hz, 1H), 6.67 (dd, J=2.4, 8.0 Hz, 1H), 6.61 (d, J=2.4 Hz, 1H), 6.41 (d, J=1.2 Hz, 1H), 3.97 (s, 3H), 3.89-3.87 (m, 4H), 3.62-3.59 (m, 4H), 2.19 (s, 3H).

Example 62: (2S)—N-{4-methyl-3-[2-(1-methylpyrazol-4-yl)-6-(morpholin-4-yl)pyridin-4-yl]phenyl}-2-(trifluoromethyl)morpholine-4-carboxamide

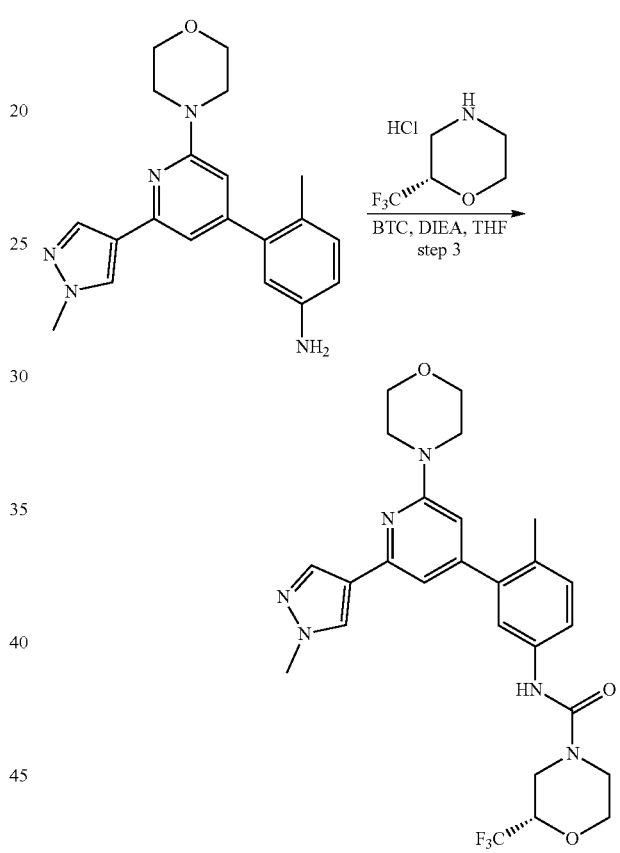

To a mixture of 4-methyl-3-[2-(1-methylpyrazol-4-yl)-6-(morpholin-4-yl)pyridin-4-yl]aniline (180 mg, 0.515 mmol) and DIEA (333 mg, 2.575 mmol) in tetrahydrofuran (12 mL) was added triphosgene (61 mg, 0.206 mmol) at room temperature. The resulting mixture was stirred for 30 min at room temperature. To this was added (2S)-2-(trifluoromethyl)morpholine hydrochloride (118 mg, 0.618 mmol). The resulting mixture was stirred for additional 16 h at room temperature and concentrated under reduced pressure. The residue was purified by reverse flash chromatography with the following conditions: column, C18 silica gel; mobile phase, CH$_3$CN in water (10 mM NH$_4$HCO$_3$), 25% to 95%; Detector, UV 254 nm to afford (2S)—N-{4-methyl-3-[2-(1-methylpyrazol-4-yl)-6-(morpholin-4-yl)pyridin-4-yl]phenyl}-2-(trifluoromethyl)morpholine-4-carboxamide (127 mg, 46%) as an off-white solid. MS ESI calculated for C$_{26}$H$_{29}$F$_3$N$_6$O$_3$ [M+H]$^+$, 531.23, found 531.20. $^1$H NMR (400 MHz, CDCl$_3$) δ 7.92-7.91 (m, 2H), 7.3-7.23 (m, 3H), 6.83 (s, 1H), 6.41-6.38 (m, 2H), 4.19-4.10 (m, 2H), 4.00-3.92 (m, 4H), 3.89-3.81 (m, 5H), 3.74-3.67 (m, 1H), 3.62-3.60 (m, 4H), 3.27-3.21 (m, 1H), 3.13-3.07 (m, 1H), 2.26 (s, 3H). $^{19}$F NMR (376 MHz, CDCl$_3$) δ −77.51 (3F).

Example 63: (2R)—N-{4-methyl-3-[2-(1-methylpyrazol-4-yl)-6-(morpholin-4-yl)pyridin-4-yl]phenyl}-2-(trifluoromethyl)morpholine-4-carboxamide

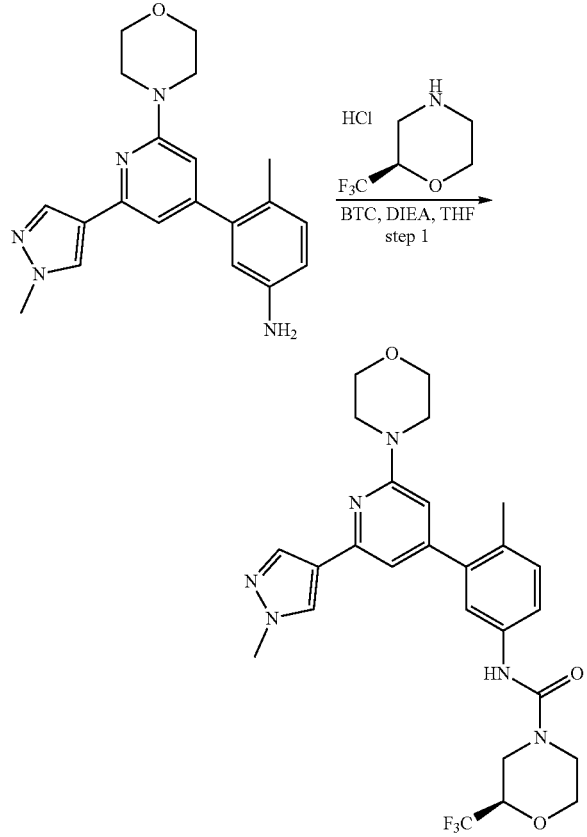

A mixture of 4-methyl-3-[2-(1-methylpyrazol-4-yl)-6-(morpholin-4-yl)pyridin-4-yl]aniline (180 mg, 0.515 mmol) and DIEA (333 mg, 2.575 mmol) in tetrahydrofuran (12 mL) was added triphosgene (61 mg, 0.206 mmol) at room temperature. The resulting mixture was stirred for 30 min at room temperature. To this was added (2R)-2-(trifluoromethyl)morpholine hydrochloride (118 mg, 0.618 mmol). The resulting mixture was stirred for additional 16 h at room temperature and concentrated under reduced pressure. The residue was purified by reverse flash chromatography with the following conditions: column, C18 silica gel; mobile phase, CH$_3$CN in water (10 mM NH$_4$HCO$_3$), 25% to 95%; Detector, UV 254 nm to afford (2R)—N-{4-methyl-3-[2-(1-methylpyrazol-4-yl)-6-(morpholin-4-yl)pyridin-4-yl]phenyl}-2-(trifluoromethyl)morpholine-4-carboxamide (103.6 mg, 38%) as an off-white solid. MS ESI calculated for C$_{26}$H$_{29}$F$_3$N$_6$O$_3$ [M+H]$^+$, 531.23, found 531.20. $^1$H NMR (400 MHz, CDCl$_3$) δ 7.92-7.89 (m, 2H), 7.31-7.28 (m, 1H), 7.24-7.22 (m, 2H), 6.81 (s, 1H), 6.49-6.39 (m, 2H), 4.18-4.08 (m, 2H), 3.96-3.80 (m, 9H), 3.72-3.58 (m, 5H), 3.25-3.17 (m, 1H), 3.12-3.05 (m, 1H), 2.26 (s, 3H). $^{19}$F NMR (376 MHz, CDCl$_3$) δ −77.50 (3F).

Example 64: (3R)—N-{4-methyl-3-[2-(1-methylpyrazol-4-yl)-6-(morpholin-4-yl)pyridin-4-yl]phenyl}-3-(trifluoromethoxy)pyrrolidine-1-carboxamide

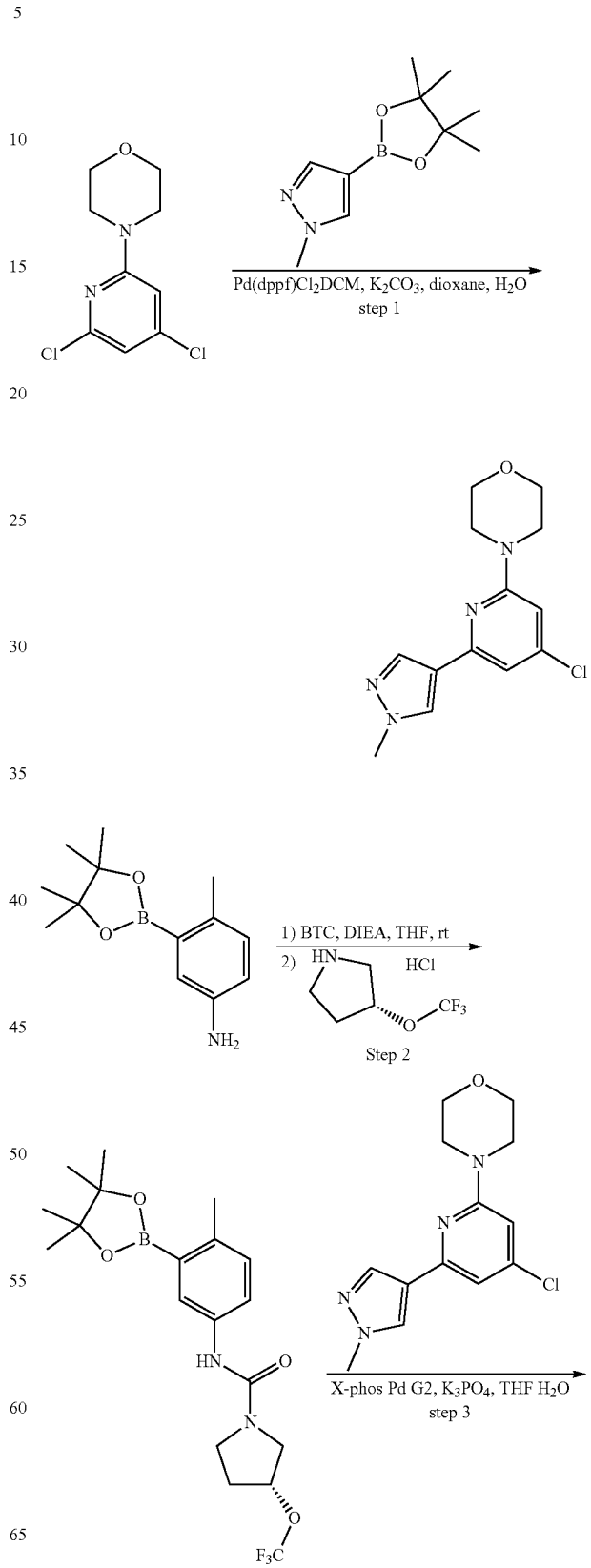

Preparation 64A: 4-[4-chloro-6-(1-methylpyrazol-4-yl)pyridin-2-yl]morpholine

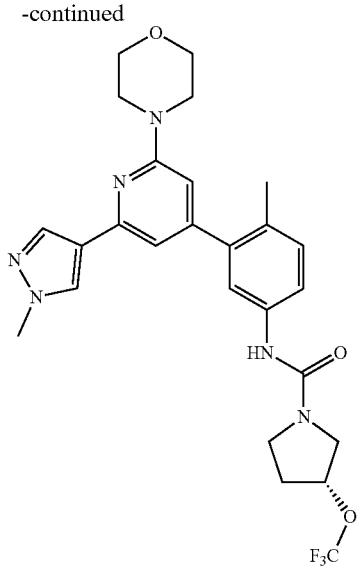

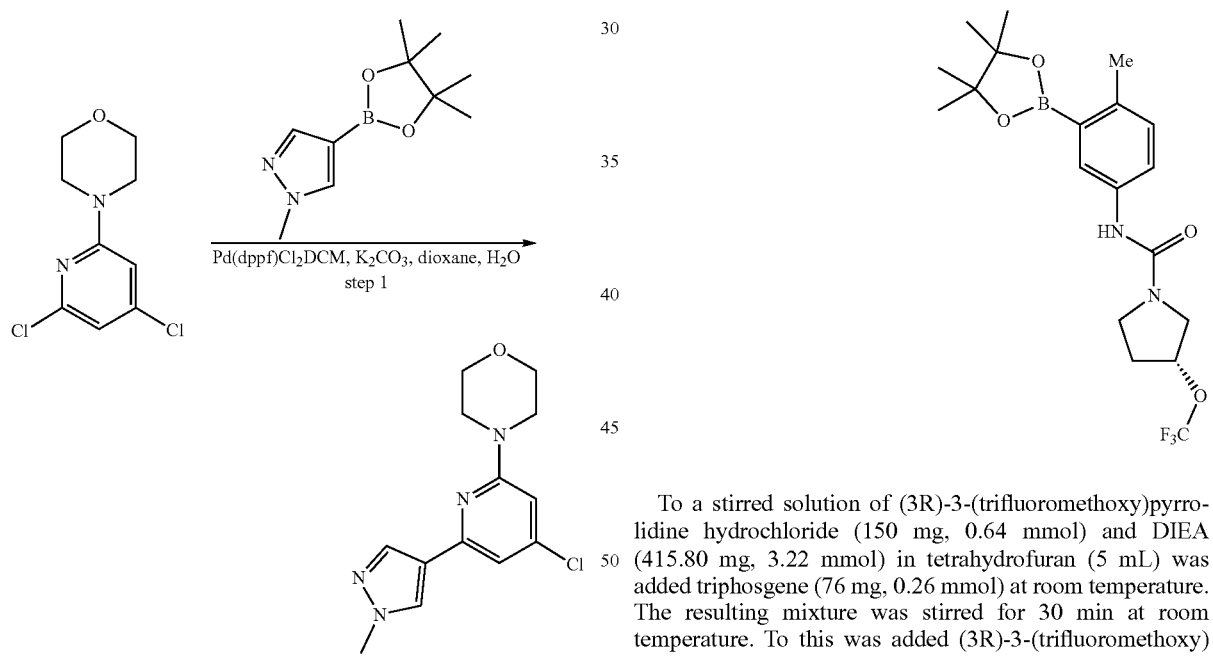

A mixture of 1-methyl-4-(4,4,5,5-tetramethyl-1,3,2-dioxaborolan-2-yl)pyrazole (1.07 g, 5.148 mmol), 4-(4,6-dichloropyridin-2-yl)morpholine (1 g, 4.290 mmol), 1,1'-bis(diphenylphosphino)ferrocene-palladium(II) dichloride dichloromethane complex (352 mg, 0.431 mmol) and potassium carbonate (1.78 g, 12.870 mmol) in dioxane (8 mL) and H$_2$O (2 mL) was stirred at 80° C. for 16 h under nitrogen atmosphere. The resulting mixture was diluted with water (50 mL) and extracted with EtOAc (3×50 mL). The combined organic layers were washed with brine (3×20 mL), dried over anhydrous Na$_2$SO$_4$. After filtration, the filtrate was concentrated under reduced pressure. The residue was purified by silica gel column chromatography, eluted with petroleum ether/EtOAc (1/1) to afford 4-[4-chloro-6-(1-methylpyrazol-4-yl)pyridin-2-yl]morpholine (892 mg, 75%) as a yellow solid. MS ESI calculated for C$_{13}$H$_{15}$ClN$_4$O [M+H]$^+$, 279.09; found 279.05. $^1$H NMR (400 MHz, CDCl$_3$) δ 7.90 (s, 1H), 7.85 (s, 1H), 6.84 (d, J=1.2 Hz, 1H), 6.45 (d, J=1.2 Hz, 1H), 3.95 (s, 3H), 3.87-3.81 (m, 4H), 3.60-3.53 (m, 4H).

Preparation 64B: (3R)—N-[4-methyl-3-(4,4,5,5-tetramethyl-1,3,2-dioxaborolan-2-yl)phenyl]-3-(trifluoromethoxy)pyrrolidine-1-carboxamide

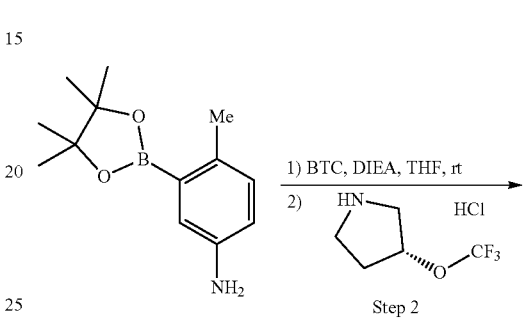

To a stirred solution of (3R)-3-(trifluoromethoxy)pyrrolidine hydrochloride (150 mg, 0.64 mmol) and DIEA (415.80 mg, 3.22 mmol) in tetrahydrofuran (5 mL) was added triphosgene (76 mg, 0.26 mmol) at room temperature. The resulting mixture was stirred for 30 min at room temperature. To this was added (3R)-3-(trifluoromethoxy)pyrrolidine hydrochloride (136 mg, 0.708 mmol). The solution was stirred for 1 h at room temperature. The resulting mixture was concentrated under vacuum. The residue was purified by silica gel column chromatography, eluted with EtOAc/petroleum ether (0~ 60%) to afford (3R)—N-[4-methyl-3-(4,4,5,5-tetramethyl-1,3,2-dioxaborolan-2-yl)phenyl]-3-(trifluoromethoxy)pyrrolidine-1-carboxamide (250 mg, 94%) as an off-white solid. MS ESI calculated for C$_{19}$H$_{26}$BF$_3$N$_2$O$_4$ [M+H]$^+$, 415.19, found 415.25. $^1$H NMR (400 MHz, CDCl$_3$) δ 7.73-7.71 (m, 1H), 7.46-7.45 (m, 1H), 7.16-7.14 (m, 1H), 6.14 (s, 1H), 4.95-4.92 (m, 1H), 3.80-3.71 (m, 2H), 3.64-3.61 (m, 2H), 2.51 (s, 3H), 2.37-2.20 (m, 2H), 1.37 (s, 12H). F-NMR (376 MHz, CDCl$_3$) δ −58.70 (3F).

Example 64: (3R)—N-{4-methyl-3-[2-(1-methylpyrazol-4-yl)-6-(morpholin-4-yl)pyridin-4-yl]phenyl}-3-(trifluoromethoxy)pyrrolidine-1-carboxamide

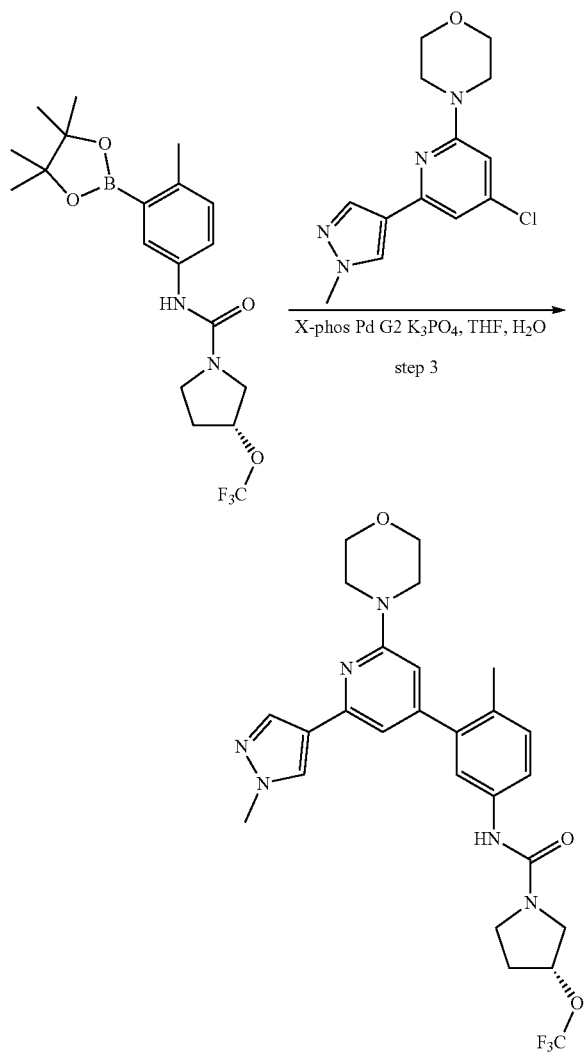

A mixture of 4-[4-chloro-6-(1-methylpyrazol-4-yl)pyridin-2-yl]morpholine (150 mg, 0.538 mmol), (3R)—N-[4-methyl-3-(4,4,5,5-tetramethyl-1,3,2-dioxaborolan-2-yl)phenyl]-3-(trifluoromethoxy)pyrrolidine-1-carboxamide (201 mg, 0.484 mmol), potassium phosphate (228 mg, 1.076 mmol), tetrahydrofuran (2 mL), H$_2$O (0.5 mL) and XPhos palladium(II) biphenyl-2-amine chloride (42 mg, 0.054 mmol) was stirred for 16 h at 80° C. under nitrogen atmosphere. The reaction was quenched by the addition of water (20 mL). The resulting mixture was extracted with EtOAc (3×20 mL). The combined organic layers were washed with saturated brine (2×30 mL), dried over anhydrous Na$_2$SO$_4$. After filtration, the filtrate was concentrated under reduced pressure. The residue was purified by HP-Flash chromatography with the following conditions: column, C18 silica gel; mobile phase, CH$_3$CN in water, 30% to 60%; Detector, UV 254 nm to afford (3R)—N-{4-methyl-3-[2-(1-methylpyrazol-4-yl)-6-(morpholin-4-yl)pyridin-4-yl]phenyl}-3-(trifluoromethoxy)pyrrolidine-1-carboxamide (79.1 mg, 28%) as a white solid. MS ESI calculated for C$_{26}$H$_{29}$F$_3$N$_6$O$_3$ [M+H]$^+$, 531.23, found 531.20. $^1$H NMR (400 MHz, DMSO-d$_6$) δ δ 8.28 (s, 1H), 8.24 (s, 1H), 7.97 (s, 1H), 7.48 (dd, J=1.6, 8.4 Hz, 1H), 7.40 (s, 1H), 7.17 (d, J 8.4 Hz, 1H), 6.92 (s, 1H), 6.50 (s, 1H), 5.16-5.14 (m, 1H), 3.87 (s, 3H), 3.72-3.41 (m, 12H), 2.30-2.11 (m, 5H). $^{19}$F NMR (376 MHz, DMSO-d$_6$) δ −56.72 (3F).

Example 65: (2R)—N-{4-methyl-3-[2-(2-methylpyrazol-3-yl)-6-(morpholin-4-yl)pyridin-4-yl]phenyl}-2-(trifluoromethyl)morpholine-4-carboxamide

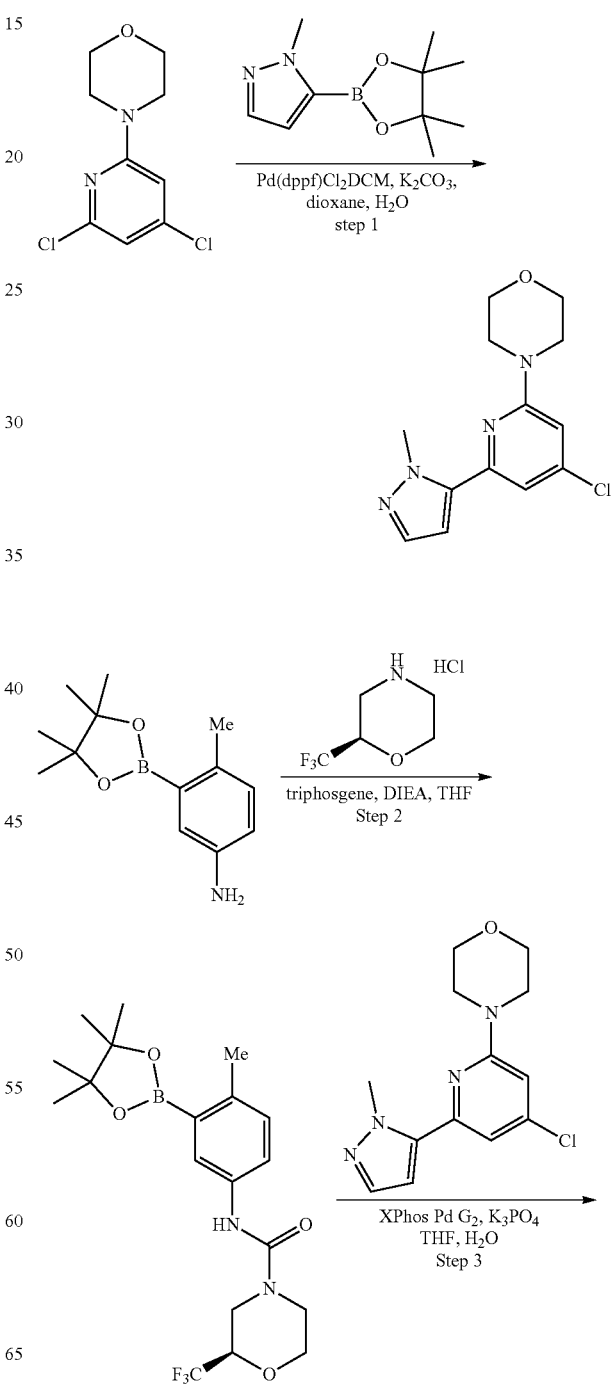

Preparation 65A: 4-[4-chloro-6-(2-methylpyrazol-3-yl)pyridin-2-yl]morpholine

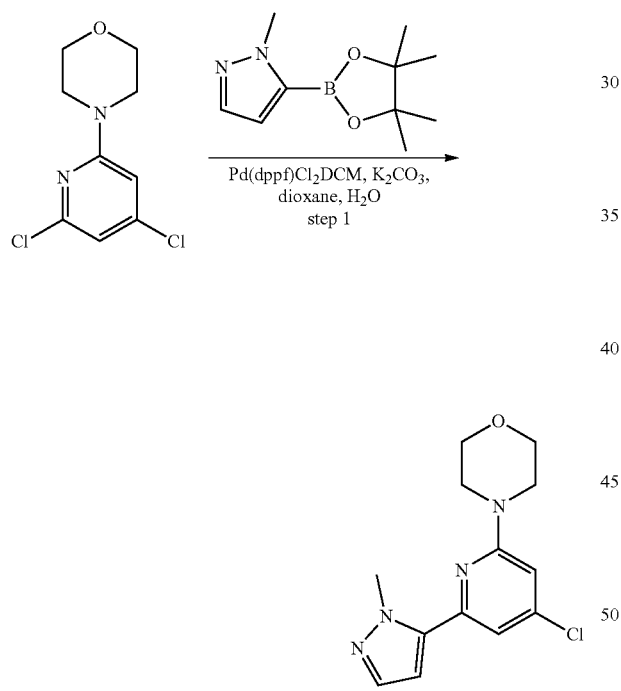

To a stirred mixture of 4-(4,6-dichloropyridin-2-yl)morpholine (300 mg, 1.287 mmol) and 1-methyl-5-(4,4,5,5-tetramethyl-1,3,2-dioxaborolan-2-yl)pyrazole (536 mg, 2.574 mmol) in dioxane (3 mL) and H₂O (0.7 mL) was added 1,1'-bis(diphenylphosphino)ferrocene-palladium(II) dichloride dichloromethane complex (105 mg, 0.129 mmol) and potassium carbonate (355 mg, 2.574 mmol). The resulting mixture was stirred for 2 h at 80° C. under nitrogen atmosphere. The reaction was diluted with water (50 mL) and extracted with EtOAc (3×50 mL). The combined organic layers were washed with brine (50 mL), dried over anhydrous Na₂SO₄. After filtration, the filtrate was concentrated under reduced pressure. The residue was purified by silica gel column chromatography, eluted with petroleum ether/EtOAc (3/2) to afford 4-[4-chloro-6-(2-methylpyrazol-3-yl)pyridin-2-yl]morpholine (150 mg, 42%) as a yellow solid. MS ESI calculated for $C_{13}H_{15}ClN_4O$ $[M+H]^+$, 279.09; found 279.10. $^1$H NMR (400 MHz, CDCl₃) δ 7.49 (s, 1H), 6.98 (s, 1H), 6.59 (s, 1H), 6.57 (s, 1H), 4.22 (s, 3H), 3.89-3.82 (m, 4H), 3.60-3.53 (m, 4H).

Preparation 65B: (2R)—N-[4-methyl-3-(4,4,5,5-tetramethyl-1,3,2-dioxaborolan-2-yl)phenyl]-2-(trifluoromethyl)morpholine-4-carboxamide

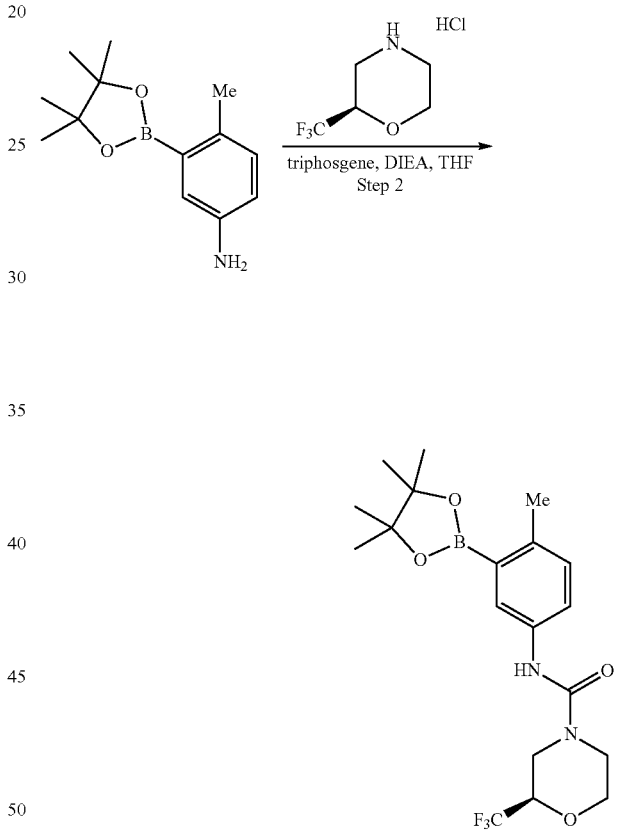

A mixture of 4-methyl-3-(4,4,5,5-tetramethyl-1,3,2-dioxaborolan-2-yl)aniline (300 mg, 1.287 mmol) and DIEA (832 mg, 6.435 mmol) in tetrahydrofuran (20 mL) were added triphosgene (153 mg, 0.515 mmol) and (2R)-2-(trifluoromethyl)morpholine (200 mg, 1.287 mmol). The resulting mixture was stirred for 2 h at room temperature. The reaction was quenched with MeOH (3 mL). The resulting mixture was concentrated under reduced pressure. The residue was purified by silica gel column chromatography, eluted with petroleum ether/EtOAc (5/1) to afford (2R)—N-[4-methyl-3-(4,4,5,5-tetramethyl-1,3,2-dioxaborolan-2-yl)phenyl]-2-(trifluoromethyl)morpholine-4-carboxamide (245 mg, crude) as an off-white solid. MS ESI calculated for $C_{19}H_{26}BF_3N_2O_4$ $[M+H]^+$ 415.19 found 415.10.

Example 65: (2R)—N-{4-methyl-3-[2-(2-methylpyrazol-3-yl)-6-(morpholin-4-yl)pyridin-4-yl]phenyl}-2-(trifluoromethyl)morpholine-4-carboxamide

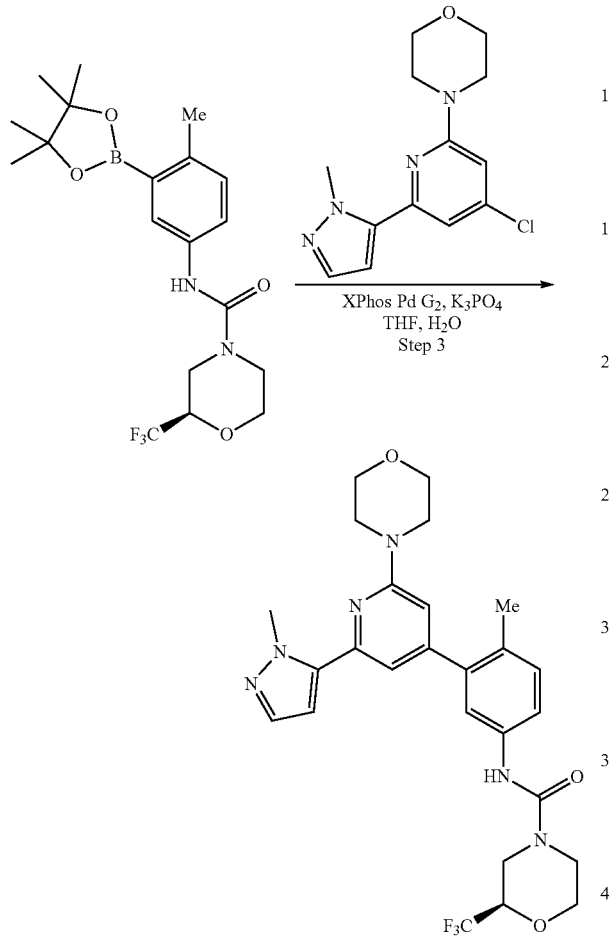

A mixture of 4-[4-chloro-6-(2-methylpyrazol-3-yl)pyridin-2-yl]morpholine (200 mg, 0.718 mmol), (2R)—N-[4-methyl-3-(4,4,5,5-tetramethyl-1,3,2-dioxaborolan-2-yl)phenyl]-2-(trifluoromethyl)morpholine-4-carboxamide (327 mg, 0.790 mmol), tetrahydrofuran (5 mL) and H₂O (0.5 mL), potassium phosphate (457 mg, 2.154 mmol) and chloro(2-dicyclohexylphosphino-2',4',6'-triisopropyl-1,1'-biphenyl)[2-(2'-amino-1,1'-biphenyl)]palladium(II) (2$^{nd}$ Generation XPhos precatalyst) (56 mg, 0.072 mmol) was stirred for 16 h at 80° C. under nitrogen atmosphere. The resulting mixture was concentrated under reduced pressure. The residue was purified by reverse flash chromatography with the following conditions: column, silica gel; mobile phase, CH₃CN in water (10 mM NH₄HCO₃), 10% to 50%; Detector, UV 254 nm to afford (2R)—N-{4-methyl-3-[2-(2-methylpyrazol-3-yl)-6-(morpholin-4-yl)pyridin-4-yl]phenyl}-2-(trifluoromethyl)morpholine-4-carboxamide (256 mg, 67%) as an off-white solid. MS ESI calculated for C₂₆H₂₉F₃N₆O₃ [M+H]⁺ 531.23; found 531.20. ¹H NMR (300 MHz, CDCl₃) δ 7.50 (s, 1H), 7.31-7.23 (m, 3H), 6.96 (m, 1H), 6.56-6.54 (m, 2H), 6.42 (s, 1H), 4.29 (s, 3H), 4.19-4.10 (m, 2H), 3.99-3.81 (m, 6H), 3.74-3.58 (m, 5H), 3.28-3.14 (m, 1H), 3.11-3.07 (m, 1H), 2.27 (s, 3H). ¹⁹F NMR (282 MHz, CDCl₃) δ −77.50 (3F).

Example 66: N-{4-methyl-3-[2-(1-methylpyrazol-4-yl)-6-(morpholin-4-yl)pyridin-4-yl]phenyl}-3-(trifluoromethyl)-2,5-dihydropyrrole-1-carboxamide

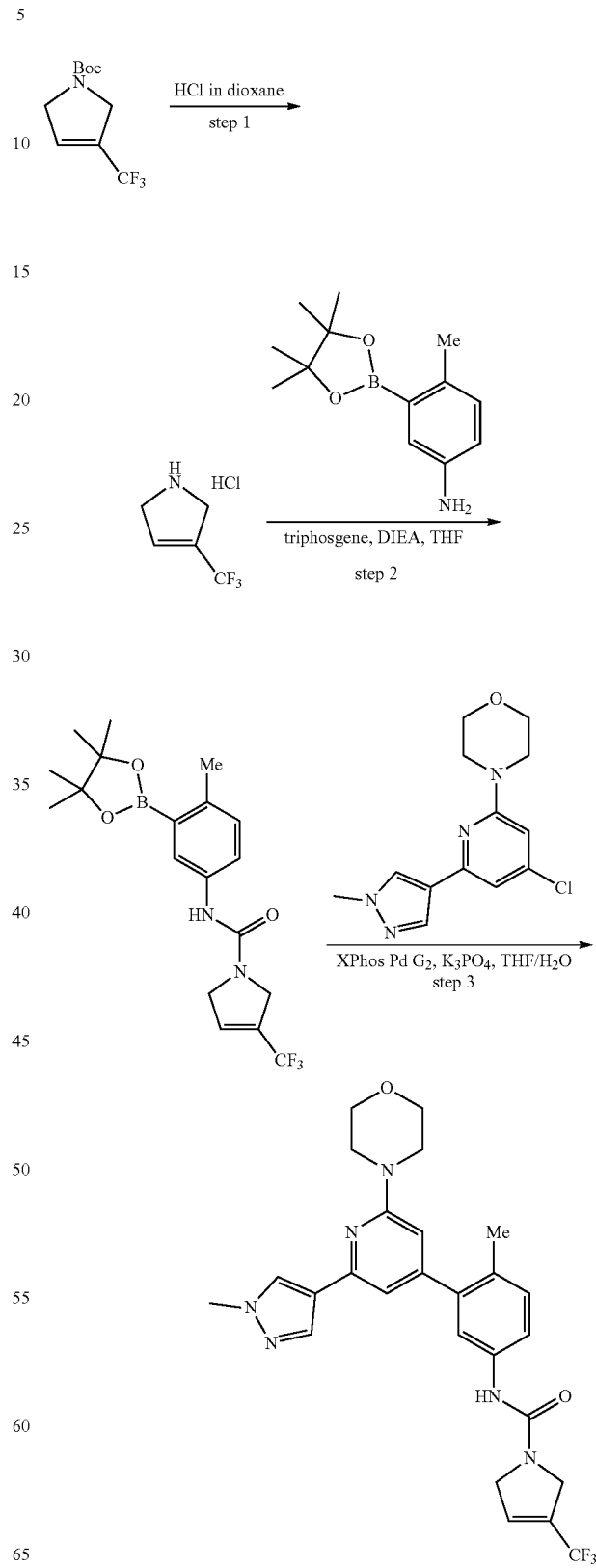

Preparation 66A: 3-(trifluoromethyl)-2,5-dihydro-1H-pyrrole hydrochloride

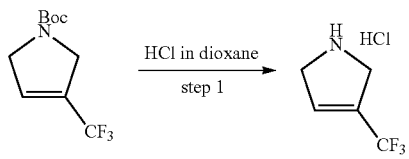

To a solution of tert-butyl 3-(trifluoromethyl)-2,5-dihydropyrrole-1-carboxylate (500 mg, 2.108 mmol) in DCM (8.0 mL) was added HCl (gas) in 1,4-dioxane (2.0 mL, 109.706 mmol). The resulting mixture was stirred for 16 h at room temperature. The resulting mixture was concentrated under reduced pressure to afford 3-(trifluoromethyl)-2,5-dihydro-1H-pyrrole hydrochloride (360 mg, crude) as a yellow solid. MS ESI calculated for $C_5H_7ClF_3N$ [M−Cl]$^+$, 138.05, found 138.05.

Preparation 66B: N-[4-methyl-3-(4,4,5,5-tetramethyl-1,3,2-dioxaborolan-2-yl)phenyl]-3-(trifluoromethyl)-2,5-dihydropyrrole-1-carboxamide

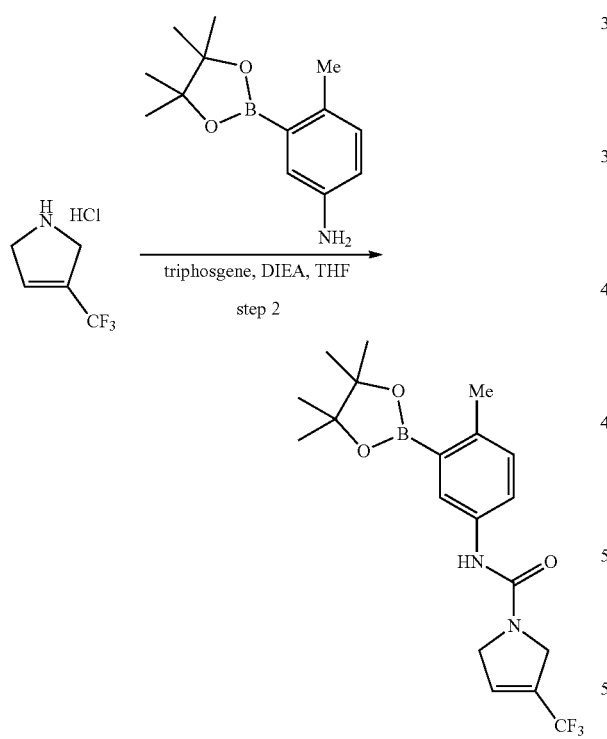

To a stirred mixture of 4-methyl-3-(4,4,5,5-tetramethyl-1,3,2-dioxaborolan-2-yl)aniline (280 mg, 1.201 mmol) and DIEA (776 mg, 6.005 mmol) in tetrahydrofuran (30 mL) were added ditrichloromethyl carbonate (142.57 mg, 0.480 mmol) at room temperature. The resulting mixture was stirred for 30 min at room temperature. To this was added 3-(trifluoromethyl)-2,5-dihydro-1H-pyrrole hydrochloride (250.16 mg, 1.441 mmol) at room temperature. The resulting mixture was stirred for 2 h at room temperature. The reaction was quenched by the addition of water (40 mL). The resulting mixture was extracted with EtOAc (3×40 mL). The combined organic layers were washed with brine (2×20 mL), dried over anhydrous $Na_2SO_4$. After filtration, the filtrate was concentrated under reduced pressure. The residue was purified by silica gel column chromatography, eluted with petroleum ether/EtOAc (1:1) to afford N-[4-methyl-3-(4,4,5,5-tetramethyl-1,3,2-dioxaborolan-2-yl)phenyl]-3-(trifluoromethyl)-2,5-dihydropyrrole-1-carboxamide (280 mg, 59%) as a white solid. MS ESI calculated for $C_{19}H_{24}BF_3N_2O_3$ [M+H]$^+$, 397.18, found 397.10. $^1$H NMR (400 MHz, CDCl$_3$) δ 7.73 (dd, J=2.4, 8.4 Hz, 1H), 7.47 (d, J=2.4 Hz, 1H), 7.16 (d, J=8.4 Hz, 1H), 6.44 (s, 1H), 6.10 (s, 1H), 4.46 (s, 4H), 2.51 (s, 3H), 1.36 (s, 12H). $^{19}$F NMR (376 MHz, CDCl$_3$) δ −65.66 (3F).

Example 66: N-{4-methyl-3-[2-(1-methylpyrazol-4-yl)-6-(morpholin-4-yl)pyridin-4-yl]phenyl}-3-(trifluoromethyl)-2,5-dihydropyrrole-1-carboxamide

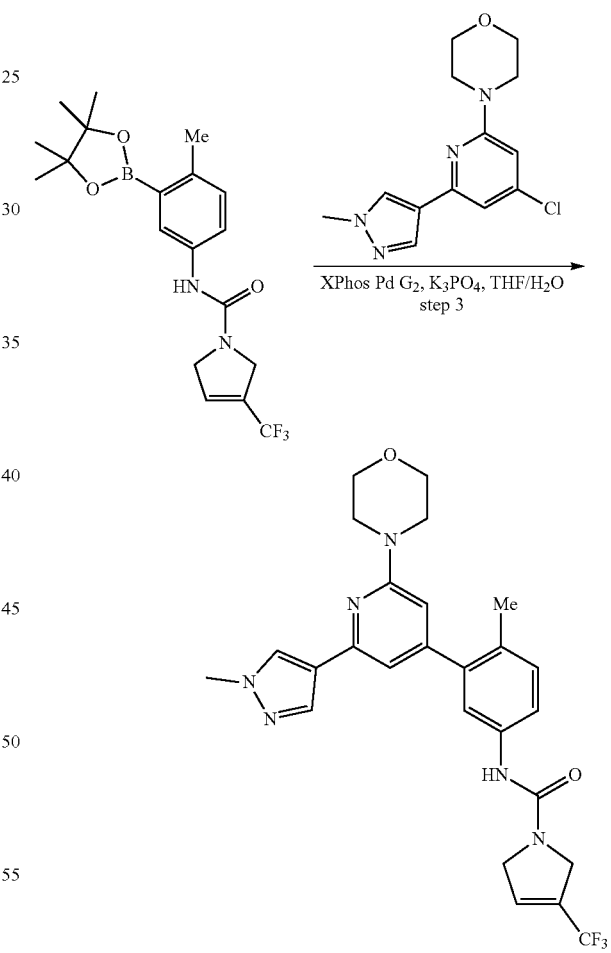

A mixture of N-[4-methyl-3-(4,4,5,5-tetramethyl-1,3,2-dioxaborolan-2-yl)phenyl]-3-(trifluoromethyl)-2,5-dihydropyrrole-1-carboxamide (150 mg, 0.379 mmol), potassium phosphate (241 mg, 1.137 mmol), 4-[4-chloro-6-(1-methylpyrazol-4-yl)pyridin-2-yl]morpholine (116 mg, 0.417 mmol), tetrahydrofuran (2 mL) and H$_2$O (0.2 mL) and chloro(2-dicyclohexylphosphino-2',4',6'-triisopropyl-1,1'-biphenyl)[2-(2'-amino-1,1'-biphenyl)]palladium(II) (2$^{nd}$ Generation XPhos precatalyst) (30 mg, 0.038 mmol) was stirred for 2 h at 80° C. under nitrogen atmosphere. The resulting mixture was concentrated under reduced pressure. The residue was purified by and reverse phase chromatography, eluted with 55% CH$_3$CN in water (10 mM NH$_4$HCO$_3$) to afford N-{4-methyl-3-[2-(1-methylpyrazol-4-yl)-6-(morpholin-4-yl)pyridin-4-yl]phenyl}-3-(trifluoromethyl)-2,5-dihydropyrrole-1-carboxamide (106.8 mg, 55%) as a white solid. MS ESI calculated for C$_{26}$H$_{27}$F$_3$N$_6$O$_2$ [M+H]$^+$, 513.21; found 513.25. $^1$H NMR (400 MHz, CDCl$_3$) δ 7.50 (s, 1H), 7.37-7.33 (m, 2H), 7.24 (d, J=8.0 Hz, 1H), 6.97 (s, 1H), 6.56 (s, 2H), 6.45 (s, 1H), 6.15 (s, 1H), 4.49-4.47 (m, 4H), 4.29 (s, 3H), 3.89-3.87 (m, 4H), 3.61-3.59 (m, 4H), 2.27 (s, 3H). $^{19}$F NMR (376 MHz, CDCl$_3$) δ −65.68 (3F).

Example 67: (2S)—N-{2-fluoro-4-methyl-5-[2-(1-methylpyrazol-4-yl)-6-(morpholin-4-yl)pyridin-4-yl]phenyl}-2-(trifluoromethyl)morpholine-4-carboxamide

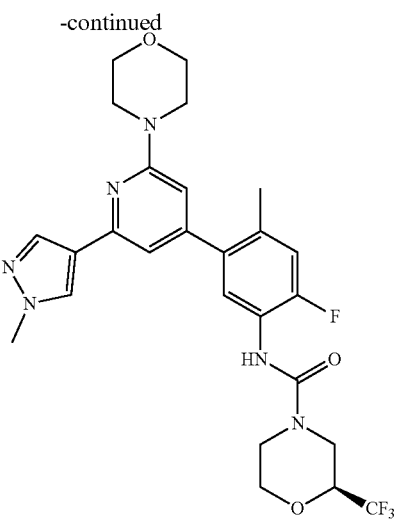

Preparation 67A: 2-fluoro-4-methyl-5-(4,4,5,5-tetramethyl-1,3,2-dioxaborolan-2-yl)aniline

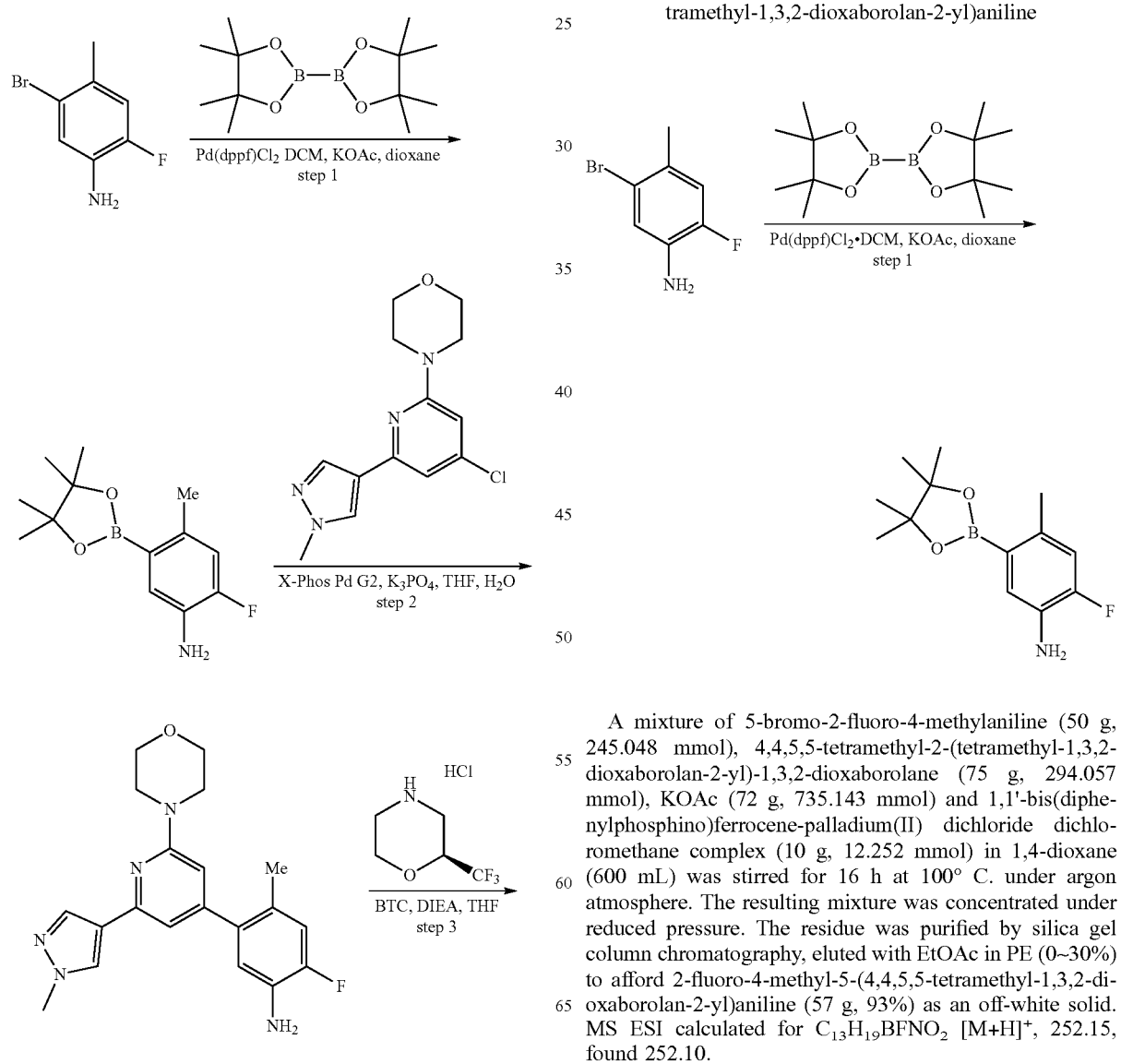

A mixture of 5-bromo-2-fluoro-4-methylaniline (50 g, 245.048 mmol), 4,4,5,5-tetramethyl-2-(tetramethyl-1,3,2-dioxaborolan-2-yl)-1,3,2-dioxaborolane (75 g, 294.057 mmol), KOAc (72 g, 735.143 mmol) and 1,1'-bis(diphenylphosphino)ferrocene-palladium(II) dichloride dichloromethane complex (10 g, 12.252 mmol) in 1,4-dioxane (600 mL) was stirred for 16 h at 100° C. under argon atmosphere. The resulting mixture was concentrated under reduced pressure. The residue was purified by silica gel column chromatography, eluted with EtOAc in PE (0~30%) to afford 2-fluoro-4-methyl-5-(4,4,5,5-tetramethyl-1,3,2-dioxaborolan-2-yl)aniline (57 g, 93%) as an off-white solid. MS ESI calculated for C$_{13}$H$_{19}$BFNO$_2$ [M+H]$^+$, 252.15, found 252.10.

305

Preparation 67B: 2-fluoro-4-methyl-5-[2-(1-methylpyrazol-4-yl)-6-(morpholin-4-yl)pyridin-4-yl]aniline

306

Example 67: (2S)—N-{2-fluoro-4-methyl-5-[2-(1-methylpyrazol-4-yl)-6-(morpholin-4-yl)pyridin-4-yl]phenyl}-2-(trifluoromethyl)morpholine-4-carboxamide

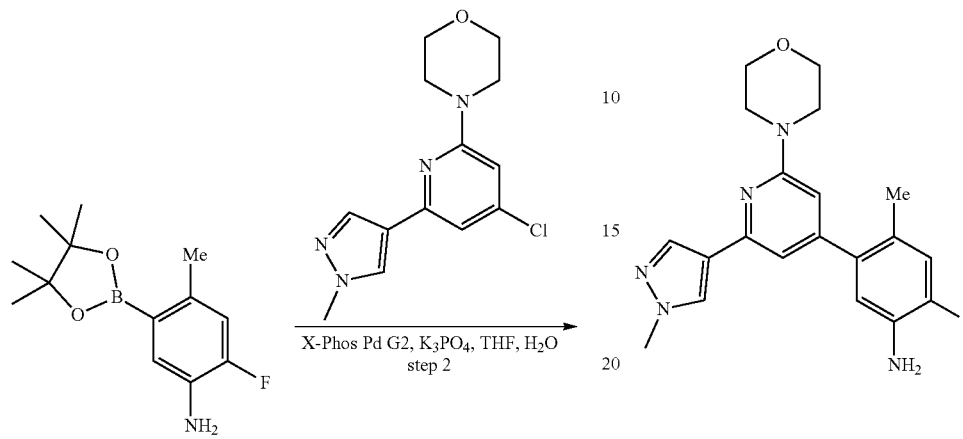

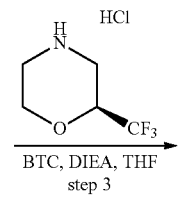

A mixture of 4-[4-chloro-6-(1-methylpyrazol-4-yl)pyridin-2-yl]morpholine (1 g, 3.588 mmol), 2-fluoro-4-methyl-5-(4,4,5,5-tetramethyl-1,3,2-dioxaborolan-2-yl)aniline (0.99 g, 3.947 mmol), chloro(2-dicyclohexylphosphino-2',4',6'-triisopropyl-1,1'-biphenyl)[2-(2'-amino-1,1'-biphenyl)]palladium(II) ($2^{nd}$ Generation XPhos precatalyst) (280 mg, 0.359 mmol) and potassium phosphate (1.52 g, 7.176 mmol) in tetrahydrofuran (10 mL) and H$_2$O (1 mL) was stirred for 2 h at 80° C. under nitrogen atmosphere. The resulting mixture was quenched with water (20 mL) and extracted with EtOAc (2×20 mL). The combined organic layers were washed with brine (10 mL), dried over anhydrous Na$_2$SO$_4$. After filtration, the filtrate was concentrated under reduced pressure. The residue was purified by silica gel column chromatography, eluted with petroleum ether/EtOAc (1/1) to afford 2-fluoro-4-methyl-5-[2-(1-methylpyrazol-4-yl)-6-(morpholin-4-yl)pyridin-4-yl]aniline (707 mg, 51%) as a light brown solid. MS ESI calculated for C$_{20}$H$_{22}$FN$_5$O [M+H]$^+$, 368.18, found 368.30. $^1$H NMR (400 MHz, CDCl$_3$) δ 7.93 (s, 1H), 7.89 (s, 1H), 6.92 (d, J=12.0 Hz, 1H), 6.81-6.80 (m, 1H), 6.69 (d, J=8.8 Hz, 1H), 6.37 (s, 1H), 3.97 (s, 3H), 3.89-3.86 (m, 4H), 3.61-3.59 (m, 4H), 2.18 (s, 3H). $^{19}$F NMR (376 MHz, CDCl$_3$) δ −136.37 (1F).

A mixture of 2-fluoro-4-methyl-5-[2-(1-methylpyrazol-4-yl)-6-(morpholin-4-yl)pyridin-4-yl]aniline (150 mg, 0.408 mmol) DIEA (264 mg, 2.041 mmol) and triphosgene (48 mg, 0.163 mmol) in tetrahydrofuran (10 mL) was stirred for 30 min at room temperature under nitrogen atmosphere. To this was added (2S)-2-(trifluoromethyl)morpholine hydrochloride (78 mg, 0.408 mmol) at room temperature. The resulting mixture was stirred for additional 2 h at room temperature. The resulting mixture was concentrated under reduced pressure. The residue was purified by silica gel column chromatography, eluted with CH$_2$Cl$_2$/EtOAc (3/2) to afford (2S)—N-{2-fluoro-4-methyl-5-[2-(1-methylpyrazol-4-yl)-6-(morpholin-4-yl)pyridin-4-yl]phenyl}-2-(trifluoromethyl)morpholine-4-carboxamide (146 mg, 63%) as an off-white solid. MS ESI calculated for C$_{26}$H$_{28}$F$_4$N$_6$O$_3$ [M+H]$^+$, 549.22, found 549.40. $^1$H NMR (400 MHz, DMSO-d$_6$) δ 8.57 (s, 1H), 8.24 (s, 1H), 7.97 (s, 1H), 7.29 (d, J=8.0 Hz, 1H), 7.19 (d, J=11.6 Hz, 1H), 6.91 (s, 1H), 6.49 (s, 1H), 4.31-4.18 (m, 2H), 4.15-3.92 (m, 2H), 3.87 (s, 3H), 3.74-3.72 (m, 4H), 3.62-3.60 (m, 1H), 3.55-3.53 (m, 4H), 3.10-2.94 (m, 2H), 2.25 (s, 3H). $^{19}$F NMR (376 MHz, DMSO-d$_6$) δ −76.14 (3F), −124.24 (1F).

307

Example 68: (2R)—N-{2-fluoro-4-methyl-5-[2-(1-methylpyrazol-4-yl)-6-(morpholin-4-yl)pyridin-4-yl]phenyl}-2-(trifluoromethyl)morpholine-4-carboxamide

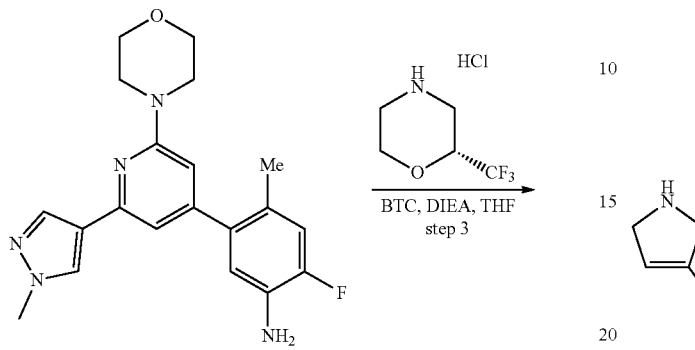

308

Example 69: N-{2-fluoro-4-methyl-5-[2-(1-methylpyrazol-4-yl)-6-(morpholin-4-yl)pyridin-4-yl]phenyl}-3-(trifluoromethyl)-2,5-dihydropyrrole-1-carboxamide

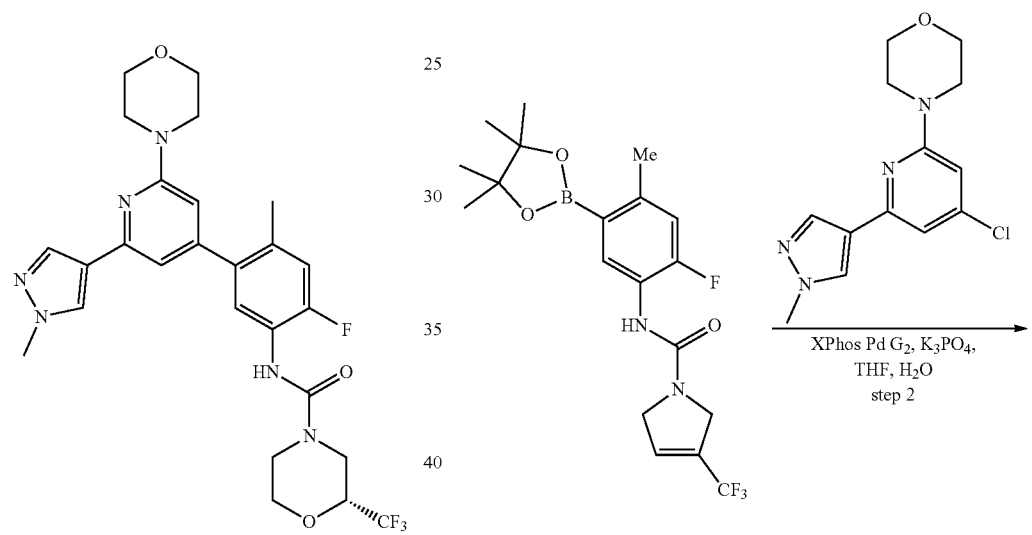

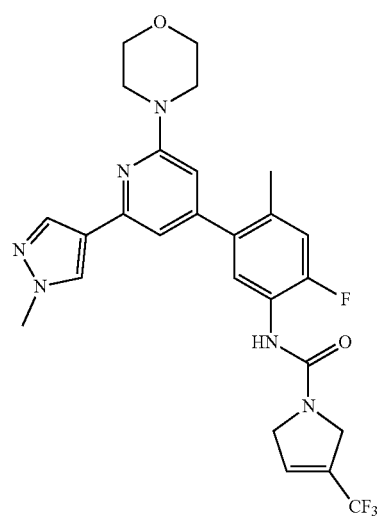

A mixture of 2-fluoro-4-methyl-5-[2-(1-methylpyrazol-4-yl)-6-(morpholin-4-yl)pyridin-4-yl]aniline (130 mg, 0.354 mmol), DIEA (228.64 mg, 1.769 mmol) and triphosgene (42 mg, 0.142 mmol) in tetrahydrofuran (8.5 mL) was stirred for 30 min at room temperature under nitrogen atmosphere. To this was added (2R)-2-(trifluoromethyl)morpholine hydrochloride (68 mg, 0.354 mmol) at room temperature. The resulting mixture was stirred for additional 2 h at room temperature. The resulting mixture was concentrated under reduced pressure. The residue was purified by silica gel column chromatography, eluted with $CH_2Cl_2$/EtOAc (3/2) to afford (2R)—N-{2-fluoro-4-methyl-5-[2-(1-methylpyrazol-4-yl)-6-(morpholin-4-yl)pyridin-4-yl]phenyl}-2-(trifluoromethyl)morpholine-4-carboxamide (148 mg, 72%) as an off-white solid. MS ESI calculated for $C_{26}H_{28}F_4N_6O_3$ [M+H]$^+$, 549.22, found 549.30. $^1$H NMR (400 MHz, DMSO-$d_6$) δ 8.57 (s, 1H), 8.24 (s, 1H), 7.97 (s, 1H), 7.29 (d, J=8.0 Hz, 1H), 7.19 (d, J=11.6 Hz, 1H), 6.91 (s, 1H), 6.49 (s, 1H), 4.23-4.18 (m, 2H), 4.15-3.96 (m, 2H), 3.92 (s, 3H), 3.87-3.72 (m, 4H), 3.65-3.62 (m, 1H), 3.59-3.53 (m, 4H), 3.08-2.94 (m, 2H), 2.25 (s, 3H). $^{19}$F NMR (376 MHz, DMSO-$d_6$) δ −76.14 (3F), −124.23 (1F).

Preparation 69A: N-[2-fluoro-4-methyl-5-(4,4,5,5-tetramethyl-1,3,2-dioxaborolan-2-yl)phenyl]-3-(trifluoromethyl)-2,5-dihydropyrrole-1-carboxamide

Example 69: N-{2-fluoro-4-methyl-5-[2-(1-methylpyrazol-4-yl)-6-(morpholin-4-yl)pyridin-4-yl]phenyl}-3-(trifluoromethyl)-2,5-dihydropyrrole-1-carboxamide

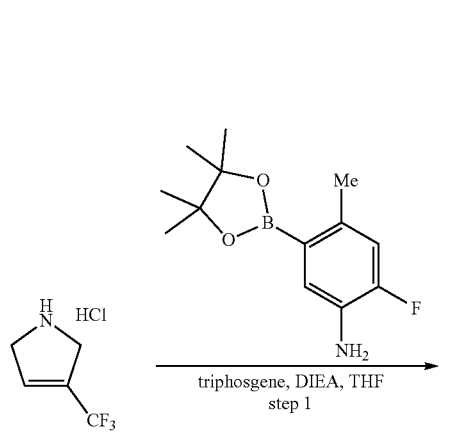

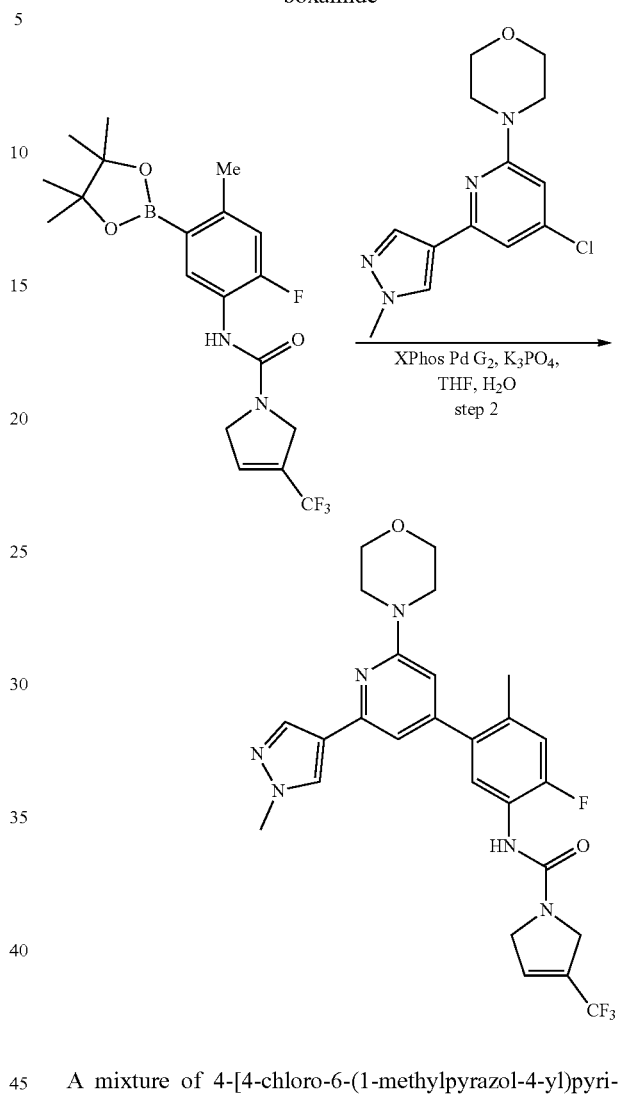

A mixture of 2-fluoro-4-methyl-5-(4,4,5,5-tetramethyl-1,3,2-dioxaborolan-2-yl)aniline (700 mg, 2.788 mmol), DIEA (1.8 g, 13.940 mmol) and triphosgene (331 mg, 1.115 mmol) in tetrahydrofuran (67 mL) was stirred for 30 min at room temperature. To this was added 3-(trifluoromethyl)-2,5-dihydro-1H-pyrrole hydrochloride (611.52 mg, 4.461 mmol) at room temperature. The resulting mixture was stirred for additional 2 h at room temperature. The resulting mixture was concentrated under reduced pressure. The residue was purified by silica gel column chromatography, eluted with petroleum ether/EtOAc/EtOH (4:3:1) to afford N-[2-fluoro-4-methyl-5-(4,4,5,5-tetramethyl-1,3,2-dioxaborolan-2-yl)phenyl]-3-(trifluoromethyl)-2,5-dihydropyrrole-1-carboxamide (794 mg, 68.76%) as an off-white solid. MS ESI calculated for $C_{19}H_{23}BF_4N_2O_3$ [M+H]$^+$, 415.17, found 415.30. $^1$H NMR (400 MHz, CDCl$_3$) δ 8.37 (d, J=9.2 Hz, 1H), 6.90 (d, J=12.4 Hz, 1H), 6.44 (s, 1H), 6.17 (s, 1H), 4.48 (s, 4H), 2.50 (s, 3H), 1.34 (s, 12H).

A mixture of 4-[4-chloro-6-(1-methylpyrazol-4-yl)pyridin-2-yl]morpholine (100 mg, 0.359 mmol), chloro(2-dicyclohexylphosphino-2',4',6'-triisopropyl-1,1'-biphenyl)[2-(2'-amino-1,1'-biphenyl)]palladium(II) (2$^{nd}$ Generation XPhos precatalyst) (28 mg, 0.036 mmol), N-[2-fluoro-4-methyl-5-(4,4,5,5-tetramethyl-1,3,2-dioxaborolan-2-yl)phenyl]-3-(trifluoromethyl)-2,5-dihydropyrrole-1-carboxamide (149 mg, 0.359 mmol) and potassium phosphate (152.30 mg, 0.718 mmol) in tetrahydrofuran (2 mL) and H$_2$O (0.2 mL) was stirred for 2 h at 80° C. under nitrogen atmosphere. The reaction was quenched with water (20 mL). The resulting mixture was diluted with EtOAc (3×10 mL) and washed with brine (2×10 mL), dried over anhydrous Na$_2$SO$_4$. After filtration, the filtrate was concentrated under reduced pressure. The residue was purified by silica gel column chromatography, eluted with petroleum ether/EtOAc/EtOH (4/3/1) to afford N-{2-fluoro-4-methyl-5-[2-(1-methylpyrazol-4-yl)-6-(morpholin-4-yl)pyridin-4-yl]phenyl}-3-(trifluoromethyl)-2,5-dihydropyrrole-1-carboxamide (46 mg, 24%) as an off-white solid. MS ESI calculated for $C_{26}H_{26}F_4N_6O_2$[M+H]$^+$, 531.21; found 531.20. $^1$H NMR (400 MHz, CDCl$_3$) δ 8.04 (d, J=8.4 Hz, 1H), 7.94 (s, 1H), 7.92 (br, 1H), 7.03 (d, J=11.6 Hz, 1H), 6.82 (s, 1H), 6.46 (s, 1H), 6.40 (s, 1H), 6.33 (d, J=3.2 Hz, 1H), 4.49 (s, 4H), 3.97 (s, 3H), 3.89-3.87 (m, 4H), 3.62-3.60 (m, 4H), 2.25 (s, 3H).
$^{19}$F NMR (376 MHz, CDCl$_3$) δ −65.66 (3F), −133.10 (1F).

Example 70: (3S)—N-{2-fluoro-4-methyl-5-[2-methyl-6-(morpholin-4-yl)pyridin-4-yl]phenyl}-3-(2,2,2-trifluoroethyl)pyrrolidine-1-carboxamide

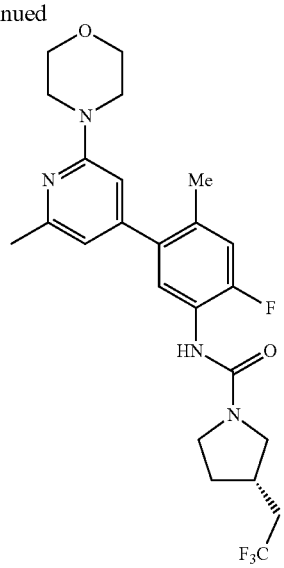

Preparation 70A: (3S)—N-[2-fluoro-4-methyl-5-(4,4,5,5-tetramethyl-1,3,2-dioxaborolan-2-yl)phenyl]-3-(2,2,2-trifluoroethyl)pyrrolidine-1-carboxamide

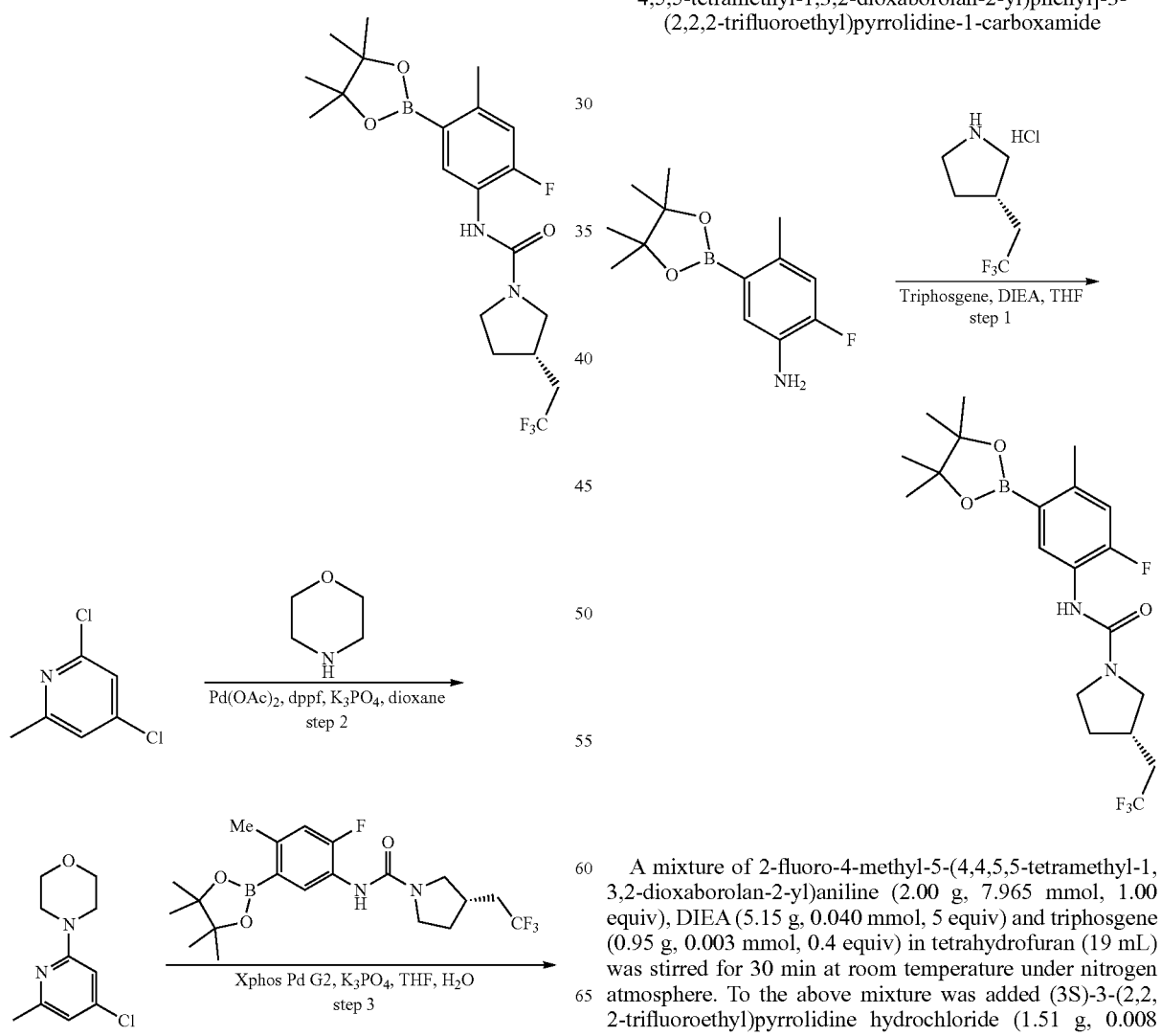

A mixture of 2-fluoro-4-methyl-5-(4,4,5,5-tetramethyl-1,3,2-dioxaborolan-2-yl)aniline (2.00 g, 7.965 mmol, 1.00 equiv), DIEA (5.15 g, 0.040 mmol, 5 equiv) and triphosgene (0.95 g, 0.003 mmol, 0.4 equiv) in tetrahydrofuran (19 mL) was stirred for 30 min at room temperature under nitrogen atmosphere. To the above mixture was added (3S)-3-(2,2,2-trifluoroethyl)pyrrolidine hydrochloride (1.51 g, 0.008 mmol, 1.00 equiv). The resulting mixture was stirred for additional 3 h at room temperature. The resulting mixture was concentrated under vacuum. The residue was purified by silica gel column chromatography, eluted with petroleum ether/EtOAc/EtOH (4/3/1) to afford (3S)—N-[2-fluoro-4-methyl-5-(4,4,5,5-tetramethyl-1,3,2-dioxaborolan-2-yl)phenyl]-3-(2,2,2-trifluoroethyl)pyrrolidine-1-carboxamide (3.2 g, 75%) as an off-white solid. MS ESI calculated for $C_{20}H_{27}BF_4N_2O_3$ [M+H]$^+$, 431.21, found 431.25. $^1$H NMR (400 MHz, CDCl$_3$) δ 8.38 (d, J=9.3 Hz, 1H), 6.88 (dd, J=12.3, 0.8 Hz, 1H), 6.20 (d, J=3.2 Hz, 1H), 3.83 (dd, J=9.9, 7.5 Hz, 1H), 3.67-3.63 (m, 1H), 3.46 (td, J=9.7, 6.8 Hz, 1H), 3.13 (t, J=9.5 Hz, 1H), 2.66-2.51 (m, 1H), 2.46 (s, 3H), 2.35-2.17 (m, 3H), 1.78-1.74 (m, 1H), 1.33 (s, 12H).

Preparation 70B:
4-(4-chloro-6-methylpyridin-2-yl)morpholine

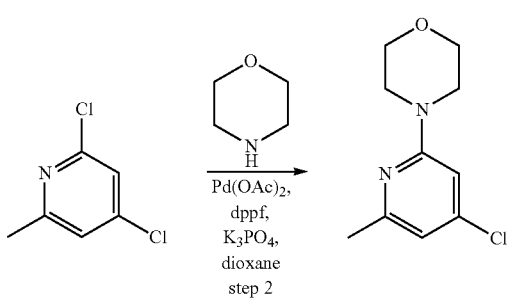

A mixture of 2,4-dichloro-6-methylpyridine (1.00 g, 6.172 mmol), morpholine (0.54 g, 6.172 mmol), 1,4-dioxane (10 mL), dppf (1.51 g, 2.734 mmol), Pd(OAc)$_2$ (0.14 g, 0.617 mmol) and potassium phosphate (3.93 g, 18.516 mmol) was stirred for 2 h at 85° C. under nitrogen atmosphere. The resulting mixture was concentrated under reduced pressure. The residue was purified by silica gel column chromatography, eluted with petroleum ether/EtOAc (1/1) to afford 4-(4-chloro-6-methylpyridin-2-yl)morpholine (1.30 g, 99%) as a white solid. MS ESI calculated for $C_{10}H_{13}Cl_1N_2O$ [M+H]$^+$ 213.07 found 213.05. $^1$H NMR (400 MHz, CDCl$_3$) δ 6.56 (d, J=1.6 Hz, 1H), 6.43 (d, J=1.6 Hz, 1H), 3.83-3.81 (m, 4H), 3.53-3.51 (m, 4H), 2.40 (s, 3H).

Example 70: (3S)—N-{2-fluoro-4-methyl-5-[2-methyl-6-(morpholin-4-yl)pyridin-4-yl]phenyl}-3-(2,2,2-trifluoroethyl)pyrrolidine-1-carboxamide

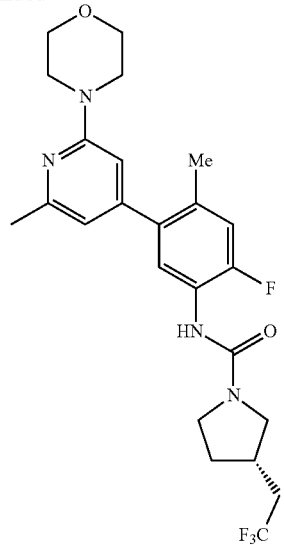

A mixture of 4-(4-chloro-6-methylpyridin-2-yl)morpholine (70 mg, 0.329 mmol), (3S)—N-[2-fluoro-4-methyl-5-(4,4,5,5-tetramethyl-1,3,2-dioxaborolan-2-yl)phenyl]-3-(2,2,2-trifluoroethyl)pyrrolidine-1-carboxamide (113 mg, 0.263 mmol) in tetrahydrofuran (1.5 mL) and H$_2$O (0.15 mL), potassium phosphate (210 mg, 0.987 mmol) and XPhos palladium(II) biphenyl-2-amine chloride (26 mg, 0.033 mmol) was stirred for 2 h at 80° C. under nitrogen atmosphere. The resulting mixture was concentrated under reduced pressure. The residue was purified by Prep-TLC with petroleum ether/EtOAc (1/1) to afford (3S)—N-{2-fluoro-4-methyl-5-[2-methyl-6-(morpholin-4-yl)pyridin-4-yl]phenyl}-3-(2,2,2-trifluoroethyl)pyrrolidine-1-carboxamide (22.7 mg, 14%) as a white solid. MS ESI calculated for $C_{24}H_{28}F_4N_4O_2$[M+H]$^+$ 481.21 found 481.35. $^1$H NMR (400 MHz, CDCl$_3$) δ 8.03 (d, J=7.2 Hz, 1H), 6.98 (d, J=12.0 Hz, 1H), 6.51 (s, 1H), 6.36-3.33 (m, 2H), 3.94-3.82 (m, 5H), 3.69-3.65 (m, 1H), 3.59-3.45 (m, 5H), 3.18-3.13 (m, 1H), 2.60-2.58 (m, 1H), 2.44 (s, 3H), 2.34-2.27 (m, 3H), 2.22 (s, 3H), 1.84-1.73 (m, 1H). $^{19}$F NMR (376 MHz, CDCl$_3$) δ −64.72 (3F), −134.57 (1F).

Example 71: (3S)—N-{5-[2-cyclopropyl-6-(morpholin-4-yl)pyridin-4-yl]-2-fluoro-4-methylphenyl}-3-(2,2,2-trifluoroethyl)pyrrolidine-1-carboxamide

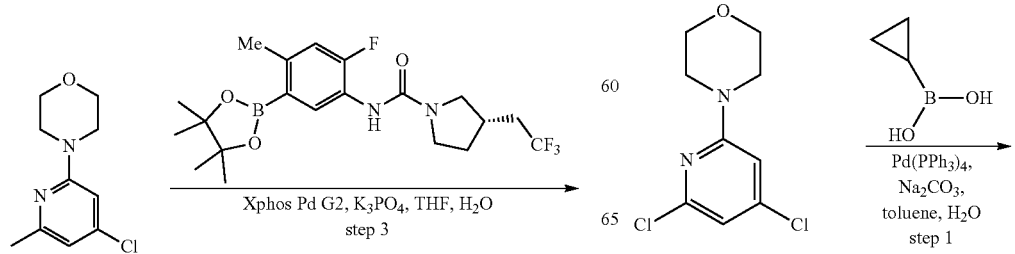

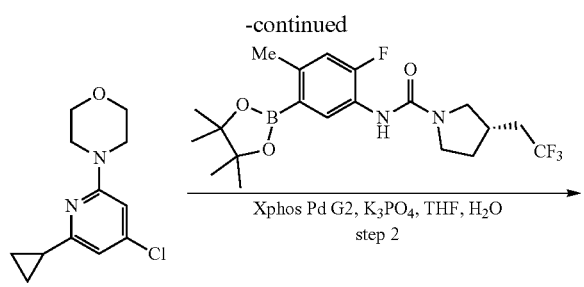

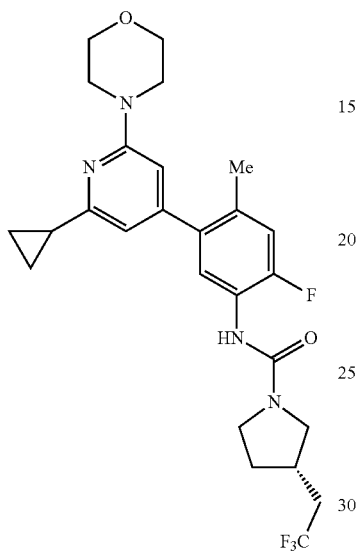

Preparation 71A:
4-(4-chloro-6-cyclopropylpyridin-2-yl)morpholine

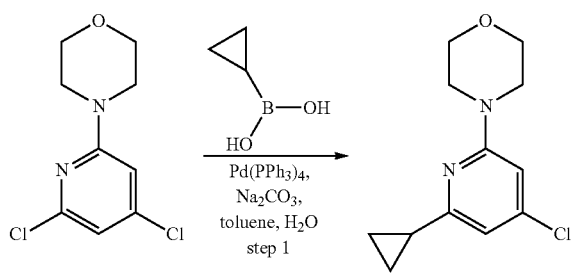 [SMILES: Clc1cc(Cl)nc(N2CCOCC2)c1 ; OB(O)C1CC1 ; Clc1cc(C2CC2)nc(N2CCOCC2)c1]

A mixture of 4-(4,6-dichloropyridin-2-yl)morpholine (500 mg, 2.145 mmol), cyclopropylboronic acid (369 mg, 4.290 mmol), Pd(PPh₃)₄ (2.47 g, 0.215 mmol) and Na₂CO₃ (682 mg, 6.435 mmol) in toluene (8 mL) and H₂O (2 mL) was stirred for 5 h at 90° C. under nitrogen atmosphere. The reaction was diluted with water (40 mL). The resulting mixture was extracted with EtOAc (3×50 mL). The combined organic layers were washed with brine (2×30 mL), dried over anhydrous Na₂SO₄. After filtration, the filtrate was concentrated under reduced pressure. The residue was purified by silica gel column chromatography, eluted with petroleum ether/EtOAc (1/1) to afford 4-(4-chloro-6-cyclopropylpyridin-2-yl)morpholine (360 mg, 70%) as a white solid. MS ESI calculated for $C_{12}H_{15}ClN_2O$ [M+H]⁺, 239.09, found 239.00. ¹H NMR (400 MHz, CDCl₃) δ 6.58 (d, J=1.6 Hz, 1H), 6.37 (d, J=1.6 Hz, 1H), 3.84-3.74 (m, 4H), 3.51-3.44 (m, 4H), 1.91-1.84 (m, 1H), 1.05-0.98 (m, 2H), 0.95-0.85 (m, 2H).

Example 71: (3S)—N-{5-[2-cyclopropyl-6-(morpholin-4-yl)pyridin-4-yl]-2-fluoro-4-methylphenyl}-3-(2,2,2-trifluoroethyl)pyrrolidine-1-carboxamide

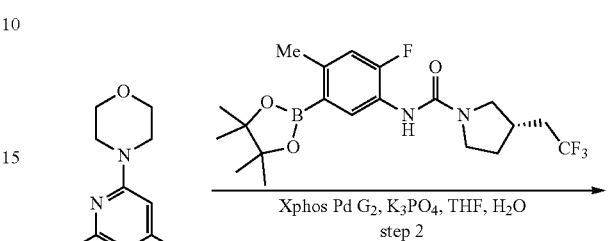

A mixture of 4-(4-chloro-6-cyclopropylpyridin-2-yl)morpholine (100 mg, 0.419 mmol), (3S)—N-[2-fluoro-4-methyl-5-(4,4,5,5-tetramethyl-1,3,2-dioxaborolan-2-yl)phenyl]-3-(2,2,2-trifluoroethyl)pyrrolidine-1-carboxamide (144 mg, 0.335 mmol) and chloro(2-dicyclohexylphosphino-2',4',6'-triisopropyl-1,1'-biphenyl)[2-(2'-amino-1,1'-biphenyl)]palladium(II) (2$^{nd}$ Generation XPhos precatalyst) (33 mg, 0.042 mmol) in tetrahydrofuran (1 mL) and potassium phosphate (2 mL, 0.5 M) was stirred for 2 h at 40° C. under nitrogen atmosphere. The reaction was diluted with water (30 mL). The resulting mixture was extracted with EtOAc (3×30 mL). The combined organic layers were washed with brine (2×20 mL), dried over anhydrous Na₂SO₄. After filtration, the filtrate was concentrated under reduced pressure. The residue was purified by silica gel column chromatography, eluted with petroleum ether/EtOAc (1/1) to afford (3S)—N-{5-[2-cyclopropyl-6-(morpholin-4-yl)pyridin-4-yl]-2-fluoro-4-methylphenyl}-3-(2,2,2-trifluoroethyl)pyrrolidine-1-carboxamide (90 mg, 42%) as a white solid. MS ESI calculated for $C_{26}H_{30}F_4N_4O_2$[M+H]⁺, 507.23, found 507.20. ¹H NMR (400 MHz, CDCl₃) 8.02 (d, J=8.4 Hz, 1H), 6.98 (d, J=12.0 Hz, 1H), 6.52 (s, 1H) 6.31-6.29 (m, 2H) 3.85-3.81 (m, 5H), 3.68-3.64 (m, 1H), 3.54-3.40 (m, 5H), 3.15 (t, J=9.2 Hz, 1H), 2.63-2.55 (m, 1H), 2.34-2.25 (m, 3H), 2.22 (s, 3H), 1.94-1.91 (m, 1H), 1.83-1.73 (m, 1H), 1.05-1.03 (m, 2H) 0.91-0.89 (m, 2H). ¹⁹F NMR (376 MHz, CDCl₃) δ −64.97 (3F), 6-134.57 (F).

Example 72: (3S)—N-{5-[2-ethyl-6-(morpholin-4-yl)pyridin-4-yl]-2-fluoro-4-methylphenyl}-3-(2,2,2-trifluoroethyl)pyrrolidine-1-carboxamide

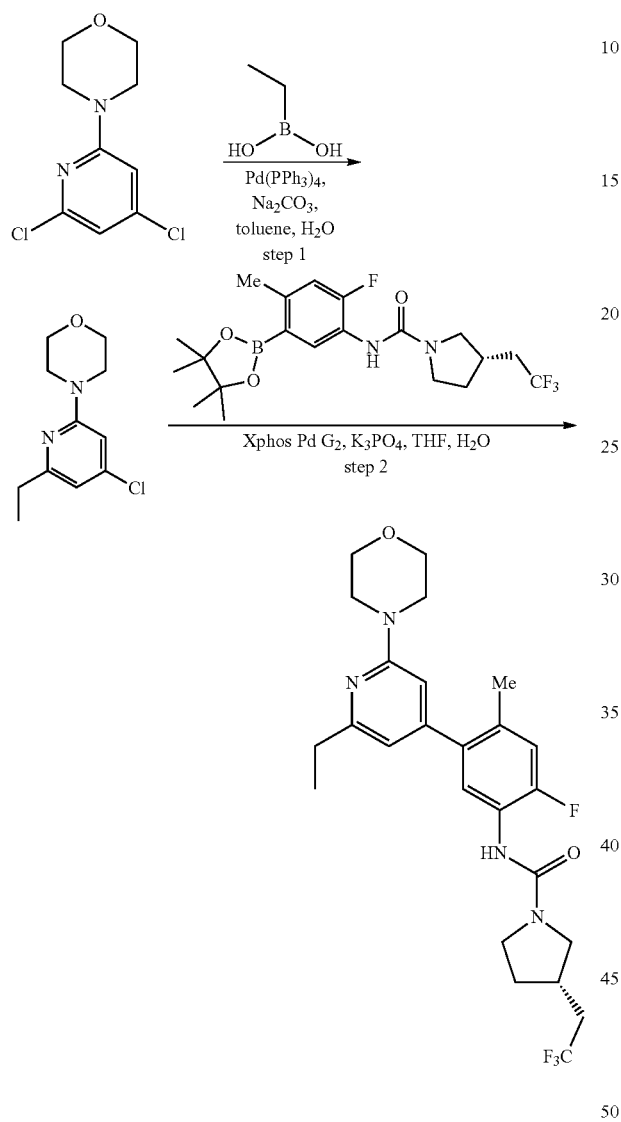

Preparation 72A:
4-(4-chloro-6-ethylpyridin-2-yl)morpholine

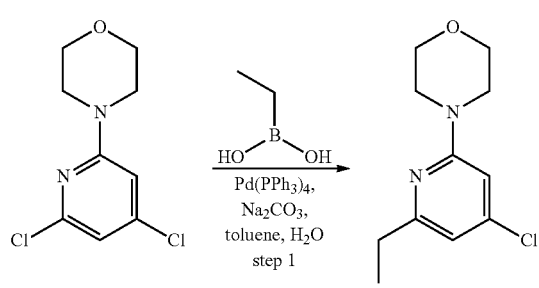

A mixture of 4-(4,6-dichloropyridin-2-yl)morpholine (1.00 g, 4.290 mmol), ethylboronic acid (0.63 g, 8.580 mmol), Pd(PPh₃)₄ (0.50 g, 0.429 mmol) and Na₂CO₃ (1.36 g, 12.870 mmol) in toluene (16 mL) and H₂O (4 mL) was stirred for 16 h at 90° C. under nitrogen atmosphere. The reaction was quenched by the addition of water (200 mL). The aqueous layer was extracted with CH₂Cl₂ (3×500 mL). The resulting mixture was concentrated under reduced pressure. The residue was purified by silica gel column chromatography, eluted with petroleum ether/EtOAc (5/1) to afford 4-(4-chloro-6-ethylpyridin-2-yl)morpholine (0.60 g, 70%) as colorless liquid. MS ESI calculated for C₁₁H₁₅ClN₂O[M+H]⁺, 227.09, found 227.05. ¹H NMR (400 MHz, CDCl₃) δ 6.56 (d, J=1.2 Hz, 1H), 6.44 (d, J=1.2 Hz, 1H), 3.84-3.81 (m, 4H), 3.54-3.51 (m, 4H), 2.66 (q, J=7.6 Hz, 2H), 1.27 (t, J=7.6 Hz, 3H).

Example 72: (3S)—N-{5-[2-ethyl-6-(morpholin-4-yl)pyridin-4-yl]-2-fluoro-4-methylphenyl}-3-(2,2,2-trifluoroethyl)pyrrolidine-1-carboxamide

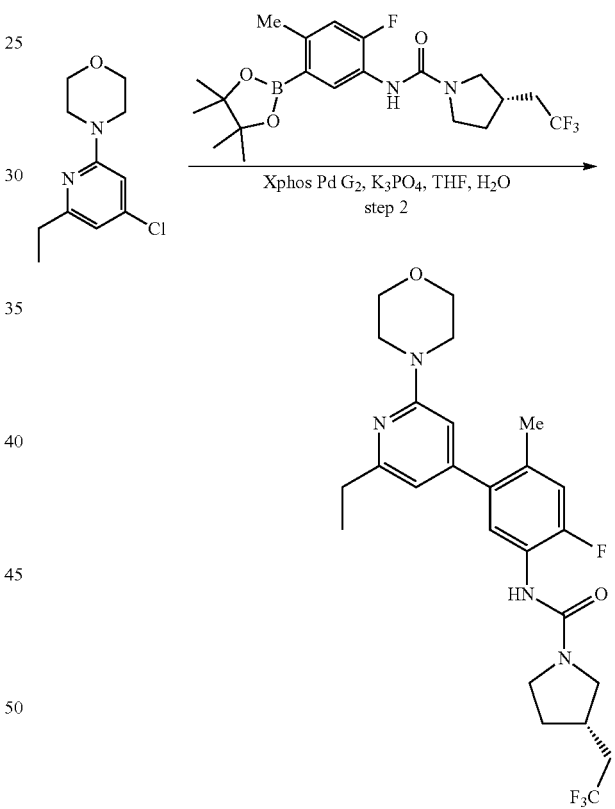

A mixture of 4-(4-chloro-6-ethylpyridin-2-yl)morpholine (100 mg, 0.441 mmol), (3S)—N-[2-fluoro-4-methyl-5-(4,4,5,5-tetramethyl-1,3,2-dioxaborolan-2-yl)phenyl]-3-(2,2,2-trifluoroethyl)pyrrolidine-1-carboxamide (152 mg, 0.353 mmol) and chloro(2-dicyclohexylphosphino-2',4',6'-triisopropyl-1,1'-biphenyl)[2-(2'-amino-1,1'-biphenyl)]palladium (II) (2ⁿᵈ Generation XPhos precatalyst) (35 mg, 0.044 mmol) in tetrahydrofuran (1 mL) and potassium phosphate (2 mL, 0.5 M) was stirred for 2 h at 40° C. under nitrogen atmosphere. The reaction was diluted with water (30 mL) at room temperature. The resulting mixture was extracted with EtOAc (3×30 mL). The combined organic layers were washed with brine (2×20 mL), dried over anhydrous Na$_2$SO$_4$. After filtration, the filtrate was concentrated under reduced pressure. The residue was purified by silica gel column chromatography, eluted with petroleum ether/EtOAc (1/1) to afford (3S)—N-{5-[2-ethyl-6-(morpholin-4-yl)pyridin-4-yl]-2-fluoro-4-methylphenyl}-3-(2,2,2-trifluoroethyl)pyrrolidine-1-carboxamide (115 mg, 53%) as a white solid. MS ESI calculated for C$_{25}$H$_{30}$F$_4$N$_4$O$_2$[M+H]$^+$, 495.23, found 495.15. $^1$H NMR (400 MHz, CDCl$_3$) δ 8.03 (d, J=8.4 Hz, 1H), 6.98 (d, J=12.0 Hz, 1H), 6.50 (s, 1H), 6.34-6.32 (m, 2H), 3.86-3.81 (m, 5H), 3.69-3.64 (m, 1H), 3.55-3.44 (m, 5H), 3.17-3.12 (m, 1H), 2.72 (q, J=7.6 Hz, 2H), 2.68-2.61 (m, 1H), 2.34-2.24 (m, 3H), 2.22 (s, 3H), 1.83-1.76 (m, 1H), 1.30 (t, J=7.6 Hz, 3H). $^{19}$F NMR (376 MHz, CDCl$_3$) δ −64.97 (3F), δ −134.58 (F).

Example 73: N-{2-fluoro-4-methyl-5-[2-(2-methylpyrazol-3-yl)-6-(morpholin-4-yl)pyridin-4-yl]phenyl}-3-(trifluoromethyl)-2,5-dihydropyrrole-1-carboxamide filtrate was concentrated under reduced pressure. The residue was purified by reverse flash chromatography with the following conditions: column, C18 silica gel; mobile phase, CH$_3$CN in water (10 mM NH$_4$HCO$_3$), 35% to 95%; UV 254 nm to afford N-{2-fluoro-4-methyl-5-[2-(2-methylpyrazol-3-yl)-6-(morpholin-4-yl)pyridin-4-yl]phenyl}-3-(trifluoromethyl)-2,5-dihydropyrrole-1-carboxamide (85 mg, 44%) as an off-white solid. MS ESI calculated for C$_{26}$H$_{26}$F$_4$N$_6$O$_2$ [M+H]$^+$, 531.21, found 531.25. $^1$H NMR (400 MHz, CDCl$_3$) δ 8.06 (d, J=8.4 Hz, 1H), 7.52 (d, J=1.6 Hz, 1H), 7.04 (d, J=12.0 Hz, 1H), 6.94 (s, 1H), 6.57-6.56 (m, 2H), 6.46 (s, 1H), 6.34 (d, J=2.8 Hz, 1H), 4.49 (s, 4H), 4.30 (s, 3H), 3.89-3.87 (m, 4H), 3.61-3.59 (m, 4H), 2.26 (s, 3H). $^{19}$F NMR (376 MHz, DMSO-d$_6$) δ −65.66 (3F), −133.61 (1F).

Example 74: (3S)—N-{2-fluoro-4-methyl-5-[2-(1-methylpyrazol-4-yl)-6-(morpholin-4-yl)pyridin-4-yl]phenyl}-3-(2,2,2-trifluoroethyl)pyrrolidine-1-carboxamide

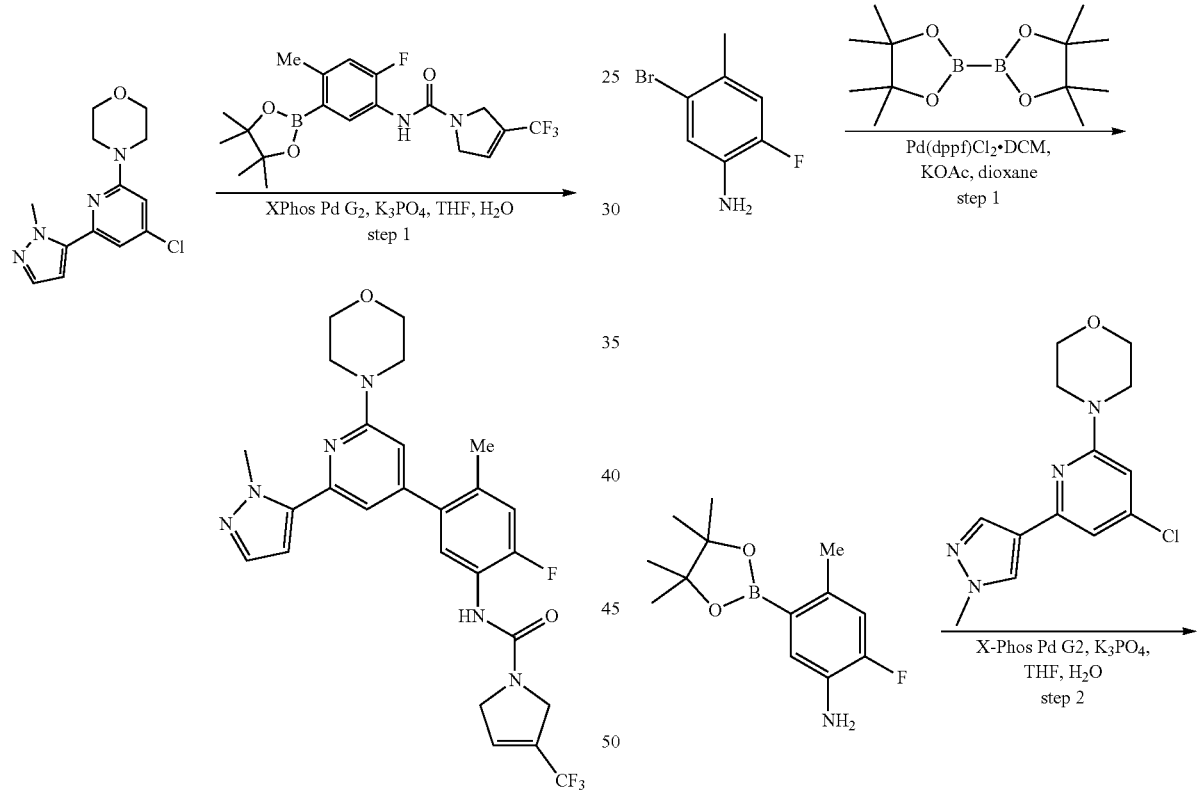

A mixture of 4-[4-chloro-6-(2-methylpyrazol-3-yl)pyridin-2-yl]morpholine (101 mg, 0.362 mmol), N-[2-fluoro-4-methyl-5-(4,4,5,5-tetramethyl-1,3,2-dioxaborolan-2-yl)phenyl]-3-(trifluoromethyl)-2,5-dihydropyrrole-1-carboxamide (120 mg, 0.290 mmol), chloro(2-dicyclohexylphosphino-2',4',6'-triisopropyl-1,1'-biphenyl)[2-(2'-amino-1,1'-biphenyl)]palladium(II) (2$^{nd}$ Generation XPhos precatalyst) (28 mg, 0.036 mmol) in tetrahydrofuran (0.6 mL) was added potassium phosphate (123 mg, 0.579 mmol) in H$_2$O (1.2 mL) was stirred for 2 h at 60° C. under nitrogen atmosphere. The resulting mixture was diluted with water (50 mL). The resulting mixture was extracted with EtOAc (3×50 mL). The combined organic layers were washed with brine (3×50 mL), dried over anhydrous Na$_2$SO$_4$. After filtration, the

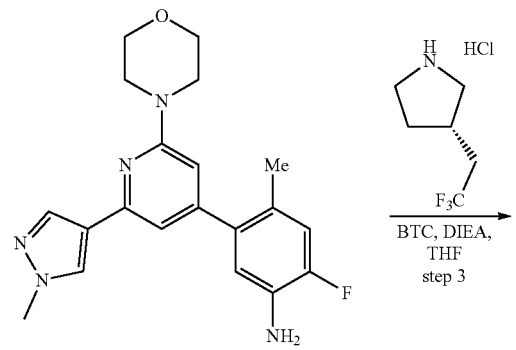

-continued

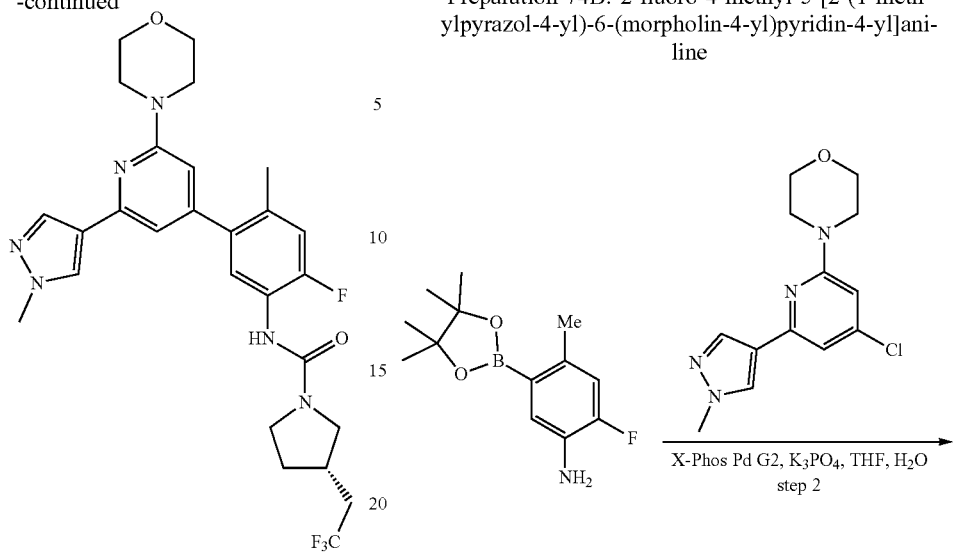

Preparation 74A: 2-fluoro-4-methyl-5-(4,4,5,5-tetramethyl-1,3,2-dioxaborolan-2-yl)aniline

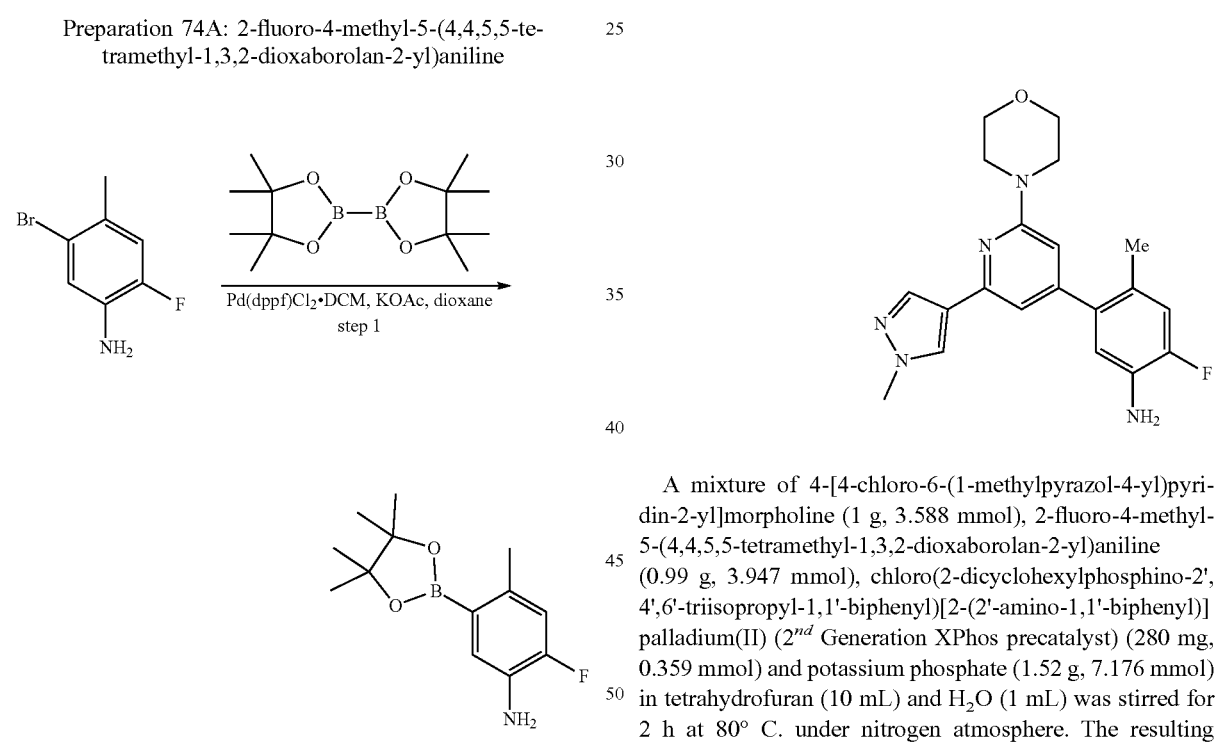

A mixture of 5-bromo-2-fluoro-4-methylaniline (50 g, 245.048 mmol), 4,4,5,5-tetramethyl-2-(tetramethyl-1,3,2-dioxaborolan-2-yl)-1,3,2-dioxaborolane (75 g, 294.057 mmol), KOAc (72 g, 735.143 mmol) and 1,1'-bis(diphenylphosphino)ferrocene-palladium(II) dichloride dichloromethane complex (10 g, 12.252 mmol) in 1,4-dioxane (600 mL) was stirred for 16 h at 100° C. under argon atmosphere. The resulting mixture was concentrated under reduced pressure. The residue was purified by silica gel column chromatography, eluted with EtOAc in PE (0~30%) to afford 2-fluoro-4-methyl-5-(4,4,5,5-tetramethyl-1,3,2-dioxaborolan-2-yl)aniline (57 g, 93%) as an off-white solid. MS ESI calculated for $C_{13}H_{19}BFNO_2$ [M+H]$^+$, 252.15, found 252.10.

Preparation 74B: 2-fluoro-4-methyl-5-[2-(1-methylpyrazol-4-yl)-6-(morpholin-4-yl)pyridin-4-yl]aniline A mixture of 4-[4-chloro-6-(1-methylpyrazol-4-yl)pyridin-2-yl]morpholine (1 g, 3.588 mmol), 2-fluoro-4-methyl-5-(4,4,5,5-tetramethyl-1,3,2-dioxaborolan-2-yl)aniline (0.99 g, 3.947 mmol), chloro(2-dicyclohexylphosphino-2',4',6'-triisopropyl-1,1'-biphenyl)[2-(2'-amino-1,1'-biphenyl)]palladium(II) (2$^{nd}$ Generation XPhos precatalyst) (280 mg, 0.359 mmol) and potassium phosphate (1.52 g, 7.176 mmol) in tetrahydrofuran (10 mL) and H$_2$O (1 mL) was stirred for 2 h at 80° C. under nitrogen atmosphere. The resulting mixture was quenched with water (20 mL) and extracted with EtOAc (2×20 mL). The combined organic layers were washed with brine (10 mL), dried over anhydrous Na$_2$SO$_4$. After filtration, the filtrate was concentrated under reduced pressure. The residue was purified by silica gel column chromatography, eluted with petroleum ether/EtOAc (1/1) to afford 2-fluoro-4-methyl-5-[2-(1-methylpyrazol-4-yl)-6-(morpholin-4-yl)pyridin-4-yl]aniline (707 mg, 51%) as a light brown solid. MS ESI calculated for $C_{20}H_{22}FN_5O$ [M+H]$^+$, 368.18, found 368.30. $^1$H NMR (400 MHz, CDCl$_3$) δ 7.93 (s, 1H), 7.89 (s, 1H), 6.92 (d, J=12.0 Hz, 1H), 6.81-6.80 (m, 1H), 6.69 (d, J=8.8 Hz, 1H), 6.37 (s, 1H), 3.97 (s, 3H), 3.89-3.86 (m, 4H), 3.61-3.59 (m, 4H), 2.18 (s, 3H). $^{19}$F NMR (376 MHz, CDCl$_3$) δ −136.37 (1F).

323

Example 74: (3S)—N-{2-fluoro-4-methyl-5-[2-(1-methylpyrazol-4-yl)-6-(morpholin-4-yl)pyridin-4-yl]phenyl}-3-(2,2,2-trifluoroethyl)pyrrolidine-1-carboxamide

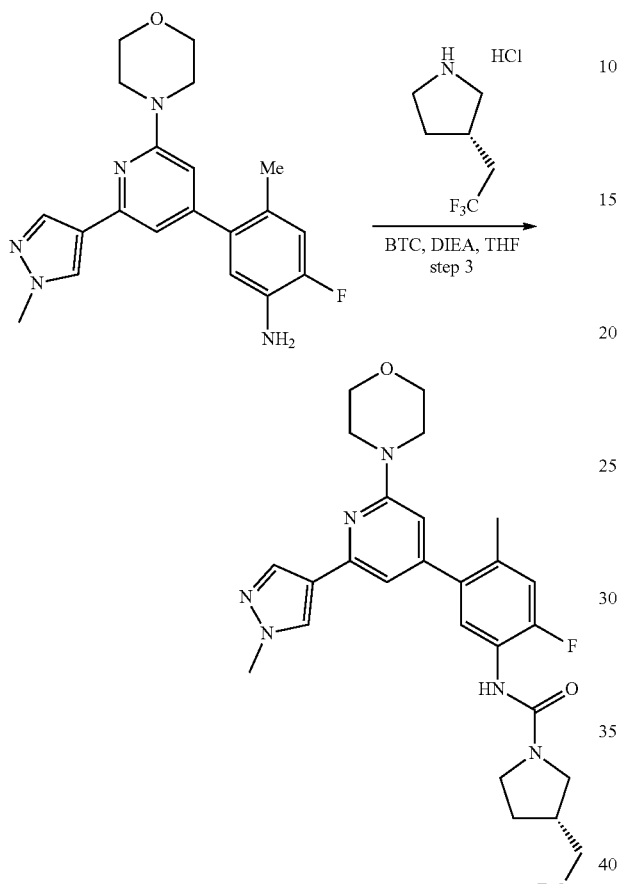

To a stirred solution of 2-fluoro-4-methyl-5-[2-(1-methylpyrazol-4-yl)-6-(morpholin-4-yl)pyridin-4-yl]aniline (100 mg, 0.272 mmol) and DIEA (175 mg, 1.360 mmol) in tetrahydrofuran (1 mL) was added triphosgene (32 mg, 0.109 mmol). The resulting mixture was stirred for 30 min at room temperature. To this was added (3 S)-3-(2,2,2-trifluoroethyl)pyrrolidine hydrochloride (45 mg, 0.299 mmol). The resulting mixture was stirred for additional 2 h at room temperature. The resulting mixture was concentrated under reduced pressure. The residue was purified by reverse phase chromatography, eluted with 52% $CH_3CN$ in water (10 mM $NH_4HCO_3$) to afford (3S)—N-{2-fluoro-4-methyl-5-[2-(1-methylpyrazol-4-yl)-6-(morpholin-4-yl)pyridin-4-yl]phenyl}-3-(2,2,2-trifluoroethyl)pyrrolidine-1-carboxamide (90.4 mg, 61%) as a white solid. MS ESI calculated for $C_{27}H_{30}F_4N_6O_2$ $[M+H]^+$, 547.24; found 547.50. $^1H$ NMR (400 MHz, DMSO-$d_6$) δ 8.25 (s, 1H), 7.97 (s, 1H), 7.92 (s, 1H), 7.37 (d, J=8.4 Hz, 1H), 7.17 (d, J=11.6 Hz, 1H), 6.91 (s, 1H), 6.49 (s, 1H), 3.87 (s, 3H), 3.79-3.63 (m, 5H), 3.54-3.49 (m, 5H), 3.30-3.28 (m, 1H), 3.03-3.00 (m, 1H), 2.50-2.33 (m, 3H), 2.24 (s, 3H), 2.11-2.08 (m, 1H), 1.69-1.64 (s, 1H). 19F NMR (376 MHz, DMSO-$d_6$) δ −63.40 (3F), −124.77 (1F).

324

Example 75: (3R)—N-{2-fluoro-4-methyl-5-[2-(1-methyl pyrazol-4-yl)-6-(morpholin-4-yl)pyridin-4-yl]phenyl}-3-(trifluoromethyl)pyrrolidine-1-carboxamide

Example 76: (3S)—N-{2-fluoro-4-methyl-5-[2-(1-methyl pyrazol-4-yl)-6-(morpholin-4-yl)pyridin-4-yl]phenyl}-3-(trifluoromethyl)pyrrolidine-1-carboxamide

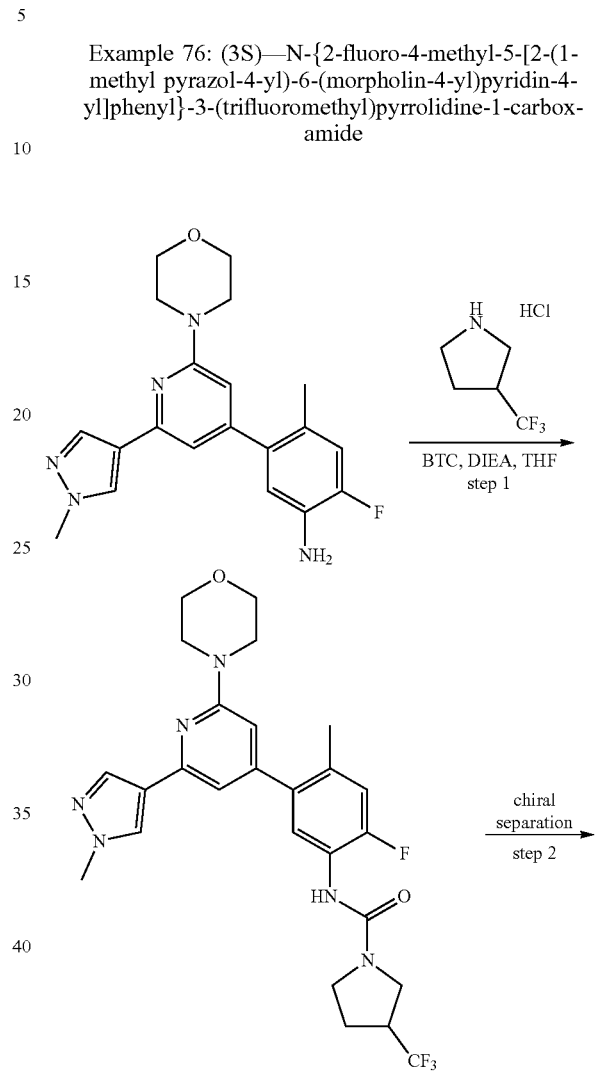

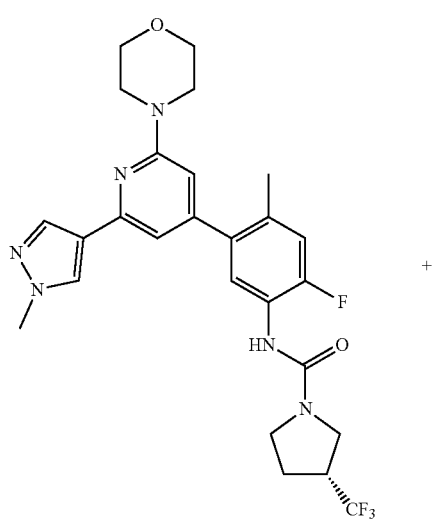

+

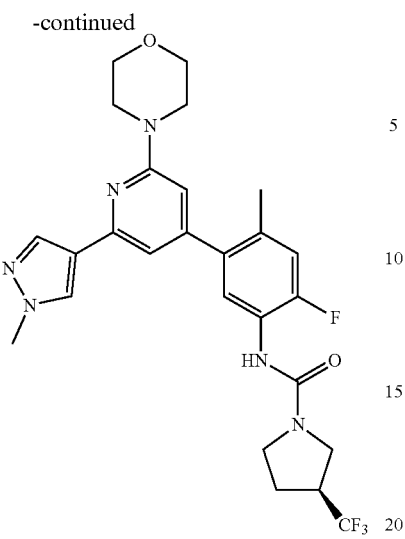

Preparation 75A: N-{2-fluoro-4-methyl-5-[2-(1-methylpyrazol-4-yl)-6-(morpholin-4-yl)pyridin-4-yl]phenyl}-3-(trifluoromethyl)pyrrolidine-1-carboxamide

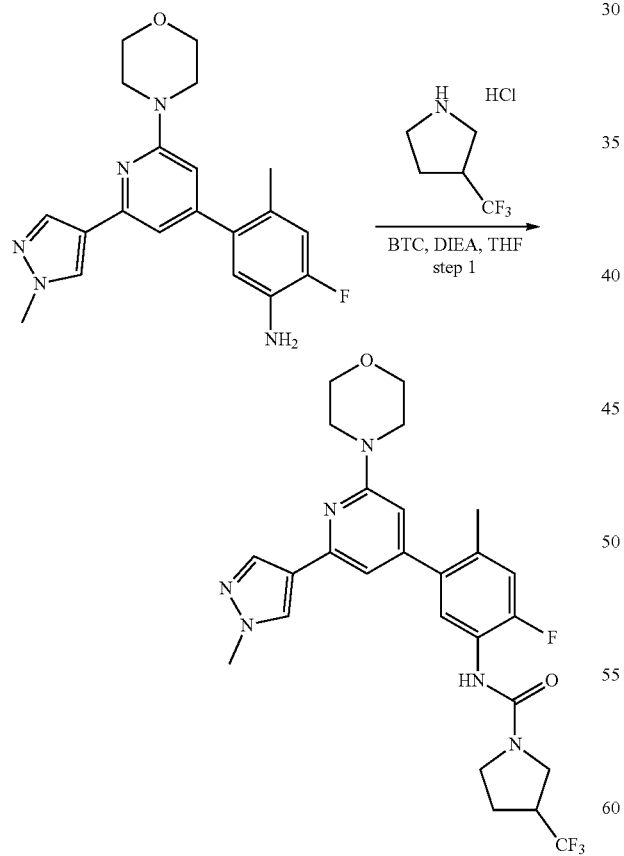

A mixture of 2-fluoro-4-methyl-5-[2-(1-methylpyrazol-4-yl)-6-(morpholin-4-yl)pyridin-4-yl]aniline (200 mg, 0.544 mmol) and DIEA (352 mg, 2.722 mmol) in tetrahydrofuran (13 mL) was stirred for 30 min at room temperature. To this was added 3-(trifluoromethyl)pyrrolidine hydrochloride (105 mg, 0.598 mmol) at room temperature. The resulting mixture was stirred for additional 2 h at room temperature. The resulting mixture was concentrated under reduced pressure. The residue was purified by silica gel column chromatography, eluted with petroleum ether/EtOAc/EtOH (8/3/1) to afford N-{2-fluoro-4-methyl-5-[2-(1-methylpyrazol-4-yl)-6-(morpholin-4-yl)pyridin-4-yl]phenyl}-3-(trifluoromethyl)pyrrolidine-1-carboxamide (280 mg, 91%) as an off-white solid. MS ESI calculated for $C_{26}H_{28}F_4N_6O_2$ $[M+H]^+$, 533.22, found 533.20.

Example 75: (3R)—N-{2-fluoro-4-methyl-5-[2-(1-methylpyrazol-4-yl)-6-(morpholin-4-yl)pyridin-4-yl]phenyl}-3-(trifluoromethyl)pyrrolidine-1-carboxamide Example 76: (3S)—N-{2-fluoro-4-methyl-5-[2-(1-methylpyrazol-4-yl)-6-(morpholin-4-yl)pyridin-4-yl]phenyl}-3-(trifluoromethyl)pyrrolidine-1-carboxamide

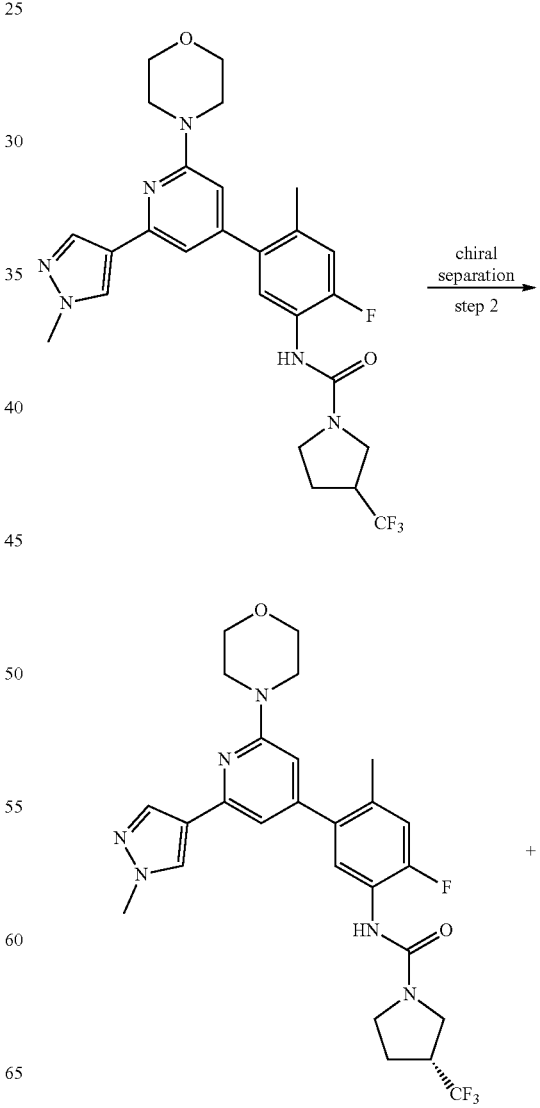

-continued

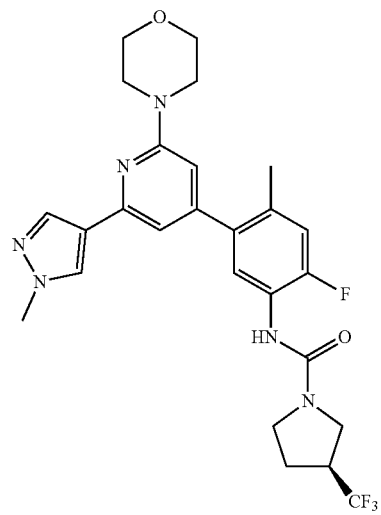 [SMILES: Cc1cc(F)c(NC(=O)N2CC[C@H](C(F)(F)F)C2)cc1-c1cc(-c2cnn(C)c2)nc(N2CCOCC2)c1]

The racemic compound (280 mg) was resolved by Chiral-HPLC with the following conditions (Column: CHIRAL-PAK IH, 2×25 cm, 5 μm; Mobile Phase: Hexane/DCM/EtOH (3/1/1); Flow rate: 20 mL/min; Detector: 220/254 nm; $RT_1$: 11.29 min to afford (3R)—N-{2-fluoro-4-methyl-5-[2-(1-methylpyrazol-4-yl)-6-(morpholin-4-yl)pyridin-4-yl]phenyl}-3-(trifluoromethyl)pyrrolidine-1-carboxamide (106 mg, 76%) as an off-white solid, MS ESI calculated for $C_{26}H_{28}F_4N_6O_2$ [M+H]$^+$, 533.22, found 533.35. $^1$H NMR (400 MHz, DMSO-$d_6$) δ 8.25 (s, 1H), 8.07 (s, 1H), 7.97 (s, 1H), 7.36 (d, J=8.4 Hz, 1H), 7.18 (d, J=11.6 Hz, 1H), 6.91 (s, 1H), 6.49 (s, 1H), 3.87 (s, 3H), 3.74-3.70 (m, 4H), 3.68-3.67 (m, 1H), 3.58-3.50 (m, 5H), 3.48-3.42 (m, 2H), 3.33-3.26 (m, 1H), 2.24 (s, 3H), 2.23-2.16 (m, 1H), 2.08-1.98 (m, 1H). $^{19}$F NMR (376 MHz, DMSO-$d_6$) δ -69.80 (3F), -124.49 (1F).

And $RT_2$: 15.60 min to afford (3S)—N-{2-fluoro-4-methyl-5-[2-(1-methylpyrazol-4-yl)-6-(morpholin-4-yl)pyridin-4-yl]phenyl}-3-(trifluoromethyl)pyrrolidine-1-carboxamide (102.6 mg, 73%), MS ESI calculated for $C_{26}H_{28}F_4N_6O_2$[M+H]$^+$, 533.22, found 533.30. $^1$H NMR (400 MHz, DMSO-$d_6$) δ 8.24 (s, 1H), 8.07 (s, 1H), 7.97 (s, 1H), 7.36 (d, J=8.4 Hz, 1H), 7.18 (d, J=11.6 Hz, 1H), 6.91 (s, 1H), 6.49 (s, 1H), 3.87 (s, 3H), 3.74-3.70 (m, 4H), 3.68-3.65 (m, 1H), 3.57-3.50 (m, 5H), 3.48-3.44 (m, 2H), 3.42-3.26 (m, 1H), 2.24 (s, 3H), 2.23-2.21 (m, 1H), 2.19-1.98 (m, 1H). $^{19}$F NMR (376 MHz, DMSO-$d_6$) δ -69.80 (3F), -124.49 (1F).

Example 77: N-{2-fluoro-4-methyl-5-[2-(1-methylpyrazol-4-yl)-6-(morpholin-4-yl)pyridin-4-yl]phenyl}-3-(2,2,2-trifluoroethyl)-2,5-dihydropyrrole-1-carboxamide

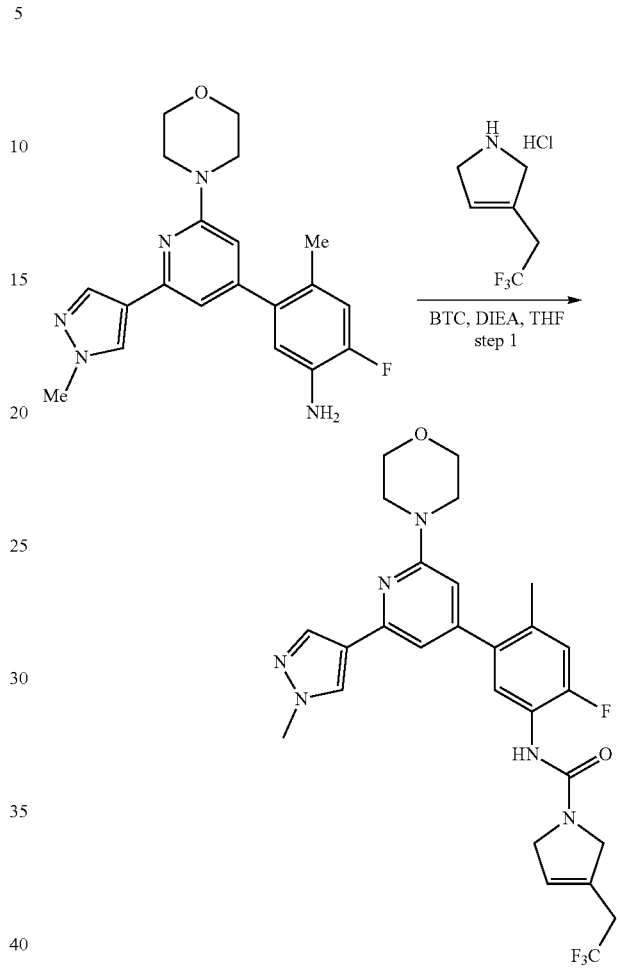

To a stirred mixture of 2-fluoro-4-methyl-5-[2-(1-methylpyrazol-4-yl)-6-(morpholin-4-yl)pyridin-4-yl]aniline (100 mg, 0.272 mmol) and DIEA (175 mg, 1.360 mmol) in tetrahydrofuran (2 mL) was added triphosgene (32 mg, 0.109 mmol) at room temperature. The resulting mixture was stirred for 30 min at room temperature. To this was added 3-(2,2,2-trifluoroethyl)-2,5-dihydro-1H-pyrrole hydrochloride (51 mg, 0.272 mmol) in tetrahydrofuran (2 mL) at room temperature. The resulting mixture was stirred for 30 min at room temperature. The resulting mixture was concentrated under reduced pressure. The residue was purified by reverse flash chromatography with the following conditions: column, silica gel; mobile phase, $CH_3CN$ in water (10 mM $NH_4HCO_3$), 35% to 75%; Detector, UV 254 nm to afford N-{2-fluoro-4-methyl-5-[2-(1-methylpyrazol-4-yl)-6-(morpholin-4-yl)pyridin-4-yl]phenyl}-3-(2,2,2-trifluoroethyl)-2,5-dihydropyrrole-1-carboxamide (80.7 mg, 54%) as a white solid. MS ESI calculated for $C_{27}H_{28}F_4N_6O_2$ [M+H]$^+$, 545.22, found 545.35. $^1$H NMR (400 MHz, DMSO-$d_6$) δ 8.26 (s, 1H), 8.01-7.94 (m, 2H), 7.40 (d, J=8.0 Hz, 1H), 7.18 (d, J=11.6 Hz, 1H), 6.93 (s, 1H), 6.51 (s, 1H), 5.94 (s, 1H), 4.22 (s, 4H), 3.87 (s, 3H), 3.74-3.72 (m, 4H), 3.69-3.52 (m, 4H), 3.35-3.27 (m, 2H), 2.24 (s, 3H). $^{19}$F NMR (376 MHz, DMSO-$d_6$) δ -63.31 (3F), 124.72 (1F).

Example 78: (3S)—N-{3-[2-(1-ethylpyrazol-4-yl)-6-(morpholin-4-yl)pyridin-4-yl]-4-methylphenyl}-3-(2,2,2-trifluoroethyl)pyrrolidine-1-carboxamide
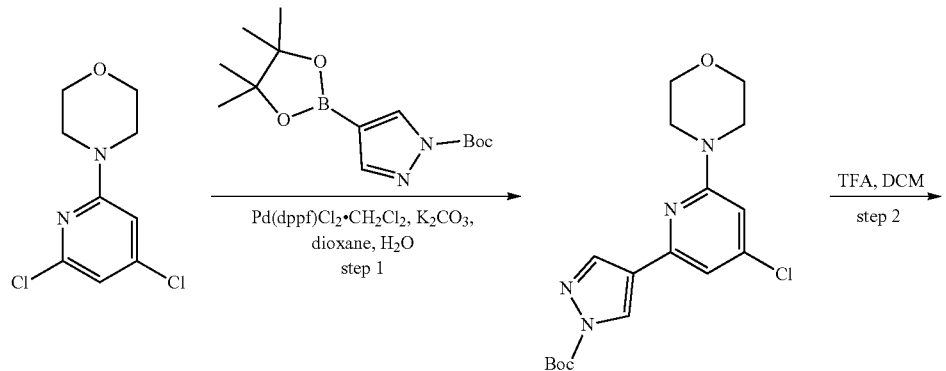
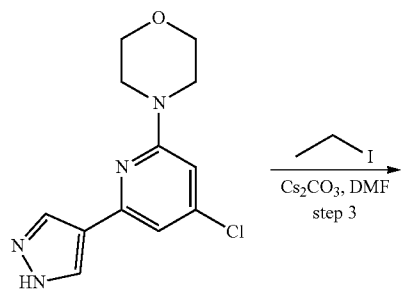
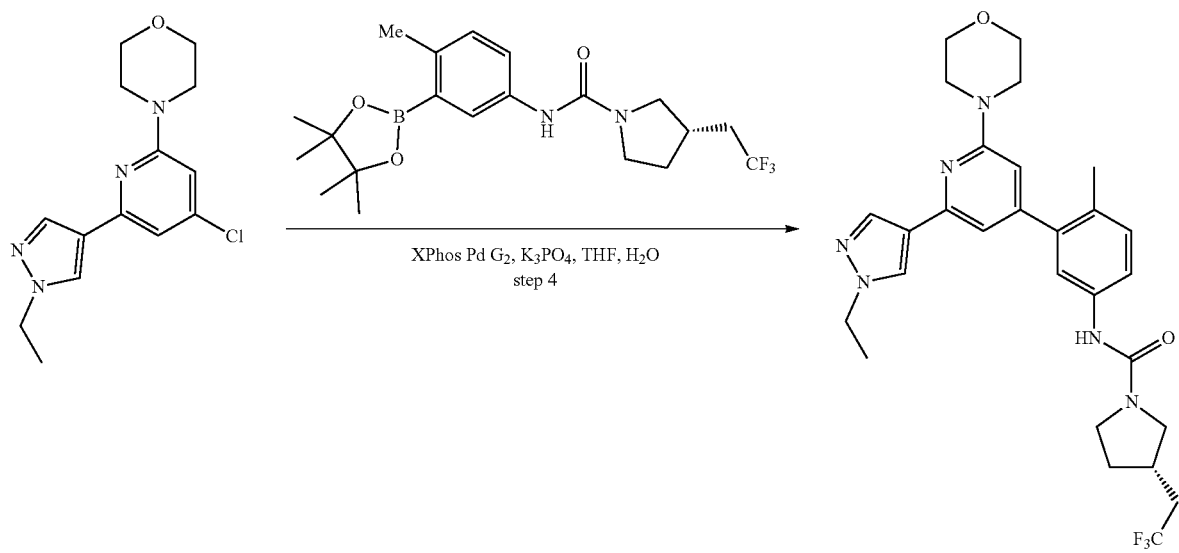

331

Preparation 78A. tert-butyl 4-[4-chloro-6-(morpholin-4-yl)pyridin-2-yl]pyrazole-1-carboxylate

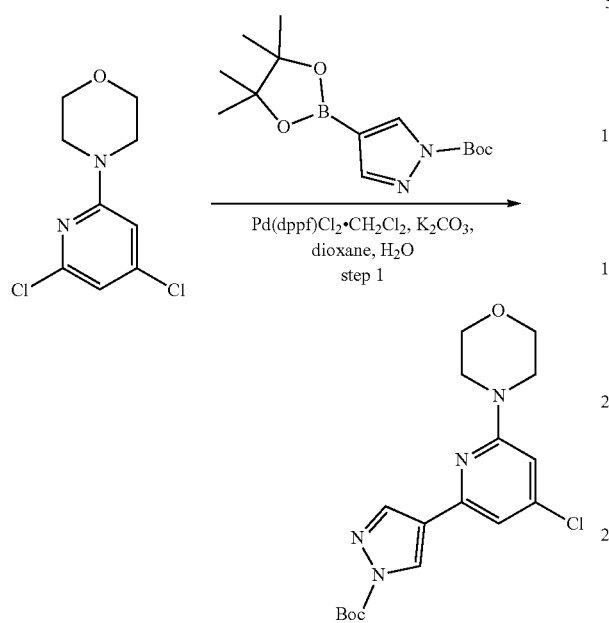

A mixture of tert-butyl 4-(4,4,5,5-tetramethyl-1,3,2-dioxaborolan-2-yl)pyrazole-1-carboxylate (1.51 g, 5.148 mmol), 4-(4,6-dichloropyridin-2-yl)morpholine (1 g, 4.290 mmol), 1,1'-bis(diphenylphosphino)ferrocene-palladium(II) dichloride dichloromethane complex (351 mg, 0.429 mmol) and potassium carbonate (1.78 g, 12.870 mmol) in dioxane (8 mL) and H$_2$O (2 mL) was stirred at 80° C. for 16 h under nitrogen atmosphere. The resulting mixture was diluted with water (20 mL) and extracted with EtOAc (20 mL). The combined organic layers were washed with brine (30 mL), dried over anhydrous Na$_2$SO$_4$. After filtration, the filtrate was concentrated under reduced pressure. The residue was purified by silica gel column chromatography, eluted with petroleum ether/EtOAc (1/1) to afford tert-butyl 4-[4-chloro-6-(morpholin-4-yl)pyridin-2-yl]pyrazole-1-carboxylate (818 mg, 52%) as a light yellow oil. MS ESI calculated for C$_{17}$H$_{21}$ClN$_4$O$_3$[M+H]$^+$, 365.13, found 365.20. $^1$H NMR (400 MHz, CDCl$_3$) δ 8.51 (s, 1H), 8.13 (s, 1H), 6.91 (s, 1H), 6.52 (s, 1H), 3.86-3.83 (m, 4H), 3.60-3.57 (m, 4H), 1.70 (s, 9H).

Preparation 78B: 4-[4-chloro-6-(1H-pyrazol-4-yl)pyridin-2-yl]morpholine

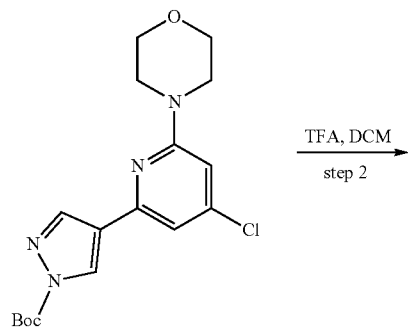

332

A mixture of tert-butyl 4-[4-chloro-6-(morpholin-4-yl)pyridin-2-yl]pyrazole-1-carboxylate (818 mg, 2.242 mmol) in DCM (5 mL) was added TFA (1 mL) was stirred at room temperature for 2 h. The mixture was basified to pH 8 with saturated NaHCO$_3$ (aq.). The resulting mixture was extracted with EtOAc (3×20 mL). The combined organic layers were washed with brine (3×20 mL), dried over anhydrous Na$_2$SO$_4$. After filtration, the filtrate was concentrated under reduced pressure. The residue was purified by silica gel column chromatography, eluted with petroleum ether/EtOAc/EtOH (4/3/1) to afford 4-[4-chloro-6-(1H-pyrazol-4-yl)pyridin-2-yl]morpholine (416 mg, 70%) as a white solid. MS ESI calculated for C12H$_{13}$ClN$_4$O [M+H]$^+$, 265.08, found 265.10.

Preparation 78C: 4-[4-chloro-6-(1-ethylpyrazol-4-yl)pyridin-2-yl]morpholine

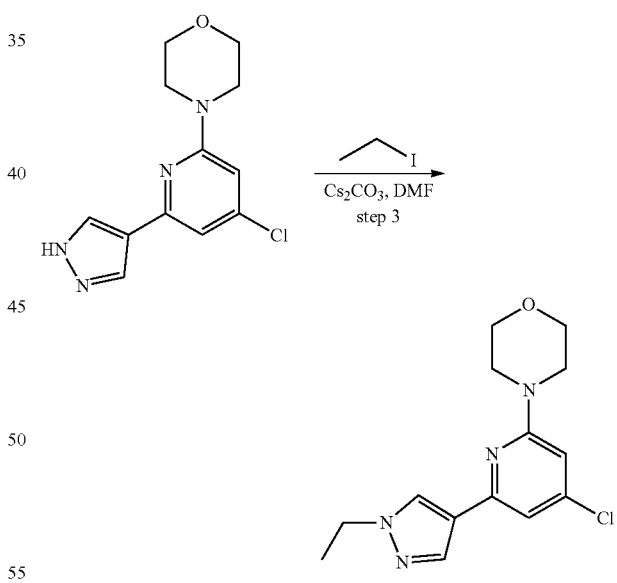

A mixture of 4-[4-chloro-6-(1H-pyrazol-4-yl)pyridin-2-yl]morpholine (1.60 g, 6.044 mmol), ethyl iodide (0.94 g, 6.044 mmol), Cs$_2$CO$_3$ (3.94 g, 12.088 mmol) and DMF (16 mL) was stirred for 16 h at 80° C. The reaction was quenched with water (100 mL) and extracted with EtOAc (3×50 mL). The combined organic layers were washed with brine (150 mL), dried over anhydrous Na$_2$SO$_4$. After filtration, the filtrate was concentrated under reduced pressure. The residue was purified by silica gel column chromatography, eluted with petroleum ether/EtOAc (1/1) to afford 4-[4-chloro-6-(1-ethylpyrazol-4-yl)pyridin-2-yl]morpholine (1.30 g, 73%) as a white solid. MS ESI calculated for $C_{14}H_{17}ClN_4O$ [M+H]$^+$, 293.11, found 293.05. $^1$H NMR (300 MHz, CDCl$_3$) δ 7.92-7.91 (m, 2H), 6.86 (d, J=1.2 Hz, 1H), 6.45 (d, J=1.5 Hz, 1H), 4.22 (q, J=7.2 Hz, 2H), 3.87-3.83 (m, 4H), 3.59-3.56 (m, 4H), 1.55 (t, J=7.2 Hz, 3H).

Example 78: (3S)—N-{3-[2-(1-ethylpyrazol-4-yl)-6-(morpholin-4-yl)pyridin-4-yl]-4-methylphenyl}-3-(2,2,2-trifluoroethyl)pyrrolidine-1-carboxamide

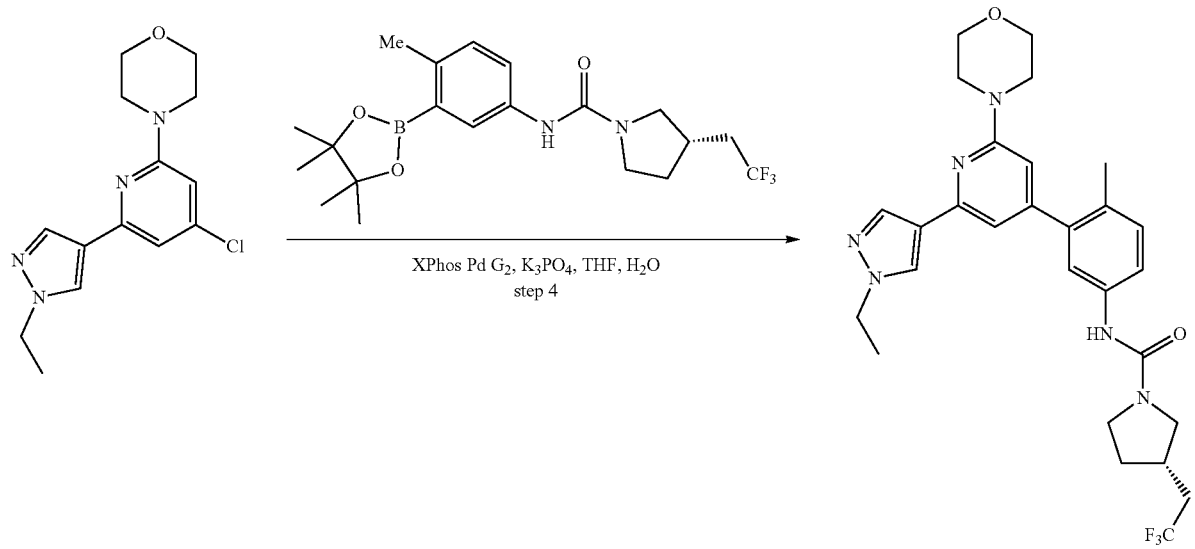 [SMILES: CCn1cc(-c2cc(Cl)cc(N3CCOCC3)n2)cn1 ; Cc1ccc(NC(=O)N2CC[C@@H](CC(F)(F)F)C2)cc1B1OC(C)(C)C(C)(C)O1 ; CCn1cc(-c2cc(-c3cc(NC(=O)N4CC[C@@H](CC(F)(F)F)C4)ccc3C)cc(N3CCOCC3)n2)cn1]

A mixture of 4-[4-chloro-6-(1-ethylpyrazol-4-yl)pyridin-2-yl]morpholine (72 mg, 0.246 mmol), (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (101 mg, 0.246 mmol), XPhos palladium(II) biphenyl-2-amine chloride (19 mg, 0.025 mmol) and potassium phosphate (104 mg, 0.492 mmol) in tetrahydrofuran (2.0 mL) and H$_2$O (0.2 mL) was stirred for 2 h at 80° C. under nitrogen atmosphere. The reaction was quenched with water (10 mL). The resulting mixture was extracted with EtOAc (2×10 mL). The combined organic layers were washed with brine (10 mL), dried over anhydrous Na$_2$SO$_4$. After filtration, the filtrate was concentrated under reduced pressure. The residue was purified by Prep-TLC (petroleum ether/EtOAc/EtOH=4/3/1) and reverse flash chromatography with the following conditions: column, C18 silica gel; mobile phase, CH$_3$CN in water (10 mM NH$_4$HCO$_3$), 35% to 70%; detector, UV 254 nm to afford (3S)—N-{3-[2-(1-ethylpyrazol-4-yl)-6-(morpholin-4-yl)pyridin-4-yl]-4-methylphenyl}-3-(2,2,2-trifluoroethyl)pyrrolidine-1-carboxamide (70 mg, 52%) as an off-white solid. MS ESI calculated for $C_{28}H_{33}F_3N_6O_2$[M+H]$^+$, 543.26 found 543.35; $^1$H NMR (400 MHz, DMSO-d$_6$) δ 8.29 (s, 1H), 8.17 (s, 1H), 7.98 (s, 1H), 7.49 (dd, J=8.4, 2.0 Hz, 1H), 7.40 (d, J=2.0 Hz, 1H), 7.15 (d, J=8.4 Hz, 1H), 6.93 (s, 1H), 6.49 (s, 1H), 4.16 (q, J=7.2 Hz, 2H), 3.74-3.65 (m, 5H), 3.55-3.51 (m, 5H), 3.32-3.28 (m, 1H), 3.05-3.00 (m, 1H), 2.47-2.38 (m, 3H), 2.19 (s, 3H), 2.13-2.05 (m, 1H), 1.70-1.61 (m, 1H), 1.40 (t, J=7.2 Hz, 3H). $^{19}$F NMR (376 MHz, DMSO-d$_6$) δ −63.37 (3F).

Example 79: N-{2-fluoro-4-methyl-5-[2-(1-methylpyrazol-4-yl)-6-(morpholin-4-yl)pyridin-4-yl]phenyl}-3-(1,1,2,2,2-pentafluoroethyl)-2,5-dihydropyrrole-1-carboxamide

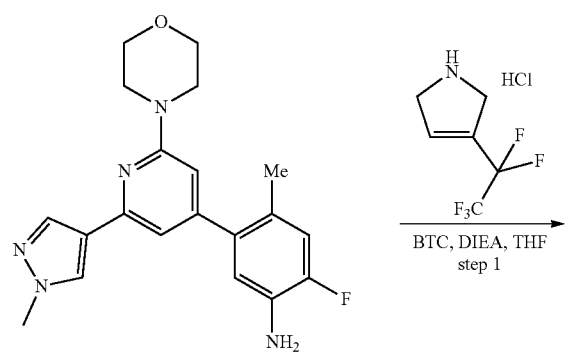

335

-continued

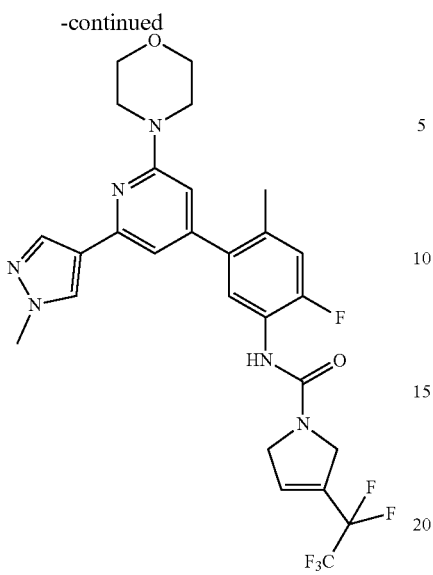

To a stirred solution of 2-fluoro-4-methyl-5-[2-(1-methylpyrazol-4-yl)-6-(morpholin-4-yl)pyridin-4-yl]aniline (100 mg, 0.272 mmol) and DIEA (176 mg, 1.360 mmol) in tetrahydrofuran (7 mL) was added triphosgene (32 mg, 0.109 mmol). The resulting mixture was stirred for 30 min at 0° C. under nitrogen atmosphere. To the above mixture was added 3-(1,1,2,2,2-pentafluoroethyl)-2,5-dihydro-1H-pyrrole hydrochloride (56 mg, 0.299 mmol) in portions at room temperature. The resulting mixture was stirred for additional 2 h at room temperature. The reaction was quenched by the addition of MeOH (3 mL) at 0° C. The mixture was purified by reverse flash chromatography with the following conditions: column, C18 silica gel; mobile phase, CH$_3$CN in water (10 mM NH$_4$HCO$_3$), 40% to 70%; detector, UV 254 nm to afford N-{2-fluoro-4-methyl-5-[2-(1-methylpyrazol-4-yl)-6-(morpholin-4-yl)pyridin-4-yl]phenyl}-3-(1,1,2,2,2-pentafluoroethyl)-2,5-dihydropyrrole-1-carboxamide (107 mg, 67%) as an off-white solid. MS ESI calculated for C27H26F6N6O2 [M+H]$^+$, 581.20 found 581.35. $^1$H NMR (400 MHz, DMSO-d$_6$) δ 8.25 (s, 1H), 8.22 (s, 1H), 7.97 (s, 1H), 7.37 (d, J=8.4 Hz, 1H), 7.20 (d, J=11.6 Hz, 1H), 6.92 (s, 1H), 6.81 (s, 1H), 6.50 (s, 1H), 4.42 (s, 4H), 3.87 (s, 3H), 3.74-3.71 (m, 4H), 3.55-3.53 (m, 4H), 2.25 (s, 3H). $^{19}$F NMR (376 MHz, DMSO-d$_6$) δ −83.54 (3F), −113.42 (2F), −124.35 (1F).

Example 80: (3R)—N-{2-fluoro-4-methyl-5-[2-(1-methylpyrazol-4-yl)-6-(morpholin-4-yl)pyridin-4-yl]phenyl}-3-(1,1,2,2,2-pentafluoroethyl)pyrrolidine-1-carboxamide Example 81: (3S)—N-{2-fluoro-4-methyl-5-[2-(1-methylpyrazol-4-yl)-6-(morpholin-4-yl)pyridin-4-yl]phenyl}-3-(1,1,2,2,2-pentafluoroethyl)pyrrolidine-1-carboxamide

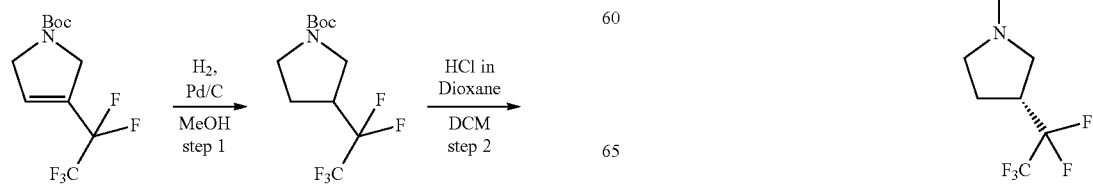

336

-continued

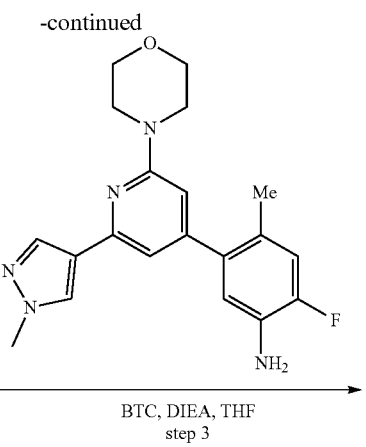

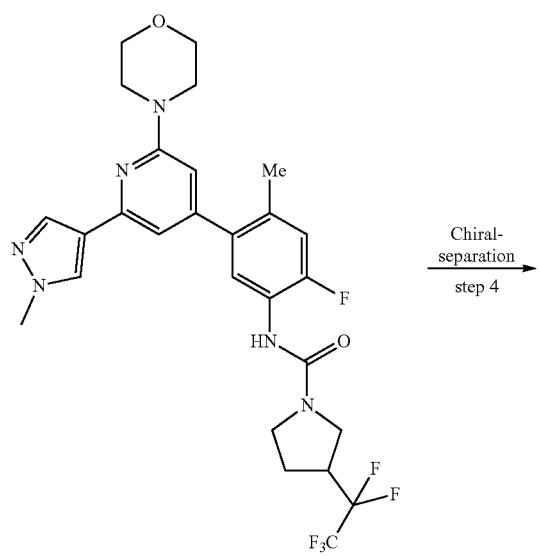

-continued

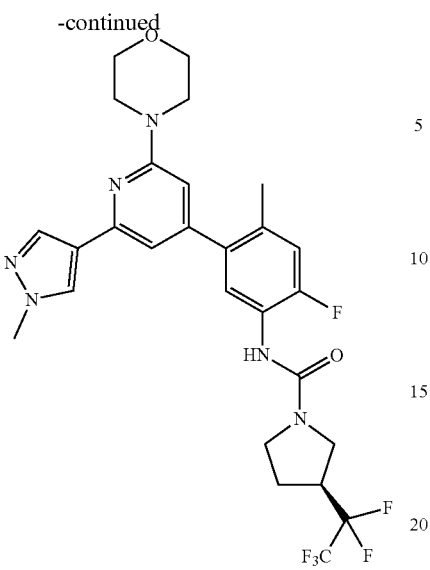

Preparation 80A: tert-butyl 3-(1,1,2,2,2-pentafluoroethyl)pyrrolidine-1-carboxylate

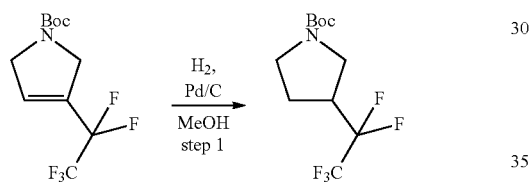

To a stirred mixture of tert-butyl 3-(1,1,2,2,2-pentafluoroethyl)-2,5-dihydropyrrole-1-carboxylate (220 mg, 0.761 mmol) in MeOH (2 mL) was added Pd/C (40 mg). The resulting mixture was stirred for 1 h at room temperature under hydrogen atmosphere. The resulting mixture was filtered, and the filter cake was washed with MeOH (5×5 mL). The filtrate was concentrated under reduced pressure to afford tert-butyl 3-(1,1,2,2,2-pentafluoroethyl)pyrrolidine-1-carboxylate (229 mg, crude) as colorless oil. MS ESI calculated for $C_{11}H_{16}F_5NO_2$ [M+H–$^t$Bu]$^+$, 234.11, found 234.10.

Preparation 80B: 3-(1,1,2,2,2-pentafluoroethyl)pyrrolidine hydrochloride

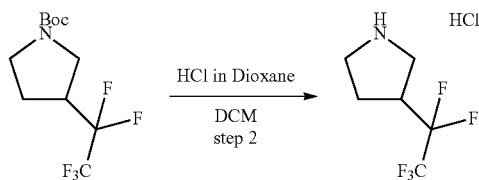

To a stirred mixture of tert-butyl 3-(1,1,2,2,2-pentafluoroethyl)pyrrolidine-1-carboxylate (229 mg, 1.0177 mmol) in DCM (2 mL) was added HCl (gas) in 1,4-dioxane (4 M, 2 mL) dropwise at 0° C. The resulting mixture was stirred for 1 h at room temperature. The resulting mixture was concentrated under reduced pressure to afford 3-(1,1,2,2,2-pentafluoroethyl)pyrrolidine hydrochloride (182 mg, crude) as colorless oil. MS ESI calculated for $C_6H_9ClF_5N$ [M–Cl]$^+$, 190.06, found 190.15.

Preparation 80C: N-{2-fluoro-4-methyl-5-[2-(1-methylpyrazol-4-yl)-6-(morpholin-4-yl)pyridin-4-yl]phenyl}-3-(1,1,2,2,2-pentafluoroethyl)pyrrolidine-1-carboxamide

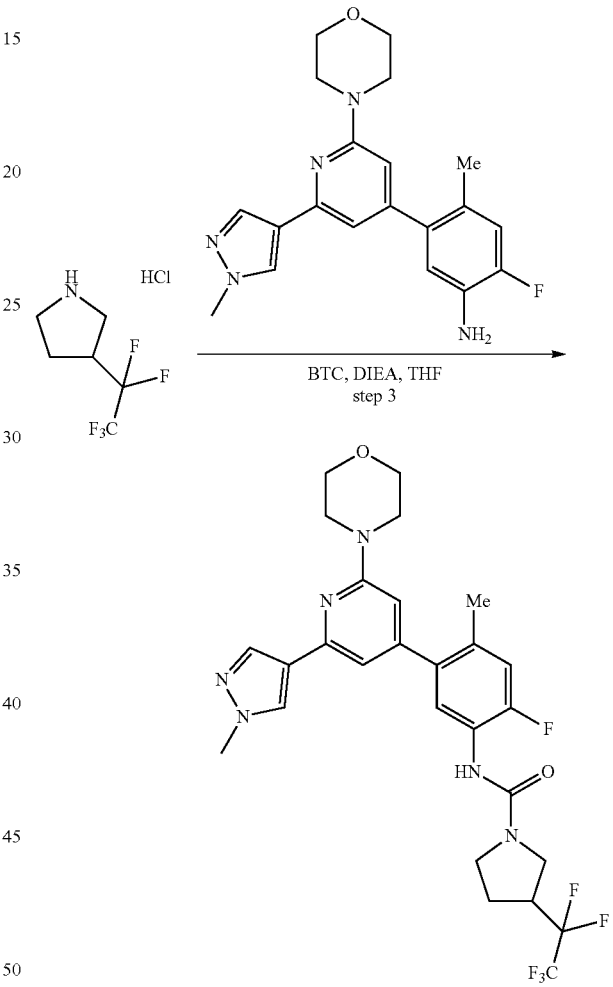

To a stirred mixture of 2-fluoro-4-methyl-5-[2-(1-methylpyrazol-4-yl)-6-(morpholin-4-yl)pyridin-4-yl]aniline (280 mg, 0.762 mmol) in tetrahydrofuran (8 mL) were added DIEA (492 mg, 3.810 mmol), triphosgene (90 mg, 0.305 mmol) in tetrahydrofuran (5 mL) at room temperature under nitrogen atmosphere. The resulting mixture was stirred for 30 min at room temperature under nitrogen atmosphere. To the above mixture was added 3-(1,1,2,2,2-pentafluoroethyl) pyrrolidine hydrochloride (171 mg, 0.762 mmol) in tetrahydrofuran (5 mL) at room temperature. The resulting mixture was stirred for additional 1 h at room temperature. The resulting mixture was concentrated under reduced pressure. The residue was purified by silica gel column chromatography, eluted with petroleum ether/EtOAc/EtOH (4/3/1) and reverse flash chromatography with the following conditions: column, silica gel; mobile phase, CH₃CN in water (10 mM NH₄HCO₃), 30% to 60%; detector, UV 254 nm to afford N-{2-fluoro-4-methyl-5-[2-(1-methylpyrazol-4-yl)-6-(morpholin-4-yl)pyridin-4-yl]phenyl}-3-(1,1,2,2,2-pentafluoroethyl)pyrrolidine-1-carboxamide (338 mg, 76%) as a white solid. MS ESI calculated for $C_{27}H_{28}F_6N_6O_2$ [M+H]⁺, 583.22, found 583.45.

Example 80: (3R)—N-{2-fluoro-4-methyl-5-[2-(1-methylpyrazol-4-yl)-6-(morpholin-4-yl)pyridin-4-yl]phenyl}-3-(1,1,2,2,2-pentafluoroethyl)pyrrolidine-1-carboxamide Example 81: (3S)—N-{2-fluoro-4-methyl-5-[2-(1-methylpyrazol-4-yl)-6-(morpholin-4-yl)pyridin-4-yl]phenyl}-3-(1,1,2,2,2-pentafluoroethyl)pyrrolidine-1-carboxamide

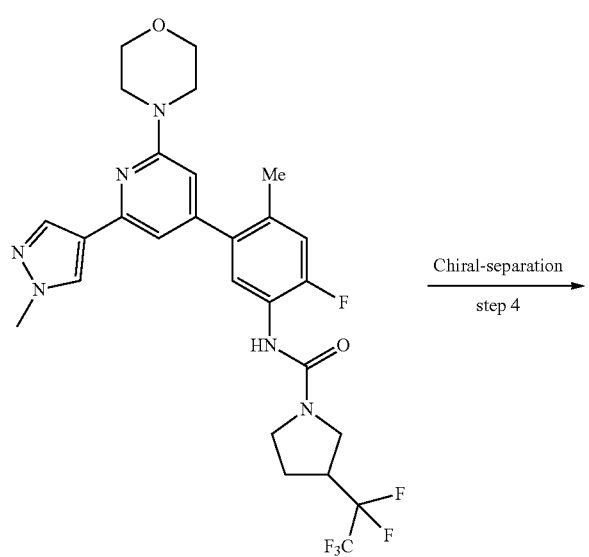

Chiral-separation
step 4

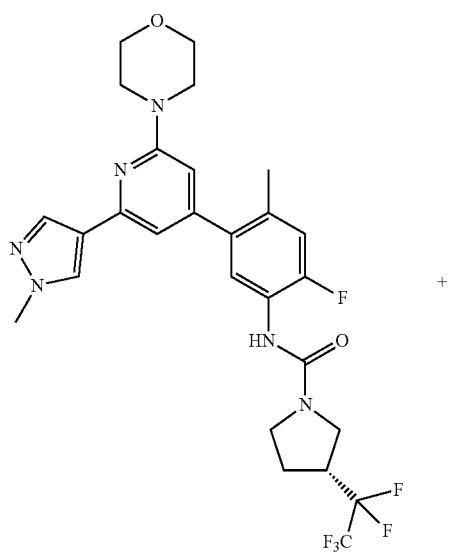

+

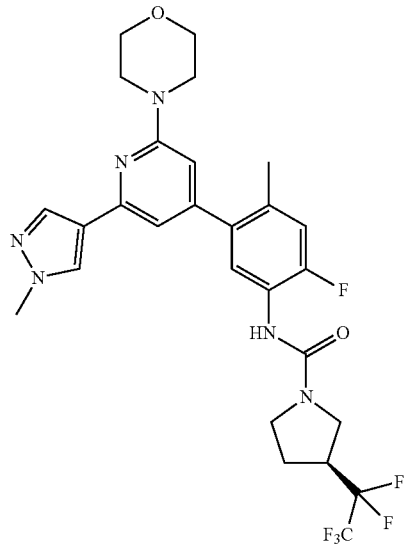

The N-{2-fluoro-4-methyl-5-[2-(1-methylpyrazol-4-yl)-6-(morpholin-4-yl)pyridin-4-yl]phenyl}-3-(1,1,2,2,2-pentafluoroethyl)pyrrolidine-1-carboxamide (320 mg, 0.549 mmol) was resolved by Prep-Chiral-HPLC with the following conditions (Column: (R, R)-WHELK-01-Kromasil, 2.11×25 cm, 5 μm; Mobile Phase A: Hexane:DCM=3:1, Mobile Phase B: EtOH; Flow rate: 20 mL/min; Gradient: 20% B; Wave Length: 220/254 nm; RT₁: 23.67 min to afford (3R)—N-{2-fluoro-4-methyl-5-[2-(1-methylpyrazol-4-yl)-6-(morpholin-4-yl)pyridin-4-yl]phenyl}-3-(1,1,2,2,2-pentafluoroethyl)pyrrolidine-1-carboxamide (120.1 mg, 75%) as a white solid. $C_{27}H_{28}F_6N_6O_2$[M+H]⁺, 583.22, found 583.25. ¹H NMR (400 MHz, DMSO-d₆) 8.25 (s, 1H), 8.13 (s, 1H), 7.97 (s, 1H), 7.34 (d, J=8.4 Hz, 1H), 7.18 (d, J=11.6 Hz, 1H), 6.91 (s, 1H), 6.49 (s, 1H), 3.86 (s, 3H), 3.75-3.66 (m, 5H), 3.64-3.62 (m, 1H), 3.55-3.52 (m, 4H), 3.44-3.40 (m, 2H), 3.38-3.34 (m, 1H), 2.24 (s, 3H), 2.21-2.15 (m, 1H), 2.06-1.96 (1H). ¹⁹F NMR (376 MHz, DMSO-d₆) δ −83.23 (3F), −120.83-121.17 (2F), 124.33 (1F).

And RT₂: 28.74 min to afford (3S)—N-{2-fluoro-4-methyl-5-[2-(1-methylpyrazol-4-yl)-6-(morpholin-4-yl)pyridin-4-yl]phenyl}-3-(1,1,2,2,2-pentafluoroethyl)pyrrolidine-1-carboxamide (112.0 mg, 70%) as a white solid. $C_{27}H_{28}F_6N_6O_2$ [M+H]⁺, 583.22, found 583.25. ¹H NMR (400 MHz, DMSO-d₆) 8.25 (s, 1H), 8.13 (s, 1H), 7.97 (s, 1H), 7.34 (d, J=8.0 Hz, 1H), 7.18 (d, J=11.6 Hz, 1H), 6.91 (s, 1H), 6.45 (s, 1H), 3.86 (s, 3H), 3.75-3.66 (m, 5H), 3.64-3.62 (m, 1H), 3.59-3.52 (m, 4H), 3.48-3.40 (m, 2H), 3.38-3.34 (m, 1H), 2.24 (s, 3H), 2.21-2.15 (m, 1H), 2.06-1.96 (1H). ¹⁹F NMR (376 MHz, DMSO-d₆) δ −83.24 (3F), 120.09-121.86 (2F), 124.32 (1F).

Example 82: (3S)-3-tert-butyl-N-{2-fluoro-4-methyl-5-[2-(1-methylpyrazol-4-yl)-6-(morpholin-4-yl)pyridin-4-yl]phenyl}pyrrolidine-1-carboxamide

Example 83: (3R)-3-tert-butyl-N-{2-fluoro-4-methyl-5-[2-(1-methylpyrazol-4-yl)-6-(morpholin-4-yl)pyridin-4-yl]phenyl}pyrrolidine-1-carboxamide

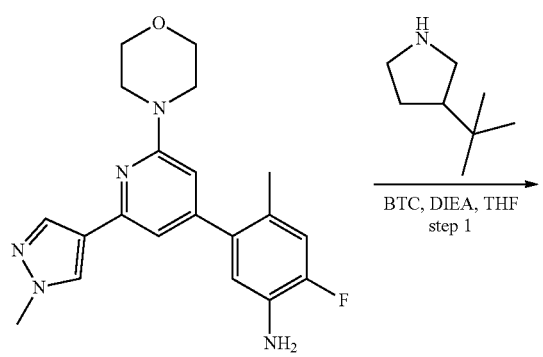

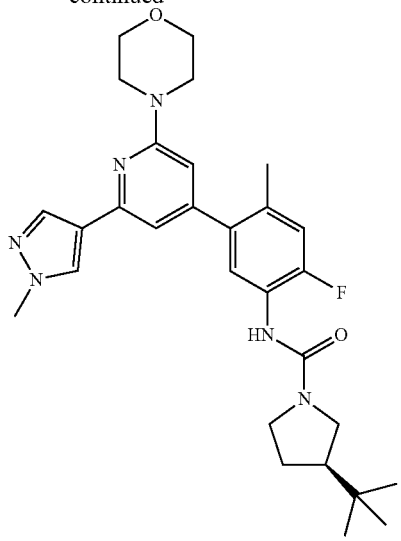

-continued

Preparation 82A: 3-tert-butyl-N-{2-fluoro-4-methyl-5-[2-(1-methylpyrazol-4-yl)-6-(morpholin-4-yl)pyridin-4-yl]phenyl}pyrrolidine-1-carboxamide

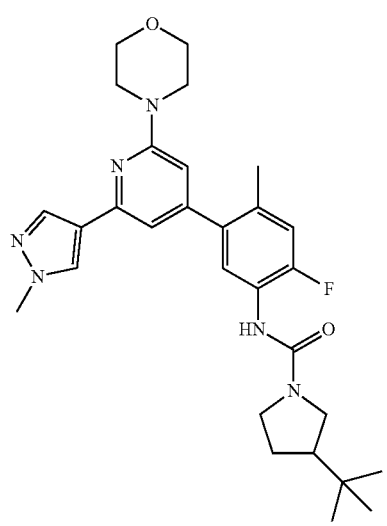 [SMILES: Cc1cc(F)c(NC(=O)N2CC[C@H](C(C)(C)C)C2)cc1-c1cc(-c2cnn(C)c2)nc(N2CCOCC2)c1]

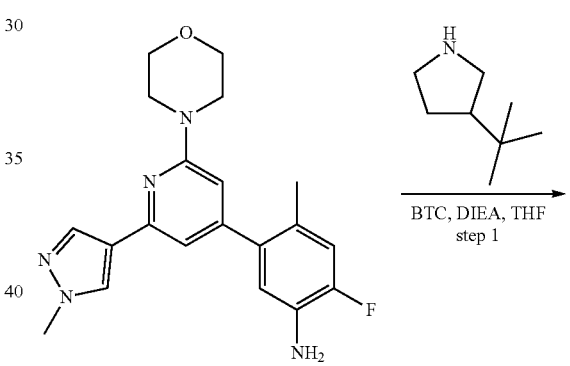

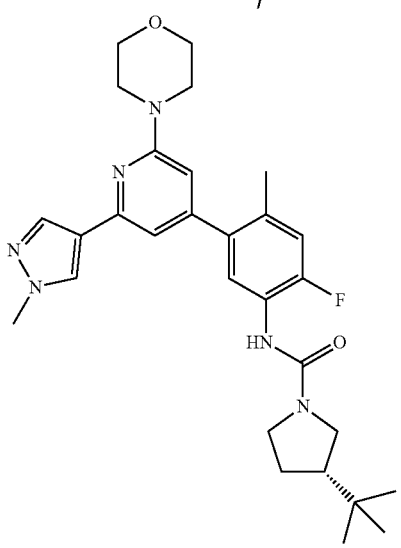

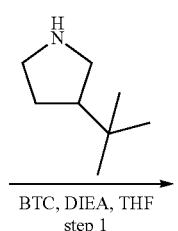

To a stirred mixture of 2-fluoro-4-methyl-5-[2-(1-methylpyrazol-4-yl)-6-(morpholin-4-yl)pyridin-4-yl]aniline (200 mg, 0.544 mmol) and DIEA (352 mg, 2.720 mmol) in tetrahydrofuran (5 mL) was added triphosgene (65 mg, 0.218 mmol). The reaction mixture was stirred for 1 h at room temperature under nitrogen atmosphere. To this was added 3-tert-butylpyrrolidine (76 mg, 0.598 mmol) in tetrahydrofuran (1 mL). The reaction mixture was stirred for 2 h at room temperature under nitrogen atmosphere. The reaction was quenched by the addition of MeOH (2 mL) at 0° C. The resulting mixture was concentrated under reduced pressure. The residue was purified by silica gel column chromatography, eluted with petroleum ether/EtOAc (1/3) to afford 3-tert-butyl-N-{2-fluoro-4-methyl-5-[2-(1-methylpyrazol-4-yl)-6-(morpholin-4-yl)pyridin-4-yl]phenyl}pyrrolidine-1-carboxamide (260 mg, 91%) as a light yellow solid. MS ESI calculated for $C_{29}H_{37}FN_6O_2$ [M+H]$^+$, 520.30; found 521.40.

Example 82: (3S)-3-tert-butyl-N-{2-fluoro-4-methyl-5-[2-(1-methylpyrazol-4-yl)-6-(morpholin-4-yl)pyridin-4-yl]phenyl}pyrrolidine-1-carboxamide Example 83: (3R)-3-tert-butyl-N-{2-fluoro-4-methyl-5-[2-(1-methylpyrazol-4-yl)-6-(morpholin-4-yl)pyridin-4-yl]phenyl}pyrrolidine-1-carboxamide

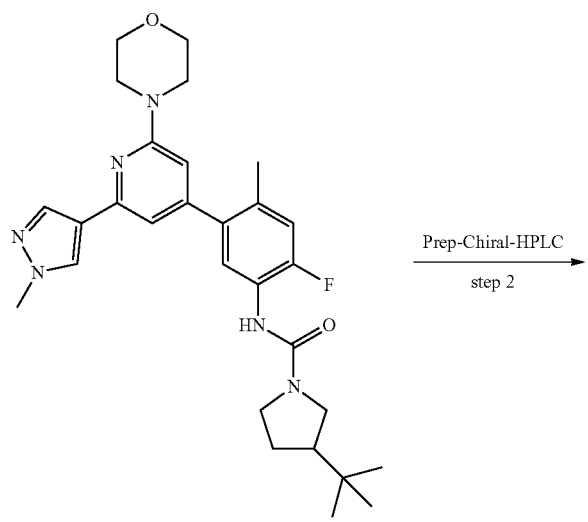

Prep-Chiral-HPLC
step 2

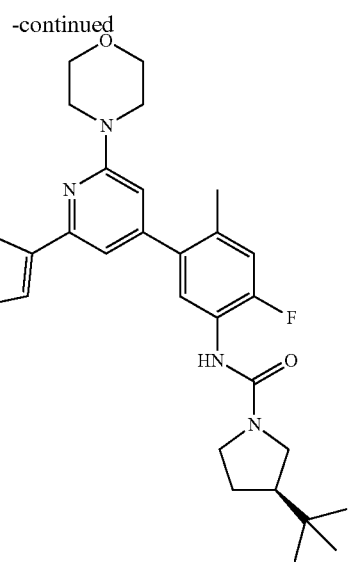

3-tert-butyl-N-{2-fluoro-4-methyl-5-[2-(1-methylpyrazol-4-yl)-6-(morpholin-4-yl)pyridin-4-yl]phenyl}pyrrolidine-1-carboxamide (250 mg, 0.480 mmol) was resolved with Chiral-HPLC (Column: CHIRAL ART Amylose-SA, 2×25 cm, 5 μm; Mobile Phase A: Hexane, Mobile Phase B: MeOH:DCM=1:1; Flow rate: 20 mL/min; Gradient: 15% B; Wave Length: 220/254 nm; RT$_1$: 22.88 min to afford (3R)-3-tert-butyl-N-{2-fluoro-4-methyl-5-[2-(1-methylpyrazol-4-yl)-6-(morpholin-4-yl)pyridin-4-yl]phenyl}pyrrolidine-1-carboxamide (50.9 mg, 20%) as off-white solid; MS ESI calculated for $C_{29}H_{37}FN_6O_2$ [M+H]$^+$, 520.30; found 521.40. $^1$H NMR (400 MHz, CDCl$_3$) δ 8.13 (d, J=8.0 Hz, 1H), 7.91 (s, 1H), 7.00 (d, J=12.0 Hz, 1H), 6.85 (s, 1H), 6.44 (s, 1H), 6.36 (d, J=3.2 Hz, 1H), 3.97 (s, 3H), 3.92-3.88 (m, 4H), 3.72-3.53 (m, 6H), 3.42-3.38 (m, 1H), 3.20-3.14 (m, 1H), 2.25 (s, 3H), 2.16-2.11 (m, 1H), 1.99-1.96 (m, 1H), 1.79-1.76 (m, 1H), 0.98 (s, 9H). $^{19}$F NMR (376 MHz, CDCl$_3$) δ −134.48 (1F).

And RT$_2$: 26.72 min to afford (3S)-3-tert-butyl-N-{2-fluoro-4-methyl-5-[2-(1-methylpyrazol-4-yl)-6-(morpholin-4-yl)pyridin-4-yl]phenyl}pyrrolidine-1-carboxamide (55.2 mg, 22%) as off-white solid; MS ESI calculated for $C_{29}H_{37}FN_6O_2$ [M+H]$^+$, 520.30; found 521.40. $^1$H NMR (400 MHz, CDCl$_3$) δ 8.13 (d, J=8.4 Hz, 1H), 7.91 (s, 1H), 7.01 (d, J=12.0 Hz, 1H), 6.85 (s, 1H), 6.44 (s, 1H), 6.36 (d, J=3.2 Hz, 1H), 3.97 (s, 3H), 3.92-3.88 (m, 4H), 3.72-3.53 (m, 6H), 3.44-3.37 (m, 1H), 3.20-3.14 (m, 1H), 2.25 (s, 3H), 2.17-2.12 (m, 1H), 1.99-1.96 (m, 1H), 1.79-1.76 (m, 1H), 0.98 (s, 9H). $^{19}$F NMR (376 MHz, CDCl$_3$) δ −134.52 (1F).

Example 84: (3R)-3-(1,1-difluoroethyl)-N-{2-fluoro-4-methyl-5-[2-(1-methylpyrazol-4-yl)-6-(morpholin-4-yl)pyridin-4-yl]phenyl}pyrrolidine-1-carboxamide

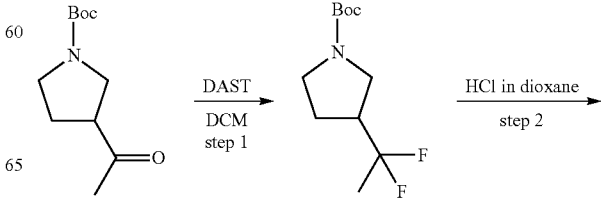

345
-continued

346
-continued

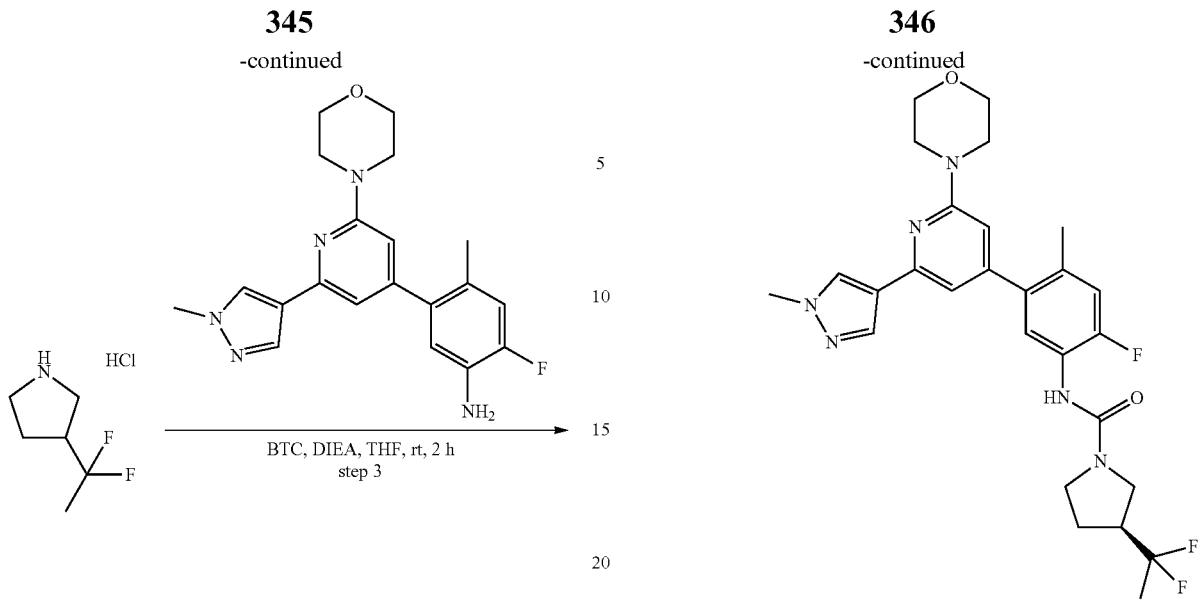

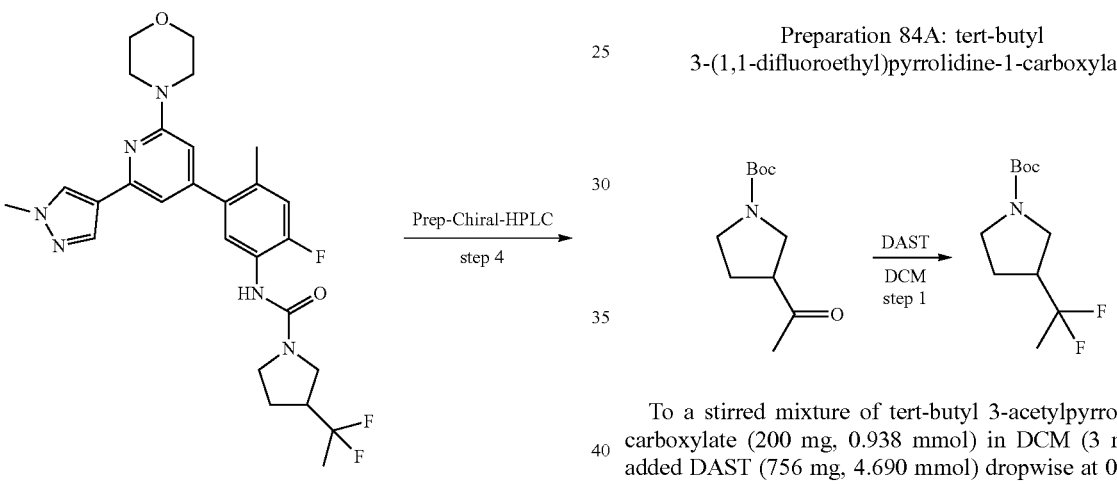

Preparation 84A: tert-butyl 3-(1,1-difluoroethyl)pyrrolidine-1-carboxylate

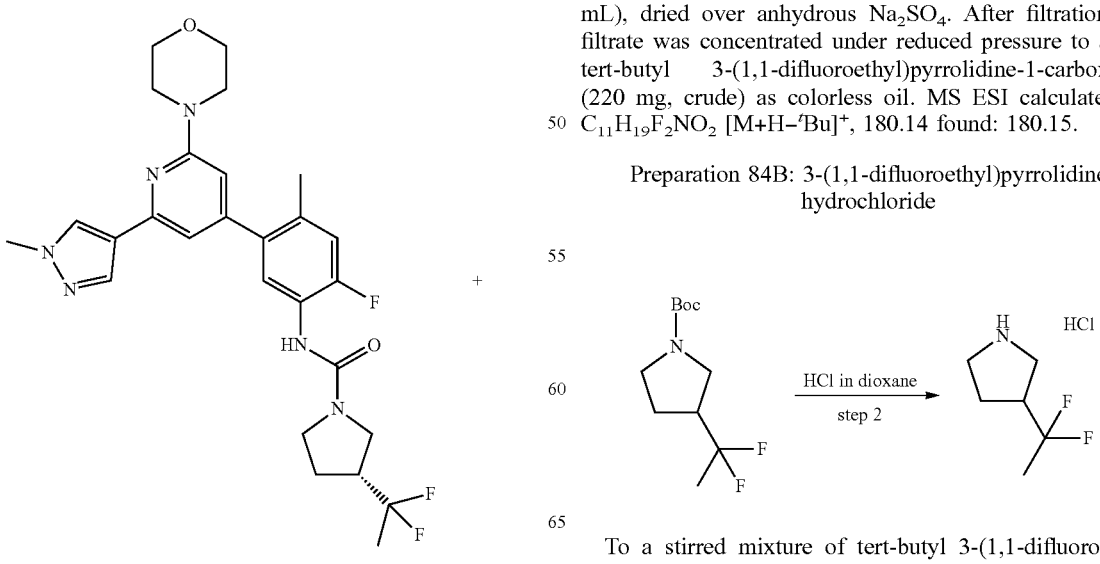

To a stirred mixture of tert-butyl 3-acetylpyrrolidine-1-carboxylate (200 mg, 0.938 mmol) in DCM (3 mL) was added DAST (756 mg, 4.690 mmol) dropwise at 0° C. The reaction mixture was stirred for 12 h at 60° C. The reaction was quenched by the addition of NaHCO$_3$ (5 mL) at 0° C. The resulting mixture was extracted with EtOAc (3×5 mL). The combined organic layers were washed with brine (3×10 mL), dried over anhydrous Na$_2$SO$_4$. After filtration, the filtrate was concentrated under reduced pressure to afford tert-butyl 3-(1,1-difluoroethyl)pyrrolidine-1-carboxylate (220 mg, crude) as colorless oil. MS ESI calculated for C$_{11}$H$_{19}$F$_2$NO$_2$ [M+H−$^t$Bu]$^+$, 180.14 found: 180.15.

Preparation 84B: 3-(1,1-difluoroethyl)pyrrolidine hydrochloride

To a stirred mixture of tert-butyl 3-(1,1-difluoroethyl) pyrrolidine-1-carboxylate (220 mg, 0.935 mmol) in dioxane (2 mL) was added HCl (gas) in 1,4-dioxane (2 mL, 4 M). The reaction mixture was stirred for 1 h at room temperature. The resulting mixture was concentrated under reduced pressure to afford 3-(1,1-difluoroethyl)pyrrolidine hydrochloride (220 mg, crude) as colorless oil. MS ESI calculated for $C_6H_{12}ClF_2N$ [M−Cl]$^+$, 135.09, found: 136.15.

Preparation 84C: 3-(1,1-difluoroethyl)-N-{2-fluoro-4-methyl-5-[2-(1-methylpyrazol-4-yl)-6-(morpholin-4-yl)pyridin-4-yl]phenyl}pyrrolidine-1-carboxamide 1 h at room temperature under nitrogen atmosphere. The reaction was quenched by the addition of MeOH (2 mL) at 0° C. and concentrated under reduced pressure. The residue was purified by silica gel column chromatography, eluted with petroleum ether/EtOAc (1/3) to afford 3-(1,1-difluoroethyl)-N-{2-fluoro-4-methyl-5-[2-(1-methylpyrazol-4-yl)-6-(morpholin-4-yl)pyridin-4-yl]phenyl}pyrrolidine-1-carboxamide (200 mg, 51%) as a light yellow solid. MS ESI calculated for $C_{27}H_{31}F_3N_6O_2$ [M+H]$^+$, 529.25; found: 529.35.

Example 84: (3R)-3-(1,1-difluoroethyl)-N-{2-fluoro-4-methyl-5-[2-(1-methylpyrazol-4-yl)-6-(morpholin-4-yl)pyridin-4-yl]phenyl}pyrrolidine-1-carboxamide

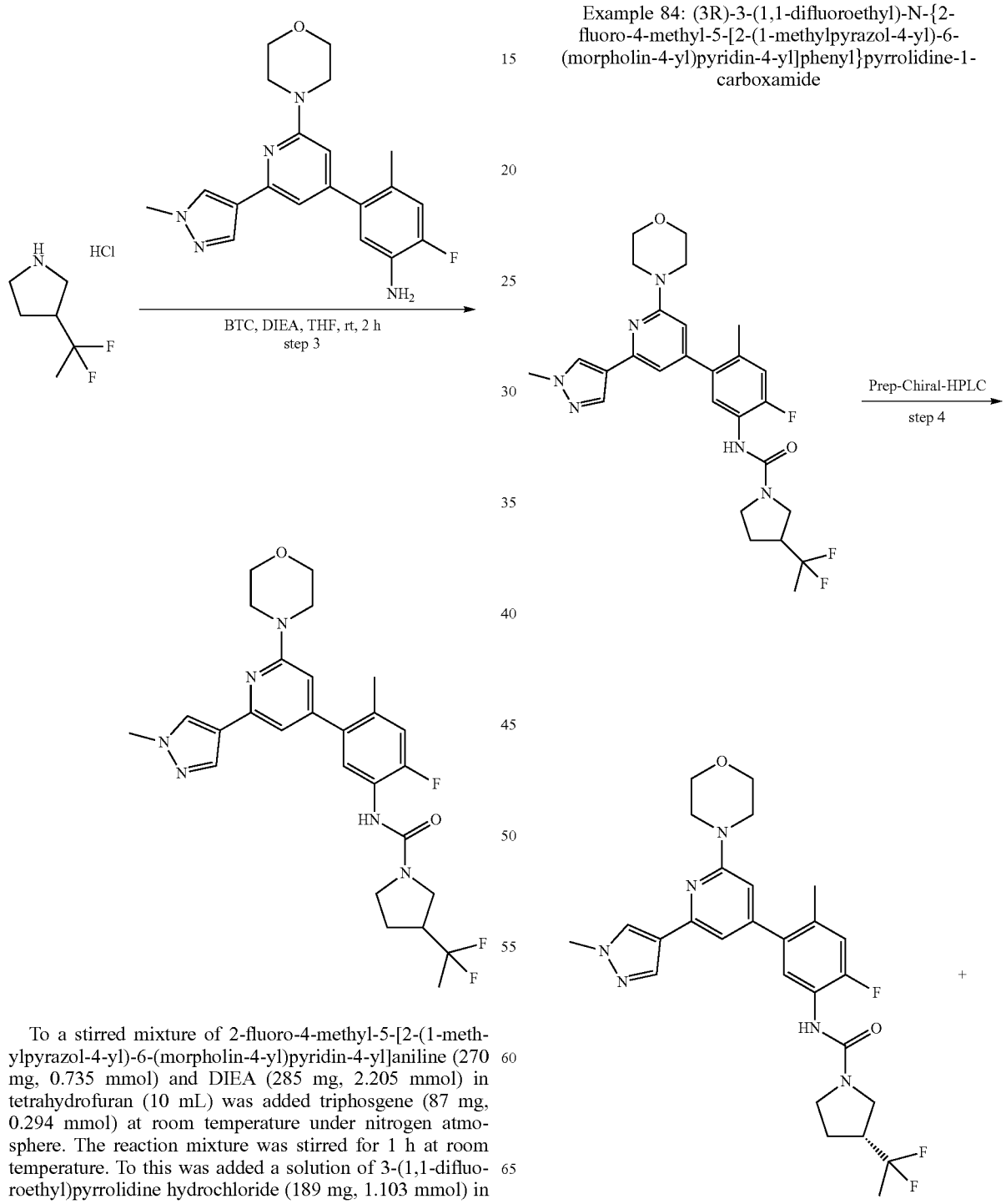

To a stirred mixture of 2-fluoro-4-methyl-5-[2-(1-methylpyrazol-4-yl)-6-(morpholin-4-yl)pyridin-4-yl]aniline (270 mg, 0.735 mmol) and DIEA (285 mg, 2.205 mmol) in tetrahydrofuran (10 mL) was added triphosgene (87 mg, 0.294 mmol) at room temperature under nitrogen atmosphere. The reaction mixture was stirred for 1 h at room temperature. To this was added a solution of 3-(1,1-difluoroethyl)pyrrolidine hydrochloride (189 mg, 1.103 mmol) in tetrahydrofuran (1 mL). The reaction mixture was stirred for

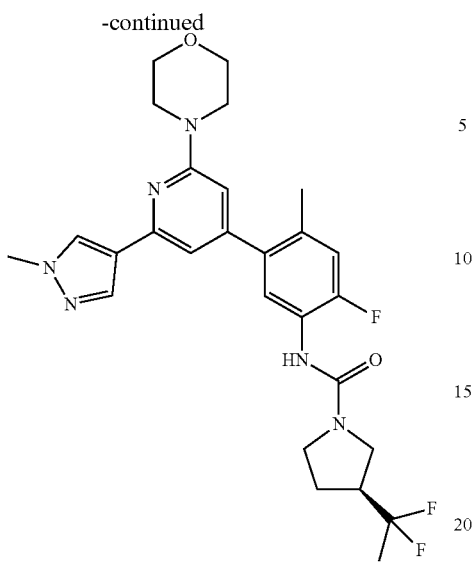

3-(1,1-difluoroethyl)-N-{2-fluoro-4-methyl-5-[2-(1-methylpyrazol-4-yl)-6-(morpholin-4-yl)pyridin-4-yl]phenyl}pyrrolidine-1-carboxamide (200 mg, 0.378 mmol) was resolved with chiral-HPLC (Column: CHIRALPAK IH, 2×25 cm, 5 μm; Mobile Phase A: MTBE, Mobile Phase B: MeOH; Flow rate: 20 mL/min; Gradient: 10% B; Wave Length: 220/254 nm; $RT_1$: 11.30 min to afford (3R)-3-(1,1-difluoroethyl)-N-{2-fluoro-4-methyl-5-[2-(1-methylpyrazol-4-yl)-6-(morpholin-4-yl)pyridin-4-yl]phenyl}pyrrolidine-1-carboxamide (70.6 mg, 34%) as off-white solid. MS ESI calculated for $C_{27}H_{31}F_3N_6O_2$ [M+H]$^+$, 529.25; found: 529.25. $^1$H NMR (400 MHz, $CDCl_3$) δ 8.08 (d, J=8.4 Hz, 1H), 7.92 (s, 1H), 7.01 (d, J=12.0 Hz, 1H), 6.83 (s, 1H), 6.42 (s, 1H), 6.36 (d, J=3.2 Hz, 1H), 3.97 (s, 3H), 3.90-3.88 (m, 4H), 3.75-3.68 (m, 2H), 3.64-3.60 (m, 4H), 3.55-3.48 (m, 2H), 2.81-2.75 (m, 1H), 2.25 (s, 3H), 2.23-2.09 (m, 2H), 1.68 (t, J=18.4 Hz, 3H). $^{19}$F NMR (376 MHz, $CDCl_3$) δ −95.93-97.99 (2F), −134.35 (1F).

And $RT_2$: 15.73 min to afford (3S)-3-(1,1-difluoroethyl)-N-{2-fluoro-4-methyl-5-[2-(1-methylpyrazol-4-yl)-6-(morpholin-4-yl)pyridin-4-yl]phenyl}pyrrolidine-1-carboxamide (77.8 mg, 37%) as off-white solid. MS ESI calculated for $C_{27}H_{31}F_3N_6O_2$ [M+H]$^+$, 529.25; found: 529.30. $^1$H NMR (400 MHz, $CDCl_3$) δ 8.08 (d, J=8.4 Hz, 1H), 7.92 (s, 1H), 7.01 (d, J=12.0 Hz, 1H), 6.83 (s, 1H), 6.42 (s, 1H), 6.36 (d, J=3.2 Hz, 1H), 3.97 (s, 3H), 3.90-3.88 (m, 4H), 3.75-3.68 (m, 2H), 3.64-3.60 (m, 4H), 3.55-3.48 (m, 2H), 2.81-2.75 (m, 1H), 2.25 (s, 3H), 2.23-2.09 (m, 2H), 1.68 (t, J=18.4 Hz, 3H). $^{19}$F NMR (376 MHz, $CDCl_3$) δ −95.92-97.40 (2F), −134.14 (1F).

Example 85: N-{2-fluoro-4-methyl-5-[2-(1-methylpyrazol-4-yl)-6-(morpholin-4-yl)pyridin-4-yl]phenyl}-3-(2-fluoropropan-2-yl)pyrrolidine-1-carboxamide

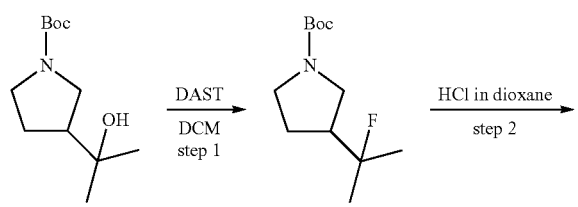

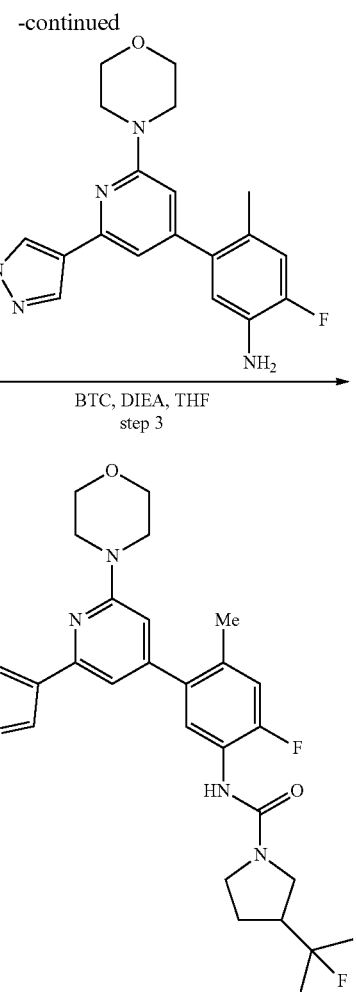

Preparation 85A: Mixture of tert-butyl 3-(2-fluoropropan-2-yl)pyrrolidine-1-carboxylate and tert-butyl 3-(propan-2-ylidene)pyrrolidine-1-carboxylate and tert-butyl 3-(prop-1-en-2-yl)pyrrolidine-1-carboxylate

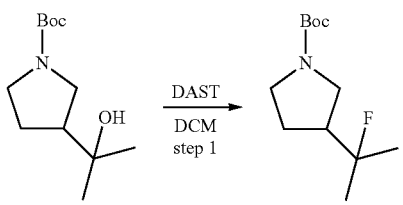

To a stirred solution of tert-butyl 3-(2-hydroxypropan-2-yl)pyrrolidine-1-carboxylate (1.00 g, 4.361 mmol) in DCM (10 mL) was added DAST (0.91 g, 5.669 mmol) dropwise at 0° C. under nitrogen atmosphere. The resulting mixture was stirred for 3 h at room temperature under nitrogen atmosphere. The resulting mixture was concentrated under reduced pressure and quenched with water (100 mL). The resulting mixture was extracted with EtOAc (3×60 mL). The combined organic layers were washed with saturated brine (50 mL), dried over anhydrous $Na_2SO_4$. After filtration, the filtrate was concentrated under reduced pressure. The residue was purified by silica gel column chromatography, eluted with petroleum ether/EtOAc (4/1) to afford tert-butyl 3-(2-fluoropropan-2-yl)pyrrolidine-1-carboxylate (50 mg, crude) as a colorless solid. MS ESI calculated for $C_{12}H_{22}FNO_2$ [M+H–$^tBu$]$^+$, 176.10, found 176.00. $^1H$ NMR (400 MHz, CDCl$_3$) δ 3.56-3.51 (m, 4H), 3.31-3.18 (m, 2H), 1.98-1.88 (m, 1H), 1.48 (s, 9H), 1.41 (d, J=2.4 Hz, 3H), 1.35 (d, J=2.4 Hz, 3H). $^{19}F$ NMR (376 MHz, CDCl$_3$) δ −148.35 (1F).

Preparation 85B: 3-(2-fluoropropan-2-yl)pyrrolidine Hydrochloride

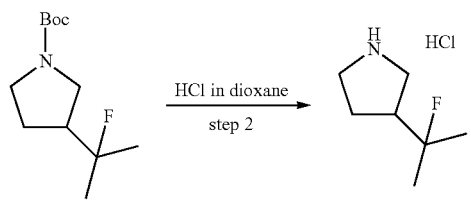

To a stirred solution of mixture of tert-butyl 3-(2-fluoropropan-2-yl)pyrrolidine-1-carboxylate (700 mg, 3.026 mmol) in dioxane (10 mL) was added HCl (gas) in 1,4-dioxane (10 mL) dropwise at 0° C. The resulting mixture was stirred for 3 h at room temperature. The resulting mixture was concentrated under reduced pressure to afford 3-(2-fluoropropan-2-yl)pyrrolidine hydrochloride (550 mg, crude) as light brown oil. The crude product was used in the next step directly without further purification. MS ESI calculated for $C_7H_{15}ClFN$ [M–Cl]$^+$, 132.11, found 132.05.

Example 85: N-{2-fluoro-4-methyl-5-[2-(1-methylpyrazol-4-yl)-6-(morpholin-4-yl)pyridin-4-yl]phenyl}-3-(2-fluoropropan-2-yl)pyrrolidine-1-carboxamide

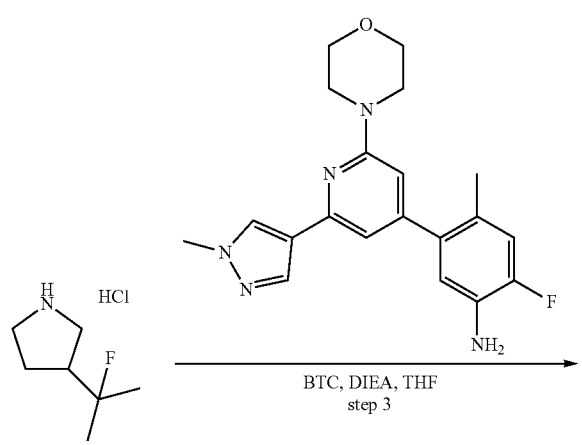

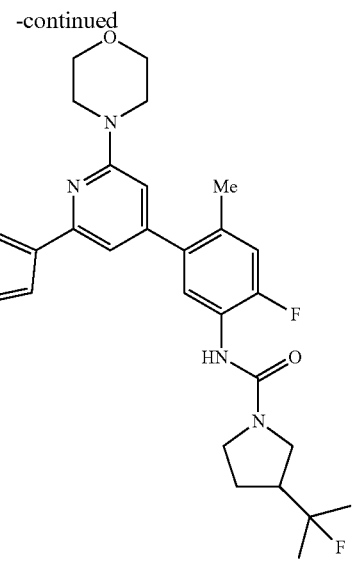

To a stirred solution of 2-fluoro-4-methyl-5-[2-(1-methylpyrazol-4-yl)-6-(morpholin-4-yl)pyridin-4-yl]aniline (0.40 g, 1.089 mmol) and DIEA (1.41 g, 10.890 mmol) in tetrahydrofuran (26 mL) was added triphosgene (0.13 g, 0.436 mmol) in portions at room temperature under nitrogen atmosphere. The resulting mixture was stirred for 30 min at room temperature under nitrogen atmosphere. To this was added 3-(2-fluoropropan-2-yl)pyrrolidine hydrochloride (0.27 g, 1.633 mmol) at room temperature. The resulting mixture was stirred for additional 2 h at room temperature. The reaction was quenched with MeOH (5 mL) and concentrated under reduced pressure. The residue was purified by silica gel column chromatography, eluted with EtOH/EtOAc/petroleum ether (1/3/4) and Prep-HPLC with the following conditions (Column: XBridge Shield RP18 OBD Column, 30×150 mm, 5 μm; Mobile Phase A: water (10 mM NH$_4$HCO$_3$), Mobile Phase B: CH$_3$CN; Flow rate: 60 mL/min; Gradient: 45% B to 60% B; Detecter: 254 nm to afford N-{2-fluoro-4-methyl-5-[2-(1-methylpyrazol-4-yl)-6-(morpholin-4-yl)pyridin-4-yl]phenyl}-3-(2-fluoropropan-2-yl)pyrrolidine-1-carboxamide (140 mg, 24%) as an off-white solid. MS ESI calculated for $C_{28}H_{34}F_2N_6O_2$[M+H]$^+$, 525.27, found 525.45. $^1H$ NMR (400 MHz, CDCl$_3$) δ 8.08 (d, J=8.4 Hz, 1H), 7.92 (s, 1H), 7.87 (s, 1H), 7.00 (d, J=12.0 Hz, 1H), 6.81 (s, 1H), 6.40 (s, 1H), 6.36 (s, 1H), 3.96 (s, 3H), 3.88. 3.85 (m, 4H), 3.78-3.66 (m, 2H), 3.61-3.58 (m, 4H), 3.49-3.37 (m, 2H), 2.55-2.41 (m, 1H), 2.24 (s, 3H), 2.12-1.97 (m, 2H), 1.45 (s, 3H), 1.40 (s, 3H). $^{19}F$ NMR (376 MHz, CDCl$_3$) δ−134.35 (1F), −149.41 (1F).

II. Biological Evaluation

Example 1: Kinase Assay Protocol

Protein Kinase Assay:
Assay platform was used to measure kinase/inhibitor interactions as described previously (Anastassiadis et al., 2011). In brief, for each reaction, kinase and substrate were mixed in a buffer containing 20 mM HEPES (pH 7.5), 10 mM MgCl2, 1 mM EGTA, 0.02% Brij35, 0.02 mg/mL BSA, 0.1 mM Na$_3$VO4, 2 mM DTT, and 1% DMSO. All compounds were solubilized in DMSO. Compounds were then added to each reaction mixture via acoustic dispense using an ECHO 550 nanoliter dispenser. For human RAF1 testing, human MEK1 (K97R) was used as a substrate at a concentration of 3 micromolar, with a final ATP concentration of 10 micromolar. For human BRAF testing, human MEK1 (K97R) was used as a substrate at 1 micromolar concentration, with a final ATP concentration of 25 micromolar. Compounds were tested in 10-dose $IC_{50}$ mode with a 3-fold serial dilution starting at 10 micromolar. After a 20-min incubation, ATP (Sigma-Aldrich, St. Louis, Mo. 63178) and [g33P] ATP (specific activity 10 microCi/microliter) purchased at PerkinElmer (Boston, Mass., 02118 Cat #BLU 003H250UC) were added at a final total concentration of 10 mM. Reactions were carried out at room temperature for 2 hr and spotted onto P81 ion exchange cellulose chromatography paper (Reaction Biology). Filter paper was washed in 0.75% phosphoric acid to remove unincorporated ATP. The percent remaining kinase activity relative to a vehicle-containing (DMSO) kinase reaction was calculated for each kinase/inhibitor pair. $IC_{50}$ values were calculated using Prism 5 (GraphPad).

Representative data for exemplary compounds is presented in Table 2.

TABLE 2

| Synthetic Chemistry Example | RAF-1 $IC_{50}$ | Synthetic Chemistry Example | RAF-1 $IC_{50}$ |
|---|---|---|---|
| 1 | B | 44 | B |
| 2 | B | 45 | B |
| 3 | B | 46 | B |
| 4 | B | 47 | B |
| 5 | B | 48 | A |
| 6 | B | 49 | A |
| 7 | A | 50 | B |
| 8 | A | 51 | B |
| 9 | B | 52 | B |
| 10 | B | 53 | B |
| 11 | B | 54 | B |
| 12 | A | 55 | B |
| 13 | A | 56 | B |
| 14 | B | 57 | B |
| 15 | B | 58 | B |
| 16 | B | 59 | B |
| 17 | B | 60 | B |
| 18 | A | 61 | B |
| 19 | A | 62 | B |
| 20 | A | 63 | B |
| 21 | A | 64 | B |
| 22 | A | 65 | A |
| 23 | A | 66 | A |
| 24 | A | 67 | A |
| 25 | A | 68 | A |
| 26 | A | 69 | A |
| 27 | C | 70 | A |
| 28 | C | 71 | A |
| 29 | B | 72 | A |
| 30 | B | 73 | A |
| 31 | C | 74 | A |
| 32 | B | 75 | A |
| 33 | A | 76 | A |
| 34 | A | 77 | A |
| 35 | B | 78 | A |
| 36 | A | 79 | B |
| 37 | B | 80 | B |
| 38 | B | 81 | B |
| 39 | B | 82 | B |
| 40 | B | 83 | B |
| 41 | B | 84 | A |
| 42 | B | 85 | B |
| 43 | B | | |

Note:
Biochemical assay $IC_{50}$ data are designated within the following ranges:
A: ≤0.001 μM  C: >0.010 μM to ≤ 0.100 μM
B: >0.001 μM to ≤ 0.010 μM  D: >0.100 μM to ≤ 1 μM III. Preparation of Pharmaceutical Dosage Forms Example 1: Oral Capsule The active ingredient is a compound of Table 1, or a pharmaceutically acceptable salt or solvate thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

Example 2: Solution for Injection

The active ingredient is a compound of Table 1, or a pharmaceutically acceptable salt thereof, and is formulated as a solution in sesame oil at a concentration of 50 mg-eq/mL.

The examples and embodiments described herein are for illustrative purposes only and various modifications or changes suggested to persons skilled in the art are to be included within the spirit and purview of this application and scope of the appended claims.

We claim:

1. A compound, or pharmaceutically acceptable salt or solvate thereof, having the structure of Formula (I):

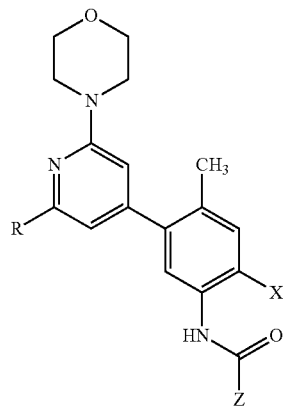

(I)

wherein,
R is selected from the group consisting of optionally substituted C1-C8 alkyl, optionally substituted C2-C8 alkenyl, optionally substituted C2-C8 alkynyl, optionally substituted C3-C6 cycloalkyl, optionally substituted C4-C8 cycloalkylalkyl, optionally substituted C3-C6 heterocyclyl, optionally substituted C4-C8 heterocyclylalkyl, optionally substituted C6 aryl, optionally substituted 5- or 6-membered heteroaryl, and —CON($R^1$)$_2$;
$R^1$ is selected from H or optionally substituted C1-C8 alkyl, wherein, optionally, two $R^1$ substituents join to form a ring;
X is H or F;
Z is selected from:
(a) —NR$^a$R$^b$, wherein R$^a$ is selected from H, optionally substituted alkyl, optionally substituted C3-C6 alkenyl, optionally substituted C3-C6 alkynyl, optionally substituted C3-C6 cycloalkyl, optionally substituted C3-C6 cycloalkylalkyl, optionally substituted heterocyclyl, or optionally substituted heterocyclylalkyl; and $R^b$ is selected from optionally substituted alkyl, optionally substituted C3-C6 alkenyl, optionally substituted C3-C6 alkynyl, optionally substituted C3-C6 cycloalkyl, optionally substituted C3-C6 cycloalkylalkyl, optionally substituted C4-C6 heterocyclyl, or optionally substituted heterocyclylalkyl;

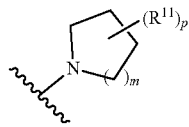

wherein m is 0, 1, 2, or 3; p is 0, 1, 2, 3, or 4; and
each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —SO$_2$alkyl, optionally substituted C3-C6 cycloalkylalkyl, optionally substituted heterocyclyl, or optionally substituted heterocyclylalkyl; or two $R^{11}$ groups together form an oxo;

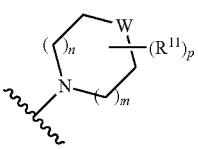

wherein m is 0, 1, 2, or 3; n is 0, 1, 2, or 3; p is 0, 1, 2, 3, or 4; W is O, S, S(O), SO$_2$, NH or N (optionally substituted C1-C6 alkyl); and
each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two $R^{11}$ groups together form an oxo;

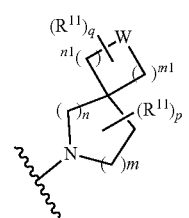

wherein m is 0, 1, or 2; n is 0, 1, or 2; m1 is 0, 1, or 2; n1 is 0, 1, or 2 provided both m1 and n1 are not both 0; p is 0, 1, or 2; and q is 0, 1 or 2;
W is O, S, S(O), SO$_2$, NH or N (optionally substituted C1-C6 alkyl), CH$_2$, CHR$^{11}$, or C(R$^{11}$)$_2$; and
each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two $R^{11}$ groups together form an oxo;

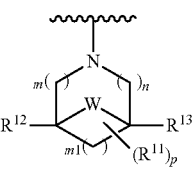

wherein m is 0, 1, or 2; n is 0, 1, or 2; m1 is 1, or 2; p is 0, 1, 2, or 3; W is O, S, S(O), SO$_2$, NH or N (optionally substituted C1-C6 alkyl), CH$_2$, CHR$^{11}$, —CH$_2$—CH$_2$—, —CH$_2$—CHR$^{11}$—, —CH$_2$—C(R$^{11}$)$_2$—, —CHR$^{11}$—CH$_2$—, —C(R$^{11}$)$_2$—CH$_2$—, —NH—CH$_2$—, —NH—CHR$^{11}$—, —NH—C(R$^{11}$)$_2$—, —CH$_2$—NH—, —CHR$^{11}$—NH—, —C(R$^{11}$)$_2$—NH—, —N(R$^{11}$)—CH$_2$—, —N(R$^{11}$)—CHR$^{11}$—, —N(R$^{11}$)—C(R$^{11}$)$_2$—, —CH$_2$—N(R$^{11}$)—, —CHR$^{11}$—N(R$^{11}$)—, —C(R$^{11}$)$_2$—N(R$^{11}$)—, —O—CH$_2$—, or —CH$_2$—O—; each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two $R^{11}$ groups together form an oxo; and $R^{12}$ and $R^{13}$ are each independently selected from H, or optionally substituted C1-C6 alkyl;

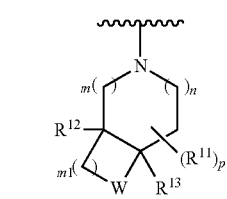

or

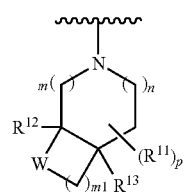

wherein m is 0, 1, or 2; n is 0, 1, or 2; m1 is 0, 1, or 2; p is 0, 1, or 2; W is O, S, S(O), SO$_2$, NH or N (optionally substituted C1-C6 alkyl), CH$_2$, CHR$^{11}$, or C(R$^{11}$)$_2$; each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two $R^{11}$ groups together form an oxo; and $R^{12}$ and $R^{13}$ are each independently selected from H, or optionally substituted C1-C6 alkyl;

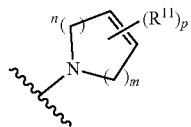

(g)

wherein m is 0, 1, 2, or 3; n is 0, 1, 2, or 3; p is 0, 1, 2, 3, or 4; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —SO$_2$alkyl, optionally substituted C3-C6 cycloalkylalkyl, optionally substituted heterocyclyl, or optionally substituted heterocyclylalkyl; or two $R^{11}$ groups together form an oxo;

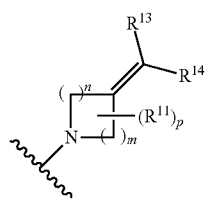

(h)

wherein m is 1, 2, or 3; n is 1, 2, or 3; p is 0, 1, or 2; and each $R^{13}$ or $R^{14}$ is independently selected from hydrogen, halogen, —CN, optionally substituted C1-C6 alkyl, or optionally substituted C3-C6 cycloalkyl; each $R^{11}$ is independently selected from —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl; or

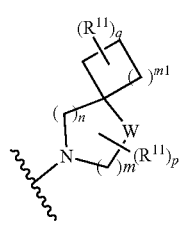

(i)

wherein m is 0, 1, or 2; n is 0, 1, or 2; m1 is 0, 1, or 2; p is 0, 1, or 2; and q is 0, 1 or 2; W is O, S, S(O), SO$_2$, NH or N (optionally substituted C1-C6 alkyl), CH$_2$, CHR$^{11}$, or C(R$^{11}$)$_2$; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two geminal $R^{11}$ groups together form an oxo.

2. The compound of claim 1, or pharmaceutically acceptable salt or solvate thereof, wherein Z is

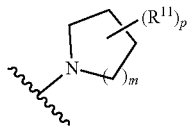

wherein m is 0, 1, 2, or 3; p is 0, 1, 2, 3, or 4; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —SO$_2$alkyl, optionally substituted C3-C6 cycloalkylalkyl, optionally substituted heterocyclyl, or optionally substituted heterocyclylalkyl; or two $R^{11}$ groups together form an oxo.

3. The compound of claim 2, or pharmaceutically acceptable salt or solvate thereof, wherein m is 1.

4. The compound of claim 2, or pharmaceutically acceptable salt or solvate thereof, wherein p is 1.

5. The compound of claim 2, or pharmaceutically acceptable salt or solvate thereof, wherein $R^{11}$ is optionally substituted C1-C6 alkyl, or optionally substituted C3-C6 cycloalkyl.

6. The compound of claim 5, or pharmaceutically acceptable salt or solvate thereof, wherein the optionally substituted C1-C6 alkyl, or optionally substituted C3-C6 cycloalkyl is substituted with at least a halogen.

7. The compound of claim 5, or pharmaceutically acceptable salt or solvate thereof, wherein the optionally substituted C1-C6 alkyl is an optionally substituted C2 alkyl substituted with at least one halogen.

8. The compound of claim 7, or pharmaceutically acceptable salt or solvate thereof, wherein the optionally substituted C2 alkyl is a 3,3,3-trifluoroethyl group.

9. The compound of claim 2, or pharmaceutically acceptable salt or solvate thereof, wherein Z is 3-(2,2,2-trifluoroethyl)pyrrolidin-1-yl.

10. The compound of claim 1, or pharmaceutically acceptable salt or solvate thereof, wherein Z is —NR$^a$R$^b$, wherein R$^a$ is selected from H, optionally substituted alkyl, optionally substituted C3-C6 alkenyl, optionally substituted C3-C6 alkynyl, optionally substituted C3-C6 cycloalkyl, optionally substituted C3-C6 cycloalkylalkyl, optionally substituted heterocyclyl, or optionally substituted heterocyclylalkyl; and R$^b$ is selected from optionally substituted alkyl, optionally substituted C3-C6 alkenyl, optionally substituted C3-C6 alkynyl, optionally substituted C3-C6 cycloalkyl, optionally substituted C3-C6 cycloalkylalkyl, optionally substituted C4-C6 heterocyclyl, or optionally substituted heterocyclylalkyl.

11. The compound of claim 1, or pharmaceutically acceptable salt or solvate thereof, wherein Z is

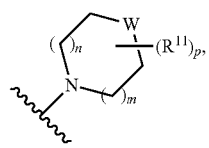

wherein m is 0, 1, 2, or 3; n is 0, 1, 2, or 3; p is 0, 1, 2, 3, or 4; W is O, S, S(O), SO₂, NH or N (optionally substituted C1-C6 alkyl); and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO₂alkyl, optionally substituted C3-C6 cycloalkylalkyl, optionally substituted heterocyclyl, or optionally substituted heterocyclylalkyl, or two $R^{11}$ groups together form an oxo.

12. The compound of claim 1, or pharmaceutically acceptable salt or solvate thereof, wherein Z is

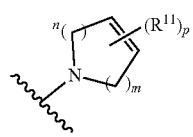

wherein m is 0, 1, 2, or 3; n is 0, 1, 2, or 3; p is 0, 1, 2, 3, or 4; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —S-alkyl, optionally substituted —SO₂alkyl, optionally substituted C3-C6 cycloalkylalkyl, optionally substituted heterocyclyl, or optionally substituted heterocyclylalkyl; or two $R^{11}$ groups together form an oxo.

13. The compound of claim 1, or pharmaceutically acceptable salt or solvate thereof, wherein R is optionally substituted C1-C8 alkyl.

14. The compound of claim 1, or pharmaceutically acceptable salt or solvate thereof, wherein R is optionally substituted C2-C8 alkenyl.

15. The compound of claim 1, or pharmaceutically acceptable salt or solvate thereof, wherein R is optionally substituted C2-C8 alkynyl.

16. The compound of claim 1, or pharmaceutically acceptable salt or solvate thereof, wherein R is optionally substituted C3-C6 cycloalkyl.

17. The compound of claim 1, or pharmaceutically acceptable salt or solvate thereof, wherein R is optionally substituted C3-C6 heterocyclyl.

18. The compound of claim 1, or pharmaceutically acceptable salt or solvate thereof, wherein R is optionally substituted 5-membered heteroaryl.

19. The compound of claim 18, or pharmaceutically acceptable salt or solvate thereof, wherein the optionally substituted 5-membered heteroaryl is an optionally substituted pyrazole, oxazole, or thiazole.

20. The compound of claim 1, or pharmaceutically acceptable salt or solvate thereof, wherein R is optionally substituted 6-membered heteroaryl.

21. The compound of claim 20, or pharmaceutically acceptable salt or solvate thereof, wherein the optionally substituted 6-membered heteroaryl is an optionally substituted pyridine or pyrimidine.

22. The compound of claim 1, or pharmaceutically acceptable salt or solvate thereof, wherein R is —CON($R^1$)₂, and $R^1$ is selected from H or optionally substituted C1-C8 alkyl.

23. The compound of claim 12, or pharmaceutically acceptable salt or solvate thereof, wherein n is 1; m is 1; p is 1; and $R^{11}$ is optionally substituted C1-C6 alkyl.

24. The compound of claim 23, or pharmaceutically acceptable salt or solvate thereof, wherein $R^{11}$ is a —CF₃ group.

25. The compound of claim 23, or pharmaceutically acceptable salt or solvate thereof, wherein R is an optionally substituted pyrazole.

26. The compound of claim 25, or pharmaceutically acceptable salt or solvate thereof, wherein R is an optionally substituted pyrazol-4-yl, or optionally substituted pyrazol-5-yl.

27. The compound of claim 26, or pharmaceutically acceptable salt or solvate thereof, wherein R is

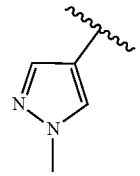 [SMILES: *c1cnn(C)c1]

or

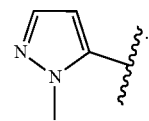

28. The compound of claim 1, or pharmaceutically acceptable salt or solvate thereof, wherein X is F.

29. The compound of claim 1, or pharmaceutically acceptable salt or solvate thereof, wherein X is H.

30. A pharmaceutical composition comprising a compound, or pharmaceutically acceptable salt or solvate thereof, as described in claim 1, and a pharmaceutically acceptable excipient.

* * * * *